(12) United States Patent
Chen et al.

(10) Patent No.: US 11,701,379 B2
(45) Date of Patent: Jul. 18, 2023

(54) IN VITRO AND IN VIVO INTRACELLULAR DELIVERY OF SIRNA VIA SELF-ASSEMBLED NANOPIECES

(71) Applicant: Rhode Island Hospital, Providence, RI (US)

(72) Inventors: Qian Chen, Barrington, RI (US); Yupeng Chen, Sharon, MA (US); Hongchuan Yu, Chestnut Hill, MA (US)

(73) Assignee: Rhode Island Hospital, Providence, RI (US)

( * ) Notice: Subject to any disclaimer, the term of this patent is extended or adjusted under 35 U.S.C. 154(b) by 0 days.

(21) Appl. No.: 17/041,399

(22) PCT Filed: Mar. 26, 2019

(86) PCT No.: PCT/US2019/024155
§ 371 (c)(1),
(2) Date: Sep. 24, 2020

(87) PCT Pub. No.: WO2019/191151
PCT Pub. Date: Oct. 3, 2019

(65) Prior Publication Data
US 2021/0023117 A1   Jan. 28, 2021

Related U.S. Application Data

(60) Provisional application No. 62/648,233, filed on Mar. 26, 2018.

(51) Int. Cl.
| | | |
|---|---|---|
| C07H 21/02 | (2006.01) |
| C07H 21/04 | (2006.01) |
| A61K 31/713 | (2006.01) |
| A61K 47/54 | (2017.01) |
| A61K 47/69 | (2017.01) |
| A61P 19/02 | (2006.01) |
| C12N 15/113 | (2010.01) |

(52) U.S. Cl.
CPC .......... *A61K 31/713* (2013.01); *A61K 47/545* (2017.08); *A61K 47/6929* (2017.08); *A61K 47/6949* (2017.08); *A61P 19/02* (2018.01); *C12N 15/1136* (2013.01); *C12N 2310/141* (2013.01); *C12N 2320/31* (2013.01)

(58) Field of Classification Search
CPC .......................... C12N 15/113; C12N 2310/14
See application file for complete search history.

(56) References Cited

U.S. PATENT DOCUMENTS

| | | | |
|---|---|---|---|
| 6,696,565 B2 | 2/2004 | Fenniri | |
| 8,795,691 B2 * | 8/2014 | Webster | A61P 19/00 544/245 |
| 2007/0281900 A1 * | 12/2007 | Cui | C12N 15/113 435/458 |
| 2014/0171482 A1 | 6/2014 | Webster et al. | |
| 2015/0017138 A1 * | 1/2015 | Fruehauf | C12N 15/111 435/351 |
| 2015/0258094 A1 | 9/2015 | Chen et al. | |

FOREIGN PATENT DOCUMENTS

| | | |
|---|---|---|
| WO | 9219195 A1 | 11/1992 |
| WO | 2016/144125 A2 | 9/2016 |
| WO | 2019191151 A1 | 10/2019 |

OTHER PUBLICATIONS

Borzsonyi et al. (J Am Chem Soc, 2010, 132, 15136-15139).*
International Search Report corresponding to International Application No. PCT/US2019/024155 dated Aug. 16, 2019 (5 pages).
Written Opinion corresponding to International Application No. PCT/US2019/024155 dated Aug. 16, 2019 (6 pages).
Zhang et al. (Mar. 1, 2009) "Arginine-Glycine-Aspartic Acid Modified Rosette Nanotube-Hydrogel Composites for Bone Tissue Engineering", Biomaterials, 30(7):1309-1320.
Khoury et al. (Aug. 2008) "Efficient Suppression of Murine Arthritis by Combined Anticytokine Small Interfering Rna Lipoplexes", Arthritis & Rheumatology, 58(8):2356-2367.
Kim et al. (May 2016) "Pentoxifylline Ameliorates Mechanical Hyperalgesia in a Rat Model of Chemotherapy-Induced Neuropathic Pain", Pain Physician, 19(4):E589-600 (12 pages).
Kole et al. (Jan. 20, 2012) "RNA Therapeutics: Beyond RNA Interference and Antisense Oligonucleotides", Nature Reviews Drug Discovery, 11(2):125-140.
Komano et al. (Jan. 2012) "Arthritic Joint-targeting Small Interfering RNA-encapsulated Liposome: Implication for Treatment Strategy for Rheumatoid Arthritis", Journal of Pharmacology and Experimental Therapeutics, 340(1):109-113.
Lee et al. (Sep. 17, 2012) "Changes in Microarchitectural Characteristics at the Tibial Epiphysis Induced by Collagen-induced Rheumatoid Arthritis Over Time", Clinical Interventions in Aging, 7:373-382.
Lee et al. (Feb. 2014) "TNF-α Gene Silencing Using Polymerized SiRNA/thiolated Glycol Chitosan Nanoparticles for Rheumatoid Arthritis", Molecular Therapy, 22(2):397-408.
Li et al. (2013) "Curcumin Attenuates Diabetic Neuropathic Pain by Downregulating TNF-α in a Rat Model", International Journal of Medical Sciences, 10(4):377-381.
Lubberts et al. (Nov. 2002) "Increase in Expression of Receptor Activator of Nuclear Factor Kappab at Sites of Bone Erosion Correlates With Progression of Inflammation in Evolving Collagen-induced Arthritis", Arthritis & Rheumatology, 46(11):3055-3064.
Luo et al. (Jun. 2017) "Adenovirus-mediated Small Interfering RNA Targeting TAK1 Ameliorates Joint Inflammation With Collagen-induced Arthritis in Mice", Inflammation, 40(3):894-903.

(Continued)

*Primary Examiner* — Amy H Bowman
(74) *Attorney, Agent, or Firm* — Adler Pollock & Sheehan P.C.

(57) ABSTRACT

The compositions and methods of the invention provide compositions and methods for preferential targeting of tissues to delivery therapeutic or diagnostic agents. For example, such compounds are useful in the treatment of joint disorders those affecting articulating joints, e.g., injury-induced osteoarthritis as well as autoimmune diseases affecting joint tissue such as rheumatoid arthritis.

2 Claims, 86 Drawing Sheets

Specification includes a Sequence Listing.

(56) References Cited

OTHER PUBLICATIONS

Marotte et al. (2007) "A 1-year case-control study in patients with rheumatoid arthritis indicates prevention of loss of bone mineral density in both responders and nonresponders to infliximab", Arthritis Research & Therapy, 9(3):R61 (7 pages).
McInnes et al. (Dec. 8, 2011) "The Pathogenesis of Rheumatoid Arthritis", The New England Journal of Medicine, 365(23):2205-2219.
Moralez et al. (Jun. 15, 2005) "Helical Rosette Nanotubes with Tunable Stability and Hierarchy", Journal of the American Chemical Society, 127(23):8307-8309 (12 pages).
Nakanishi et al. (Jun. 13, 2016) "Go-sha-jinki-gan (GJG) Ameliorates Allodynia in Chronic Constriction Injury-model Mice via Suppression of TNF-α Expression in the Spinal Cord", Molecular Pain, 12:(16 pages).
Okamura et al. (Jul. 2015) "Efficacy at 52 Weeks of Daily Clinical Use of Iguratimod in Patients With Rheumatoid Arthritis", Modern Rheumatology, 25(4):534-539.
Okamura et al. (Mar. 2015) "Efficacy of the Clinical Use of Iguratimod Therapy in Patients With Rheumatoid Arthritis", Modern Rheumatology, 25(2):235-240.
Okamura et al. (Nov. 22, 2014) "Evaluation of Tocilizumab Therapy in Patients With Rheumatoid Arthritis Based on FDG-PET/CT", BMC Musculoskeletal Disorders, 15:393 (7 pages).
Okamura et al. (Aug. 2012) "The Assessment of Biologic Treatment in Patients With Rheumatoid Arthritis Using FFDG-PET/CT", Rheumatology (Oxford), 51(8):1484-1491.
Saidenberg et al. (Nov. 2004) "TNF-alpha Antibodies and Osteoprotegerin Decrease Systemic Bone Loss Associated With Inflammation Through Distinct Mechanisms in Collagen-induced Arthritis", Bone, 35(5):1200-1207.
Scheinman et al. (Dec. 2011) "Functionalized STAT 1 SiRNA Nanoparticles Regress Rheumatoid Arthritis in a Mouse Model", Nanomedicine (Lond), 6(10):1669-1682.
Van Schouwenburg et al. (Mar. 2013) "Immunogenicity of Anti-TNF Biologic Therapies for Rheumatoid Arthritis", Nature Reviews Rheumatology, 9(3):164-172.
Seeuws et al. (2010, e-published Aug. 23, 2010) "A Multiparameter Approach to Monitor Disease Activity in Collagen-induced Arthritis", Arthritis Research & Therapy, 12(4):R160 (10 pages).
Shvedova et al. (Jun. 10, 2005) "Unusual Inflammatory and Fibrogenic Pulmonary Responses to Single-Walled Carbon Nanotubes in Mice", American Journal of Physiology-Lung Cellular and Molecular Physiology, 289(5):L698-L708.
Takagishi et al. (Apr. 1986) "Effects of Cyclosporin on Collagen Induced Arthritis in Mice", Annals of the Rheumatic Diseases, 45(4):339-344.
Torzilli et al. (Sep. 1997) "Effect of Proteoglycan Removal on Solute Mobility in Articular Cartilage", Journal of Biomechanics, 30(9):895-902.
Tyagi et al. (Jan. 1998) "Multicolor Molecular Beacons for Allele Discrimination", Nature Biotechnology, 16 (1):49-53.
Baddack-Werncke et al. (Feb. 6, 2017) "Cytotoxic T cells Modulate Inflammation and Endogenous Opioid Analgesia in Chronic Arthritis", Journal of Neuroinflammation, 14(1):30 (11 pages).
Wijbrandts et al. (Mar. 2009) "Bone Mineral Density in Rheumatoid Arthritis Patients 1 Year After Adalimumab Therapy: Arrest of Bone Loss", Annals of the Rheumatic Diseases, 68(3):373-376.
Wu et al. (Sep. 2016) "Secondary Osteoporosis in Collagen-induced Arthritis Rats", Journal of Bone and Minera Metabolism, 34(5):500-516.
Yi et al. (Jun. 2014) "Induced Production of Anti-etanercept Antibody in Collagen-induced Arthritis", Molecular Medicine Reports, 9(6):2301-2308.
Yonemoto et al. (2016) "Comparison of Golimumab 100-mg Monotherapy to Golimumab 50 Mg Plus Methotrexate in Patients With Rheumatoid Arthritis: Results From a Multicenter, Cohort Study", Modern Rheumatology, 26(1):24-28.
Taketa et al. (2008) "Selective Cyclooxygenase-2 Inhibitor Prevents Reduction of Trabecular Bone Mass in Collagen-induced Arthritic Mice in Association With Suppression of RANKL/OPG Ratio and IL-6 mRNA Expression in Synovial Tissues but Not in Bone Marrow Cells", Journal of Bone and Mineral Metabolism, 26(2):143-151.
Database Genbank (Oct. 9, 2016) "A Disintegrin and Metalloproteinase with Thrombospondin Motifs 4 Isoform 1 Preproprotein [*Homo sapiens*]", GenBank Accession No. NP_005090.3, 4 pages.
Kato et al. (Sep. 12, 2015) "The Inhibitory Effects of a Rankl-binding Peptide on Articular and Periarticular Bone Loss in a Murine Model of Collagen-induced Arthritis: a Bone Histomorphometric Study", Arthritis Research & Therapy, 17(1):251 (15 pages).
Database Genbank (Oct. 6, 2016) "*Homo sapiens* TNFRSF1A Associated Via Death Domain (TRADD), Transcript Variant 1, mRNA", GenBank Accession No. NM_003789.3, 4 pages.
Database Genbank (Nov. 7, 2015) "*Homo sapiens* Transforming Growth Factor Beta 2 (TGFB2), Transcript Variant 1, mRNA", GenBank Accession No. NM_001135599.2, 6 pages.
Database Genbank (Oct. 17, 2015) "*Homo sapiens* Transforming Growth Factor, Beta 1 (TGFB1), mRNA", Genbank Accession No. NM_000660.5, 4 pages.
Database Genbank (Oct. 6, 2016) "*Homo sapiens* Tumor Necrosis Factor (TNF), mRNA", GenBank Accession No. NM_000594.3, 6 pages.
Database Genbank (Jun. 6, 2006) "*Homo sapiens* Tumor Necrosis Factor, Alpha-Induced Protein 3, mRNA (cDNA clone MGC:138687 IMAGE:40036692), Complete Cds", GenBank Accession No. BC114480.1, 3 pages.
Database Genbank (Oct. 6, 2016) "*Homo sapiens* Vascular Endothelial Growth Factor A (VEGFA), Transcript Variant 1, mRNA", GenBank Accession No. NM_001025366.2, 7 pages.
Database Genbank (May 24, 1995) "Human Cell Death Protein (RIP) mRNA, partial cds", GenBank Accession No. U25994.1, 1 page.
Database Genbank (Nov. 1, 1994) "Human dipeptidyl peptidase IV (CD26) mRNA, complete cds", Genbank Accession No. M74777.1, 2 pages.
Database Genbank (Sep. 3, 1994) "Human Tumor Necrosis Factor Receptor II (TNFrII) mRNA, Complete xis", GenBank Accession No. M55994.1, 2 pages.
Database Genbank (Nov. 25, 2015) "Insulin-like Growth Factor I Isoform 4 Preproprotein [*Homo sapiens*]", GenBank Accession No. NP_000609.1, 4 pages.
Database Genbank (Jul. 15, 2006) "Interleukin 15 [*Homo sapiens*]", GenBank Accession No. AAH18149.1, 2 pages.
Database Genbank (Oct. 2, 2016) "Interleukin-1 Alpha Precursor [*Homo sapiens*]", GenBank Accession No. NP_000566.3, 3 pages.
Database Genbank (Oct. 6, 2016) "Interleukin-1 Beta Proprotein [*Homo sapiens*]", GenBank Accession No. NP_000567.1, 3 pages.
Database Genbank (Oct. 7, 2016) "Interleukin-1 Receptor Antagonist Protein Isoform 3 [*Homo sapiens*]", GenBank Accession No. NP_000568.1, 3 pages.
Database Genbank (Oct. 15, 2016) "Interleukin-1 Receptor type 1 Isoform 1 Precursor [*Homo sapiens*]", GenBank Accession No. NP_000868.1, 3 pages.
Database Genbank (Jul. 24, 2020) "Interleukin-2 Receptor Subunit Alpha Isoform 1 Precursor [*Homo sapiens*]", Genbank Accession No. NP_000408.1, 3 Pages.
Database Genbank (Aug. 16, 2021) "Interleukin-20 isoform 1 Precursor [*Homo sapiens*]", Genbank Accession No. NP_061194.2, 3 pages.
Database Genbank (Sep. 5, 2016) "Interleukin-6 Isoform 1 Precursor [*Homo sapiens*]", GenBank Accession No. NP_000591.1, 3 pages.
Database Genbank (Oct. 6, 2016) "Interleukin-8 Isoform 1 Precursor [*Homo sapiens*]", GenBank Accession No. NP_000575.1, 4 pages.
Database Genbank (Oct. 7, 2016) "Interstitial Collagenase Isoform 2 [*Homo sapiens*]", GenBank Accession No. NP_001139410.1, 3 pages.

(56) References Cited

OTHER PUBLICATIONS

Database Genbank (Oct. 24, 1996) "Il6476.seq.F Human fetal heart, Lambda ZAP Express Homo sapiens cDNA 5', mRNA Sequence", Genbank Accession No. AA092293.1, 1 page.
Database Genbank (Mar. 15, 2015) "Matrix Metalloproteinase-9 Preproprotein [*Homo sapiens*]", GenBank Accession No. NP_004985. 2, 5 pages.
Database Genbank (Oct. 21, 2011) "MHC Class II Antigen [*Homo sapiens*]", GenBank Accession No. ADZ73424.1, 1 page.
Database Genbank (Oct. 18, 2021) "Mus Musculus MicroRNA 181a-2 (Mir181a-2), MicroRNA", Genbank Accession No. NR_029568. 1, 3 pages.
Database Genbank (Nov. 18, 2016) "Prolyl Endopeptidase FAP Isoform 2 [*Homo sapiens*]", GenBank Accession No. NP_001278736. 1, 3 pages.
Database Genbank (Apr. 9, 2016) "Protein-Arginine Deiminase Type-2 [*Homo sapiens*]", NCBI Reference Sequence: NP_031391. 2, 4 pages.
Database Genbank (Apr. 9, 2016) "Protein-Arginine Deiminase Type-3 [*Homo sapiens*]", GenBank Accession No. NP_057317.2, 4 pages.
Database Genbank (Apr. 9, 2016) "Protein-Arginine Deiminase Type-4 [*Homo sapiens*]", GenBank Accession No. NP_036519.2, 4 pages.
Database Genbank (May 24, 1995) "RIP, partial [*Homo sapiens*]", GenBank Accession No. AAC50137.1, 1 page.
Database Genbank (Jun. 6, 2006) "Send to: Tumor Necrosis Factor, Alpha-induced Protein 3 [*Homo sapiens*]", Genbank Accession No. AAI14481.1, 2 pages.
Database Genbank (Aug. 3, 1996) "Signal Transducer and Activator of Transcription 4 [*Homo sapiens*]", GenBank Accession No. AAB05605.1, 2 pages.
Database Genbank (Oct. 8, 2016) "Stromelysin-1 Preproprotein [*Homo sapiens*]", GenBank Accession No. NP_002413.1, 4 pages.
Database Genbank (Mar. 3, 2015) "TPA: Homo sapiens MicroRNA Hsa-mir-125a Precursor", Genbank Accession No. LM608509.1, 1 page.
Database Genbank (Sep. 5, 2016) "Transforming Growth Factor Beta-1 Proprotein Preproprotein [*Homo sapiens*]", GenBank Accession No. NP_000651.3, 3 pages.
Database Genbank (Sep. 11, 2016) "Transforming Growth Factor Beta-2 Proprotein Isoform 1 Precursor [*Homo sapiens*]", GenBank Accession No. NP_001129071.1, 3 pages.
Database Genbank (Oct. 6, 2016) "Tumor Necrosis Factor [*Homo sapiens*]", GenBank Accession No. NP_000585.2, 4 pages.
Database Genbank (Sep. 3, 1994) "Tumor Necrosis Factor Receptor [*Homo sapiens*]", GenBank Accession No. AAA36755.1, 2 pages.
Database Genbank (Oct. 9, 2016) "Tumor Necrosis Factor Receptor Superfamily Member 1A isoform 1 Precursor [*Homo sapiens*]", GenBank Accession No. NP_001056.1, 4 pages.
Database Genbank (Oct. 6, 2016) "Vascular Endothelial Growth Factor A Isoform a [*Homo sapiens*]", GenBank Accession No. NP_001020537.2, 4 pages.
Fenniri et al. (Apr. 25, 2001) "Helical Rosette Nanotubes: Design, Self-Assembly, and Characterization", Journal of the American Chemical Society, 123(16):3854-3855 (7 pages).
Fine et al. (Apr. 20, 2009) "Enhanced Endothelial Cell Functions on Rosette Nanotube-Coated Titanium Vascular Stents", International Journal of Nanomedicine, 4:91-97.
Gao et al. (Jun. 2015) "A Store-operated Calcium Channel Inhibitor Attenuates Collagen-induced Arthritis", British Journal of Pharmacology, 172(12):2991-3002.
Database Genbank (Mar. 15, 2015) "*Homo sapiens* Interleukin 1, Alpha (IL1A), mRNA", NCBI Reference Sequence: NM 000575.3, 6 pages.
Howard et al. (Jan. 2009) "Chitosan/sima Nanoparticle-mediated Tnf-alpha Knockdown in Peritoneal Macrophages for Anti-inflammatory Treatment in a Murine Arthritis Model", Molecular Therapy, 7(1):162-168.

Inoue et al. (2009) "Comparison of Anti-rheumatic Effects of Local Rnai-based Therapy in Collagen Induced Arthritis Rats Using Various Cytokine Genes as Molecular Targets", Modern Rheumatology,19(2):125-133.
Journeay et al. (Jun. 2008) "Low Inflammatory Activation by Self-Assembling Rosette Nanotubes in Human Calu-3 Pulmonary Epithelial Cells", Small, 4(6):817-823.
Journeay et al. (2008) "Rosette Nanotubes Show Low Acute Pulmonary Toxicity in Vivo", International Journal of Nanomedicine, 3(3):373-383.
Kanazawa et al. (Dec. 30, 2016) "Systemic Delivery of Small Interfering RNA Targeting Nuclear Factor KB in Mice With Collagen-induced Arthritis Using Arginine-histidine-cysteine Based Oligopeptide-modified Polymer Nanomicelles", International Journal of Pharmaceutics, 515(1-2):315-323.
Khoury et al. (Jun. 2006) "Efficient New Cationic Liposome Formulation for Systemic Delivery of Small Interfering RNA Silencing Tumor Necrosis Factor Alpha in Experimental Arthritis", Arthritis & Rheumatology, 54(6):1867-1877.
Bertoldi et al. (Dec. 7, 2013) "Disease Activity and Bone Mineral Density of MCP Joints in Patients with Rheumatoid and Psoriatic Arthritis: Is There a Correlation?—A Study in Patients Treated with Methotrexate and an Anti-TNF α Agent", ISRN Rheumatology, 2013:708323 (6 pages).
Choy et al. (Mar. 22, 2001) "Cytokine pathways and joint inflammation in rheumatoid arthritis", The New England Journal of Medicine, 344(12):907-916.
Comper (1991) "Physiochemical Aspects of Cartilage Extra Cellular Matrix", Cartilage: Molecular Aspects, 59-96.
Database Genbank (Nov. 14, 2021) "A Disintegrin and Metalloproteinase with Thrombospondin Motifs 5 Preproprotein", Genbank Accession No. NP_008969.2, 4 pages.
Database Genbank (Oct. 8, 2016) "Bone Morphogenetic Protein 2 Preproprotein [*Homo sapiens*]", Genbank Accession No. NP_001191. 1, 3 pages.
Database Genbank (Dec. 21, 2016) "Bone Morphogenetic Protein 4 Isoform a Preproprotein [*Homo sapiens*]", GenBank Accession No. NP_001193.2, 3 pages.
Database Genbank (Oct. 8, 2016) "Bone Morphogenetic Protein 7 Preproprotein [*Homo sapiens*]", Genbank Accession No. NP_001710. 1, 3 pages.
Database Genbank (Aug. 7, 2016) "Collagenase 3 Preproprotein [*Homo sapiens*]", GenBank Accession No. NP_002418.1, 4 Pages.
Database Genbank (Nov. 8, 2021) "Dipeptidyl peptidase 4 isoform 1 [*Homo sapiens*]", Genbank Accession No. NP_001926.2, 4 pages.
Database Genbank (Dec. 6, 2016) "Dipeptidyl Peptidase IV [*Homo sapiens*]", GenBank Accession No. AAA51943.1, 1 page.
Database Genbank (Sep. 15, 2016) "Forkhead Box Protein O3 [*Homo sapiens*]", GenBank Accession No. NP_001446.1, 6 pages.
Database Genbank (May 9, 2007) "FOXP3 [*Homo sapiens*]", GenBank Accession No. ABQ15210.1, 1 page.
Database Genbank (Nov. 11, 2015) "*Homo sapiens* ADAM metallopeptidase with thrombospondin type 1 motif 4 (ADAMTS4), mRNA", Genbank Accession No. NM_005099.4, 4 pages.
Database Genbank (Nov. 11, 2015) "*Homo sapiens* ADAM metallopeptidase with thrombospondin type 1 motif 5 (ADAMTS5), mRNA", GenBank Accession No. NM_007038.3, 6 pages.
Database Genbank (Mar. 15, 2015) "*Homo sapiens* Bone Morphogenetic Protein 2 (BMP2), mRNA", GenBank Accession No. NM_001200.2, 5 pages.
Database Genbank (Nov. 18, 2015) "*Homo sapiens* Bone Morphogenetic Protein 4 (BMP4), Transcript Variant 1, mRNA", GenBank Accession No. NM_001202.3, 5 pages.
Database Genbank (Oct. 8, 2016) "*Homo sapiens* Bone Morphogenetic Protein 7 (BMP7), mRNA", GenBank Accession No. NM_001719.2, 5 pages.
Database Genbank (Apr. 13, 2003) "*Homo sapiens* Chemokine (C-C motif) Receptor 6 (CCR6) mRNA, Complete cds", GenBank Accession No. AY242126.1, 1 page.
Database Genbank (Oct. 6, 2016) "*Homo sapiens* C-X-C Motif Chemokine Ligand 8 (CXCL8), Transcript Variant 1, mRNA", GenBank Accession No. NM_000584.3, 6 pages.

(56) References Cited

OTHER PUBLICATIONS

Database Genbank (Oct. 6, 2016) "*Homo sapiens* Dipeptidyl Peptidase 4 (DPP4), mRNA", GenBank Accession No. NM_001935.3, 7 pages.
Database Genbank (Oct. 8, 2016) "*Homo sapiens* Fibroblast Activation Protein Alpha (FAP), Transcript Variant 2, mRNA", GenBank Accession No. NM_001291807.1, 6 pages.
Database Genbank (Sep. 15, 2016) "*Homo sapiens* Forkhead Box O3 (FOXO3), Transcript Variant 1, mRNA", GenBank Accession No. NM_001455.3, 10 pages.
Database Genbank (May 9, 2007) "*Homo sapiens* FOXP3 mRNA, Complete cds", GenBank Accession No. EF534714.1, 1 page.
Database Genbank (Mar. 15, 2015) "*Homo sapiens* Insulin-like Growth Factor 1 (somatomedin C) (IGF1), Transcript Variant 4, mRNA", Genbank Accession No. NM_000618.3, 5 pages.
Database Genbank (May 2, 2019) "*Homo sapiens* interleukin 1 beta (IL1B), mRNA", Genbank Accession No. NM_000576.2, 4 pages.
Database Genbank (Oct. 7, 2016) "*Homo sapiens* Interleukin 1 Receptor Antagonist (IL1RN), Transcript Variant 3, mRNA", GenBank Accession No. NM_000577.4, 5 pages.
Database Genbank (Jun. 3, 2018) "*Homo sapiens* interleukin 1 receptor type 1 (IL1R1), transcript variant 1, mRNA", Genbank Accession No. NM_000877.3, 5 pages.
Database Genbank (Jul. 15, 2006) "*Homo sapiens* Interleukin 15, mRNA (cDNA clone MGC:9721 IMAGE:3851514), Complete cds", GenBank Accession No. BC018149.2, 2 pages.
Database Genbank (Aug. 11, 2019) "*Homo sapiens* interleukin 2 receptor subunit alpha (IL2RA), transcript variant 1, mRNA", Genbank Accession No. NM_000417.2, 5 pages.
Database Genbank (Oct. 6, 2016) "*Homo sapiens* Interleukin 20 (IL20), mRNA", GenBank Accession No. NM_018724.3, 4 pages.
Database Genbank (Mar. 15, 2015) "*Homo sapiens* Interleukin 6 (IL6), mRNA", Genbank Accession No. NM_000600.3, 3 pages.
Database Genbank (Oct. 7, 2016) "*Homo sapiens* Matrix Metallopeptidase 1 (MMP1), Transcript Variant 2, mRNA", GenBank Accession No. NM_001145938.1, 5 pages.
Database Genbank (Nov. 17, 2018) "*Homo sapiens* Matrix Metallopeptidase 13 (MMP13), mRNA", Genbank Accession No. NM_002427.3, 4 pages.
Database Genbank (Mar. 15, 2015) "*Homo sapiens* Matrix Metallopeptidase 3 (MMP3), mRNA", GenBank Accession No. NM_002422.3, 6 pages.
Database Genbank (Mar. 15, 2015) "*Homo sapiens* Matrix Metallopeptidase 9 (MMP9), mRNA", Genbank Accession No. NM_004994.2, 6 pages.
Database Genbank (Oct. 21, 2011) "*Homo sapiens* MHC Class II Antigen (HLA-DRB1) mRNA, HLA-DRB1*10:01:01 Allele, Complete cds", GenBank Accession No. HQ267233.1, 1 page.
Database Genbank (May 21, 2015) "*Homo sapiens* MicroRNA 125a (MIR125A), microRNA", GenBank Accession No. NR_029693.1, 3 pages.
Database Genbank (May 21, 2015) "*Homo sapiens* MicroRNA 140 (MIR140), microRNA", GenBank Accession No. NR_029681.1, 3 pages.
Database Genbank (Oct. 3, 2021) "*Homo sapiens* microRNA 181a-2 (MIR181A2), microRNA", Genbank Accession_NR_029611.1, 3 pages.
Database Genbank (May 21, 2015) "*Homo sapiens* MicroRNA 203a (MIR203A), MicroRNA", Genbank Accession No. NR_029620.1, 3 pages.
Database Genbank (Oct. 8, 2016) "*Homo sapiens* MicroRNA 27a (MIR27A), MicroRNA", GenBank Accession No. NR_029501.1, 3 pages.
Database Genbank (May 21, 2015) "*Homo sapiens* MicroRNA 365a (MIR365A), microRNA", NCBI Reference Sequence: NR_029854.1, 3 pages.
Database Genbank (May 1, 2002) "*Homo sapiens* MicroRNA miR-24 gene, complete sequence", Genbank Accession No. AF480527.1, 1 page.
Database Genbank (Apr. 9, 2016) "*Homo sapiens* Peptidyl Arginine Deiminase 2 (PADI2), mRNA", GenBank Accession No. NM_007365.2, 6 pages.
Database Genbank (Apr. 9, 2016) "*Homo sapiens* Peptidyl Arginine Deiminase 3 (PADI3), mRNA", GenBank Accession No. NM_016233.2, 6 pages.
Database Genbank (Apr. 9, 2016) "*Homo sapiens* Peptidyl Arginine Deiminase 4 (PADI4), mRNA", GenBank Accession No. NM_012387.2, 6 pages.
Database Genbank (Jun. 26, 2004) "*Homo sapiens* Protein Tyrosine Phosphatase, Non-Receptor type 22 (lymphoid), mRNA (cDNA clone MGC:87871 IMAGE:5497108), complete cds", GenBank Accession No. BC071670.1, 2 pages.
Database Genbank (May 7, 2012) "*Homo sapiens* Sirtuin 1 (SIRT1) mRNA, partial cds", GenBank Accession No. JQ768366.1, 1 page.
Database Genbank (Aug. 3, 1996) "*Homo sapiens* STAT4 mRNA, Complete cds", GenBank Accession No. L78440.1, 2 pages.
Database Genbank (Oct. 9, 2016) "*Homo sapiens* TNF Receptor Superfamily Member 1A (TNFRSF1A), Transcript Variant 1, mRNA", GenBank Accession No. NM_001065.3, 6 pages.

\* cited by examiner

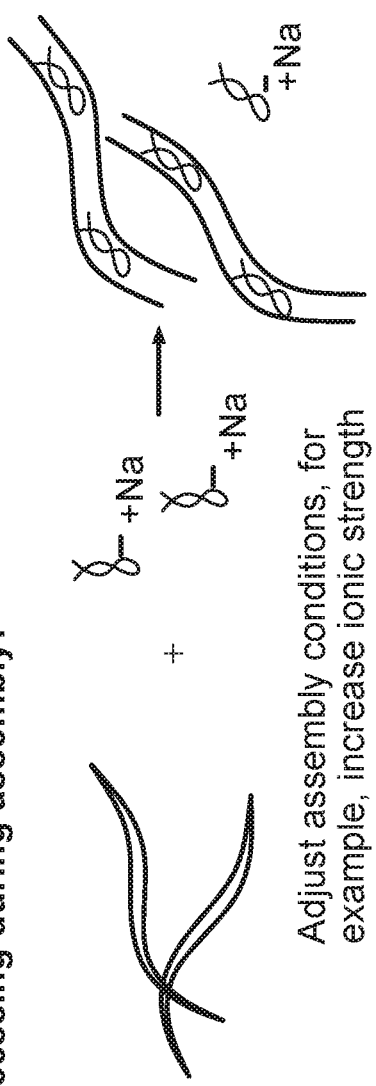
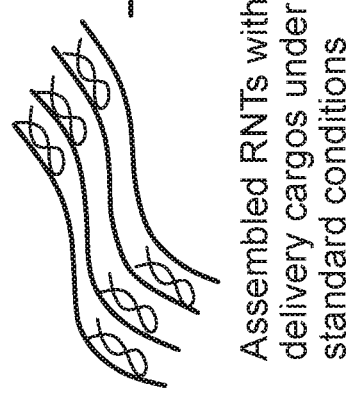
FIG. 4 (continued)

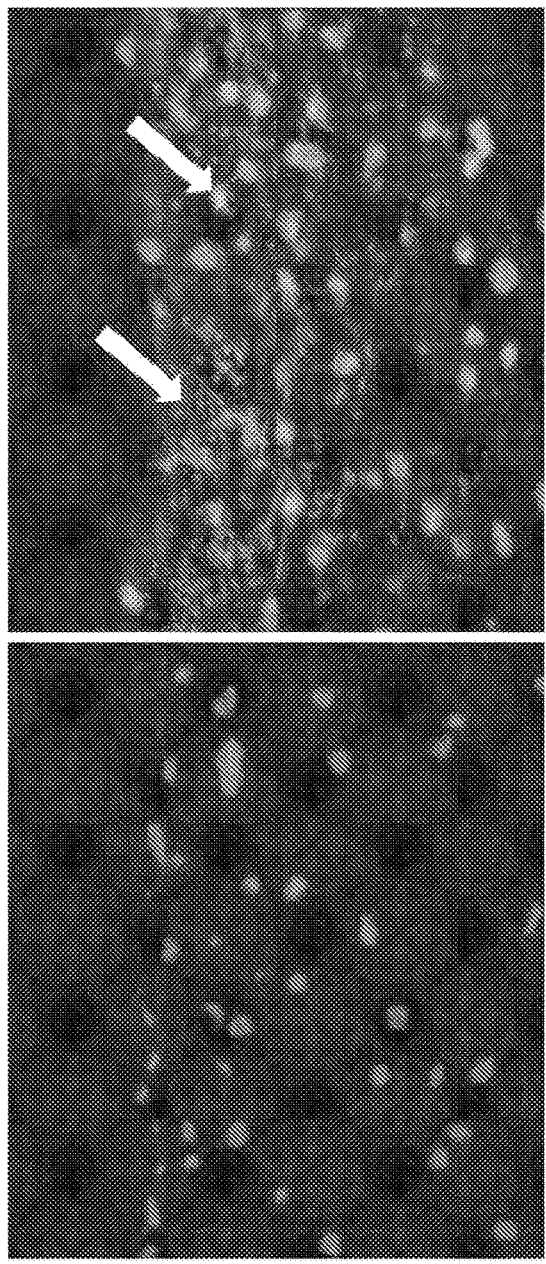
FIG. 13
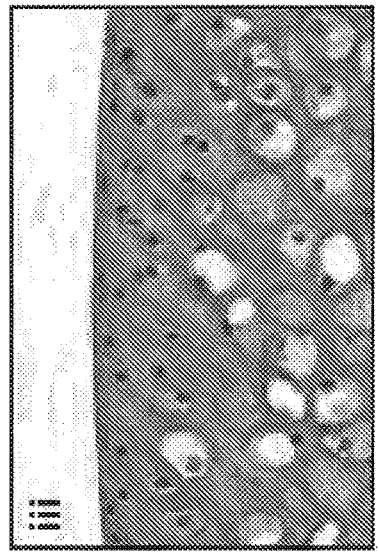
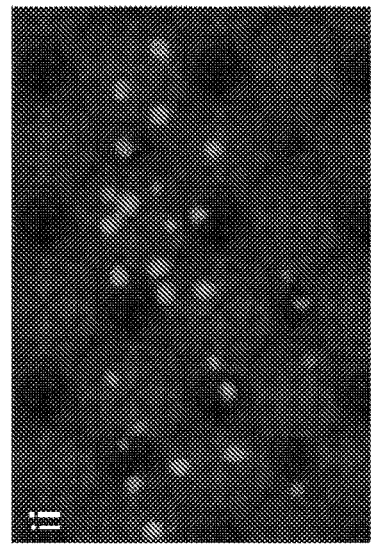
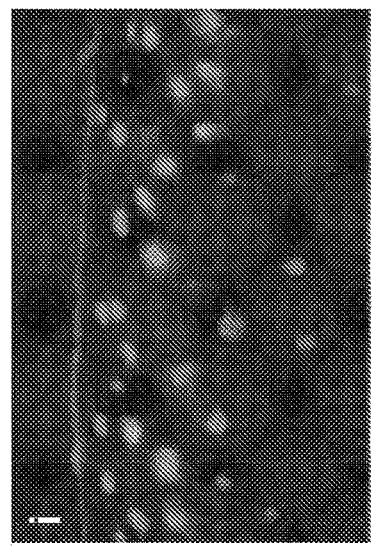
FIG. 14

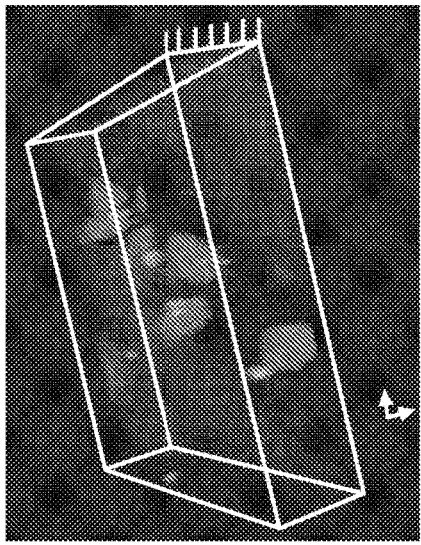
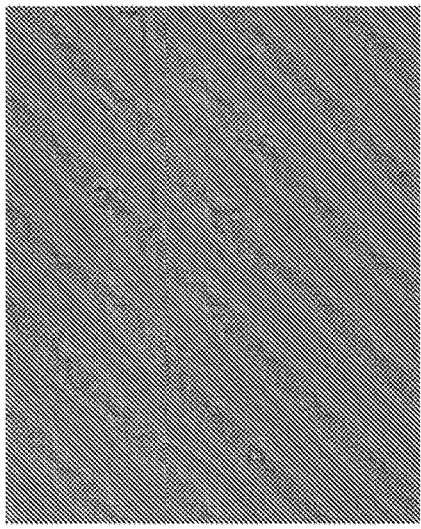
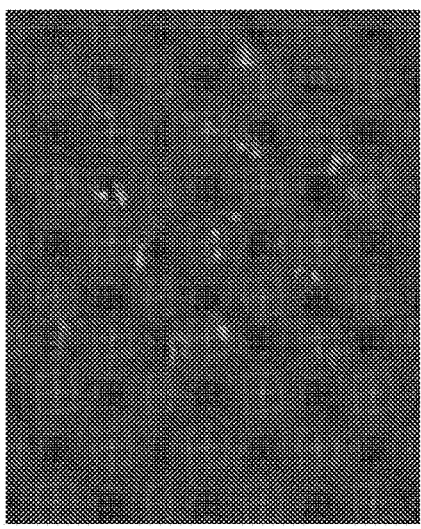
FIG. 15
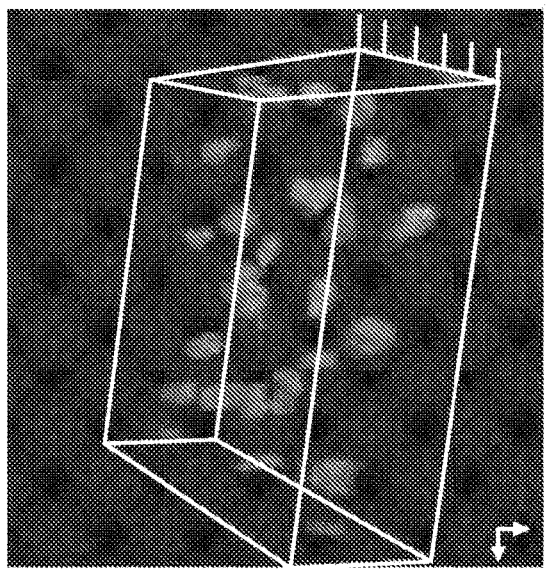
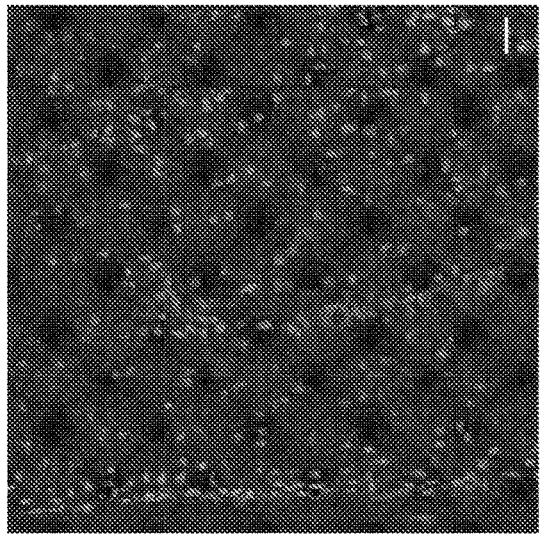
FIG. 16

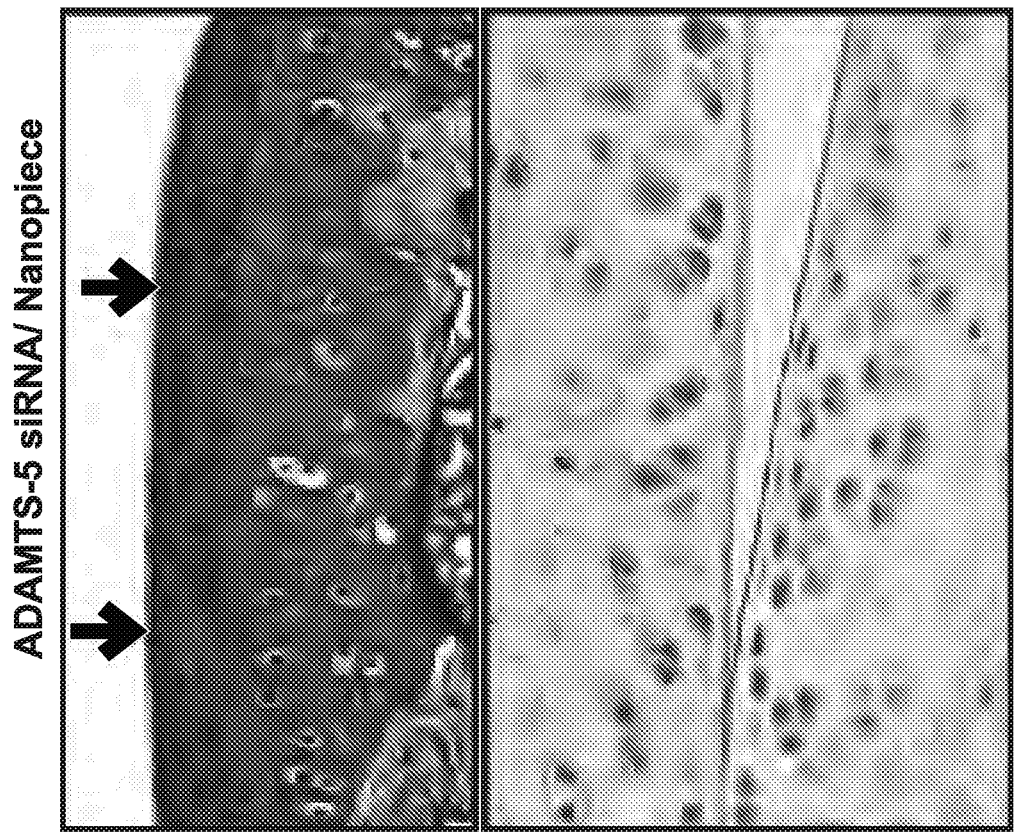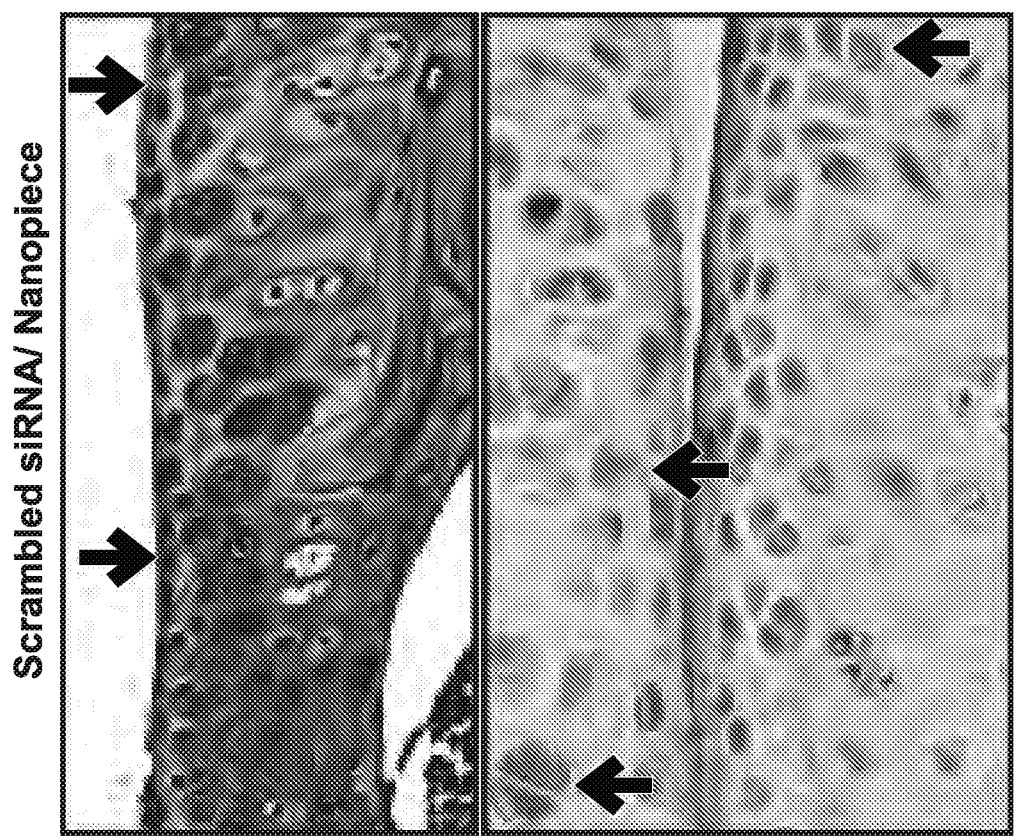
FIG. 34

FIG. 38 DMM knee 30 days after surgery

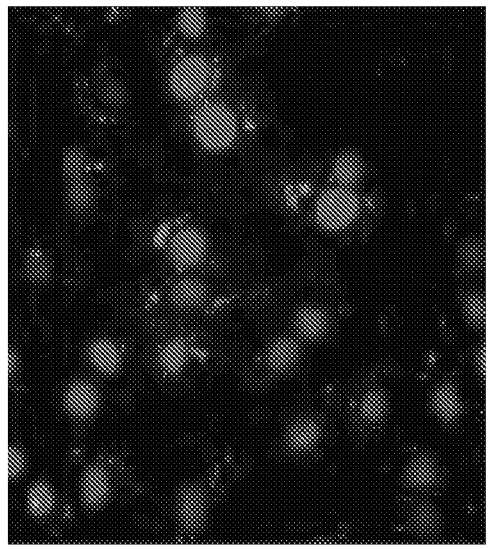
Red + Green
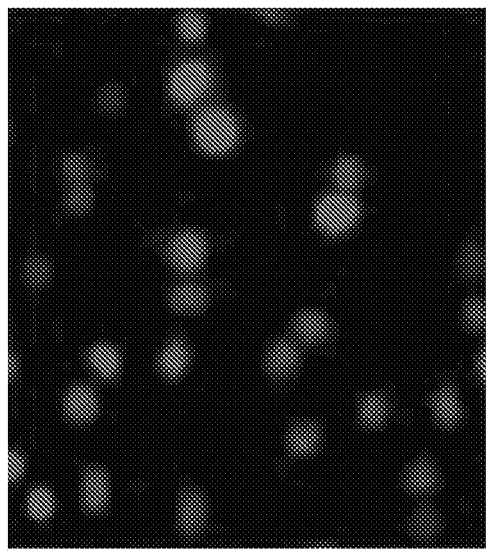
Green channel
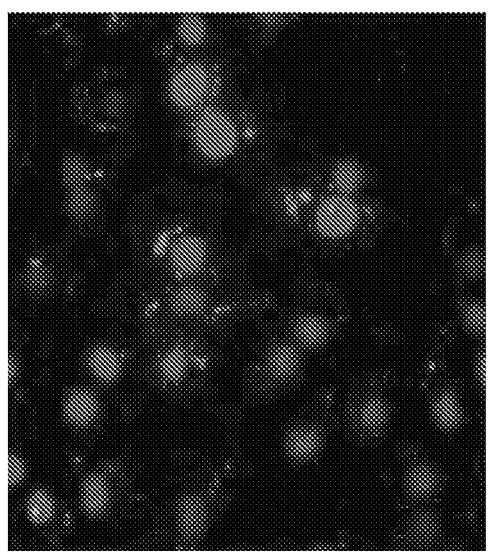
Red channel
| Stimulation | GAPDH | ADAMTS-5 | Scrambled |
|---|---|---|---|
| - | + | + | - |
FIG. 40

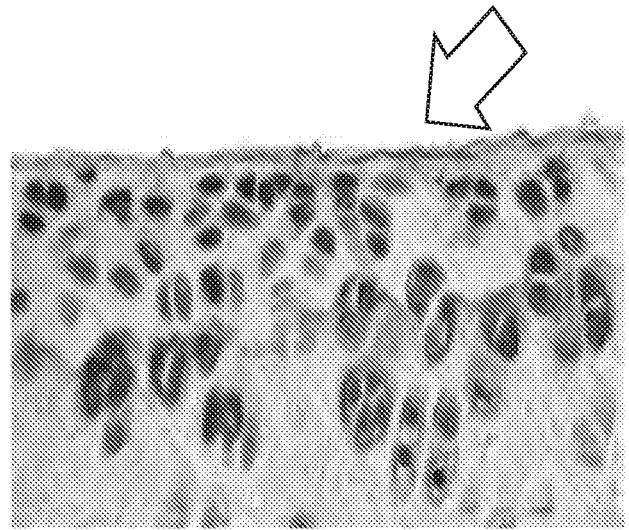
Sham with ADAMTS5 siRNA/NPs
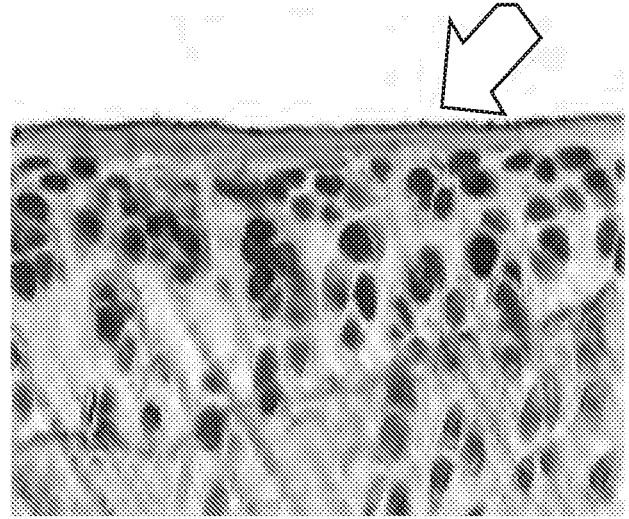
DMM with non-targeting siRNA/NPs
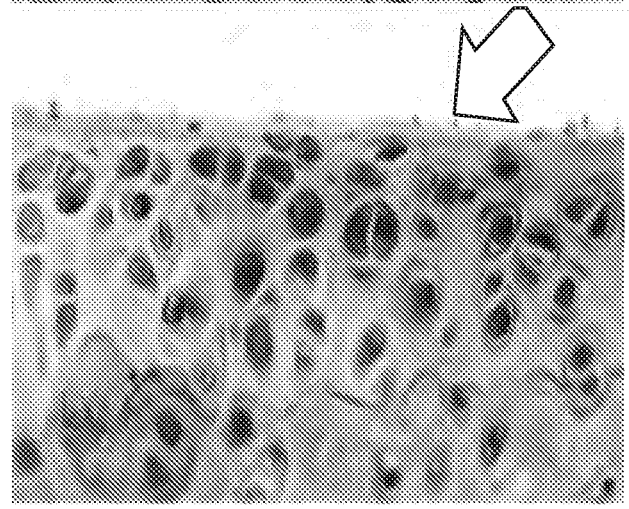
DMM with ADAMTS5 siRNA/NPs
FIG. 46

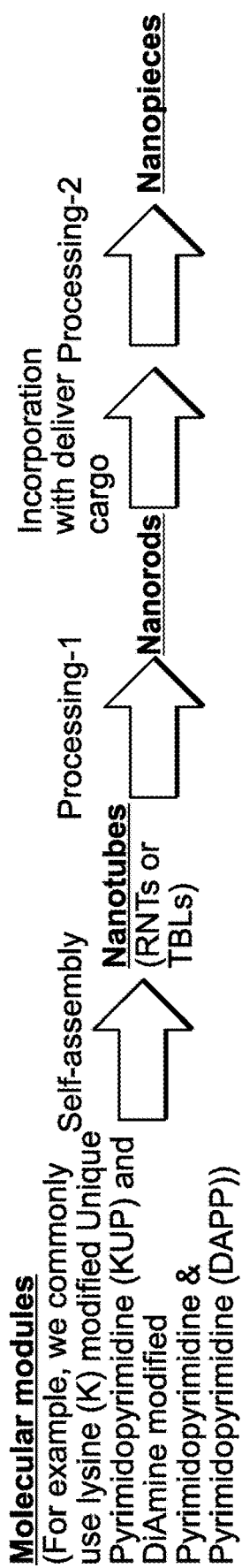
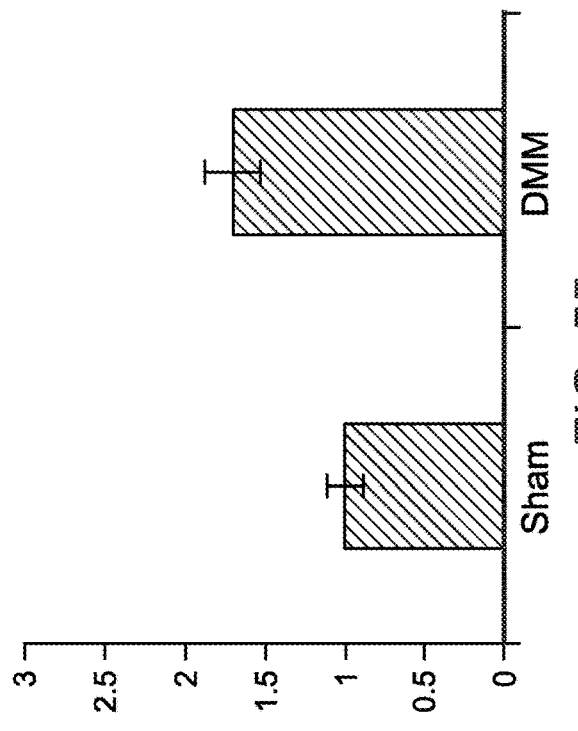
FIG. 53
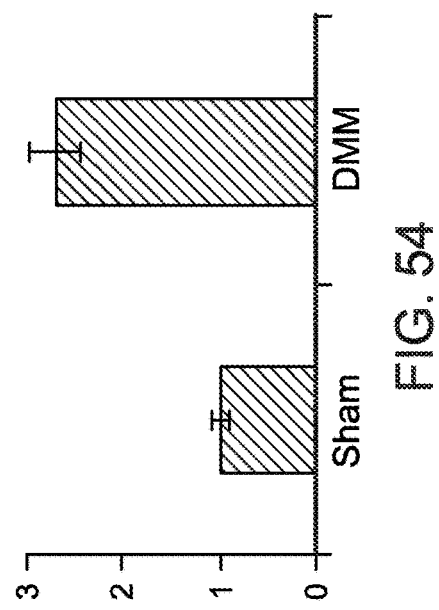
FIG. 54
FIG. 55

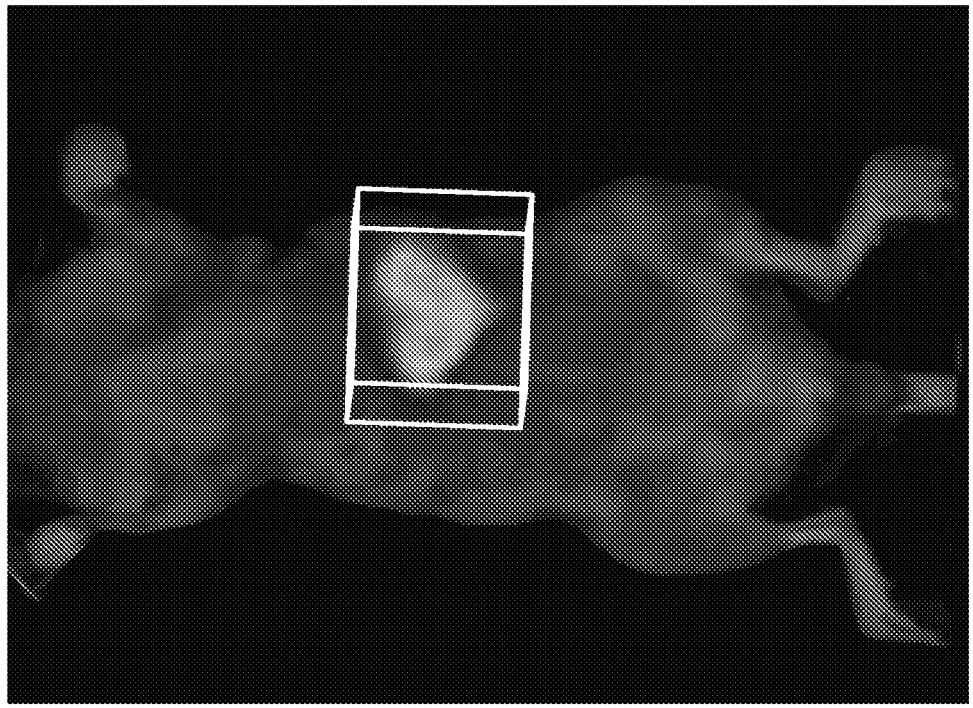
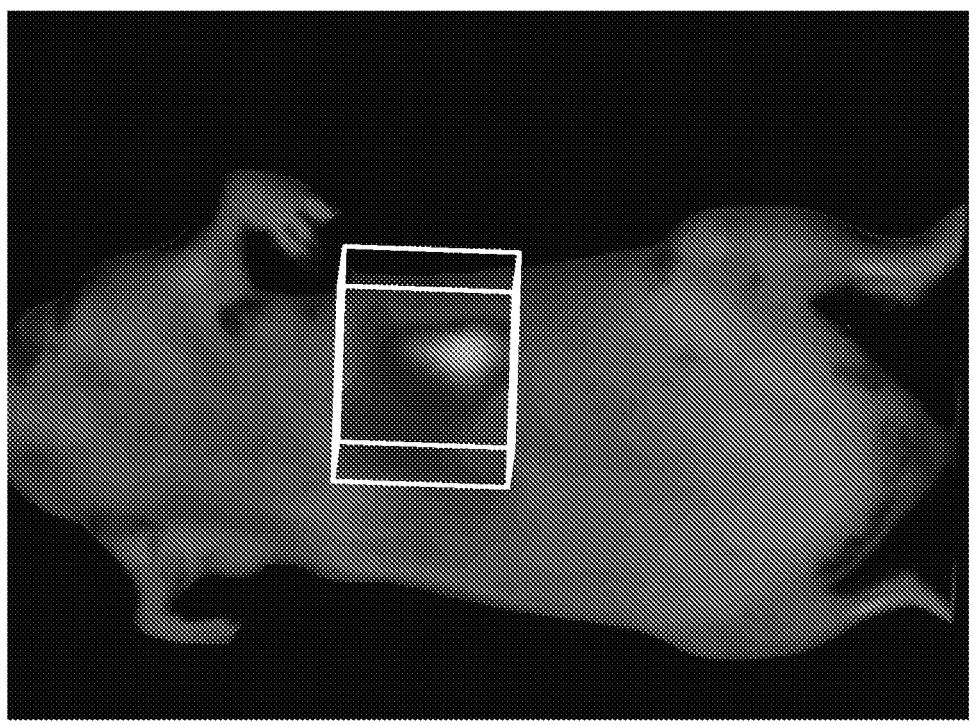
FIG. 62

- Specializing in developing RNA therapeutics delivery
- Focusing on non-liver and hard-to-reach tissues
- Targeting diseases without current effective therapeutics

Nanopieces™ Delivery Platform

- Smart
  - ☐ Nanopieces™ self-assemble and disassemble for targeted RNA release
- Small
  - ☐ Smaller than conventional nanoparticles, Nanopieces™ deliver into a variety of body tissues
- Safe
  - ☐ Biocompatible, biodegradable, and proven non-toxic in animal models

FIG. 71

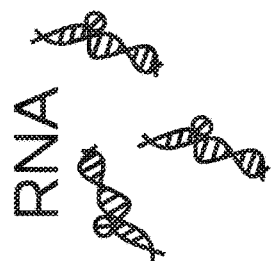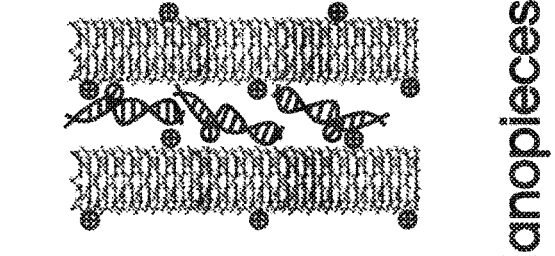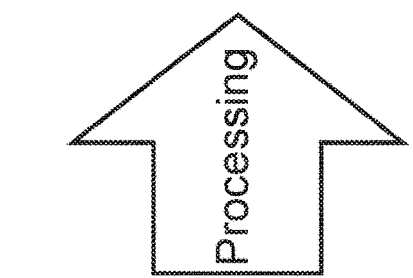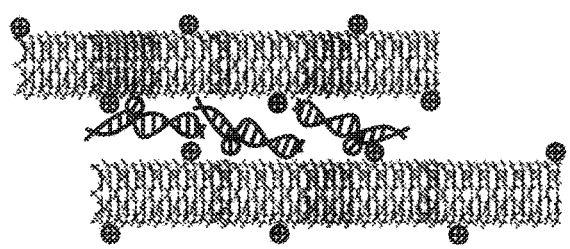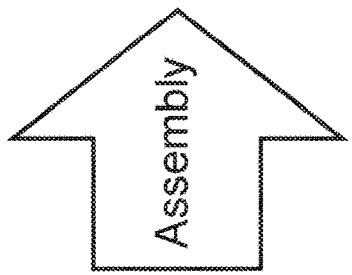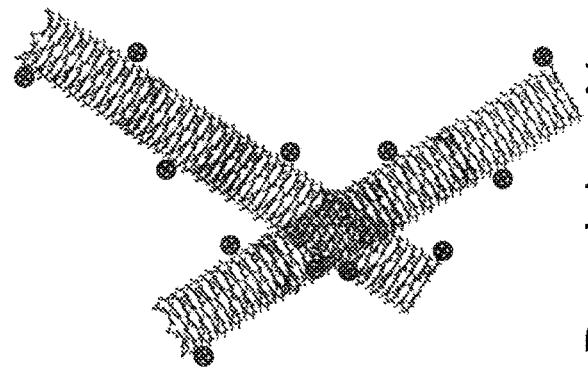
FIG. 73

Post-Traumatic Joint Injury (PTJI)

- No disease modifying drugs available
  - Corticosteroids and NSAIDS only relieve symptoms

- NPs™ treat underlying disease by:
  - Reducing risk of osteoarthritis
  - Relieving pain and inflammation

FIG. 77

PTJI: *In Vivo* Localized Delivery
- Delivery of IL-1R siRNA/NPs™ to treat meniscus injury induced joint degeneration
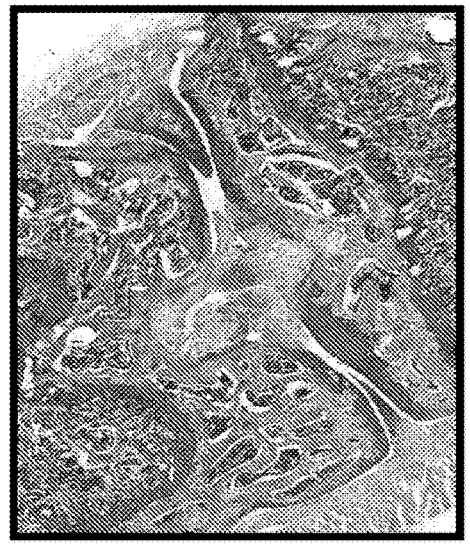
Meniscus injury and joint degeneration
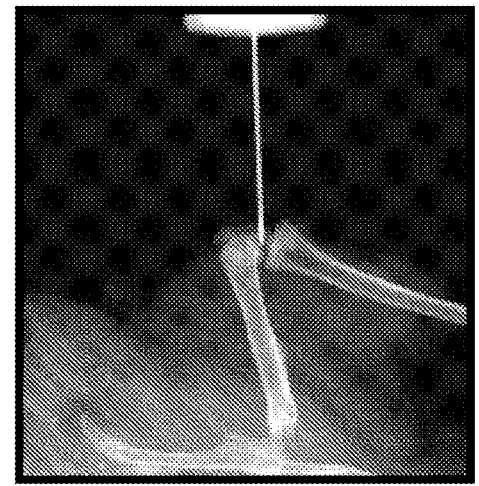
Injection of NPs™ into knee joints
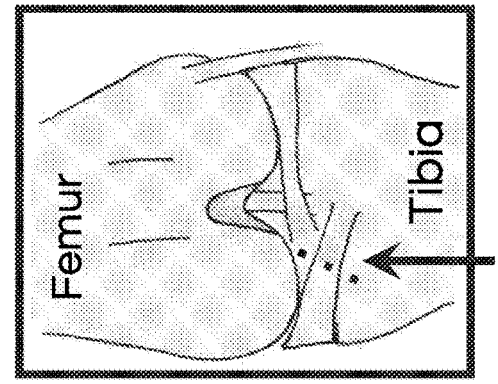
Histology confirms therapeutic outcomes
FIG. 79

Chondrosarcoma

- Accounts for 40% of bone cancers in adults
- No specific, effective drugs available
  □ Radiation ineffective
  □ Prone to metastases
  □ High mortality at late stage
  □ Early stage resection somewhat effective

FIG. 81

Chondrosarcoma: *In Vivo* Data
Inhibiting Tumor Growth:
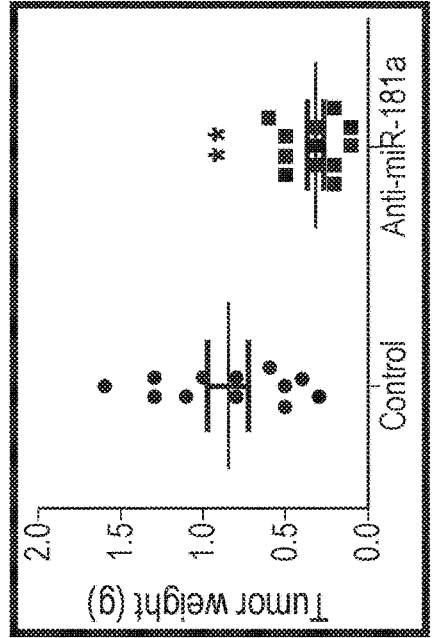
Inhibiting Tumor Metastasis:
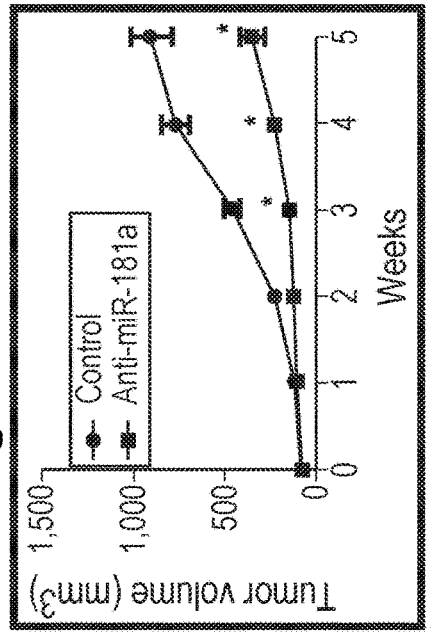
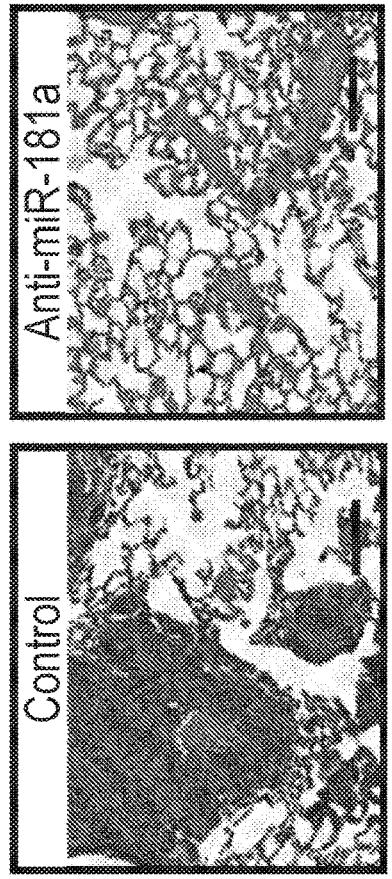
FIG. 82

Rheumatoid Arthritis (RA)
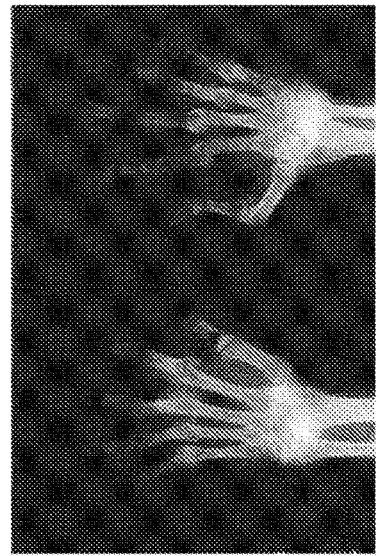
- Affects approximately 1.6 million Americans.
- Synovial inflammation and hyperplasia ("swelling")
- Cartilage and bone destruction ("deformity")
- Current anti-TNF protein drugs are not effective for some patients
- New therapeutics are needed
FIG. 83

Therapeutic Approach

- Inhibiting TNF-α gene expression, which is responsible for progression of RA, by delivering siRNA into collagen induced arthritis (CIA) mice.

- SiRNAs are difficult to infiltrate joints by systemic delivery; this challenge was overcome by a novel Nanopieces (NPs) delivery system.

siRNA administration using NPs

- TNF-α RNAi/NP therapy was highly efficacious in inhibiting TNF-α expression in the joint and progression of arthritis in mouse RA model.

- This systemic siRNA administration technology has great potential to be translated for treatment of RA patients.

FIG. 87

Nanopieces™ Nucleic Acid Delivery Advantages

| | Nanopieces™ | Lipid Nanoparticle | Polymer Nanoparticle | Viral Delivery | Peptide Modification |
|---|---|---|---|---|---|
| Non-covalent | ✓ | ✓ | | ✓ | |
| Penetrates matrix | ✓ | | ✓ | ✓ | ✓ |
| Non-toxic | ✓ | | | | ✓ |
| Biodegradable | ✓ | ✓ | | ✓ | ✓ |

```
                            SEQUENCE LISTING

<160> NUMBER OF SEQ ID NOS: 231

<210> SEQ ID NO 1
<211> LENGTH: 9660
<212> TYPE: DNA
<213> ORGANISM: Homo sapiens

<400> SEQUENCE: 1
ataaattcat tgttccacct cctcgcatct tcacagcgct cgcgctgctc tcggcgctcg      60
cagctgccga ctggggatga cggcgggcag gaggagaccg cagccgaagg gacacagaca     120
cgccgcttca ccagctcgcc tcaggctgcc ccctgcatt tttgttttaa ttttacggc      180 tttttcccct ctctttcttc ccttcctcct ggtcccagca gagccaagga aacccacaaa    240
ataagaaagg aagtgggccc cggagcttgg aacctccaca gccggcttgt ccagcgcagc    300 gcggggcgg gaggctgcgc gcaccagttg ccagcccggt gcgcggtacc tttccttact     360
tttcttgaaa cagcgatcgt gcctgcattt ggtggttttt tggttttgt ttttttcctt    420 ttcccgtatt tgctgaatct ccactatccg actttttttt tttaatcttt tctttccccc     480
cccccccacc ccacctcttt ctggagcacg aatccaaaca ttttcccaag caacaaagaa    540
aagttcgcac gctggcaccg cagcccggac aggctggcgc tgctgccggg ccccctccc     600 tccgacactt gactcaatcc tgcaagcaag tgtgtgtgtg tccccatccc ccgccccgtt    660
aacttcatag caaataacaa atacccataa agtcccagtc gcgcagcccc tccccgcggg    720
cagcgcacta tgctgctcgg gtgggcgtcc ctgctgctgt gcgcgttccg cctgcccctg    780
gccgcggtcg gccccgccgc gacacctgcc caggataaag ccgggcagcc tccgactgct    840
gcagcagccg cccagccccg ccggcggcag ggggaggagg tgcaggagcg agccgagcct    900
cccggccacc cgcaccccct ggcgcagcgg cgcaggagca aggggctggt gcagaacatc    960
gaccaactct actccggcgg cggcaaggtg ggctacctcg tctacgcggg cggccggagg   1020
ttcctcttgg acctggagcg agatggttcg gtgggcattg ctggcttcgt gcccgcagga   1080
ggcgggacga gtgcgcctg gcgccaccgg agccactgct tctatcgggg cacagtggac   1140
ggtagtcccc gctctctggc tgtctttgac ctctgtgggg gtctcgacgg cttcttcgcg   1200
gtcaagcacg cgcgctacac cctaaagcca ctgctgcgcg gacccgggc ggaggaagaa    1260 aagggcgcg tgtacgggga tgggtccgca cggatcctgc acgtctacac ccgcgagggc   1320
ttcagcttcg aggccctgcc gccgcgcgcc agctgcgaaa ccccgcgtc cacaccggag   1380 gcccacgagc atgctccggc gcacagcaac ccgagcggac gcgcagcact ggcctcgcag   1440
ctcttggacc agtccgctct ctcgcccgct gggggctcag gaccgcagac gtggtggcgg   1500
cggcggcgcc gctccatctc ccgggcccgc caggtggagc tgcttctggt ggctgacgcg   1560
tccatggcgc ggttgtatgg ccggggcctg cagcattacc tgctgaccct ggcctccatc   1620
gccaataggc tgtacagcca tgctagcatc gagaaccaca tccgcctggc cgtggtgaag   1680
gtggtggtgc taggcgacaa ggacaagagc ctggaagtga gcaagaacgc tgccaccaca   1740
ctcaagaact tttgcaagtg gcagcaccaa cacaaccagc tgggagatga ccatgaggag   1800
```

```
cactacgatg cagctatcct gtttactcgg gaggatttat gtgggcatca ttcatgtgac   1860
accctgggaa tggcagacgt tgggaccata tgttctccag agcgcagctg tgctgtgatt   1920
gaagacgatg gcctccacgc agccttcact gtggctcacg aaatcggaca tttacttggc   1980
ctctcccatg acgattccaa attctgtgaa gagacctttg gttccacaga agataagcgc   2040
ttaatgtctt ccatccttac cagcattgat gcatctaagc cctggtccaa atgcacttca   2100
gccaccatca cagaattcct ggatgatggc catggtaact gtttgctgga cctaccacga   2160
aagcagatcc tgggccccga agaactccca ggacagacct acgatgccac ccagcagtgc   2220
aacctgacat tcgggcctga gtactccgtg tgtcccggca tggatgtctg tgctcgcctg   2280
tggtgtgctg tggtacgcca gggccagatg gtctgtctga ccaagaagct gcctgcggtg   2340
gaagggacgc cttgtggaaa ggggagaatc tgcctgcagg gcaaatgtgt ggacaaaacc   2400
aagaaaaaat attattcaac gtcaagccat ggcaactggg gatcttgggg atcctggggc   2460
cagtgttctc gctcatgtgg aggaggagtg cagtttgcct atcgtcactg taataaccct   2520
gctcccagaa acaacggacg ctactgcaca gggaagaggg ccatctaccg ctcctgcagt   2580
ctcatgccct gcccacccaa tggtaaatca tttcgtcatg aacagtgtga ggccaaaaat   2640
ggctatcagt ctgatgcaaa aggagtcaaa acttttgtgg aatgggttcc caaatatgca   2700
ggtgtcctgc cagcggatgt gtgcaagctg acctgcagag ccaagggcac tggctactat   2760
gtggtatttt ctccaaaggt gaccgatggc actgaatgta ggctgtacag taattccgtc   2820
tgcgtccggg ggaagtgtgt gagaactggc tgtgacggca tcattggctc aaagctgcag   2880
tatgacaagt gcggagtatg tggaggagac aactccagct gtacaaagat tgttggaacc   2940
tttaataaga aaagtaaggg ttacactgac gtggtgagga ttcctgaagg ggcaacccac   3000
ataaaagttc gacagttcaa agccaaagac cagactagat tcactgccta tttagccctg   3060
aaaaagaaaa acggtgagta ccttatcaat ggaaagtaca tgatctccac ttcagagact   3120
atcattgaca tcaatggaac agtcatgaac tatagcggtt ggagccacag ggatgacttc   3180
ctgcatggca tgggctactc tgccacgaag gaaattctaa tagtgcagat tcttgcaaca   3240
gaccccacta aaccattaga tgtccgttat agcttttttg ttcccaagaa gtccactcca   3300
aaagtaaact ctgtcactag tcatggcagc aataaagtgg gatcacacac ttcgcagccg   3360
cagtgggtca cgggcccatg gctcgcctgc tctaggacct gtgacacagg ttggcacacc   3420
agaacggtgc agtgccagga tggaaaccgg aagttagcaa aaggatgtcc tctctcccaa   3480
aggccttctg cgtttaagca atgcttgttg aagaaatgtt agcctgtggt tatgatctta   3540
tgcacaaaga taactggagg attcagcact gatgcagtcg tggtgaacag gaggtctacc   3600
taacgcacac aaagtcatgc ttcagtgaca ttgtcaacag gagtccaatt atgggcagaa   3660
tctgctctct gtgaccaaaa gaggatgtgc actgcttcac gtgacagtgg tgaccttgca   3720
atatagaaaa acttgggagt tattgaacat cccctgggct acaagaaaac actgatgaat   3780
gtaaaatcag gggacatttg aagatggcag aactgtctcc cccttgtcac ctacctctga   3840
tagaatgtct ttaatggtat cataatcatt ttcacccata atacacagta gcttcttctt   3900
actgtttgta aatacattct cccttggtat gtcactttat atcccctggt tctattaaaa   3960
tatccatata tatttctata aaaaagtgt ttgaccaaag taggtctgca gctatttcaa   4020
cttccttccg tttccagaaa gagctgtgga tattttactg gaaattaaga acttgctgct   4080
gttttaataa gatgtagtat attttctgac tacaggagat aaaatttcag tcaaaaaacc   4140
```

```
attttgacag caagtatctt ctgagaaatt ttgaaaagta aatagatctc agtgtatcta    4200
gtcacttaaa tacatacacg ggttcattta cttaaacctt tgactgcctg tatttttttc    4260
aggtagctag ccaaattaat gcataatttc agatgtagaa gtagggtttg cgtgtgtgtg    4320
tgtgatcata ctcaagagtc taaaaactag tttccttgtg ttggaaattt aaaaggaaaa    4380
aaatcgtatt tcactgtgtt ttcaatttat attttcacaa ctactttctc tctccagagc    4440
tttcatctga tatctcacaa tgtatgatat acgtacaaaa cacacagcaa gttttctatc    4500
atgtccaaca cattcaacac tggtatacct cctaccagca agcctttaaa atgcatttgt    4560
gtttgcttat ttgttttgtt caagggttca gtaagaccta caatgttttg tatttcttga    4620
cttattttat tagaaacatt aaagatcact tggtagttag ccacattgag aagtggttat    4680
cattgttaat gtggttaatg ccaaaaagtg gttaatatta ataagactgt ttccacacca    4740
taggcaataa tttcttaatt taaaaaatct aagtatattc ctattgtact aaatattttt    4800
cccaactgga aagcacttga ttgtacccgt aagtgtttga gtgatgacat gtgatgattt    4860
tcagaaagtt gttgttttg tttccatagc ctgtttaagt aggttgtaag tttgaatagt    4920
tagacatgga aattatttta taagcacaca cctaaagata tcttttttaga tgataaaatg    4980 tacaccccc catcaccaac ctcacaactt agaaaatcta agttgtttga tttctttggg    5040
atttcttttg ttgtgaaaca ctgcaaagcc aattttctct tataaaaatt catagtaatc    5100
ctgccaaatg tgcctattgt taaagatttg catgtgaaga tcttagggaa ccactgtttg    5160
agttctacaa gctcatgaga gtttattttt attataagat gttttttaata taaaagaatt    5220 atgtaactga tcactatatt acatcatttc agtgggccag gaaatagat gtcttgctgt    5280 tttcagtatt ttcttaagaa attgctttta aaacaaataa ttgttttaca aaaccaataa    5340
ttatcctttg aattttcata gactgacttt gcttttgacg tagaaatttt ttttctcaat    5400
aaattatcac tttgagaaat gaggcctgta caaggctgat aacctatatg tgatggagat    5460
cacccaatgc caagggcaga aagcaaacct agttaaatag gtgagaaaaa aaataataat    5520
cccagtgcca tttgtctgtg caaagagaat taggagagag gttaatgtta cttttttcca    5580
ttttggaaat aattttaatc aagtaactca aatgtgacaa aatttatttt tattttttgt    5640
ggttatattc ccaacaacat taaaaaatac tcgaggcata aatgtagttg tctcctactc    5700
tgcttctctt actatactca tacatttta atatggttta tcaatgattc atgtttccct    5760
caaatagtga tggtttacac ctgtcatgga aacaatccta gagagctcag agcaattaaa    5820
ccactattcc atgcttttaa gtagttttct ccaccttttt cttatgagtc tcactagatt    5880
gactgaggaa tgtatgtcta aattcctgga gaagatgata tggattggaa actgaaattc    5940
agagaaatgg agtgttcaat agataccacg aattgtgaac aaagggaaaa ttctatacaa    6000

ctcaatctaa gтсагтссaс tttgacttcg tactgtcttt cаcсттттccа ttgttgcatc    6060

ttgaattttt taaaatgtct адааттcagg ата gcta gggg ctactt cttt aaaaaaaaaa    6120

ааааааада аттсgтстga аатgстсаg gttt gta aga atcta atctc астт асатаа    6180

стаа gсастс сатаатаа gт ттт аттаа gт асаа gggа g ccagaaaaa тgасаттт at    6240

ttcttctaga tcagaaaaat ttaaatta a g ccc тgсттg ct g тта gаа atat gt gggс    6300

аттgт тат aa тттатт caat aaa tttat gt tcctttgcct tcctgtggaa acagtttat    6360

сссаста ааc ta ggaatta g gggа таа атс асааа саааа ааа а gттgс а gсастgааа    6420

ааа а gt аатт tattgttttt gcaactggta tgt gaattt g тgт gа тааааа тта тттат тс    6480

ттаттт а аса ааатат gтт саа атттттс тата тттааа ат gtttt gct gttgtcctac    6540
```

```
tttttaattt atgcttcatg tttgtgtata aagtacactt ttacactttg tgagtttaca   6600
taatatacag cactggttgc ttttgtattt ttttacagaa agctttctgt gtgaagcagg   6660
tgtatatgta tatattcctc atgtattctt attctgatac tatcattttt ctttccaagg   6720 aaatttaat ctgtcatgac caatagtgtt cattacttgt gcctatgata ataggttttt    6780
tacatcacat taacactatt ttttccaagt cacaaataag aaaaacactt attcaatgaa   6840
acaaggtgca agtttaaat ttgggtacac aaatagccta gaagcttcct acagacgcta    6900
agacacagcc aataatcaga tcctttcact tcatcgagaa acttggacaa gtcgatattg   6960
atgtattaga tgaaagttgt ctacacacaa cttctgaggg atacaaacga taataaaacc   7020
aaatgttgtc tgtttctcct ttagaaacac ctcctaaaat taatatcatt tagtctctag   7080
tgtctgtagg attctacaga tgagcacaaa tagattgggg ttgtataaca aatgctaata   7140
gtcataactg tttctacaaa tatggggtgt ccattaagag aatgtgatgt tttcctactg   7200
ctgttgaatc ccatggggtg attataggac ttgaaatagg cagagtcacc tctgatgaca   7260
tcagcttgcc tctgtgattt cacagtctga tcctggcaac aagacaaagc acccttggac   7320
acacagccaa tctctggttg tgatatttcc ccattgattc cttccttgtt aacaaggtca   7380
ttttaatggt tcaggtgagg acagcagcca gattcaaagt ccagaatttg tgctgttaca   7440
tagagttcac actgtcaaat aacattgaat ttaataatga tcaaattttt ctagtagtct   7500
ttggcagagt gtataatctc attggcatga ttggtgaata ttactaatct ctttataatg   7560
aaagatgctt tacaaatacc ttatatttgc taacatttca aaactactaa ataaatgaaa   7620
tagccatgtg tacagaaatg gtcatttaaa gctttaatag aaccaaattc aagacaatgt   7680
atcatttaga cacacagaaa aggaacttgt atgttttccc tattatttt ctcatttgcc    7740 aacaatctat agttttaggt tatcaaacag atagatcaac ttaactggct agtacattga   7800
aaaatcttcc taagaatcct tgttagcat aatctataga gataatttct caaattatat    7860
catcatgatg catataaact ctataatgta taattgtgtt tcatttattt aatgtatgag   7920
aacatattga aatacaaaac catgcattag ccaaaaaatt ggaatacagg tagtgttcag   7980
atcagcaaaa cattcagtct ggtaaatgcc tgcctggggc tatgatatca ttctcaatgc   8040
aggttttatg gaaaaactaa agaaatatgt tgttagatga tgttggtttt gaaaaaaaaa   8100
agacattaac atacacatta gttagcccag ttaattgcat tctactaata tagttgcaca   8160
ttagcaataa ttttgctgtc tctggtcttt attttgtggc ttcaactaac tggaccatgt   8220
ggactgtaaa ggtcaaatgg aaaaaacgag cagtggcccc tcatcctgta aggtactgct   8280
acatcagagt gacctaaaag tctaacactg tgaggaaaac tgtgatttgt aggaaaaaaa   8340
aaaaaaacaa ataaaaaaca gggcatgctt tttaattttt ttccactttc ctttggcaca   8400
cccaatgaac aattctaatt tttattgagg tgctaacatc tttcgtgacc gactgtcaaa   8460
tgtggtattt ttgagttact attttctac atgattttac agtttgcaag aaagacctct    8520
aagctttgtg tcacggtagg gcacaacttg atactcaaaa tttgaaaaat aagcacatcc   8580
aatgattgtt ttgaccaaca gtggtcagtg acgtaaactg catgtgcatc tgaggacatt   8640 taagggtca ttaaaatttg aggagcatca ggccggagta gcagactttt agatgagtca    8700
tatttcagca ttcactaagt cctcagcatt ccattcaaac tgtcgtgtat atttggcctg   8760
attttttttc aagctttgca ataatttatg ttattggtaa acacttggtg actatatctc   8820
agccttttct ttaacaactc acaatatatt agaaacacgt ctacctatac tgagagtata   8880
```

-continued

```
tttacaatag aagaacatac tgtatgtgac tttgtaaagc tagactttg attaagaaat    8940 atataatctc tggatgctat ttttgcatta tacactcagg cacaacgtaa accttgatgg    9000
ctcatcttgc tacaattacg agttgaaaaa cactacttac gtatttgtat gacctattag    9060
tcagaggaaa tcatacatat gctttgtaaa tagactttgc agataactaa atagactgaa    9120
gaaatatgtt gcatttgata gaagcaattg cataaatatt tggtttctat attagagtct    9180
gtgagtaaag tcaagtaata aacctaagta ggtataacag attttttaaac cttgaaactt    9240 gctttgatgg tagagaaaat cattgaagat ttacatactg tatataagat gtaaaatgta    9300
cgctgcttat taccctcaat tttccagaag caatggtata taatgcagtt gaaaaaccaa    9360
aaatcttgga aaactaagac gggtcttgtt taaaatgtct ctcagctttg caaccttca    9420 aatcttaatc aactatttaa agcattactg tgtcttgtag cctgcattcc acaacagctc    9480
tgttattcag gtaaaagact tgaactgagc cgtttgggac ctatactgta atattttcat    9540
tgaggaacaa tatcctattt tgtaaagcat ttccctatgt gtgactttaa actgtaaaat    9600
taaacactgc ttttgtgggt tcagtgggca taataaaatat aaattgtaaa ctaggttaaa    9660
```

<210> SEQ ID NO 2
<211> LENGTH: 930
<212> TYPE: PRT
<213> ORGANISM: Homo sapiens

<400> SEQUENCE: 2

```
Met Leu Leu Gly Trp Ala Ser Leu Leu Leu Cys Ala Phe Arg Leu Pro
1               5                   10                  15

Leu Ala Ala Val Gly Pro Ala Ala Thr Pro Ala Gln Asp Lys Ala Gly
            20                  25                  30

Gln Pro Pro Thr Ala Ala Ala Ala Gln Pro Arg Arg Arg Gln Gly
        35                  40                  45

Glu Glu Val Gln Glu Arg Ala Glu Pro Pro Gly His Pro His Pro Leu
    50                  55                  60

Ala Gln Arg Arg Arg Ser Lys Gly Leu Val Gln Asn Ile Asp Gln Leu
65                  70                  75                  80

Tyr Ser Gly Gly Lys Val Gly Tyr Leu Val Tyr Ala Gly Gly Arg
                85                  90                  95

Arg Phe Leu Leu Asp Leu Glu Arg Asp Gly Ser Val Gly Ile Ala Gly
            100                 105                 110

Phe Val Pro Ala Gly Gly Gly Thr Ser Ala Pro Trp Arg His Arg Ser
        115                 120                 125

His Cys Phe Tyr Arg Gly Thr Val Asp Gly Ser Pro Arg Ser Leu Ala
    130                 135                 140

Val Phe Asp Leu Cys Gly Gly Leu Asp Gly Phe Phe Ala Val Lys His
145                 150                 155                 160

Ala Arg Tyr Thr Leu Lys Pro Leu Leu Arg Gly Pro Trp Ala Glu Glu
                165                 170                 175

Glu Lys Gly Arg Val Tyr Gly Asp Gly Ser Ala Arg Ile Leu His Val
            180                 185                 190

Tyr Thr Arg Glu Gly Phe Ser Phe Glu Ala Leu Pro Pro Arg Ala Ser
        195                 200                 205

Cys Glu Thr Pro Ala Ser Thr Pro Glu Ala His Glu His Ala Pro Ala
    210                 215                 220

His Ser Asn Pro Ser Gly Arg Ala Ala Leu Ala Ser Gln Leu Leu Asp
225                 230                 235                 240
```

```
Gln Ser Ala Leu Ser Pro Ala Gly Gly Ser Gly Pro Gln Thr Trp Trp
                245                 250                 255

Arg Arg Arg Arg Arg Ser Ile Ser Arg Ala Arg Gln Val Glu Leu Leu
            260                 265                 270

Leu Val Ala Asp Ala Ser Met Ala Arg Leu Tyr Gly Arg Gly Leu Gln
        275                 280                 285

His Tyr Leu Leu Thr Leu Ala Ser Ile Ala Asn Arg Leu Tyr Ser His
    290                 295                 300

Ala Ser Ile Glu Asn His Ile Arg Leu Ala Val Val Lys Val Val
305                 310                 315                 320

Leu Gly Asp Lys Asp Lys Ser Leu Glu Val Ser Lys Asn Ala Ala Thr
                325                 330                 335

Thr Leu Lys Asn Phe Cys Lys Trp Gln His Gln His Asn Gln Leu Gly
            340                 345                 350

Asp Asp His Glu Glu His Tyr Asp Ala Ala Ile Leu Phe Thr Arg Glu
        355                 360                 365

Asp Leu Cys Gly His His Ser Cys Asp Thr Leu Gly Met Ala Asp Val
    370                 375                 380

Gly Thr Ile Cys Ser Pro Glu Arg Ser Cys Ala Val Ile Glu Asp Asp
385                 390                 395                 400

Gly Leu His Ala Ala Phe Thr Val Ala His Glu Ile Gly His Leu Leu
                405                 410                 415

Gly Leu Ser His Asp Asp Ser Lys Phe Cys Glu Glu Thr Phe Gly Ser
            420                 425                 430

Thr Glu Asp Lys Arg Leu Met Ser Ser Ile Leu Thr Ser Ile Asp Ala
        435                 440                 445

Ser Lys Pro Trp Ser Lys Cys Thr Ser Ala Thr Ile Thr Glu Phe Leu
    450                 455                 460

Asp Asp Gly His Gly Asn Cys Leu Leu Asp Leu Pro Arg Lys Gln Ile
465                 470                 475                 480

Leu Gly Pro Glu Glu Leu Pro Gly Gln Thr Tyr Asp Ala Thr Gln Gln
                485                 490                 495

Cys Asn Leu Thr Phe Gly Pro Glu Tyr Ser Val Cys Pro Gly Met Asp
            500                 505                 510

Val Cys Ala Arg Leu Trp Cys Ala Val Val Arg Gln Gly Gln Met Val
        515                 520                 525

Cys Leu Thr Lys Lys Leu Pro Ala Val Glu Gly Thr Pro Cys Gly Lys
    530                 535                 540

Gly Arg Ile Cys Leu Gln Gly Lys Cys Val Asp Lys Thr Lys Lys Lys
545                 550                 555                 560

Tyr Tyr Ser Thr Ser Ser His Gly Asn Trp Gly Ser Trp Gly Ser Trp
                565                 570                 575

Gly Gln Cys Ser Arg Ser Cys Gly Gly Val Gln Phe Ala Tyr Arg
            580                 585                 590

His Cys Asn Asn Pro Ala Pro Arg Asn Gly Arg Tyr Cys Thr Gly
        595                 600                 605

Lys Arg Ala Ile Tyr Arg Ser Cys Ser Leu Met Pro Cys Pro Pro Asn
    610                 615                 620

Gly Lys Ser Phe Arg His Glu Gln Cys Glu Ala Lys Asn Gly Tyr Gln
625                 630                 635                 640

Ser Asp Ala Lys Gly Val Lys Thr Phe Val Glu Trp Val Pro Lys Tyr
                645                 650                 655

Ala Gly Val Leu Pro Ala Asp Val Cys Lys Leu Thr Cys Arg Ala Lys
```

660                 665                 670
Gly Thr Gly Tyr Tyr Val Val Phe Ser Pro Lys Val Thr Asp Gly Thr
            675                 680                 685

Glu Cys Arg Leu Tyr Ser Asn Ser Val Cys Val Arg Gly Lys Cys Val
            690                 695                 700

Arg Thr Gly Cys Asp Gly Ile Ile Gly Ser Lys Leu Gln Tyr Asp Lys
705                 710                 715                 720

Cys Gly Val Cys Gly Gly Asp Asn Ser Ser Cys Thr Lys Ile Val Gly
            725                 730                 735

Thr Phe Asn Lys Lys Ser Lys Gly Tyr Thr Asp Val Val Arg Ile Pro
            740                 745                 750

Glu Gly Ala Thr His Ile Lys Val Arg Gln Phe Lys Ala Lys Asp Gln
            755                 760                 765

Thr Arg Phe Thr Ala Tyr Leu Ala Leu Lys Lys Lys Asn Gly Glu Tyr
            770                 775                 780

Leu Ile Asn Gly Lys Tyr Met Ile Ser Thr Ser Glu Thr Ile Ile Asp
785                 790                 795                 800

Ile Asn Gly Thr Val Met Asn Tyr Ser Gly Trp Ser His Arg Asp Asp
                805                 810                 815

Phe Leu His Gly Met Gly Tyr Ser Ala Thr Lys Glu Ile Leu Ile Val
                820                 825                 830

Gln Ile Leu Ala Thr Asp Pro Thr Lys Pro Leu Asp Val Arg Tyr Ser
            835                 840                 845

Phe Phe Val Pro Lys Lys Ser Thr Pro Lys Val Asn Ser Val Thr Ser
            850                 855                 860

His Gly Ser Asn Lys Val Gly Ser His Thr Ser Gln Pro Gln Trp Val
865                 870                 875                 880

Thr Gly Pro Trp Leu Ala Cys Ser Arg Thr Cys Asp Thr Gly Trp His
                885                 890                 895

Thr Arg Thr Val Gln Cys Gln Asp Gly Asn Arg Lys Leu Ala Lys Gly
                900                 905                 910

Cys Pro Leu Ser Gln Arg Pro Ser Ala Phe Lys Gln Cys Leu Leu Lys
            915                 920                 925

Lys Cys
    930

<210> SEQ ID NO 3
<211> LENGTH: 19
<212> TYPE: RNA
<213> ORGANISM: Artificial Sequence
<220> FEATURE:
<223> OTHER INFORMATION: synthetic construct

<400> SEQUENCE: 3
gcucaaagcu gcaguauga                                              19

<210> SEQ ID NO 4
<211> LENGTH: 19
<212> TYPE: RNA
<213> ORGANISM: Artificial Sequence
<220> FEATURE:
<223> OTHER INFORMATION: synthetic construct

<400> SEQUENCE: 4
gaaguccacu ccaaaagua                                              19

<210> SEQ ID NO 5

```
<211> LENGTH: 19
<212> TYPE: RNA
<213> ORGANISM: Artificial Sequence
<220> FEATURE:
<223> OTHER INFORMATION: synthetic construct

<400> SEQUENCE: 5
gcacuacgau gcagcuauc                                                  19

<210> SEQ ID NO 6
<211> LENGTH: 19
<212> TYPE: RNA
<213> ORGANISM: Artificial Sequence
<220> FEATURE:
<223> OTHER INFORMATION: synthetic construct

<400> SEQUENCE: 6
cgaaggaaau ucuaauagu                                                  19

<210> SEQ ID NO 7
<211> LENGTH: 32
<212> TYPE: DNA
<213> ORGANISM: Artificial Sequence
<220> FEATURE:
<223> OTHER INFORMATION: synthetic construct

<400> SEQUENCE: 7
ccggtctaac atttcttcaa caagcagacc gg                                   32

<210> SEQ ID NO 8
<211> LENGTH: 32
<212> TYPE: DNA
<213> ORGANISM: Artificial Sequence
<220> FEATURE:
<223> OTHER INFORMATION: synthetic construct

<400> SEQUENCE: 8
ccggtcttat acacaaacat gaagcagacc gg                                   32

<210> SEQ ID NO 9
<211> LENGTH: 32
<212> TYPE: DNA
<213> ORGANISM: Artificial Sequence
<220> FEATURE:
<223> OTHER INFORMATION: synthetic construct

<400> SEQUENCE: 9
ccggtctaca tcttattaaa acagcagacc gg                                   32

<210> SEQ ID NO 10
<211> LENGTH: 4410
<212> TYPE: DNA
<213> ORGANISM: Homo sapiens

<400> SEQUENCE: 10
ggggagaacc cacagggaga cccacagaca catatgcacg agagagacag aggaggaaag      60
agacagagac aaaggcacag cggaagaagg cagagacagg gcaggcacag aagcggccca     120
gacagagtcc tacagaggga gaggccgag  aagctgcaga agacacaggc agggagagac     180
aaagatccag gaaaggaggg ctcaggagga gagtttggag aagccagacc cctgggcacc     240
tctcccaagc ccaaggacta agttttctcc atttcctttta acggtcctca gcccttctga     300
aaactttgcc tctgaccttg gcaggagtcc aagcccccag gctacagaga ggagctttcc     360
aaagctaggg tgtggaggac ttggtgccct agacggcctc agtccctccc agctgcagta     420
```

-continued

```
ccagtgccat gtcccagaca ggctcgcatc ccgggagggg cttggcaggg cgctggctgt      480
ggggagccca accctgcctc ctgctcccca ttgtgccgct ctcctggctg gtgtggctgc      540
ttctgctact gctggcctct ctcctgccct cagcccggct ggccagcccc ctcccccggg      600
aggaggagat cgtgtttcca gagaagctca acggcagcgt cctgcctggc tcgggcgccc      660
ctgccaggct gttgtgccgc ttgcaggcct ttggggagac gctgctacta gagctggagc      720
aggactccgg tgtgcaggtc gaggggctga cagtgcagta cctgggccag cgcctgagc      780 tgctgggtgg agcagagcct ggcacctacc tgactggcac catcaatgga gatccggagt      840
cggtggcatc tctgcactgg gatggggag ccctgttagg cgtgttacaa tatcgggggg      900
ctgaactcca cctccagccc ctggagggag gcacccctaa ctctgctggg ggacctgggg      960
ctcacatcct acgccggaag agtcctgcca gcggtcaagg tcccatgtgc aacgtcaagg     1020
ctcctcttgg aagcccagc cccagacccc gaagagccaa gcgctttgct tcactgagta     1080
gatttgtgga cactggtg gtggcagatg acaagatggc cgcattccac ggtgcgggc      1140 taaagcgcta cctgctaaca gtgatggcag cagcagccaa ggccttcaag cacccaagca     1200
tccgcaatcc tgtcagcttg gtggtgactc ggctagtgat cctggggtca ggcgaggagg     1260
ggccccaagt ggggcccagt gctgcccaga ccctgcgcag cttctgtgcc tggcagcggg     1320
gcctcaacac ccctgaggac tcggaccctg accactttga cacagccatt ctgtttaccc     1380
gtcaggacct gtgtggagtc tccacttgcg acacgctggg tatggctgat gtgggcaccg     1440
tctgtgaccc ggctcggagc tgtgccattg tggaggatga tgggctccag tcagccttca     1500
ctgctgctca tgaactgggt catgtcttca acatgctcca tgacaactcc aagccatgca     1560
tcagtttgaa tgggcctttg agcacctctc gccatgtcat ggcccctgtg atggctcatg     1620
tggatcctga ggagccctgg tccccctgca gtgcccgctt catcactgac ttcctggaca     1680
atggctatgg gcactgtctc ttagacaaac cagaggctcc attgcatctg cctgtgactt     1740
tccctggcaa ggactatgat gctgaccgcc agtgccagct gaccttcggg cccgactcac     1800
gccattgtcc acagctgccg ccgccctgtg ctgccctctg gtgctctggc cacctcaatg     1860
gccatgccat gtgccagacc aaacactcgc cctgggccga tggcacaccc tgcgggcccg     1920
cacaggcctg catgggtggt cgctgcctcc acatggacca gctccaggac ttcaatattc     1980
cacaggctgg tggctgggt ccttggggac catggggtga ctgctctcgg acctgtgggg     2040
gtggtgtcca gttctcctcc cgagactgca gcgaggcctgt ccccggaat ggtggcaagt     2100 actgtgaggg ccgccgtacc cgcttccgct cctgcaacac tgaggactgc ccaactggct     2160
cagccctgac cttccgcgag gagcagtgtg ctgcctacaa ccaccgcacc gacctcttca     2220
agagcttccc agggccatg gactgggttc ctcgctacac aggcgtggcc cccaggacc     2280 agtgcaaact cacctgccag gcccaggcac tgggctacta ctatgtgctg agccacgggg     2340
tggtagatgg gacccctgt tccccggaca gctcctcggt ctgtgtccag ggccgatgca     2400
tccatgctgg ctgtgatcgc atcattggct ccaagaagaa gtttgacaag tgcatggtgt     2460
gcggagggga cggttctggt tgcagcaagc agtcaggctc cttcaggaaa ttcaggtacg     2520
gatacaacaa tgtggtcact atcccgcgg gggccaccca cattcttgtc cggcagcagg     2580
gaaaccctgg ccaccggagc atctacttgg ccctgaagct gccagatggc tcctatgccc     2640
tcaatggtga atacacgctg atgccctccc ccacagatgt ggtactgcct ggggcagtca     2700
gcttgcgcta cagcggggcc actgcagcct cagagacact gtcaggccat gggccactgg     2760
```

```
cccagccttt gacactgcaa gtcctagtgg ctggcaaccc ccaggacaca cgcctccgat    2820
acagcttctt cgtgccccgg ccgacccctt caacgccacg ccccactccc caggactggc    2880
tgcaccgaag agcacagatt ctggagatcc ttcggcggcg ccctgggcg gcaggaaat     2940 aacctcacta tcccggctgc cctttctggg caccggggcc tcggacttag ctgggagaaa    3000
gagagagctt ctgttgctgc ctcatgctaa gactcagtgg ggaggggctg tgggcgtgag    3060
acctgcccct cctctctgcc ctaatgcgca ggctggccct gccctggttt cctgccctgg    3120
gaggcagtga tgggttagtg gatggaaggg gctgacagac agccctccat ctaaactgcc    3180
ccctctgccc tgcgggtcac aggagggagg gggaaggcag ggagggcctg ggccccagtt    3240
gtatttattt agtatttatt cacttttatt tagcaccagg gaaggggaca aggactaggg    3300
tcctggggaa cctgaccect gaccectcat agccctcacc ctggggctag gaaatccagg    3360
gtggtggtga taggtataag tggtgtgtgt atgcgtgtgt gtgtgtgtga aaatgtgtgt    3420
gtgcttatgt atgaggtaca acctgttctg cttcctctct cctgaatttt atttttgg     3480 aaaagaaaag tcaagggtag ggtgggcctt cagggagtga gggattatct ttttttttt    3540 ttctttcttt cttctttttt ttttttgag acagaatctc gctctgtcgc ccaggctgga    3600
gtgcaatggc acaatctcgg ctcactgcat cctccgcctc ccgggttcaa gtgattctca    3660
tgcctcagcc tcctgagtag ctgggattac aggctcctgc caccacgccc ggctaatttt    3720
tgttttgttt tgtttggaga cagagtctcg ctattgtcac cagggctgga atgatttcag    3780
ctcactgcaa ccttcgccac ctgggttcca gcaattctcc tgcctcagcc tcccgagtag    3840
ctgagattat aggcacctac caccacgccc ggctaatttt tgtattttta gtagagacgg    3900
ggtttcacca tgttggccag gctggtctcg aactcctgac cttaggtgat ccactcgcct    3960
tcatctccca aagtgctggg attacaggcg tgagccaccg tgcctggcca cgcccaacta    4020
atttttgtat ttttagtaga cagggtttt caccatgttg gccaggctgc tcttgaactc     4080
ctgacctcag gtaatcgacc tgcctcggcc tcccaaagtg ctgggattac aggtgtgagc    4140
caccacgccc ggtacatatt ttttaaattg aattctacta tttatgtgat ccttttggag    4200
tcagacagat gtggttgcat cctaactcca tgtctctgag cattagattt ctcatttgcc    4260
aataataata cctcccttag aagtttgttg tgaggattaa ataatgtaaa taagaacta     4320 gcataacact caaaaaaaaa aaaaaaaaaa aaaaaaaaaa aaaaaaaaaa aaaaaaaaa     4380 aaaaaaaaaa aaaaaaaaa aaaaaaaaa                                      4410

<210> SEQ ID NO 11
<211> LENGTH: 837
<212> TYPE: PRT
<213> ORGANISM: Homo sapiens

<400> SEQUENCE: 11

Met Ser Gln Thr Gly Ser His Pro Gly Arg Gly Leu Ala Gly Arg Trp
1               5                   10                  15

Leu Trp Gly Ala Gln Pro Cys Leu Leu Leu Pro Ile Val Pro Leu Ser
            20                  25                  30

Trp Leu Val Trp Leu Leu Leu Leu Leu Ala Ser Leu Leu Pro Ser
        35                  40                  45

Ala Arg Leu Ala Ser Pro Leu Pro Arg Glu Glu Glu Ile Val Phe Pro
    50                  55                  60

Glu Lys Leu Asn Gly Ser Val Leu Pro Gly Ser Gly Ala Pro Ala Arg
65                  70                  75                  80
```

```
Leu Leu Cys Arg Leu Gln Ala Phe Gly Glu Thr Leu Leu Glu Leu
                85                  90                  95
Glu Gln Asp Ser Gly Val Gln Val Glu Gly Leu Thr Val Gln Tyr Leu
            100                 105                 110
Gly Gln Ala Pro Glu Leu Leu Gly Gly Ala Glu Pro Gly Thr Tyr Leu
            115                 120                 125
Thr Gly Thr Ile Asn Gly Asp Pro Glu Ser Val Ala Ser Leu His Trp
        130                 135                 140
Asp Gly Gly Ala Leu Leu Gly Val Leu Gln Tyr Arg Gly Ala Glu Leu
145                 150                 155                 160
His Leu Gln Pro Leu Glu Gly Gly Thr Pro Asn Ser Ala Gly Gly Pro
                165                 170                 175
Gly Ala His Ile Leu Arg Arg Lys Ser Pro Ala Ser Gly Gln Gly Pro
            180                 185                 190
Met Cys Asn Val Lys Ala Pro Leu Gly Ser Pro Ser Pro Arg Pro Arg
            195                 200                 205
Arg Ala Lys Arg Phe Ala Ser Leu Ser Arg Phe Val Glu Thr Leu Val
        210                 215                 220
Val Ala Asp Asp Lys Met Ala Ala Phe His Gly Ala Gly Leu Lys Arg
225                 230                 235                 240
Tyr Leu Leu Thr Val Met Ala Ala Ala Ala Lys Ala Phe Lys His Pro
                245                 250                 255
Ser Ile Arg Asn Pro Val Ser Leu Val Val Thr Arg Leu Val Ile Leu
            260                 265                 270
Gly Ser Gly Glu Glu Gly Pro Gln Val Gly Pro Ser Ala Ala Gln Thr
        275                 280                 285
Leu Arg Ser Phe Cys Ala Trp Gln Arg Gly Leu Asn Thr Pro Glu Asp
    290                 295                 300
Ser Asp Pro Asp His Phe Asp Thr Ala Ile Leu Phe Thr Arg Gln Asp
305                 310                 315                 320
Leu Cys Gly Val Ser Thr Cys Asp Thr Leu Gly Met Ala Asp Val Gly
                325                 330                 335
Thr Val Cys Asp Pro Ala Arg Ser Cys Ala Ile Val Glu Asp Asp Gly
            340                 345                 350
Leu Gln Ser Ala Phe Thr Ala Ala His Glu Leu Gly His Val Phe Asn
        355                 360                 365
Met Leu His Asp Asn Ser Lys Pro Cys Ile Ser Leu Asn Gly Pro Leu
    370                 375                 380
Ser Thr Ser Arg His Val Met Ala Pro Val Met Ala His Val Asp Pro
385                 390                 395                 400
Glu Glu Pro Trp Ser Pro Cys Ser Ala Arg Phe Ile Thr Asp Phe Leu
                405                 410                 415
Asp Asn Gly Tyr Gly His Cys Leu Leu Asp Lys Pro Glu Ala Pro Leu
            420                 425                 430
His Leu Pro Val Thr Phe Pro Gly Lys Asp Tyr Asp Ala Asp Arg Gln
        435                 440                 445
Cys Gln Leu Thr Phe Gly Pro Asp Ser Arg His Cys Pro Gln Leu Pro
    450                 455                 460
Pro Pro Cys Ala Ala Leu Trp Cys Ser Gly His Leu Asn Gly His Ala
465                 470                 475                 480
Met Cys Gln Thr Lys His Ser Pro Trp Ala Asp Gly Thr Pro Cys Gly
                485                 490                 495
Pro Ala Gln Ala Cys Met Gly Gly Arg Cys Leu His Met Asp Gln Leu
```

```
            500                 505                 510
Gln Asp Phe Asn Ile Pro Gln Ala Gly Gly Trp Gly Pro Trp Gly Pro
        515                 520                 525

Trp Gly Asp Cys Ser Arg Thr Cys Gly Gly Val Gln Phe Ser Ser
        530                 535                 540

Arg Asp Cys Thr Arg Pro Val Pro Arg Asn Gly Lys Tyr Cys Glu
545                 550                 555                 560

Gly Arg Arg Thr Arg Phe Arg Ser Cys Asn Thr Glu Asp Cys Pro Thr
                565                 570                 575

Gly Ser Ala Leu Thr Phe Arg Glu Glu Gln Cys Ala Ala Tyr Asn His
        580                 585                 590

Arg Thr Asp Leu Phe Lys Ser Phe Pro Gly Pro Met Asp Trp Val Pro
        595                 600                 605

Arg Tyr Thr Gly Val Ala Pro Gln Asp Gln Cys Lys Leu Thr Cys Gln
        610                 615                 620

Ala Gln Ala Leu Gly Tyr Tyr Tyr Val Leu Glu Pro Arg Val Val Asp
625                 630                 635                 640

Gly Thr Pro Cys Ser Pro Asp Ser Ser Val Cys Val Gln Gly Arg
                645                 650                 655

Cys Ile His Ala Gly Cys Asp Arg Ile Ile Gly Ser Lys Lys Phe
        660                 665                 670

Asp Lys Cys Met Val Cys Gly Gly Asp Gly Ser Gly Cys Ser Lys Gln
        675                 680                 685

Ser Gly Ser Phe Arg Lys Phe Arg Tyr Gly Tyr Asn Asn Val Val Thr
        690                 695                 700

Ile Pro Ala Gly Ala Thr His Ile Leu Val Arg Gln Gln Gly Asn Pro
705                 710                 715                 720

Gly His Arg Ser Ile Tyr Leu Ala Leu Lys Leu Pro Asp Gly Ser Tyr
                725                 730                 735

Ala Leu Asn Gly Glu Tyr Thr Leu Met Pro Ser Pro Thr Asp Val Val
                740                 745                 750

Leu Pro Gly Ala Val Ser Leu Arg Tyr Ser Gly Ala Thr Ala Ala Ser
        755                 760                 765

Glu Thr Leu Ser Gly His Gly Pro Leu Ala Gln Pro Leu Thr Leu Gln
        770                 775                 780

Val Leu Val Ala Gly Asn Pro Gln Asp Thr Arg Leu Arg Tyr Ser Phe
785                 790                 795                 800

Phe Val Pro Arg Pro Thr Pro Ser Thr Pro Arg Pro Thr Pro Gln Asp
                805                 810                 815

Trp Leu His Arg Arg Ala Gln Ile Leu Glu Ile Leu Arg Arg Arg Pro
        820                 825                 830

Trp Ala Gly Arg Lys
        835

<210> SEQ ID NO 12
<211> LENGTH: 19
<212> TYPE: RNA
<213> ORGANISM: Artificial Sequence
<220> FEATURE:
<223> OTHER INFORMATION: synthetic construct

<400> SEQUENCE: 12
ccgcaauccu gucagcuug                                                  19

<210> SEQ ID NO 13
```

```
<211> LENGTH: 19
<212> TYPE: RNA
<213> ORGANISM: Artificial Sequence
<220> FEATURE:
<223> OTHER INFORMATION: synthetic construct

<400> SEQUENCE: 13
gcgcuuugcu ucacugagu                                                19

<210> SEQ ID NO 14
<211> LENGTH: 19
<212> TYPE: RNA
<213> ORGANISM: Artificial Sequence
<220> FEATURE:
<223> OTHER INFORMATION: synthetic construct

<400> SEQUENCE: 14
ggacacacgc cuccgauac                                                19

<210> SEQ ID NO 15
<211> LENGTH: 19
<212> TYPE: RNA
<213> ORGANISM: Artificial Sequence
<220> FEATURE:
<223> OTHER INFORMATION: synthetic construct

<400> SEQUENCE: 15
gcaccgaaga gcacagauu                                                19

<210> SEQ ID NO 16
<211> LENGTH: 32
<212> TYPE: DNA
<213> ORGANISM: Artificial Sequence
<220> FEATURE:
<223> OTHER INFORMATION: synthetic construct

<400> SEQUENCE: 16
ccggtctttt cacacacaca cacacggacc gg                                 32

<210> SEQ ID NO 17
<211> LENGTH: 32
<212> TYPE: DNA
<213> ORGANISM: Artificial Sequence
<220> FEATURE:
<223> OTHER INFORMATION: synthetic construct

<400> SEQUENCE: 17
ccggtctaaa aatacaaaaa ttagccgacc gg                                 32

<210> SEQ ID NO 18
<211> LENGTH: 32
<212> TYPE: DNA
<213> ORGANISM: Artificial Sequence
<220> FEATURE:
<223> OTHER INFORMATION: synthetic construct

<400> SEQUENCE: 18
ccggtcttgt ctctgtctct ttcctcgacc gg                                 32

<210> SEQ ID NO 19
<211> LENGTH: 2735
<212> TYPE: DNA
<213> ORGANISM: Homo sapiens

<400> SEQUENCE: 19
acaacagtcc ccaggcatca ccattcaaga tgcatccagg ggtcctggct gccttcctct    60
```

```
tcttgagctg gactcattgt cgggccctgc cccttcccag tggtggtgat gaagatgatt     120
tgtctgagga agacctccag tttgcagagc gctacctgag atcatactac catcctacaa     180
atctcgcggg aatcctgaag gagaatgcag caagctccat gactgagagg ctccgagaaa     240
tgcagtcttt cttcggctta gaggtgactg gcaaacttga cgataacacc ttagatgtca     300
tgaaaaagcc aagatgcggg gttcctgatg tgggtgaata caatgttttc cctcgaactc     360
ttaaatggtc caaaatgaat ttaacctaca gaattgtgaa ttacacccct gatatgactc     420
attctgaagt cgaaaaggca ttcaaaaaag ccttcaaagt ttggtccgat gtaactcctc     480
tgaattttac cagacttcac gatggcattg ctgacatcat gatctctttt ggaattaagg     540
agcatggcga cttctaccca tttgatgggc cctctggcct gctggctcat gcttttcctc     600
ctgggccaaa ttatggagga gatgcccatt ttgatgatga tgaaacctgg acaagtagtt     660
ccaaaggcta caacttgttt cttgttgctg cgcatgagtt cggccactcc ttaggtcttg     720
accactccaa ggaccctgga gcactcatgt ttcctatcta cacctacacc ggcaaaagcc     780
actttatgct tcctgatgac gatgtacaag ggatccagtc tctctatggt ccaggagatg     840
aagaccccaa ccctaaacat ccaaaaacgc cagacaaatg tgacccttcc ttatcccttg     900
atgccattac cagtctccga ggagaaacaa tgatctttaa agacagattc ttctggcgcc     960
tgcatcctca gcaggttgat gcggagctgt ttttaacgaa atcattttgg ccagaacttc    1020
ccaaccgtat tgatgctgca tatgagcacc cttctcatga cctcatcttc atcttcagag    1080
gtagaaaatt ttgggctctt aatggttatg acattctgga aggttatccc aaaaaaaatat    1140 ctgaactggg tcttccaaaa gaagttaaga agataagtgc agctgttcac tttgaggata    1200
caggcaagac tctcctgttc tcaggaaacc aggtctggag atatgatgat actaaccata    1260
ttatggataa agactatccg agactaatag aagaagactt cccaggaatt ggtgataaag    1320
tagatgctgt ctatgagaaa aatggttata tctatttttt caacggaccc atacagtttg    1380
aatacagcat ctggagtaac cgtattgttc gcgtcatgcc agcaaattcc attttgtggt    1440
gttaagtgtc ttttttaaaaa ttgttattta aatcctgaag agcatttggg gtaatacttc    1500
cagaagtgcg gggtagggga agaagagcta tcaggagaaa gcttggttct gtgaacaagc    1560
ttcagtaagt tatctttgaa tatgtagtat ctatatgact atgcgtggct ggaaccacat    1620
tgaagaatgt tagagtaatg aaatggagga tctctaaaga gcatctgatt cttgttgctg    1680
tacaaaagca atggttgatg atacttccca caccacaaat gggacacatg gtctgtcaat    1740
gagagcataa tttaaaaata tatttataag gaaattttac aagggcataa agtaaataca    1800
tgcatataat gaataaatca ttcttactaa aaagtataaa atagtatgaa atggaaatt    1860 tgggagagcc atacataaaa gaaataaacc aaaggaaaat gtctgtaata atagactgta    1920
acttccaaat aaataatttt cattttgcac tgaggatatt cagatgtatg tgcccttctt    1980
cacacagaca ctaacgaaat atcaaagtca ttaaagacag gagacaaaag agcagtggta    2040
agaatagtag atgtggcctt tgaattctgt ttaattttca cttttggcaa tgactcaaag    2100
tctgctctca tataagacaa atattccttt gcatattata aaggataaag aaggatgatg    2160 tcttttatt aaaatatttc aggttcttca gaagtcacac attacaaagt taaaattgtt    2220
atcaaaatag tctaaggcca tggcatccct ttttcataaa ttatttgatt atttaagact    2280
aaaagttgca tttaaccct attttaccta gctaattatt taattgtcca gtttgtcttg    2340
gatatatagg ctatttttcta aagacttgta tagcatgaaa taaaatatat cttataaagt    2400
```

```
ggaagtatgt atattaaaaa agagacatcc aaatttttt ttaaagcagt ctactagatt    2460
gtgatccctt gagatatgga aggatgcctt tttttctctg catttaaaaa aatccccag     2520 cacttcccac agtgcctatt gatacttggg gagggtgctt ggcacttatt gaatatatga    2580
tcggccatca aggaagaac tattgtgctc agagacactg ttgataaaaa ctcaggcaaa     2640
gaaaatgaaa tgcatatttg caaagtgtat taggaagtgt ttatgttgtt tataataaaa    2700
atatattttc aacagacaaa aaaaaaaaaa aaaaa                               2735
```

<210> SEQ ID NO 20
<211> LENGTH: 471
<212> TYPE: PRT
<213> ORGANISM: Homo sapiens

<400> SEQUENCE: 20

```
Met His Pro Gly Val Leu Ala Ala Phe Leu Phe Leu Ser Trp Thr His
1               5                   10                  15

Cys Arg Ala Leu Pro Leu Pro Ser Gly Gly Asp Glu Asp Asp Leu Ser
            20                  25                  30

Glu Glu Asp Leu Gln Phe Ala Glu Arg Tyr Leu Arg Ser Tyr Tyr His
        35                  40                  45

Pro Thr Asn Leu Ala Gly Ile Leu Lys Glu Asn Ala Ala Ser Ser Met
    50                  55                  60

Thr Glu Arg Leu Arg Glu Met Gln Ser Phe Phe Gly Leu Glu Val Thr
65                  70                  75                  80

Gly Lys Leu Asp Asp Asn Thr Leu Asp Val Met Lys Lys Pro Arg Cys
                85                  90                  95

Gly Val Pro Asp Val Gly Glu Tyr Asn Val Phe Pro Arg Thr Leu Lys
            100                 105                 110

Trp Ser Lys Met Asn Leu Thr Tyr Arg Ile Val Asn Tyr Thr Pro Asp
        115                 120                 125

Met Thr His Ser Glu Val Glu Lys Ala Phe Lys Lys Ala Phe Lys Val
    130                 135                 140

Trp Ser Asp Val Thr Pro Leu Asn Phe Thr Arg Leu His Asp Gly Ile
145                 150                 155                 160

Ala Asp Ile Met Ile Ser Phe Gly Ile Lys Glu His Gly Asp Phe Tyr
                165                 170                 175

Pro Phe Asp Gly Pro Ser Gly Leu Leu Ala His Ala Phe Pro Pro Gly
            180                 185                 190

Pro Asn Tyr Gly Gly Asp Ala His Phe Asp Asp Glu Thr Trp Thr
        195                 200                 205

Ser Ser Ser Lys Gly Tyr Asn Leu Phe Leu Val Ala Ala His Glu Phe
    210                 215                 220

Gly His Ser Leu Gly Leu Asp His Ser Lys Asp Pro Gly Ala Leu Met
225                 230                 235                 240

Phe Pro Ile Tyr Thr Tyr Thr Gly Lys Ser His Phe Met Leu Pro Asp
                245                 250                 255

Asp Asp Val Gln Gly Ile Gln Ser Leu Tyr Gly Pro Gly Asp Glu Asp
            260                 265                 270

Pro Asn Pro Lys His Pro Lys Thr Pro Asp Lys Cys Asp Pro Ser Leu
        275                 280                 285

Ser Leu Asp Ala Ile Thr Ser Leu Arg Gly Glu Thr Met Ile Phe Lys
    290                 295                 300

Asp Arg Phe Phe Trp Arg Leu His Pro Gln Gln Val Asp Ala Glu Leu
305                 310                 315                 320
```

```
Phe Leu Thr Lys Ser Phe Trp Pro Glu Leu Pro Asn Arg Ile Asp Ala
            325                 330                 335

Ala Tyr Glu His Pro Ser His Asp Leu Ile Phe Ile Phe Arg Gly Arg
        340                 345                 350

Lys Phe Trp Ala Leu Asn Gly Tyr Asp Ile Leu Glu Gly Tyr Pro Lys
    355                 360                 365

Lys Ile Ser Glu Leu Gly Leu Pro Lys Glu Val Lys Lys Ile Ser Ala
370                 375                 380

Ala Val His Phe Glu Asp Thr Gly Lys Thr Leu Leu Phe Ser Gly Asn
385                 390                 395                 400

Gln Val Trp Arg Tyr Asp Thr Asn His Ile Met Asp Lys Asp Tyr
            405                 410                 415

Pro Arg Leu Ile Glu Glu Asp Phe Pro Gly Ile Gly Asp Lys Val Asp
        420                 425                 430

Ala Val Tyr Glu Lys Asn Gly Tyr Ile Tyr Phe Phe Asn Gly Pro Ile
    435                 440                 445

Gln Phe Glu Tyr Ser Ile Trp Ser Asn Arg Ile Val Arg Val Met Pro
450                 455                 460

Ala Asn Ser Ile Leu Trp Cys
465                 470

<210> SEQ ID NO 21
<211> LENGTH: 20
<212> TYPE: RNA
<213> ORGANISM: Artificial Sequence
<220> FEATURE:
<223> OTHER INFORMATION: synthetic construct

<400> SEQUENCE: 21
uuucacacac acacacacgc                                                   20

<210> SEQ ID NO 22
<211> LENGTH: 20
<212> TYPE: RNA
<213> ORGANISM: Artificial Sequence
<220> FEATURE:
<223> OTHER INFORMATION: synthetic construct

<400> SEQUENCE: 22
uuuucacaca cacacacacg                                                   20

<210> SEQ ID NO 23
<211> LENGTH: 20
<212> TYPE: RNA
<213> ORGANISM: Artificial Sequence
<220> FEATURE:
<223> OTHER INFORMATION: synthetic construct

<400> SEQUENCE: 23
uaaaaauaca aaaauuagcc                                                   20

<210> SEQ ID NO 24
<211> LENGTH: 20
<212> TYPE: RNA
<213> ORGANISM: Artificial Sequence
<220> FEATURE:
<223> OTHER INFORMATION: synthetic construct

<400> SEQUENCE: 24
uuugucucug ucucuuuccu                                                   20
```

<210> SEQ ID NO 25
<211> LENGTH: 32
<212> TYPE: DNA
<213> ORGANISM: Artificial Sequence
<220> FEATURE:
<223> OTHER INFORMATION: synthetic construct

<400> SEQUENCE: 25
ccggtctaca cacaccactt atacctgacc gg                          32

<210> SEQ ID NO 26
<211> LENGTH: 32
<212> TYPE: DNA
<213> ORGANISM: Artificial Sequence
<220> FEATURE:
<223> OTHER INFORMATION: synthetic construct

<400> SEQUENCE: 26
ccggtctata atctcagcta ctcggggacc gg                          32

<210> SEQ ID NO 27
<211> LENGTH: 32
<212> TYPE: DNA
<213> ORGANISM: Artificial Sequence
<220> FEATURE:
<223> OTHER INFORMATION: synthetic construct

<400> SEQUENCE: 27
ccggtcaaac aaaacaaaaa ttagccgacc gg                          32

<210> SEQ ID NO 28
<211> LENGTH: 1903
<212> TYPE: DNA
<213> ORGANISM: Homo sapiens

<400> SEQUENCE: 28
agcatgagtc agacagcctc tggctttctg gaagggcaag gactctatat atacagaggg      60
agcttcctag ctgggatatt ggagcagcaa gaggctggga agccatcact taccttgcac     120
tgagaaagaa gacaaaggca agttgaaaag cggagaaata gtgcccagt ggttgaaaaa      180
ttgaagcaaa tgcaggaatt cttggctg aaagtgactg ggaaaccaga tgctgaaacc       240
ctgaaggtga tgaagcagcc cagatgtgga gtgcctgatg tggctcagtt tgtcctcact     300
gagggggaacc ctcgctggga gcaaacacat ctgacctaca ggattgaaaa ttacacgcca    360
gatttgccaa gagcagatgt ggaccatgcc attgagaaag ccttccaact ctggagtaat    420
gtcacacctc tgacattcac caaggtctct gagggtcaag cagacatcat gatatctttt    480
gtcaggggag atcatcggga caactctcct tttgatggac ctggaggaaa tcttgctcat    540
gcttttcaac caggcccagg tattggaggg gatgctcatt ttgatgaaga tgaaaggtgg    600
accaacaatt tcagagagta caacttacat cgtgttgcag ctcatgaact cggccattct    660
cttggactct cccattctac tgatatcggg gctttgatgt accctagcta caccttcagt    720
ggtgatgttc agctagctca ggatgacatt gatggcatcc aagccatata tggacgttcc    780
caaaatcctg tccagcccat cggcccacaa accccaaaag cgtgtgacag taagctaacc    840
tttgatgcta taactacgat tcggggagaa gtgatgttct taaagacag attctacatg    900
cgcacaaatc ccttctaccc ggaagttgag ctcaatttca tttctgtttt ctggccacaa    960
ctgccaaatg ggcttgaagc tgcttacgaa tttgccgaca gagatgaagt ccggtttttc    1020
aaagggaata agtactgggc tgttcaggga cagaatgtgc tacacggata ccccaaggac   1080

-continued

```
atctacagct cctttggctt ccctagaact gtgaagcata tcgatgctgc tctttctgag    1140
gaaaacactg gaaaaaccta cttctttgtt gctaacaaat actggaggta tgatgaatat    1200
aaacgatcta tggatccagg ttatcccaaa atgatagcac atgactttcc tggaattggc    1260
cacaaagttg atgcagtttt catgaaagat ggattttcct atttctttca tggaacaaga    1320
caatacaaat ttgatcctaa aacgaagaga attttgactc tccagaaagc taatagctgg    1380
ttcaactgca ggaaaaattg aacattacta atttgaatgg aaaacacatg gtgtgagtcc    1440
aaagaaggtg ttttcctgaa gaactgtcta ttttctcagt cattttaac ctctagagtc     1500 actgatacac agaatataat cttatttata cctcagtttg catattttt tactatttag     1560 aatgtagccc tttttgtact gatataattt agttccacaa atggtgggta caaaaagtca    1620
agtttgtggc ttatggattc atataggcca gagttgcaaa gatcttttcc agagtatgca    1680
actctgacgt tgatcccaga gagcagcttc agtgacaaac atatcctttc aagacagaaa    1740
gagacaggag acatgagtct ttgccggagg aaaagcagct caagaacaca tgtgcagtca    1800
ctggtgtcac cctggatagg caagggataa ctcttctaac acaaataag tgttttatgt      1860 ttggaataaa gtcaaccttg tttctactgt tttatacact ttc                      1903
```

<210> SEQ ID NO 29
<211> LENGTH: 403
<212> TYPE: PRT
<213> ORGANISM: Homo sapiens

<400> SEQUENCE: 29

```
Met Gln Glu Phe Phe Gly Leu Lys Val Thr Gly Lys Pro Asp Ala Glu
1               5                   10                  15

Thr Leu Lys Val Met Lys Gln Pro Arg Cys Gly Val Pro Asp Val Ala
            20                  25                  30

Gln Phe Val Leu Thr Glu Gly Asn Pro Arg Trp Glu Gln Thr His Leu
        35                  40                  45

Thr Tyr Arg Ile Glu Asn Tyr Thr Pro Asp Leu Pro Arg Ala Asp Val
    50                  55                  60

Asp His Ala Ile Glu Lys Ala Phe Gln Leu Trp Ser Asn Val Thr Pro
65                  70                  75                  80

Leu Thr Phe Thr Lys Val Ser Glu Gly Gln Ala Asp Ile Met Ile Ser
                85                  90                  95

Phe Val Arg Gly Asp His Arg Asp Asn Ser Pro Phe Asp Gly Pro Gly
            100                 105                 110

Gly Asn Leu Ala His Ala Phe Gln Pro Gly Pro Gly Ile Gly Gly Asp
        115                 120                 125

Ala His Phe Asp Glu Asp Glu Arg Trp Thr Asn Asn Phe Arg Glu Tyr
    130                 135                 140

Asn Leu His Arg Val Ala Ala His Glu Leu Gly His Ser Leu Gly Leu
145                 150                 155                 160

Ser His Ser Thr Asp Ile Gly Ala Leu Met Tyr Pro Ser Tyr Thr Phe
                165                 170                 175

Ser Gly Asp Val Gln Leu Ala Gln Asp Asp Ile Asp Gly Ile Gln Ala
            180                 185                 190

Ile Tyr Gly Arg Ser Gln Asn Pro Val Gln Pro Ile Gly Pro Gln Thr
        195                 200                 205

Pro Lys Ala Cys Asp Ser Lys Leu Thr Phe Asp Ala Ile Thr Thr Ile
    210                 215                 220
```

-continued

Arg Gly Glu Val Met Phe Phe Lys Asp Arg Phe Tyr Met Arg Thr Asn
225                 230                 235                 240

Pro Phe Tyr Pro Glu Val Glu Leu Asn Phe Ile Ser Val Phe Trp Pro
            245                 250                 255

Gln Leu Pro Asn Gly Leu Glu Ala Ala Tyr Glu Phe Ala Asp Arg Asp
            260                 265                 270

Glu Val Arg Phe Phe Lys Gly Asn Lys Tyr Trp Ala Val Gln Gly Gln
        275                 280                 285

Asn Val Leu His Gly Tyr Pro Lys Asp Ile Tyr Ser Ser Phe Gly Phe
    290                 295                 300

Pro Arg Thr Val Lys His Ile Asp Ala Ala Leu Ser Glu Glu Asn Thr
305                 310                 315                 320

Gly Lys Thr Tyr Phe Phe Val Ala Asn Lys Tyr Trp Arg Tyr Asp Glu
                325                 330                 335

Tyr Lys Arg Ser Met Asp Pro Gly Tyr Pro Lys Met Ile Ala His Asp
                340                 345                 350

Phe Pro Gly Ile Gly His Lys Val Asp Ala Val Phe Met Lys Asp Gly
            355                 360                 365

Phe Phe Tyr Phe Phe His Gly Thr Arg Gln Tyr Lys Phe Asp Pro Lys
370                 375                 380

Thr Lys Arg Ile Leu Thr Leu Gln Lys Ala Asn Ser Trp Phe Asn Cys
385                 390                 395                 400

Arg Lys Asn

<210> SEQ ID NO 30
<211> LENGTH: 19
<212> TYPE: RNA
<213> ORGANISM: Artificial Sequence
<220> FEATURE:
<223> OTHER INFORMATION: synthetic construct

<400> SEQUENCE: 30
uuagcuuacu gucacacgc                                                  19

<210> SEQ ID NO 31
<211> LENGTH: 19
<212> TYPE: RNA
<213> ORGANISM: Artificial Sequence
<220> FEATURE:
<223> OTHER INFORMATION: synthetic construct

<400> SEQUENCE: 31
uuauauucau cauaccucc                                                  19

<210> SEQ ID NO 32
<211> LENGTH: 19
<212> TYPE: RNA
<213> ORGANISM: Artificial Sequence
<220> FEATURE:
<223> OTHER INFORMATION: synthetic construct

<400> SEQUENCE: 32
uugucuucuu ucucagugc                                                  19

<210> SEQ ID NO 33
<211> LENGTH: 19
<212> TYPE: RNA
<213> ORGANISM: Artificial Sequence
<220> FEATURE:
<223> OTHER INFORMATION: synthetic construct

<400> SEQUENCE: 33
uucguaagca gcuucaagc                                                   19

<210> SEQ ID NO 34
<211> LENGTH: 31
<212> TYPE: DNA
<213> ORGANISM: Artificial Sequence
<220> FEATURE:
<223> OTHER INFORMATION: synthetic construct

<400> SEQUENCE: 34
ccggtcttcg taagcagctt caagcgaccg g                                     31

<210> SEQ ID NO 35
<211> LENGTH: 30
<212> TYPE: DNA
<213> ORGANISM: Artificial Sequence
<220> FEATURE:
<223> OTHER INFORMATION: synthetic construct

<400> SEQUENCE: 35
ccggtctaaa gaacatcact ttccgaccgg                                       30

<210> SEQ ID NO 36
<211> LENGTH: 31
<212> TYPE: DNA
<213> ORGANISM: Artificial Sequence
<220> FEATURE:
<223> OTHER INFORMATION: synthetic construct

<400> SEQUENCE: 36
ccggtctaaa acagtagaaa caagggaccg g                                     31

<210> SEQ ID NO 37
<211> LENGTH: 2387
<212> TYPE: DNA
<213> ORGANISM: Homo sapiens

<400> SEQUENCE: 37
agacacctct gccctcacca tgagcctctg gcagccctg gtcctggtgc tcctggtgct       60
gggctgctgc tttgctgccc cagacagcg ccagtccacc cttgtgctct ccctggaga      120 cctgagaacc aatctcaccg acaggcagct ggcagaggaa tacctgtacc gctatggtta    180
cactcgggtg gcagagatgc gtggagagtc gaaatctctg gggcctgcgc tgctgcttct    240
ccagaagcaa ctgtccctgc ccgagaccgg tgagctggat agcgccacgc tgaaggccat    300 gcgaaccca cggtgcgggg tcccagacct gggcagattc caaacctttg agggcgacct    360
caagtggcac caccacaaca tcacctattg gatccaaaac tactcggaag acttgccgcg    420
ggcggtgatt gacgacgcct tgcccgcgc cttcgcactg tggagcgcgg tgacgccgct    480
caccttcact cgcgtgtaca gccgggacgc agacatcgtc atccagtttg tgtcgcgga    540 gcacggagac gggtatccct tcgacgggaa ggacgggctc tggcacacg cctttcctcc    600 tggccccggc attcagggag acgcccattt cgacgatgac gagttgtggt ccctgggcaa    660
gggcgtcgtg gttccaactc ggtttggaaa cgcagatggc cgcggctgcc acttcccctt    720
catcttcgag ggccgctcct actctgcctg caccaccgac ggtcgctccg acggcttgcc    780
ctggtgcagt accacggcca actacgacac cgacgaccgg tttggcttct gccccagcga    840
gagactctac acccaggacg gcaatgctga tgggaaaccc tgccagtttc cattcatctt    900
ccaaggccaa tcctactccg cctgcaccac ggacggtcgc tccgacggct accgctggtg    960

```
cgccaccacc gccaactacg accgggacaa gctcttcggc ttctgcccga cccgagctga    1020
ctcgacggtg atggggggca actcggcggg ggagctgtgc gtcttcccct tcactttcct    1080
gggtaaggag tactcgacct gtaccagcga gggccgcgga gatgggcgcc tctggtgcgc    1140
taccacctcg aactttgaca gcgacaagaa gtggggcttc tgcccggacc aaggatacag    1200
tttgttcctc gtggcggcgc atgagttcgg ccacgcgctg gcttagatc attcctcagt     1260 gccggaggcg ctcatgtacc ctatgtaccg cttcactgag gggcccccct tgcataagga    1320
cgacgtgaat ggcatccggc acctctatgg tcctcgcccc gaacctgagc acggcctcc     1380 aaccaccacc acaccgcagc ccacggctcc cccgacggtc tgccccaccg acccccccac    1440
tgtccacccc tcagagcgcc ccacagctgg ccccacaggt ccccccctcag ctggccccac   1500 aggtcccccc actgctggcc cttctacggc cactactgtg cctttgagtc cggtggacga    1560
tgcctgcaac gtgaacatct tcgacgccat cgcggagatt gggaaccagc tgtatttgtt    1620
caaggatggg aagtactggc gattctctga gggcaggggg agccggccgc agggccctt     1680 ccttatcgcc gacaagtggc ccgcgctgcc ccgcaagctg gactcggtct ttgaggagcg    1740
gctctccaag aagcttttct tcttctctgg gcgccaggtg tgggtgtaca caggcgcgtc    1800
ggtgctgggc ccgaggcgtc tggacaagct gggcctggga gccgacgtgg cccaggtgac    1860
cggggccctc cggagtggca gggggaagat gctgctgttc agcggggcggc gcctctggag   1920 gttcgacgtg aaggcgcaga tggtggatcc ccggagcgcc agcgaggtgg accggatgtt    1980 ccccgggggtg cctttggaca cgcacgacgt cttccagtac cgagagaaag cctatttctg    2040
ccaggaccgc ttctactggc gcgtgagttc ccggagtgag ttgaaccagg tggaccaagt    2100
gggctacgtg acctatgaca tcctgcagtg ccctgaggac tagggctccc gtcctgcttt    2160
ggcagtgcca tgtaaatccc cactgggacc aaccctgggg aaggagccag tttgccggat    2220
acaaactggt attctgttct ggaggaaagg gaggagtgga ggtgggctgg gccctctctt    2280
ctcacctttg ttttttgttg gagtgtttct aataaacttg gattctctaa cctttaaaaa    2340
aaaaaaaaaa aaaaaaaaaa aaaaaaaaaa aaaaaaaaaa aaaaaaa               2387
```

<210> SEQ ID NO 38
<211> LENGTH: 707
<212> TYPE: PRT
<213> ORGANISM: Homo sapiens

<400> SEQUENCE: 38

```
Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
            20                  25                  30

Gly Asp Leu Arg Thr Asn Leu Thr Asp Arg Gln Leu Ala Glu Glu Tyr
        35                  40                  45

Leu Tyr Arg Tyr Gly Tyr Thr Arg Val Ala Glu Met Arg Gly Glu Ser
    50                  55                  60

Lys Ser Leu Gly Pro Ala Leu Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
```

```
            115                 120                 125
Ser Glu Asp Leu Pro Arg Ala Val Ile Asp Ala Phe Ala Arg Ala
    130                 135                 140
Phe Ala Leu Trp Ser Ala Val Thr Pro Leu Thr Phe Thr Arg Val Tyr
145                 150                 155                 160
Ser Arg Asp Ala Asp Ile Val Ile Gln Phe Gly Val Ala Glu His Gly
                    165                 170                 175
Asp Gly Tyr Pro Phe Asp Gly Lys Asp Gly Leu Leu Ala His Ala Phe
            180                 185                 190
Pro Pro Gly Pro Gly Ile Gln Gly Asp Ala His Phe Asp Asp Asp Glu
        195                 200                 205
Leu Trp Ser Leu Gly Lys Gly Val Val Pro Thr Arg Phe Gly Asn
    210                 215                 220
Ala Asp Gly Ala Ala Cys His Phe Pro Phe Ile Phe Glu Gly Arg Ser
225                 230                 235                 240
Tyr Ser Ala Cys Thr Thr Asp Gly Arg Ser Asp Gly Leu Pro Trp Cys
                    245                 250                 255
Ser Thr Thr Ala Asn Tyr Asp Thr Asp Asp Arg Phe Gly Phe Cys Pro
            260                 265                 270
Ser Glu Arg Leu Tyr Thr Gln Asp Gly Asn Ala Asp Gly Lys Pro Cys
        275                 280                 285
Gln Phe Pro Phe Ile Phe Gln Gly Gln Ser Tyr Ser Ala Cys Thr Thr
    290                 295                 300
Asp Gly Arg Ser Asp Gly Tyr Arg Trp Cys Ala Thr Thr Ala Asn Tyr
305                 310                 315                 320
Asp Arg Asp Lys Leu Phe Gly Phe Cys Pro Thr Arg Ala Asp Ser Thr
                    325                 330                 335
Val Met Gly Gly Asn Ser Ala Gly Glu Leu Cys Val Phe Pro Phe Thr
            340                 345                 350
Phe Leu Gly Lys Glu Tyr Ser Thr Cys Thr Ser Glu Gly Arg Gly Asp
        355                 360                 365
Gly Arg Leu Trp Cys Ala Thr Thr Ser Asn Phe Asp Ser Asp Lys Lys
    370                 375                 380
Trp Gly Phe Cys Pro Asp Gln Gly Tyr Ser Leu Phe Leu Val Ala Ala
385                 390                 395                 400
His Glu Phe Gly His Ala Leu Gly Leu Asp His Ser Ser Val Pro Glu
                    405                 410                 415
Ala Leu Met Tyr Pro Met Tyr Arg Phe Thr Glu Gly Pro Pro Leu His
            420                 425                 430
Lys Asp Asp Val Asn Gly Ile Arg His Leu Tyr Gly Pro Arg Pro Glu
        435                 440                 445
Pro Glu Pro Arg Pro Pro Thr Thr Thr Pro Gln Pro Thr Ala Pro
    450                 455                 460
Pro Thr Val Cys Pro Thr Gly Pro Pro Thr Val His Pro Ser Glu Arg
465                 470                 475                 480
Pro Thr Ala Gly Pro Thr Gly Pro Pro Ser Ala Gly Pro Thr Gly Pro
                    485                 490                 495
Pro Thr Ala Gly Pro Ser Thr Ala Thr Thr Val Pro Leu Ser Pro Val
            500                 505                 510
Asp Asp Ala Cys Asn Val Asn Ile Phe Asp Ala Ile Ala Glu Ile Gly
        515                 520                 525
Asn Gln Leu Tyr Leu Phe Lys Asp Gly Lys Tyr Trp Arg Phe Ser Glu
    530                 535                 540
```

```
Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Arg Leu Ser
            565                 570                 575

Lys Lys Leu Phe Phe Phe Ser Gly Arg Gln Val Trp Val Tyr Thr Gly
        580                 585                 590

Ala Ser Val Leu Gly Pro Arg Arg Leu Asp Lys Leu Gly Leu Gly Ala
    595                 600                 605

Asp Val Ala Gln Val Thr Gly Ala Leu Arg Ser Gly Arg Gly Lys Met
610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
            660                 665                 670

Phe Cys Gln Asp Arg Phe Tyr Trp Arg Val Ser Ser Arg Ser Glu Leu
        675                 680                 685

Asn Gln Val Asp Gln Val Gly Tyr Val Thr Tyr Asp Ile Leu Gln Cys
    690                 695                 700

Pro Glu Asp
705

<210> SEQ ID NO 39
<211> LENGTH: 21
<212> TYPE: RNA
<213> ORGANISM: Artificial Sequence
<220> FEATURE:
<223> OTHER INFORMATION: synthetic construct

<400> SEQUENCE: 39
uugucgcugu caaaguucga g                                           21

<210> SEQ ID NO 40
<211> LENGTH: 21
<212> TYPE: RNA
<213> ORGANISM: Artificial Sequence
<220> FEATURE:
<223> OTHER INFORMATION: synthetic construct

<400> SEQUENCE: 40
uucuugucgc ugucaaaguu c                                           21

<210> SEQ ID NO 41
<211> LENGTH: 21
<212> TYPE: RNA
<213> ORGANISM: Artificial Sequence
<220> FEATURE:
<223> OTHER INFORMATION: synthetic construct

<400> SEQUENCE: 41
uucaacucac uccgggaacu c                                           21

<210> SEQ ID NO 42
<211> LENGTH: 21
<212> TYPE: RNA
<213> ORGANISM: Artificial Sequence
<220> FEATURE:
<223> OTHER INFORMATION: synthetic construct

<400> SEQUENCE: 42
```
uucacgucgu ccuuaugcaa g    21

<210> SEQ ID NO 43
<211> LENGTH: 31
<212> TYPE: DNA
<213> ORGANISM: Artificial Sequence
<220> FEATURE:
<223> OTHER INFORMATION: synthetic construct

<400> SEQUENCE: 43
ccggtcttgt cgctgtcaaa gttcggaccg g    31

<210> SEQ ID NO 44
<211> LENGTH: 31
<212> TYPE: DNA
<213> ORGANISM: Artificial Sequence
<220> FEATURE:
<223> OTHER INFORMATION: synthetic construct

<400> SEQUENCE: 44
ccggtcttat tagaaacact ccaacgaccg g    31

<210> SEQ ID NO 45
<211> LENGTH: 31
<212> TYPE: DNA
<213> ORGANISM: Artificial Sequence
<220> FEATURE:
<223> OTHER INFORMATION: synthetic construct

<400> SEQUENCE: 45
ccggtcattc acgtcgtcct tatgcgaccg g    31

<210> SEQ ID NO 46
<211> LENGTH: 1828
<212> TYPE: DNA
<213> ORGANISM: Homo sapiens

<400> SEQUENCE: 46
ctacaaggag gcaggcaaga cagcaaggca tagagacaac atagagctaa gtaaagccag    60
tggaaatgaa gagtcttcca atcctactgt tgctgtgcgt ggcagtttgc tcagcctatc    120
cattggatgg agctgcaagg ggtgaggaca ccagcatgaa ccttgttcag aaatatctag    180
aaaactacta cgacctcaaa aaagatgtga acagtttgt taggagaaag acagtggtc    240
ctgttgttaa aaaaatccga gaaatgcaga agttccttgg attggaggtg acggggaagc    300
tggactccga cactctggag gtgatgcgca agcccaggtg tggagttcct gatgttggtc    360
acttcagaac ctttcctggc atcccgaagt ggaggaaaac ccaccttaca tacaggattg    420
tgaattatac accagatttg ccaaaagatg ctgttgattc tgctgttgag aaagctctga    480
aagtctggga gaggtgact ccactcacat tctccaggct gtatgaagga gaggctgata    540
taatgatctc ttttgcagtt agagaacatg gagactttta ccctttgat ggacctggaa    600
atgttttggc ccatgcctat gcccctgggc agggattaa tggagatgcc cactttgatg    660
atgatgaaca atggacaaag gatacaacag gaccaatttt atttctcgtt gctgctcatg    720
aaattggcca ctccctgggt ctctttcact cagccaacac tgaagctttg atgtacccac    780
tctatcactc actcacagac ctgactcggt tccgcctgtc tcaagatgat ataaatggca    840
ttcagtccct ctatggacct ccccctgact cccctgagac cccctggta cccacgaaac    900
ctgtccctcc agaacctggg acgccagcca actgtgatcc tgctttgtcc tttgatgctg    960

```
tcagcactct gaggggagaa atcctgatct ttaaagacag gcacttttgg cgcaaatccc    1020
tcaggaagct tgaacctgaa ttgcatttga tctcttcatt ttggccatct cttccttcag    1080
gcgtggatgc cgcatatgaa gttactagca aggacctcgt tttcattttt aaaggaaatc    1140
aattctgggc tatcagagga aatgaggtac gagctggata cccaagaggc atccacaccc    1200
taggtttccc tccaaccgtg aggaaaatcg atgcagccat ttctgataag gaaaagaaca    1260
aaacatattt ctttgtagag gacaaatact ggagatttga tgagaagaga aattccatgg    1320
agccaggctt tcccaagcaa atagctgaag actttccagg gattgactca aagattgatg    1380
ctgtttttga agaatttggg ttcttttatt tctttactgg atcttcacag ttggagtttg    1440
acccaaatgc aaagaaagtg acacacactt tgaagagtaa cagctggctt aattgttgaa    1500
agagatatgt agaaggcaca atatgggcac tttaaatgaa gctaataatt cttcacctaa    1560
gtctctgtga attgaaatgt tcgttttctc ctgcctgtgc tgtgactcga gtcacactca    1620
agggaacttg agcgtgaatc tgtatcttgc cggtcatttt tatgttatta cagggcattc    1680
aaatgggctg ctgcttagct tgcaccttgt cacatagagt gatctttccc aagagaaggg    1740
gaagcactcg tgtgcaacag acaagtgact gtatctgtgt agactatttg cttatttaat    1800
aaagacgatt tgtcagttat tttatctt                                       1828
```

<210> SEQ ID NO 47
<211> LENGTH: 477
<212> TYPE: PRT
<213> ORGANISM: Homo sapiens

<400> SEQUENCE: 47

```
Met Lys Ser Leu Pro Ile Leu Leu Leu Cys Val Ala Val Cys Ser
1               5                   10                  15

Ala Tyr Pro Leu Asp Gly Ala Ala Arg Gly Glu Asp Thr Ser Met Asn
                20                  25                  30

Leu Val Gln Lys Tyr Leu Glu Asn Tyr Tyr Asp Leu Lys Lys Asp Val
            35                  40                  45

Lys Gln Phe Val Arg Arg Lys Asp Ser Gly Pro Val Val Lys Lys Ile
        50                  55                  60

Arg Glu Met Gln Lys Phe Leu Gly Leu Glu Val Thr Gly Lys Leu Asp
65                  70                  75                  80

Ser Asp Thr Leu Glu Val Met Arg Lys Pro Arg Cys Gly Val Pro Asp
                85                  90                  95

Val Gly His Phe Arg Thr Phe Pro Gly Ile Pro Lys Trp Arg Lys Thr
                100                 105                 110

His Leu Thr Tyr Arg Ile Val Asn Tyr Thr Pro Asp Leu Pro Lys Asp
            115                 120                 125

Ala Val Asp Ser Ala Val Glu Lys Ala Leu Lys Val Trp Glu Glu Val
        130                 135                 140

Thr Pro Leu Thr Phe Ser Arg Leu Tyr Glu Gly Glu Ala Asp Ile Met
145                 150                 155                 160

Ile Ser Phe Ala Val Arg Glu His Gly Asp Phe Tyr Pro Phe Asp Gly
                165                 170                 175

Pro Gly Asn Val Leu Ala His Ala Tyr Ala Pro Gly Pro Gly Ile Asn
            180                 185                 190

Gly Asp Ala His Phe Asp Asp Glu Gln Trp Thr Lys Asp Thr Thr
        195                 200                 205

Gly Thr Asn Leu Phe Leu Val Ala Ala His Glu Ile Gly His Ser Leu
    210                 215                 220
```

-continued

Gly Leu Phe His Ser Ala Asn Thr Glu Ala Leu Met Tyr Pro Leu Tyr
225                 230                 235                 240

His Ser Leu Thr Asp Leu Thr Arg Phe Arg Leu Ser Gln Asp Asp Ile
            245                 250                 255

Asn Gly Ile Gln Ser Leu Tyr Gly Pro Pro Asp Ser Pro Glu Thr
        260                 265                 270

Pro Leu Val Pro Thr Glu Pro Val Pro Glu Pro Gly Thr Pro Ala
        275                 280                 285

Asn Cys Asp Pro Ala Leu Ser Phe Asp Ala Val Ser Thr Leu Arg Gly
290                 295                 300

Glu Ile Leu Ile Phe Lys Asp Arg His Phe Trp Arg Lys Ser Leu Arg
305                 310                 315                 320

Lys Leu Glu Pro Glu Leu His Leu Ile Ser Ser Phe Trp Pro Ser Leu
            325                 330                 335

Pro Ser Gly Val Asp Ala Ala Tyr Glu Val Thr Ser Lys Asp Leu Val
            340                 345                 350

Phe Ile Phe Lys Gly Asn Gln Phe Trp Ala Ile Arg Gly Asn Glu Val
        355                 360                 365

Arg Ala Gly Tyr Pro Arg Gly Ile His Thr Leu Gly Phe Pro Pro Thr
370                 375                 380

Val Arg Lys Ile Asp Ala Ala Ile Ser Asp Lys Glu Lys Asn Lys Thr
385                 390                 395                 400

Tyr Phe Phe Val Glu Asp Lys Tyr Trp Arg Phe Asp Glu Lys Arg Asn
            405                 410                 415

Ser Met Glu Pro Gly Phe Pro Lys Gln Ile Ala Glu Asp Phe Pro Gly
            420                 425                 430

Ile Asp Ser Lys Ile Asp Ala Val Phe Glu Glu Phe Gly Phe Tyr
        435                 440                 445

Phe Phe Thr Gly Ser Ser Gln Leu Glu Phe Asp Pro Asn Ala Lys Lys
        450                 455                 460

Val Thr His Thr Leu Lys Ser Asn Ser Trp Leu Asn Cys
465                 470                 475

<210> SEQ ID NO 48
<211> LENGTH: 20
<212> TYPE: RNA
<213> ORGANISM: Artificial Sequence
<220> FEATURE:
<223> OTHER INFORMATION: synthetic construct

<400> SEQUENCE: 48
uucaucauca ucaaaguggg                                              20

<210> SEQ ID NO 49
<211> LENGTH: 20
<212> TYPE: RNA
<213> ORGANISM: Artificial Sequence
<220> FEATURE:
<223> OTHER INFORMATION: synthetic construct

<400> SEQUENCE: 49
uaauaacaua aaaaugaccg                                              20

<210> SEQ ID NO 50
<211> LENGTH: 20
<212> TYPE: RNA
<213> ORGANISM: Artificial Sequence
<220> FEATURE:

<223> OTHER INFORMATION: synthetic construct

<400> SEQUENCE: 50
uagucuacac agauacaguc              20

<210> SEQ ID NO 51
<211> LENGTH: 20
<212> TYPE: RNA
<213> ORGANISM: Artificial Sequence
<220> FEATURE:
<223> OTHER INFORMATION: synthetic construct

<400> SEQUENCE: 51
uauaucaucu ugagacaggc              20

<210> SEQ ID NO 52
<211> LENGTH: 32
<212> TYPE: DNA
<213> ORGANISM: Artificial Sequence
<220> FEATURE:
<223> OTHER INFORMATION: synthetic construct

<400> SEQUENCE: 52
ccggtctata tcatcttgag acaggcgacc gg              32

<210> SEQ ID NO 53
<211> LENGTH: 32
<212> TYPE: DNA
<213> ORGANISM: Artificial Sequence
<220> FEATURE:
<223> OTHER INFORMATION: synthetic construct

<400> SEQUENCE: 53
ccggtctttc tcttctcatc aaatctgacc gg              32

<210> SEQ ID NO 54
<211> LENGTH: 32
<212> TYPE: DNA
<213> ORGANISM: Artificial Sequence
<220> FEATURE:
<223> OTHER INFORMATION: synthetic construct

<400> SEQUENCE: 54
ccggtctaac aaactgtttc acatctgacc gg              32

<210> SEQ ID NO 55
<211> LENGTH: 2943
<212> TYPE: DNA
<213> ORGANISM: Homo sapiens

<400> SEQUENCE: 55
accaggcaac accattgaag gctcatatgt aaaaatccat gccttccttt ctcccaatct      60
ccattcccaa acttagccac tggcttctgg ctgaggcctt acgcataccct cccgggggctt    120 gcacacacct tcttctacag aagacacacc ttgggcatat cctacagaag accaggcttc    180
tctctggtcc ttggtagagg gctactttac tgtaacaggg ccagggtgga gagttctctc    240
ctgaagctcc atcccctcta taggaaatgt gttgacaata ttcagaagag taagaggatc    300
aagacttctt tgtgctcaaa taccactgtt ctcttctcta ccctgcccta accaggagct    360 tgtcaccca aactctgagg tgatttatgc cttaatcaag caaacttccc tcttcagaaa      420
agatggctca ttttccctca aaagttgcca ggagctgcca agtattctgc caattcaccc    480
tggagcacaa tcaacaaatt cagccagaac acaactacag ctactattag aactattatt    540

```
attaataaat tcctctccaa atctagcccc ttgacttcgg atttcacgat ttctcccttc    600
ctcctagaaa cttgataagt ttcccgcgct tccctttttc taagactaca tgtttgtcat    660
cttataaagc aaaggggtga ataaatgaac caaatcaata acttctggaa tatctgcaaa    720
caacaataat atcagctatg ccatctttca ctattttagc cagtatcgag ttgaatgaac    780
atagaaaaat acaaaactga attcttccct gtaaattccc cgttttgacg acgcacttgt    840
agccacgtag ccacgcctac ttaagacaat tacaaaaggc gaagaagact gactcaggct    900
taagctgcca gccagagagg gagtcatttc attggcgttt gagtcagcaa agaagtcaag    960
atggccaaag ttccagacat gtttgaagac ctgaagaact gttacagtga aaatgaagaa   1020
gacagttcct ccattgatca tctgtctctg aatcagaaat ccttctatca tgtaagctat   1080
ggcccactcc atgaaggctg catggatcaa tctgtgtctc tgagtatctc tgaaacctct   1140
aaaacatcca agcttacctt caaggagagc atggtggtag tagcaaccaa cgggaaggtt   1200
ctgaagaaga gacggttgag tttaagccaa tccatcactg atgatgacct ggaggccatc   1260
gccaatgact cagaggaaga atcatcaag cctaggtcag cacctttag cttcctgagc   1320
aatgtgaaat acaactttat gaggatcatc aaatacgaat tcatcctgaa tgacgccctc   1380
aatcaaagta taattcgagc caatgatcag tacctcacgg ctgctgcatt acataatctg   1440
gatgaagcag tgaaatttga catgggtgct tataagtcat caaggatga tgctaaaatt   1500
accgtgattc taagaatctc aaaaactcaa ttgtatgtga ctgcccaaga tgaagaccaa   1560
ccagtgctgc tgaaggagat gcctgagata cccaaaacca tcacaggtag tgagaccaac   1620
ctcctcttct tctgggaaac tcacggcact aagaactatt tcacatcagt tgcccatcca   1680
aacttgttta ttgccacaaa gcaagactac tgggtgtgct tggcagggg gccaccctct   1740
atcactgact ttcagatact ggaaaaccag gcgtaggtct ggagtctcac ttgtctcact   1800
tgtgcagtgt tgacagttca tatgtaccat gtacatgaag aagctaaatc ctttactgtt   1860
agtcatttgc tgagcatgta ctgagccttg taattctaaa tgaatgttta cactctttgt   1920
aagagtggaa ccaacactaa catataatgt tgttatttaa agaacaccct atattttgca   1980
tagtaccaat cattttaatt attattcttc ataacaattt taggaggacc agagctactg   2040
actatggcta ccaaaaagac tctacccata ttacagatgg gcaaattaag gcataagaaa   2100
actaagaaat atgcacaata gcagttgaaa caagaagcca cagacctagg atttcatgat   2160
ttcatttcaa ctgtttgcct tctactttta agttgctgat gaactcttaa tcaaatagca   2220
taagtttctg ggacctcagt tttatcattt tcaaaatgga gggaataata cctaagcctt   2280
cctgccgcaa cagttttta tgctaatcag ggaggtcatt ttggtaaaat acttcttgaa   2340
gccgagcctc aagatgaagg caaagcacga aatgttattt tttaattatt atttatatat   2400
gtatttataa atatatttaa gataattata atatactata tttatgggaa ccccttcatc   2460
ctctgagtgt gaccaggcat cctccacaat agcagacagt gttttctggg ataagtaagt   2520
ttgatttcat taatacaggg catttttggtc caagttgtgc ttatcccata gccaggaaac   2580
tctgcattct agtactgggg agacctgtaa tcatataata aatgtacatt aattaccttg   2640
agccagtaat tggtccgatc tttgactctt ttgccattaa acttacctgg gcattcttgt   2700
ttcaattcca cctgcaatca agtcctacaa gctaaaatta gatgaactca actttgacaa   2760
ccatgagacc actgttatca aaactttctt ttctggaatg taatcaatgt ttcttctagg   2820
ttctaaaaat tgtgatcaga ccataatgtt acattattat caacaatagt gattgataga   2880
```

-continued

```
gtgttatcag tcataactaa ataaagcttg caacaaaatt ctctgacaaa aaaaaaaaaa      2940
aaa                                                                    2943
```

<210> SEQ ID NO 56
<211> LENGTH: 271
<212> TYPE: PRT
<213> ORGANISM: Homo sapiens

<400> SEQUENCE: 56

```
Met Ala Lys Val Pro Asp Met Phe Glu Asp Leu Lys Asn Cys Tyr Ser
1               5                   10                  15

Glu Asn Glu Glu Asp Ser Ser Ser Ile Asp His Leu Ser Leu Asn Gln
            20                  25                  30

Lys Ser Phe Tyr His Val Ser Tyr Gly Pro Leu His Glu Gly Cys Met
        35                  40                  45

Asp Gln Ser Val Ser Leu Ser Ile Ser Glu Thr Ser Lys Thr Ser Lys
    50                  55                  60

Leu Thr Phe Lys Glu Ser Met Val Val Ala Thr Asn Gly Lys Val
65                  70                  75                  80

Leu Lys Lys Arg Arg Leu Ser Leu Ser Gln Ser Ile Thr Asp Asp Asp
                85                  90                  95

Leu Glu Ala Ile Ala Asn Asp Ser Glu Glu Ile Ile Lys Pro Arg
            100                 105                 110

Ser Ala Pro Phe Ser Phe Leu Ser Asn Val Lys Tyr Asn Phe Met Arg
        115                 120                 125

Ile Ile Lys Tyr Glu Phe Ile Leu Asn Asp Ala Leu Asn Gln Ser Ile
    130                 135                 140

Ile Arg Ala Asn Asp Gln Tyr Leu Thr Ala Ala Ala Leu His Asn Leu
145                 150                 155                 160

Asp Glu Ala Val Lys Phe Asp Met Gly Ala Tyr Lys Ser Ser Lys Asp
                165                 170                 175

Asp Ala Lys Ile Thr Val Ile Leu Arg Ile Ser Lys Thr Gln Leu Tyr
            180                 185                 190

Val Thr Ala Gln Asp Glu Asp Gln Pro Val Leu Leu Lys Glu Met Pro
        195                 200                 205

Glu Ile Pro Lys Thr Ile Thr Gly Ser Glu Thr Asn Leu Leu Phe Phe
    210                 215                 220

Trp Glu Thr His Gly Thr Lys Asn Tyr Phe Thr Ser Val Ala His Pro
225                 230                 235                 240

Asn Leu Phe Ile Ala Thr Lys Gln Asp Tyr Trp Val Cys Leu Ala Gly
                245                 250                 255

Gly Pro Pro Ser Ile Thr Asp Phe Gln Ile Leu Glu Asn Gln Ala
            260                 265                 270
```

<210> SEQ ID NO 57
<211> LENGTH: 20
<212> TYPE: RNA
<213> ORGANISM: Artificial Sequence
<220> FEATURE:
<223> OTHER INFORMATION: synthetic construct

<400> SEQUENCE: 57

```
uuucuauguu cauucaacuc                                                    20
```

<210> SEQ ID NO 58
<211> LENGTH: 20
<212> TYPE: RNA

```
<213> ORGANISM: Artificial Sequence
<220> FEATURE:
<223> OTHER INFORMATION: synthetic construct

<400> SEQUENCE: 58
ucauucaacu cgauacuggc                                              20

<210> SEQ ID NO 59
<211> LENGTH: 20
<212> TYPE: RNA
<213> ORGANISM: Artificial Sequence
<220> FEATURE:
<223> OTHER INFORMATION: synthetic construct

<400> SEQUENCE: 59
uucauucaac ucgauacugg                                              20

<210> SEQ ID NO 60
<211> LENGTH: 20
<212> TYPE: RNA
<213> ORGANISM: Artificial Sequence
<220> FEATURE:
<223> OTHER INFORMATION: synthetic construct

<400> SEQUENCE: 60
uaauaguucu aauaguagcu                                              20

<210> SEQ ID NO 61
<211> LENGTH: 32
<212> TYPE: DNA
<213> ORGANISM: Artificial Sequence
<220> FEATURE:
<223> OTHER INFORMATION: synthetic construct

<400> SEQUENCE: 61
ccggtctttc ttagtttcct tatgccgacc gg                                32

<210> SEQ ID NO 62
<211> LENGTH: 31
<212> TYPE: DNA
<213> ORGANISM: Artificial Sequence
<220> FEATURE:
<223> OTHER INFORMATION: synthetic construct

<400> SEQUENCE: 62
ccggtctaat agttctaata gtagcgaccg g                                 31

<210> SEQ ID NO 63
<211> LENGTH: 31
<212> TYPE: DNA
<213> ORGANISM: Artificial Sequence
<220> FEATURE:
<223> OTHER INFORMATION: synthetic cosntruct

<400> SEQUENCE: 63
ccggtctatg aactgtcaac actgcgaccg g                                 31

<210> SEQ ID NO 64
<211> LENGTH: 1498
<212> TYPE: DNA
<213> ORGANISM: Homo sapiens

<400> SEQUENCE: 64
accaaacctc ttcgaggcac aaggcacaac aggctgctct gggattctct tcagccaatc    60
ttcattgctc aagtgtctga agcagccatg gcagaagtac ctgagctcgc cagtgaaatg   120
```

```
atggcttatt acagtggcaa tgaggatgac ttgttctttg aagctgatgg ccctaaacag    180
atgaagtgct ccttccagga cctggacctc tgccctctgg atggcggcat ccagctacga    240
atctccgacc accactacag caagggcttc aggcaggccg cgtcagttgt tgtggccatg    300
gacaagctga ggaagatgct ggttccctgc ccacagacct tccaggagaa tgacctgagc    360
accttctttc ccttcatctt tgaagaagaa cctatcttct tcgacacatg ggataacgag    420
gcttatgtgc acgatgcacc tgtacgatca ctgaactgca cgctccggga ctcacagcaa    480
aaaagcttgg tgatgtctgg tccatatgaa ctgaaagctc tccacctcca gggacaggat    540
atggagcaac aagtggtgtt ctccatgtcc tttgtacaag gagaagaaag taatgacaaa    600
atacctgtgg ccttgggcct caaggaaaag aatctgtacc tgtcctgcgt gttgaaagat    660
gataagccca ctctacagct ggagagtgta gatcccaaaa attacccaaa gaagaagatg    720
gaaaagcgat ttgtcttcaa caagatagaa atcaataaca agctggaatt tgagtctgcc    780
cagttcccca actggtacat cagcaccctc caagcagaaa acatgcccgt cttcctggga    840
gggaccaaag gcggccagga tataactgac ttcaccatgc aatttgtgtc ttcctaaaga    900
gagctgtacc cagagagtcc tgtgctgaat gtggactcaa tccctagggc tggcagaaag    960
ggaacagaaa ggttttttgag tacggctata gcctggactt tcctgttgtc tacaccaatg   1020
cccaactgcc tgccttaggg tagtgctaag aggatctcct gtccatcagc caggacagtc   1080
agctctctcc tttcagggcc aatccccagc ccttttgttg agccaggcct ctctcacctc   1140
tcctactcac ttaaagcccg cctgacagaa accacggcca catttggttc taagaaaccc   1200
tctgtcattc gctcccacat tctgatgagc aaccgcttcc ctatttattt atttatttgt   1260
ttgtttgttt tattcattgg tctaatttat tcaaaggggg caagaagtag cagtgtctgt   1320
aaaagagcct agttttttaat agctatgaaa tcaattcaat ttggactggt gtgctctctt   1380
taaatcaagt cctttaatta agactgaaaa tatataagct cagattattt aaatgggaat   1440
atttataaat gagcaaatat catactgttc aatggttctg aaataaactt cactgaag      1498
```

<210> SEQ ID NO 65
<211> LENGTH: 269
<212> TYPE: PRT
<213> ORGANISM: Homo sapiens

<400> SEQUENCE: 65

```
Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp
        115                 120                 125
```

Ser Gln Gln Lys Ser Leu Val Met Ser Gly Pro Tyr Glu Leu Lys Ala
            130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
            195                 200                 205

Lys Lys Met Glu Lys Arg Phe Val Phe Asn Lys Ile Glu Ile Asn Asn
        210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
            260                 265

<210> SEQ ID NO 66
<211> LENGTH: 21
<212> TYPE: RNA
<213> ORGANISM: Artificial Sequence
<220> FEATURE:
<223> OTHER INFORMATION: synthetic construct

<400> SEQUENCE: 66
uuaucaucuu ucaacacgca g                                          21

<210> SEQ ID NO 67
<211> LENGTH: 21
<212> TYPE: RNA
<213> ORGANISM: Artificial Sequence
<220> FEATURE:
<223> OTHER INFORMATION: synthetic construct

<400> SEQUENCE: 67
uuuuacagac acugcuacuu c                                          21

<210> SEQ ID NO 68
<211> LENGTH: 21
<212> TYPE: RNA
<213> ORGANISM: Artificial Sequence
<220> FEATURE:
<223> OTHER INFORMATION: synthetic construct

<400> SEQUENCE: 68
uuugucauua cuuucuucuc c                                          21

<210> SEQ ID NO 69
<211> LENGTH: 21
<212> TYPE: RNA
<213> ORGANISM: Artificial Sequence
<220> FEATURE:
<223> OTHER INFORMATION: synthetic construct

<400> SEQUENCE: 69
uacagacacu gcuacuucuu g                                          21

<210> SEQ ID NO 70
<211> LENGTH: 33
<212> TYPE: DNA

```
<213> ORGANISM: Artificial Sequence
<220> FEATURE:
<223> OTHER INFORMATION: synthetic construct

<400> SEQUENCE: 70
ccggtctttt gtcattactt tcttctcgac cgg                                33

<210> SEQ ID NO 71
<211> LENGTH: 33
<212> TYPE: DNA
<213> ORGANISM: Artificial Sequence
<220> FEATURE:
<223> OTHER INFORMATION: synthetic construct

<400> SEQUENCE: 71
ccggtctttc agtcttaatt aaaggacgac cgg                                33

<210> SEQ ID NO 72
<211> LENGTH: 32
<212> TYPE: DNA
<213> ORGANISM: Artificial Sequence
<220> FEATURE:
<223> OTHER INFORMATION: synthetic construct

<400> SEQUENCE: 72
ccggtcttac ataaattaac tcagctgacc gg                                 32

<210> SEQ ID NO 73
<211> LENGTH: 1201
<212> TYPE: DNA
<213> ORGANISM: Homo sapiens

<400> SEQUENCE: 73
aatattagag tctcaacccc caataaatat aggactggag atgtctgagg ctcattctgc     60
cctcgagccc accgggaacg aaagagaagc tctatctccc ctccaggagc ccagctatga    120
actccttctc cacaagcgcc ttcggtccag ttgccttctc cctggggctg ctcctggtgt    180
tgcctgctgc cttccctgcc ccagtacccc caggagaaga ttccaaagat gtagccgccc    240
cacacagaca gccactcacc tcttcagaac gaattgacaa acaaattcgg tacatcctcg    300
acggcatctc agccctgaga aggagacat gtaacaagag taacatgtgt gaaagcagca    360
aagaggcact ggcagaaaac aacctgaacc ttccaaagat ggctgaaaaa gatggatgct    420
tccaatctgg attcaatgag gagacttgcc tggtgaaaat catcactggt cttttggagt    480
ttgaggtata cctagagtac ctccagaaca gatttgagag tagtgaggaa caagccagag    540
ctgtgcagat gagtacaaaa gtcctgatcc agttcctgca gaaaaaggca aagaatctag    600
atgcaataac caccccctgac ccaaccacaa atgccagcct gctgacgaag ctgcaggcac    660
agaaccagtg gctgcaggac atgacaactc atctcattct gcgcagcttt aaggagttcc    720
tgcagtccag cctgagggct cttcggcaaa tgtagcatgg gcacctcaga ttgttgttgt    780
taatgggcat tccttcttct ggtcagaaac ctgtccactg gcacagaac ttatgttgtt    840 ctctatggag aactaaaagt atgagcgtta ggacactatt ttaattattt ttaatttatt    900
aatatttaaa tatgtgaagc tgagttaatt tatgtaagtc atatttatat ttttaagaag    960
taccacttga acatttat gtattagttt tgaataata atggaaagtg gctatgcagt   1020
ttgaatatcc tttgtttcag agccagatca tttcttggaa agtgtaggct tacctcaaat   1080
aaatggctaa cttatacata ttttaaaga aatatttata ttgtatttat ataatgtata   1140
aatggttttt ataccaataa atggcatttt aaaaaattca gcaaaaaaaa aaaaaaaaa    1200
``` a                                                                        1201

<210> SEQ ID NO 74
<211> LENGTH: 212
<212> TYPE: PRT
<213> ORGANISM: Homo sapiens

<400> SEQUENCE: 74

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
                20                  25                  30

Gly Glu Asp Ser Lys Asp Val Ala Ala Pro His Arg Gln Pro Leu Thr
            35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 75
<211> LENGTH: 21
<212> TYPE: RNA
<213> ORGANISM: Artificial Sequence
<220> FEATURE:
<223> OTHER INFORMATION: synthetic construct

<400> SEQUENCE: 75
uaaaauagug uccuaacgcu c                                                    21

<210> SEQ ID NO 76
<211> LENGTH: 21
<212> TYPE: RNA
<213> ORGANISM: Artificial Sequence
<220> FEATURE:
<223> OTHER INFORMATION: synthetic construct

<400> SEQUENCE: 76
ucacuacucu caaaucuguu c                                                    21

<210> SEQ ID NO 77

```
<211> LENGTH: 21
<212> TYPE: RNA
<213> ORGANISM: Artificial Sequence
<220> FEATURE:
<223> OTHER INFORMATION: synthetic construct

<400> SEQUENCE: 77
uuacucuugu uacaugucuc c                                              21

<210> SEQ ID NO 78
<211> LENGTH: 21
<212> TYPE: RNA
<213> ORGANISM: Artificial Sequence
<220> FEATURE:
<223> OTHER INFORMATION: synthetic construct

<400> SEQUENCE: 78
uaacgcucau acuuuuaguu c                                              21

<210> SEQ ID NO 79
<211> LENGTH: 33
<212> TYPE: DNA
<213> ORGANISM: Artificial Sequence
<220> FEATURE:
<223> OTHER INFORMATION: synthetic construct

<400> SEQUENCE: 79
ccggtcttac tcttgttaca tgtcyccgac ctt                                 33

<210> SEQ ID NO 80
<211> LENGTH: 33
<212> TYPE: DNA
<213> ORGANISM: Artificial Sequence
<220> FEATURE:
<223> OTHER INFORMATION: synthetic construct

<400> SEQUENCE: 80
ccggtcttac tcttgttaca tgtctccgac ctt                                 33

<210> SEQ ID NO 81
<211> LENGTH: 33
<212> TYPE: DNA
<213> ORGANISM: Artificial Sequence
<220> FEATURE:
<223> OTHER INFORMATION: synthetic construct

<400> SEQUENCE: 81
ccggtctaca taaaatgttt caagtgggac ctt                                 33

<210> SEQ ID NO 82
<211> LENGTH: 1718
<212> TYPE: DNA
<213> ORGANISM: Homo sapiens

<400> SEQUENCE: 82
gagggtgcat aagttctcta gtagggtgat gatataaaaa gccaccggag cactccataa     60
ggcacaaact ttcagagaca gcagagcaca caagcttcta ggacaagagc caggaagaaa    120
ccaccggaag gaaccatctc actgtgtgta acatgactt ccaagctggc cgtggctctc    180
ttggcagcct tcctgatttc tgcagctctg tgtgaaggtg cagttttgcc aaggagtgct    240
aaagaactta gatgtcagtg cataaagaca tactccaaac cttccacccc caaatttatc    300
aaagaactga gagtgattga gagtggacca cactgcgcca acacagaaat tattgtaaag    360
ctttctgatg gaagagagct ctgtctggac cccaaggaaa actgggtgca gagggttgtg    420
```

```
gagaagttttt tgaagagggc tgagaattca taaaaaaatt cattctctgt ggtatccaag      480
aatcagtgaa gatgccagtg aaacttcaag caaatctact tcaacacttc atgtattgtg      540
tgggtctgtt gtagggttgc cagatgcaat acaagattcc tggttaaatt tgaatttcag      600
taaacaatga atagttttc attgtaccat gaaatatcca gaacatactt atatgtaaag       660
tattatttat ttgaatctac aaaaaacaac aaataatttt taaatataag gattttccta     720
gatattgcac gggagaatat acaaatagca aaattgaggc caagggccaa gagaatatcc      780
gaactttaat ttcaggaatt gaatgggttt gctagaatgt gatatttgaa gcatcacata     840
aaaatgatgg gacaataaat tttgccataa agtcaaattt agctggaaat cctggatttt      900
tttctgttaa atctggcaac cctagtctgc tagccaggat ccacaagtcc ttgttccact      960
gtgccttggt ttctccttta tttctaagtg gaaaaagtat tagccaccat cttacctcac      1020
agtgatgttg tgaggacatg tggaagcact ttaagttttt tcatcataac ataaattatt      1080
ttcaagtgta acttattaac ctatttatta tttatgtatt tatttaagca tcaaatattt      1140
gtgcaagaat ttggaaaaat agaagatgaa tcattgattg aatagttata aagatgttat      1200
agtaaattta ttttatttta gatattaaat gatgttttat tagataaatt tcaatcaggg      1260
tttttagatt aaacaaacaa acaattgggt acccagttaa attttcattt cagataaaca      1320
acaaataatt tttagtata agtacattat tgtttatctg aaatttaat tgaactaaca        1380 atcctagttt gatactccca gtcttgtcat tgccagctgt gttggtagtg ctgtgttgaa      1440
ttacggaata atgagttaga actattaaaa cagccaaaac tccacagtca atattagtaa      1500
tttcttgctg gttgaaactt gtttattatg tacaaataga ttcttataat attatttaaa     1560
tgactgcatt tttaaataca aggctttata tttttaactt taagatgttt ttatgtgctc     1620
tccaaatttt ttttactgtt tctgattgta tggaaatata aaagtaaata tgaaacattt      1680
aaaatataat ttgttgtcaa agtaaaaaaa aaaaaaaa                              1718
```

<210> SEQ ID NO 83
<211> LENGTH: 99
<212> TYPE: PRT
<213> ORGANISM: Homo sapiens

<400> SEQUENCE: 83

```
Met Thr Ser Lys Leu Ala Val Ala Leu Leu Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser
```

<210> SEQ ID NO 84
<211> LENGTH: 20
<212> TYPE: RNA
<213> ORGANISM: Artificial Sequence
<220> FEATURE:

-continued

<223> OTHER INFORMATION: synthetic construct

<400> SEQUENCE: 84
uuuguuuaau cuaaaaaccc                                           20

<210> SEQ ID NO 85
<211> LENGTH: 20
<212> TYPE: RNA
<213> ORGANISM: Artificial Sequence
<220> FEATURE:
<223> OTHER INFORMATION: synthetic construct

<400> SEQUENCE: 85
uuuacacaca gugagauggu                                           20

<210> SEQ ID NO 86
<211> LENGTH: 20
<212> TYPE: RNA
<213> ORGANISM: Artificial Sequence
<220> FEATURE:
<223> OTHER INFORMATION: synthetic construct

<400> SEQUENCE: 86
uucaaauauc acauucuagc                                           20

<210> SEQ ID NO 87
<211> LENGTH: 20
<212> TYPE: RNA
<213> ORGANISM: Artificial Sequence
<220> FEATURE:
<223> OTHER INFORMATION: synthetic construct

<400> SEQUENCE: 87
uuaugcacug acaucuaagu                                           20

<210> SEQ ID NO 88
<211> LENGTH: 32
<212> TYPE: DNA
<213> ORGANISM: Artificial Sequence
<220> FEATURE:
<223> OTHER INFORMATION: synthetic construct

<400> SEQUENCE: 88
ccggtctatc acattctagc aaacccgacc gg                             32

<210> SEQ ID NO 89
<211> LENGTH: 32
<212> TYPE: DNA
<213> ORGANISM: Artificial Sequence
<220> FEATURE:
<223> OTHER INFORMATION: synthetic construct

<400> SEQUENCE: 89
ccggtctact agagaactta tgcaccgacc gg                             32

<210> SEQ ID NO 90
<211> LENGTH: 32
<212> TYPE: DNA
<213> ORGANISM: Artificial Sequence
<220> FEATURE:
<223> OTHER INFORMATION: synthetic construct

<400> SEQUENCE: 90
ccggtctagt tctaactcat tattccgacc gg                             32

```
<210> SEQ ID NO 91
<211> LENGTH: 5170
<212> TYPE: DNA
<213> ORGANISM: Homo sapiens

<400> SEQUENCE: 91
gtggccggcg gccggagccg actcggagcg cgcggcgccg gccgggagga gccggagagc      60
ggccgggccg ggcggtgggg gcgccggcct gccccgcgcg ccccagggag cggcaggaat     120
gtgacaatcg cgcgcccgcg caccgaagca ctcctcgctc ggctcctagg gctctcgccc     180
ctctgagctg agccgggttc cgcccggggc tgggatccca tcaccctcca cggccgtccg     240
tccaggtaga cgcaccctct gaagatggtg actccctcct gagaagctgg accccttggt     300
aaaagacaag gccttctcca agaagaatat gaaagtgtta ctcagactta tttgtttcat     360
agctctactg atttcttctc tggaggctga taaatgcaag gaacgtgaag aaaaaataat     420
tttagtgtca tctgcaaatg aaattgatgt tcgtccctgt cctcttaacc caaatgaaca     480
caaaggcact ataacttggt ataaagatga cagcaagaca cctgtatcta cagaacaagc     540
ctccaggatt catcaacaca agagaaaact ttggtttgtt cctgctaagg tggaggattc     600
aggacattac tattgcgtgg taagaaattc atcttactgc ctcagaatta aaataagtgc     660
aaaatttgtg gagaatgagc ctaacttatg ttataatgca caagccatat ttaagcagaa     720
actacccgtt gcaggagacg gaggacttgt gtgcccttat atggagtttt ttaaaaatga     780
aaataatgag ttacctaaat tacagtggta taaggattgc aaacctctac ttcttgacaa     840
tatacacttt agtggagtca agataggct catcgtgatg aatgtggctg aaaagcatag     900
agggaactat acttgtcatg catcctacac atacttgggc aagcaatatc ctattacccg     960
ggtaatagaa tttattactc tagaggaaaa caaacccaca aggcctgtga ttgtgagccc    1020
agctaatgag acaatggaag tagacttggg atcccagata caattgatct gtaatgtcac    1080
cggccagttg agtgacattg cttactgaa gtggaatggg tcagtaattg atgaagatga    1140
cccagtgcta ggggaagact attacagtgt ggaaaatcct gcaaacaaaa gaaggagtac    1200
cctcatcaca gtgctaata tatcggaaat tgaaagtaga ttttataaac atccatttac    1260
ctgttttgcc aagaatacac atggtataga tgcagcatat atccagttaa tatatccagt    1320
cactaatttc cagaagcaca tgattggtat atgtgtcacg ttgacagtca taattgtgtg    1380
ttctgttttc atctataaaa tcttcaagat tgacattgtg ctttggtaca gggattcctg    1440
ctatgatttt ctcccaataa aagcttcaga tggaaagacc tatgacgcat atatactgta    1500
tccaaagact gttggggaag gtctacctc tgactgtgat attttgtgt ttaaagtctt    1560 gcctgaggtc ttggaaaaac agtgtggata taagctgttc atttatggaa gggatgacta    1620
cgttggggaa gacattgttg aggtcattaa tgaaaacgta aagaaaagca gaagactgat    1680 tatcattta gtcagagaaa catcaggctt cagctggctg ggtggttcat ctgaagagca    1740
aatagccatg tataatgctc ttgttcagga tggaattaaa gttgtcctgc ttgagctgga    1800
gaaaatccaa gactatgaga aaatgccaga atcgattaaa ttcattaagc agaaacatgg    1860
ggctatccgc tggtcagggg actttacaca gggaccacag tctgcaaaga caaggttctg    1920
gaagaatgtc aggtaccaca tgccagtcca gcgacggtca ccttcatcta acaccagtt    1980 actgtcacca gccactaagg agaaactgca agagaggct cacgtgcctc tcgggtagca    2040
tggagaagtt gccaagagtt ctttaggtgc ctcctgtctt atggcgttgc aggccaggtt    2100
atgcctcatg ctgacttgca gagttcatgg aatgtaacta tatcatcctt tatccctgag    2160
```

```
gtcacctgga atcagattat aagggaata agccatgacg tcaatagcag cccagggcac      2220
ttcagagtag agggcttggg aagatctttt aaaaaggcag taggcccggt gtggtggctc      2280
acgcctataa tcccagcact tgggaggct gaagtgggtg gatcaccaga ggtcaggagt      2340
tcgagaccag cccagccaac atggcaaaac cccatctcta ctaaaaatac aaaaatgagc      2400
taggcatggt ggcacacgcc tgtaatccca gctacacctg aggctgaggc aggagaattg      2460
cttgaaccgg ggagacggag gttgcagtga gccgagtttg gccactgca ctctagcctg      2520 gcaacagagc aagactccgt ctcaaaaaaa gggcaataaa tgccctctct gaatgtttga      2580
actgccaaga aaaggcatgg agacagcgaa ctagaagaaa gggcaagaag gaaatagcca      2640
ccgtctacag atggcttagt taagtcatcc acagcccaag ggcggggcta tgccttgtct      2700
ggggaccctg tagagtcact gaccctggag cggctctcct gagaggtgct gcaggcaaag      2760
tgagactgac acctcactga ggaagggaga catattcttg gagaactttc catctgcttg      2820
tattttccat acacatcccc agccagaagt tagtgtccga agaccgaatt ttattttaca      2880
gagcttgaaa actcacttca atgaacaaag ggattctcca ggattccaaa gttttgaagt      2940
catcttagct ttccacagga gggagagaac ttaaaaaagc aacagtagca gggaattgat      3000
ccacttctta atgctttcct ccctggcatg accatcctgt cctttgttat tatcctgcat      3060
tttacgtctt tggaggaaca gctccctagt ggcttcctcc gtctgcaatg tcccttgcac      3120
agcccacaca tgaaccatcc ttcccatgat gccgctcttc tgtcatcccg ctcctgctga      3180
aacacctccc aggggctcca cctgttcagg agctgaagcc catgctttcc caccagcatg      3240
tcactcccag accacctccc tgccctgtcc tccagcttcc cctcgctgtc ctgctgtgtg      3300
aattcccagg ttggcctggt ggccatgtcg cctgccccca gcactcctct gtctctgctc      3360
ttgcctgcac ccttcctcct cctttgccta ggaggccttc tcgcattttc tctagctgat      3420
cagaatttta ccaaaattca gaacatcctc caattccaca gtctctggga actttccct      3480 aagaggcgac ttcctctcca gccttctctc tctggtcagg cccactgcag agatggtggt      3540
gagcacatct gggaggctgg tctccctcca gctggaattg ctgctctctg agggagaggc      3600
tgtggtggct gtctctgtcc ctcactgcct tccaggagca atttgcacat gtaacataga      3660
tttatgtaat gctttatgtt taaaaacatt ccccaattat cttatttaat ttttgcaatt      3720
attctaattt tatatataga gaaagtgacc tattttttaa aaaaatcaca ctctaagttc      3780
tattgaacct aggacttgag cctccatttc tggcttctag tctggtgttc tgagtacttg      3840
atttcaggtc aataacggtc ccccctcact ccacactggc acgtttgtga gaagaaatga      3900
cattttgcta ggaagtgacc gagtctagga atgcttttat tcaagacacc aaattccaaa      3960
cttctaaatg ttggaatttt caaaaattgt gtttagattt tatgaaaaac tcttctactt      4020
tcatctattc tttccctaga ggcaaacatt tcttaaaatg tttcattttc attaaaaatg      4080
aaagccaaat ttatatgcca ccgattgcag gacacaagca cagttttaag agttgtatga      4140
acatggagag gactttt ggt ttttatattt ctcgtattta atatgggtga acaccaactt      4200
ttatttggaa taataatttt cctcctaaac aaaaacacat tgagtttaag tctctgactc      4260
ttgcctttcc acctgctttc tcctgggccc gctttgcctg cttgaaggaa cagtgctgtt      4320
ctggagctgc tgttccaaca gacagggcct agctttcatt tgacacacag actacagcca      4380
gaagcccatg gagcagggat gtcacgtctt gaaaagccta ttgatgtttt tacaaattta      4440
attttgcaga ttattttagt ctgtcatcca gaaaatgtgt cagcatgcat agtgctaaga      4500
aagcaagcca atttggaaac ttaggttagt gacaaaattg gccagagagt gggggtgatg      4560
```

```
atgaccaaga attacaagta gaatggcagc tggaatttaa ggagggacaa gaatcaatgg    4620
ataagcgtgg gtggaggaag atccaaacag aaaagtgcaa agttattccc catcttccaa    4680
gggttgaatt ctggaggaag aagacacatt cctagttccc cgtgaacttc ctttgactta    4740
ttgtccccac taaaacaaaa caaaaaactt ttaatgcctt ccacattaat tagattttct    4800
tgcagttttt ttatggcatt ttttaaaga tgccctaagt gttgaagaag agtttgcaaa    4860
tgcaacaaaa tatttaatta ccggttgtta aaactggttt agcacaattt atattttccc    4920
tctcttgcct ttcttatttg caataaaagg tattgagcca ttttttaaat gacattttg     4980 ataaattatg tttgtactag ttgatgaagg agttttttt aacctgttta tataattttg     5040
cagcagaagc caaatttttt gtatattaaa gcaccaaatt catgtacagc atgcatcacg    5100
gatcaataga ctgtacttat tttccaataa aattttcaaa ctttgtactg ttaaaaaaaa    5160
aaaaaaaaa                                                             5170
```

<210> SEQ ID NO 92
<211> LENGTH: 569
<212> TYPE: PRT
<213> ORGANISM: Homo sapiens

<400> SEQUENCE: 92

```
Met Lys Val Leu Leu Arg Leu Ile Cys Phe Ile Ala Leu Leu Ile Ser
 1               5                  10                  15

Ser Leu Glu Ala Asp Lys Cys Lys Glu Arg Glu Lys Ile Ile Leu
            20                  25                  30

Val Ser Ser Ala Asn Glu Ile Asp Val Arg Pro Cys Pro Leu Asn Pro
        35                  40                  45

Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Lys Leu Pro Val Ala Gly Asp Gly Gly Leu Val Cys Pro Tyr
    130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255
```

Ile Ala Tyr Trp Lys Trp Asn Gly Ser Val Ile Asp Glu Asp Pro
            260                 265                 270

Val Leu Gly Glu Asp Tyr Tyr Ser Val Glu Asn Pro Ala Asn Lys Arg
            275                 280                 285

Arg Ser Thr Leu Ile Thr Val Leu Asn Ile Ser Glu Ile Glu Ser Arg
        290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
                325                 330                 335

His Met Ile Gly Ile Cys Val Thr Leu Thr Val Ile Ile Val Cys Ser
            340                 345                 350

Val Phe Ile Tyr Lys Ile Phe Lys Ile Asp Ile Val Leu Trp Tyr Arg
            355                 360                 365

Asp Ser Cys Tyr Asp Phe Leu Pro Ile Lys Ala Ser Asp Gly Lys Thr
        370                 375                 380

Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
                405                 410                 415

Lys Gln Cys Gly Tyr Lys Leu Phe Ile Tyr Gly Arg Asp Asp Tyr Val
            420                 425                 430

Gly Glu Asp Ile Val Glu Val Ile Asn Glu Asn Val Lys Lys Ser Arg
        435                 440                 445

Arg Leu Ile Ile Ile Leu Val Arg Glu Thr Ser Gly Phe Ser Trp Leu
    450                 455                 460

Gly Gly Ser Ser Glu Glu Gln Ile Ala Met Tyr Asn Ala Leu Val Gln
465                 470                 475                 480

Asp Gly Ile Lys Val Val Leu Leu Glu Leu Glu Lys Ile Gln Asp Tyr
                485                 490                 495

Glu Lys Met Pro Glu Ser Ile Lys Phe Ile Lys Gln Lys His Gly Ala
            500                 505                 510

Ile Arg Trp Ser Gly Asp Phe Thr Gln Gly Pro Gln Ser Ala Lys Thr
        515                 520                 525

Arg Phe Trp Lys Asn Val Arg Tyr His Met Pro Val Gln Arg Arg Ser
530                 535                 540

Pro Ser Ser Lys His Gln Leu Leu Ser Pro Ala Thr Lys Glu Lys Leu
545                 550                 555                 560

Gln Arg Glu Ala His Val Pro Leu Gly
                565

```
<210> SEQ ID NO 93
<211> LENGTH: 20
<212> TYPE: RNA
<213> ORGANISM: Artificial Sequence
<220> FEATURE:
<223> OTHER INFORMATION: synthetic construct

<400> SEQUENCE: 93
uuucuucuca caaacgugcc                                              20

<210> SEQ ID NO 94
<211> LENGTH: 20
<212> TYPE: RNA
<213> ORGANISM: Artificial Sequence
<220> FEATURE:
<223> OTHER INFORMATION: synthetic construct
```

<400> SEQUENCE: 94
uuauaccaag uuauagugcc                                                    20

<210> SEQ ID NO 95
<211> LENGTH: 20
<212> TYPE: RNA
<213> ORGANISM: Artificial Sequence
<220> FEATURE:
<223> OTHER INFORMATION: synthetic construct

<400> SEQUENCE: 95
uuguaaaaca ucuaauaggc                                                    20

<210> SEQ ID NO 96
<211> LENGTH: 20
<212> TYPE: RNA
<213> ORGANISM: Artificial Sequence
<220> FEATURE:
<223> OTHER INFORMATION: synthetic construct

<400> SEQUENCE: 96
uuuccacacu guaauagucu                                                    20

<210> SEQ ID NO 97
<211> LENGTH: 31
<212> TYPE: DNA
<213> ORGANISM: Artificial Sequence
<220> FEATURE:
<223> OTHER INFORMATION: synthetic construct

<400> SEQUENCE: 97
ccggtctttc ttctcacaaa cgtgcgaccg g                                       31

<210> SEQ ID NO 98
<211> LENGTH: 31
<212> TYPE: DNA
<213> ORGANISM: Artificial Sequence
<220> FEATURE:
<223> OTHER INFORMATION: synthetic construct

<400> SEQUENCE: 98
ccggtcttaa acacaaaaat atcacgaccg g                                       31

<210> SEQ ID NO 99
<211> LENGTH: 31
<212> TYPE: DNA
<213> ORGANISM: Artificial Sequence
<220> FEATURE:
<223> OTHER INFORMATION: synthetic construct

<400> SEQUENCE: 99
ccggtctttc cacactgtaa tagtcgaccg g                                       31

<210> SEQ ID NO 100
<211> LENGTH: 1686
<212> TYPE: DNA
<213> ORGANISM: Homo sapiens

<400> SEQUENCE: 100
cagacgctcc ctcagcaagg acagcagagg accagctaag agggagagaa gcaactacag        60
accccccctg aaaacaaccc tcagacgcca catcccctga caagctgcca ggcaggttct       120
cttcctctca catactgacc cacggctcca ccctctctcc cctggaaagg acaccatgag       180

```
cactgaaagc atgatccggg acgtggagct ggccgaggag gcgctcccca agaagacagg    240
ggggccccag ggctccaggc ggtgcttgtt cctcagcctc ttctccttcc tgatcgtggc    300
aggcgccacc acgctcttct gcctgctgca ctttggagtg atcggccccc agagggaaga    360
gttccccagg gacctctctc taatcagccc tctggcccag gcagtcagat catcttctcg    420
aaccccgagt gacaagcctg tagcccatgt tgtagcaaac cctcaagctg aggggcagct    480
ccagtggctg aaccgccggg ccaatgccct cctggccaat ggcgtggagc tgagagataa    540
ccagctggtg gtgccatcag agggcctgta cctcatctac tcccaggtcc tcttcaaggg    600
ccaaggctgc ccctccaccc atgtgctcct cacccacacc atcagccgca tcgccgtctc    660
ctaccagacc aaggtcaacc tcctctctgc catcaagagc ccctgccaga gggagacccc    720
agaggggggct gaggccaagc cctggtatga gcccatctat ctgggagggg tcttccagct    780
ggagaagggt gaccgactca gcgctgagat caatcggccc gactatctcg actttgccga    840
gtctgggcag gtctactttg ggatcattgc cctgtgagga ggacgaacat ccaaccttcc    900
caaacgcctc ccctgcccca atccctttat taccccctcc ttcagacacc ctcaacctct    960
tctggctcaa aaagagaatt gggggcttag ggtcggaacc caagcttaga actttaagca   1020
acaagaccac cacttcgaaa cctgggattc aggaatgtgt ggcctgcaca gtgaagtgct   1080
ggcaaccact aagaattcaa actggggcct ccagaactca ctggggccta cagctttgat   1140
ccctgacatc tggaatctgg agaccaggga gcctttggtt ctggccagaa tgctgcagga   1200
cttgagaaga cctcacctag aaattgacac aagtggacct taggccttcc tctctccaga   1260
tgtttccaga cttccttgag acacggagcc cagcccctcc catggagcca gctccctcta   1320
tttatgtttg cacttgtgat tatttattat ttatttatta tttatttatt tacagatgaa   1380
tgtatttatt tgggagaccg gggtatcctg ggggacccaa tgtaggagct gccttggctc   1440
agacatgttt tccgtgaaaa cggagctgaa caataggctg ttcccatgta gccccctggc   1500
ctctgtgcct tcttttgatt atgttttta aaatatttat ctgattaagt tgtctaaaca   1560
atgctgattt ggtgaccaac tgtcactcat tgctgagcct ctgctcccca ggggagttgt   1620
gtctgtaatc gccctactat tcagtggcga gaaataaagt ttgcttagaa aagaaaaaaa   1680
aaaaaa                                                               1686
```

<210> SEQ ID NO 101
<211> LENGTH: 233
<212> TYPE: PRT
<213> ORGANISM: Homo sapiens

<400> SEQUENCE: 101

```
Met Ser Thr Glu Ser Met Ile Arg Asp Val Glu Leu Ala Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
        50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
```

```
                    100                 105                 110
Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
            210                 215                 220

Gln Val Tyr Phe Gly Ile Ile Ala Leu
225                 230

<210> SEQ ID NO 102
<211> LENGTH: 19
<212> TYPE: RNA
<213> ORGANISM: Artificial Sequence
<220> FEATURE:
<223> OTHER INFORMATION: synthetic construct

<400> SEQUENCE: 102
aauaaauaau cacaagugc                                               19

<210> SEQ ID NO 103
<211> LENGTH: 19
<212> TYPE: RNA
<213> ORGANISM: Artificial Sequence
<220> FEATURE:
<223> OTHER INFORMATION: synthetic construct

<400> SEQUENCE: 103
uaaaaaacau aaucaaaag                                               19

<210> SEQ ID NO 104
<211> LENGTH: 19
<212> TYPE: RNA
<213> ORGANISM: Artificial Sequence
<220> FEATURE:
<223> OTHER INFORMATION: synthetic construct

<400> SEQUENCE: 104
uaauaaauaa ucacaagug                                               19

<210> SEQ ID NO 105
<211> LENGTH: 19
<212> TYPE: RNA
<213> ORGANISM: Artificial Sequence
<220> FEATURE:
<223> OTHER INFORMATION: synthetic construct

<400> SEQUENCE: 105
uuuucuuuuc uaagcaaac                                               19

<210> SEQ ID NO 106
<211> LENGTH: 31
<212> TYPE: DNA
<213> ORGANISM: Artificial Sequence
```

```
<220> FEATURE:
<223> OTHER INFORMATION: synthetic construct

<400> SEQUENCE: 106
ccggtcaaac ataatcaaaa gaagggaccg g                                    31

<210> SEQ ID NO 107
<211> LENGTH: 31
<212> TYPE: DNA
<213> ORGANISM: Artificial Sequence
<220> FEATURE:
<223> OTHER INFORMATION: synthetic construct

<400> SEQUENCE: 107
ccggtctaaa aaacataatc aaaaggaccg g                                    31

<210> SEQ ID NO 108
<211> LENGTH: 31
<212> TYPE: DNA
<213> ORGANISM: Artificial Sequence
<220> FEATURE:
<223> OTHER INFORMATION: synthetic construct

<400> SEQUENCE: 108
ccggtctatt ttaaaaaaca taatcgaccg g                                    31

<210> SEQ ID NO 109
<211> LENGTH: 3677
<212> TYPE: DNA
<213> ORGANISM: Homo sapiens

<400> SEQUENCE: 109
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa     180 cattttttt taaaactgta ttgtttctcg ttttaattta ttttgcttg ccattcccca       240 cttgaatcgg gccgacggct tggggagatt gctctacttc cccaaatcac tgtggatttt     300
ggaaaccagc agaaagagga aagaggtagc aagagctcca gagagaagtc gaggaagaga     360
gagacggggt cagagagagc gcgcgggcgt gcgagcagcg aaagcgacag gggcaaagtg     420
agtgacctgc ttttgggggt gaccgccgga gcgcggcgtg agccctcccc cttgggatcc     480
cgcagctgac cagtcgcgct gacggacaga cagacagaca ccgcccccag ccccagctac     540
cacctcctcc ccggccggcg gcggacagtg gacgcggcgg cgagccgcgg gcaggggccg     600
gagcccgcgc ccggaggcgg ggtggagggg gtcgggctc gcggcgtcgc actgaaactt      660
ttcgtccaac ttctgggctg ttctcgcttc ggaggagccg tggtccgcgc ggggggaagcc    720 gagccgagcg gagccgcgag aagtgctagc tcggccgggg aggagccgca gccggaggag    780 gggaggagg aagaagagaa ggaagaggag agggggccgc agtggcgact cggcgctcgg     840
aagccgggct catggacggg tgaggcggcg gtgtgcgcag acagtgctcc agccgcgcgc    900
gctccccagg ccctggcccg ggcctcgggc cggggaggaa gagtagctcg ccgaggcgcc    960
gaggagagcg ggccgcccca gccccgagc cggagaggga gcgcgagccg cgccggcccc   1020
ggtcgggcct ccgaaaccat gaactttctg ctgtcttggg tgcattggag ccttgccttg    1080
ctgctctacc tccaccatgc caagtggtcc caggctgcac ccatggcaga aggaggaggg    1140
cagaatcatc acgaagtggt gaagttcatg gatgtctatc agcgcagcta ctgccatcca    1200
```

```
atcgagaccc tggtggacat cttccaggag taccctgatg agatcgagta catcttcaag    1260
ccatcctgtg tgcccctgat gcgatgcggg ggctgctgca atgacgaggg cctggagtgt    1320
gtgcccactg aggagtccaa catcaccatg cagattatgc ggatcaaacc tcaccaaggc    1380
cagcacatag agagatgag cttcctacag cacaacaaat gtgaatgcag accaaagaaa     1440
gatagagcaa gacaagaaaa aaaatcagtt cgaggaaagg gaaagggca aaaacgaaag     1500 cgcaagaaat cccggtataa gtcctggagc gtgtacgttg gtgcccgctg ctgtctaatg    1560
ccctggagcc tccctggccc ccatccctgt gggccttgct cagagcggag aaagcatttg    1620
tttgtacaag atccgcagac gtgtaaatgt tcctgcaaaa acacagactc gcgttgcaag    1680
gcgaggcagc ttgagttaaa cgaacgtact tgcagatgtg acaagccgag gcggtgagcc    1740
gggcaggagg aaggagcctc cctcagggtt tcgggaacca gatctctcac caggaaagac    1800
tgatacagaa cgatcgatac agaaaccacg ctgccgccac cacaccatca ccatcgacag    1860
aacagtcctt aatccagaaa cctgaaatga aggaagagga gactctgcgc agagcacttt    1920
gggtccggag ggcgagactc cggcggaagc attcccgggc gggtgaccca gcacggtccc    1980
tcttggaatt ggattcgcca tttattttt cttgctgcta aatcaccgag cccggaagat     2040
tagagagttt tatttctggg attcctgtag acacacccac ccatacat acatttatat      2100 atatatatat tatatatata taaaaataaa tatctctatt ttatatatat aaaatatata    2160
tattcttttt ttaaattaac agtgctaatg ttattggtgt cttcactgga tgtatttgac    2220
tgctgtggac ttgagttggg aggggaatgt tcccactcag atcctgacag ggaagaggag    2280
gagatgagag actctggcat gatcttttt ttgtcccact tggtggggcc agggtcctct     2340
cccctgccca ggaatgtgca aggccagggc atggggcaa atatgaccca gttttgggaa     2400
caccgacaaa cccagccctg gcgctgagcc tctctacccc aggtcagacg gacagaaaga    2460
cagatcacag gtacagggat gaggacaccg gctctgacca ggagtttggg gagcttcagg    2520
acattgctgt gctttgggga ttccctccac atgctgcacg cgcatctcgc ccccagggc     2580 actgcctgga agattcagga gcctgggcgg ccttcgctta ctctcacctg cttctgagtt    2640
gcccaggaga ccactggcag atgtcccggc gaagagaaga gacacattgt tggaagaagc    2700
agcccatgac agctccccctt cctgggactc gccctcatcc tcttcctgct ccccttcctg   2760
gggtgcagcc taaaaggacc tatgtcctca caccattgaa accactagtt ctgtcccccc    2820
aggagacctg gttgtgtgtg tgtgagtggt tgaccttcct ccatcccctg gtccttccct    2880
tcccttcccg aggcacagag agacagggca ggatccacgt gcccattgtg gaggcagaga    2940
aaagagaaag tgtttatat acggtactta tttaatatcc ctttttaatt agaaattaaa     3000
acagttaatt taattaaaga gtagggtttt ttttcagtat tcttggttaa tatttaatttt   3060 caactattta tgagatgtat cttttgctct ctcttgctct cttatttgta ccggttttttg   3120 tatataaaat tcatgtttcc aatctctctc tccctgatcg gtgacagtca ctagcttatc    3180
ttgaacagat atttaatttt gctaacactc agctctgccc tccccgatcc cctggctccc    3240
cagcacacat tcctttgaaa taaggtttca atatacatct acatactata tatatatttg    3300
gcaacttgta tttgtgtgta tatatatata tatgtgttta tgtatatatg tgattctgat    3360
aaaatagaca ttgctattct gttttttata tgtaaaaaca aaacaagaaa aaatagagaa    3420
ttctacatac taaatctctc tcctttttta atttaat ttgttatcat ttatttattg       3480
gtgctactgt ttatccgtaa taattgtggg gaaaagatat taacatcacg tctttgtctc    3540
tagtgcagtt tttcgagata ttccgtagta catatttatt tttaaacaac gacaaagaaa    3600
```

```
tacagatata tcttaaaaaa aaaaaagcat tttgtattaa agaatttaat tctgatctca    3660
aaaaaaaaaa aaaaaaa                                                   3677
```

<210> SEQ ID NO 110
<211> LENGTH: 412
<212> TYPE: PRT
<213> ORGANISM: Homo sapiens

<400> SEQUENCE: 110

```
Met Thr Asp Arg Gln Thr Asp Thr Ala Pro Ser Pro Ser Tyr His Leu
1               5                   10                  15

Leu Pro Gly Arg Arg Thr Val Asp Ala Ala Ala Ser Arg Gly Gln
            20                  25                  30

Gly Pro Glu Pro Ala Pro Gly Gly Val Glu Gly Val Gly Ala Arg
        35                  40                  45

Gly Val Ala Leu Lys Leu Phe Val Gln Leu Leu Gly Cys Ser Arg Phe
50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
    130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
    290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Tyr Lys Ser Trp Ser Val Tyr Val Gly Ala Arg Cys Cys
            340                 345                 350
```

```
Leu Met Pro Trp Ser Leu Pro Gly Pro His Pro Cys Gly Pro Cys Ser
        355                 360                 365

Glu Arg Arg Lys His Leu Phe Val Gln Asp Pro Gln Thr Cys Lys Cys
    370                 375                 380

Ser Cys Lys Asn Thr Asp Ser Arg Cys Lys Ala Arg Gln Leu Glu Leu
385                 390                 395                 400

Asn Glu Arg Thr Cys Arg Cys Asp Lys Pro Arg Arg
                405                 410

<210> SEQ ID NO 111
<211> LENGTH: 21
<212> TYPE: RNA
<213> ORGANISM: Artificial Sequence
<220> FEATURE:
<223> OTHER INFORMATION: synthetic construct

<400> SEQUENCE: 111
uaaaacucuc uaaucuuccg g                                          21

<210> SEQ ID NO 112
<211> LENGTH: 21
<212> TYPE: RNA
<213> ORGANISM: Artificial Sequence
<220> FEATURE:
<223> OTHER INFORMATION: synthetic construct

<400> SEQUENCE: 112
uuccuucucu ucuuccuccu c                                          21

<210> SEQ ID NO 113
<211> LENGTH: 21
<212> TYPE: RNA
<213> ORGANISM: Artificial Sequence
<220> FEATURE:
<223> OTHER INFORMATION: synthetic construct

<400> SEQUENCE: 113
uauacacaca aauacaaguu g                                          21

<210> SEQ ID NO 114
<211> LENGTH: 21
<212> TYPE: RNA
<213> ORGANISM: Artificial Sequence
<220> FEATURE:
<223> OTHER INFORMATION: synthetic construct

<400> SEQUENCE: 114
uuaaaacgag aaacaauaca g                                          21

<210> SEQ ID NO 115
<211> LENGTH: 31
<212> TYPE: DNA
<213> ORGANISM: Artificial Sequence
<220> FEATURE:
<223> OTHER INFORMATION: synthetic construct

<400> SEQUENCE: 115
ccggtctaaa actctctaat cttccgaccg g                               31

<210> SEQ ID NO 116
<211> LENGTH: 31
<212> TYPE: DNA
<213> ORGANISM: Artificial Sequence
<220> FEATURE:
<223> OTHER INFORMATION: synthetic construct
```

<400> SEQUENCE: 116
ccggtctttg atccgcataa tctgcgaccg g                              31

<210> SEQ ID NO 117
<211> LENGTH: 31
<212> TYPE: DNA
<213> ORGANISM: Artificial Sequence
<220> FEATURE:
<223> OTHER INFORMATION: synthetic construct

<400> SEQUENCE: 117
ccggtcttga aattaaatat taaccgaccg g                              31

<210> SEQ ID NO 118
<211> LENGTH: 2583
<212> TYPE: DNA
<213> ORGANISM: Homo sapiens

<400> SEQUENCE: 118

| | | |
|---|---|---|
| agccggtccc cgccgccgcc gcccttcgcg ccctgggcca tctccctccc acctccctcc | 60 |
| gcggagcagc cagacagcga gggccccggc cggggggcagg gggacgccc cgtccggggc | 120 |
| accccccgg ctctgagccg cccgcggggc cggcctcggc ccggagcgga ggaaggagtc | 180 |
| gccgaggagc agcctgaggc cccagagtct gagacgagcc gccgccgccc ccgccactgc | 240 |
| ggggaggagg gggaggagga gcgggaggag ggacgagctg gtcgggagaa gaggaaaaaa | 300 |
| acttttgaga cttttccgtt gccgctggga gccggaggcg cggggacctc ttggcgcgac | 360 |
| gctgccccgc gaggaggcag gacttgggga ccccagaccg cctcccttttg ccgccgggga | 420 |
| cgcttgctcc ctccctgccc cctacacggc gtccctcagg cgcccccatt ccggaccagc | 480 |
| cctcgggagt cgccgacccg gcctcccgca aagacttttc cccagacctc gggcgcaccc | 540 |
| cctgcacgcc gccttcatcc ccggcctgtc tcctgagccc ccgcgcatcc tagacccttt | 600 |
| ctcctccagg agacggatct ctctccgacc tgccacagat cccctattca agaccaccca | 660 |
| ccttctggta ccagatcgcg cccatctagg ttatttccgt gggatactga gacacccccg | 720 |
| gtccaagcct ccctccacc actgcgccct tctccctgag gacctcagct ttccctcgag | 780 |
| gccctcctac cttttgccgg gagacccca gccctgcag gggcggggcc tccccaccac | 840 |
| accagccctg ttcgcgctct cggcagtgcc gggggcgcc gctcccccca tgccgccctc | 900 |
| cgggctgcgg ctgctgccgc tgctgctacc gctgctgtgg ctactggtgc tgacgcctgg | 960 |
| ccggccggcc gcgggactat ccacctgcaa gactatcgac atggagctgg tgaagcggaa | 1020 |
| gcgcatcgag gccatccgcg gccagatcct gtccaagctg cggctcgcca gccccccgag | 1080 |
| ccaggggag gtgccgcccg gccgctgcc cgaggccgtg ctcgcccgt acaacagcac | 1140 |
| ccgcgaccgg gtggccgggg agagtgcaga accggagccc gagcctgagg ccgactacta | 1200 |
| cgccaaggag gtcacccgcg tgctaatggt ggaaacccac aacgaaatct atgacaagtt | 1260 |
| caagcagagt acacacagca tatatatgtt cttcaacaca tcagagctcc gagaagcggt | 1320 |
| acctgaaccc gtgttgctct cccgggcaga gctgcgtctg ctgaggctca agttaaaagt | 1380 |
| ggagcagcac gtggagctgt accagaaata cagcaacaat tcctggcgat acctcagcaa | 1440 |
| ccggctgctg gcaccagcg actcgccaga gtggttatct tttgatgtca ccggagttgt | 1500 |
| gcggcagtgg ttgagccgtg gaggggaaat tgagggctt cgccttagcg cccactgctc | 1560 |
| ctgtgacagc agggataaca cactgcaagt ggacatcaac gggttcacta ccggccgccg | 1620 |

-continued

```
aggtgacctg gccaccattc atggcatgaa ccggcctttc ctgcttctca tggccacccc    1680
gctggagagg gcccagcatc tgcaaagctc ccggcaccgc cgagccctgg acaccaacta    1740
ttgcttcagc tccacggaga agaactgctg cgtgcggcag ctgtacattg acttccgcaa    1800
ggacctcggc tggaagtgga tccacgagcc caagggctac catgccaact tctgcctcgg    1860
gccctgcccc tacatttgga gcctggacac gcagtacagc aaggtcctgg ccctgtacaa    1920
ccagcataac ccgggcgcct cggcggcgcc gtgctgcgtg ccgcaggcgc tggagccgct    1980
gcccatcgtg tactacgtgg gccgcaagcc caaggtggag cagctgtcca acatgatcgt    2040
gcgctcctgc aagtgcagct gaggtcccgc cccgccccgc ccgccccgg caggcccggc    2100
cccacccgc ccgcccccg ctgccttgcc catgggggct gtatttaagg acaccgtgc        2160
cccaagccca cctggggccc cattaaagat ggagagagga ctgcggatct ctgtgtcatt    2220
gggcgcctgc ctggggtctc catccctgac gttcccccac tcccactccc tctctctccc    2280
tctctgcctc ctcctgcctg tctgcactat tcctttgccc ggcatcaagg cacaggggac    2340
cagtggggaa cactactgta gttagatcta tttattgagc accttgggca ctgttgaagt    2400
gccttacatt aatgaactca ttcagtcacc atagcaacac tctgagatgc agggactctg    2460
ataacaccca ttttaaaggt gaggaaacaa gcccagagag gttaagggag gagttcctgc    2520
ccaccaggaa cctgctttag tgggggatag tgaagaagac aataaaagat agtagttcag    2580
gcc                                                                  2583
```

<210> SEQ ID NO 119
<211> LENGTH: 390
<212> TYPE: PRT
<213> ORGANISM: Homo sapiens

<400> SEQUENCE: 119

```
Met Pro Pro Ser Gly Leu Arg Leu Leu Pro Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
```

```
                195                 200                 205
Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 120
<211> LENGTH: 19
<212> TYPE: RNA
<213> ORGANISM: Artificial Sequence
<220> FEATURE:
<223> OTHER INFORMATION: synthetic construct

<400> SEQUENCE: 120
uauugucuuc uucacuauc                                                  19

<210> SEQ ID NO 121
<211> LENGTH: 19
<212> TYPE: RNA
<213> ORGANISM: Artificial Sequence
<220> FEATURE:
<223> OTHER INFORMATION: synthetic construct

<400> SEQUENCE: 121
uagaucuaac uacaguagu                                                  19

<210> SEQ ID NO 122
<211> LENGTH: 19
<212> TYPE: RNA
<213> ORGANISM: Artificial Sequence
<220> FEATURE:
<223> OTHER INFORMATION: synthetic construct

<400> SEQUENCE: 122
uauaugcugu guguacucu                                                  19

<210> SEQ ID NO 123
<211> LENGTH: 19
<212> TYPE: RNA
<213> ORGANISM: Artificial Sequence
```

```
<220> FEATURE:
<223> OTHER INFORMATION: synthetic construct

<400> SEQUENCE: 123
uauauaugcu guguguacu                                                    19

<210> SEQ ID NO 124
<211> LENGTH: 31
<212> TYPE: DNA
<213> ORGANISM: Artificial Sequence
<220> FEATURE:
<223> OTHER INFORMATION: synthetic construct

<400> SEQUENCE: 124
ccggtcatat atgctgtgtg tactcgaccg g                                      31

<210> SEQ ID NO 125
<211> LENGTH: 31
<212> TYPE: DNA
<213> ORGANISM: Artificial Sequence
<220> FEATURE:
<223> OTHER INFORMATION: synthetic construct

<400> SEQUENCE: 125
ccggtctttt attgtcttct tcactgaccg g                                      31

<210> SEQ ID NO 126
<211> LENGTH: 31
<212> TYPE: DNA
<213> ORGANISM: Artificial Sequence
<220> FEATURE:
<223> OTHER INFORMATION: synthetic construct

<400> SEQUENCE: 126
ccggtctata tatgctgtgt gtactgaccg g                                      31

<210> SEQ ID NO 127
<211> LENGTH: 5966
<212> TYPE: DNA
<213> ORGANISM: Homo sapiens

<400> SEQUENCE: 127
gtgatgttat ctgctggcag cagaaggttc gctccgagcg gagctccaga agctcctgac      60
aagagaaaga cagattgaga tagagataga aagagaaaga gagaaagaga cagcagagcg     120
agagcgcaag tgaaagaggc aggggagggg gatggagaat attagcctga cggtctaggg     180
agtcatccag gaacaaactg aggggctgcc cggctgcaga caggaggaga cagagaggat     240
ctattttagg gtggcaagtg cctacctacc ctaagcgagc aattccacgt tggggagaag     300
ccagcagagg ttgggaaagg gtgggagtcc aagggagccc ctgcgcaacc ccctcaggaa     360
taaaactccc cagccagggt gtcgcaaggg ctgccgttgt gatccgcagg gggtgaacgc     420
aaccgcgacg gctgatcgtc tgtggctggg ttggcgtttg gagcaagaga aggaggagca     480
ggagaaggag ggagctggag gctggaagcg tttgcaagcg gcggcggcag caacgtggag     540
taaccaagcg ggtcagcgcg cgcccgccag ggtgtaggcc acggagcgca gctcccagag     600
caggatccgc gccgcctcag cagcctctgc ggccctgcg gcacccgacc gagtaccgag     660
cgccctgcga agcgcaccct cctcccgcg gtgcgctggg ctcgccccca gcgcgcgcac     720
acgcacacac acacacacac acacacacgc acgcacacac gtgtgcgctt ctctgctccg     780
gagctgctgc tgctcctgct ctcagcgccg cagtggaagg caggaccgaa ccgctccttc     840
```

-continued

```
tttaaatata taaatttcag cccaggtcag cctcggcggc cccctcacc gcgctcccgg    900
cgccctccc gtcagttcgc cagctgccag ccccgggacc ttttcatctc ttcccttttg    960
gccggaggag ccgagttcag atccgccact ccgcacccga gactgacaca ctgaactcca   1020
cttcctcctc ttaaatttat ttctacttaa tagccactcg tctcttttt tccccatctc   1080
attgctccaa gaattttttt cttcttactc gccaaagtca gggttccctc tgcccgtccc   1140
gtattaatat ttccactttt ggaactactg gccttttctt tttaaaggaa ttcaagcagg   1200
atacgttttt ctgttgggca ttgactagat tgtttgcaaa agtttcgcat caaaaacaac   1260
aacaacaaaa aaccaaacaa ctctccttga tctatacttt gagaattgtt gatttctttt   1320
ttttattctg acttttaaaa acaacttttt tttccactttt tttaaaaaat gcactactgt   1380
gtgctgagcg cttttctgat cctgcatctg tcacggtcg cgctcagcct gtctacctgc    1440
agcacactcg atatggacca gttcatgcgc aagaggatcg aggcgatccg cgggcagatc   1500
ctgagcaagc tgaagctcac cagtccccca gaagactatc ctgagcccga ggaagtcccc   1560
ccggaggtga tttccatcta caacagcacc agggacttgc tccaggagaa ggcgagccgg   1620
agggcggccg cctgcgagcg cgagaggagc gacgaagagt actacgccaa ggaggtttac   1680
aaaatagaca tgccgccctt cttccctcc gaaactgtct gcccagttgt tacaacaccc    1740
tctggctcag tgggcagctt gtgctccaga cagtcccagg tgctctgtgg gtaccttgat   1800
gccatcccgc ccactttcta cagaccctac ttcagaattg ttcgatttga cgtctcagca   1860
atggagaaga atgcttccaa tttggtgaaa gcagagttca gagtctttcg tttgcagaac   1920
ccaaaagcca gagtgcctga acaacggatt gagctatatc agattctcaa gtccaaagat   1980
ttaacatctc caacccagcg ctacatcgac agcaaagttg tgaaaacaag agcagaaggc   2040
gaatggctct ccttcgatgt aactgatgct gttcatgaat ggcttcacca taaagacagg   2100
aacctgggat ttaaaataag cttacactgt ccctgctgca cttttgtacc atctaataat   2160
tacatcatcc caaataaaag tgaagaacta gaagcaagat ttgcaggtat tgatggcacc   2220
tccacatata ccagtggtga tcagaaaact ataaagtcca ctaggaaaaa aaacagtggg   2280
aagaccccac atctcctgct aatgttattg ccctcctaca gacttgagtc acaacagacc   2340
aaccggcgga agaagcgtgc tttggatgcg gcctattgct ttagaaatgt gcaggataat   2400
tgctgcctac gtccactttta cattgatttc aagagggatc tagggtggaa atggatacac   2460
gaacccaaag ggtacaatgc caacttctgt gctggagcat gcccgtattt atggagttca   2520
gacactcagc acagcagggt cctgagctta tataatacca taaatccaga agcatctgct   2580
tctccttgct gcgtgtccca agatttagaa cctctaacca ttctctacta cattggcaaa   2640
acacccaaga ttgaacagct ttctaatatg attgtaaagt cttgcaaatg cagctaaaat   2700
tcttggaaaa gtggcaagac caaaatgaca atgatgatga taatgatgat gacgacgaca   2760
acgatgatgc ttgtaacaag aaaacataag agagccttgg ttcatcagtg ttaaaaaatt   2820
tttgaaaagg cggtactagt tcagacactt tggaagtttg tgttctgttt gttaaaactg   2880
gcatctgaca caaaaaaagt tgaaggcctt attctacatt tcacctactt tgtaagtgag   2940
agagacaaga agcaaatttt ttttaaagaa aaaataaac actggaagaa tttattagtg    3000
ttaattatgt gaacaacgac aacaacaaca acaacaacaa acaggaaaat cccattaagt   3060
ggagttgctg tacgtaccgt tcctatcccg cgcctcactt gatttttctg tattgctatg   3120
caataggcac ccttcccatt cttactctta gagttaacag tgagttattt attgtgtgtt   3180
actatataat gaacgtttca ttgcccttgg aaaataaaac aggtgtataa agtggagacc   3240
```

```
aaatactttg ccagaaactc atggatggct taaggaactt gaactcaaac gagccagaaa    3300
aaaagaggtc atattaatgg gatgaaaacc caagtgagtt attatatgac cgagaaagtc    3360
tgcattaaga taaagaccct gaaaacacat gttatgtatc agctgcctaa ggaagcttct    3420
tgtaaggtcc aaaaactaaa aagactgtta ataaaagaaa ctttcagtca gaataagtct    3480
gtaagttttt ttttttcttt ttaattgtaa atggttcttt gtcagtttag taaaccagtg    3540
aaatgttgaa atgttttgac atgtactggt caaacttcag accttaaaat attgctgtat    3600
agctatgcta taggttttt cctttgtttt ggtatatgta accataccta tattattaaa    3660
atagatggat atagaagcca gcataattga aaacacatct gcagatctct tttgcaaact    3720
attaaatcaa acattaact actttatgtg taatgtgtaa attttacca tatttttat    3780 attctgtaat aatgtcaact atgatttaga ttgacttaaa tttgggctct ttttaatgat    3840
cactcacaaa tgtatgtttc ttttagctgg ccagtacttt tgagtaaagc ccctatagtt    3900
tgacttgcac tacaaatgca ttttttttt aataacattt gccctacttg tgctttgtgt    3960
ttctttcatt attatgacat aagctacctg ggtccacttg tcttttcttt tttttgtttc    4020
acagaaaaga tgggttcgag ttcagtggtc ttcatcttcc aagcatcatt actaaccaag    4080
tcagacgtta acaaattttt atgttaggaa aaggaggaat gttatagata catagaaaat    4140
tgaagtaaaa tgttttcatt ttagcaagga tttagggttc taactaaaac tcagaatctt    4200
tattgagtta agaaaagttt ctctaccttg gtttaatcaa tattttgta aaatcctatt    4260 gttattacaa agaggacact tcataggaaa catcttttc tttagtcagg tttttaatat    4320 tcaggggaa attgaaagat atatattta gtcgattttt caaaggggga aaaaagtcca    4380
ggtcagcata agtcattttg tgtatttcac tgaagttata aggtttttat aaatgttctt    4440
tgaaggggaa aaggcacaag ccaattttc ctatgatcaa aaaattcttt ctttcctctg    4500
agtgagagtt atctatatct gaggctaaag tttaccttgc tttaataaat aatttgccac    4560
atcattgcag aagaggtatc ctcatgctgg ggttaataga atatgtcagt ttatcacttg    4620
tcgcttattt agctttaaaa taaaaattaa taggcaaagc aatggaatat ttgcagtttc    4680
acctaaagag cagcataagg aggcgggaat ccaaagtgaa gttgtttgat atggtctact    4740
tcttttttgg aatttcctga ccattaatta aagaattgga tttgcaagtt tgaaaactgg    4800
aaaagcaaga gatgggatgc cataatagta aacagcccct tgtgttggatg taacccaatc    4860 ccagatttga gtgtgtgttg attattttt tgtcttccac ttttctatta tgtgtaaatc    4920
acttttattt ctgcagacat tttcctctca gataggatga catttgttt tgtattattt    4980 tgtctttcct catgaatgca ctgataatat tttaaatgct ctattttaag atctcttgaa    5040 tctgttttt tttttttaa tttggggggt ctgtaaggtc tttatttccc ataagtaaat    5100
attgccatgg gagggggtg gaggtggcaa ggaagggtg aagtgctagt atgcaagtgg    5160
gcagcaatta tttttgtgtt aatcagcagt acaatttgat cgttggcatg gttaaaaaat    5220
ggaatataag attagctgtt ttgtattttg atgaccaatt acgctgtatt ttaacacgat    5280
gtatgtctgt ttttgtggtg ctctagtggt aaataaatta tttcgatgat atgtggatgt    5340 cttttttccta tcagtaccat catcgagtct agaaaacacc tgtgatgcaa taagactatc    5400
tcaagctgga aaagtcatac cacctttccg attgccctct gtgctttctc ccttaaggac    5460
agtcacttca gaagtcatgc tttaaagcac aagagtcagg ccatatccat caaggataga    5520
agaaatccct gtgccgtctt tttattccct tatttattgc tatttggtaa ttgtttgaga    5580
```

-continued

```
tttagttttcc atccagcttg actgccgacc agaaaaaatg cagagagatg tttgcaccat    5640
gctttggctt tctggttcta tgttctgcca acgccagggc caaaagaact ggtctagaca    5700
gtatcccctg tagccccata acttggatag ttgctgagcc agccagatat aacaagagcc    5760
acgtgctttc tggggttggt tgtttgggat cagctacttg cctgtcagtt tcactggtac    5820
cactgcacca caaacaaaaa aacccaccct atttcctcca atttttttgg ctgctaccta    5880
caagaccaga ctcctcaaac gagttgccaa tctcttaata aataggatta ataaaaaaag    5940
taattgtgac tcaaaaaaaa aaaaaa                                         5966
```

<210> SEQ ID NO 128
<211> LENGTH: 442
<212> TYPE: PRT
<213> ORGANISM: Homo sapiens

<400> SEQUENCE: 128

```
Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
        35                  40                  45

Lys Leu Thr Ser Pro Pro Glu Asp Tyr Pro Glu Pro Glu Glu Val Pro
    50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
            100                 105                 110

Pro Ser Glu Thr Val Cys Pro Val Val Thr Thr Pro Ser Gly Ser Val
        115                 120                 125

Gly Ser Leu Cys Ser Arg Gln Ser Gln Val Leu Cys Gly Tyr Leu Asp
    130                 135                 140

Ala Ile Pro Pro Thr Phe Tyr Arg Pro Tyr Phe Arg Ile Val Arg Phe
145                 150                 155                 160

Asp Val Ser Ala Met Glu Lys Asn Ala Ser Asn Leu Val Lys Ala Glu
                165                 170                 175

Phe Arg Val Phe Arg Leu Gln Asn Pro Lys Ala Arg Val Pro Glu Gln
            180                 185                 190

Arg Ile Glu Leu Tyr Gln Ile Leu Lys Ser Lys Asp Leu Thr Ser Pro
        195                 200                 205

Thr Gln Arg Tyr Ile Asp Ser Lys Val Val Lys Thr Arg Ala Glu Gly
    210                 215                 220

Glu Trp Leu Ser Phe Asp Val Thr Asp Ala Val His Glu Trp Leu His
225                 230                 235                 240

His Lys Asp Arg Asn Leu Gly Phe Lys Ile Ser Leu His Cys Pro Cys
                245                 250                 255

Cys Thr Phe Val Pro Ser Asn Asn Tyr Ile Ile Pro Asn Lys Ser Glu
            260                 265                 270

Glu Leu Glu Ala Arg Phe Ala Gly Ile Asp Gly Thr Ser Thr Tyr Thr
        275                 280                 285

Ser Gly Asp Gln Lys Thr Ile Lys Ser Thr Arg Lys Lys Asn Ser Gly
    290                 295                 300
```

-continued

```
Lys Thr Pro His Leu Leu Leu Met Leu Leu Pro Ser Tyr Arg Leu Glu
305                 310                 315                 320

Ser Gln Gln Thr Asn Arg Arg Lys Lys Arg Ala Leu Asp Ala Ala Tyr
            325                 330                 335

Cys Phe Arg Asn Val Gln Asp Asn Cys Cys Leu Arg Pro Leu Tyr Ile
        340                 345                 350

Asp Phe Lys Arg Asp Leu Gly Trp Lys Trp Ile His Glu Pro Lys Gly
    355                 360                 365

Tyr Asn Ala Asn Phe Cys Ala Gly Ala Cys Pro Tyr Leu Trp Ser Ser
370                 375                 380

Asp Thr Gln His Ser Arg Val Leu Ser Leu Tyr Asn Thr Ile Asn Pro
385                 390                 395                 400

Glu Ala Ser Ala Ser Pro Cys Cys Val Ser Gln Asp Leu Glu Pro Leu
            405                 410                 415

Thr Ile Leu Tyr Tyr Ile Gly Lys Thr Pro Lys Ile Glu Gln Leu Ser
        420                 425                 430

Asn Met Ile Val Lys Ser Cys Lys Cys Ser
            435                 440
```

```
<210> SEQ ID NO 129
<211> LENGTH: 20
<212> TYPE: RNA
<213> ORGANISM: Artificial Sequence
<220> FEATURE:
<223> OTHER INFORMATION: synthetic construct

<400> SEQUENCE: 129
uaucucuauc ucaaucuguc                                              20

<210> SEQ ID NO 130
<211> LENGTH: 20
<212> TYPE: RNA
<213> ORGANISM: Artificial Sequence
<220> FEATURE:
<223> OTHER INFORMATION: synthetic construct

<400> SEQUENCE: 130
uucuaucucu aucucaaucu                                              20

<210> SEQ ID NO 131
<211> LENGTH: 20
<212> TYPE: RNA
<213> ORGANISM: Artificial Sequence
<220> FEATURE:
<223> OTHER INFORMATION: synthetic construct

<400> SEQUENCE: 131
uucucuuucu aucucuaucu                                              20

<210> SEQ ID NO 132
<211> LENGTH: 20
<212> TYPE: RNA
<213> ORGANISM: Artificial Sequence
<220> FEATURE:
<223> OTHER INFORMATION: synthetic construct

<400> SEQUENCE: 132
ucuaucucua ucucaaucug                                              20

<210> SEQ ID NO 133
<211> LENGTH: 31
<212> TYPE: DNA
```

<213> ORGANISM: Artificial Sequence
<220> FEATURE:
<223> OTHER INFORMATION: synthetic construct

<400> SEQUENCE: 133
ccggtcttct atctctatct caatcgaccg g         31

<210> SEQ ID NO 134
<211> LENGTH: 31
<212> TYPE: DNA
<213> ORGANISM: Artificial Sequence
<220> FEATURE:
<223> OTHER INFORMATION: synthetic construct

<400> SEQUENCE: 134
ccggtctatc tctatctcaa tctgtgaccg g         31

<210> SEQ ID NO 135
<211> LENGTH: 31
<212> TYPE: DNA
<213> ORGANISM: Artificial Sequence
<220> FEATURE:
<223> OTHER INFORMATION: synthetic construct

<400> SEQUENCE: 135
ccggtcttct ctttctatct ctatcgaccg g         31

<210> SEQ ID NO 136
<211> LENGTH: 7321
<212> TYPE: DNA
<213> ORGANISM: Homo sapiens

<400> SEQUENCE: 136

```
ttttgtagat aaatgtgagg attttctcta aatccctctt ctgtttgcta aatctcactg    60
tcactgctaa attcagagca gatagagcct gcgcaatgga ataaagtcct caaaattgaa   120
atgtgacatt gctctcaaca tctcccatct ctctggattt cttttgctt cattattcct    180
gctaaccaat tcattttcag actttgtact tcagaagcaa tgggaaaaat cagcagtctt   240
ccaacccaat tatttaagtg ctgcttttgt gatttcttga aggtgaagat gcacaccatg   300
tcctcctcgc atctcttcta cctggcgctg tgcctgctca ccttcaccag ctctgccacg   360
gctggaccgg agacgctctg cggggctgag ctggtggatg ctcttcagtt cgtgtgtgga   420
gacaggggct tttatttcaa caagcccaca gggtatggct ccagcagtcg gagggcgcct   480
cagacaggca tcgtggatga gtgctgcttc cggagctgtg atctaaggag gctggagatg   540
tattgcgcac ccctcaagcc tgccaagtca gctcgctctg tccgtgccca gcgccacacc   600
gacatgccca gacccagaa ggaagtacat ttgaagaacg caagtagagg gagtgcagga   660
aacaagaact acaggatgta ggaagaccct cctgaggagt gaagagtgac atgccaccgc   720
aggatccttt gctctgcacg agttacctgt taaactttgg aacacctacc aaaaaataag   780
tttgataaca tttaaaagat gggcgtttcc cccaatgaaa tacacaagta acattccaa    840
cattgtcttt aggagtgatt tgcaccttgc aaaaatggtc ctggagttgg tagattgctg   900
ttgatctttt atcaataatg ttctatagaa aagaaaaaaa aatatatat atatatatat   960
cttagtccct gcctctcaag agccacaaat gcatgggtgt tgtatagatc cagttgcact  1020
aaattcctct ctgaatcttg gctgctggag ccattcattc agcaaccttg tctaagtggt  1080
ttatgaattg tttccttatt tgcacttctt tctacacaac tcgggctgtt tgttttacag  1140
tgtctgataa tcttgttagt ctatacccac cacctcctt cataacctt atatttgccg   1200
```

-continued

| | |
|---|---|
| aatttggcct cctcaaaagc agcagcaagt cgtcaagaag cacaccaatt ctaacccaca | 1260 |
| agattccatc tgtggcattt gtaccaaata taagttggat gcattttatt ttagacacaa | 1320 |
| agctttattt ttccacatca tgcttacaaa aagaataat gcaaatagtt gcaactttga | 1380 |
| ggccaatcat ttttaggcat atgttttaaa catagaaagt ttcttcaact caaaagagtt | 1440 |
| ccttcaaatg atgagttaat gtgcaaccta attagtaact ttcctctttt tattttttcc | 1500 |
| atatagagca ctatgtaaat ttagcatatc aattatacag gatatatcaa acagtatgta | 1560 |
| aaactctgtt ttttagtata atggtgctat tttgtagttt gttatatgaa agagtctggc | 1620 |
| caaaacggta atacgtgaaa gcaaaacaat aggggaagcc tggagccaaa gatgacacaa | 1680 |
| ggggaagggt actgaaaaca ccatccattt gggaagaag gcaaagtccc cccagttatg | 1740 |
| ccttccaaga ggaacttcag acacaaaagt ccactgatgc aaattggact ggcgagtcca | 1800 |
| gagaggaaac tgtggaatgg aaaaagcaga aggctaggaa ttttagcagt cctggtttct | 1860 |
| ttttctcatg gaagaaatga acatctgcca gctgtgtcat ggactcacca ctgtgtgacc | 1920 |
| ttgggcaagt cacttcacct ctctgtgcct cagtttcctc atctgcaaaa tggggggcaat | 1980 |
| atgtcatcta cctacctcaa aggggtggta taaggtttaa aaagataaag attcagattt | 2040 |
| ttttacccct gggttgctgt aagggtgcaa catcagggcg cttgagttgc tgagatgcaa | 2100 |
| ggaattctat aaataaccca ttcatagcat agctagagat tggtgaattg aatgctcctg | 2160 |
| acatctcagt tcttgtcagt gaagctatcc aaataactgg ccaactagtt gttaaaagct | 2220 |
| aacagctcaa tctcttaaaa cacttttcaa aatatgtggg aagcatttga ttttcaattt | 2280 |
| gattttgaat tctgcatttg gttttatgaa tacaaagata agtgaaaaga gagaaaggaa | 2340 |
| aagaaaaagg agaaaaacaa agagattct accagtgaaa ggggaattaa ttactctttg | 2400 |
| ttagcactca ctgactcttc tatgcagtta ctacatatct agtaaaacct cgtttaatac | 2460 |
| tataaataat attctattca ttttgaaaaa cacaatgatt ccttcttttc taggcaatat | 2520 |
| aaggaaagtg atccaaaatt tgaaatatta aaataatatc taataaaaag tcacaaagtt | 2580 |
| atcttcttta acaaacttta ctcttattct tagctgtata tacattttt taaaagtttg | 2640 |
| ttaaaatatg cttgactaga gtttccagtt gaaaggcaaa aacttccatc acaacaagaa | 2700 |
| atttcccatg cctgctcaga agggtagccc ctagctctct gtgaatgtgt tttatccatt | 2760 |
| caactgaaaa ttggtatcaa gaaagtccac tggttagtgt actagtccat catagcctag | 2820 |
| aaaatgatcc ctatctgcag atcaagattt tctcattaga acaatgaatt atccagcatt | 2880 |
| cagatctttc tagtcacctt agaactttt ggttaaaagt acccaggctt gattatttca | 2940 |
| tgcaaattct atattttaca ttcttggaaa gtctatatga aaacaaaaa taacatcttc | 3000 |
| agttttctc ccactgggtc acctcaagga tcagaggcca ggaaaaaaaa aaaaagact | 3060 |
| ccctggatct ctgaatatat gcaaaagaa ggccccattt agtggagcca gcaatcctgt | 3120 |
| tcagtcaaca agtattttaa ctctcagtcc aacattattt gaattgagca cctcaagcat | 3180 |
| gcttagcaat gttctaatca ctatggacag atgtaaaaga aactatacat cattttgcc | 3240 |
| ctctgcctgt tttccagaca tacaggttct gtggaataag atactggact cctcttccca | 3300 |
| agatggcact tcttttat tcttgtcccc agtgtgtacc tttaaaatt attccctctc | 3360 |
| aacaaaactt tataggcagt cttctgcaga cttaacgtgt tttctgtcat agttagatgt | 3420 |
| gataattcta agagtgtcta tgacttattt ccttcactta attctatcca cagtcaaaaa | 3480 |
| tcccccaagg aggaaagctg aaagatgcac tgccatatta tctttcttaa cttttttccaa | 3540 |

```
cacataatcc tctccaactg gattataaat aaattgaaaa taactcatta taccaattca    3600
ctattttatt ttttaatgaa ttaaaactag aaaacaaatt gatgcaaacc ctggaagtca    3660
gttgattact atatactaca gcagaatgac tcagatttca tagaaaggag caaccaaaat    3720
gtcacaaccc aaaactttac aagctttgct tcagaattag attgctttat aattcttgaa    3780
tgaggcaatt tcaagatatt tgtaaaagaa cagtaaacat tggtaagaat gagctttcaa    3840
ctcataggct tatttccaat ttaattgacc atactggata cttaggtcaa atttctgttc    3900
tctcttcccc aaataatatt aaagtattat ttgaactttt taagatgagg cagttcccct    3960
gaaaaagtta atgcagctct ccatcagaat ccactcttct agggatatga aaatctctta    4020
acacccaccc tacatacaca gacacacaca cacacacaca cacacacaca cacacacaca    4080
ttcaccctaa ggatccaatg gaatactgaa aagaaatcac ttccttgaaa attttattaa    4140
aaaacaaaca aacaaacaaa aagcctgtcc acccttgaga atccttcctc tccttggaac    4200
gtcaatgttt gtgtagatga aaccatctca tgctctgtgg ctccagggtt tctgttacta    4260
ttttatgcac ttgggagaag gcttagaata aaagatgtag cacattttgc tttcccattt    4320
attgtttggc cagctatgcc aatgtggtgc tattgtttct ttaagaaagt acttgactaa    4380
aaaaaaaaga aaaaagaaa aaaaagaaag catagacata ttttttttaaa gtataaaaac    4440 aacaattcta tagatagatg gcttaataaa atagcattag gtctatctag ccaccaccac    4500
ctttcaactt tttatcactc acaagtagtg tactgttcac caaattgtga atttgggggt    4560 gcagggcag gagttggaaa ttttttaaag ttagaaggct ccattgtttt gttggctctc    4620
aaacttagca aaaattagcaa tatattatcc aatcttctga acttgatcaa gagcatggag    4680
aataaacgcg ggaaaaaaga tcttataggc aaatagaaga atttaaaaga taagtaagtt    4740
ccttattgat ttttgtgcac tctgctctaa acagatatt cagcaagtgg agaaaataag    4800
aacaaagaga aaaaatacat agatttacct gcaaaaaata gcttctgcca aatcccccctt    4860 gggtattctt tggcatttac tggtttatag aagacattct cccttcaccc agacatctca    4920
aagagcagta gctctcatga aaagcaatca ctgatctcat ttgggaaatg ttggaaagta    4980
tttccttatg agatggggt tatctactga taaagaaaga attttatgaga aattgttgaa    5040 agagatggct aacaatctgt gaagattttt tgtttcttgt ttttgttttt tttttttttt    5100
tactttatac agtctttatg aatttcttaa tgttcaaaat gacttggttc ttttcttctt    5160
tttttatatc agaatgagga ataataagtt aaacccacat agactcttta aaactatagg    5220
ctagatagaa atgtatgttt gacttgttga agctataatc agactattta aaatgttttg    5280 ctattttttaa tcttaaaaga ttgtgctaat ttattagagc agaacctgtt tggctctcct    5340
cagaagaaag aatctttcca ttcaaatcac atggctttcc accaatattt tcaaagata    5400 aatctgattt atgcaatggc atcatttatt ttaaaacaga agaattgtga agtttatgc    5460 ccctcccttg caaagaccat aaagtccaga tctggtaggg gggcaacaac aaaaggaaaa    5520
tgttgttgat tcttggtttt ggattttgtt ttgttttcaa tgctagtgtt taatcctgta    5580
gtacatattt gcttattgct attttaatat tttataagac cttcctgtta ggtattagaa    5640
agtgatacat agatatcttt tttgtgtaat ttctatttaa aaaagagaga agactgtcag    5700
aagctttaag tgcatatggt acaggataaa gatatcaatt taaataacca attcctatct    5760
ggaacaatgc ttttgttttt taagaaacc tctcacagat aagacagagg cccagggat    5820 ttttgaagct gtctttattc tgcccccatc ccacccagc ccttattatt ttagtatctg    5880
cctcagaatt ttatagaggg ctgaccaagc tgaaactcta gaattaaagg aacctcactg    5940
```

```
aaaacatata tttcacgtgt tccctctttt ttttttttcct ttttgtgaga tggggtctcg  6000
cactgtcccc caggctggag tgcagtggca tgatctcggc tcactgcaac ctccacctcc  6060
tgggtttaag cgattctcct gcctcagcct cctgagtagc tgggattaca ggcacccacc  6120
actatgcccg gctaattttt tggattttta atagagacgg ggttttacca tgttggccag  6180
gttggtctca aactcctgac cttgtgattt gcccgcctca gcctcccaaa ttgctgggat  6240
tacaggcatg agccaccaca ccctgcccat gtgttccctc ttaatgtatg attacatgga  6300
tcttaaacat gatccttctc tcctcattct tcaactatct tgatggggt ctttcaaggg  6360
gaaaaaaatc caagcttttt taaagtaaaa aaaaaaaag agaggacaca aaaccaaatg  6420
ttactgctca actgaaatat gagttaagat ggagacagag tttctcctaa taaccggagc  6480
tgaattacct ttcactttca aaacatgac cttccacaat ccttagaatc tgccttttt  6540
tatattactg aggcctaaaa gtaaacatta ctcattttat tttgcccaaa atgcactgat  6600
gtaaagtagg aaaaataaaa acagagctct aaaatcccctt tcaagccacc cattgacccc  6660
actcaccaac tcatagcaaa gtcacttctg ttaatcccctt aatctgattt tgtttggata  6720
tttatcttgt acccgctgct aaacacactg caggagggac tctgaaacct caagctgtct  6780
acttacatct tttatctgtg tctgtgtatc atgaaaatgt ctattcaaaa tatcaaaacc  6840
tttcaaatat cacgcagctt atattcagtt tacataaagg ccccaaatac catgtcagat  6900
cttttttggta aaagagttaa tgaactatga gaattgggat tacatcatgt attttgcctc  6960
atgtatttttt atcacactta taggccaagt gtgataaata aacttacaga cactgaatta  7020
atttcccctg ctactttgaa accagaaaat aatgactggc cattcgttac atctgtctta  7080
gttgaaaagc atattttttta ttaaattaat tctgattgta tttgaaatta ttattcaatt  7140
cacttatggc agaggaatat caatcctaat gacttctaaa aatgtaacta attgaatcat  7200
tatcttacat ttactgttta ataagcatat tttgaaaatg tatggctaga gtgtcataat  7260
aaaatggtat atctttcttt agtaattaca ttaaaattag tcatgtttga ttaattagtt  7320
c                                                                  7321
```

<210> SEQ ID NO 137
<211> LENGTH: 153
<212> TYPE: PRT
<213> ORGANISM: Homo sapiens

<400> SEQUENCE: 137

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
                20                  25                  30

Phe Tyr Leu Ala Leu Cys Leu Leu Thr Phe Thr Ser Ser Ala Thr Ala
            35                  40                  45

Gly Pro Glu Thr Leu Cys Gly Ala Glu Leu Val Asp Ala Leu Gln Phe
        50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp

```
              115                 120                 125
Met Pro Lys Thr Gln Lys Glu Val His Leu Lys Asn Ala Ser Arg Gly
     130                 135                 140

Ser Ala Gly Asn Lys Asn Tyr Arg Met
145                 150
```

<210> SEQ ID NO 138
<211> LENGTH: 19
<212> TYPE: RNA
<213> ORGANISM: Artificial Sequence
<220> FEATURE:
<223> OTHER INFORMATION: synthetic construct

<400> SEQUENCE: 138
uaaacugaau auaagcugc                                              19

<210> SEQ ID NO 139
<211> LENGTH: 19
<212> TYPE: RNA
<213> ORGANISM: Artificial Sequence
<220> FEATURE:
<223> OTHER INFORMATION: synthetic construct

<400> SEQUENCE: 139
uaaaaaaaua ugucuaugc                                              19

<210> SEQ ID NO 140
<211> LENGTH: 19
<212> TYPE: RNA
<213> ORGANISM: Artificial Sequence
<220> FEATURE:
<223> OTHER INFORMATION: synthetic construct

<400> SEQUENCE: 140
uuuaacaggu aacucgugc                                              19

<210> SEQ ID NO 141
<211> LENGTH: 19
<212> TYPE: RNA
<213> ORGANISM: Artificial Sequence
<220> FEATURE:
<223> OTHER INFORMATION: synthetic construct

<400> SEQUENCE: 141
uaacaaacua caaaauagc                                              19

<210> SEQ ID NO 142
<211> LENGTH: 32
<212> TYPE: DNA
<213> ORGANISM: Artificial Sequence
<220> FEATURE:
<223> OTHER INFORMATION: synthetic construct

<400> SEQUENCE: 142
ccggtctaaa ctgaatataa gctgcggacc gg                               32

<210> SEQ ID NO 143
<211> LENGTH: 32
<212> TYPE: DNA
<213> ORGANISM: Artificial Sequence
<220> FEATURE:
<223> OTHER INFORMATION: synthetic construct

<400> SEQUENCE: 143
ccggtctttc aattcttcta tttgccgacc gg                               32

<210> SEQ ID NO 144
<211> LENGTH: 32
<212> TYPE: DNA
<213> ORGANISM: Artificial Sequence
<220> FEATURE:
<223> OTHER INFORMATION: synthetic construct

<400> SEQUENCE: 144

```
ccggtctaat caactgactt ccaggggacc gg                                 32
```

<210> SEQ ID NO 145
<211> LENGTH: 3150
<212> TYPE: DNA
<213> ORGANISM: Homo sapiens

<400> SEQUENCE: 145

```
ccacaaaggg cacttggccc cagggctagg agagcgaggg gagagcacag ccacccgcct     60
cggcggcccg ggactcggct cgactcgccg gagaatgcgc ccgaggacga cggggcgcca    120
gagccgcggt gctttcaact ggcgagcgcg aatgggggtg cactggagta aggcagagtg    180
atgcgggggg gcaactcgcc tggcaccgag atcgccgccg tgcccttccc tggacccggc    240
gtcgcccagg atggctgccc cgagccatgg gccgcggcgg agctagcgcg gagcgcccga    300
ccctcgaccc ccgagtcccg gagccggccc cgcgcggggc cacgcgtccc tcgggcgctg    360
gttcctaagg aggacgacag caccagcttc tcctttctcc cttcccttcc ctgccccgca    420
ctcctccccc tgctcgctgt tgttgtgtgt cagcacttgg ctggggactt cttgaacttg    480
cagggagaat aacttgcgca ccccactttg cgccggtgcc tttgcccag cggagcctgc    540
ttcgccatct ccgagcccca ccgcccctcc actcctcggc cttgcccgac actgagacgc    600
tgttcccagc gtgaaaagag agactgcgcg gccggcaccc gggagaagga ggaggcaaag    660
aaaaggaacg gacattcggt ccttgcgcca ggtcctttga ccagagttttt tccatgtgga    720
cgctctttca atgacgtgt ccccgcgtgc ttcttagacg gactgcggtc tcctaaaggt    780
cgaccatggt ggccgggacc cgctgtcttc tagcgttgct gcttcccag gtcctcctgg    840
gcggcgcggc tggcctcgtt ccggagctgg gccgcaggaa gttcgcggcg cgtcgtcgg    900
gccgccctc atcccagccc tctgacgagg tcctgagcga gttcgagttg cggctgctca    960
gcatgttcgg cctgaaacag agacccaccc ccagcaggga cgccgtggtg ccccctaca   1020
tgctagacct gtatcgcagg cactcaggtc agccgggctc acccgcccca gaccaccggt   1080
tggagagggc agccagccga gccaacactg tgcgcagctt ccaccatgaa gaatctttgg   1140
aagaactacc agaaacgagt gggaaaacaa cccggagatt cttctttaat ttaagttcta   1200
tccccacgga ggagtttatc acctcagcag agcttcaggt tttccgagaa cagatgcaag   1260
atgctttagg aaacaatagc agtttccatc accgaattaa tatttatgaa atcataaaac   1320
ctgcaacagc caactcgaaa ttccccgtga ccagactttt ggacaccagg ttggtgaatc   1380
agaatgcaag caggtgggaa agtttttgatg tcaccccccgc tgtgatgcgg tggactgcac   1440
agggacacgc caaccatgga ttcgtggtgg aagtggccca cttggaggag aaacaaggtg   1500
tctccaagag acatgttagg ataagcaggt ctttgcacca agatgaacac agctggtcac   1560
agataaggcc attgctagta acttttggcc atgatggaaa agggcatcct ctccacaaaa   1620
gagaaaaacg tcaagccaaa cacaaacagc ggaaacgcct taagtccagc tgtaagagac   1680
acccttttgta cgtggacttc agtgacgtgg ggtggaatga ctggattgtg gctccccgg   1740
```

| | |
|---|---|
| ggtatcacgc cttttactgc cacggagaat gccctttttcc tctggctgat catctgaact | 1800 |
| ccactaatca tgccattgtt cagacgttgg tcaactctgt taactctaag attcctaagg | 1860 |
| catgctgtgt cccgacagaa ctcagtgcta tctcgatgct gtaccttgac gagaatgaaa | 1920 |
| aggttgtatt aaagaactat caggacatgg ttgtgggggg ttgtgggtgt cgctagtaca | 1980 |
| gcaaaattaa atacataaat atatatatat atatatattt tagaaaaaag aaaaaaacaa | 2040 |
| acaaacaaaa aaaccccacc ccagttgaca ctttaatatt tcccaatgaa gactttattt | 2100 |
| atggaatgga atgaaaaaa aaacagctat tttgaaaata tatttatatc tacgaaaaga | 2160 |
| agttgggaaa acaaatattt taatcagaga attattcctt aaagatttaa aatgtattta | 2220 |
| gttgtacatt ttatatgggt tcaaccccag cacatgaagt ataatggtca gatttatttt | 2280 |
| gtatttattt actattataa ccactttta ggaaaaaaat agctaatttg tatttatatg | 2340 |
| taatcaaaag aagtatcggg tttgtacata attttccaaa aattgtagtt gttttcagtt | 2400 |
| gtgtgtattt aagatgaaaa gtctacatgg aaggttactc tggcaaagtg cttagcacgt | 2460 |
| ttgcttttt gcagtgctac tgttgagttc acaagttcaa gtccagaaaa aaaagtgga | 2520 |
| taatccactc tgctgacttt caagattatt atattattca attctcagga atgttgcaga | 2580 |
| gtgattgtcc aatccatgag aatttacatc cttattaggt ggaatatttg gataagaacc | 2640 |
| agacattgct gatctattat agaaactctc ctcctgccc ttaatttaca gaaagaataa | 2700 |
| agcaggatcc atagaaataa ttaggaaaac gatgaacctg caggaaagtg aatgatggtt | 2760 |
| tgttgttctt ctttcctaaa ttagtgatcc cttcaaaggg gctgatctgg ccaaagtatt | 2820 |
| caataaaacg taagatttct tcattattga tattgtggtc atatatattt aaaattgata | 2880 |
| tctcgtggcc ctcatcaagg gttggaaatt tatttgtgtt ttaccttttac ctcatctgag | 2940 |
| agctctttat tctccaaaga acccagtttt ctaactttt gcccaacacg cagcaaaatt | 3000 |
| atgcacatcg tgttttctgc ccaccctctg ttctctgacc tatcagcttg cttttctttc | 3060 |
| caaggttgtg tgtttgaaca catttctcca aatgttaaac ctatttcaga taataaatat | 3120 |
| caaatctctg gcatttcatt ctataaagtc | 3150 |

<210> SEQ ID NO 146
<211> LENGTH: 396
<212> TYPE: PRT
<213> ORGANISM: Homo sapiens

<400> SEQUENCE: 146

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
    370                 375                 380

Tyr Gln Asp Met Val Val Glu Gly Cys Gly Cys Arg
385                 390                 395

<210> SEQ ID NO 147
<211> LENGTH: 19
<212> TYPE: RNA
<213> ORGANISM: Artificial Sequence
<220> FEATURE:
<223> OTHER INFORMATION: synthetic construct

<400> SEQUENCE: 147
uugugaacuc aacaguagc                                                  19

<210> SEQ ID NO 148
<211> LENGTH: 19
<212> TYPE: RNA
<213> ORGANISM: Artificial Sequence
<220> FEATURE:
<223> OTHER INFORMATION: synthetic construct

<400> SEQUENCE: 148
uuaauuuugc uguacuagc                                                  19

<210> SEQ ID NO 149
<211> LENGTH: 19

```
<212> TYPE: RNA
<213> ORGANISM: Artificial Sequence
<220> FEATURE:
<223> OTHER INFORMATION: synthetic construct

<400> SEQUENCE: 149
uaaaacacaa auaaauuuc                                              19

<210> SEQ ID NO 150
<211> LENGTH: 19
<212> TYPE: RNA
<213> ORGANISM: Artificial Sequence
<220> FEATURE:
<223> OTHER INFORMATION: synthetic construct

<400> SEQUENCE: 150
uucuuucugu aaauuaagg                                              19

<210> SEQ ID NO 151
<211> LENGTH: 30
<212> TYPE: DNA
<213> ORGANISM: Artificial Sequence
<220> FEATURE:
<223> OTHER INFORMATION: synthetic construct

<400> SEQUENCE: 151
ccggtctaat acaaaataaa tctggaccgg                                  30

<210> SEQ ID NO 152
<211> LENGTH: 31
<212> TYPE: DNA
<213> ORGANISM: Artificial Sequence
<220> FEATURE:
<223> OTHER INFORMATION: synthetic construct

<400> SEQUENCE: 152
ccggtcaaaa cacaaataaa tttccgaccg g                                31

<210> SEQ ID NO 153
<211> LENGTH: 31
<212> TYPE: DNA
<213> ORGANISM: Artificial Sequence
<220> FEATURE:
<223> OTHER INFORMATION: synthetic construct

<400> SEQUENCE: 153
ccggtcttca ttctcgtcaa ggtacgaccg g                                31

<210> SEQ ID NO 154
<211> LENGTH: 1957
<212> TYPE: DNA
<213> ORGANISM: Homo sapiens

<400> SEQUENCE: 154
aagaggagga aggaagatgc gagaaggcag aggaggaggg agggagggaa ggagcgcgga    60
gcccggcccg gaagctaggt gagtgtggca tccgagctga gggacgcgag cctgagacgc   120
cgctgctgct ccggctgagt atctagcttg tctccccgat gggattcccg tccaagctat   180
ctcgagcctg cagcgccaca gtccccggcc ctcgcccagg ttcactgcaa ccgttcagag   240
gtccccagga gctgctgctg gcgagcccgc tactgcaggg acctatggag ccattccgta   300
gtgccatccc gagcaacgca ctgctgcagc ttccctgagc cttccagca agtttgttca    360 agattggctg tcaagaatca tggactgtta ttatatgcct tgttttctgt caagacacca   420
```

-continued

```
tgattcctgg taaccgaatg ctgatggtcg ttttattatg ccaagtcctg ctaggaggcg      480
cgagccatgc tagtttgata cctgagacgg gaagaaaaa agtcgccgag attcagggcc       540
acgcgggagg acgccgctca gggcagagcc atgagctcct gcgggacttc gaggcgacac      600
ttctgcagat gtttgggctg cgccgccgcc cgcagcctag caagagtgcc gtcattccgg      660
actacatgcg ggatctttac cggcttcagt ctggggagga ggaggaagag cagatccaca      720
gcactggtct tgagtatcct gagcgccgg ccagccgggc aacaccgtg aggagcttcc        780 accacgaaga acatctggag aacatcccag ggaccagtga aaactctgct tttcgtttcc      840
tctttaacct cagcagcatc cctgagaacg aggtgatctc ctctgcagag cttcggctct      900
tccgggagca ggtggaccag ggccctgatt gggaagggg cttccaccgt ataaacattt       960
atgaggttat gaagccccca gcagaagtgg tgcctgggca cctcatcaca cgactactgg     1020
acacgagact ggtccaccac aatgtgacac ggtgggaaac ttttgatgtg agccctgcgg     1080
tccttcgctg gacccgggag aagcagccaa actatgggct agccattgag gtgactcacc     1140
tccatcagac tcggacccac cagggccagc atgtcaggat tagccgatcg ttacctcaag     1200
ggagtgggaa ttgggcccag ctccggcccc tcctggtcac ctttggccat gatggccggg     1260
gccatgcctt gacccgacgc cggagggcca agcgtagccc taagcatcac tcacagcggg     1320
ccaggaagaa gaataagaac tgccggcgcc actcgctcta tgtggacttc agcgatgtgg     1380
gctggaatga ctggattgtg gccccaccag gctaccaggc cttctactgc catgggact      1440 gccccttttcc actggctgac cacctcaact caaccaacca tgccattgtg cagaccctgg     1500
tcaattctgt caattccagt atccccaaag cctgttgtgt gcccactgaa ctgagtgcca     1560
tctccatgct gtacctggat gagtatgata aggtggtact gaaaaattat caggagatgg     1620
tagtagaggg atgtgggtgc cgctgagatc aggcagtcct tgaggataga cagatataca     1680
caccacacac acacaccaca taccacacac acacgttc ccatccactc acccacacac       1740
tacacagact gcttccttat agctggactt ttatttaaaa aaaaaaaaa aaaaggaaaa       1800 aatccctaaa cattcacctt gaccttattt atgactttac gtgcaaatgt tttgaccata     1860
ttgatcatat attttgacaa aatatattta taactacgta ttaaaagaaa aaataaaat     1920 gagtcattat tttaaaggta aaaaaaaaa aaaaaaa                                1957
```

<210> SEQ ID NO 155
<211> LENGTH: 408
<212> TYPE: PRT
<213> ORGANISM: Homo sapiens

<400> SEQUENCE: 155

```
Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
```

-continued

```
                100                 105                 110
Arg Ala Asn Thr Val Arg Ser Phe His His Glu Glu His Leu Glu Asn
            115                 120                 125
Ile Pro Gly Thr Ser Glu Asn Ser Ala Phe Arg Phe Leu Phe Asn Leu
        130                 135                 140
Ser Ser Ile Pro Glu Asn Glu Val Ile Ser Ala Glu Leu Arg Leu
145                 150                 155                 160
Phe Arg Glu Gln Val Asp Gln Gly Pro Asp Trp Glu Arg Gly Phe His
                165                 170                 175
Arg Ile Asn Ile Tyr Glu Val Met Lys Pro Ala Glu Val Val Pro
            180                 185                 190
Gly His Leu Ile Thr Arg Leu Leu Asp Thr Arg Leu Val His His Asn
        195                 200                 205
Val Thr Arg Trp Glu Thr Phe Asp Val Ser Pro Ala Val Leu Arg Trp
210                 215                 220
Thr Arg Glu Lys Gln Pro Asn Tyr Gly Leu Ala Ile Glu Val Thr His
225                 230                 235                 240
Leu His Gln Thr Arg Thr His Gln Gly Gln His Val Arg Ile Ser Arg
                245                 250                 255
Ser Leu Pro Gln Gly Ser Gly Asn Trp Ala Gln Leu Arg Pro Leu Leu
            260                 265                 270
Val Thr Phe Gly His Asp Gly Arg Gly His Ala Leu Thr Arg Arg Arg
        275                 280                 285
Arg Ala Lys Arg Ser Pro Lys His His Ser Gln Arg Ala Arg Lys Lys
    290                 295                 300
Asn Lys Asn Cys Arg Arg His Ser Leu Tyr Val Asp Phe Ser Asp Val
305                 310                 315                 320
Gly Trp Asn Asp Trp Ile Val Ala Pro Pro Gly Tyr Gln Ala Phe Tyr
                325                 330                 335
Cys His Gly Asp Cys Pro Phe Pro Leu Ala Asp His Leu Asn Ser Thr
            340                 345                 350
Asn His Ala Ile Val Gln Thr Leu Val Asn Ser Val Asn Ser Ser Ile
        355                 360                 365
Pro Lys Ala Cys Cys Val Pro Thr Glu Leu Ser Ala Ile Ser Met Leu
    370                 375                 380
Tyr Leu Asp Glu Tyr Asp Lys Val Val Leu Lys Asn Tyr Gln Glu Met
385                 390                 395                 400
Val Val Glu Gly Cys Gly Cys Arg
                405
```

<210> SEQ ID NO 156
<211> LENGTH: 20
<212> TYPE: RNA
<213> ORGANISM: Artificial Sequence
<220> FEATURE:
<223> OTHER INFORMATION: synthetic construct

<400> SEQUENCE: 156
uaauaaaacg accaucagca                      20

<210> SEQ ID NO 157
<211> LENGTH: 20
<212> TYPE: RNA
<213> ORGANISM: Artificial Sequence
<220> FEATURE:
<223> OTHER INFORMATION: synthetic construct

```
<400> SEQUENCE: 157
uaucugucua uccucaagga                                              20

<210> SEQ ID NO 158
<211> LENGTH: 20
<212> TYPE: RNA
<213> ORGANISM: Artificial Sequence
<220> FEATURE:
<223> OTHER INFORMATION: synthetic construct

<400> SEQUENCE: 158
uucuuauucu ucuuccuggc                                              20

<210> SEQ ID NO 159
<211> LENGTH: 19
<212> TYPE: RNA
<213> ORGANISM: Artificial Sequence
<220> FEATURE:
<223> OTHER INFORMATION: synthetic construct

<400> SEQUENCE: 159
uaauaaaacg accaucagc                                               19

<210> SEQ ID NO 160
<211> LENGTH: 31
<212> TYPE: DNA
<213> ORGANISM: Artificial Sequence
<220> FEATURE:
<223> OTHER INFORMATION: synthetic construct

<400> SEQUENCE: 160
ccggtctatc tgtctatcct caagggaccg g                                 31

<210> SEQ ID NO 161
<211> LENGTH: 31
<212> TYPE: DNA
<213> ORGANISM: Artificial Sequence
<220> FEATURE:
<223> OTHER INFORMATION: synthetic construct

<400> SEQUENCE: 161
ccggtctctc aggtatcaaa ctagcgaccg g                                 31

<210> SEQ ID NO 162
<211> LENGTH: 31
<212> TYPE: DNA
<213> ORGANISM: Artificial Sequence
<220> FEATURE:
<223> OTHER INFORMATION: synthetic construct

<400> SEQUENCE: 162
ccggtctttg tcaaaatata tgatcgaccg g                                 31

<210> SEQ ID NO 163
<211> LENGTH: 4049
<212> TYPE: DNA
<213> ORGANISM: Homo sapiens

<400> SEQUENCE: 163
agcgcgtacc actctggcgc tcccgaggcg gcctcttgtg cgatccaggg cgcacaaggc    60
tgggagagcg ccccgggggcc cctgctatcc gcgccggagg ttggaagagg gtgggttgcc   120
gccgcccgag ggcgagagcg ccagaggagc gggaagaagg agcgctcgcc cgcccgcctg   180
cctcctcgct gcctccccgg cgttggctct ctggactcct aggcttgctg gctgctcctc   240
```

-continued

```
ccacccgcgc ccgcctcctc actcgccttt tcgttcgccg gggctgcttt ccaagccctg    300
cggtgcgccc gggcgagtgc ggggcgaggg gcccggggcc agcaccgagc aggggcgggg    360
ggtccgggca gagcgcggcc ggccggggag gggccatgtc tggcgcgggc gcagcggggc    420
ccgtctgcag caagtgaccg agcggcgcgg acggccgcct gccccctctg ccacctgggg    480
cggtgcgggc ccggagcccg gagcccgggt agcgcgtaga gccggcgcga tgcacgtgcg    540
ctcactgcga gctgcggcgc cgcacagctt cgtggcgctc tgggcacccc tgttcctgct    600
gcgctccgcc ctggccgact tcagcctgga caacgaggtg cactcgagct tcatccaccg    660
gcgcctccgc agccaggagc ggcgggagat gcagcgcgag atcctctcca ttttgggctt    720
gccccaccgc ccgcgcccgc acctccaggg caagcacaac tcggcaccca tgttcatgct    780
ggacctgtac aacgccatgg cggtggagga gggcggcggg cccggcggcc agggcttctc    840
ctaccccTac aaggccgtct tcagtaccca gggcccccct ctggccagcc tgcaagatag    900
ccatttcctc accgacgccg acatggtcat gagcttcgtc aacctcgtgg aacatgacaa    960
ggaattcttc cacccacgct accaccatcg agagttccgg tttgatcttt ccaagatccc    1020
agaaggggaa gctgtcacgg cagccgaatt ccggatctac aaggactaca tccgggaacg    1080
cttcgacaat gagacgttcc ggatcagcgt ttatcaggtg ctccaggagc acttgggcag    1140
ggaatcggat ctcttcctgc tcgacagccg taccctctgg gcctcggagg agggctggct    1200
ggtgtttgac atcacagcca ccagcaacca ctgggtggtc aatccgcggc acaacctggg    1260
cctgcagctc tcggtggaga cgctggatgg gcagagcatc aacccaagt ggcgggcct     1320 gattgggcgg cacgggcccc agaacaagca gcccttcatg gtggctttct tcaaggccac    1380
ggaggtccac ttccgcagca tccggtccac ggggagcaaa cagcgcagcc agaaccgctc    1440
caagacgccc aagaaccagg aagccctgcg gatggccaac gtggcagaga acagcagcag    1500
cgaccagagg caggcctgta agaagcacga gctgtatgtc agcttccgag acctgggctg    1560
gcaggactgg atcatcgcgc ctgaaggcta cgccgcctac tactgtgagg gggagtgtgc    1620
cttccctctg aactcctaca tgaacgccac caaccacgcc atcgtgcaga cgctggtcca    1680
cttcatcaac ccgaaacgg tgcccaagcc ctgctgtgcg cccacgcagc tcaatgccat    1740
ctccgtcctc tacttcgatg acagctccaa cgtcatcctg aagaaatacă gaaacatggt    1800 ggtccgggcc tgtggctgcc actagctcct ccgagaattc agacccttg gggccaagtt    1860 tttctggatc ctccattgct cgccttggcc aggaaccagc agaccaactg ccttttgtga    1920
gaccttcccc tccctatccc caactttaaa ggtgtgagag tattaggaaa catgagcagc    1980
atatggcttt tgatcagttt ttcagtggca gcatccaatg aacaagatcc tacaagctgt    2040
gcaggcaaaa cctagcagga aaaaaaaaca acgcataaag aaaaatggcc gggccaggtc    2100
attggctggg aagtctcagc catgcacgga ctcgtttcca gaggtaatta tgagcgccta    2160
ccagccaggc cacccagccg tgggaggaag ggggcgtggc aaggggtggg cacattggtg    2220
tctgtgcgaa aggaaaattg acccggaagt tcctgtaata aatgtcacaa taaaacgaat    2280
gaatgaaaat ggttaggacg ttacagatat atttttcctaa acaatttatc cccatttctc    2340
ggtttatcct gatgcgtaaa cagaagctgt gtcaagtgga gggcggggag gtccctctcc    2400
attccctaca gttttcatcc tgaggcttgc agaggcccag tgtttaccga ggtttgccca    2460
aatccaagat ctagtgggag gggaaagagc aaatgtctgc tccgaggagg gcggtgtgtt    2520
gatctttgga ggaaaaatat gttctgttgt tcagctggat ttgccgtggc agaaatgaaa    2580
```

| | |
|---|---|
| ctaggtgtgt gaaatacccg cagacatttg ggattggctt ttcacctcgc cccagtggta | 2640 |
| gtaaatccat gtgaaattgc agaggggaca aggacagcaa gtaggatgga acttgcaact | 2700 |
| caaccctgtt gttaagaagc accaatgggc cgggcacagt agctcccacc tgtaatccca | 2760 |
| gcactttggg aggctgaggt gggcggatca tttgaggtca ggagttcgag accagcctgg | 2820 |
| ccaacatggt gaaaccccat ctctactaaa aatacaaaaa ttagccgggc atggtggcac | 2880 |
| gcacctgtaa tcccagctac tctggaggct gaggcaggag aattgcttga acccagagg | 2940 |
| tggaggttgc agtgagccaa gatcgtccca ctgcactcca gcttgggtga caaaacaaga | 3000 |
| ctccatctca aagaaaaaa aaaacagcac caatgaagcc tagttctcca cgggagtggg | 3060 |
| gtgagcagga gcactgcaca tcgccccagt ggaccctctg gtctttgtct gcagtggcat | 3120 |
| tccaaggctg ggccctggca agggcacccg tggctgtctc ttcatttgca gaccctgatc | 3180 |
| agaagtctct gcaaacaaat tgctccttg aattaagggg gagatggcat aataggaggt | 3240 |
| ctgatgggtg caggatgtgc tggacttaca ttgcaaatag aagccttgtt gagggtgaca | 3300 |
| tcctaaccaa gtgtcccgat ttggaggtgg catttctgac gtggctcttg gtgtaagcct | 3360 |
| gccttgcctt ggctggtgag tcccataaat agtatgcact cagcctccgg ccacaaacac | 3420 |
| aaggcctagg ggagggctag actgtctgca acgttttct gcatctgtaa agaaaacaag | 3480 |
| gtgatcgaaa actgtggcca tgtggaaccc ggtcttgtgg gggactgttt ctccatcttg | 3540 |
| actcagacag ttcctggaaa caccgggct ctgtttttat tttctttgat gttttcttc | 3600 |
| tttagtagct tgggctgcag cctccactct ctagtcactg gggaggagta ttttttgtta | 3660 |
| tgtttggttt catttgctgg cagagctggg gcttttgtg tgatccctct tggtgtgagt | 3720 |
| tttctgaccc aaccagcctc tggttagcat catttgtaca tttaaacctg taaatagttg | 3780 |
| ttacaaagca aagagattat ttatttccat ccaaagctct tttgaacacc cccccccctt | 3840 |
| taatccctcg ttcaggacga tgagcttgct ttccttcaac ctgtttgttt tcttatttaa | 3900 |
| gactatttat taatggttgg accaatgtac tcacagctgt tgcgtcgagc agtccttagt | 3960 |
| gaaaattctg tataaataga caaatgaaa agggtttgac cttgcaataa aaggagacgt | 4020 |
| ttggttctgg caaaaaaaaa aaaaaaaaa | 4049 |

<210> SEQ ID NO 164
<211> LENGTH: 431
<212> TYPE: PRT
<213> ORGANISM: Homo sapiens

<400> SEQUENCE: 164

```
Met His Val Arg Ser Leu Arg Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110
```

```
Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 165
<211> LENGTH: 19
<212> TYPE: RNA
<213> ORGANISM: Artificial Sequence
<220> FEATURE:
<223> OTHER INFORMATION: synthetic construct

<400> SEQUENCE: 165
uuccuaauac ucucacacc                                                  19

<210> SEQ ID NO 166
<211> LENGTH: 19
<212> TYPE: RNA
<213> ORGANISM: Artificial Sequence
<220> FEATURE:
<223> OTHER INFORMATION: synthetic construct
```

<400> SEQUENCE: 166
uaacaaaaaa uacuccucc							19

<210> SEQ ID NO 167
<211> LENGTH: 20
<212> TYPE: RNA
<213> ORGANISM: Artificial Sequence
<220> FEATURE:
<223> OTHER INFORMATION: synthetic construct

<400> SEQUENCE: 167
uaaauaagaa aacaaacagg							20

<210> SEQ ID NO 168
<211> LENGTH: 20
<212> TYPE: RNA
<213> ORGANISM: Artificial Sequence
<220> FEATURE:
<223> OTHER INFORMATION: synthetic construct

<400> SEQUENCE: 168
uuccuaauac ucucacaccu							20

<210> SEQ ID NO 169
<211> LENGTH: 32
<212> TYPE: DNA
<213> ORGANISM: Artificial Sequence
<220> FEATURE:
<223> OTHER INFORMATION: synthetic construct

<400> SEQUENCE: 169
ccggtctaac aaaaaatact cctcccgacc gg					32

<210> SEQ ID NO 170
<211> LENGTH: 32
<212> TYPE: DNA
<213> ORGANISM: Artificial Sequence
<220> FEATURE:
<223> OTHER INFORMATION: synthetic construct

<400> SEQUENCE: 170
ccggtcttgt aacaacuatt tacagggacc gg					32

<210> SEQ ID NO 171
<211> LENGTH: 31
<212> TYPE: DNA
<213> ORGANISM: Artificial Sequence
<220> FEATURE:
<223> OTHER INFORMATION: synthetic construct

<400> SEQUENCE: 171
ccggtctaaa taagaaaaca aacaggaccg g					31

<210> SEQ ID NO 172
<211> LENGTH: 1802
<212> TYPE: DNA
<213> ORGANISM: Homo sapiens

<400> SEQUENCE: 172
gggcagctcc accctgggag ggactgtggc ccaggtactg cccgggtgct actttatggg		60 cagcagctca gttgagttag agtctggaag acctcagaag acctcctgtc ctatgaggcc		120 ctcccccatgg ctttagagac gatctgccga ccctctggga gaaaatccag caagatgcaa	180

```
gccttcagaa tctgggatgt taaccagaag accttctatc tgaggaacaa ccaactagtt      240
gctggatact tgcaaggacc aaatgtcaat ttagaagaaa agatagatgt ggtacccatt      300
gagcctcatg ctctgttctt gggaatccat ggagggaaga tgtgcctgtc ctgtgtcaag      360
tctggtgatg agaccagact ccagctggag gcagttaaca tcactgacct gagcgagaac      420
agaaagcagg acaagcgctt cgccttcatc cgctcagaca gtggcccac caccagtttt      480 gagtctgccg cctgccccgg ttggttcctc tgcacagcga tggaagctga ccagcccgtc      540
agcctcacca atatgcctga cgaaggcgtc atggtcacca aattctactt ccaggaggac      600
gagtagtact gcccaggcct gcctgttccc attcttgcat ggcaaggact gcagggactg      660
ccagtccccc tgcccaggg ctcccggcta tgggggcact gaggaccagc cattgagggg      720
tggaccctca gaaggcgtca caacaacctg gtcacaggac tctgcctcct cttcaactga      780
ccagcctcca tgctgcctcc agaatggtct ttctaatgtg tgaatcagag cacagcagcc      840
cctgcacaaa gccttccat gtcgcctctg cattcaggat caaacccga ccacctgccc      900 aacctgctct cctcttgcca ctgcctcttc ctccctcatt ccaccttccc atgccctgga      960
tccatcaggc cacttgatga cccccaacca agtggctccc acaccctgtt ttacaaaaaa      1020
gaaaagacca gtccatgagg gaggttttta agggtttgtg gaaaatgaaa attaggattt      1080
catgattttt ttttttcagt ccccgtgaag gagagccctt catttggaga ttatgttctt      1140
tcggggagag gctgaggact taaaatattc ctgcatttgt gaaatgatgg tgaaagtaag      1200
tggtagcttt tcccttcttt ttcttctttt tttgtgatgt cccaacttgt aaaaattaaa      1260
agttatggta ctatgttagc cccataattt ttttttcct tttaaaacac ttccataatc      1320
tggactcctc tgtccaggca ctgctgccca gcctccaagc tccatctcca ctccagattt      1380
tttacagctg cctgcagtac tttacctcct atcagaagtt tctcagctcc caaggctctg      1440
agcaaatgtg gctcctgggg gttctttctt cctctgctga aggaataaat tgctccttga      1500
cattgtagag cttctggcac ttggagactt gtatgaaaga tggctgtgcc tctgcctgtc      1560
tcccccaccg ggctgggagc tctgcagagc aggaaacatg actcgtatat gtctcaggtc      1620
cctgcagggc caagcaccta gcctcgctct tggcaggtac tcagcgaatg aatgctgtat      1680
atgttgggtg caaagttccc tacttcctgt gacttcagct ctgttttaca ataaaatctt      1740
gaaaatgcct aaaaaaaaaa aaaaaaaaaa aaaaaaaaaa aaaaaaaaaa aaaaaaaaaa      1800
aa                                                                    1802
```

<210> SEQ ID NO 173
<211> LENGTH: 159
<212> TYPE: PRT
<213> ORGANISM: Homo sapiens

<400> SEQUENCE: 173

```
Met Ala Leu Glu Thr Ile Cys Arg Pro Ser Gly Arg Lys Ser Lys
1               5                   10                  15

Met Gln Ala Phe Arg Ile Trp Asp Val Asn Gln Lys Thr Phe Tyr Leu
            20                  25                  30

Arg Asn Asn Gln Leu Val Ala Gly Tyr Leu Gln Gly Pro Asn Val Asn
        35                  40                  45

Leu Glu Glu Lys Ile Asp Val Val Pro Ile Glu Pro His Ala Leu Phe
    50                  55                  60

Leu Gly Ile His Gly Gly Lys Met Cys Leu Ser Cys Val Lys Ser Gly
65                  70                  75                  80
```

```
Asp Glu Thr Arg Leu Gln Leu Glu Ala Val Asn Ile Thr Asp Leu Ser
                 85                  90                  95

Glu Asn Arg Lys Gln Asp Lys Arg Phe Ala Phe Ile Arg Ser Asp Ser
            100                 105                 110

Gly Pro Thr Thr Ser Phe Glu Ser Ala Ala Cys Pro Gly Trp Phe Leu
        115                 120                 125

Cys Thr Ala Met Glu Ala Asp Gln Pro Val Ser Leu Thr Asn Met Pro
130             135                 140

Asp Glu Gly Val Met Val Thr Lys Phe Tyr Phe Gln Glu Asp Glu
145                 150                 155

<210> SEQ ID NO 174
<211> LENGTH: 100
<212> TYPE: RNA
<213> ORGANISM: Artificial Sequence
<220> FEATURE:
<223> OTHER INFORMATION: synthetic construct

<400> SEQUENCE: 174
ugugucucuc ucuguguccu gccagugguu uuacccuaug guagguuacg ucaugcuguu      60
cuaccacagg guagaaccac ggacaggaua ccggggcacc                          100

<210> SEQ ID NO 175
<211> LENGTH: 22
<212> TYPE: RNA
<213> ORGANISM: Artificial Sequence
<220> FEATURE:
<223> OTHER INFORMATION: synthetic construct

<400> SEQUENCE: 175
cagugguuuu acccuauggu ag                                              22

<210> SEQ ID NO 176
<211> LENGTH: 87
<212> TYPE: RNA
<213> ORGANISM: Homo sapiens

<400> SEQUENCE: 176
accgcaggga aaaugaggga cuuuuggggg cagauguguu uccauuccac uaucauaaug      60
ccccuaaaaa uccuuauugc ucuugca                                         87

<210> SEQ ID NO 177
<211> LENGTH: 23
<212> TYPE: RNA
<213> ORGANISM: Artificial Sequence
<220> FEATURE:
<223> OTHER INFORMATION: synthetic construct

<400> SEQUENCE: 177
agggacuuuu gggggcagau gug                                             23

<210> SEQ ID NO 178
<211> LENGTH: 86
<212> TYPE: RNA
<213> ORGANISM: Homo sapiens

<400> SEQUENCE: 178
ugccagucuc uaggucccug agacccuuua accugugagg acauccaggg ucacagguga      60
gguucuuggg agccuggcgu cuggcc                                          86

<210> SEQ ID NO 179
```

```
<211> LENGTH: 24
<212> TYPE: RNA
<213> ORGANISM: Artificial Sequence
<220> FEATURE:
<223> OTHER INFORMATION: synthetic construct

<400> SEQUENCE: 179
ucccugagac ccuuuaaccu guga                                            24

<210> SEQ ID NO 180
<211> LENGTH: 22
<212> TYPE: RNA
<213> ORGANISM: Artificial Sequence
<220> FEATURE:
<223> OTHER INFORMATION: synthetic construct

<400> SEQUENCE: 180
acaggugagg uucuugggag cc                                              22

<210> SEQ ID NO 181
<211> LENGTH: 1968
<212> TYPE: DNA
<213> ORGANISM: Homo sapiens

<400> SEQUENCE: 181
actccgggtg gcaggcgccc gggggaatcc cagctgactc gctcactgcc ttcgaagtcc     60
ggcgcccccc gggagggaac tgggtggccg caccctcccg gctgcggtgg ctgtcgcccc    120
ccaccctgca gccaggactc gatggaggta cagagctcgg cttctttgcc ttgggagggg    180
agtggtggtg gttgaaaggg cgatggaatt tccccgaaa gcctacgccc agggcccctc     240
ccagctccag cgttacccctc cggtctatcc tactggccga gctgccccgc cttctcatgg   300
ggaaaactta gccgcaactt caattttgg tttttccttt aatgacactt ctgaggctct     360
cctagccatc ctcccgcttc cggaggagcg cagatcgcag gtcccttgc ccctggcgtg    420 cgactcccta ctgcgctgcg ctcttacggc gttccaggct gctggctagc gcaaggcggg    480
ccgggcaccc cgcgctccgc tgggaggtg agggacgcgc gtctggcggc cccagccaag    540
ctgcgggttt ctgagaagac gctgtcccgc agccctgagg gctgagttct gcacccagtc   600
aagctcagga aggccaagaa aagaatccat tccaatatat ggccatgtgg ctctttggag    660
caatgttcca tcatgttcca tgctgctgac gtcacatgga gcacagaaat caatgttagc   720
agatagccag cccatacaag atcgtattgt attgtaggag gcatcgtgga tggatggctg    780
ctggaaaccc cttgccatag ccagctcttc ttcaatactt aaggatttac cgtggctttg    840
agtaatgaga atttcgaaac cacatttgag aagtatttcc atccagtgct acttgtgttt    900
acttctaaac agtcatttc taactgaagc tggcattcat gtcttcattt tgggctgttt     960
cagtgcaggg cttcctaaaa cagaagccaa ctgggtgaat gtaataagtg atttgaaaaa   1020
aattgaagat cttattcaat ctatgcatat tgatgctact ttatatacgg aaagtgatgt   1080
tcaccccagt tgcaaagtaa cagcaatgaa gtgcttctc ttggagttac aagttatttc    1140
acttgagtcc ggagatgcaa gtattcatga tacagtagaa aatctgatca tcctagcaaa   1200
caacagtttg tcttctaatg ggaatgtaac agaatctgga tgcaaagaat gtgaggaact   1260
ggaggaaaaa aatattaaag aattttttgca gagttttgta catattgtcc aaatgttcat  1320
caacacttct tgattgcaat tgattctttt taaagtgttt ctgttattaa caaacatcac   1380
tctgctgctt agacataaca aaacactcgg catttcaaat gtgctgtcaa acaagtttt   1440 tctgtcaaga agatgatcag accttggatc agatgaactc ttagaaatga aggcagaaaa  1500
```

-continued

```
atgtcattga gtaatatagt gactatgaac ttctctcaga cttactttac tcattttttt      1560
aatttattat tgaaattgta catatttgtg gaataatgta aaatgttgaa taaaaatatg      1620
tacaagtgtt gttttttaag ttgcactgat attttacctc ttattgcaaa atagcatttg      1680
tttaagggtg atagtcaaat tatgtattgg tggggctggg taccaatgct gcaggtcaac      1740
agctatgctg gtaggctcct gcctgtgtgg aaccactgac tactggctct cattgacttc      1800
cttactaagc atagcaaaca gaggaagaat ttgttatcag taagaaaaag aagaactata      1860
tgtgaatcct cttctttaca ctgtaattta gttattgatg tataaagcaa ctgttatgaa      1920
ataaagaaat tgcaataact ggcaaaaaaa aaaaaaaaa aaaaaaaa                    1968

<210> SEQ ID NO 182
<211> LENGTH: 162
<212> TYPE: PRT
<213> ORGANISM: Homo sapiens

<400> SEQUENCE: 182

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
        50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 183
<211> LENGTH: 1252
<212> TYPE: DNA
<213> ORGANISM: Homo sapiens

<400> SEQUENCE: 183
ctttgaattc ctagctcctg tggtctccag atttcaggcc taagatgaaa gcctctagtc        60
ttgccttcag ccttctctct gctgcgtttt atctcctatg gactccttcc actggactga       120
agacactcaa tttgggaagc tgtgtgatcg ccacaaacct tcaggaaata cgaaatggat       180
tttctgagat acggggcagt gtgcaagcca agatgaaa cattgacatc agaatcttaa        240
ggaggactga gtctttgcaa gacacaaagc ctgcgaatcg atgctgcctc ctgcgccatt       300
tgctaagact ctatctggac agggtattta aaaactacca gaccctgac cattatactc        360 tccggaagat cagcagcctc gccaattcct ttcttaccat caagaaggac ctccggctct       420
```

| | |
|---|---|
| gtcatgccca catgacatgc cattgtgggg aggaagcaat gaagaaatac agccagattc | 480 |
| tgagtcactt tgaaaagctg aaccctcagg cagcagttgt gaaggctttg ggggaactag | 540 |
| acattcttct gcaatggatg gaggagacag aataggagga aagtgatgct gctgctaaga | 600 |
| atattcgagg tcaagagctc cagtcttcaa tacctgcaga ggaggcatga ccccaaacca | 660 |
| ccatctcttt actgtactag tcttgtgctg gtcacagtgt atcttattta tgcattactt | 720 |
| gcttccttgc atgattgtct ttatgcatcc ccaatcttaa ttgagaccat acttgtataa | 780 |
| gattttgta atatctttct gctattggat atatttatta gttaatatat ttatttattt | 840 |
| tttgctattt aatgtattta ttttttact tggacatgaa actttaaaaa aattcacaga | 900 |
| ttatatttat aacctgacta gagcaggtga tgtatttta tacagtaaaa aaaaaaaacc | 960 |
| ttgtaaattc tagaagagtg gctagggggg ttattcattt gtattcaact aaggacatat | 1020 |
| ttactcatgc tgatgctctg tgagatattt gaaattgaac caatgactac ttaggatggg | 1080 |
| ttgtggaata agttttgatg tggaattgca catctaccct acaattactg accatcccca | 1140 |
| gtagactccc cagtcccata attgtgtatc ttccagccag gaatcctaca cggccagcat | 1200 |
| gtatttctac aaataaagtt ttcttttgcat aacaaaaaaa aaaaaaaaaa aa | 1252 |

```
<210> SEQ ID NO 184
<211> LENGTH: 176
<212> TYPE: PRT
<213> ORGANISM: Homo sapiens

<400> SEQUENCE: 184

Met Lys Ala Ser Ser Leu Ala Phe Ser Leu Leu Ser Ala Ala Phe Tyr
  1               5                  10                  15

Leu Leu Trp Thr Pro Ser Thr Gly Leu Lys Thr Leu Asn Leu Gly Ser
             20                  25                  30

Cys Val Ile Ala Thr Asn Leu Gln Glu Ile Arg Asn Gly Phe Ser Glu
         35                  40                  45

Ile Arg Gly Ser Val Gln Ala Lys Asp Gly Asn Ile Asp Ile Arg Ile
     50                  55                  60

Leu Arg Arg Thr Glu Ser Leu Gln Asp Thr Lys Pro Ala Asn Arg Cys
 65                  70                  75                  80

Cys Leu Leu Arg His Leu Leu Arg Leu Tyr Leu Asp Arg Val Phe Lys
                 85                  90                  95

Asn Tyr Gln Thr Pro Asp His Tyr Thr Leu Arg Lys Ile Ser Ser Leu
            100                 105                 110

Ala Asn Ser Phe Leu Thr Ile Lys Lys Asp Leu Arg Leu Cys His Ala
        115                 120                 125

His Met Thr Cys His Cys Gly Glu Glu Ala Met Lys Lys Tyr Ser Gln
    130                 135                 140

Ile Leu Ser His Phe Glu Lys Leu Glu Pro Gln Ala Ala Val Val Lys
145                 150                 155                 160

Ala Leu Gly Glu Leu Asp Ile Leu Leu Gln Trp Met Glu Glu Thr Glu
                165                 170                 175

<210> SEQ ID NO 185
<211> LENGTH: 2265
<212> TYPE: DNA
<213> ORGANISM: Homo sapiens

<400> SEQUENCE: 185
```

| | |
|---|---|
| acagccagag ggacgagcta gcccgacgat ggcccagggg acattgatcc gtgtgacccc | 60 |

```
agagcagccc acccatgccg tgtgtgtgct gggcaccttg actcagcttg acatctgcag    120
ctctgcccct gaggactgca cgtccttcag catcaacgcc tccccagggg tggtcgtgga    180
tattgcccac ggccctccag ccaagaagaa atccacaggt tcctccacat ggcccctgga    240
ccctggggta gaggtgaccc tgacgatgaa agtggccagt ggtagcacag gcgaccagaa    300
ggttcagatt tcatactacg acccaagac tccaccagtc aaagctctac tctacctcac     360
cggggtggaa atctccttgt gcgcagacat caccgcacc ggcaaagtga agccaaccag     420
agctgtgaaa gatcagagga cctggacctg gggcccttgt ggacagggtg ccatcctgct    480
ggtgaactgt gacagagaca atctcgaatc ttctgccatg gactgcgagg atgatgaagt    540
gcttgacagc gaagacctgc aggacatgtc gctgatgacc ctgagcacga agaccccaa     600 ggacttcttc acaaaccata cactggtgct ccacgtggcc aggtctgaga tggacaaagt    660
gagggtgttt caggccacac ggggcaaact gtcctccaag tgcagcgtag tcttgggtcc    720
caagtggccc tctcactacc tgatggtccc cggtggaaag cacaacatgg acttctacgt    780
ggaggccctc gctttccgg acaccgactt cccgggctc attaccctca ccatctccct      840
gctggacacg tccaacctgg agctccccga ggctgtggtg ttccaagaca gcgtggtctt    900
ccgcgtggcg ccctggatca tgaccccaa cacccagccc ccgcaggagg tgtacgcgtg     960
cagtattttt gaaaatgagg acttcctgaa gtcagtgact actctggcca tgaaagccaa    1020
gtgcaagctg accatctgcc tgaggagga gaacatggat gaccagtgga tgcaggatga     1080
aatggagatc ggctacatcc aagccccaca caaaacgctg cccgtggtct tcgactctcc    1140
aaggaacaga ggcctgaagg agtttcccat caaacgcgtg atgggtccag attttggcta    1200
tgtaactcga gggccccaaa caggggtat cagtggactg gactcctttg ggaacctgga     1260
agtgagcccc ccagtcacag tcaggggcaa ggaatacccg ctgggcagga ttctcttcgg    1320
ggacagctgt tatcccagca atgacagccg gcagatgcac caggccctgc aggacttcct    1380
cagtgcccag caggtgcagg cccctgtgaa gctctattct gactggctgt ccgtgggcca    1440
cgtggacgag ttcctgagct tgtgccagc acccgacagg aagggcttcc ggctgctcct     1500
ggccagcccc aggtcctgct acaaactgtt ccaggagcag cagaatgagg ccacggggga    1560
ggccctgctg ttcgaaggga tcaagaaaaa aaacagcag aaaataaaga acattctgtc     1620
aaacaagaca ttgagagaac ataattcatt tgtggagaga tgcatcgact ggaaccgcga    1680
gctgctgaag cgggagctgg gcctggccga gagtgacatc attgacatcc gcagctctt     1740 caagctcaaa gagttctcta aggcggaagc tttttttccc aacatggtga acatgctggt    1800
gctagggaag caccctgggca tccccaagcc cttcgggccc gtcatcaacg ccgctgctg    1860 cctggaggag aaggtgtgtt ccctgctgga gccactgggc ctccagtgca ccttcatcaa    1920
cgacttcttc acctaccaca tcaggcatgg ggaggtgcac tgcggcacca acgtgcgcag    1980
aaagcccttc tccttcaagt ggtggaacat ggtgccctga gcccatcttc cctgcgtcc     2040 tctccctcct ggccagatgt cgctgggtcc tctgcagtgt ggcaagcaag agctcttgtg    2100
aatattgtgg ctccctgggg gcggccagcc ctcccagcag tggcttgctt tcttctcctg    2160
tgatgtccca gtttcccact ctgaagatcc caacatggtc ctagcactgc acactcagtt    2220
ctgctctaag aagctgcaat aaagttttt taagtcactt tgtac                     2265
```

<210> SEQ ID NO 186
<211> LENGTH: 663
<212> TYPE: PRT
<213> ORGANISM: Homo sapiens

```
<400> SEQUENCE: 186

Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser
            20                  25                  30

Ala Pro Glu Asp Cys Thr Ser Phe Ser Ile Asn Ala Ser Pro Gly Val
        35                  40                  45

Val Val Asp Ile Ala His Gly Pro Pro Ala Lys Lys Lys Ser Thr Gly
    50                  55                  60

Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Gly
            100                 105                 110

Val Glu Ile Ser Leu Cys Ala Asp Ile Thr Arg Thr Gly Lys Val Lys
            115                 120                 125

Pro Thr Arg Ala Val Lys Asp Gln Arg Thr Trp Thr Trp Gly Pro Cys
130                 135                 140

Gly Gln Gly Ala Ile Leu Leu Val Asn Cys Asp Arg Asp Asn Leu Glu
145                 150                 155                 160

Ser Ser Ala Met Asp Cys Glu Asp Glu Val Leu Asp Ser Glu Asp
                165                 170                 175

Leu Gln Asp Met Ser Leu Met Thr Leu Ser Thr Lys Thr Pro Lys Asp
            180                 185                 190

Phe Phe Thr Asn His Thr Leu Val Leu His Val Ala Arg Ser Glu Met
            195                 200                 205

Asp Lys Val Arg Val Phe Gln Ala Thr Arg Gly Lys Leu Ser Ser Lys
210                 215                 220

Cys Ser Val Val Leu Gly Pro Lys Trp Pro Ser His Tyr Leu Met Val
225                 230                 235                 240

Pro Gly Gly Lys His Asn Met Asp Phe Tyr Val Glu Ala Leu Ala Phe
            245                 250                 255

Pro Asp Thr Asp Phe Pro Gly Leu Ile Thr Leu Thr Ile Ser Leu Leu
            260                 265                 270

Asp Thr Ser Asn Leu Glu Leu Pro Glu Ala Val Val Phe Gln Asp Ser
            275                 280                 285

Val Val Phe Arg Val Ala Pro Trp Ile Met Thr Pro Asn Thr Gln Pro
290                 295                 300

Pro Gln Glu Val Tyr Ala Cys Ser Ile Phe Glu Asn Glu Asp Phe Leu
305                 310                 315                 320

Lys Ser Val Thr Thr Leu Ala Met Lys Ala Lys Cys Lys Leu Thr Ile
            325                 330                 335

Cys Pro Glu Glu Glu Asn Met Asp Asp Gln Trp Met Gln Asp Glu Met
            340                 345                 350

Glu Ile Gly Tyr Ile Gln Ala Pro His Lys Thr Leu Pro Val Val Phe
            355                 360                 365

Asp Ser Pro Arg Asn Arg Gly Leu Lys Glu Phe Pro Ile Lys Arg Val
            370                 375                 380

Met Gly Pro Asp Phe Gly Tyr Val Thr Arg Gly Pro Gln Thr Gly Gly
385                 390                 395                 400

Ile Ser Gly Leu Asp Ser Phe Gly Asn Leu Glu Val Ser Pro Pro Val
```

```
            405                 410                 415
Thr Val Arg Gly Lys Glu Tyr Pro Leu Gly Arg Ile Leu Phe Gly Asp
            420                 425                 430

Ser Cys Tyr Pro Ser Asn Asp Ser Arg Gln Met His Gln Ala Leu Gln
            435                 440                 445

Asp Phe Leu Ser Ala Gln Gln Val Gln Ala Pro Val Lys Leu Tyr Ser
        450                 455                 460

Asp Trp Leu Ser Val Gly His Val Asp Glu Phe Leu Ser Phe Val Pro
465                 470                 475                 480

Ala Pro Asp Arg Lys Gly Phe Arg Leu Leu Leu Ala Ser Pro Arg Ser
                485                 490                 495

Cys Tyr Lys Leu Phe Gln Glu Gln Gln Asn Glu Gly His Gly Glu Ala
            500                 505                 510

Leu Leu Phe Glu Gly Ile Lys Lys Lys Gln Gln Lys Ile Lys Asn
            515                 520                 525

Ile Leu Ser Asn Lys Thr Leu Arg Glu His Asn Ser Phe Val Glu Arg
        530                 535                 540

Cys Ile Asp Trp Asn Arg Glu Leu Leu Lys Arg Glu Leu Gly Leu Ala
545                 550                 555                 560

Glu Ser Asp Ile Ile Asp Ile Pro Gln Leu Phe Lys Leu Lys Glu Phe
                565                 570                 575

Ser Lys Ala Glu Ala Phe Phe Pro Asn Met Val Asn Met Leu Val Leu
            580                 585                 590

Gly Lys His Leu Gly Ile Pro Lys Pro Phe Gly Pro Val Ile Asn Gly
            595                 600                 605

Arg Cys Cys Leu Glu Glu Lys Val Cys Ser Leu Leu Glu Pro Leu Gly
        610                 615                 620

Leu Gln Cys Thr Phe Ile Asn Asp Phe Phe Thr Tyr His Ile Arg His
625                 630                 635                 640

Gly Glu Val His Cys Gly Thr Asn Val Arg Arg Lys Pro Phe Ser Phe
                645                 650                 655

Lys Trp Trp Asn Met Val Pro
            660

<210> SEQ ID NO 187
<211> LENGTH: 801
<212> TYPE: DNA
<213> ORGANISM: Homo sapiens

<400> SEQUENCE: 187
atggtgtgtc tgaggctccc tggaggctcc tgcatggcag ttctgacagt gacactgatg      60
gtgctgagct ccccactggc tttggctggg acaccagac cacgtttctt ggaggaggtt     120
aagtttgagt gtcatttctt caacgggacg agcgggtgc ggttgctgga aagacgcgtc     180
cataaccaag aggagtacgc gcgctacgac agcgacgtgg gggagtaccg ggcggtgacg     240
gagctggggc ggcctgatgc cgagtactgg aacagccaga aggacctcct ggagcggagg     300
cgtgccgcgg tggacaccta ctgcagacac aactacgggg ttggtgagag cttcacagtg     360
cagcggcgag ttcaacctaa ggtgactgtg tatccttcaa agaccagcc cctgcagcac     420 cacaacctcc tggtctgttc tgtgaatggt ttctatccag gcagcattga agtcaggtgg     480
ttccggaacg gccaggaaga gaagactggg gtggtgtcca cgggcctgat ccagaatgga     540
gactggacct tccagaccct ggtgatgctg gaaacagttc ctcagagtgg agaggtttac     600
acctgccaag tggagcaccc aagtgtgatg agccctctca cagtggaatg agagcacgg      660
```

```
tctgaatctg cacagagcaa gatgctgagt ggagtcgggg gctttgtgct gggcctgctc      720
ttccttgggg ccgggctgtt catctacttc aggaatcaga aaggacactc tggacttccg      780
ccaacaggat tcctgagctg a                                                801
```

<210> SEQ ID NO 188
<211> LENGTH: 266
<212> TYPE: PRT
<213> ORGANISM: Homo sapiens

<400> SEQUENCE: 188

```
Met Val Cys Leu Arg Leu Pro Gly Gly Ser Cys Met Ala Val Leu Thr
1               5                   10                  15

Val Thr Leu Met Val Leu Ser Ser Pro Leu Ala Leu Ala Gly Asp Thr
            20                  25                  30

Arg Pro Arg Phe Leu Glu Glu Val Lys Phe Glu Cys His Phe Phe Asn
        35                  40                  45

Gly Thr Glu Arg Val Arg Leu Leu Glu Arg Arg Val His Asn Gln Glu
    50                  55                  60

Glu Tyr Ala Arg Tyr Asp Ser Asp Val Gly Glu Tyr Arg Ala Val Thr
65                  70                  75                  80

Glu Leu Gly Arg Pro Asp Ala Glu Tyr Trp Asn Ser Gln Lys Asp Leu
                85                  90                  95

Leu Glu Arg Arg Arg Ala Ala Val Asp Thr Tyr Cys Arg His Asn Tyr
            100                 105                 110

Gly Val Gly Glu Ser Phe Thr Val Gln Arg Arg Val Gln Pro Lys Val
        115                 120                 125

Thr Val Tyr Pro Ser Lys Thr Gln Pro Leu Gln His His Asn Leu Leu
    130                 135                 140

Val Cys Ser Val Asn Gly Phe Tyr Pro Gly Ser Ile Glu Val Arg Trp
145                 150                 155                 160

Phe Arg Asn Gly Gln Glu Glu Lys Thr Gly Val Val Ser Thr Gly Leu
                165                 170                 175

Ile Gln Asn Gly Asp Trp Thr Phe Gln Thr Leu Val Met Leu Glu Thr
            180                 185                 190

Val Pro Gln Ser Gly Glu Val Tyr Thr Cys Gln Val Glu His Pro Ser
        195                 200                 205

Val Met Ser Pro Leu Thr Val Glu Trp Arg Ala Arg Ser Glu Ser Ala
    210                 215                 220

Gln Ser Lys Met Leu Ser Gly Val Gly Gly Phe Val Leu Gly Leu Leu
225                 230                 235                 240

Phe Leu Gly Ala Gly Leu Phe Ile Tyr Phe Arg Asn Gln Lys Gly His
                245                 250                 255

Ser Gly Leu Pro Pro Thr Gly Phe Leu Ser
            260                 265
```

<210> SEQ ID NO 189
<211> LENGTH: 3436
<212> TYPE: DNA
<213> ORGANISM: Homo sapiens

<400> SEQUENCE: 189

```
ggtgtctcgg ccatgacaca catttgacat gccctccctc aacctactta tagactattt       60
ttcttgctct gcagcatgga ccaaagagaa attctgcaga agttcctgga tgaggcccaa      120
agcaagaaaa ttactaaaga ggagtttgcc aatgaatttc tgaagctgaa aaggcaatct      180
```

-continued

```
accaagtaca aggcagacaa aacctatcct acaactgtgg ctgagaagcc caagaatatc      240
aagaaaaaca gatataagga tattttgccc tatgattata gccgggtaga actatccctg      300
ataacctctg atgaggattc cagctacatc aatgccaact tcattaaggg agtttatgga      360
cccaaggctt atattgccac ccagggtcct ttatctacaa ccctcctgga cttctggagg      420
atgatttggg aatatagtgt ccttatcatt gttatggcat gcatggagta tgaaatggga      480
aagaaaaagt gtgagcgcta ctgggctgag ccaggagaga tgcagctgga atttggccct      540
ttctctgtat cctgtgaagc tgaaaaaagg aaatctgatt atataatcag gactctaaaa      600
gttaagttca atagtgaaac tcgaactatc taccagtttc attacaagaa ttggccagac      660
catgatgtac cttcatctat agaccctatt cttgagctca tctgggatgt acgttgttac      720
caagaggatg acagtgttcc catatgcatt cactgcagtg ctggctgtgg aaggactggt      780
gttatttgtg ctattgatta tacatggatg ttgctaaaag atgggagtca agcaaagcat      840
tgtattcctg agaaaaatca cactctccaa gcagactctt attctcctaa tttaccaaaa      900
agtaccacaa aagcagcaaa aatgatgaac caacaaagga caaaaatgga aatcaaagaa      960
tcttcttcct ttgactttag gacttctgaa ataagtgcaa aagaagagct agttttgcac     1020
cctgctaaat caagcacttc ttttgacttt ctggagctaa attacagttt tgacaaaaat     1080
gctgacacaa ccatgaaatg gcagacaaag gcatttccaa tagttgggga gcctcttcag     1140
aagcatcaaa gtttggattt gggctctctt ttgtttgagg gatgttctaa ttctaaacct     1200
gtaaatgcag caggaagata ttttaattca aaggtgccaa taacacggac caaatcaact     1260
ccttttgaat tgatacagca gagagaaacc aaggaggtgg acagcaagga aaactttctt     1320
tatttggaat ctcaaccaca tgattcttgt tttgtagaga tgcaggctca aaaagtaatg     1380
catgtttctt cagcagaact gaattattca ctgccatatg actctaaaca ccaaatacgt     1440
aatgcctcta atgtaaagca ccatgactct agtgctcttg gtgtatattc ttacataccc     1500
ttagtggaaa atccttattt ttcatcatgg cctccaagtg gtaccagttc taagatgtct     1560
cttgatttac ctgagaagca agatggaact gttttttcctt cttctctgtt gccaacatcc     1620
tctacatccc tcttctctta ttacaattca catgattctt tatcactgaa ttctccaacc     1680
aatatttcct cactattgaa ccaggagtca gctgtactag caactgctcc aaggatagat     1740
gatgaaatcc cccctccact tcctgtacgg acacctgaat catttattgt ggttgaggaa     1800
gctggagaat tctcaccaaa tgttcccaaa tccttatcct cagctgtgaa ggtaaaaatt     1860
ggaacatcac tggaatgggg tggaacatct gaaccaaaga aatttgatga ctctgtgata     1920
cttagaccaa gcaagagtgt aaaactccga agtcctaaat cagaactaca tcaagatcgt     1980
tcttctcccc cacctcctct cccagaaaga actctagagt ccttctttct tgccgatgaa     2040
gattgtatgc aggcccaatc tatagaaaca tattctacta gctatcctga caccatggaa     2100
aattcaacat cttcaaaaca gacactgaag actcctggaa aaagtttcac aaggagtaag     2160
agtttgaaaa ttttgcgaaa catgaaaaag agtatctgta attcttgccc accaaacaag     2220
cctgcagaat ctgttcagtc aaataactcc agctcatttc tgaattttgg ttttgcaaac     2280 cgttttttcaa aacccaaagg accaaggaat ccaccaccaa cttggaatat ttaataaaac     2340
tccagattta taataatatg ggctgcaagt acacctgcaa ataaaactac tagaatactg     2400
ctagttaaaa taagtgctct atatgcataa tatcaaatat gaagatatgc taatgtgtta     2460
atagctttta aagaaaagc aaaatgccaa taagtgccag ttttgcattt tcatatcatt     2520
```

```
tgcattgagt tgaaaactgc aaataaaagt ttgtcacttg agcttatgta cagaatgcta    2580
tatgagaaac acttttagaa tggatttatt tttcattttt gccagttatt tttattttct    2640 tttactttt tacataaaca taaacttcaa aaggtttgta agatttggat ctcaactaat     2700
ttctacattg ccagaatata ctataaaaag ttaaaaaaaa aacttacttt gtgggttgca    2760
atacaaactg ctcttgacaa tgactattcc ctgacagtta tttttgccta aatggagtat    2820
accttgtaaa tcttcccaaa tgttgtggaa aactggaata ttaagaaaat gagaaattat    2880
atttattaga ataaaatgtg caaataatga caattatttg aatgtaacaa ggaattcaac    2940
tgaaatcctg ataagttta accaaagtca ttaaattacc aattctagaa aagtaatcaa     3000
tgaaatataa tagctatctt ttggtagcaa aagatataaa ttgtatatgt ttatacagga    3060
tctttcagat catgtgcaat ttttatctaa ccaatcagaa atactagttt aaaatgaatt    3120
tctatatgaa tatggatctg ccataagaaa atctagttca actctaattt tatgtagtaa    3180
ataaattggc aggtaattgt ttttacaaag aatccacctg acttccccta atgcattaaa    3240 aatatttta tttaaataac tttatttata acttttagaa acatgtagta ttgtttaaac     3300
atcatttgtt cttcagtatt tttcatttgg aagtccaata gggcaaattg aatgaagtat    3360
tattatctgt ctcttgtagt acaatgtatc caacagacac tcaataaact ttttggttgt    3420
taaaaaaaaa aaaaaa                                                    3436

<210> SEQ ID NO 190
<211> LENGTH: 752
<212> TYPE: PRT
<213> ORGANISM: Homo sapiens

<400> SEQUENCE: 190

Met Asp Gln Arg Glu Ile Leu Gln Lys Phe Leu Asp Glu Ala Gln Ser
1               5                   10                  15

Lys Lys Ile Thr Lys Glu Glu Phe Ala Asn Glu Phe Leu Lys Leu Lys
            20                  25                  30

Arg Gln Ser Thr Lys Tyr Lys Ala Asp Lys Thr Tyr Pro Thr Thr Val
        35                  40                  45

Ala Glu Lys Pro Lys Asn Ile Lys Lys Asn Arg Tyr Lys Asp Ile Leu
    50                  55                  60

Pro Tyr Asp Tyr Ser Arg Val Glu Leu Ser Leu Ile Thr Ser Asp Glu
65                  70                  75                  80

Asp Ser Ser Tyr Ile Asn Ala Asn Phe Ile Lys Gly Val Tyr Gly Pro
                85                  90                  95

Lys Ala Tyr Ile Ala Thr Gln Gly Pro Leu Ser Thr Thr Leu Leu Asp
            100                 105                 110

Phe Trp Arg Met Ile Trp Glu Tyr Ser Val Leu Ile Ile Val Met Ala
        115                 120                 125

Cys Met Glu Tyr Glu Met Gly Lys Lys Cys Glu Arg Tyr Trp Ala
    130                 135                 140

Glu Pro Gly Glu Met Gln Leu Glu Phe Gly Pro Phe Ser Val Ser Cys
145                 150                 155                 160

Glu Ala Glu Lys Arg Lys Ser Asp Tyr Ile Ile Arg Thr Leu Lys Val
                165                 170                 175

Lys Phe Asn Ser Glu Thr Arg Thr Ile Tyr Gln Phe His Tyr Lys Asn
            180                 185                 190

Trp Pro Asp His Asp Val Pro Ser Ser Ile Asp Pro Ile Leu Glu Leu
        195                 200                 205
```

```
Ile Trp Asp Val Arg Cys Tyr Gln Glu Asp Asp Ser Val Pro Ile Cys
    210                 215                 220
Ile His Cys Ser Ala Gly Cys Gly Arg Thr Gly Val Ile Cys Ala Ile
225                 230                 235                 240
Asp Tyr Thr Trp Met Leu Leu Lys Asp Gly Ser Gln Ala Lys His Cys
                245                 250                 255
Ile Pro Glu Lys Asn His Thr Leu Gln Ala Asp Ser Tyr Ser Pro Asn
            260                 265                 270
Leu Pro Lys Ser Thr Thr Lys Ala Ala Lys Met Met Asn Gln Gln Arg
        275                 280                 285
Thr Lys Met Glu Ile Lys Glu Ser Ser Phe Asp Phe Arg Thr Ser
    290                 295                 300
Glu Ile Ser Ala Lys Glu Leu Val Leu His Pro Ala Lys Ser Ser
305                 310                 315                 320
Thr Ser Phe Asp Phe Leu Glu Leu Asn Tyr Ser Phe Asp Lys Asn Ala
                325                 330                 335
Asp Thr Thr Met Lys Trp Gln Thr Lys Ala Phe Pro Ile Val Gly Glu
            340                 345                 350
Pro Leu Gln Lys His Gln Ser Leu Asp Leu Gly Ser Leu Leu Phe Glu
        355                 360                 365
Gly Cys Ser Asn Ser Lys Pro Val Asn Ala Ala Gly Arg Tyr Phe Asn
    370                 375                 380
Ser Lys Val Pro Ile Thr Arg Thr Lys Ser Thr Pro Phe Glu Leu Ile
385                 390                 395                 400
Gln Gln Arg Glu Thr Lys Glu Val Asp Ser Lys Glu Asn Phe Ser Tyr
                405                 410                 415
Leu Glu Ser Gln Pro His Asp Ser Cys Phe Val Glu Met Gln Ala Gln
            420                 425                 430
Lys Val Met His Val Ser Ser Ala Glu Leu Asn Tyr Ser Leu Pro Tyr
        435                 440                 445
Asp Ser Lys His Gln Ile Arg Asn Ala Ser Asn Val Lys His His Asp
    450                 455                 460
Ser Ser Ala Leu Gly Val Tyr Ser Tyr Ile Pro Leu Val Glu Asn Pro
465                 470                 475                 480
Tyr Phe Ser Ser Trp Pro Pro Ser Gly Thr Ser Ser Lys Met Ser Leu
                485                 490                 495
Asp Leu Pro Glu Lys Gln Asp Gly Thr Val Phe Pro Ser Ser Leu Leu
            500                 505                 510
Pro Thr Ser Ser Thr Ser Leu Phe Ser Tyr Tyr Asn Ser His Asp Ser
        515                 520                 525
Leu Ser Leu Asn Ser Pro Thr Asn Ile Ser Ser Leu Leu Asn Gln Glu
    530                 535                 540
Ser Ala Val Leu Ala Thr Ala Pro Arg Ile Asp Asp Glu Ile Pro Pro
545                 550                 555                 560
Pro Leu Pro Val Arg Thr Pro Glu Ser Phe Ile Val Val Glu Glu Ala
                565                 570                 575
Gly Glu Phe Ser Pro Asn Val Pro Lys Ser Leu Ser Ser Ala Val Lys
            580                 585                 590
Val Lys Ile Gly Thr Ser Leu Glu Trp Gly Gly Thr Ser Glu Pro Lys
        595                 600                 605
Lys Phe Asp Asp Ser Val Ile Leu Arg Pro Ser Lys Ser Val Lys Leu
    610                 615                 620
Arg Ser Pro Lys Ser Glu Leu His Gln Asp Arg Ser Ser Pro Pro Pro
```

```
                625                 630                 635                 640
            Pro Leu Pro Glu Arg Thr Leu Glu Ser Phe Phe Leu Ala Asp Glu Asp
                            645                 650                 655

Cys Met Gln Ala Gln Ser Ile Glu Thr Tyr Ser Thr Ser Tyr Pro Asp
                        660                 665                 670

Thr Met Glu Asn Ser Thr Ser Ser Lys Gln Thr Leu Lys Thr Pro Gly
                        675                 680                 685

Lys Ser Phe Thr Arg Ser Lys Ser Leu Lys Ile Leu Arg Asn Met Lys
                    690                 695                 700

Lys Ser Ile Cys Asn Ser Cys Pro Pro Asn Lys Pro Ala Glu Ser Val
            705                 710                 715                 720

Gln Ser Asn Asn Ser Ser Ser Phe Leu Asn Phe Gly Phe Ala Asn Arg
                            725                 730                 735

Phe Ser Lys Pro Lys Gly Pro Arg Asn Pro Pro Thr Trp Asn Ile
                        740                 745                 750

<210> SEQ ID NO 191
<211> LENGTH: 3825
<212> TYPE: DNA
<213> ORGANISM: Homo sapiens

<400> SEQUENCE: 191
ccggagaggt gttggagagc acaatggctg aacaagtcct tcctcaggct ttgtatttga      60
gcaatatgcg gaaagctgtg aagatacggg agagaactcc agaagacatt tttaaaccta    120
ctaatgggat cattcatcat tttaaaacca tgcaccgata cacactggaa atgttcagaa    180
cttgccagtt ttgtcctcag tttcgggaga tcatccacaa agccctcatc gacagaaaca    240
tccaggccac cctggaaagc agaagaaac tcaactggtg tcgagaagtc cggaagcttg     300
tggcgctgaa aacgaacggt gacggcaatt gcctcatgca tgccacttct cagtacatgt    360
ggggcgttca ggacacagac ttggtactga ggaaggcgct gttcagcacg ctcaaggaaa    420
cagacacacg caactttaaa ttccgctggc aactggagtc tctcaaatct caggaatttg    480
ttgaaacggg gctttgctat gatactcgga actggaatga tgaatgggac aatcttatca    540
aaatggcttc cacagacaca cccatggccc gaagtggact tcagtacaac tcactggaag    600
aaatacacat atttgtcctt tgcaacatcc tcagaaggcc aatcattgtc atttcagaca    660
aaatgctaag aagtttggaa tcaggttcca atttcgcccc tttgaaagtg ggtggaattt    720
acttgcctct ccactggcct gcccaggaat gctacagata ccccattgtt ctcggctatg    780
acagccatca ttttgtaccc ttggtgaccc tgaaggacag tgggcctgaa atccgagctg    840
ttccacttgt taacagagac cggggaagat tgaagactt aaaagttcac ttttttgacag    900 atcctgaaaa tgagatgaag gagaagctct taaagagta cttaatggtg atagaaatcc    960
ccgtccaagg ctgggaccat ggcacaactc atctcatcaa tgccgcaaag ttggatgaag   1020
ctaacttacc aaaagaaatc aatctggtag atgattactt tgaacttgtt cagcatgagt   1080
acaagaaatg gcaggaaaac agcgagcagg ggaggagaga ggggcacgcc cagaatccca   1140
tggaaccttc cgtgcccag ctttctctca tggatgtaaa atgtgaaacg cccaactgcc    1200
ccttcttcat gtctgtgaac acccagcctt tatgccatga gtgctcagag aggcggcaaa   1260
agaatcaaaa caaactccca aagctgaact ccaagccggg ccctgagggg ctccctggca   1320
tggcgctcgg ggcctctcgg ggagaagcct atgagccctt ggcgtggaac ctgaggagt    1380 ccactggggg gcctcattcg gccccaccga cagcacccag cccttttctg ttcagtgaga   1440
```

```
ccactgccat gaagtgcagg agccccggct gccccttcac actgaatgtg cagcacaacg   1500
gattttgtga acgttgccac aacgcccggc aacttcacgc cagccacgcc ccagaccaca   1560
caaggcactt ggatcccggg aagtgccaag cctgcctcca ggatgttacc aggacattta   1620
atgggatctg cagtacttgc ttcaaaagga ctacagcaga ggcctcctcc agcctcagca   1680
ccagcctccc tccttcctgt caccagcgtt ccaagtcaga tccctcgcgg ctcgtccgga   1740
gcccctcccc gcattcttgc cacagagctg gaaacgacgc ccctgctggc tgcctgtctc   1800
aagctgcacg gactcctggg gacaggacgg ggacgagcaa gtgcagaaaa gccggctgcg   1860
tgtattttgg gactccagaa acaagggct tttgcacact gtgtttcatc gagtacagag   1920
aaaacaaaca ttttgctgct gcctcaggga aagtcagtcc cacagcgtcc aggttccaga   1980
acaccattcc gtgcctgggg agggaatgcg gcacccttgg aagcaccatg tttgaaggat   2040
actgccagaa gtgtttcatt gaagctcaga atcagagatt tcatgaggcc aaaaggacag   2100
aagagcaact gagatcgagc cagcgcagag atgtgcctcg aaccacacaa agcacctcaa   2160
ggcccaagtg cgcccgggcc tcctgcaaga acatcctggc ctgccgcagc gaggagctct   2220
gcatggagtg tcagcatccc aaccagagga tgggccctgg ggcccaccgg ggtgagcctg   2280
cccccgaaga ccccccaag cagcgttgcc gggccccgc ctgtgatcat tttggcaatg   2340
ccaagtgcaa cggctactgc aacgaatgct tcagttcaa gcagatgtat ggctaaccgg   2400
aaacaggtgg gtcacctcct gcaagaagtg gggcctcgag ctgtcagtca tcatggtgct   2460
atcctctgaa cccctcagct gccactgcaa cagtgggctt aagggtgtct gagcaggaga   2520
ggaaagataa gctcttcgtg gtgcccacga tgctcaggtt tggtaacccg ggagtgttcc   2580
caggtggcct tagaaagcaa agcttgtaac tggcaaggga tgatgtcaga ttcagcccaa   2640
ggttcctcct ctcctaccaa gcaggaggcc aggaacttct ttggacttgg aaggtgtgcg   2700
gggactggcc gaggcccctg caccctgcgc atcaggactg cttcatcgtc ttggctgaga   2760
aagggaaaag acacacaagt cgcgtgggtt ggagaagcca gagccattcc acctcccctc   2820
ccccagcatc tctcagagat gtgaagccag atcctcatgg cagcgaggcc ctctgcaaga   2880
agctcaagga agctcaggga aaatggacgt attcagagag tgtttgtagt tcatggtttt   2940
tccctacctg cccggttcct ttcctgagga cccggcagaa atgcagaacc atccatggac   3000
tgtgattctg aggctgctga gactgaacat gttcacattg acagaaaaac aagctgctct   3060
ttataatatg cacctttaa aaaattagaa tattttactg ggaagacgtg taactctttg   3120
ggttattact gtctttactt ctaaagaagt tagcttgaac tgaggagtaa agtgtgtac   3180
atatataata taccttaca ttatgtatga gggattttt taaattatat tgaaatgctg   3240
ccctagaagt acaataggaa ggctaaataa taataacctg ttttctggtt gttgttgggg   3300
catgagcttg tgtatacact gcttgcataa actcaaccag ctgccttttt aaagggagct   3360
ctagtccttt ttgtgtaatt cacttttattt atttttattac aaacttcaag attatttaag   3420
cgaagatatt tcttcagctc tggggaaaat gccacagtgt tctcctgaga gaacatcctt   3480
gctttgagtc aggctgtggg caagttcctg accacaggga gtaaattggc ctctttgata   3540
cacttttgct tgcctcccca ggaaagaagg aattgcatcc aagtatacaa tacatattca   3600
tcgatgtttc gtgcttctcc ttatgaaact ccagctatgt aataaaaac tatactctgt   3660
gttctgttaa tgcctctgag tgtcctacct ccttggagat gagataggga aggagcaggg   3720
atgagactgg caatggtcac agggaaagat gtggcctttt tgtgatggttt tattttctgt   3780
taacactgtg tcctgggggg gctgggaagt cccctgcatc ccatg           3825
```

<210> SEQ ID NO 192
<211> LENGTH: 790
<212> TYPE: PRT
<213> ORGANISM: Homo sapiens

<400> SEQUENCE: 192

```
Met Ala Glu Gln Val Leu Pro Gln Ala Leu Tyr Leu Ser Asn Met Arg
1               5                   10                  15

Lys Ala Val Lys Ile Arg Glu Arg Thr Pro Glu Asp Ile Phe Lys Pro
                20                  25                  30

Thr Asn Gly Ile Ile His His Phe Lys Thr Met His Arg Tyr Thr Leu
            35                  40                  45

Glu Met Phe Arg Thr Cys Gln Phe Cys Pro Gln Phe Arg Glu Ile Ile
50                  55                  60

His Lys Ala Leu Ile Asp Arg Asn Ile Gln Ala Thr Leu Glu Ser Gln
65                  70                  75                  80

Lys Lys Leu Asn Trp Cys Arg Glu Val Arg Lys Leu Val Ala Leu Lys
                85                  90                  95

Thr Asn Gly Asp Gly Asn Cys Leu Met His Ala Thr Ser Gln Tyr Met
            100                 105                 110

Trp Gly Val Gln Asp Thr Asp Leu Val Leu Arg Lys Ala Leu Phe Ser
        115                 120                 125

Thr Leu Lys Glu Thr Asp Thr Arg Asn Phe Lys Phe Arg Trp Gln Leu
130                 135                 140

Glu Ser Leu Lys Ser Gln Glu Phe Val Glu Thr Gly Leu Cys Tyr Asp
145                 150                 155                 160

Thr Arg Asn Trp Asn Asp Glu Trp Asp Asn Leu Ile Lys Met Ala Ser
                165                 170                 175

Thr Asp Thr Pro Met Ala Arg Ser Gly Leu Gln Tyr Asn Ser Leu Glu
            180                 185                 190

Glu Ile His Ile Phe Val Leu Cys Asn Ile Leu Arg Arg Pro Ile Ile
        195                 200                 205

Val Ile Ser Asp Lys Met Leu Arg Ser Leu Glu Ser Gly Ser Asn Phe
210                 215                 220

Ala Pro Leu Lys Val Gly Gly Ile Tyr Leu Pro Leu His Trp Pro Ala
225                 230                 235                 240

Gln Glu Cys Tyr Arg Tyr Pro Ile Val Leu Gly Tyr Asp Ser His His
                245                 250                 255

Phe Val Pro Leu Val Thr Leu Lys Asp Ser Gly Pro Glu Ile Arg Ala
            260                 265                 270

Val Pro Leu Val Asn Arg Asp Arg Gly Arg Phe Glu Asp Leu Lys Val
        275                 280                 285

His Phe Leu Thr Asp Pro Glu Asn Glu Met Lys Glu Lys Leu Leu Lys
290                 295                 300

Glu Tyr Leu Met Val Ile Glu Ile Pro Val Gln Gly Trp Asp His Gly
305                 310                 315                 320

Thr Thr His Leu Ile Asn Ala Ala Lys Leu Asp Glu Ala Asn Leu Pro
                325                 330                 335

Lys Glu Ile Asn Leu Val Asp Asp Tyr Phe Glu Leu Val Gln His Glu
            340                 345                 350

Tyr Lys Lys Trp Gln Glu Asn Ser Glu Gln Gly Arg Arg Glu Gly His
        355                 360                 365

Ala Gln Asn Pro Met Glu Pro Ser Val Pro Gln Leu Ser Leu Met Asp
```

```
              370                 375                 380
Val Lys Cys Glu Thr Pro Asn Cys Pro Phe Phe Met Ser Val Asn Thr
385                 390                 395                 400

Gln Pro Leu Cys His Glu Cys Ser Glu Arg Arg Gln Lys Asn Gln Asn
                405                 410                 415

Lys Leu Pro Lys Leu Asn Ser Lys Pro Gly Pro Glu Gly Leu Pro Gly
                420                 425                 430

Met Ala Leu Gly Ala Ser Arg Gly Glu Ala Tyr Glu Pro Leu Ala Trp
                435                 440                 445

Asn Pro Glu Glu Ser Thr Gly Gly Pro His Ser Ala Pro Pro Thr Ala
            450                 455                 460

Pro Ser Pro Phe Leu Phe Ser Glu Thr Thr Ala Met Lys Cys Arg Ser
465                 470                 475                 480

Pro Gly Cys Pro Phe Thr Leu Asn Val Gln His Asn Gly Phe Cys Glu
                485                 490                 495

Arg Cys His Asn Ala Arg Gln Leu His Ala Ser His Ala Pro Asp His
                500                 505                 510

Thr Arg His Leu Asp Pro Gly Lys Cys Gln Ala Cys Leu Gln Asp Val
            515                 520                 525

Thr Arg Thr Phe Asn Gly Ile Cys Ser Thr Cys Phe Lys Arg Thr Thr
            530                 535                 540

Ala Glu Ala Ser Ser Ser Leu Ser Thr Ser Leu Pro Pro Ser Cys His
545                 550                 555                 560

Gln Arg Ser Lys Ser Asp Pro Ser Arg Leu Val Arg Ser Pro Ser Pro
                565                 570                 575

His Ser Cys His Arg Ala Gly Asn Asp Ala Pro Ala Gly Cys Leu Ser
                580                 585                 590

Gln Ala Ala Arg Thr Pro Gly Asp Arg Thr Gly Thr Ser Lys Cys Arg
            595                 600                 605

Lys Ala Gly Cys Val Tyr Phe Gly Thr Pro Glu Asn Lys Gly Phe Cys
            610                 615                 620

Thr Leu Cys Phe Ile Glu Tyr Arg Glu Asn Lys His Phe Ala Ala Ala
625                 630                 635                 640

Ser Gly Lys Val Ser Pro Thr Ala Ser Arg Phe Gln Asn Thr Ile Pro
                645                 650                 655

Cys Leu Gly Arg Glu Cys Gly Thr Leu Gly Ser Thr Met Phe Glu Gly
                660                 665                 670

Tyr Cys Gln Lys Cys Phe Ile Glu Ala Gln Asn Gln Arg Phe His Glu
                675                 680                 685

Ala Lys Arg Thr Glu Glu Gln Leu Arg Ser Ser Gln Arg Arg Asp Val
            690                 695                 700

Pro Arg Thr Thr Gln Ser Thr Ser Arg Pro Lys Cys Ala Arg Ala Ser
705                 710                 715                 720

Cys Lys Asn Ile Leu Ala Cys Arg Ser Glu Glu Leu Cys Met Glu Cys
                725                 730                 735

Gln His Pro Asn Gln Arg Met Gly Pro Gly Ala His Arg Gly Glu Pro
                740                 745                 750

Ala Pro Glu Asp Pro Lys Gln Arg Cys Arg Ala Pro Ala Cys Asp
                755                 760                 765

His Phe Gly Asn Ala Lys Cys Asn Gly Tyr Cys Asn Glu Cys Phe Gln
            770                 775                 780

Phe Lys Gln Met Tyr Gly
785                 790
```

<210> SEQ ID NO 193
<211> LENGTH: 2588
<212> TYPE: DNA
<213> ORGANISM: Homo sapiens

<400> SEQUENCE: 193

| | | | | | |
|---|---|---|---|---|---|
| gctttctcct | agggactgtg | aggggcgctt | ctgactttgg | acttgagcac | tgcctgggac | 60 |
| ctgtgctgag | agagcgctag | catgtctcag | tggaatcaag | tccaacagtt | agaaatcaag | 120 |
| tttttggagc | aggtggatca | attctatgat | gacaactttc | ccatggaaat | tcggcatctg | 180 |
| ttggcccaat | ggattgaaaa | tcaagactgg | gaggcagctt | ctaacaatga | aaccatggca | 240 |
| acgattcttc | ttcaaaactt | gttaatacaa | ctggatgaac | agttaggtcg | tgtttccaaa | 300 |
| gagaaaaacc | tactcttgat | acacaatcta | aaaagaatta | ggaaggtcct | tcagggaaaa | 360 |
| tttcatggaa | atccaatgca | tgtagctgtg | gttatttcaa | actgtttaag | ggaagagagg | 420 |
| agaatattgg | ctgcagccaa | catgcctgtc | caggggcctc | tagagaaatc | cttacaaagt | 480 |
| tcttcagttt | cagaaagaca | gaggaatgtg | gagcacaaag | tggctgccat | taaaaacagt | 540 |
| gtgcagatga | cagaacaaga | taccaaatac | ttagaagatc | tgcaagacga | atttgactac | 600 |
| aggtatataa | caattcagac | aatggatcag | agtgacaaga | atagtgccat | ggtgaatcag | 660 |
| gaagttttga | cactgcagga | aatgcttaac | agcctcgatt | tcaagagaaa | ggaggctctc | 720 |
| agtaaaatga | cccaaatcat | ccatgagaca | gacctgttaa | tgaacaccat | gctcatagaa | 780 |
| gagctgcaag | actggaagcg | gcggcagcaa | atcgcctgca | tcgggggtcc | actccacaat | 840 |
| gggctcgacc | agcttcagaa | ctgctttaca | ctattggcag | aaagtctttt | ccaactgaga | 900 |
| aggcaattgg | agaaactaga | ggagcaatct | accaaaatga | catatgaagg | tgatcccatt | 960 |
| ccaatgcaaa | gaactcacat | gctagaaaga | gtcaccttct | tgatctacaa | ccttttcaag | 1020 |
| aactcatttg | tggttgagcg | acagccatgt | atgccaaccc | accctcagag | gccgttggta | 1080 |
| cttaaaaccc | taattcagtt | cactgtaaaa | ctaaggctac | taataaaatt | gccagaacta | 1140 |
| aactatcagg | taaaggttaa | ggcatcaatt | gacaagaatg | tttcaactct | aagcaaccga | 1200 |
| agatttgtac | tttgtggaac | taatgtcaaa | gccatgtcta | ttgaagaatc | ttccaatggg | 1260 |
| agtctctcag | tagaatttcg | acatttgcaa | ccaaaggaaa | tgaagtccag | tgctggaggt | 1320 |
| aaaggaaatg | agggctgtca | catggtgact | gaagaacttc | attccataac | gtttgaaaca | 1380 |
| cagatctgcc | tctatggcct | gaccatagat | ttggagacca | gctcattgcc | tgtggtgatg | 1440 |
| atttccaatg | tcagtcagtt | acctaatgct | gggcatccaa | tcatttggta | caacgtgtca | 1500 |
| accaacgatt | cccagaactt | ggttttcttt | aataatcctc | cacctgccac | attgagtcaa | 1560 |
| ctactggagg | tgatgagctg | gcagttttca | tcgtacgttg | gtcgtggtct | taactcagat | 1620 |
| caactccata | tgctggcaga | gaagcttaca | gtccaatcta | gctacagtga | tggtcaccctc | 1680 |
| acctgggcca | agtctgcaa | ggaacattta | cctggtaaat | catttacctt | ttggacatgg | 1740 |
| cttgaagcaa | tattggatct | aattaagaaa | cacattcttc | ccctttggat | tgatgggtat | 1800 |
| gtcatgggct | ttgttagcaa | agagaaggaa | cggctgttgc | taaaggataa | aatgcctggc | 1860 |
| acctttttat | taagattcag | tgaaagccat | ctcggaggaa | taactttcac | ctgggtggac | 1920 |
| cattctgaaa | gtgggaagt | gagattccac | tctgtagaac | cctacaataa | aggccggttg | 1980 |
| tctgctctgc | cattcgctga | catcctgcga | gactacaaag | ttattatggc | tgaaaacatt | 2040 |
| cctgaaaacc | ctctgaagta | cctatatcct | gacattccca | aagacaaagc | cttcggtaaa | 2100 |

```
cactacagct ctcagccttg cgaagtttca agaccaacag aaagggggtga caaaggttat    2160 gttccttctg tttttatccc catctcaaca atccgaagtg attcaacaga gccacattct    2220
ccatcagacc ttcttcccat gtctccaagt gtgtatgcgg tgttgagaga aaacctgagt    2280
cccacaacaa ttgaaactgc aatgaagtct ccttattctg ctgaatgaca ggataaactc    2340
tgacgcacca agaaggaag caaatgaaaa agtttaaaga ctgttctttg cccaataacc    2400 acatttatt tcttcagctt tgtaaatacc aggttctagg aaatgtttga catctgaagc    2460
tctcttcaca ctcccgtggc actcctcaat tgggagtgtt gtgactgaaa tgcttgaaac    2520
caaagcttca gataaacttg caagataaga caactttaag aaaccagtgt taataacaat    2580
attaacag                                                             2588
```

<210> SEQ ID NO 194
<211> LENGTH: 748
<212> TYPE: PRT
<213> ORGANISM: Homo sapiens

<400> SEQUENCE: 194

```
Met Ser Gln Trp Asn Gln Val Gln Gln Leu Glu Ile Lys Phe Leu Glu
1               5                   10                  15

Gln Val Asp Gln Phe Tyr Asp Asp Asn Phe Pro Met Glu Ile Arg His
            20                  25                  30

Leu Leu Ala Gln Trp Ile Glu Asn Gln Asp Trp Glu Ala Ala Ser Asn
        35                  40                  45

Asn Glu Thr Met Ala Thr Ile Leu Leu Gln Asn Leu Leu Ile Gln Leu
    50                  55                  60

Asp Glu Gln Leu Gly Arg Val Ser Lys Glu Lys Asn Leu Leu Leu Ile
65                  70                  75                  80

His Asn Leu Lys Arg Ile Arg Lys Val Leu Gln Gly Lys Phe His Gly
                85                  90                  95

Asn Pro Met His Val Ala Val Val Ile Ser Asn Cys Leu Arg Glu Glu
            100                 105                 110

Arg Arg Ile Leu Ala Ala Ala Asn Met Pro Val Gln Gly Pro Leu Glu
        115                 120                 125

Lys Ser Leu Gln Ser Ser Ser Val Ser Glu Arg Gln Arg Asn Val Glu
    130                 135                 140

His Lys Val Ala Ala Ile Lys Asn Ser Val Gln Met Thr Glu Gln Asp
145                 150                 155                 160

Thr Lys Tyr Leu Glu Asp Leu Gln Asp Glu Phe Asp Tyr Arg Tyr Lys
                165                 170                 175

Thr Ile Gln Thr Met Asp Gln Ser Asp Lys Asn Ser Ala Met Val Asn
            180                 185                 190

Gln Glu Val Leu Thr Leu Gln Glu Met Leu Asn Ser Leu Asp Phe Lys
        195                 200                 205

Arg Lys Glu Ala Leu Ser Lys Met Thr Gln Ile Ile His Glu Thr Asp
    210                 215                 220

Leu Leu Met Asn Thr Met Leu Ile Glu Glu Leu Gln Asp Trp Lys Arg
225                 230                 235                 240

Arg Gln Gln Ile Ala Cys Ile Gly Gly Pro Leu His Asn Gly Leu Asp
                245                 250                 255

Gln Leu Gln Asn Cys Phe Thr Leu Leu Ala Glu Ser Leu Phe Gln Leu
            260                 265                 270

Arg Arg Gln Leu Glu Lys Leu Glu Glu Gln Ser Thr Lys Met Thr Tyr
        275                 280                 285
```

-continued

```
Glu Gly Asp Pro Ile Pro Met Gln Arg Thr His Met Leu Glu Arg Val
        290                 295                 300

Thr Phe Leu Ile Tyr Asn Leu Phe Lys Asn Ser Phe Val Val Glu Arg
305                 310                 315                 320

Gln Pro Cys Met Pro Thr His Pro Gln Arg Pro Leu Val Leu Lys Thr
                325                 330                 335

Leu Ile Gln Phe Thr Val Lys Leu Arg Leu Leu Ile Lys Leu Pro Glu
                340                 345                 350

Leu Asn Tyr Gln Val Lys Val Lys Ala Ser Ile Asp Lys Asn Val Ser
            355                 360                 365

Thr Leu Ser Asn Arg Arg Phe Val Leu Cys Gly Thr Asn Val Lys Ala
    370                 375                 380

Met Ser Ile Glu Glu Ser Ser Asn Gly Ser Leu Ser Val Glu Phe Arg
385                 390                 395                 400

His Leu Gln Pro Lys Glu Met Lys Ser Ser Ala Gly Gly Lys Gly Asn
                405                 410                 415

Glu Gly Cys His Met Val Thr Glu Glu Leu His Ser Ile Thr Phe Glu
                420                 425                 430

Thr Gln Ile Cys Leu Tyr Gly Leu Thr Ile Asp Leu Glu Thr Ser Ser
            435                 440                 445

Leu Pro Val Val Met Ile Ser Asn Val Ser Gln Leu Pro Asn Ala Trp
    450                 455                 460

Ala Ser Ile Ile Trp Tyr Asn Val Ser Thr Asn Asp Ser Gln Asn Leu
465                 470                 475                 480

Val Phe Phe Asn Asn Pro Pro Ala Thr Leu Ser Gln Leu Leu Glu
                485                 490                 495

Val Met Ser Trp Gln Phe Ser Ser Tyr Val Gly Arg Gly Leu Asn Ser
                500                 505                 510

Asp Gln Leu His Met Leu Ala Glu Lys Leu Thr Val Gln Ser Ser Tyr
            515                 520                 525

Ser Asp Gly His Leu Thr Trp Ala Lys Phe Cys Lys Glu His Leu Pro
    530                 535                 540

Gly Lys Ser Phe Thr Phe Trp Thr Trp Leu Glu Ala Ile Leu Asp Leu
545                 550                 555                 560

Ile Lys Lys His Ile Leu Pro Leu Trp Ile Asp Gly Tyr Val Met Gly
                565                 570                 575

Phe Val Ser Lys Glu Lys Glu Arg Leu Leu Leu Lys Asp Lys Met Pro
                580                 585                 590

Gly Thr Phe Leu Leu Arg Phe Ser Glu Ser His Leu Gly Gly Ile Thr
            595                 600                 605

Phe Thr Trp Val Asp His Ser Glu Ser Gly Glu Val Arg Phe His Ser
    610                 615                 620

Val Glu Pro Tyr Asn Lys Gly Arg Leu Ser Ala Leu Pro Phe Ala Asp
625                 630                 635                 640

Ile Leu Arg Asp Tyr Lys Val Ile Met Ala Glu Asn Ile Pro Glu Asn
                645                 650                 655

Pro Leu Lys Tyr Leu Tyr Pro Asp Ile Pro Lys Asp Lys Ala Phe Gly
                660                 665                 670

Lys His Tyr Ser Ser Gln Pro Cys Glu Val Ser Arg Pro Thr Glu Arg
            675                 680                 685

Gly Asp Lys Gly Tyr Val Pro Ser Val Phe Ile Pro Ile Ser Thr Ile
    690                 695                 700
```

Arg Ser Asp Ser Thr Glu Pro His Ser Pro Ser Asp Leu Leu Pro Met
705                 710                 715                 720

Ser Pro Ser Val Tyr Ala Val Leu Arg Glu Asn Leu Ser Pro Thr Thr
            725                 730                 735

Ile Glu Thr Ala Met Lys Ser Pro Tyr Ser Ala Glu
            740                 745

<210> SEQ ID NO 195
<211> LENGTH: 1125
<212> TYPE: DNA
<213> ORGANISM: Homo sapiens

<400> SEQUENCE: 195

```
atgagcgggg aatcaatgaa tttcagcgat gttttcgact ccagtgaaga ttattttgtg     60
tcagtcaata cttcatatta ctcagttgat tctgagatgt tactgtgctc cttgcaggag    120
gtcaggcagt tctccaggct atttgtaccg attgcctact ccttgatctg tgtctttggc    180
ctcctgggga atattctggt ggtgatcacc tttgcttttt ataagaaggc caggtctatg    240
acagacgtct atctcttgaa catggccatt gcagacatcc tctttgttct tactctccca    300
ttctgggcag tgagtcatgc cactggtgcg tgggttttca gcaatgccac gtgcaagttg    360
ctaaaaggca tctatgccat caactttaac tgcgggatgc tgctcctgac ttgcattagc    420
atggaccggt acatcgccat tgtacaggcg actaagtcat tccggctccg atccagaaca    480
ctaccgcgca gcaaaatcat ctgccttgtt gtgtgggggc tgtcagtcat catctccagc    540
tcaacttttg tcttcaacca aaaatacaac acccaaggca cgatgtctg tgaacccaag    600
taccagactg tctcggagcc catcaggtgg aagctgctga tgttggggct tgagctactc    660
tttggtttct ttatcccttt gatgttcatg atattttgtt acacgttcat tgtcaaaacc    720
ttggtgcaag ctcagaattc taaaaggcac aaagccatcc gtgtaatcat agctgtggtg    780
cttgtgtttc tggcttgtca gattcctcat aacatggtcc tgcttgtgac ggctgcaaat    840
ttgggtaaaa tgaaccgatc ctgccagagc gaaaagctaa ttggctatac gaaaactgtc    900
acagaagtcc tggctttcct gcactgctgc ctgaaccctg tgctctacgc ttttattggg    960
cagaagttca gaaactactt tctgaagatc ttgaaggacc tgtggtgtgt gagaaggaag   1020
tacaagtcct caggcttctc ctgtgccggg aggtactcag aaaacatttc tcggcagacc   1080
agtgagaccg cagataacga caatgcgtcg tccttcacta tgtga               1125
```

<210> SEQ ID NO 196
<211> LENGTH: 374
<212> TYPE: PRT
<213> ORGANISM: Homo sapiens

<400> SEQUENCE: 196

Met Ser Gly Glu Ser Met Asn Phe Ser Asp Val Phe Asp Ser Ser Glu
1               5                   10                  15

Asp Tyr Phe Val Ser Val Asn Thr Ser Tyr Tyr Ser Val Asp Ser Glu
            20                  25                  30

Met Leu Leu Cys Ser Leu Gln Glu Val Arg Gln Phe Ser Arg Leu Phe
        35                  40                  45

Val Pro Ile Ala Tyr Ser Leu Ile Cys Val Phe Gly Leu Leu Gly Asn
    50                  55                  60

Ile Leu Val Val Ile Thr Phe Ala Phe Tyr Lys Lys Ala Arg Ser Met
65                  70                  75                  80

Thr Asp Val Tyr Leu Leu Asn Met Ala Ile Ala Asp Ile Leu Phe Val

```
                    85                  90                  95
Leu Thr Leu Pro Phe Trp Ala Val Ser His Ala Thr Gly Ala Trp Val
                100                 105                 110
Phe Ser Asn Ala Thr Cys Lys Leu Leu Lys Gly Ile Tyr Ala Ile Asn
            115                 120                 125
Phe Asn Cys Gly Met Leu Leu Leu Thr Cys Ile Ser Met Asp Arg Tyr
        130                 135                 140
Ile Ala Ile Val Gln Ala Thr Lys Ser Phe Arg Leu Arg Ser Arg Thr
145                 150                 155                 160
Leu Pro Arg Ser Lys Ile Ile Cys Leu Val Val Trp Gly Leu Ser Val
                165                 170                 175
Ile Ile Ser Ser Ser Thr Phe Val Phe Asn Gln Lys Tyr Asn Thr Gln
                180                 185                 190
Gly Ser Asp Val Cys Glu Pro Lys Tyr Gln Thr Val Ser Glu Pro Ile
            195                 200                 205
Arg Trp Lys Leu Leu Met Leu Gly Leu Glu Leu Leu Phe Gly Phe Phe
        210                 215                 220
Ile Pro Leu Met Phe Met Ile Phe Cys Tyr Thr Phe Ile Val Lys Thr
225                 230                 235                 240
Leu Val Gln Ala Gln Asn Ser Lys Arg His Lys Ala Ile Arg Val Ile
                245                 250                 255
Ile Ala Val Val Leu Val Phe Leu Ala Cys Gln Ile Pro His Asn Met
            260                 265                 270
Val Leu Leu Val Thr Ala Ala Asn Leu Gly Lys Met Asn Arg Ser Cys
        275                 280                 285
Gln Ser Glu Lys Leu Ile Gly Tyr Thr Lys Thr Val Thr Glu Val Leu
290                 295                 300
Ala Phe Leu His Cys Cys Leu Asn Pro Val Leu Tyr Ala Phe Ile Gly
305                 310                 315                 320
Gln Lys Phe Arg Asn Tyr Phe Leu Lys Ile Leu Lys Asp Leu Trp Cys
                325                 330                 335
Val Arg Arg Lys Tyr Lys Ser Ser Gly Phe Ser Cys Ala Gly Arg Tyr
            340                 345                 350
Ser Glu Asn Ile Ser Arg Gln Thr Ser Glu Thr Ala Asp Asn Asp Asn
        355                 360                 365
Ala Ser Ser Phe Thr Met
        370

<210> SEQ ID NO 197
<211> LENGTH: 2258
<212> TYPE: DNA
<213> ORGANISM: Homo sapiens

<400> SEQUENCE: 197
ctcctccagc tcttcctgtc ccgctgttgc aacactgcct cactcttccc ctcccacctt      60
ctctcccctc tctctgctt taattttctc agaattctct ggactgaggc tccagttctg     120
gcctttgggg ttcaagatca ctgggaccag gccgtgatct ctatgcccga gtctcaaccc     180
tcaactgtca ccccaaggca cttgggacgt cctggacaga ccgagtcccg ggaagcccca     240
gcactgccgc tgccacactg ccctgagccc aaatggggga gtgagaggcc atagctgtct     300
ggcatgggcc tctccaccgt gcctgacctg ctgctgccac tggtgctcct ggagctgttg     360
gtgggaatat acccctcagg ggttattgga ctggtccctc acctagggga cagggagaag     420
agagatagtg tgtgtcccca aggaaaatat atccacccct aaaataattc gatttgctgt     480
```

```
accaagtgcc acaaaggaac ctacttgtac aatgactgtc caggcccggg gcaggatacg    540
gactgcaggg agtgtgagag cggctccttc accgcttcag aaaaccacct cagacactgc    600
ctcagctgct ccaaatgccg aaaggaaatg ggtcaggtgg agatctcttc ttgcacagtg    660
gaccgggaca ccgtgtgtgg ctgcaggaag aaccagtacc ggcattattg gagtgaaaac    720
cttttccagt gcttcaattg cagcctctgc ctcaatggga ccgtgcacct ctcctgccag    780
gagaaacaga acaccgtgtg cacctgccat gcaggtttct ttctaagaga aaacgagtgt    840
gtctcctgta gtaactgtaa gaaaagcctg gagtgcacga agttgtgcct accccagatt    900
gagaatgtta agggcactga ggactcaggc accacagtgc tgttgcccct ggtcattttc    960
tttggtcttt gccttttatc cctcctcttc attggtttaa tgtatcgcta ccaacggtgg   1020
aagtccaagc tctactccat tgtttgtggg aaatcgacac ctgaaaaaga ggggagctt    1080 gaaggaacta ctactaagcc cctggcccca acccaagct tcagtcccac tccaggcttc    1140 accccaccc tgggcttcag tcccgtgccc agttccacct tcacctccag ctccacctat   1200 accccggtg actgtcccaa ctttgcggct ccccgcagag aggtggcacc accctatcag   1260
ggggctgacc ccatccttgc gacagccctc gcctccgacc ccatccccaa cccccttcag   1320
aagtgggagg acagcgccca aagccacag agcctagaca ctgatgaccc cgcgacgctg   1380
tacgccgtgg tggagaacgt gcccccgttg cgctggaagg aattcgtgcg cgcctaggg    1440 ctgagcgacc acgagatcga tcggctggag ctgcagaacg ggcgctgcct gcgcgaggcg   1500
caatacagca tgctggcgac ctggaggcgg cgcacgccgc ggcgcgaggc cacgctggag   1560
ctgctgggac gcgtgctccg cgacatggac ctgctgggct gcctggagga catcgaggag   1620
gcgctttgcg gccccgccgc cctcccgccc gcgcccagtc ttctcagatg aggctgcgcc   1680
cctgcgggca gctctaagga ccgtcctgcg agatcgcctt ccaaccccac ttttttctgg   1740
aaaggagggg tcctgcaggg gcaagcagga gctagcagcc gcctacttgg tgctaacccc   1800
tcgatgtaca tagcttttct cagctgcctg cgcgccgccg acagtcagcg ctgtgcgcgc   1860
ggagagaggt gcgccgtggg ctcaagagcc tgagtgggtg gtttgcgagg atgagggacg   1920
ctatgcctca tgcccgtttt gggtgtcctc accagcaagg ctgctcgggg gcccctggtt   1980
cgtccctgag cctttttcac agtgcataag cagttttttt tgttttttgtt ttgttttgtt   2040 ttgtttttaa atcaatcatg ttacactaat agaaacttgg cactcctgtg ccctctgcct   2100
ggacaagcac atagcaagct gaactgtcct aaggcagggg cgagcacgga caatggggc    2160 cttcagctgg agctgtggac ttttgtacat acactaaaat tctgaagtta aagctctgct   2220
cttggaaaaa aaaaaaaaa aaaaaaaaa aaaaaaa                               2258
```

<210> SEQ ID NO 198
<211> LENGTH: 455
<212> TYPE: PRT
<213> ORGANISM: Homo sapiens

<400> SEQUENCE: 198

```
Met Gly Leu Ser Thr Val Pro Asp Leu Leu Pro Leu Val Leu Leu
1               5                   10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
```

-continued

```
                50                  55                  60
Gly Thr Tyr Leu Tyr Asn Asp Cys Pro Gly Pro Gly Gln Asp Thr Asp
 65                  70                  75                  80

Cys Arg Glu Cys Glu Ser Gly Ser Phe Thr Ala Ser Glu Asn His Leu
                 85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445

Pro Ala Pro Ser Leu Leu Arg
450                 455

<210> SEQ ID NO 199
```

<211> LENGTH: 2394
<212> TYPE: DNA
<213> ORGANISM: Homo sapiens

<400> SEQUENCE: 199

```
gaattcggcg cagcggagcc tggagagaag gcgctgggct gcgagggcgc gagggcgcga      60
gggcagggg  caaccggacc ccgcccgcac ccatggcgcc cgtcgccgtc tgggccgcgc     120
tggccgtcgg actggagctc tgggctgcgg cgcacgcctt gccgcccag  gtggcattta     180
caccctacgc cccggagccc gggagcacat gccggctcag agaatactat gaccagacag     240
ctcagatgtg ctgcagcaag tgctcgccgg gccaacatgc aaaagtcttc tgtaccaaga     300
cctcggacac cgtgtgtgac tcctgtgagg acagcacata cacccagctc tggaactggg     360
ttcccgagtg cttgagctgt ggctcccgct gtagctctga ccaggtggaa actcaagcct     420
gcactcggga acagaaccgc atctgcacct gcaggcccgg ctggtactgc gcgctgagca     480
agcaggaggg gtgccggctg tgcgcgccgc tgcgcaagtg ccgcccgggc ttcggcgtgg     540
ccagaccagg aactgaaaca tcagacgtgg tgtgcaagcc ctgtgccccg gggacgttct     600
ccaacacgac ttcatccacg atatttgca  ggccccacca gatctgtaac gtggtggcca     660
tccctgggaa tgcaagcagg gatgcagtct gcacgtccac gtcccccacc cggagtatgg     720
ccccaggggc agtacactta ccccagccag tgtccacacg atcccaacac acgcagccaa     780
ctccagaacc cagcactgct ccaagcacct ccttcctgct cccaatgggc cccagccccc     840
cagctgaagg gagcactggc gacttcgctc ttccagttgg actgattgtg ggtgtgacag     900
ccttgggtct actaataata ggagtggtga actgtgtcat catgacccag gtgaaaaaga     960
agccccttgtg cctgcagaga gaagccaagg tgcctcactt gcctgccgat aaggcccggg    1020
gtacacaggg ccccgagcag cagcacctgc tgatcacagc gccgagctcc agcagcagct    1080
ccctggagag ctcggccagt gcgttggaca aagggcgcc cactcggaac cagccacagg    1140
caccaggcgt ggaggccagt ggggccgggg aggcccgggc cagcaccggg agctcagatt    1200
cttcccctgg tggccatggg acccaggtca atgtcacctg catcgtgaac gtctgtagca    1260
gctctgacca cagctcacag tgctcctccc aagccagctc acaatgggga gacacagatt    1320
ccagcccctc ggagtccccg aaggacgagc aggtcccctt ctccaaggag aatgtgcct    1380
ttcggtcaca gctggagacg ccagagaccc tgctggggag caccgaagag aagcccctgc    1440
cccttggagt gcctgatgct gggatgaagc ccagttaacc aggccggtgt gggctgtgtc    1500
gtagccaagg tgggctgagc cctggcagga tgacctgcg  aagggccct  ggtccttcca    1560
ggcccccacc actaggactc tgaggctctt tctgggccaa gttcctctag tgccctccac    1620
agccgcagcc tccctctgac ctgcaggcca agagcagagg cagcgggttg tggaaagcct    1680
ctgctgccat ggtgtgtccc tctcggaagg ctggctgggc atggacgttc ggggcatgct    1740
ggggcaagtc cctgactctc tgtgacctgc ccgcccagc  tgcacctgcc agcctggctt    1800
ctggagccct tgggtttttt gtttgtttgt ttgtttgttt gtttgtttct ccccctgggc    1860
tctgccccag ctctggcttc cagaaaaccc cagcatcctt ttctgcagag gggctttctg    1920
gagaggaggg atgctgcctg agtcacccat gaagacagga cagtgcttca gcctgaggct    1980
gagactgcgg gatggtcctg gggctctgtg cagggaggag gtggcagccc tgtagggaac    2040
ggggtccttc aagttagctc aggaggcttg gaaagcatca cctcaggcca ggtgcagtcc    2100
ctcacgccta tgatcccagc actttgggag gctgaggcgg gtggatcacc tgaggttagg    2160
agttcgagac cagcctggcc aacatggtaa accccatct  ctactaaaaa tacagaaatt    2220
```

```
agccgggcgt ggtggcgggc acctatagtc ccagctactc agaagcctga ggctgggaaa    2280
tcgtttgaac ccgggaagcg gaggttgcag ggagccgaga tcacgccact gcactccagc    2340
ctgggcgaca gagcgagagt ctgtctcaaa agaaaaaaaa aaaaaaccga attc          2394
```

<210> SEQ ID NO 200
<211> LENGTH: 461
<212> TYPE: PRT
<213> ORGANISM: Homo sapiens

<400> SEQUENCE: 200

```
Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Arg Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
        275                 280                 285

Lys Lys Pro Leu Cys Leu Gln Arg Glu Ala Lys Val Pro His Leu Pro
    290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
```

```
                340             345             350
Val Glu Ala Ser Gly Ala Gly Glu Ala Arg Ala Ser Thr Gly Ser Ser
            355                 360                 365

Asp Ser Ser Pro Gly Gly His Gly Thr Gln Val Asn Val Thr Cys Ile
        370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
            420                 425                 430

Gln Leu Glu Thr Pro Glu Thr Leu Leu Gly Ser Thr Glu Glu Lys Pro
        435                 440                 445

Leu Pro Leu Gly Val Pro Asp Ala Gly Met Lys Pro Ser
            450                 455                 460
```

<210> SEQ ID NO 201
<211> LENGTH: 1240
<212> TYPE: DNA
<213> ORGANISM: Homo sapiens

<400> SEQUENCE: 201

| | | | | | |
|---|---|---|---|---|---|
| gacgtgaaga | gtttaaagaa | agagtattca | aacgaaaatg | cagttgtgaa | gagaatgcag | 60 |
| tctcttcaac | ttgattgtgt | ggcagtacct | tcaagccggt | caaattcagc | cacagaacag | 120 |
| cctggttcac | tgcacagttc | ccagggactt | gggatgggtc | ctgtggagga | gtcctggttt | 180 |
| gctccttccc | tggagcaccc | acaagaagag | aatgagccca | gcctgcagag | taaactccaa | 240 |
| gacgaagcca | actaccatct | ttatggcagc | cgcatggaca | gcagacgaa | acagcagccc | 300 |
| agacagaatg | tggcttacaa | cagagaggag | gaaaggagac | gcagggtctc | ccatgaccct | 360 |
| tttgcacagc | aaagacctta | cgagaatttt | cagaatacag | agggaaaagg | cactgtttat | 420 |
| tccagtgcag | ccagtcatgg | taatgcagtg | caccagccat | cagggctcac | cagccaacct | 480 |
| caagtactgt | atcagaacaa | tggattatat | agctcacatg | gctttggaac | aagaccactg | 540 |
| gatccaggaa | cagcaggtcc | cagagtttgg | tacaggccaa | ttccaagtca | tatgcctagt | 600 |
| ctgcataata | tcccagtgcc | tgagaccaac | tatctaggaa | attctcccac | catgccattc | 660 |
| agctccttgc | caccaacaga | tgaatctata | aaatatacca | tatacaatag | tactggcatt | 720 |
| cagattggag | cctacaatta | tatggagatt | ggtgggacga | gttcatcact | actagacagc | 780 |
| acaaatacga | acttcaaaga | agagccagct | gctaagtacc | aagctatctt | tgataatacc | 840 |
| actagtctga | cggataaaca | cctggaccca | atcagggaaa | atctgggaaa | gcactggaaa | 900 |
| aactgtgccc | gtaaactggg | cttcacacag | tctcagattg | atgaaattga | ccatgactat | 960 |
| gagcgagatg | gactgaaaga | aaaggtttac | cagatgctcc | aaaagtgggt | gatgagggaa | 1020 |
| ggcataaagg | gagccacggt | ggggaagctg | gcccaggcgc | tccaccagtg | ttccaggatc | 1080 |
| gaccttctga | gcagcttgat | ttacgtcagc | cagaactaac | cctggatggg | ctacggcagc | 1140 |
| tgaagtggac | gcctcactta | gtggataacc | ccagaaagtt | ggctgcctca | gagcattcag | 1200 |
| aattctgtcc | tcactgatag | gggttctgtg | tctgcagaaa | | | 1240 |

<210> SEQ ID NO 202
<211> LENGTH: 372
<212> TYPE: PRT
<213> ORGANISM: Homo sapiens

```
<400> SEQUENCE: 202

Asp Val Lys Ser Leu Lys Lys Glu Tyr Ser Asn Glu Asn Ala Val Val
1               5                   10                  15

Lys Arg Met Gln Ser Leu Gln Leu Asp Cys Val Ala Val Pro Ser Ser
            20                  25                  30

Arg Ser Asn Ser Ala Thr Glu Gln Pro Gly Ser Leu His Ser Ser Gln
        35                  40                  45

Gly Leu Gly Met Gly Pro Val Glu Glu Ser Trp Phe Ala Pro Ser Leu
    50                  55                  60

Glu His Pro Gln Glu Glu Asn Glu Pro Ser Leu Gln Ser Lys Leu Gln
65                  70                  75                  80

Asp Glu Ala Asn Tyr His Leu Tyr Gly Ser Arg Met Asp Arg Gln Thr
                85                  90                  95

Lys Gln Gln Pro Arg Gln Asn Val Ala Tyr Asn Arg Glu Glu Arg
            100                 105                 110

Arg Arg Arg Val Ser His Asp Pro Phe Ala Gln Gln Arg Pro Tyr Glu
        115                 120                 125

Asn Phe Gln Asn Thr Glu Gly Lys Gly Thr Val Tyr Ser Ser Ala Ala
    130                 135                 140

Ser His Gly Asn Ala Val His Gln Pro Ser Gly Leu Thr Ser Gln Pro
145                 150                 155                 160

Gln Val Leu Tyr Gln Asn Asn Gly Leu Tyr Ser Ser His Gly Phe Gly
                165                 170                 175

Thr Arg Pro Leu Asp Pro Gly Thr Ala Gly Pro Arg Val Trp Tyr Arg
            180                 185                 190

Pro Ile Pro Ser His Met Pro Ser Leu His Asn Ile Pro Val Pro Glu
        195                 200                 205

Thr Asn Tyr Leu Gly Asn Ser Pro Thr Met Pro Phe Ser Ser Leu Pro
    210                 215                 220

Pro Thr Asp Glu Ser Ile Lys Tyr Thr Ile Tyr Asn Ser Thr Gly Ile
225                 230                 235                 240

Gln Ile Gly Ala Tyr Asn Tyr Met Glu Ile Gly Gly Thr Ser Ser Ser
                245                 250                 255

Leu Leu Asp Ser Thr Asn Thr Asn Phe Lys Glu Pro Ala Ala Lys
            260                 265                 270

Tyr Gln Ala Ile Phe Asp Asn Thr Thr Ser Leu Thr Asp Lys His Leu
        275                 280                 285

Asp Pro Ile Arg Glu Asn Leu Gly Lys His Trp Lys Asn Cys Ala Arg
    290                 295                 300

Lys Leu Gly Phe Thr Gln Ser Gln Ile Asp Glu Ile Asp His Asp Tyr
305                 310                 315                 320

Glu Arg Asp Gly Leu Lys Glu Lys Val Tyr Gln Met Leu Gln Lys Trp
                325                 330                 335

Val Met Arg Glu Gly Ile Lys Gly Ala Thr Val Gly Lys Leu Ala Gln
            340                 345                 350

Ala Leu His Gln Cys Ser Arg Ile Asp Leu Leu Ser Ser Leu Ile Tyr
        355                 360                 365

Val Ser Gln Asn
    370

<210> SEQ ID NO 203
<211> LENGTH: 1496
<212> TYPE: DNA
<213> ORGANISM: Homo sapiens
```

<400> SEQUENCE: 203

```
gcacacccgg aagcggcgga gtagagcgga gcctggcggg cgtgggaacc caggccccgc      60
cgaggcggcc aggaggtgag atggcagctg gcaaaatggg cacgaagag tgggtgggca      120
gcgcatacct gtttgtggag tcctcgctgg acaaggtggt cctgtcggat gcctacgcgc      180
accccccagca gaaggtggca gtgtacaggg ctctgcaggc tgccttggca gagagcggcg      240
ggagcccgga cgtgctgcag atgctgaaga tccaccgcag cgacccgcag ctgatcgtgc      300
agctgcgatt ctgcgggcgg cagccctgtg gccgcttcct ccgcgcctac cgcgaggggg      360
cgctgcgcgc cgcgctgcag aggagcctgg cggccgcgct cgcccagcac tcggtgccgc      420
tgcaactgga gctgcgcgcc ggcgccgagc ggctggacgc tttgctggcg gacgaggagc      480
gctgtttgag ttgcatccta gcccagcagc ccgaccggct ccgggatgaa gaactggctg      540
agctggagga tgcgctgcga atctgaagt gcggctcggg ggcccggggt ggcgacgggg      600
aggtcgcttc ggccccttg cagccccgg tgccctctct gtcggaggtg aagccgccgc      660
cgccgccgcc acctgcccag actttctgt tccagggtca gcctgtagtg aatcggccgc      720
tgagcctgaa ggaccaacag acgttcgcgc gctctgtggg tctcaaatgg cgcaaggtgg      780
ggcgctcact gcagcgaggc tgccgggcgc tgcgggaccc ggcgctggac tcgctggcct      840
acgagtacga gcgcgaggga ctgtacgagc aggccttcca gctgctgcgg cgcttcgtgc      900
aggccgaggg ccgccgcgcc acgctgcagc gcctggtgga ggcactcgag gagaacgagc      960
tcaccagcct ggcagaggac ttgctgggcc tgaccgatcc caatggcggc ctggcctaga      1020
ccaggggtgc agccagcttt tggagaacct ggatggcctt agggttcctt ctgcggctat      1080
tgctgaaccc ctgtccatcc acgggaccct gaaactccac ttggcctatc tgctggacct      1140
gctggggcag agttgattgc cttccccagg agccagacca ctgggggtgc atcattgggg      1200
attctgcctc aggtactttg atagagtgtg gggtgggggg gacctgcttt ggagatcagc      1260
ctcaccttct cccatcccag aagcggggct tacagccagc ccttacagtt tcactcatga      1320
agcaccttga tctttggtgt cctggacttc atcctgggtg ctgcagatac tgcagtgaag      1380
taaaacagga atcaatcttg cctgccccca gctcacactc agcgtgggac cccgaatgtt      1440
aagcaatgat aataaagtat aacacggatt ttgatgtgag aaaaaaaaaa aaaaaa      1496
```

<210> SEQ ID NO 204
<211> LENGTH: 312
<212> TYPE: PRT
<213> ORGANISM: Homo sapiens

<400> SEQUENCE: 204

```
Met Ala Ala Gly Gln Asn Gly His Glu Glu Trp Val Gly Ser Ala Tyr
1               5                   10                  15

Leu Phe Val Glu Ser Ser Leu Asp Lys Val Val Leu Ser Asp Ala Tyr
                20                  25                  30

Ala His Pro Gln Gln Lys Val Ala Val Tyr Arg Ala Leu Gln Ala Ala
            35                  40                  45

Leu Ala Glu Ser Gly Gly Ser Pro Asp Val Leu Gln Met Leu Lys Ile
        50                  55                  60

His Arg Ser Asp Pro Gln Leu Ile Val Gln Leu Arg Phe Cys Gly Arg
65                  70                  75                  80

Gln Pro Cys Gly Arg Phe Leu Arg Ala Tyr Arg Glu Gly Ala Leu Arg
                85                  90                  95
```

```
Ala Ala Leu Gln Arg Ser Leu Ala Ala Ala Leu Ala Gln His Ser Val
            100                 105                 110

Pro Leu Gln Leu Glu Leu Arg Ala Gly Ala Glu Arg Leu Asp Ala Leu
        115                 120                 125

Leu Ala Asp Glu Glu Arg Cys Leu Ser Cys Ile Leu Ala Gln Gln Pro
    130                 135                 140

Asp Arg Leu Arg Asp Glu Glu Leu Ala Glu Leu Asp Ala Leu Arg
145                 150                 155                 160

Asn Leu Lys Cys Gly Ser Gly Ala Arg Gly Gly Asp Gly Glu Val Ala
                165                 170                 175

Ser Ala Pro Leu Gln Pro Pro Val Pro Ser Leu Ser Glu Val Lys Pro
            180                 185                 190

Pro Pro Pro Pro Pro Pro Ala Gln Thr Phe Leu Phe Gln Gly Gln Pro
        195                 200                 205

Val Val Asn Arg Pro Leu Ser Leu Lys Asp Gln Gln Thr Phe Ala Arg
    210                 215                 220

Ser Val Gly Leu Lys Trp Arg Lys Val Gly Arg Ser Leu Gln Arg Gly
225                 230                 235                 240

Cys Arg Ala Leu Arg Asp Pro Ala Leu Asp Ser Leu Ala Tyr Glu Tyr
                245                 250                 255

Glu Arg Glu Gly Leu Tyr Glu Gln Ala Phe Gln Leu Leu Arg Arg Phe
            260                 265                 270

Val Gln Ala Glu Gly Arg Arg Ala Thr Leu Gln Arg Leu Val Glu Ala
        275                 280                 285

Leu Glu Glu Asn Glu Leu Thr Ser Leu Ala Glu Asp Leu Leu Gly Leu
    290                 295                 300

Thr Asp Pro Asn Gly Gly Leu Ala
305                 310

<210> SEQ ID NO 205
<211> LENGTH: 4363
<212> TYPE: DNA
<213> ORGANISM: Homo sapiens

<400> SEQUENCE: 205
gcaggctgct ggagaaggcg cacctgctgc aggtgctccc ggccgccccg gaccagcgag    60
cgcgggcact gcggcgggga ggatgctgcg cgagcggacc gtgcggctgc agtacgggag   120
ccgcgtggag gcggtgtacg tgctgggcac ctacctctgg accgatgtct acagcgcggc   180
cccagccggg gcccaaacct tcagcctgaa gcactcggaa cacgtgtggg tggaggtggt   240
gcgtgatggg gaggctgagg aggtggccac caatggcaag cagcgctggc ttctctcgcc   300
cagcaccacc ctgcgggtca ccatgagcca ggcgagcacc gaggccagca gtgacaaggt   360
caccgtcaac tactatgacg aggaagggag cattcccatc gaccaggcgg ggctcttcct   420
cacagccatt gagatctccc tggatgtgga cgcagaccgg gatggtgtgg tggagaagaa   480
caacccaaag aaggcatcct ggacctgggg ccccgagggc caggggggcca tcctgctggt   540 gaactgtgac cgagagacac cctggttgcc caaggaggac tgccgtgatg agaaggtcta   600
cagcaaggaa gatctcaagg acatgtccca gatgatcctg cggaccaaag gccccgaccg   660
cctccccgcc ggatacgaga tagttctgta catttccatg tcagactcag acaaagtggg   720
cgtgttctac gtggagaacc cgttcttcgg ccaacgctat atccacatcc tgggccggcg   780
gaagctctac catgtggtca agtacacggg tggctccgcg gagctgctgt tcttcgtgga   840
aggcctctgt ttccccgacg agggcttctc aggcctggtc tccatccatg tcagcctgct   900
```

```
ggagtacatg gcccaggaca ttcccctgac tcccatcttc acggacaccg tgatattccg    960
gattgctccg tggatcatga cccccaacat cctgcctccc gtgtcggtgt ttgtgtgctg   1020
catgaaggat aattacctgt tcctgaaaga ggtgaagaac cttgtggaga aaaccaactg   1080
tgagctgaag gtctgcttcc agtacctaaa ccgaggcgat cgctggatcc aggatgaaat   1140
tgagtttggc tacatcgagg cccccccataa aggcttcccc gtggtgctgg actctccccg   1200
agatggaaac ctaaaggact tccctgtgaa ggagctcctg ggcccagatt ttggctacgt   1260
gacccgggag cccctctttg agtctgtcac cagccttgac tcatttggaa acctggaggt   1320
cagtccccca gtgaccgtga acggcaagac atacccgctt ggccgcatcc tcatcgggag   1380
cagctttcct ctgtctggtg gtcggaggat gaccaaggtg gtgcgtgact tcctgaaggc   1440
ccagcaggtg caggcgcccg tggagctcta ctcagactgg ctgactgtgg gccacgtgga   1500
tgagttcatg tcctttgtcc ccatccccgg cacaaagaaa ttcctgctac tcatggccag   1560
cacctcggcc tgctacaagc tcttccgaga gaagcagaag gacggccatg agaggccat   1620 catgttcaaa ggcttgggtg ggatgagcag caagcgaatc accatcaaca agattctgtc   1680
caacgagagc cttgtgcagg agaacctgta cttccagcgc tgcctagact ggaaccgtga   1740
catcctcaag aaggagctgg gactgacaga gcaggacatc attgacctgc ccgctctgtt   1800
caagatggac gaggaccacc gtgccagagc cttcttccca aacatggtga acatgatcgt   1860
gctggacaag gacctgggca tccccaagcc attcgggcca caggttgagg aggaatgctg   1920
cctggagatg cacgtgcgtg gcctcctgga gcccctgggc ctcgaatgca ccttcatcga   1980
cgacatttct gcctaccaca aatttctggg ggaagtccac tgtggcacca acgtccgcag   2040
gaagcccttc accttcaagt ggtggcacat ggtgccctga cctgccaggg gccctggcgt   2100
ttgcctcctt cgcttagttc tccagaccct ccctcacacg cccagagcct tctgctgaca   2160
tggactggac agccccgctg ggagaccttt gggacgtggg gtggaatttg gggtatctgt   2220
gccttgccct ccctgagagg ggcctcagtg tcctctgaag ccatccccag tgagcctcga   2280
ctctgtccct gctgaaaata gctgggccag tgtctctgta gccctgacat aaggaacaga   2340
acacaacaaa acacagcaaa ccatgtgccc aaactgctcc ccaaagaatt ttgagtctct   2400
aatctgacac tgaatgaggg gagaagggaa ggagattctg ggattgccag ttcttccagc   2460
agccatgctc tgaaaatcaa ggtagaatcc atggaaaggg accccaggac cccgggaccc   2520
tagacgtatc ttgaactgcc atcgtcattt caaatacatc tccctcaggg tttccaggtg   2580 gccacccccca attattcatt ccttaccaac ctctcaaatc ctcttggctt tctctctgca   2640
gtgtggacac tgttggctag tcctccccac tccctgaggg tccagtaagt tagcttagaa   2700
ccttcctgga aacatttcat ctgagcaggt ttccccacgt gtgggatgct ccttttgcct   2760
catctgtctc agggatgcag gctcccccgc atgcatgggg atttctcccc agaccagcat   2820
acttgtgacc tgagagttca atgcgtaaag atgcccctgg tcagccatat ccatcttctc   2880
ttgcctggtc cttgattctc tggccgctcc ctgaccttcc tccttccact gccttgactt   2940
tcttcctttt tattcctggt gccatctgtc caggcagcta gacaagaact tgttcgccag   3000
cagccagatt caggccttcc caggggcata ataagtgacc agcccctcct ctccggacat   3060
cagatccaac acataaggac cctggcctac cctccagccc aacagccagt tctgggtcag   3120
ctgccaactt agggggtggtt tgattatccc attgaaattc accagtgcct ttgccaaaga   3180
ccctctcatt tggacatacc cagattcatt ccctggctcc aactgaaaag actcagtttc   3240
```

```
aatcgttaaa agttcctta gggccagaag aataaatgaa ttataatccc attttgaaga    3300
accgatttat aaccaatgaa aaggttataa tgtaatttat attcttggag gaacaagatt    3360
ttcatttggg attatttcct tcaaccattc aacaaacatt tgttgtatgc cactaagcgc    3420
caggcacggc gttgggctct gcaaacacag tggttagtag cagtctggac ctggtcccta    3480
ctggcatgga acccatcact ccccaacatg caaagcccac atttaaaggc cagcctctgc    3540
cccttcagtg atgcgctctt tagaaatgcc agtccactat attcagaaat ccgcagggca    3600
caaaacttcc agcaagtcac tgttgtggtg aaatgggcag tgggggtggg gggtcttctt    3660
taaacaggcc cccttcccat ctacctagcc agtacccatc caatgagtcc ccagagcctc    3720
cagaagctgt tgtctcctct ctggggacag cagctcctgc ctttggaggc caaagcccca    3780
gatctctcca gccccagagc tgaaaacacc aagtgcctat ttgagggtgt ctgtctggag    3840
acttagagtt tgtcatgtgt gtgtgtgtgt ttggttaatg tgggtttatg ggttttcttt    3900 ctttttttc ttttttttt tagtctacat taggggaag tgagcgcctc ccatgtgcag    3960
acagtgtgtc tttatagatt tttctaaggc tttccccaat gatgtcggta atttctgatg    4020
tttctgaagt tcccaggact cacacacccg ttcccatctc acttgcccac ccagtgtgac    4080
aaccctcggt gtggatatac ccccgtggac tcatggctct tccccacccc cacttttctat    4140 aaatgtaggc ctagaatacg cttctctgtt gcaaaactca gctaagttcc tgcttccacc    4200
ttgatgttga aatatcttat gtaagagggc aggggatgtc gtgaagatgg caagaagaac    4260
acagtttcaa atttctggaa aagagcctgt ggtggagatc taaagatgtt tagggaagag    4320
ctcgactaaa gaacaatgaa ataaatggtc caaggggaag tca                    4363

<210> SEQ ID NO 206
<211> LENGTH: 665
<212> TYPE: PRT
<213> ORGANISM: Homo sapiens

<400> SEQUENCE: 206

Met Leu Arg Glu Arg Thr Val Arg Leu Gln Tyr Gly Ser Arg Val Glu
1               5                   10                  15

Ala Val Tyr Val Leu Gly Thr Tyr Leu Trp Thr Asp Val Tyr Ser Ala
            20                  25                  30

Ala Pro Ala Gly Ala Gln Thr Phe Ser Leu Lys His Ser Glu His Val
        35                  40                  45

Trp Val Glu Val Val Arg Asp Gly Glu Ala Glu Val Ala Thr Asn
    50                  55                  60

Gly Lys Gln Arg Trp Leu Leu Ser Pro Ser Thr Thr Leu Arg Val Thr
65                  70                  75                  80

Met Ser Gln Ala Ser Thr Glu Ala Ser Ser Asp Lys Val Thr Val Asn
                85                  90                  95

Tyr Tyr Asp Glu Glu Gly Ser Ile Pro Ile Asp Gln Ala Gly Leu Phe
            100                 105                 110

Leu Thr Ala Ile Glu Ile Ser Leu Asp Val Asp Ala Asp Arg Asp Gly
        115                 120                 125

Val Val Glu Lys Asn Asn Pro Lys Lys Ala Ser Trp Thr Trp Gly Pro
    130                 135                 140

Glu Gly Gln Gly Ala Ile Leu Leu Val Asn Cys Asp Arg Glu Thr Pro
145                 150                 155                 160

Trp Leu Pro Lys Glu Asp Cys Arg Asp Glu Lys Val Tyr Ser Lys Glu
                165                 170                 175
```

```
Asp Leu Lys Asp Met Ser Gln Met Ile Leu Arg Thr Lys Gly Pro Asp
            180                 185                 190

Arg Leu Pro Ala Gly Tyr Glu Ile Val Leu Tyr Ile Ser Met Ser Asp
            195                 200                 205

Ser Asp Lys Val Gly Val Phe Tyr Val Glu Asn Pro Phe Phe Gly Gln
            210                 215                 220

Arg Tyr Ile His Ile Leu Gly Arg Arg Lys Leu Tyr His Val Val Lys
225                 230                 235                 240

Tyr Thr Gly Gly Ser Ala Glu Leu Leu Phe Val Glu Gly Leu Cys
                245                 250                 255

Phe Pro Asp Glu Gly Phe Ser Gly Leu Val Ser Ile His Val Ser Leu
            260                 265                 270

Leu Glu Tyr Met Ala Gln Asp Ile Pro Leu Thr Pro Ile Phe Thr Asp
            275                 280                 285

Thr Val Ile Phe Arg Ile Ala Pro Trp Ile Met Thr Pro Asn Ile Leu
            290                 295                 300

Pro Pro Val Ser Val Phe Val Cys Cys Met Lys Asp Asn Tyr Leu Phe
305                 310                 315                 320

Leu Lys Glu Val Lys Asn Leu Val Glu Lys Thr Asn Cys Glu Leu Lys
                325                 330                 335

Val Cys Phe Gln Tyr Leu Asn Arg Gly Asp Arg Trp Ile Gln Asp Glu
            340                 345                 350

Ile Glu Phe Gly Tyr Ile Glu Ala Pro His Lys Gly Phe Pro Val Val
                355                 360                 365

Leu Asp Ser Pro Arg Asp Gly Asn Leu Lys Asp Phe Pro Val Lys Glu
            370                 375                 380

Leu Leu Gly Pro Asp Phe Gly Tyr Val Thr Arg Glu Pro Leu Phe Glu
385                 390                 395                 400

Ser Val Thr Ser Leu Asp Ser Phe Gly Asn Leu Glu Val Ser Pro Pro
                405                 410                 415

Val Thr Val Asn Gly Lys Thr Tyr Pro Leu Gly Arg Ile Leu Ile Gly
            420                 425                 430

Ser Ser Phe Pro Leu Ser Gly Gly Arg Arg Met Thr Lys Val Val Arg
            435                 440                 445

Asp Phe Leu Lys Ala Gln Gln Val Gln Ala Pro Val Glu Leu Tyr Ser
            450                 455                 460

Asp Trp Leu Thr Val Gly His Val Asp Glu Phe Met Ser Phe Val Pro
465                 470                 475                 480

Ile Pro Gly Thr Lys Lys Phe Leu Leu Leu Met Ala Ser Thr Ser Ala
                485                 490                 495

Cys Tyr Lys Leu Phe Arg Glu Lys Gln Lys Asp Gly His Gly Glu Ala
                500                 505                 510

Ile Met Phe Lys Gly Leu Gly Gly Met Ser Ser Lys Arg Ile Thr Ile
            515                 520                 525

Asn Lys Ile Leu Ser Asn Glu Ser Leu Val Gln Glu Asn Leu Tyr Phe
            530                 535                 540

Gln Arg Cys Leu Asp Trp Asn Arg Asp Ile Leu Lys Lys Glu Leu Gly
545                 550                 555                 560

Leu Thr Glu Gln Asp Ile Ile Asp Leu Pro Ala Leu Phe Lys Met Asp
                565                 570                 575

Glu Asp His Arg Ala Arg Ala Phe Phe Pro Asn Met Val Asn Met Ile
            580                 585                 590

Val Leu Asp Lys Asp Leu Gly Ile Pro Lys Pro Phe Gly Pro Gln Val
```

```
              595                 600                 605
Glu Glu Glu Cys Cys Leu Glu Met His Val Arg Gly Leu Leu Glu Pro
    610                 615                 620
Leu Gly Leu Glu Cys Thr Phe Ile Asp Asp Ile Ser Ala Tyr His Lys
625                 630                 635                 640
Phe Leu Gly Glu Val His Cys Gly Thr Asn Val Arg Arg Lys Pro Phe
                645                 650                 655
Thr Phe Lys Trp Trp His Met Val Pro
            660                 665

<210> SEQ ID NO 207
<211> LENGTH: 3189
<212> TYPE: DNA
<213> ORGANISM: Homo sapiens

<400> SEQUENCE: 207
```

| | | | | | |
|---|---|---|---|---|---|
| agtgttgggg | ttggcggcca | cagctaagtc | caacaccagc | atgtcgctgc | agagaatcgt | 60 |
| gcgtgtgtcc | ctggagcatc | ccaccagcgc | ggtgtgtgtg | gctggcgtgg | agaccctcgt | 120 |
| ggacatttat | gggtcagtgc | ctgagggcac | agaaatgttt | gaggtctatg | gacgcctgg | 180 |
| cgtggacatc | tacatctctc | ccaacatgga | gggggccgg | gagcgtgcag | acaccaggcg | 240 |
| gtggcgcttt | gacgcgactt | tggagatcat | cgtggtcatg | aactccccca | gcaatgacct | 300 |
| caacgacagc | catgttcaga | tttcctacca | ctccagccat | gagcctctgc | ccctggccta | 360 |
| tgcggtgctc | tacctcacct | gtgttgacat | ctctctggat | tgcgacctga | actgtgaggg | 420 |
| aaggcaggac | aggaactttg | tagacaagcg | gcagtgggtc | tgggggccca | gtgggtatgg | 480 |
| cggcatcttg | ctggtgaact | gtgaccgtga | tgatccgagc | tgtgatgtcc | aggacaattg | 540 |
| tgaccagcac | gtgcactgcc | tgcaagacct | ggaagacatg | tctgtcatgg | tcctgcggac | 600 |
| gcagggccct | gcagccctct | tgatgacca | caaacttgtc | ctccataccct | ccagctatga | 660 |
| tgccaaacgg | gcacaggtct | tccacatctg | cggtcctgag | gatgtgtgtg | aggcctatag | 720 |
| gcatgtgctg | ggccaagata | aggtgtccta | tgaggtaccc | cgcttgcatg | ggatgaggaa | 780 |
| gcgcttcttc | gtggaaggcc | tgtccttccc | tgatgccggc | ttcacaggac | tcatctcctt | 840 |
| ccatgtcact | ctgctggacg | actccaacga | ggatttctcg | gcatccccta | tcttcactga | 900 |
| cactgtggtg | ttccgagtgg | caccctggat | catgacgccc | agcactctgc | caccccctaga | 960 |
| ggtgtatgtg | tgccgtgtga | ggaacaacac | gtgttttgtg | gatgcggtgg | cagagctggc | 1020 |
| caggaaggcc | ggctgcaagc | tgaccatctg | cccacaggcc | gagaaccgca | acgaccgctg | 1080 |
| gatccaggat | gagatggagc | tgggctacgt | tcaggcgccg | cacaagaccc | tcccggtggt | 1140 |
| ctttgactcc | ccaaggaatg | ggaactgca | ggatttccct | tacaaaagaa | tcctgggtcc | 1200 |
| agattttggt | tacgtgactc | gggaaccacg | cgacaggtct | gtgagtggcc | tggactcctt | 1260 |
| tgggaacctg | gaggtcagcc | ctccagtggt | ggccaatggg | aaagagtacc | ccctggggag | 1320 |
| gatcctcatt | gggggcaacc | tgcctgggtc | aagtggccgc | agggtcaccc | aggtggtgcg | 1380 |
| ggacttcctc | catgcccaga | aggtgcagcc | cccgtggag | ctctttgtgg | actggttggc | 1440 |
| cgtgggccat | gtggatgagt | ttctgagctt | tgtccctgcc | cccgatggga | agggcttccg | 1500 |
| gatgctcctg | ccagccctg | gggcctgctt | caagctcttc | caggaaaagc | agaagtgtgg | 1560 |
| ccacggagg | gccctcctgt | tccagggggt | tgttgatgat | gagcaggtca | agaccatctc | 1620 |
| catcaaccag | gtgctctcca | ataaagacct | catcaactac | aataagtttg | tgcagagctg | 1680 |
| catcgactgg | aaccgtgagg | tgctgaagcg | ggagctgggc | ctggcagagt | gtgacatcat | 1740 |

```
tgacatccca cagctcttca agaccgagag gaaaaaagca acggccttct tccctgactt    1800
ggtgaacatg ctggtgctgg ggaagcacct gggcatcccc aagcccttg ggcccatcat     1860 caatggctgc tgctgcctgg aggagaaggt gcggtccctg ctggagccgc tgggcctcca    1920
ctgcaccttc attgatgact tcactccata ccacatgctg catggggagg tgcactgtgg    1980
caccaatgtg tgcagaaagc ccttctcttt caagtggtgg aacatggtgc cctgagacag    2040
ctcccaccca ccatcctgtc cccctgggc gggcattggc ccaggtggtg agacagaga     2100 caggcccctg aacgataagc accaagagac cccaaggctc cagatggaac actgagggtg    2160
accgtccctc tcagaagcct tttccctgga agtgtccatg cctcacctgc aacccatgtg    2220
gttctcagac ttgaatcttc tcggcccccc aaaaagaagg acctcatttc ttatagcctc    2280
tcctgtgatt caacacaacc catggagatg tccccttctc actctgaaat catccatttg    2340
gggacaaatc cacattgggg tctagaaaca tccacgtatc tcatcagcca tcttgtcctg    2400
tgcatcctaa cagaggaagg atccatgatt ctgctttggt ccaattgctt cctctctgca    2460
gaggaacaac cctaaaacca gaccactcca cgcaggacag gcaggagaga ttcttcctaa    2520
agcctccccc ataaaaaggg agctgtggat ccacttagat cagggcggaa ccatctttca    2580
cccggccaag ctcctgccca gatgttgacc ctcacccagc gtgagctgtc acatagtagg    2640
agcttctaga tgcatgtgga agcaatgaga gttgtcccct agccttataa actccccatg    2700
atctgacatg cagaaatcca gccttgtcca gaatcctcct ggaatttctt ggagacgaaa    2760
gtatctgggg gattgttggg tactagggag actgggtaca agggtgaaaa gtagttccca    2820
taatacacat ggttgactat ggtgatccac cttgtgatgg ttaatattag gtgtctggag    2880
aaggttgctt cattggccct gggacttctc tctgcaggag gagagaacgc tgcctctcct    2940
ctggattggt ctcaggctct ctgttggcct ttggtcagcg tttccacatc ctgctctgct    3000
gcaggagagg gggctaaggg gctggatcca ccaaggcagc tcacagcggg aaaactctgg    3060
gaatgaacca ctgaattcag gggatggggg tggggggcg gttctcgagg tgtgtgccag     3120
ctacacgtgt gttctgtatg ggtccagctg cgtttccatc actcgctaat aaatcaacag    3180
aaacacaaa                                                            3189
```

<210> SEQ ID NO 208
<211> LENGTH: 664
<212> TYPE: PRT
<213> ORGANISM: Homo sapiens

<400> SEQUENCE: 208

```
Met Ser Leu Gln Arg Ile Val Arg Val Ser Leu Glu His Pro Thr Ser
1               5                   10                  15

Ala Val Cys Val Ala Gly Val Glu Thr Leu Val Asp Ile Tyr Gly Ser
                20                  25                  30

Val Pro Glu Gly Thr Glu Met Phe Glu Val Tyr Gly Thr Pro Gly Val
            35                  40                  45

Asp Ile Tyr Ile Ser Pro Asn Met Glu Arg Gly Arg Glu Arg Ala Asp
        50                  55                  60

Thr Arg Arg Trp Arg Phe Asp Ala Thr Leu Glu Ile Ile Val Val Met
65                  70                  75                  80

Asn Ser Pro Ser Asn Asp Leu Asn Asp Ser His Val Gln Ile Ser Tyr
                85                  90                  95

His Ser Ser His Glu Pro Leu Pro Leu Ala Tyr Ala Val Leu Tyr Leu
            100                 105                 110
```

```
Thr Cys Val Asp Ile Ser Leu Asp Cys Asp Leu Asn Cys Glu Gly Arg
            115                 120                 125

Gln Asp Arg Asn Phe Val Asp Lys Arg Gln Trp Val Trp Gly Pro Ser
    130                 135                 140

Gly Tyr Gly Gly Ile Leu Leu Val Asn Cys Asp Arg Asp Asp Pro Ser
145                 150                 155                 160

Cys Asp Val Gln Asp Asn Cys Asp Gln His Val His Cys Leu Gln Asp
                165                 170                 175

Leu Glu Asp Met Ser Val Met Val Leu Arg Thr Gln Gly Pro Ala Ala
                180                 185                 190

Leu Phe Asp Asp His Lys Leu Val Leu His Thr Ser Ser Tyr Asp Ala
            195                 200                 205

Lys Arg Ala Gln Val Phe His Ile Cys Gly Pro Glu Asp Val Cys Glu
    210                 215                 220

Ala Tyr Arg His Val Leu Gly Gln Asp Lys Val Ser Tyr Glu Val Pro
225                 230                 235                 240

Arg Leu His Gly Asp Glu Arg Phe Phe Val Glu Gly Leu Ser Phe
                245                 250                 255

Pro Asp Ala Gly Phe Thr Gly Leu Ile Ser Phe His Val Thr Leu Leu
                260                 265                 270

Asp Asp Ser Asn Glu Asp Phe Ser Ala Ser Pro Ile Phe Thr Asp Thr
            275                 280                 285

Val Val Phe Arg Val Ala Pro Trp Ile Met Thr Pro Ser Thr Leu Pro
    290                 295                 300

Pro Leu Glu Val Tyr Val Cys Arg Val Arg Asn Asn Thr Cys Phe Val
305                 310                 315                 320

Asp Ala Val Ala Glu Leu Ala Arg Lys Ala Gly Cys Lys Leu Thr Ile
                325                 330                 335

Cys Pro Gln Ala Glu Asn Arg Asn Asp Arg Trp Ile Gln Asp Glu Met
            340                 345                 350

Glu Leu Gly Tyr Val Gln Ala Pro His Lys Thr Leu Pro Val Val Phe
    355                 360                 365

Asp Ser Pro Arg Asn Gly Glu Leu Gln Asp Phe Pro Tyr Lys Arg Ile
370                 375                 380

Leu Gly Pro Asp Phe Gly Tyr Val Thr Arg Glu Pro Arg Asp Arg Ser
385                 390                 395                 400

Val Ser Gly Leu Asp Ser Phe Gly Asn Leu Glu Val Ser Pro Pro Val
                405                 410                 415

Val Ala Asn Gly Lys Glu Tyr Pro Leu Gly Arg Ile Leu Ile Gly Gly
            420                 425                 430

Asn Leu Pro Gly Ser Ser Gly Arg Arg Val Thr Gln Val Val Arg Asp
    435                 440                 445

Phe Leu His Ala Gln Lys Val Gln Pro Pro Val Glu Leu Phe Val Asp
    450                 455                 460

Trp Leu Ala Val Gly His Val Asp Glu Phe Leu Ser Phe Val Pro Ala
465                 470                 475                 480

Pro Asp Gly Lys Gly Phe Arg Met Leu Leu Ala Ser Pro Gly Ala Cys
                485                 490                 495

Phe Lys Leu Phe Gln Glu Lys Gln Lys Cys Gly His Gly Arg Ala Leu
            500                 505                 510

Leu Phe Gln Gly Val Val Asp Asp Glu Gln Val Lys Thr Ile Ser Ile
            515                 520                 525
```

```
Asn Gln Val Leu Ser Asn Lys Asp Leu Ile Asn Tyr Asn Lys Phe Val
            530                 535                 540

Gln Ser Cys Ile Asp Trp Asn Arg Glu Val Leu Lys Arg Glu Leu Gly
545                 550                 555                 560

Leu Ala Glu Cys Asp Ile Ile Asp Ile Pro Gln Leu Phe Lys Thr Glu
                565                 570                 575

Arg Lys Lys Ala Thr Ala Phe Phe Pro Asp Leu Val Asn Met Leu Val
            580                 585                 590

Leu Gly Lys His Leu Gly Ile Pro Lys Pro Phe Gly Pro Ile Ile Asn
            595                 600                 605

Gly Cys Cys Cys Leu Glu Glu Lys Val Arg Ser Leu Leu Glu Pro Leu
            610                 615                 620

Gly Leu His Cys Thr Phe Ile Asp Asp Phe Thr Pro Tyr His Met Leu
625                 630                 635                 640

His Gly Glu Val His Cys Gly Thr Asn Val Cys Arg Lys Pro Phe Ser
                645                 650                 655

Phe Lys Trp Trp Asn Met Val Pro
            660
```

```
<210> SEQ ID NO 209
<211> LENGTH: 1296
<212> TYPE: DNA
<213> ORGANISM: Homo sapiens

<400> SEQUENCE: 209
atgcccaacc ccaggcctgg caagccctcg gcccctcct tggcccttgg cccatcccca      60
ggagcctcgc ccagctggag ggctgcaccc aaagcctcag acctgctggg ggcccggggc     120
ccagggggaa ccttccaggg ccgagatctt cgaggcgggg cccatgcctc ctcttcttcc     180
ttgaacccca tgccaccatc gcagctgcag ctgcccacac tgccctagt catggtggca      240 ccctccgggg cacggctggg cccttgccc acttacagg cactcctcca ggacaggcca      300
catttcatgc accagctctc aacggtggat gcccacgccc ggacccctgt gctgcaggtg     360
caccccctgg agagcccagc catgatcagc ctcacaccac caccaccgc cactggggtc      420 ttctccctca aggcccggcc tggcctccca cctgggatca acgtggccag cctggaatgg     480
gtgtccaggg agccggcact gctctgcacc ttcccaaatc ccagtgcacc aggaaggac      540 agcacccttt cggctgtgcc ccagagctcc tacccactgc tggcaaatgg tgtctgcaag     600
tggcccggat gtgagaaggt cttcgaagag ccagaggact tcctcaagca ctgccaggcg     660
gaccatcttc tggatgagaa gggcagggca caatgtctcc tccagagaga gatggtacag     720
tctctggagc agcagctggt gctggagaag gagaagctga gtgccatgca ggcccacctg     780
gctgggaaaa tggcactgac caaggcttca tctgtggcat catccgacaa gggctcctgc     840
tgcatcgtag ctgctggcag ccaaggccct gtcgtcccag cctggtctgg ccccgggag      900 gcccctgaca gcctgtttgc tgtccggagg cacctgtggg gtagccatgg aaacagcaca     960
ttcccagagt cctccacaa catggactac ttcaagttcc acaacatgcg ccccctttc      1020 acctacgcca cgctcatccg ctgggccatc ctggaggctc cagagaagca gcggacactc     1080
aatgagatct accactggtt cacacgcatg tttgccttct tcagaaacca tcctgccacc     1140
tggaagaacg ccatccgcca aacctgagt ctgcacaagt gctttgtgcg ggtggagagc     1200 gagaagggg ctgtgtggac cgtggatgag ctggagttcc gcaagaaacg gagccagagg     1260
cccagcaggt gttccaaccc tacacctggc ccctga                              1296
```

<210> SEQ ID NO 210
<211> LENGTH: 431
<212> TYPE: PRT
<213> ORGANISM: Homo sapiens

<400> SEQUENCE: 210

```
Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
    290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
    370                 375                 380
```

```
Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
            405                 410                 415

Arg Ser Gln Arg Pro Ser Arg Cys Ser Asn Pro Thr Pro Gly Pro
        420                 425                 430

<210> SEQ ID NO 211
<211> LENGTH: 3216
<212> TYPE: DNA
<213> ORGANISM: Homo sapiens

<400> SEQUENCE: 211
ggcagtttcc tggctgaaca cgccagccca atacttaaag agagcaactc ctgactccga      60
tagagactgg atggacccac aagggtgaca gcccaggcgg accgatcttc ccatcccaca     120
tcctccggcg cgatgccaaa agaggctgac ggcaactgg gccttctgca gagaaagacc      180
tccgcttcac tgccccggct ggtcccaagg gtcaggaaga tggattcata cctgctgatg     240 tgggactgc tcacgttcat catggtgcct ggctgccagg cagagctctg tgacgatgac      300
ccgccagaga tcccacacgc cacattcaaa gccatggcct acaaggaagg aaccatgttg     360
aactgtgaat gcaagagagg tttccgcaga taaaaagcg gtcactcta tgctctgt       420 acaggaaact ctagccactc gtcctgggac aaccaatgtc aatgcacaag ctctgccact     480
cggaacacaa cgaaacaagt gacacctcaa cctgaagaac agaagaaag gaaaaccaca      540 gaaatgcaaa gtccaatgca gccagtggac caagcgagcc ttccaggtca ctgcagggaa     600
cctccaccat gggaaaatga agccacagag agaatttatc atttcgtggt ggggcagatg     660
gtttattatc agtgcgtcca gggatacagg gctctacaca gaggtcctgc tgagagcgtc     720
tgcaaaatga cccacgggaa gacaaggtgg acccagcccc agctcatatg cacaggtgaa     780
atggagacca gtcagtttcc aggtgaagag aagcctcagg caagcccga aggccgtcct      840 gagagtgaga cttcctgcct cgtcacaaca acagattttc aaatacagac agaaatggct     900
gcaaccatgg agacgtccat atttacaaca gagtaccagg tagcagtggc cggctgtgtt     960
ttcctgctga tcagcgtcct cctcctgagt gggctcacct ggcagcggag acagaggaag    1020
agtagaagaa caatctagaa aaccaaaaga acaagaattt cttggtaaga agccgggaac    1080
agacaacaga agtcatgaag cccaagtgaa atcaaaggtg ctaaatggtc gcccaggaga    1140
catccgttgt gcttgcctgc gttttggaag ctctgaagtc acatcacagg acacggggca    1200
gtggcaacct tgtctctatg ccagctcagt cccatcagag agcgagcgct acccacttct    1260
aaatagcaat ttcgccgttg aagaggaagg gcaaaaccac tagaactctc catcttattt    1320
tcatgtatat gtgttcatta aagcatgaat ggtatggaac tctctccacc ctatatgtag    1380
tataaagaaa gtaggtttta cattcatctc attccaactt cccagttcag gagtcccaag    1440
gaaagcccca gcactaacgt aaatacacaa cacacacact ctaccctata caactggaca    1500
ttgtctgcgt ggttcctttc tcagccgctt ctgactgctg attctcccgt tcacgttgcc    1560
taataaacat ccttcaagaa ctctgggctg ctacccagaa atcattttac ccttggctca    1620
atcctctaag ctaacccect tctactgagc cttcagtctt gaatttctaa aaacagagg     1680 ccatggcaga ataatctttg ggtaacttca aaacggggca gccaaaccca tgaggcaatg    1740
tcaggaacag aaggatgaat gaggtcccag gcagagaatc atacttagca aagttttacc    1800
tgtgcgttac taattggcct cttttaagagt tagtttcttt gggattgcta tgaatgatac    1860
```

```
cctgaatttg gcctgcacta atttgatgtt tacaggtgga cacacaaggt gcaaatcaat      1920
gcgtacgttt cctgagaagt gtctaaaaac accaaaaagg gatccgtaca ttcaatgttt      1980
atgcaaggaa ggaaagaaag aaggaagtga agagggagaa gggatggagg tcacactggt      2040
agaacgtaac cacggaaaag agcgcatcag gcctggcacg gtggctcagg cctataaccc      2100
cagctcccta ggagaccaag gcgggagcat ctcttgaggc caggagtttg agaccagcct      2160
gggcagcata gcaagacaca tccctacaaa aaattagaaa ttggctggat gtggtggcat      2220
acgcctgtag tcctagccac tcaggaggct gaggcaggag gattgcttga gcccaggagt      2280
tcgaggctgc agtcagtcat gatggcacca ctgcactcca gcctgggcaa cagagcaaga      2340
tcctgtcttt aaggaaaaaa agacaagatg agcataccag cagtccttga acattatcaa      2400
aaagttcagc atattagaat caccggggag ccttgttaaa agagttcgct gggcccatct      2460
tcagagtctc tgagttgttg gtctggaata gagccaaatg ttttgtgtgt ctaacaattc      2520
ccaggtgctg ttgctgctgc tactattcca ggaacacact tgagaacca ttgtgttatt       2580 gctctgcacg cccaccccact ctcaactccc acgaaaaaaa tcaacttcca gagctaagat     2640
ttcggtggaa gtcctggttc catatctggt gcaagatctc ccctcacgaa tcagttgagt      2700
caacattcta gctcaacaac atcacacgat taacattaac gaaaattatt catttgggaa      2760
actatcagcc agttttcact tctgaagggg caggagagtg ttatgagaaa tcacggcagt      2820
tttcagcagg gtccagattc agattaaata actatttct gtcatttctg tgaccaacca      2880
catacaaaca gactcatctg tgcactctcc ccctccccct tcaggtatat gttttctgag      2940
taaagttgaa aagaatctca gaccagaaaa tatagatata tatttaaatc ttacttgagt      3000
agaactgatt acgactttg ggtgttgagg ggtctataag atcaaaactt ttccatgata       3060
atactaagat gttatcgacc atttatctgt ccttctctca aaagtgtatg gtggaatttt      3120
ccagaagcta tgtgatacgt gatgatgtca tcactctgct gttaacatat aataaattta     3180
ttgctattgt ttataaaaga ataaatgata ttttttt                               3216
```

<210> SEQ ID NO 212
<211> LENGTH: 272
<212> TYPE: PRT
<213> ORGANISM: Homo sapiens

<400> SEQUENCE: 212

```
Met Asp Ser Tyr Leu Leu Met Trp Gly Leu Leu Thr Phe Ile Met Val
1               5                   10                  15

Pro Gly Cys Gln Ala Glu Leu Cys Asp Asp Pro Pro Glu Ile Pro
            20                  25                  30

His Ala Thr Phe Lys Ala Met Ala Tyr Lys Glu Gly Thr Met Leu Asn
        35                  40                  45

Cys Glu Cys Lys Arg Gly Phe Arg Arg Ile Lys Ser Gly Ser Leu Tyr
    50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
        115                 120                 125
```

```
Pro Pro Trp Glu Asn Glu Ala Thr Glu Arg Ile Tyr His Phe Val Val
    130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
                180                 185                 190

Phe Pro Gly Glu Glu Lys Pro Gln Ala Ser Pro Glu Gly Arg Pro Glu
            195                 200                 205

Ser Glu Thr Ser Cys Leu Val Thr Thr Thr Asp Phe Gln Ile Gln Thr
    210                 215                 220

Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
            260                 265                 270

<210> SEQ ID NO 213
<211> LENGTH: 2740
<212> TYPE: DNA
<213> ORGANISM: Homo sapiens

<400> SEQUENCE: 213
aagaacgccc ccaaaatctg tttctaattt tacagaaatc ttttgaaact tggcacggta      60
ttcaaaagtc cgtggaaaga aaaaaacctt gtcctggctt cagcttccaa ctacaaagac     120
agacttggtc cttttcaacg gttttcacag atccagtgac ccacgctctg aagacagaat     180
tagctaactt tcaaaaacat ctggaaaaat gaagacttgg gtaaaaatcg tatttggagt     240
tgccacctct gctgtgcttg ccttattggt gatgtgcatt gtcttacgcc cttcaagagt     300
tcataactct gaagaaaata caatgagagc actcacactg aaggatattt taaatggaac     360
attttcttat aaaacatttt ttccaaactg gatttcagga caagaatatc ttcatcaatc     420
tgcagataac aatatagtac tttataatat tgaaacagga caatcatata ccatttttgag     480 taatagaacc atgctttgga gatactctta cacagcaaca tattcatct atgaccttag     540 caatggagaa tttgtaagag gaaatgagct tcctcgtcca attcagtatt tatgctggtc     600
gcctgttggg agtaaattag catatgtcta tcaaaacaat atctatttga aacaaagacc     660
aggagatcca cctttccaaa taacatttaa tggaagagaa aataaaatat ttaatggaat     720
cccagactgg gtttatgaag aggaaatgct tgctacaaaa tatgctctct ggtggtctcc     780
taatggaaaa tttttggcat atgcggaatt taatgatacg atataccag ttattgccta     840 ttcctattat ggcgatgaac aatatcctag aacaataaat attccatacc caaaggctgg     900
agctaagaat cccgttgttc ggatatttat tatcgatacc acttaccctg cgtatgtagg     960
tccccaggaa gtgcctgttc cagcaatgat agcctcaagt gattattatt tcagttggct    1020
cacgtgggtt actgatgaac gagtatgttt gcagtggcta aaaagagtcc agaatgtttc    1080
ggtcctgtct atatgtgact tcaggggaaga ctggcagaca tgggattgtc caagacccca   1140
ggagcatata gaagaaagca gaactggatg gctggtgga ttctttgttt caacaccagt    1200
tttcagctat gatgccattt cgtactacaa aatatttagt gacaaggatg ctcaaaaca    1260 tattcactat atcaaagaca ctgtggaaaa tgctattcaa attacaagtg gcaagtggga   1320
```

```
ggccataaat atattcagag taacacagga ttcactgttt tattctagca atgaatttga    1380 agaatacct ggaagaagaa acatctacag aattagcatt ggaagctatc ctccaagcaa    1440
gaagtgtgtt acttgccatc taaggaaaga aaggtgccaa tattacacag caagtttcag    1500
cgactacgcc aagtactatg cacttgtctg ctacggccca ggcatcccca tttccaccct    1560
tcatgatgga cgcactgatc aagaaattaa atcctggaa gaaaacaagg aattggaaaa    1620
tgctttgaaa aatatccagc tgcctaaaga ggaaattaag aaacttgaag tagatgaaat    1680
tactttatgg tacaagatga ttcttcctcc tcaatttgac agatcaaaga gtatccctt    1740 gctaattcaa gtgtatggtg gtccctgcag tcagagtgta aggtctgtat ttgctgttaa    1800
ttggatatct tatcttgcaa gtaaggaagg gatggtcatt gccttggtgg atggtcgagg    1860
aacagctttc caaggtgaca aactcctcta tgcagtgtat cgaaagctgg gtgtttatga    1920
agttgaagac cagattacag ctgtcagaaa attcatagaa atgggtttca ttgatgaaaa    1980
aagaatagcc atgggggct ggtcctatgg aggatacgtt tcatcactgg cccttgcatc    2040
tggaactggt cttttcaaat gtggtatagc agtggctcca gtctccagct gggaatatta    2100
cgcgtctgtc tacacagaga gattcatggg tctcccaaca aaggatgata atcttgagca    2160
ctataagaat tcaactgtga tggcaagagc agaatatttc agaaatgtag actatcttct    2220
catccacgga acagcagatg ataatgtgca ctttcaaaac tcagcacaga ttgctaaagc    2280
tctggttaat gcacaagtgg atttccaggc aatgtggtac tctgaccaga accacggctt    2340
atccggcctg tccacgaacc acttatacac ccacatgacc cacttcctaa gcagtgttt    2400 ctctttgtca gactaaaaac gatgcagatg caagcctgta tcagaatctg aaaaccttat    2460
ataaacccct cagacagttt gcttatttta tttttatgt tgtaaaatgc tagtataaac    2520
aaacaaatta atgttgttct aaaggctgtt aaaaaaaaga tgaggactca gaagttcaag    2580
ctaaatattg tttacatttt ctggtactct gtgaaagaag agaaaaggga gtcatgcatt    2640
ttgctttgga cacagtgttt tatcacctgt tcatttgaag aaaaataata aagtcagaag    2700
ttcaagtgct aaaaaaaaaa aaaaaaaaaa aaaaaaaaa                          2740
```

<210> SEQ ID NO 214
<211> LENGTH: 735
<212> TYPE: PRT
<213> ORGANISM: Homo sapiens

<400> SEQUENCE: 214

```
Met Lys Thr Trp Val Lys Ile Val Phe Gly Val Ala Thr Ser Ala Val
1               5                   10                  15

Leu Ala Leu Leu Val Met Cys Ile Val Leu Arg Pro Ser Arg Val His
                20                  25                  30

Asn Ser Glu Glu Asn Thr Met Arg Ala Leu Thr Leu Lys Asp Ile Leu
            35                  40                  45

Asn Gly Thr Phe Ser Tyr Lys Thr Phe Phe Pro Asn Trp Ile Ser Gly
        50                  55                  60

Gln Glu Tyr Leu His Gln Ser Ala Asp Asn Asn Ile Val Leu Tyr Asn
65                  70                  75                  80

Ile Glu Thr Gly Gln Ser Tyr Thr Ile Leu Ser Asn Arg Thr Met Leu
                85                  90                  95

Trp Arg Tyr Ser Tyr Thr Ala Thr Tyr Tyr Ile Tyr Asp Leu Ser Asn
            100                 105                 110

Gly Glu Phe Val Arg Gly Asn Glu Leu Pro Arg Pro Ile Gln Tyr Leu
        115                 120                 125
```

-continued

```
Cys Trp Ser Pro Val Gly Ser Lys Leu Ala Tyr Val Tyr Gln Asn Asn
            130                 135                 140

Ile Tyr Leu Lys Gln Arg Pro Gly Asp Pro Pro Phe Gln Ile Thr Phe
145                 150                 155                 160

Asn Gly Arg Glu Asn Lys Ile Phe Asn Gly Ile Pro Asp Trp Val Tyr
                165                 170                 175

Glu Glu Glu Met Leu Ala Thr Lys Tyr Ala Leu Trp Trp Ser Pro Asn
            180                 185                 190

Gly Lys Phe Leu Ala Tyr Ala Glu Phe Asn Asp Thr Asp Ile Pro Val
        195                 200                 205

Ile Ala Tyr Ser Tyr Tyr Gly Asp Glu Gln Tyr Pro Arg Thr Ile Asn
210                 215                 220

Ile Pro Tyr Pro Lys Ala Gly Ala Lys Asn Pro Val Val Arg Ile Phe
225                 230                 235                 240

Ile Ile Asp Thr Thr Tyr Pro Ala Tyr Val Gly Pro Gln Glu Val Pro
                245                 250                 255

Val Pro Ala Met Ile Ala Ser Ser Asp Tyr Tyr Phe Ser Trp Leu Thr
            260                 265                 270

Trp Val Thr Asp Glu Arg Val Cys Leu Gln Trp Leu Lys Arg Val Gln
        275                 280                 285

Asn Val Ser Val Leu Ser Ile Cys Asp Phe Arg Glu Asp Trp Gln Thr
290                 295                 300

Trp Asp Cys Pro Lys Thr Gln Glu His Ile Glu Glu Ser Arg Thr Gly
305                 310                 315                 320

Trp Ala Gly Gly Phe Phe Val Ser Thr Pro Val Phe Ser Tyr Asp Ala
                325                 330                 335

Ile Ser Tyr Tyr Lys Ile Phe Ser Asp Lys Asp Gly Tyr Lys His Ile
            340                 345                 350

His Tyr Ile Lys Asp Thr Val Glu Asn Ala Ile Gln Ile Thr Ser Gly
        355                 360                 365

Lys Trp Glu Ala Ile Asn Ile Phe Arg Val Thr Gln Asp Ser Leu Phe
370                 375                 380

Tyr Ser Ser Asn Glu Phe Glu Glu Tyr Pro Gly Arg Arg Asn Ile Tyr
385                 390                 395                 400

Arg Ile Ser Ile Gly Ser Tyr Pro Pro Ser Lys Lys Cys Val Thr Cys
                405                 410                 415

His Leu Arg Lys Glu Arg Cys Gln Tyr Tyr Thr Ala Ser Phe Ser Asp
            420                 425                 430

Tyr Ala Lys Tyr Tyr Ala Leu Val Cys Tyr Gly Pro Gly Ile Pro Ile
        435                 440                 445

Ser Thr Leu His Asp Gly Arg Thr Asp Gln Glu Ile Lys Ile Leu Glu
450                 455                 460

Glu Asn Lys Glu Leu Glu Asn Ala Leu Lys Asn Ile Gln Leu Pro Lys
465                 470                 475                 480

Glu Glu Ile Lys Lys Leu Glu Val Asp Glu Ile Thr Leu Trp Tyr Lys
                485                 490                 495

Met Ile Leu Pro Pro Gln Phe Asp Arg Ser Lys Lys Tyr Pro Leu Leu
            500                 505                 510

Ile Gln Val Tyr Gly Gly Pro Cys Ser Gln Ser Val Arg Ser Val Phe
        515                 520                 525

Ala Val Asn Trp Ile Ser Tyr Leu Ala Ser Lys Glu Gly Met Val Ile
530                 535                 540
```

Ala Leu Val Asp Gly Arg Gly Thr Ala Phe Gln Gly Asp Lys Leu Leu
545                 550                 555                 560

Tyr Ala Val Tyr Arg Lys Leu Gly Val Tyr Glu Val Glu Asp Gln Ile
                565                 570                 575

Thr Ala Val Arg Lys Phe Ile Glu Met Gly Phe Ile Asp Glu Lys Arg
            580                 585                 590

Ile Ala Ile Trp Gly Trp Ser Tyr Gly Gly Tyr Val Ser Ser Leu Ala
        595                 600                 605

Leu Ala Ser Gly Thr Gly Leu Phe Lys Cys Gly Ile Ala Val Ala Pro
    610                 615                 620

Val Ser Ser Trp Glu Tyr Tyr Ala Ser Val Tyr Thr Glu Arg Phe Met
625                 630                 635                 640

Gly Leu Pro Thr Lys Asp Asp Asn Leu Glu His Tyr Lys Asn Ser Thr
                645                 650                 655

Val Met Ala Arg Ala Glu Tyr Phe Arg Asn Val Asp Tyr Leu Leu Ile
            660                 665                 670

His Gly Thr Ala Asp Asp Asn Val His Phe Gln Asn Ser Ala Gln Ile
        675                 680                 685

Ala Lys Ala Leu Val Asn Ala Gln Val Asp Phe Gln Ala Met Trp Tyr
    690                 695                 700

Ser Asp Gln Asn His Gly Leu Ser Gly Leu Ser Thr Asn His Leu Tyr
705                 710                 715                 720

Thr His Met Thr His Phe Leu Lys Gln Cys Phe Ser Leu Ser Asp
                725                 730                 735

<210> SEQ ID NO 215
<211> LENGTH: 3913
<212> TYPE: DNA
<213> ORGANISM: Homo sapiens

<400> SEQUENCE: 215

```
ctttcactgg caagagacgg agtcctgggt ttcagttcca gttgcctgcg gtgggctgtg      60
tgagtttgcc aaagtcccct gccctctctg ggtctcggtt ccctcgcctg tccacgtgag     120
gttggaggag ctgaacgccg acgtcatttt tagctaagag ggagcagggt ccccgagtcg     180
ccggcccagg gtctgcgcat ccgaggccgc gcgcccttc ccctccccca cggctcctcc      240
gggccccgca ctctgcgccc cggctgccgc ccagcgccct acaccgccct caggggccc      300
tcgcgggctc ccccggccg ggatgccagt gccccgcgcc acgcgcgcct gctcccgcgc      360
cgcctgccct gcagcctgcc cgcggcgcct ttataccccag cgggctcggc gctcactaat     420
gtttaactcg gggccgaaac ttgccagcgg cgagtgactc caccgcccgg agcagcggtg     480
caggacgcgc gtctccgccg cccgcggtga cttctgcctg cgctccttct ctgaacgctc     540
acttccgagg agacgccgac gatgaagaca ccgtggaagg ttcttctggg actgctgggt     600
gctgctcgc ttgtcaccat catcaccgtg cccgtggttc tgctgaacaa aggcacagat      660
gatgctacag ctgacagtcg caaaacttac actctaactg attacttaaa aaatacttat     720
agactgaagt tatactccct aagatggatt tcagatcatg aatatctcta caaacaagaa     780
aataatatct tggtattcaa tgctgaatat ggaaacagct cagttttctt ggagaacagt     840
acatttgatg agtttggaca ttctatcaat gattattcaa tatctcctga tgggcagttt     900
attctcttag aatacaacta cgtgaagcaa tggaggcatt cctacacagc ttcatatgac     960
atttatgatt taaataaaag gcagctgatt acagaagaga ggattccaaa caacacacag    1020
tgggtcacat ggtcaccagt gggtcataaa ttggcatatg tttggaacaa tgacatttat    1080
```

-continued

```
gttaaaattg aaccaaattt accaagttac agaatcacat ggacggggaa agaagatata    1140
atatataatg gaataactga ctgggtttat gaagaggaag tcttcagtgc ctactctgct    1200
ctgtggtggt ctccaaacgg cacttttta gcatatgccc aatttaacga cacagaagtc     1260
ccacttattg aatactcctt ctactctgat gagtcactgc agtacccaaa gactgtacgg    1320
gttccatatc caaaggcagg agctgtgaat ccaactgtaa agttctttgt tgtaaataca    1380
gactctctca gctcagtcac caatgcaact tccatacaaa tcactgctcc tgcttctatg    1440
ttgatagggg atcactactt gtgtgatgtg acatgggcaa cacaagaaag aatttctttg    1500
cagtggctca ggaggattca gaactattcg gtcatggata tttgtgacta tgatgaatcc    1560
agtggaagat ggaactgctt agtggcacgg caacacattg aaatgagtac tactggctgg    1620
gttggaagat ttaggccttc agaacctcat tttacccttg atggtaatag cttctacaag    1680
atcatcagca atgaagaagg ttacagacac atttgctatt ccaaataga taaaaaagac     1740
tgcacattta ttacaaaagg cacctgggaa gtcatcggga tagaagctct aaccagtgat    1800
tatctatact acattagtaa tgaatataaa ggaatgccag gaggaaggaa tctttataaa    1860
atccaactta gtgactatac aaaagtgaca tgcctcagtt gtgagctgaa tccggaaagg    1920
tgtcagtact attctgtgtc attcagtaaa gaggcgaagt attatcagct gagatgttcc    1980
ggtcctggtc tgcccctcta tactctacac agcagcgtga atgataaagg ctgagagtc    2040
ctggaagaca attcagcttt ggataaaatg ctgcagaatg tccagatgcc ctccaaaaaa    2100
ctggacttca ttattttgaa tgaaacaaaa ttttggtatc agatgatctt gcctcctcat    2160
tttgataaat ccaagaaata tcctctacta ttagatgtgt atgcaggccc atgtagtcaa    2220
aaagcagaca ctgtcttcag actgaactgg gccacttacc ttgcaagcac agaaaacatt    2280
atagtagcta gctttgatgg cagaggaagt ggttaccaag gagataagat catgcatgca    2340
atcaacagaa gactgggaac atttgaagtt gaagatcaaa ttgaagcagc cagacaattt    2400
tcaaaaatgg gatttgtgga caacaaacga attgcaattt ggggctggtc atatggaggg    2460
tacgtaacct caatggtcct gggatcggga agtggcgtgt tcaagtgtgg aatagccgtg    2520
gcgcctgtat cccggtggga gtactatgac tcagtgtaca cagaacgtta catgggtctc    2580
ccaactccag aagacaacct tgaccattac agaaattcaa cagtcatgag cagagctgaa    2640
aattttaaac aagttgagta cctccttatt catggaacag cagatgataa cgttcacttt    2700
cagcagtcag ctcagatctc caaagccctg gtcgatgttg gagtggattt ccaggcaatg    2760
tggtatactg atgaagacca tggaatagct agcagcacag cacaccaaca tatatatacc    2820
cacatgagcc acttcataaa acaatgtttc tctttacctt agcacctcaa aataccatgc    2880
catttaaagc ttattaaaac tcattttgt tttcattatc tcaaaactgc actgtcaaga     2940
tgatgatgat ctttaaaata cacactcaaa tcaagaaact taaggttacc tttgttccca    3000
aatttcatac ctatcatctt aagtagggac ttctgtcttc acaacagatt attaccttac    3060
agaagtttga attatccggt cgggttttat tgtttaaaat catttctgca tcagctgctg    3120
aaacaacaaa taggaattgt ttttatggag gctttgcata gattccctga gcaggatttt    3180
aatcttttc taactggact ggttcaaatg ttgttctctt ctttaaaggg atggcaagat     3240
gtgggcagtg atgtcactag ggcagggaca ggataagagg gattagggag agaagatagc    3300
agggcatggc tgggaaccca gtccaagca taccaacacg agcaggctac tgtcagctcc     3360
cctcggagaa gagctgttca cagccagact ggcacagttt tctgagaaag actattcaaa    3420
```

-continued

```
cagtctcagg aaatcaaata tgcaaagcac tgacttctaa gtaaaaccac agcagttgaa      3480
aagactccaa agaaatgtaa gggaaactgc cagcaacgca ggccccccagg tgccagttat      3540 ggctataggt gctacaaaaa cacagcaagg gtgatgggaa agcattgtaa atgtgctttt      3600
aaaaaaaaat actgatgttc ctagtgaaag aggcagcttg aaactgagat gtgaacacat      3660
cagcttgccc tgttaaaaga tgaaaatatt tgtatcacaa atcttaactt gaaggagtcc      3720
ttgcatcaat ttttcttatt tcatttcttt gagtgtctta attaaaagaa tattttaact      3780
tccttggact cattttaaaa aatggaacat aaaatacaat gttatgtatt attattccca      3840
ttctacatac tatggaattt ctcccagtca tttaataaat gtgccttcat tttttcagaa      3900
aaaaaaaaaa aaa                                                         3913
```

<210> SEQ ID NO 216
<211> LENGTH: 766
<212> TYPE: PRT
<213> ORGANISM: Homo sapiens

<400> SEQUENCE: 216

```
Met Lys Thr Pro Trp Lys Val Leu Leu Gly Leu Leu Ala Ala Ala
1               5                   10                  15

Leu Val Thr Ile Ile Thr Val Pro Val Val Leu Leu Asn Lys Gly Thr
                20                  25                  30

Asp Asp Ala Thr Ala Asp Ser Arg Lys Thr Tyr Thr Leu Thr Asp Tyr
35                  40                  45

Leu Lys Asn Thr Tyr Arg Leu Lys Leu Tyr Ser Leu Arg Trp Ile Ser
50                  55                  60

Asp His Glu Tyr Leu Tyr Lys Gln Glu Asn Asn Ile Leu Val Phe Asn
65                  70                  75                  80

Ala Glu Tyr Gly Asn Ser Ser Val Phe Leu Glu Asn Ser Thr Phe Asp
                85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
            180                 185                 190

Ile Ile Tyr Asn Gly Ile Thr Asp Trp Val Tyr Glu Glu Glu Val Phe
        195                 200                 205

Ser Ala Tyr Ser Ala Leu Trp Trp Ser Pro Asn Gly Thr Phe Leu Ala
    210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
            260                 265                 270

Thr Asp Ser Leu Ser Ser Val Thr Asn Ala Thr Ser Ile Gln Ile Thr
        275                 280                 285
```

```
Ala Pro Ala Ser Met Leu Ile Gly Asp His Tyr Leu Cys Asp Val Thr
290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
            340                 345                 350

Trp Val Gly Arg Phe Arg Pro Ser Glu Pro His Phe Thr Leu Asp Gly
        355                 360                 365

Asn Ser Phe Tyr Lys Ile Ser Asn Glu Glu Gly Tyr Arg His Ile
370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Gly Arg Asn Leu Tyr
                420                 425                 430

Lys Ile Gln Leu Ser Asp Tyr Thr Lys Val Thr Cys Leu Ser Cys Glu
            435                 440                 445

Leu Asn Pro Glu Arg Cys Gln Tyr Tyr Ser Val Ser Phe Ser Lys Glu
450                 455                 460

Ala Lys Tyr Tyr Gln Leu Arg Cys Ser Gly Pro Gly Leu Pro Leu Tyr
465                 470                 475                 480

Thr Leu His Ser Ser Val Asn Asp Lys Gly Leu Arg Val Leu Glu Asp
                485                 490                 495

Asn Ser Ala Leu Asp Lys Met Leu Gln Asn Val Gln Met Pro Ser Lys
            500                 505                 510

Lys Leu Asp Phe Ile Ile Leu Asn Glu Thr Lys Phe Trp Tyr Gln Met
        515                 520                 525

Ile Leu Pro Pro His Phe Asp Lys Ser Lys Lys Tyr Pro Leu Leu Leu
530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
                580                 585                 590

Ala Ile Asn Arg Arg Leu Gly Thr Phe Glu Val Glu Asp Gln Ile Glu
            595                 600                 605

Ala Ala Arg Gln Phe Ser Lys Met Gly Phe Val Asp Asn Lys Arg Ile
610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                645                 650                 655

Ser Arg Trp Glu Tyr Tyr Asp Ser Val Tyr Thr Glu Arg Tyr Met Gly
                660                 665                 670

Leu Pro Thr Pro Glu Asp Asn Leu Asp His Tyr Arg Asn Ser Thr Val
            675                 680                 685

Met Ser Arg Ala Glu Asn Phe Lys Gln Val Glu Tyr Leu Leu Ile His
690                 695                 700
```

```
Gly Thr Ala Asp Asp Asn Val His Phe Gln Gln Ser Ala Gln Ile Ser
705                 710                 715                 720

Lys Ala Leu Val Asp Val Gly Val Asp Phe Gln Ala Met Trp Tyr Thr
                725                 730                 735

Asp Glu Asp His Gly Ile Ala Ser Ser Thr Ala His Gln His Ile Tyr
            740                 745                 750

Thr His Met Ser His Phe Ile Lys Gln Cys Phe Ser Leu Pro
        755                 760                 765

<210> SEQ ID NO 217
<211> LENGTH: 2924
<212> TYPE: DNA
<213> ORGANISM: Homo sapiens

<400> SEQUENCE: 217
```

| | | | | | |
|---|---|---|---|---|---|
| gacgccgacg | atgaagacac | cgtggaaggt | tcttctggga | ctgctgggtg | ctgctgcgct | 60 |
| tgtcaccatc | atcaccgtgc | ccgtggttct | gctgaacaaa | ggcacagatg | atgctacagc | 120 |
| tgacagtcgc | aaaacttaca | ctctaactga | ttacttaaaa | atacttata | gactgaagtt | 180 |
| atactcctta | agatggattt | cagatcatga | atatctctac | aaacaagaaa | ataatatctt | 240 |
| ggtattcaat | gctgaatatg | aaacagctc | agttttcttg | gagaacagta | catttgatga | 300 |
| gtttggacat | tctatcaatg | attattcaat | atctcctgat | gggcagttta | ttctcttaga | 360 |
| atacaactac | gtgaagcaat | ggaggcattc | ctacacagct | tcatatgaca | tttatgattt | 420 |
| aaataaaagg | cagctgatta | cagaagagag | gattccaaac | aacacacagt | gggtcacatg | 480 |
| gtcaccagtg | ggtcataaat | tggcatatgt | ttggaacaat | gacatttatg | ttaaaattga | 540 |
| accaaattta | ccaagttaca | gaatcacatg | gacggggaaa | gaagatataa | tatataatgg | 600 |
| aataactgac | tgggtttatg | aagaggaagt | cttcagtgcc | tactctgctc | tgtggtggtc | 660 |
| tccaaacggc | actttttag | catatgccca | atttaacgac | acagaagtcc | cacttattga | 720 |
| atactccttc | tactctgatg | agtcactgca | gtacccaaag | actgtacggg | ttccatatcc | 780 |
| aaaggcagga | gctgtgaatc | caactgtaaa | gttctttgtt | gtaaatacag | actctctcag | 840 |
| ctcagtcacc | aatgcaactt | ccatacaaat | cactgctcct | gcttctatgt | tgataggga | 900 |
| tcactacttg | tgtgatgtga | catgggcaac | acaagaaaga | atttctttgc | agtggctcag | 960 |
| gaggattcag | aactattcgg | tcatggatat | ttgtgactat | gatgaatcca | gtggaagatg | 1020 |
| gaactgctta | gtggcacggc | aacacattga | aatgagtact | actggctggg | ttggaagatt | 1080 |
| taggccttca | gaacctcatt | ttaccccttga | tggtaatagc | ttctacaaga | tcatcagcaa | 1140 |
| tgaagaaggt | tacagacaca | tttgctatt | ccaaatagat | aaaaaagact | gcacatttat | 1200 |
| tacaaaaggc | acctgggaag | tcatcgggat | agaagctcta | accagtgatt | atctatacta | 1260 |
| cattagtaat | gaatataaag | gaatgccagg | aggaaggaat | ctttataaaa | tccaacttag | 1320 |
| tgactataca | aaagtgacat | gcctcagttg | tgagctgaat | ccggaaaggt | gtcagtacta | 1380 |
| ttctgtgtca | ttcagtaaag | aggcgaagta | ttatcagctg | agatgttccg | gtcctggtct | 1440 |
| gcccctctat | actctacaca | gcagcgtgaa | tgataaaggg | ctgagagtcc | tggaagacaa | 1500 |
| ttcagctttg | gataaaatgc | tgcagaatgt | ccagatgccc | tccaaaaaac | tggacttcat | 1560 |
| tatttgaat | gaaacaaaat | tttggtatca | gatgatcttg | cctcctcatt | ttgataaatc | 1620 |
| caagaaatat | cctctactat | agatgtgta | tgcaggccca | tgtagtcaaa | aagcagacac | 1680 |
| tgtcttcaga | ctgaactggg | ccacttacct | tgcaagcaca | gaaaacatta | tagtagctag | 1740 |
| ctttgatggc | agaggaagtg | gttaccaagg | agataagatc | atgcatgcaa | tcaacagaag | 1800 |

```
actgggaaca tttgaagttg aagatcaaat tgaagcagcc agacaatttt caaaaatggg    1860
atttgtggac aacaaacgaa ttgcaatttg gggctggtca tatggagggt acgtaacctc    1920
aatggtcctg ggatcaggaa gtggcgtgtt caagtgtgga atagccgtgg cgcctgtatc    1980
ccggtgggag tactatgact cagtgtacac agaacgttac atgggtctcc caactccaga    2040
agacaacctt gaccattaca gaaattcaac agtcatgagc agagctgaaa attttaaaca    2100
agttgagtac ctcctattc atggaacagc agatgataac gttcactttc agcagtcagc    2160
tcagatctcc aaagccctgg tcgatgttgg agtggatttc caggcaatgt ggtatactga    2220
tgaagaccat ggaatagcta gcagcacagc acaccaacat atatataccc acatgagcca    2280
cttcataaaa caatgtttct ctttaccttta gcacctcaaa ataccatgcc atttaaagct    2340
tattaaaact cattttttgtt ttcattatct caaaactgca ctgtcaagat gatgatgatc    2400
tttaaaatac acactcaaat caagaaactt aaggttacct ttgttcccaa atttcatacc    2460
tatcatctta agtagggact tctgtcttca aacagatta ttaccttaca gaagtttgaa    2520
ttatccggtc gggttttatt gtttaaaatc atttctgcat cagctgctga acaacaaat    2580 aggaattgtt tttatggagg ctttgcatag attccctgag caggatttta atcttttct    2640 aactggactg gttcaaatgt tgttctcttc tttaaaggga tggcaagatg tgggcagtga    2700
tgtcactagg gcagggacag gataagaggg attagggaga gaagatagca gggcatggct    2760
gggaacccaa gtccaagcat accaacacga ccaggctact gtcagctccc ctcggagaaa    2820
actgtgcagt ctgcgtgtga acagctcttc tcctttagag cacaatggat ctcgagggat    2880
cttccatacc taccagttct gcgcctcgag gccgcgactc taga                     2924
```

<210> SEQ ID NO 218
<211> LENGTH: 766
<212> TYPE: PRT
<213> ORGANISM: Homo sapiens

<400> SEQUENCE: 218

Met Lys Thr Pro Trp Lys Val Leu Leu Gly Leu Leu Ala Ala Ala
1               5                   10                  15

Leu Val Thr Ile Ile Thr Val Pro Val Val Leu Leu Asn Lys Gly Thr
            20                  25                  30

Asp Asp Ala Thr Ala Asp Ser Arg Lys Thr Tyr Thr Leu Thr Asp Tyr
        35                  40                  45

Leu Lys Asn Thr Tyr Arg Leu Lys Leu Tyr Ser Leu Arg Trp Ile Ser
    50                  55                  60

Asp His Glu Tyr Leu Tyr Lys Gln Glu Asn Asn Ile Leu Val Phe Asn
65                  70                  75                  80

Ala Glu Tyr Gly Asn Ser Ser Val Phe Leu Glu Asn Ser Thr Phe Asp
                85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

```
Glu Pro Asn Leu Pro Ser Tyr Arg Ile Thr Trp Thr Gly Lys Glu Asp
                180                 185                 190

Ile Ile Tyr Asn Gly Ile Thr Asp Trp Val Tyr Glu Glu Val Phe
            195                 200             205

Ser Ala Tyr Ser Ala Leu Trp Trp Ser Pro Asn Gly Thr Phe Leu Ala
        210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
            260                 265                 270

Thr Asp Ser Leu Ser Ser Val Thr Asn Ala Thr Ser Ile Gln Ile Thr
        275                 280                 285

Ala Pro Ala Ser Met Leu Ile Gly Asp His Tyr Leu Cys Asp Val Thr
    290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
            340                 345                 350

Trp Val Gly Arg Phe Arg Pro Ser Glu Pro His Phe Thr Leu Asp Gly
        355                 360                 365

Asn Ser Phe Tyr Lys Ile Ile Ser Asn Glu Glu Gly Tyr Arg His Ile
    370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Gly Arg Asn Leu Tyr
            420                 425                 430

Lys Ile Gln Leu Ser Asp Tyr Thr Lys Val Thr Cys Leu Ser Cys Glu
        435                 440                 445

Leu Asn Pro Glu Arg Cys Gln Tyr Tyr Ser Val Ser Phe Ser Lys Glu
    450                 455                 460

Ala Lys Tyr Tyr Gln Leu Arg Cys Ser Gly Pro Gly Leu Pro Leu Tyr
465                 470                 475                 480

Thr Leu His Ser Ser Val Asn Asp Lys Gly Leu Arg Val Leu Glu Asp
                485                 490                 495

Asn Ser Ala Leu Asp Lys Met Leu Gln Asn Val Gln Met Pro Ser Lys
            500                 505                 510

Lys Leu Asp Phe Ile Ile Leu Asn Glu Thr Lys Phe Trp Tyr Gln Met
        515                 520                 525

Ile Leu Pro Pro His Phe Asp Lys Ser Lys Lys Tyr Pro Leu Leu Leu
    530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
            580                 585                 590
```

```
Ala Ile Asn Arg Arg Leu Gly Thr Phe Glu Val Glu Asp Gln Ile Glu
            595                 600                 605

Ala Ala Arg Gln Phe Ser Lys Met Gly Phe Val Asp Asn Lys Arg Ile
        610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                645                 650                 655

Ser Arg Trp Glu Tyr Tyr Asp Ser Val Tyr Thr Glu Arg Tyr Met Gly
            660                 665                 670

Leu Pro Thr Pro Glu Asp Asn Leu Asp His Tyr Arg Asn Ser Thr Val
        675                 680                 685

Met Ser Arg Ala Glu Asn Phe Lys Gln Val Glu Tyr Leu Leu Ile His
    690                 695                 700

Gly Thr Ala Asp Asp Asn Val His Phe Gln Gln Ser Ala Gln Ile Ser
705                 710                 715                 720

Lys Ala Leu Val Asp Val Gly Val Asp Phe Gln Ala Met Trp Tyr Thr
                725                 730                 735

Asp Glu Asp His Gly Ile Ala Ser Ser Thr Ala His Gln His Ile Tyr
            740                 745                 750

Thr His Met Ser His Phe Ile Lys Gln Cys Phe Ser Leu Pro
        755                 760                 765

<210> SEQ ID NO 219
<211> LENGTH: 1260
<212> TYPE: DNA
<213> ORGANISM: Homo sapiens

<400> SEQUENCE: 219
atgattggca cagatcctcg aacaattctt aaagatttat tgccggaaac aatacctcca      60
cctgagttgg atgatatgac actgtggcag attgttatta atatcctttc agaaccacca     120
aaaaggaaaa aagaaaaga tattaataca attgaagatg ctgtgaaatt actgcaagag     180
tgcaaaaaaa ttatagttct aactggagct ggggtgtctg tttcatgtgg aatacctgac     240
ttcaggtcaa gggatggtat ttatgctcgc cttgctgtag acttcccaga tcttccagat     300
cctcaagcga tgtttgatat tgaatatttc agaaaagatc caagaccatt cttcaagttt     360
gcaaaggaaa tatatcctgg acaattccag ccatctctct gtcacaaatt catagccttg     420
tcagataagg aaggaaaact acttcgcaac tatacccaga acatagacac gctggaacag     480
gttgcgggaa tccaaaggat aattcagtgt catggttcct ttgcaacagc atcttgcctg     540
atttgtaaat acaaagttga ctgtgaagct gtacgaggag ctctttttag tcaggtagtt     600
cctcgatgtc ctaggtgccc agctgatgaa ccgcttgcta tcatgaaacc agagattgtg     660
ttttttggtg aaaatttacc agaacagttt catagagcca tgaagtatga caaagatgaa     720
gttgacctcc tcattgttat tgggtcttcc ctcaaagtaa gaccagtagc actaattcca     780
agttccatac cccatgaagt gcctcagata ttaattaata gagaacctt gcctcatctg     840 cattttgatg tagagcttct tggagactgt gatgtcataa ttaatgaatt gtgtcatagg     900
ttaggtggtg aatatgccaa actttgctgt aaccctgtaa agctttcaga aattactgaa     960
aaacctccac gaacacaaaa agaattggct tatttgtcag agttgccacc cacacctctt    1020
catgtttcag aagactcaag ttcaccagaa agaacttcac caccagattc ttcagtgatt    1080
gtcacacttt tagaccaagc agctaagagt aatgatgatt tagatgtgtc tgaatcaaaa    1140
```

```
ggttgtatgg aagaaaaacc acaggaagta caaacttcta ggaatgttga agtattgct       1200 gaacagatgg aaaatccgga tttgaagaat gttggttcta gtactgggga gaaaaatgaa     1260
```

<210> SEQ ID NO 220
<211> LENGTH: 420
<212> TYPE: PRT
<213> ORGANISM: Homo sapiens

<400> SEQUENCE: 220

```
Met Ile Gly Thr Asp Pro Arg Thr Ile Leu Lys Asp Leu Leu Pro Glu
1               5                   10                  15

Thr Ile Pro Pro Glu Leu Asp Asp Met Thr Leu Trp Gln Ile Val
            20                  25                  30

Ile Asn Ile Leu Ser Glu Pro Pro Lys Arg Lys Lys Arg Lys Asp Ile
        35                  40                  45

Asn Thr Ile Glu Asp Ala Val Lys Leu Leu Gln Glu Cys Lys Lys Ile
    50                  55                  60

Ile Val Leu Thr Gly Ala Gly Val Ser Val Ser Cys Gly Ile Pro Asp
65                  70                  75                  80

Phe Arg Ser Arg Asp Gly Ile Tyr Ala Arg Leu Ala Val Asp Phe Pro
                85                  90                  95

Asp Leu Pro Asp Pro Gln Ala Met Phe Asp Ile Glu Tyr Phe Arg Lys
            100                 105                 110

Asp Pro Arg Pro Phe Phe Lys Phe Ala Lys Glu Ile Tyr Pro Gly Gln
        115                 120                 125

Phe Gln Pro Ser Leu Cys His Lys Phe Ile Ala Leu Ser Asp Lys Glu
    130                 135                 140

Gly Lys Leu Leu Arg Asn Tyr Thr Gln Asn Ile Asp Thr Leu Glu Gln
145                 150                 155                 160

Val Ala Gly Ile Gln Arg Ile Ile Gln Cys His Gly Ser Phe Ala Thr
                165                 170                 175

Ala Ser Cys Leu Ile Cys Lys Tyr Lys Val Asp Cys Glu Ala Val Arg
            180                 185                 190

Gly Ala Leu Phe Ser Gln Val Val Pro Arg Cys Pro Arg Cys Pro Ala
        195                 200                 205

Asp Glu Pro Leu Ala Ile Met Lys Pro Glu Ile Val Phe Phe Gly Glu
    210                 215                 220

Asn Leu Pro Glu Gln Phe His Arg Ala Met Lys Tyr Asp Lys Asp Glu
225                 230                 235                 240

Val Asp Leu Leu Ile Val Ile Gly Ser Ser Leu Lys Val Arg Pro Val
                245                 250                 255

Ala Leu Ile Pro Ser Ser Ile Pro His Glu Val Pro Gln Ile Leu Ile
            260                 265                 270

Asn Arg Glu Pro Leu Pro His Leu His Phe Asp Val Glu Leu Leu Gly
        275                 280                 285

Asp Cys Asp Val Ile Ile Asn Glu Leu Cys His Arg Leu Gly Gly Glu
    290                 295                 300

Tyr Ala Lys Leu Cys Cys Asn Pro Val Lys Leu Ser Glu Ile Thr Glu
305                 310                 315                 320

Lys Pro Pro Arg Thr Gln Lys Glu Leu Ala Tyr Leu Ser Glu Leu Pro
                325                 330                 335

Pro Thr Pro Leu His Val Ser Glu Asp Ser Ser Ser Pro Glu Arg Thr
            340                 345                 350

Ser Pro Pro Asp Ser Ser Val Ile Val Thr Leu Leu Asp Gln Ala Ala
```

|     |     | 355 |     |     |     | 360 |     |     |     | 365 |     |
| --- | --- | --- | --- | --- | --- | --- | --- | --- | --- | --- | --- |

Lys Ser Asn Asp Asp Leu Asp Val Ser Glu Ser Lys Gly Cys Met Glu
    370                    375                    380

Glu Lys Pro Gln Glu Val Gln Thr Ser Arg Asn Val Glu Ser Ile Ala
385                    390                    395                    400

Glu Gln Met Glu Asn Pro Asp Leu Lys Asn Val Gly Ser Ser Thr Gly
                405                    410                    415

Glu Lys Asn Glu
            420

<210> SEQ ID NO 221
<211> LENGTH: 7341
<212> TYPE: DNA
<213> ORGANISM: Homo sapiens

<400> SEQUENCE: 221

| | | | | |
|---|---|---|---|---|
| gcgcgaggcc | gtcgattcgc | tcgcggctcc | atcgcggcct | ggccggggggg | cggtgtctgc | 60 |
| tgcgccaggt | tcgctggccg | cacgtcttca | ggtcctcctg | ttcctgggag | gcgggcgcgg | 120 |
| caggactggg | aggtggcggc | agcgggcgag | gactcgccga | ggacgggggct | ccggcccggg | 180 |
| ataaccaact | ctccttctct | cttctttggt | gcttccccag | gcggcggcgg | cggcgcccgg | 240 |
| gagccggagc | cttcgcggcg | tccacgtccc | tcccccgctg | caccccgccc | cggcgcgaga | 300 |
| ggagagcgcg | agagccccag | ccgcgggcgg | gcgggcggcg | aagatggcag | aggcaccggc | 360 |
| ttccccggcc | ccgctctctc | cgctcgaagt | ggagctggac | ccggagttcg | agccccagag | 420 |
| ccgtccgcga | tcctgtacgt | ggcccctgca | aaggccggag | ctccaagcga | gccctgccaa | 480 |
| gccctcgggg | gagacggccc | ccgactccat | gatccccgag | gaggaggacg | atgaagacga | 540 |
| cgaggacggc | gggggacggg | ccggctcggc | catggcgatc | ggcggcggcg | gcgggagcgg | 600 |
| cacgctgggc | tccgggctgc | tccttgagga | ctcggcccgg | gtgctggcac | ccggagggca | 660 |
| agaccccggg | tctgggccag | ccaccgcggc | gggcgggctg | agcgggggta | cacaggcgct | 720 |
| gctgcagcct | cagcaaccgc | tgccaccgcc | gcagccgggg | gcggctgggg | gctccgggca | 780 |
| gccgaggaaa | tgttcgtcgc | ggcggaacgc | ctggggaaac | ctgtcctacg | cggacctgat | 840 |
| cacccgcgcc | atcgagagct | ccccggacaa | acggctcact | ctgtcccaga | tctacgagtg | 900 |
| gatggtgcgt | tgcgtgccct | acttcaagga | taagggcgac | agcaacagct | ctgccggctg | 960 |
| gaagaactcc | atccggcaca | acctgtcact | gcatagtcga | ttcatgcggg | tccagaatga | 1020 |
| gggaactggc | aagagctctt | ggtggatcat | caaccctgat | ggggggaaga | gcggaaaagc | 1080 |
| cccccggcgg | cgggctgtct | ccatggacaa | tagcaacaag | tataccaaga | gccgtggccg | 1140 |
| cgcagccaag | aagaaggcag | ccctgcagac | agccccgaa | tcagctgacg | acagtccctc | 1200 |
| ccagctctcc | aagtggcctg | gcagccccac | gtcacgcagc | agtgatgagc | tggatgcgtg | 1260 |
| gacggacttc | cgttcacgca | ccaattctaa | cgccagcaca | gtcagtggcc | gcctgtcgcc | 1320 |
| catcatggca | agcacagagt | tggatgaagt | ccaggacgat | gatgcgcctc | tctcgcccat | 1380 |
| gctctacagc | agctcagcca | gcctgtcacc | ttcagtaagc | aagccgtgca | cggtggaact | 1440 |
| gccacggctg | actgatatgg | caggcaccat | gaatctgaat | gatgggctga | ctgaaaacct | 1500 |
| catggacgac | ctgctggata | acatcacgct | cccgccatcc | cagccatcgc | ccactggggg | 1560 |
| actcatgcag | cggagctcta | gcttcccgta | taccaccaag | ggctcgggcc | tgggctcccc | 1620 |
| aaccagctcc | tttaacagca | cggtgttcgg | accttcatct | ctgaactccc | tacgccagtc | 1680 |
| tcccatgcag | accatccaag | agaacaagcc | agctaccttc | tcttccatgt | cacactatgg | 1740 |

```
taaccagaca ctccaggacc tgctcacttc ggactcactt agccacacgc atgtcatgat    1800
gacacagtcg gaccccttga tgtctcaggc cagcaccgct gtgtctgccc agaattcccg    1860
ccggaacgtg atgcttcgca atgatccgat gatgtccttt gctgcccagc ctaaccaggg    1920
aagtttggtc aatcagaact tgctccacca ccagcaccaa acccagggcg ctcttggtgg    1980
cagccgtgcc ttgtcgaatt ctgtcagcaa catgggcttg agtgagtcca gcagccttgg    2040
gtcagccaaa caccagcagc agtctcctgt cagccagtct atgcaaaccc tctcggactc    2100
tctctcaggc tcctccttgt actcaactag tgcaaacctg cccgtcatgg gccatgagaa    2160
gttccccagc gacttggacc tggacatgtt caatgggagc ttggaatgtg acatggagtc    2220
cattatccgt agtgaactca tggatgctga tgggttggat tttaactttg attccctcat    2280
ctccacacag aatgttgttg gtttgaacgt ggggaacttc actggtgcta agcaggcctc    2340
atctcagagc tgggtgccag gctgaaggat cactgaggaa ggggaagtgg gcaaagcaga    2400
ccctcaaact gacacaagac ctacagagaa aacccttttgc caaatctgct ctcagcaagt    2460
ggacagtgat accgtttaca gcttaacacc tttgtgaatc ccacgccatt ttcctaaccc    2520
agcagagact gttaatggcc ccttaccctg ggtgaagcac ttacccttgg aacagaactc    2580
taaaaagtat gcaaaatctt ccttgtacag ggtggtgagc cgcctgccag tggaggacag    2640
cacccctcag caccacccac cctcattcag agcacaccgt gagcccccgt cggccattct    2700
gtggtgtttt aatattgcga tggtttatgg gacgttttaa gtgttgttct tgtgtttgtt    2760
ttcctttgac tttctgagtt tttcacatgc attaacttgc ggtattttc tgttaaaatg    2820 ttaaccgtcc ttccctagc aaatttaaaa acagaaagaa aatgttgtac cagttaccat    2880
tccgggttcg agcatcacaa gcttttgagc gcatggaact ccataaacta acaaattaca    2940
taaactaaag ggggattttc tttcttcttt tgtttggtag aaaattatcc ttttctaaaa    3000
actgaacaat ggcacaattg tttgctatgt gcacccgtcc aggacagaac cgtgcatagg    3060
caaaaggagt ggagcacagc gtccggccca gtgtgtttcc ggttctgagt cagggtgatc    3120
tgtggacggg accccagcac caagtctacg ggtgccagat cagtagggcc tgtgatttcc    3180
tgtcagtgtc ctcagctaat gtgaacagtg ttggtctgct ggttagaaac tagaatattg    3240
atattttcag gaaagaaatc agctcagctc tccactcatt gccaaatgtc actaaagggt    3300
ttagttttaa ggagaaagaa aaggaaaaaa aaaaaaaaca aaaagtcct gttttgcttt    3360 gcagaacaaa tgaacttaca ggtgagcatt aagcttgcag tgagaaatgt gcgaagagta    3420
aaaacccaag tcaatgctga ggcagttcta acttcactgt tttcctaaat acacatcctt    3480
gattattttc agccttgcta tataatctga tctgctagaa gtgtatgagt gagaggcaat    3540
agcatacaaa ctgatttttt aaatataagc ttaggttgta attgtacaag tgactcaatg    3600
gaagtacaaa atagggcagt tttaactttt ttttctgctt ctatggatt cattttgttg     3660 tgttttcaaa aagttatggt gctgtatagg tgcttctgt ttaacctgga aagtgtgatt    3720
atattcgtta ccttctttgg tagacggaat agttgggacc acctttggta cataagaaat    3780
tggtataacg atgctctgat tagcacagta tatgcatact tctccaaagt gatatatgaa    3840
gactcttttc tttgcataaa aagcattagg catataaatg tataaatata ttttatcatg    3900
tacagtacaa aaatggaacc ttatgcatgg gccttaggaa tacaggctag tatttcagca    3960
cagacttccc tgcttgagtt cttgctgatg cttgcaccgt gacagtgggc accaacacag    4020
acgtgccacc caacccctg cacacaccac cggccaccag gggcccccttt gtgcgccttg    4080
```

```
gctttataac tcctctgggg gtgatattgg tggtgatcac agctcctagc ataatgagag    4140
ttccatttgg tattgtcaca cgtctcctgc ctcgcttggg ttgccatgtt tgagcgatgg    4200
ccctgttgat ttcaccctgc cttttactga atctgtaaat tgttgtgcaa ttgtggttat    4260
agtagactgt agcacattgc cttttctaaa ctgctacatg tttataatct tcattttta    4320 agtatgtgta attttttaa gtatgtattc tattcatatg gtctgcttgt cagtgagcca    4380
gacttgctta ctatattcct ttataataat gctagccact tcctggattc tttagtaatg    4440
tgctgtatgc aagaactttc cagtagcagt gaaggagggt tgcctctcca agcttcctaa    4500
gggatgctgc cctgtgtggg gatgcattgc agaggcacta gtagcatggg ggctagagtg    4560
gggagcgaga tgtaaaaggg tgggggata ggagaattcc agagtgcttc cagcattagg    4620
gtcctgagaa cttctgagtt cagagaaaca tgcaaagtga ctaacaaaat agctacttac    4680 cttttgcagtt ttacagaccc tgggagctgc tttgggagtg agaaaggcaa ccctccaatg    4740
tgtttcaact ttaaaatgtt gaattctttt cagacatggt atctcattta ttctcctttt    4800
ctagcgtttg ttgaatttca ggcagaatgt cttacagaat gtcctagaac cagattatca    4860
tttaatctga aacagctgag gaagggacag agaaggtaca agggcaaggc agcacaaaac    4920
agatcaggag aatgaagagg gaatgctttg gtttttgtt ttgttttgtt ttttctttt    4980 caagtaacta aaacagcatc tacatgtaga gtgttgtgga gagctgagac cagggtaaag    5040
tcaagtgcag catcagtact gcgagaccca ccagcccctg gagagggtca gccgagaatc    5100
tggtagtgaa gcctgtctag ggtcccggca ccctcacccct cagccacctg cagagaggcc    5160
agggccccag agactagcct ggttctgaag tgggcagggg tgctgccaga gccctctgcc    5220
ccttatgttg agaccctgct ttcaggacag gccagccgtt ggccaccatg tcacattctg    5280
agtgagtgtc acaggtccct aacaataatt ttctgatctg gagcatatca gcagaatgct    5340
tagcctcaag gggcctggca gctgtaatgt ttgatttatg atgagaacta tccgaggcca    5400
cccttggcct ctaaataagc tgctctaggg agccgcctac tttttgatga gaaattagaa    5460
gagtacctaa tgttgaaaac atgacatgcg ctcttgggat ctgctgttct tccagggct    5520 ccagaacctg atacctgtta ccaaagctag gaaagagctt tatcacaagc cttcactgtc    5580
ctggcatgag aactggctgc caggctcagt gtaccccatt aactgtgaat gaatctgagc    5640
ttggtttcct ttattgcttc ctctgcaata tgattgctga acacatttt aaaaattcag    5700 aagcttgtca ctcctgttaa tgggaggatc agtcacacat gtgtagtaca aggcggactt    5760
tgtgtttgtt tttggtgtta attttagca ttgtgtgtgt tgcttcccca ccctgaggag    5820
aggacaccat ggcttactac tcaggacaag tatgccccgc tcagggtgtg atttcaggtg    5880
gcttccaaac ttgtacgcag tttaaagatg gtggggacag actttgcctc tacctagtga    5940
accccactta agaataagg agcatttgaa tctcttggaa aaggccatga agaataaagc    6000
agtcaaaaag aagtcctcca tgttggtgcc aaggacttgc gaggggaaat aaaaatgtta    6060
tccagcctga ccaacatgga gaaacccgt ctccattaaa aatacaaaat tagcctggca    6120
tggtggcgca tgcctgtaat cccagctact ctggaggctg aggcaggaga atcgcttgaa    6180
cccaggaggc ggaggtcgca gtgagccgag atcatgccag tgcactccag cctgggtaac    6240
aagagtgaaa ctccgtgtca aaaaaaaaa aaaatgtta ctcatcctct ctgaaagcaa    6300
aaaggaaacc ctaacagctc tgaactctgg ttttattttt cttgctgtat ttgggtgaac    6360
attgtatgat taggcataat gttaaaaaa aaatttttt tttggtagaa atgcaatcac    6420
cagtaaagag gtacgaaaaa gctagcctct ctcagagacc ggggaggcag agtactacta    6480
```

```
gaggaagtga agttctgatg aatcatgcc tgtcaaatga ggtcttgaag cggatgccca    6540
aataaaagag tatattttat ctaaatctta agtgggtaac attttatgca gtttaaatga    6600
atggaatatt ttcctcttgt ttagttgtat ctgtttgtat ttttctttga tgaatgattg    6660
gtcatgaggc ctcttgccac actccagaaa tacgtgtgcg gctgctttta agaactatgt    6720
gtctggtcac ttatttctct aaaattatct cattgcctgg caatcagtct tctcttgtat    6780
acttgtccta gcacattatg tacatgggaa atgtaaacaa atgtgaagga ggaccagaaa    6840
aattagttaa tatttaaaaa aatgtattgt gcattttggc ttcacatgtt taactttttt    6900
taagaaaaaa gttgcatgaa tggaaaaaaa aatctgtata cagtatctgt aaaaactatc    6960
ttatctgttt caattccttg ctcatatccc ataatctta aactaaata tggtgtgtgg    7020 ccatatttaa acacctgaga gtcaagcagt tgagactttg atttgaagca cctcatcctt    7080
ctttcaatgc gaacactatc atatggcatt cttactgagg attttgtcta accatatgtt    7140
gccatgaatt aactctgccg cctttcttaa ggatcaaaac cagtttgatt tgggaatctt    7200 ccccttttcca aatgaaatag agatgcagta cttaactttc cttggtgttt gtagatattg    7260
ccttgtgtat tccacttaaa accgtaatct agtttgtaaa agagatggtg acgcatgtaa    7320
ataaagcatc agtgacactc t                                              7341
```

<210> SEQ ID NO 222
<211> LENGTH: 673
<212> TYPE: PRT
<213> ORGANISM: Homo sapiens

<400> SEQUENCE: 222

```
Met Ala Glu Ala Pro Ala Ser Pro Ala Pro Leu Ser Pro Leu Glu Val
1               5                   10                  15

Glu Leu Asp Pro Glu Phe Glu Pro Gln Ser Arg Pro Arg Ser Cys Thr
            20                  25                  30

Trp Pro Leu Gln Arg Pro Glu Leu Gln Ala Ser Pro Ala Lys Pro Ser
        35                  40                  45

Gly Glu Thr Ala Ala Asp Ser Met Ile Pro Glu Glu Asp Asp Glu
    50                  55                  60

Asp Asp Glu Asp Gly Gly Gly Arg Ala Gly Ser Ala Met Ala Ile Gly
65                  70                  75                  80

Gly Gly Gly Gly Ser Gly Thr Leu Gly Ser Gly Leu Leu Leu Glu Asp
                85                  90                  95

Ser Ala Arg Val Leu Ala Pro Gly Gly Gln Asp Pro Gly Ser Gly Pro
            100                 105                 110

Ala Thr Ala Ala Gly Gly Leu Ser Gly Gly Thr Gln Ala Leu Leu Gln
        115                 120                 125

Pro Gln Gln Pro Leu Pro Pro Gln Pro Gly Ala Ala Gly Gly Ser
    130                 135                 140

Gly Gln Pro Arg Lys Cys Ser Arg Arg Asn Ala Trp Gly Asn Leu
145                 150                 155                 160

Ser Tyr Ala Asp Leu Ile Thr Arg Ala Ile Glu Ser Ser Pro Asp Lys
                165                 170                 175

Arg Leu Thr Leu Ser Gln Ile Tyr Glu Trp Met Val Arg Cys Val Pro
            180                 185                 190

Tyr Phe Lys Asp Lys Gly Asp Ser Asn Ser Ser Ala Gly Trp Lys Asn
        195                 200                 205

Ser Ile Arg His Asn Leu Ser Leu His Ser Arg Phe Met Arg Val Gln
```

```
                210                 215                 220
Asn Glu Gly Thr Gly Lys Ser Ser Trp Trp Ile Ile Asn Pro Asp Gly
225                 230                 235                 240

Gly Lys Ser Gly Lys Ala Pro Arg Arg Arg Ala Val Ser Met Asp Asn
                245                 250                 255

Ser Asn Lys Tyr Thr Lys Ser Arg Gly Arg Ala Ala Lys Lys Lys Ala
                260                 265                 270

Ala Leu Gln Thr Ala Pro Glu Ser Ala Asp Asp Ser Pro Ser Gln Leu
                275                 280                 285

Ser Lys Trp Pro Gly Ser Pro Thr Ser Arg Ser Ser Asp Glu Leu Asp
290                 295                 300

Ala Trp Thr Asp Phe Arg Ser Arg Thr Asn Ser Asn Ala Ser Thr Val
305                 310                 315                 320

Ser Gly Arg Leu Ser Pro Ile Met Ala Ser Thr Glu Leu Asp Glu Val
                325                 330                 335

Gln Asp Asp Asp Ala Pro Leu Ser Pro Met Leu Tyr Ser Ser Ser Ala
                340                 345                 350

Ser Leu Ser Pro Ser Val Ser Lys Pro Cys Thr Val Glu Leu Pro Arg
                355                 360                 365

Leu Thr Asp Met Ala Gly Thr Met Asn Leu Asn Asp Gly Leu Thr Glu
                370                 375                 380

Asn Leu Met Asp Asp Leu Leu Asp Asn Ile Thr Leu Pro Pro Ser Gln
385                 390                 395                 400

Pro Ser Pro Thr Gly Gly Leu Met Gln Arg Ser Ser Ser Phe Pro Tyr
                405                 410                 415

Thr Thr Lys Gly Ser Gly Leu Gly Ser Pro Thr Ser Ser Phe Asn Ser
                420                 425                 430

Thr Val Phe Gly Pro Ser Ser Leu Asn Ser Leu Arg Gln Ser Pro Met
                435                 440                 445

Gln Thr Ile Gln Glu Asn Lys Pro Ala Thr Phe Ser Ser Met Ser His
                450                 455                 460

Tyr Gly Asn Gln Thr Leu Gln Asp Leu Leu Thr Ser Asp Ser Leu Ser
465                 470                 475                 480

His Ser Asp Val Met Met Thr Gln Ser Asp Pro Leu Met Ser Gln Ala
                485                 490                 495

Ser Thr Ala Val Ser Ala Gln Asn Ser Arg Arg Asn Val Met Leu Arg
                500                 505                 510

Asn Asp Pro Met Met Ser Phe Ala Ala Gln Pro Asn Gln Gly Ser Leu
                515                 520                 525

Val Asn Gln Asn Leu Leu His His Gln His Gln Thr Gln Gly Ala Leu
                530                 535                 540

Gly Gly Ser Arg Ala Leu Ser Asn Ser Val Ser Asn Met Gly Leu Ser
545                 550                 555                 560

Glu Ser Ser Ser Leu Gly Ser Ala Lys His Gln Gln Gln Ser Pro Val
                565                 570                 575

Ser Gln Ser Met Gln Thr Leu Ser Asp Ser Leu Ser Gly Ser Ser Leu
                580                 585                 590

Tyr Ser Thr Ser Ala Asn Leu Pro Val Met Gly His Glu Lys Phe Pro
                595                 600                 605

Ser Asp Leu Asp Leu Asp Met Phe Asn Gly Ser Leu Glu Cys Asp Met
                610                 615                 620

Glu Ser Ile Ile Arg Ser Glu Leu Met Asp Ala Asp Gly Leu Asp Phe
625                 630                 635                 640
```

Asn Phe Asp Ser Leu Ile Ser Thr Gln Asn Val Val Gly Leu Asn Val
            645                 650                 655

Gly Asn Phe Thr Gly Ala Lys Gln Ala Ser Ser Gln Ser Trp Val Pro
        660                 665                 670

Gly

<210> SEQ ID NO 223
<211> LENGTH: 22
<212> TYPE: DNA
<213> ORGANISM: Homo sapiens

<400> SEQUENCE: 223
tggctcagtt cagcaggaac ag                                            22

<210> SEQ ID NO 224
<211> LENGTH: 86
<212> TYPE: DNA
<213> ORGANISM: Homo sapiens

<400> SEQUENCE: 224
tgccagtctc taggtccctg agacccttta acctgtgagg acatccaggg tcacaggtga    60
ggttcttggg agcctggcgt ctggcc                                        86

<210> SEQ ID NO 225
<211> LENGTH: 110
<212> TYPE: DNA
<213> ORGANISM: Homo sapiens

<400> SEQUENCE: 225
gtgttgggga ctcgcgcgct gggtccagtg gttcttaaca gttcaacagt tctgtagcgc    60
aattgtgaaa tgtttaggac cactagaccc ggcgggcgcg gcgacagcga               110

<210> SEQ ID NO 226
<211> LENGTH: 100
<212> TYPE: DNA
<213> ORGANISM: Homo sapiens

<400> SEQUENCE: 226
tgtgtctctc tctgtgtcct gccagtggtt ttaccctatg gtaggttacg tcatgctgtt    60
ctaccacagg gtagaaccac ggacaggata ccggggcacc                         100

<210> SEQ ID NO 227
<211> LENGTH: 78
<212> TYPE: DNA
<213> ORGANISM: Homo sapiens

<400> SEQUENCE: 227
ctgaggagca gggcttagct gcttgtgagc agggtccaca ccaagtcgtg ttcacagtgg    60
ctaagttccg cccccccag                                                78

<210> SEQ ID NO 228
<211> LENGTH: 110
<212> TYPE: DNA
<213> ORGANISM: Homo sapiens

<400> SEQUENCE: 228
agaagggcta tcaggccagc cttcagagga ctccaaggaa cattcaacgc tgtcggtgag    60
tttgggattt gaaaaaacca ctgaccgttg actgtacctt ggggtcctta               110

```
<210> SEQ ID NO 229
<211> LENGTH: 21
<212> TYPE: DNA
<213> ORGANISM: Artificial Sequence
<220> FEATURE:
<223> OTHER INFORMATION: synthetic construct

<400> SEQUENCE: 229
aagcctgtag cccacgtcgt a                                              21

<210> SEQ ID NO 230
<211> LENGTH: 24
<212> TYPE: DNA
<213> ORGANISM: Artificial Sequence
<220> FEATURE:
<223> OTHER INFORMATION: synthetic construct

<400> SEQUENCE: 230
ggcaccacta gttggttgtc tttg                                           24

<210> SEQ ID NO 231
<211> LENGTH: 76
<212> TYPE: DNA
<213> ORGANISM: Mus musculus

<400> SEQUENCE: 231
ccatggaaca ttcaacgctg tcggtgagtt tgggattcaa aaacaaaaaa accaccgacc    60
gttgactgta ccttgg                                                    76
```

IN VITRO AND IN VIVO INTRACELLULAR DELIVERY OF SIRNA VIA SELF-ASSEMBLED NANOPIECES

RELATED APPLICATIONS

This application is a national stage application filed under 35 U.S.C. § 371 of International Patent Application No. PCT/US2019/024155, filed Mar. 26, 2019, which claims the benefit of and priority under 35 U.S.C. § 119(e) to U.S. Provisional Application No. 62/648,233, filed Mar. 26, 2018, the entire contents of which are incorporated herein by reference in their entirety.

STATEMENT OF GOVERNMENT INTERESTS

This invention was made with government support under P20 RR024484 and P20 GM104937 awarded by the National Institutes of Health. The Government has certain rights in the invention.

INCORPORATION BY REFERENCE OF SEQUENCE LISTING

The contents of the sequence listing text file named "21486-640001WO_ST25.txt", which was created on Mar. 26, 2019 and is 359,426 bytes in size, is hereby incorporated by reference in its entirety.

FIELD OF THE INVENTION

This invention relates to nanoparticles for delivering agents into cells or bodily tissues.

BACKGROUND

Although progress in drug delivery using nanotechnology has been documented, several challenges remain, particularly with regard to targeting and toxicity. Current delivery systems suffer from significant hindrances such as low targeting efficiency.

SUMMARY OF THE INVENTION

The compositions and methods of the invention provide a solution to long standing challenges in selective delivery of agents using nanotechnology. Accordingly, the invention features compounds, assemblies of such compounds, a system, or method for selective drug delivery to a cell or any bodily tissue (including those that include extracellular matrix tissue) comprising a nanoparticle. Nanoparticles such as rosette nanopieces, lipid nanoparticles, and polymeric nanoparticles composition comprise a cargo compound, wherein a positively-charged nanoparticle and cargo complex composition with net positive charge at pH 7-7.5 localizes or penetrates a negatively-charged tissue or wherein a negatively-charged (or weakly positively-charged) nanoparticle and cargo complex composition with net negative (or weak positive) charge at pH 7-7.5 localizes to or penetrates a positively-charged cell or tissue. "Negatively charged" means zeta-potential of equal or smaller than 0 mV (which is minus "−" mV). "Positively charged" means zeta-potential of equal or larger than 0 mV (which is plus "+" mV). "Weakly positive" means zeta potential of 0 mV to +30 mV. The nanoparticle is tuned to preferentially localize to and deliver its cargo (e.g., a drug) to a target bodily tissue. For example, a relatively negatively charged nanoparticle is used to preferentially localize to, accumulate, and/or penetrate a positively-charged tissue; a relatively positively charged nanoparticle is used to preferentially localize to, accumulate, and/or penetrate a negatively-charged tissue. For example, localization of the cargo-containing nanopiece is at least 10%, 20%, 50%, 75%, 2-fold, 5-fold, 8-fold, 10-fold or more to a target tissue compared to the level of localization/delivery of the cargo in the absence of the nanoparticle. Thus, the nanopieces are selectively localized to a desired bodily tissue and deliver the cargo there.

As described herein, the system for selective drug delivery to a cell or bodily tissue may include a cargo compound. In exemplary embodiments, the cargo compound is tumor necrosis factor-alpha (TNF-α) small interfering ribonucleic acid (siRNA); e.g., TNF-α siRNA. In other exemplary embodiments, the system for selective drug delivery to a cell includes delivery to a macrophage cell.

The drug or agent delivered comprises a diagnostic reagent or a therapeutic compound. In one example, a net positive charge comprises a Zeta potential in the range of +0 mV and +60 mV (e.g., 0.1 mV, 1, 5, 10, 20, 30, 45, 60 mV); exemplary negatively charged tissues include cartilage tissue or a chondrocyte cell. In another example, a charge comprising a Zeta potential in the range of −60 mV and +30 mV (e.g., −60, −50, −40, −30, −20, −10, 1, 10, 20, 30 mV) is used to selectively or preferentially target positively charged tissues; exemplary positively charged tissues include neuronal tissue or a neuron.

Also within the invention is a system for selective drug delivery to a bodily tissue comprising a nanoparticle composition comprising a cargo compound (e.g., a drug), the composition being sized to localize or penetrate a target tissue. The nanoparticle is at least 0.1 nm in at least one dimension. For example, a size of ≤150 nm (e.g., 0.1, 10, 25, 50, 75, 100, 125, 150 nm) in at least one dimension localizes to or penetrates synovium, ocular tissue, dermatologic tissue, mucosal tissue, or pulmonary tissue, a size of ≤100 nm (e.g., 0.1, 10, 25, 50, 75, 100 nm) in at least one dimension localizes to or penetrates kidney tissue, or a size of ≤30 nm (0.1, 2, 5, 10, 20, 25, 30 nm) in at least one dimension localizes to or penetrates heart tissue. A size of ≤90 nm (0.1, 2, 5, 10, 25, 50, 75, 80, 90 nm) in at least one dimension localizes to or penetrates cartilage with inflammation or defect, and a size of ≤30 nm (0.1, 2, 5, 10, 20, 25, 30 nm) in at least one dimension localizes to or penetrates healthy, intact cartilage.

The system or method includes the treatment of joint disorders those affecting articulating joints, e.g., injury-induced osteoarthritis as well as autoimmune diseases affecting joint tissue such as rheumatoid arthritis. The compositions and methods of the invention further provide a solution to long standing challenges in the treatment of diseases and/or disorders affecting the epithelial, connective, muscles and/or nervous tissues in the body. The invention provides methods of introducing a therapeutic or diagnostic agent into a cell or tissue or tissue matrix using rosette nanotubes or components of rosette nanotubes. Embodiments of the present disclosure include the formation of a composite or complex or combination of one or more agents, such as therapeutic or diagnostic agents, and a rosette nanotube or a component of a rosette nanotube, where the one or more agents are attached to or otherwise bound to the rosette nanotube or component of a rosette nanotube. Embodiments of the present disclosure are further directed to a product made by the process of mixing together rosette nanotubes as described herein or modules forming rosette nanotubes as described herein and one or more agents in aqueous media under conditions which cause the rosette nanotubes or components of rosette nanotubes to combine with the one or more agents to form a complex or combination in aqueous media where the one or more agents are attached or otherwise bound through steric, ionic, or other forces to the rosette nanotube a component of a rosette nanotube. According to one aspect, the one or more agents are bound by noncovalent forces.

The methods described herein can be used to treat a joint disease, and exemplary joint diseases include TNF-α mediated autoimmune diseases. TNF-α mediated autoimmune diseases include, for example, rheumatoid arthritis.

The nanopiece compositions are made from nanotubes made from modules that self-assemble, e.g., compounds comprising Formula I (module I) or compounds comprising Formula II (module II). Nanotubes according to the present disclosure include compounds of Formula I, or a salt thereof, below:

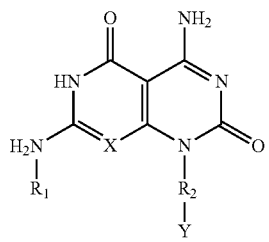

wherein X is CH or nitrogen; n is an integer of, 1, 2, 3, or 4; $R_2$ is hydrogen or a linker group for example $(CH_2)_n$ or other linker groups described herein; Y is absent when $R_2$ is hydrogen or is an amino acid or polypeptide having an amino group covalently bound to an α-carbon of the amino acid and the amino group is covalently bound to the linker group $R_2$; and $R_1$ is hydrogen or an aliphatic moiety, such as alkyl, straight or branched chain, saturated or unsaturated; and salts thereof. Preferably $R_1$ is $C_1$ to $C_{10}$ alkyl, $C_1$ to $C_5$ alkyl, $C_1$ to $C_3$ alkyl, or methyl. For example, one subset of compounds of formula (I), or a salt thereof, includes those in which X is nitrogen. In another example, one subset of compounds of formula (I) includes those in which $(CH_2)_n$ is the linker group. In another embodiment, one subset of compounds of formula (I) includes those in which $(CH_2)_n$ is the linker group and n is 2. In another example, one subset of compounds of formula (I), or a salt thereof, includes those in which Y is an amino acid selected from lysine, arginine and histidine. In another embodiment, one subset of compounds of formula (I), or a salt thereof, includes those in which X is nitrogen, $(CH_2)_n$ is the linker group, n is 2 and Y is an amino acid selected from lysine, arginine and histidine.

Compounds within the scope of the invention include those where the Y group can be connected to the linker group either by the amino group or the carboxyl group of the amino acid or polypeptide. An exemplary linker group is shown in the formula below.

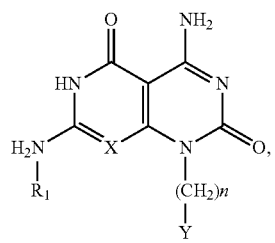

or a salt thereof.

An exemplary module within the scope of formula I is shown in FIG. 1 along with a schematic representation of a nanotube and an image of nanotubes formed from the exemplary module.

Alternative linker groups $R_2$ can join the Y group to the carbon of the $(CH_2)_n$ group or the N atom either by the amino group or the carboxyl group of the amino acid or polypeptide.

Alternative $R_2$ groups within the scope of the present disclosure are selected from a group comprising:

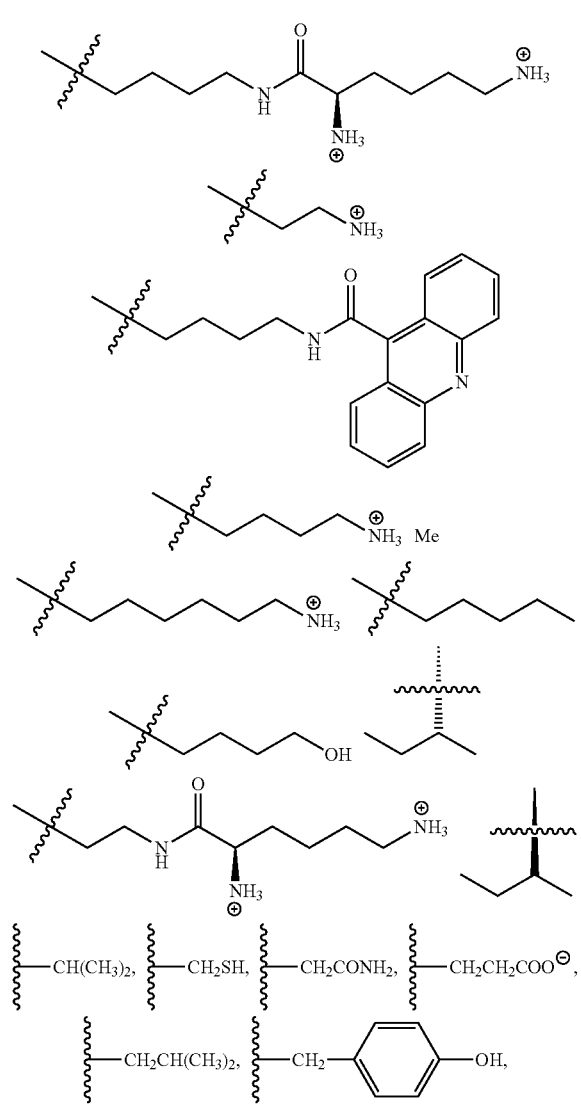

-continued

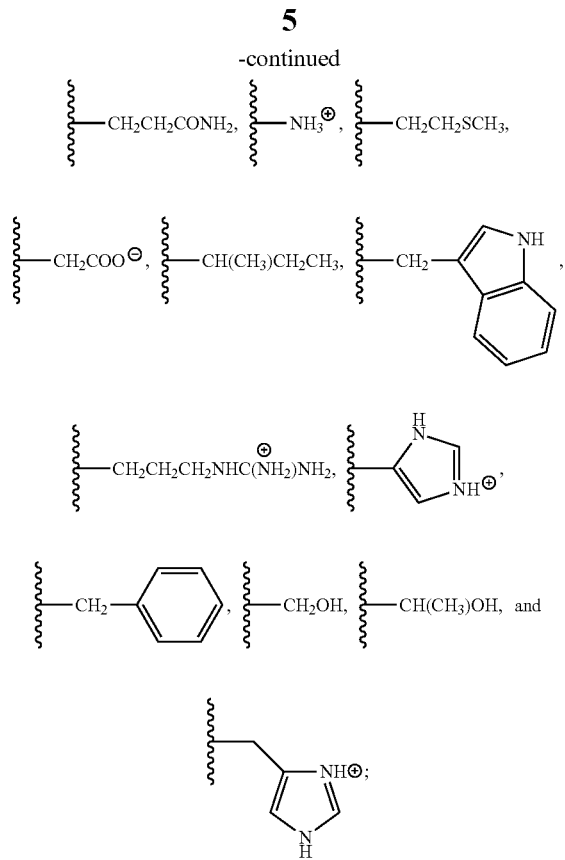

wherein Y is absent.

Compounds of Formula I can be prepared by the methods described in U.S. Pat. No. 6,696,565 hereby incorporated by reference herein in its entirety alone or combined with methods known to those of skill in the art. Additional description is provided in U.S. Pat. No. 8,795,691 and/or U.S. Patent Publication 20140171482 (U.S. Ser. No. 13/977, 138), each of which is hereby incorporated by reference. Rosette nanotubes are made by assembly of compounds of Formula (I).

Exemplary compounds of Formula I are shown below:

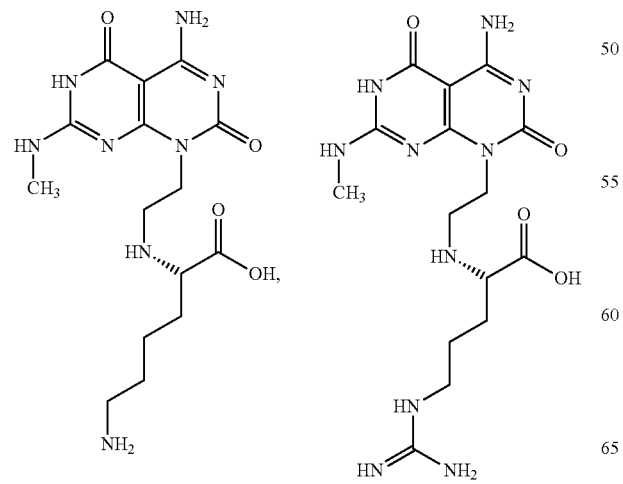

-continued

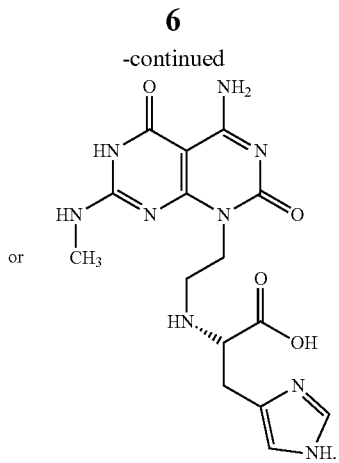

In certain embodiments, the compounds of Formula I are present in zwitterion form. The compounds are shown as below:

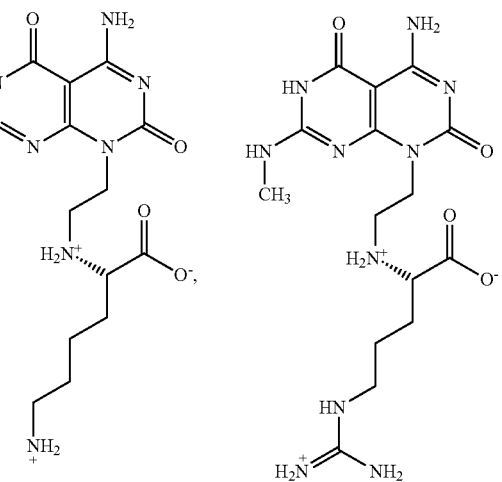

and 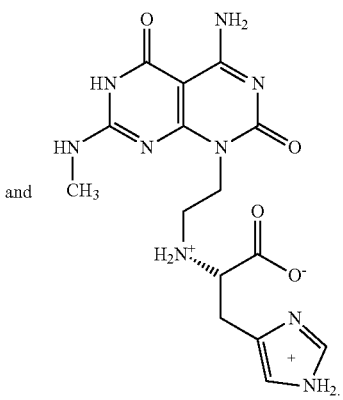

The salt forms thereof may be presented as follows:

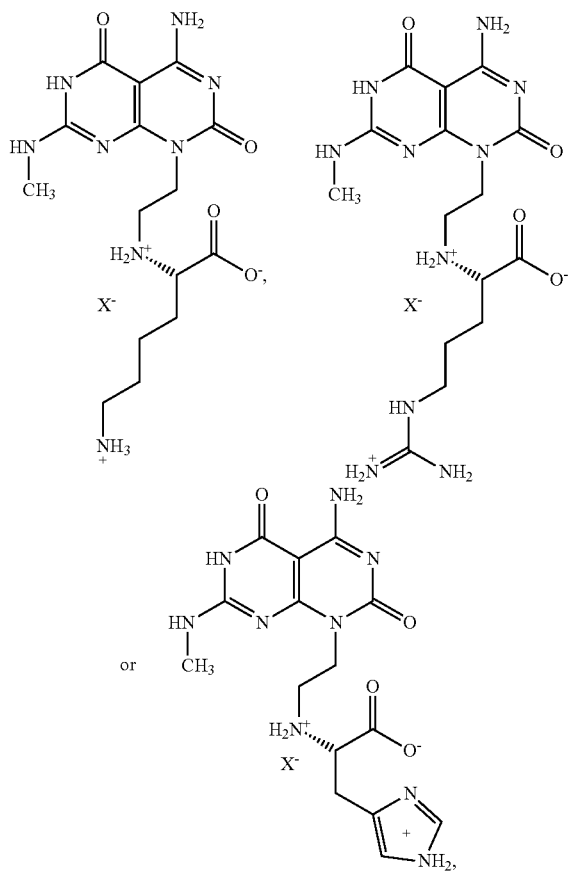

wherein X⁻ can be anion such as Cl⁻, or other anionic organic acids.

Modules according to the present disclosure also include compounds of Formula II below:

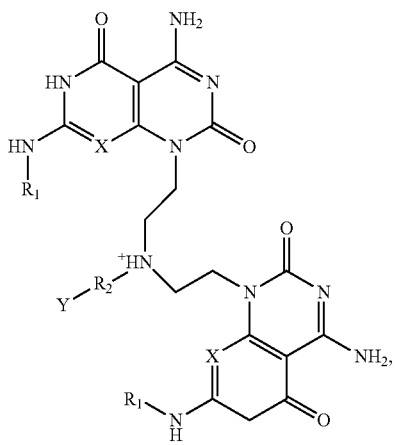

or a salt thereof.

wherein X is CH or nitrogen; $R_2$ is hydrogen or a linker group for example $(CH_2)_n$ where n is an integer of, 1, 2, 3, or 4 or $(CH_2)_3CO$ other linker groups described herein; Y is absent when $R_2$ is hydrogen or is an amino acid or polypeptide having an amino group covalently bound to an α-carbon of the amino acid and the amino group is covalently bound to the linker group $R_2$; and $R_1$ is hydrogen or an aliphatic moiety, such alkyl, straight or branched chain, saturated or unsaturated; and salts thereof. For example, one subset of compounds of formula (II) includes those in which X is nitrogen. In another example, one subset of compounds of formula (II) includes those in which $(CH_2)_n$ is the linker group. In another embodiment, one subset of compounds of formula (II) includes those in which $(CH_2)_n$ is the linker group and n is 2. In another example, one subset of compounds of formula (II) includes those in which Y is an amino acid selected from lysine, arginine and histidine. In another embodiment, one subset of compounds of formula (II) includes those in which X is nitrogen, $(CH_2)_n$ is the linker group, n is 2 and Y is an amino acid selected from lysine, arginine and histidine.

Preferably $R_1$ is $C_1$ to $C_{10}$ alkyl, $C_1$ to $C_5$ alkyl, $C_1$ to $C_3$ alkyl, or methyl. An exemplary linker group is shown in the formula below.

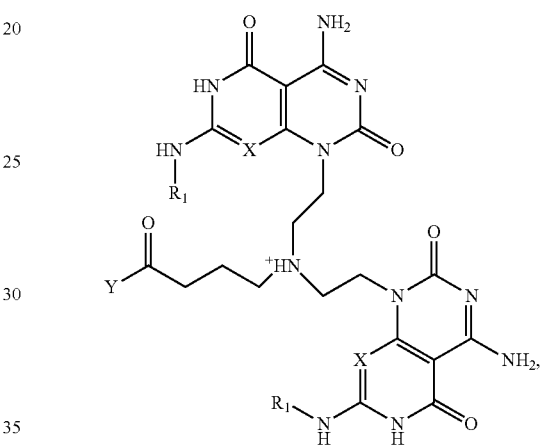

or a salt thereof.

Compounds within the scope of the present disclosure include those where the Y group can be connected to the linker group either by the amino group or the carboxyl group of the amino acid or polypeptide. Alternative $R_2$ groups within the scope of the present disclosure are selected from a group comprising:

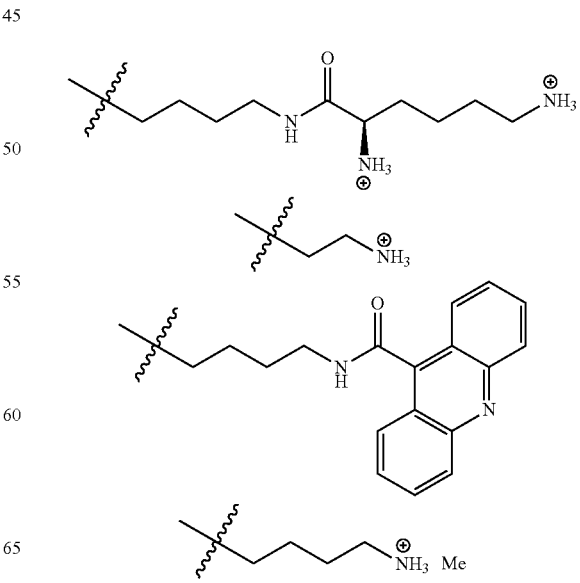

-continued
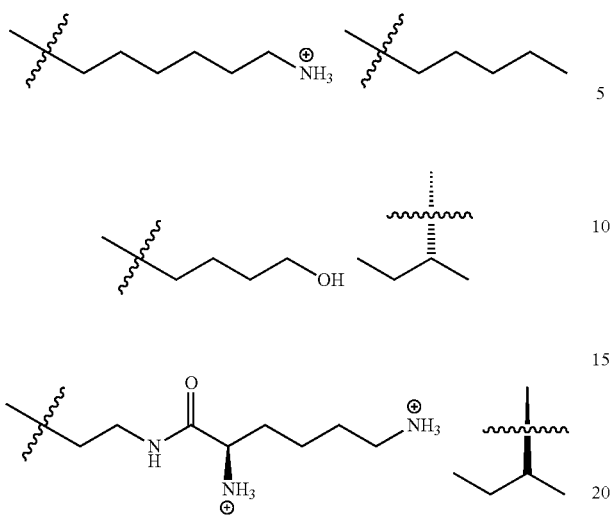
wherein Y is absent. TBL structures are made by the assembly of compounds of Formula (II).
Exemplary compounds of Formula II are shown below:
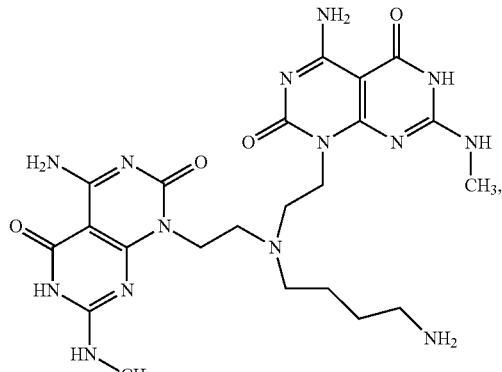
Lysine Functional Group Construct
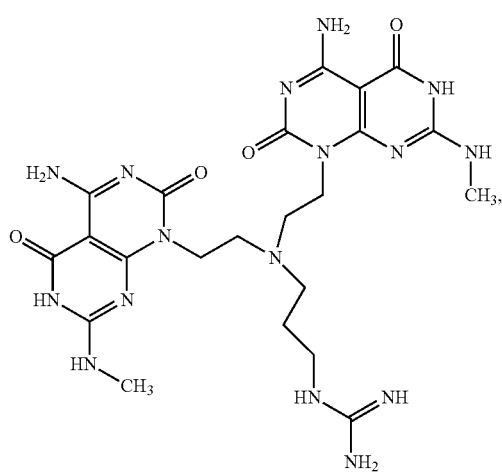
Arginine Functional Group Construct
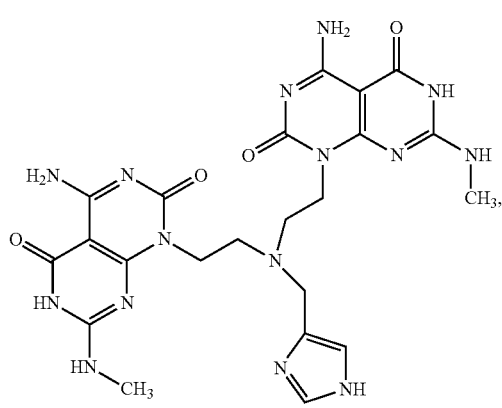
Histidine Functional Group Construct

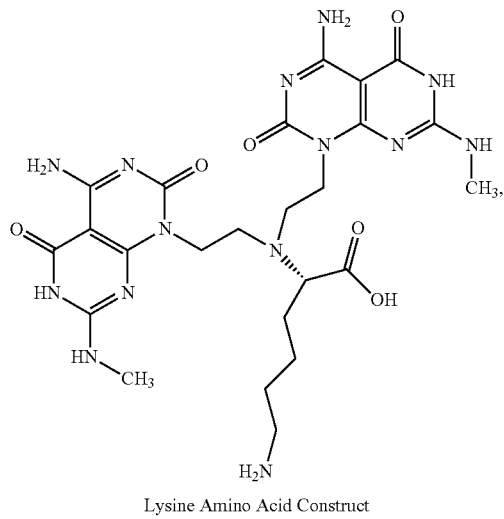

Lysine Amino Acid Construct

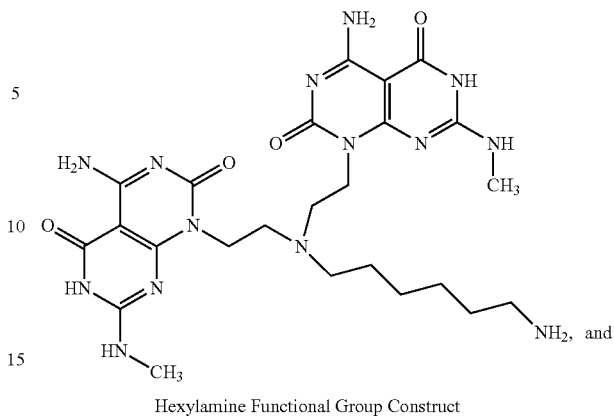

Hexylamine Functional Group Construct

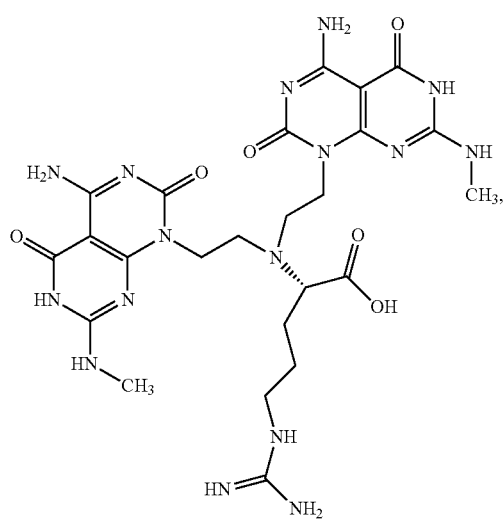

Arginine Amino Acid Construct

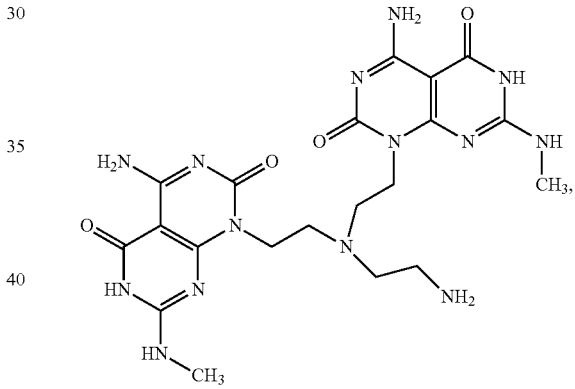

Ethylamine Functional Group Construct

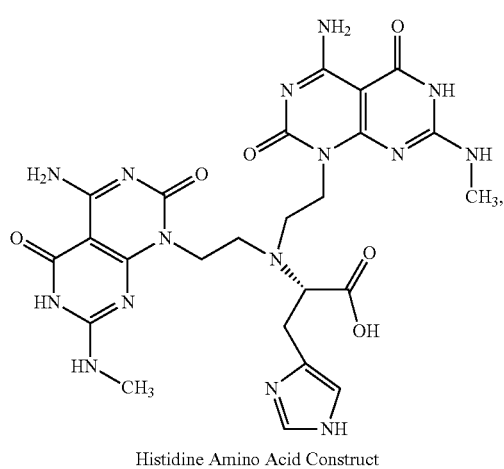

Histidine Amino Acid Construct or a salt thereof.

In some embodiments, compounds of formula II comprise amino acid functional group constructs. These compounds contain functional groups present in natural occurring amino acid side chains or may contain the entire amino acid side chain. For example, the lysine functional group constructs contains the entire amino acid side chain functionality ($-CH_2CH_2CH_2CH_2NH_3^+$), whereas the histidine functional group constructs contains the entire side chain or only contains the heteroaryl imidazole group present in histidine.

In some embodiments, compounds of formula II comprise amino acid constructs. These compounds contain the entire the amino acid or may contain modified and/or unnatural amino acids. For example, the lysine amino acid analog contains the entire amino acid functionality of lysine, whereas the histidine amino acid constructs contains a modified histidine amino acid.

In some embodiments the compound of formula II is the Lysine Functional Group Construct

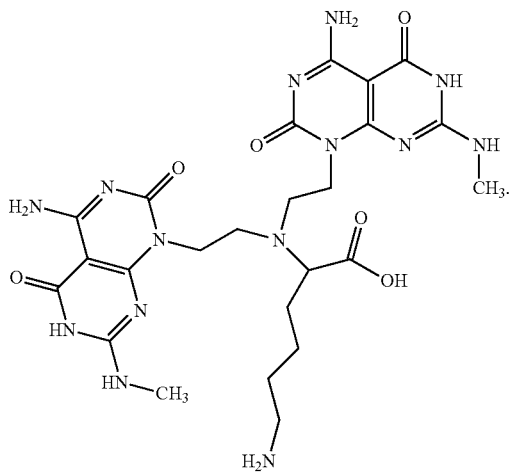 [SMILES: CNc1nc2c(c(N)nc(=O)n2CCN(CCn2c(=O)nc(N)c3c(=O)[nH]c(NC)nc32)C(CCCCN)C(=O)O)c(=O)[nH]1]

In some embodiments, the nanoparticles are constructed from lipid and/or polymeric components.

A three-dimensional representation of such modules is shown in FIG. 65. Embodiments further include delivering the composite into living cells. Embodiments further include a method of treating an individual requiring treatment comprising administering a complex of a rosette nanotube or a component of a rosette nanotube and one or more therapeutic agents to the individual in a manner to introduce the complex into cells or tissues of the individual. Embodiments further include a method of diagnosing an individual requiring diagnosis comprising administering a complex of a rosette nanotube or a component of a rosette nanotube and one or more diagnostic agents to the individual in a manner to introduce the complex into cells or tissues of the individual.

Rosette nanotubes or RNTs include nanotubes formed from modules having twin bases with a linker or TBL. Such rosette nanotubes may be referred to herein as "TBLs." According to this aspect, the agent is delivered into the cell. According to one aspect, the agent is released from the rosette nanotube after entry into the cell. According to an additional aspect, the agent remains attached to, bound to, or complexed with or combined with the rosette nanotube or component of a rosette nanotube.

Lipid nanoparticles comprise a lipid core and surfactant, in which the lipid core may include fatty acids, acrylglycerols, steroids, waxes, and mixtures of all above; and surfactants may contain a positively charged amino group, negatively charged phosphate or carboxylic acid. According to one aspect, a complex is produced by combining modules of a self-assembled rosette nanotube and one or more agents in media where the modules self-assemble into a rosette nanotube or components of a rosette nanotube which incorporates the one or more agents to form a complex of a rosette nanotube or component of a rosette nanotube and the one or more agents. According to an additional aspect, a complex is produced by combining a self-assembled rosette nanotube and one or more agents in media whereupon the one or more agents are incorporated into the rosette nanotube to form a complex of a rosette nanotube and one or more agents. The complex may then be contacted to cells whereupon the complex enters the cells. Without wishing to be bound by scientific theory, it is believes that the complex may enter cells by endocytosis. According to certain embodiments, the cells may be transformed cells, recombinant cells, malignant cells, or cells from primary cell lines. The transfection method may be performed on cells in vitro or in vivo.

The modules may be any of those known to persons of ordinary skill in the art such as G/\C motifs and A/\T motifs, unmodified or modified to include moieties or side chains, which self-assemble into helical rosette nanotubes. According to one embodiment, modules are placed into an aqueous medium where they self-assemble into a substructure such as a ring structure, such as a rosette, and the ring structures then self-assemble by stacking one on top of another to form a tubular structure, commonly referred to as a nanotube. Such modules, substructures and nanometer scale molecular structures and their self-assembly is described in U.S. Pat. No. 6,696,565, Fenniri et al, *J. Am. Chem. Soc.* 2001, 123, 3854-3855, Moralez et al., *J. Am. Chem. Soc.*, 2005, 127, 8307-8309, Fine et al., *International Journal of Nanomedicine* 2009:4 91-97; and Zhang et al., *Biomaterials* 2009; 30(7):1309-1320 each of which are hereby incorporated by reference in their entireties for all purposes.

Rosette nanotubes of the present disclosure are very stable in water and lack virus-related safety concerns and toxicity at amounts of about 1 μg/ml. See *Int. J. Nanomedicine*, 2008, 3(3):373-383; *Small.* 2008, 4(6):817-823; and *Am. J. Physiol Lung Cell Mol. Physiol.* 2005, November, 289(5): L698-708 each of which are hereby incorporated by reference in their entireties.

According to one aspect of the present disclosure, methods are provided where the self-assembly of precursors or modules incorporates the agent into or otherwise complexes the agent with, the self-assembled rosette nanotube or components of the rosette nanotube. According to another aspect, fully assembled rosette nanotubes can be incubated with one or more or a plurality of agents and the one or more or plurality of agents can complex with the fully assembled rosette nanotube to form a composite. According to one further aspect, the one or more or plurality of agents are joined to or bound to the self-assembled rosette nanotube through steric, ionic, van der Waals, dispersion or other noncovalent interactions to form a rosette nanotube or component of a rosette nanotube and agent complex useful as a complex to be administered to an individual. In another aspect of the invention, the agents comprise a therapeutic agent such as nucleic acid, peptide or small molecule. In an aspect of the invention, the therapeutic agent comprises a nucleic acid, wherein the nucleic acid comprises siRNA. In other aspects, the nucleic acid comprises TNF-α siRNA. In another embodiment, the nucleic acid comprises the sequence comprising of: AAG CCT GTA GCC CAC GTC GTA (SEQ ID NO: 229) and GGC ACC ACT AGT TGG TTG TCT TTG-3' (SEQ ID NO: 230). In a further aspect of the invention, the therapeutic agent comprises an IL-1 receptor antagonist. In yet a further aspect of the invention, the agent comprises a diagnostic agent such as a molecular probe or a molecular beacon. For example, the molecular beacon or probe comprises MMP-13 or ADAMTS-5.

According to certain aspects of the invention, a method for treating joint disease comprises administration of an effective amount of a composition containing a nanotube rosette-agent complex. Such a method of diagnosing joint disease comprises administration of an effective amount of a composition containing a nanotube rosette-agent complex. Another aspect of the invention comprises joint disease such as autoimmune, degenerative, inflammatory, infectious, cancerous, viral, fungal, injured, trauma, genetic, trauma, mechanical, nutritional or mal-alignment derived. Another embodiment of the invention describes joint disease comprising rheumatoid arthritis, osteoarthritis, juvenile onset of rheumatoid arthritis (JRA), psoriatic arthritis, reactive arthritis, septic arthritis, tendinitis, or herniation. Therapeutic agents are used to treat joint disease, e.g., such agents include analgesic agents, anti-inflammatory agents, immunosuppresive agents, antifungal agents, antibiotic agents, lubricants, anti-cancer agents, NMDA receptor antagonists, or antiviral agents.

According to certain aspects of the invention, a method for treating tissue and/or organ disease comprises administration of an effective amount of a composition containing a nanotube rosette-agent complex. Such a method of diagnosing tissue and/or organ disease comprises administration of an effective amount of a composition containing a nanotube rosette-agent complex. Another aspect of the invention comprises a tissue and/or organ disease such as autoimmune, degenerative, inflammatory, infectious, cancerous, viral, fungal, injured, trauma, genetic, trauma, mechanical, nutritional or mal-alignment derived. Another embodiment of the invention describes tissue and/or muscle disease comprising the eye, skin, brain, spine, intestine, kidney, liver, and stomach. Another aspect of the invention describes therapeutic agents to treat joint, tissue and/or organ disease, e.g., agents include analgesic agents, anti-inflammatory agents, immunosuppresive agents, antifungal agents, antibiotic agents, lubricants, anti-cancer agents, NMDA receptor antagonists, or antiviral agents.

According to certain aspects, rosette nanotubes are functionalized with a nucleic acid, such as DNA or small RNA to form a complex, for example RNA is bound to the rosette nanotube, the complex is translocated into a cell or tissue, and the intracellular small RNA (e.g., siRNA) is present within the cell in an amount sufficient for gene silencing resulting in the inhibition of the production of target proteins. In this aspect, the rosette nanotube is a delivery vehicle or carrier for the small RNA into a cell for RNA interference purposes. Alternatively, the nucleic acid can be expressed by the cell. For example, the cell comprises synoviocytes or chondrocytes. Alternatively, the target tissue is cartilage. According to certain aspects, methods and technologies are provided to process and assemble rosette nanotubes (RNTs) for cargo delivery for diagnostic and therapeutic purpose. Methods are directed to achieve inter-/intra-cellular delivery in vitro and in vivo. According to certain aspects, a complex of rosette nanotubes (RNTs) and cargo agents are prepared. The cargo agents include diagnostic molecules, for instance, oligomer based molecular beacons; or therapeutic molecules such as nucleic acid, peptide, or small molecules. Such diagnostic agents and therapeutic agents are well known to those of skill in the art. Such incorporation between RNTs and the cargo reagent are facilitated by electrostatic force, π-π interactions or hydrophilic/hydrophobic effects to form relatively stable entities, which are referred to herein as "Nanopieces". According to certain aspects, methods are provided to make rosette nanotubes of certain size (with or without an agent (e.g., cargo composition) that are suitable for trans-matrix e.g., extracellular matrix, tissue delivery. For example, methods are provided for altering at least one dimension or other parameter of Nanopieces such as width to infiltrate the pore size of the target tissue matrix. In an aspect of the invention, the rosette nanotubes are functionalized with a nucleic acid (e.g., an siRNA), and in particular embodiments, TNF-α siRNA. In embodiments, the nucleic acid comprises the sequence comprising of: AAG CCT GTA GCC CAC GTC GTA (SEQ ID NO: 229) and GGC ACC ACT AGT TGG TTG TCT TTG-3' (SEQ ID NO: 230).

In other examples, the methods for treating a joint disease described herein can include administering an effective amount of a rosette nanopiece, and the nanopiece can include a TNF-α siRNA. As provided herein, the nanopiece for trading a joint disease can enter the macrophage of a cell. In other exemplary embodiments, the nanopiece can be administered systemically.

According to certain aspects, methods and technologies are provided to process and assemble rosette nanotubes (RNTs) for cargo delivery for diagnostic and therapeutic purpose. Methods are directed to achieve inter-/intra-cellular delivery in vitro and in vivo. According to certain aspects, a complex of rosette nanotubes (RNTs) and cargo agents are prepared. The cargo agents include diagnostic molecules, for instance, oligomer based molecular beacons; or therapeutic molecules such as nucleic acid, peptide, or small molecules. In an aspect of the invention, the therapeutic agent comprises a nucleic acid, wherein the nucleic acid comprises siRNA. In other aspects, the nucleic acid comprises TNF-α siRNA. In another embodiment, the nucleic acid comprises the sequence comprising of: AAG CCT GTA GCC CAC GTC GTA (SEQ ID NO: 229) and GGC ACC ACT AGT TGG TTG TCT TTG-3' (SEQ ID NO: 230). Such diagnostic agents and therapeutic agents are well known to those of skill in the art. Such incorporation between RNTs and the cargo reagent are facilitated by electrostatic force, π-π interactions or hydrophilic/hydrophobic effects to form relatively stable entities, which are referred to herein as "Nanopieces". According to certain aspects, methods are provided to make rosette nanotubes of certain size with or without an agent that are suitable for trans-matrix tissue delivery. For example, methods are provided for altering at least one dimension parameter of Nanopieces such as width to infiltrate the pore size of the target tissue matrix.

According to certain aspects, methods are provided for making rosette nanotubes of certain lengths and size parameters such as 1) before assembly, controlling the length and bundle of RNTs via changing physical and/or chemical conditions such as temperature, molecule motion/vibration (like sonication) and pH; 2) during assembly, adjusting assembly conditions via changing physical and/or chemical conditions including concentrations, pH and ionic strength to enhance/reduce the formation and stacking of Nanopieces; 3) after assembly, breaking long or stacked Nanopieces by via changing physical and/or chemical conditions including enhancing molecule motion/vibration (like sonication).

According to certain aspects, methods are provided for trans-matrix/tissue delivery or a complex of a rosette nanotube or component or piece thereof by controlling the ratio between RNTs and cargo reagents so that the forming Nanopieces present surface charges that are suitable for attraction, localization, penetration, or retention in the tissue or one or more cells of the tissue. For example, since many tissues or cells contain negatively charged molecules (like proteoglycan), positively charged RNT can be fabricated and used to assemble with negatively charged nucleic acid cargo in certain ratios, resulting in a positive charged Nanopiece for delivery. In this manner, Nanopieces localize to, bind to, and accumulate onto/into the matrix/tissue resulting in much longer retention time to achieve more effective delivery. Therefore, the highly effective and versatile trans-matrix/tissue delivery was achieved by processed Nanopieces. The term "Nanopiece" may be used herein to refer to rosette nanotubes which may be processed into certain dimensions or components of rosette nanotubes.

According to certain aspects, methods are provided for the use of rosette nanotubes or Nanopieces for diagnostic applications insofar as molecular probes can be delivered via Nanopieces to detect a specific gene expression (or protein activity). By co-delivery of a negative control for non-specific signal and an internal positive control, a target gene expression can be accurately diagnosed in a real-time, in-situ and non-invasive manner.

According to certain aspects, therapeutic applications are envisioned, such as knocking down one or multiple disease gene expression (such as via siRNA, miRNA or anti-sense delivery), e.g., inhibiting the expression of one or more genes or gene products associated with aberrantly high expression in a disease state compared to a normal state up-regulating one or multiple beneficial gene/protein (such as via DNA, mRNA or protein delivery); or through a combination of both.

According to certain aspects, methods are provided for making rosette nanotubes of certain lengths and size parameters such as 1) before assembly, controlling the length and bundle of RNTs via changing physical and/or chemical conditions such as temperature, molecule motion/vibration (like sonication) and pH; 2) during assembly, adjusting assembly conditions via changing physical and/or chemical conditions including concentrations, pH and ionic strength to enhance/reduce the formation and stacking of Nanopieces; 3) after assembly, breaking long or stacked Nanopieces by via changing physical and/or chemical conditions including enhancing molecule motion/vibration (like sonication).

According to certain aspects, method are provided for trans-matrix/tissue delivery or a complex of a rosette nanotube or component or piece thereof by controlling the ratio between RNTs and cargo reagents so that the forming Nanopieces present surface charges that are suitable for retention in the tissue. For example, since many tissues or cells contain negatively charged molecules (like proteoglycan), positively charged RNT can be used to assemble with negatively charged nucleic acid cargo in certain ratios, resulting in a positive charged Nanopiece for delivery (see Table 1). In this manner, Nanopieces associate with, bind to and/or accumulate onto/into the matrix/tissue resulting in much longer retention time to achieve more effective delivery. Therefore, the highly effective and versatile trans-matrix/tissue delivery was achieved by processed Nanopieces.

According to certain aspects, methods are provided for the use of rosette nanotubes or Nanopieces for diagnostic applications insofar as molecular probes can be delivered via Nanopieces to detect a specific gene expression (or protein activity). By co-delivery of a negative control for non-specific signal and an internal positive control, a target gene expression can be accurately diagnosed in a real-time, in-situ and non-invasive manner.

According to certain aspects, therapeutic applications are envisioned, such as knocking down one or multiple disease gene expression (such as via siRNA delivery); up-regulating one or multiple beneficial gene/protein (such as via DNA, mRNA or protein delivery); or through a combination of both.

According to certain aspects, depending on the processing conditions, different sizes of rosette nanotubes, e. g. Nanopieces can be created for different delivery proposes, such as to enter a cellular or tissue matrix. For example, cartilage tissue matrix has about 60 nm mesh size of the collagen II fibrillar network (Comper et al in *Cartilage*: Molecular Aspects (eds Hall, B. & Newman, S.) 59-96 (CRC Press, Boston, 1991)) and about 20 nm spacing between the side chains of the proteoglycan network (Torzilli et al *J. Biomech*. 30, 895-902 (1997)). Nanopieces with small sizes (at least one dimension smaller than 60 nm and/or 20 nm) showed excellent efficiency and function in intra-cartilage matrix delivery of siRNA. Secondly, through adjusting the ratio between RNTs and cargo reagents, overall positive charged surface enabled Nanopieces to adhere with negatively charged matrix/tissue components resulting longer retention time. Thirdly, Nanopieces can deliver a variety of cargo types and can deliver multiple cargo reagents at the same time. Fourthly, using non-covalent or covalent coating on Nanopieces can achieve a longer stability in the systemic circulation and penetrate into the targeted tissue matrix and/or organ more efficiently. Lastly, processed Nanopieces demonstrated successful delivery under conditions: in vitro, ex vivo and in vivo. Therefore, methods are provided for the use of Nanopieces for trans-matrix/tissue delivery.

According to certain aspects, complexes of rosette nanotubes or components of nanotubes or Nanopieces and agents can be used for research purposes as well as used for an effective delivery agent (especially in vivo) for molecular diagnosis and therapeutics. According to certain aspects, complexes of rosette nanotubes or components of nanotubes or Nanopieces and agents can be used for therapeutic purposes for treating various diseases, such as by delivery of interleukin-1 receptor antagonist (IL-1Ra), the natural protein inhibitor of IL-1, to modulate IL-1-based inflammation as a therapy for arthritis. For example, the cargo comprises IL-1R SiRNA. Complexes of rosette nanotubes or components of nanotubes or Nanopieces and agents can be used to deliver siRNA to knockdown the disease protein to achieve effective treatment.

According to certain aspects, complexes of rosette nanotubes or components of nanotubes or Nanopieces and agents can be used for diagnostics, such as by delivery of molecular probes or molecular beacons. Methods are provided to deliver molecular beacons into chondrocytes inside cartilage matrix as well as tissues and/or organs such as heart, stomach, kidney, liver, lung, spleen, brain, intestine, spine, rib cage, and limb. With co-delivery of multiple molecular beacons to detect disease gene expression as target, non-specific signal as negative control and house-keeping gene as internal positive control, target gene expression level can be quantified in a real-time, in-situ and non-invasive manner.

Embodiments of the present disclosure are directed to complexes of a self-assembled rosette nanotube and one or more or a plurality of agents. Such agents include biologically active agents and/or diagnostic agents. The complexes are administered to an individual where the biologically active agent and/or diagnostic agent are delivered to a site within the individual, including into the cell of an individual, and are made available for therapeutic or diagnostic purposes. According to one aspect, the agent dissociates from the rosette nanotube to treat an individual or to provide a diagnostic capability. According to an additional aspect, the agent remains attached to, bound to, or complexed with or combined with the rosette nanotube.

According to one aspect, a delivery complex is produced by combining modules of a self-assembled rosette nanotube and one or more agents, such as therapeutic or diagnostic agents, in media where the modules self-assemble into a rosette nanotube which incorporates the one or more agents to form a complex of a rosette nanotube and the one or more agents. According to an additional aspect, a delivery complex is produced by combining a self-assembled rosette nanotube and one or more agents, such as therapeutic or diagnostic agents, in media whereupon the one or more agents are incorporated into the rosette nanotube to form a complex of a rosette nanotube and one or more agents. The delivery complex may then be administered to an individual for therapeutic or diagnostic purposes. It is a further object of the present invention to create complexes of agents rosette nanotubes or components of rosette nanotubes that can be delivered into target cells and intracellular matrices where the agent can function. It is a further object of the present invention to provide methods of treating individuals using a delivery system of a complex of rosette nanotubes or components of rosette nanotubes and agents, where the agent enters the cell. These and other objects, features, and advantages of the invention or certain embodiments of the invention will be apparent to those skilled in the art from the following disclosure and description of exemplary embodiments.

It is a further object of the present invention to create complexes of agents rosette nanotubes or components of rosette nanotubes that can be delivered into target cells and intracellular matrices where the agent can function. It is a further object of the present invention to provide methods of treating individuals using a delivery system of a complex of rosette nanotubes or components of rosette nanotubes and agents, where the agent enters the cell. Thus, the invention encompasses a composition comprising a cargo molecule and a nanostructure comprising Formula I or Formula II for selective, e.g., preferential, delivery of a therapeutic drug or diagnostic agent to a target bodily tissue. Alternatively, the non-structure comprises a lipid or a polymer rather than a compound or Formula I or II.

In further examples, provided herein is a system for selective drug delivery to a bodily tissue. The system includes, for example a rosette nanopiece composition comprising a cargo compound. In further embodiments, the composition can sized to localize or penetrate a cell or target tissue. In other embodiments, a size of <100 nm in at least one dimension localizes or penetrates a phagocytic cell, synovium, ocular tissue, dermatologic tissue, mucosal tissue, or pulmonary tissue; a size of <90 nm in at least one dimension localizes or penetrates cartilage with inflammation or defect; a size of <50 nm in at least one dimension localizes or penetrates kidney tissue; a size of <30 nm in at least one dimension localizes or penetrates healthy, intact cartilage; or a size of <20 nm in at least one dimension localizes or penetrates heart tissue. In embodiments, as described herein, the phagocytic cell includes a macrophage.

Methods for treating a joint disease are also provided, wherein the method includes administering a composition comprising a nanopiece and a nucleic acid. In embodiments, the nanopiece includes a compound of Formula I or Formula II, or a salt thereof, or a combination thereof, and ii) a nucleic acid. In examples, the joint disease includes a TNF-α mediated autoimmune disease, e.g., rheumatoid arthritis. In other embodiments, the nanopiece for treating a joint disease enters a macrophage cell.

The methods and compositions for treating a joint disease include administering a composition including a nanopiece and a nucleic acid. In some examples, the nucleic acid comprises siRNA. In further embodiments, the siRNA is TNF-α siRNA, and the nucleic acid sequence of the TNF-α siRNA is AAG CCT GTA GCC CAC GTC GTA (SEQ ID NO: 229) and GGC ACC ACT AGT TGG TTG TCT TTG (SEQ ID NO: 230). In other embodiments, the nucleic acid is TNF-α. The joint disease can include rheumatoid arthritis or a cancer in the joint. The cancer can include sarcoma, hemangiopericytoma, connective tissue neoplasm, chondroma, or chondrosarcoma. In other examples, the nucleic acid is anti-miR-181a, and the anti-miR-181a nucleic acid sequence is SEQ ID NO: 228 or SEQ ID NO: 229.

Also provided and described herein are compositions for selective delivery of a therapeutic drug or diagnostic agent to a target cell or a bodily tissue. The composition can include a cargo molecule and a nanostructure comprising Formula I or Formula II, or a salt thereof. In other embodiments, the composition for selective drug delivery can further include a nucleic acid molecule (e.g., an siRNA). In exemplary embodiments, the siRNA is TNF-α siRNA, e.g., with the sequence comprising of: AAG CCT GTA GCC CAC GTC GTA (SEQ ID NO: 229) and GGC ACC ACT AGT TGG TTG TCT TTG (SEQ ID NO: 230). In other embodiments, the compositions can target a cell, e.g., a phagocytic cell. In further examples, the phagocytic cell includes a macrophage.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 13 is a series of images showing fluorescence labeled siRNA/RNT Nanopieces were delivered into porcine cartilage (Right) compared with controls (siRNA only).

FIG. 14 is a series of images showing effective delivery of processed GAPDH molecular beacon/RNT Nanopieces into mouse cartilage tissue matrix and inside chondrocytes.

FIG. 15 is a series of images showing effective delivery of processed GAPDH molecular beacon/RNT Nanopieces into human cartilage tissue matrix and inside chondrocytes.

FIG. 16 is a series of images showing effective delivery of processed GAPDH molecular beacon/RNT Nanopieces into chicken cartilage tissue matrix and inside chondrocytes.

FIG. 34 is a series of images showing histology (medium grey staining is proteoglycan) and immunohistochemistry (dark grey staining is epitope from aggrecan cleavage) of mouse knee joints. ADAMTS-5 siRNA/Nanopiece greatly inhibited cartilage degeneration and Aggrecan cleavage with cytokine stimulation.

FIG. 40 is a series of images showing GAPDH and ADAMTS-5 molecular beacon delivered by Nanopieces into chondrocytes without stimulation.

FIG. 46 is a series of images showing immunohistochemistry results (staining is epitope from aggrecan cleavage) of mouse knee joints. ADAMTS-5 siRNA/Nanopieces greatly inhibited Aggrecan cleavage after DMM surgery.

FIG. 53 is flow design of self-assembly, processing-1, processing-2 to yield nanopieces.

FIG. 54 is a graph showing MMP expression increase 4 days after surgery.

FIG. 55 is a graph showing MMP-expression increase 11 days after surgery.

FIG. 62 is an image showing the decreased liver capture with small Nanopieces compared with lipid vehicles.

FIG. 71 is a schematic showing a Nanopiece™ (NP) delivery platform.

FIG. 73 is a schematic showing a Nanopiece™ assembly and processing.

FIG. 77 is a schematic showing problems and solutions associated with the clinical indication of post-traumatic joint injury (PTJI).

FIG. 79 is a schematic showing in vivo localized delivery for PTJI.

FIG. 81 is a brief description of chondrosarcoma and clinical needs.

FIG. 82 is a schematic showing in vivo data pertaining to inhibition of tumor growth and metastasis.

FIG. 83 is a brief description of rheumatoid arthritis (RA).

FIG. 87 is a description of siRNA administration using NPs.

FIG. 88 is a schematic showing nucleic acid delivery advantages using Nanopiece™.

FIG. 89A is an image of the design of JBaK nanotube and formation of NP Rosette Nanotube. FIG. 89B is an image of the Nanopiece (side and top view). FIG. 89C are images of Nanopieces in TEM; TEM=Transmission electron microscopy.

FIG. 90A are a series of graphs showing TNF-α mRNA expression of each group in PECs from the abdominal cavity (a—far left graph), knee joints (b—middle graph) and hind paws (c—far right graph) after twice injection of siRNA/NPs. In the mice with siTNF, the TNF-α mRNA expression was significantly knocked down. FIG. 90B is a graph showing the serum TNF-α levels of each group at 8 week. Serum TNF-α levels between siTNF and scrRNA mice were not significantly different. PECs: Peritoneal exudate cell macrophages, scrRNA: non-target siRNA, siTNF: TNF-α siRNA, CIA: collagen induced arthritis, $*p<0.05$, $\#p<0.005$.

FIG. 91A is a graph showing the total arthritis score (n=6, each) of each treatment group of CIA mice with each treatment. $*p<0.05$, scrRNA: non-target siRNA, siTNF: TNF-α siRNA, CIA: collagen induced arthritis. FIG. 91B is a graph depicting the mechanical pain threshold of each treatment group of CIA mice with each treatment. $*p<0.05$, scrRNA: non-target siRNA, siTNF: TNF-α siRNA, CIA: collagen induced arthritis.

FIG. 92A-92D are a series of representative X-ray and 3D μCT images of CIA mice with each treatment. FIGS. 92A and 92 B are X-ray and 3D μCT images of the hind paw. FIGS. 92C and 92B are X-ray and 3D μCT images of the knee joint. In scRNA groups, there were multiple erosions at metatarsal joints and sever tarsal bone destruction. There were also many erosions on the surface of knee joints from mice with scrRNA treatment. CIA: collagen induced arthritis, siTNF: TNF-α siRNA, scrRNA: non-target siRNA

DETAILED DESCRIPTION

Figure 1:
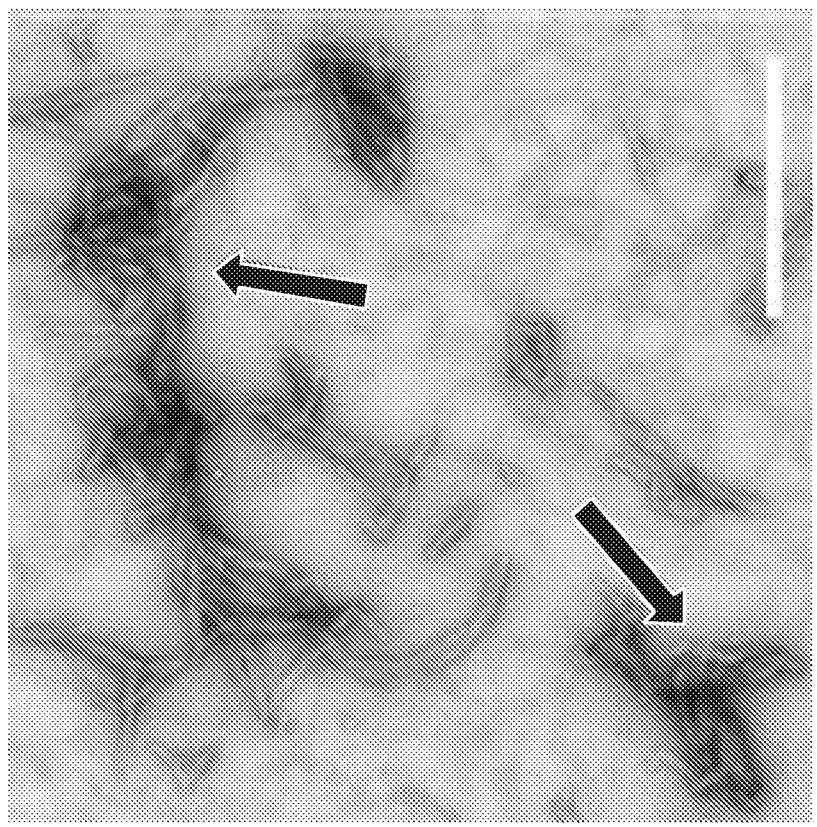
FIG. 1 is an illustration showing an assembly between RNTs with siRNA.

The compositions and methods of the invention provide compositions and methods for preferential targeting of tissues to delivery therapeutic agents. The structures, e.g., nanopieces, are constructed to comprise a charge and/or size such that the structures preferentially associate with or bind to specific bodily tissues. For example, the invention provides methods for the delivery of Nanopieces and their cargo to target cells, tissues, or organs.

Nanopieces for Treatment of Autoimmune Disease

TNF-α is a proinflammatory cytokine that is elevated in certain autoimmune diseases or disorders. Pathological deregulation characterizes those autoimmune diseases. TNF-α-mediated disease include rheumatoid arthritis, a debilitating autoimmune joint disease that is distinguished from osteoarthritis (which is not characterized as an autoimmune disease). Anti-TNF therapy has been used as a treatment for immune-inflammatory diseases, such as rheumatoid arthritis, juvenile RA, ankylosing spondylitis, psoriatic arthritis, Crohn's disease, ulcerative colitis, and psoriasis. These existing therapies use an anti-TNF-α antibody that neutralizes TNF-α function. In contrast, NP/TNF-α-siRNA described herein blocks the synthesis of TNF-α. The NP-mediated delivery system for TNF-α siRNA is associated with numerous important advantages including deep penetration into extracellular matrix-rich joint synovium and bone tissues that harbor macrophages, high efficiency in knocking down TNF-α synthesis, and low systemic toxicity.

In contrast to treatment for osteoarthritis, NP-mediated delivery for treatment of rheumatoid arthritis is carried out by systemic administration. Preferably, the treatment does not comprises local administration to a joint or joint space, e.g., does not comprise intra-articular administration. In contrast to treatment of osteoarthritis that targets joint cells such as chondrocytes, synovial cells, bone cells, joint capsule cells, and/or ligament cells, NP-mediated treatment for rheumatoid arthritis targets phagocytic cells such as macrophages, e.g., negatively-charged macrophages. Macrophages may be identified by one or more of the following markers: CD14, CD16, CD64, CD68, CD71, CCR5, CD11b, CD68, and/or CD163.

The rheumatoid arthritis (or other TNF-α-mediated autoimmune disease) therapy described herein targets and affects macrophages, i.e., the cells that produce TNF-α (which is the underlying defect of the pathology). The level of TNF-α production is therefore reduced or knocked down by the NP-mediated delivery of TNF-α siRNA to circulating macrophages or tissue-associated macrophages throughout the body. NP-mediated treatment for rheumatoid arthritis is preferably carried out by intravenous injection or infusion for treatment of numerous locations/tissues in the body that are affected by the disease.

The nanopieces described herein are positively charged. For example, the cargo, e.g., a nucleic acid such as a siRNA is negatively charged; however, when complexed with nanopieces (which are positively charged due to the presence of the positively-charged lysine of the nanopiece), the net charge of the complex is positive. The positively-charged NP-TNF-α siRNA complex associates with the negatively-charged macrophage cell and enters the cell, e.g., by endocytosis. In addition to entering cells by endocytosis, another advantage of the methods is when targeting macrophages, the cargo-loaded nanopieces may enter the cells by a second process, phagocytosis by macrophages—another advantage over previous approaches.

NP-Based Delivery to Cargo to Cells or Bodily Tissue

A successful delivery into cells does not always necessarily mean that a successful delivery into tissue is achieved to obtain an efficacious therapeutic or diagnostic outcome. One major reason is that tissues unlike cells have an extracellular matrix. For example, Nanopieces with large size or inappropriate surface charge may not penetrate the tissue efficiently enough to cause a therapeutic or diagnostic response. Drug molecules released from nanotubes prior to tissue penetration do not diffuse into enough depth of the tissue to reach a significant amount of cells. The invention solves such problems and provides methods to package drug molecules within nanotubes/nanorods that are selectively designed to alter their surface charge and/or their size to be small enough to penetrate the tissue matrix. So in this manner it is not the drug molecules that are released from the nanotubes and then diffuse into the tissue but it is the actual Nanopieces/nanorods (containing cargo, e.g., drug) that penetrate the tissue. The invention further provides methods of processing nanotubes/nanorods to control of size and other properties of Nanopieces (like surface charge and coating), in order to efficiently deliver their cargo into joints, tissues and/or organs to achieve an effective therapy or diagnosis.

These Nanopieces (Nanopieces) may contain nucleic acid, peptides, proteins and aromatic or negatively charged small molecules. Because different tissues have different surface charge, it is important to control the surface charge of Nanopieces via the ratio of delivery cargos and amount of nanorods. Nanopieces, which are too large may have difficulties in penetrating the tissue matrix and improper surface charge of Nanopieces may be repulsive to the target tissue matrix or perhaps the Nanopieces are not stable in the bodily fluids or blood. The table below describes exemplary nanopieces for preferential localization to and delivery to exemplary bodily tissues.

Selective Delivery of Nanopieces to Target Tissues

TABLE 1

| Target Tissue/Cell Type | Nanopiece Structure Size | Nanopiece Charge (Zeta potential) | Processing details to achieve desired length/width/charge* | Preferred payload/cargo | Other/notes |
|---|---|---|---|---|---|
| Cartilage/chondrocyte | General range: at least one dimension between 1 nm and 90 nm Preferred range: at least one dimension between 1 nm and 30 nm | General range: between +0 mV and +60 mV Preferred range: between +8 mV and +40 mV | Ratio: 4.4~30 μg RNTs per 0.1 nmol RNA (Preferred ratio: 6.6~20 μg RNTs per 0.1 nmol RNA) Sonication power: 10%~100% (for a 700 W | siRNA, other nucleic acids, molecular beacons and peptides/proteins (ADAMTS-5 siRNA, MMP-13 | Negatively charged |

TABLE 1-continued

| Target Tissue/Cell Type | Nanopiece Structure Size | Nanopiece Charge (Zeta potential) | Processing details to achieve desired length/width/charge* | Preferred payload/cargo | Other/notes |
|---|---|---|---|---|---|
| | | | sonicator) Sonication time: 10 s~30 mins Ionic strength of assembly solution: 0~308 mmol/L At least one of pre-processing methods (such as heating, sonication or quench): required | oligo molecular beacon, IL-1Ra protein) | |
| Synovium | General range: at least one dimension between 1 nm and 150 nm Preferred range: at least one dimension between 10 nm and 100 nm | General range: between +0 mV and +60 mV Preferred range: between +0 mV and +40 mV | Ratio: 4.4~30 µg RNTs per 0.1 nmol RNA (Preferred ratio: 4.4~20 µg RNTs per 0.1 nmol RNA) Sonication power: 1~100% (for a 700 W sonicator) Sonication time: 5 s~30 mins Ionic strength of assembly solution: no requirement At least one of pre-processing methods (such as heating, sonication or quench): not required | siRNA, other nucleic acids, molecular beacons and peptides/ proteins (IL-1 or TNF-α siRNA, IL-1 or TNF-α oligo molecular beacon, IL-1Ra protein) | |
| Neurons | General range: at least one dimension between 1 nm and 150 nm Preferred range: at least one dimension between 10 nm and 100 nm | General range: between −60 mV and +30 mV Preferred range: between −40 mV and +30 mV | Ratio: 0.1~15 µg RNTs per 0.1 nmol RNA (Preferred ratio: 1~15 µg RNTs per 0.1 nmol RNA) Sonication power: 1~100% (for a 700 W sonicator) Sonication time: 5 s~30 mins Ionic strength of assembly solution: no requirement At least one of pre-processing methods (such as heating, sonication or quench): not required | siRNA, other nucleic acids, molecular beacons and peptides/ proteins | Neurons generally positively charged |
| Brain/BBB | General range: at least one dimension between 1 nm and 100 nm Preferred range: at least one dimension between 1 nm and 30 nm | General range: between 30 mV and +40 mV Preferred range: between +8 mV and +40 mV | Ratio: 1~20 µg RNTs per 0.1 nmol RNA (Preferred ratio: 4.4~20 µg RNTs per 0.1 nmol RNA) Sonication power: 10~100% (for a 700 W sonicator) Sonication time: | siRNA, other nucleic acids, molecular beacons and peptides/ proteins | |

TABLE 1-continued

| Target Tissue/Cell Type | Nanopiece Structure Size | Nanopiece Charge (Zeta potential) | Processing details to achieve desired length/width/charge* | Preferred payload/cargo | Other/notes |
|---|---|---|---|---|---|
| | | | 10 s~30 mins Ionic strength of assembly solution: 0~308 mmol/L At least one of pre-processing methods (such as heating, sonication or quench): required | | |
| Ocular tissue | General range: at least one dimension between 1 nm and 150 nm Preferred range: at least one dimension between 10 nm and 100 nm | General range: between +0 mV and +60 mV Preferred range: between +0 mV and +40 mV | Ratio: 4.4~30 µg RNTs per 0.1 nmol RNA (Preferred ratio: 4.4~20 µg RNTs per 0.1 nmol RNA) Sonication power: 1~100% (for a 700 W sonicator) Sonication time: 5 s~30 mins Ionic strength of assembly solution: no requirement At least one of pre-processing methods (such as heating, sonication or quench): not required | siRNA, other nucleic acids, molecular beacons and peptides/proteins | |
| Derm tissue, skin, etc. | General range: at least one dimension between 1 nm and 150 nm Preferred range: at least one dimension between 10 nm and 100 nm | General range: between +0 mV and +60 mV Preferred range: between +0 mV and +40 mV | Ratio: 4.4~30 µg RNTs per 0.1 nmol RNA (Preferred ratio: 4.4~20 µg RNTs per 0.1 nmol RNA) Sonication power: 1~100% (for a 700 W sonicator) Sonication time: 5 s~30 mins Ionic strength of assembly solution: no requirement At least one of pre-processing methods (such as heating, sonication or quench): not required | siRNA, other nucleic acids, molecular beacons and peptides/proteins | |
| Tumor | General range: at least one dimension between 1 nm and 1200 nm Preferred range: at least one dimension between 10 nm and 200 nm | General range: between −60 mV and +60 mV Preferred range: between −30 mV and +60 mV | Ratio: 0.1~30 µg RNTs per 0.1 nmol RNA (Preferred ratio: 1~30 µg RNTs per 0.1 nmol RNA) Sonication power: 1~100% (for a 700 W sonicator) Sonication time: 5 s~30 mins Ionic strength of | siRNA, other nucleic acids, molecular beacons and peptides/proteins | Tumors may be acidic |

TABLE 1-continued

| Target Tissue/Cell Type | Nanopiece Structure Size | Nanopiece Charge (Zeta potential) | Processing details to achieve desired length/width/charge* | Preferred payload/ cargo | Other/ notes |
|---|---|---|---|---|---|
| | | | assembly solution: no requirement At least one of pre-processing methods (such as heating, sonication or quench): not required | | |
| Kidney | General range: at least one dimension between 1 nm and 100 nm Preferred range: at least one dimension between 10 nm and 200 nm | General range: between +0 mV and +60 mV Preferred range: between +0 mV and +40 mV | Ratio: 4.4~30 µg RNTs per 0.1 nmol RNA (Preferred ratio: 4.4~20 µg RNTs per 0.1 nmol RNA) Sonication power: 5~100% (for a 700 W sonicator) Sonication time: 5 s~30 mins Ionic strength of assembly solution: no requirement At least one of pre-processing methods (such as heating, sonication or quench): not required | siRNA, other nucleic acids, molecular beacons and peptides/ proteins | |
| Mucous membrane | General range: at least one dimension between 1 nm and 150 nm Preferred range: at least one dimension between 10 nm and 100 nm | General range: between +0 mV and +60 mV Preferred range: between +0 mV and +40 mV | Ratio: 4.4~30 µg RNTs per 0.1 nmol RNA (Preferred ratio: 4.4~20 µg RNTs per 0.1 nmol RNA) Sonication power: 1~100% (for a 700 W sonicator) Sonication time: 5 s~30 mins Ionic strength of assembly solution: no requirement At least one of pre-processing methods (such as heating, sonication or quench): not required | siRNA, other nucleic acids, molecular beacons and peptides/ proteins | |
| Lung | General range: at least one dimension between 10 nm and 150 nm Preferred range: at least one dimension between 20 nm and 100 nm | General range: between +0 mV and +60 mV Preferred range: between +0 mV and +40 mV | Ratio: 4.4~30 µg RNTs per 0.1 nmol RNA (Preferred ratio: 4.4~20 µg RNTs per 0.1 nmol RNA) Sonication power: 1~50% (for a 700 W sonicator) Sonication time: 5 s~3 mins Ionic strength of assembly solution: no | siRNA, other nucleic acids, molecular beacons and peptides/ proteins | |

TABLE 1-continued

| Target Tissue/Cell Type | Nanopiece Structure Size | Nanopiece Charge (Zeta potential) | Processing details to achieve desired length/width/charge* | Preferred payload/cargo | Other/notes |
|---|---|---|---|---|---|
| | | | requirement At least one of pre-processing methods (such as heating, sonication or quench): not required | | |
| Heart | General range: at least one dimension between 1 nm and 90 nm Preferred range: at least one dimension between 1 nm and 30 nm | General range: between +0 mV and +60 mV Preferred range: between +8 mV and +40 mV | Ratio: 4.4~30 µg RNTs per 0.1 nmol RNA (Preferred ratio: 6.6~20 µg RNTs per 0.1 nmol RNA) Sonication power: 10%~100% (for a 700 W sonicator) Sonication time: 10 s~30 mins Ionic strength of assembly solution: 0~308 mmol/L At least one of pre-processing methods (such as heating, sonication or quench): required | siRNA, other nucleic acids, molecular beacons and peptides/proteins | |

Diagnostic Applications

Molecular beacons or molecular beacon probes are oligonucleotide hybridization probes that report the presence of specific nucleic acids. Molecular beacons are hairpin shaped molecules with an internally quenched fluorophore whose fluorescence is restored when they bind to a target nucleic acid sequence. The use of molecular beacons is a non-radioactive method for detecting specific sequences of nucleic acids. They are useful in situations where it is either not possible or desirable to isolate the probe-target hybrids from an excess of the hybridization probes such as in the context of clinical diagnostics.

A typical molecular beacon probe is 25 nucleotides long. The middle 15 nucleotides are complementary to the target DNA or RNA and do not base pair with one another, while the five nucleotides at each terminus are complementary to each other rather than to the target DNA. A typical molecular beacon structure can be divided in 4 parts. Loop: a 18-30 base pair region of the molecular beacon that is complementary to the target sequence. Stem: the beacon stem is formed by the attachment, to both termini of the loop, of two short (5 to 7 nucleotide residues) oligonucleotides that are complementary to each other. 5' fluorophore: located at the 5' end of the molecular beacon, a fluorescent dye is covalently attached. 3' quencher (non-fluorescent): the quencher dye part of the beacon is covalently attached to the 3' end of the molecular beacon. When the beacon is in closed loop shape, the quencher resides in proximity to the fluorophore, which results in quenching the fluorescent emission of the latter.

If the nucleic acid to be detected is complementary to the strand in the loop, the event of hybridization occurs. The duplex formed between the nucleic acid and the loop is more stable than that of the stem because the former duplex involves more base pairs. This causes the separation of the stem and hence of the fluorophore and the quencher. Once the fluorophore is distanced from the quencher, illumination of the hybrid with light results in the fluorescent emission. The presence of the emission reports that the event of hybridization has occurred and hence the target nucleic acid sequence is present in the test sample. Molecular beacons are useful in SNP detection, real-time nucleic acid detection, real-time PCR quantification, allelic discrimination and identification, multiplex PCR assays, and for diagnostics. Nanopieces containing molecular beacons or other non-radioactive or radioactive detectable markers are particularly useful in diagnostic clinical assays.

MMP

MMP13 is involved in the progression of osteoarthritis. Matrix metalloproteinase (MMP) 13 is a major enzyme that targets cartilage for degradation. Compared to other MMPs, the expression of MMP13 is relatively more restricted to connective tissue. It not only targets type II collagen in cartilage for degradation, but also degrades proteoglycan, types IV and type IX collagen, osteonectin and perlecan in cartilage. Clinical investigation revealed that patients with articular cartilage destruction have high MMP13 expression, indicating that increased MMP13 is associated with cartilage degradation. MMP13-overexpressing transgenic mice developed a spontaneous OA-like articular cartilage destruction phenotype. The ADAMTS (a disintegrin and metalloproteinase with thrombospondin motifs) family of aggrecanases also contributes to proteoglycan/aggrecan depletion and are associated with cartilage degradation during OA. ADAMTS4 and 5 were identified as the major aggrecanases during OA development.

ADAMTS5

ADAMTS5 is a member of the ADAMTS (a disintegrin and metalloproteinase with thrombospondin motifs) protein family and a major aggrecanase in human cartilage. Members of the family share several distinct protein modules, including a propeptide region, a metalloproteinase domain, a disintegrin-like domain, and a thrombospondin type 1 (TS) motif. Individual members of this family differ in the number of C-terminal TS motifs, and some have unique C-terminal domains. The enzyme encoded by this gene contains two C-terminal TS motifs and functions as aggrecanase to cleave aggrecan, a major proteoglycan of cartilage.

ADAMTS5 plays a role in arthritis, e.g., it plays a key role in aggrecan degradation in cartilage. For example, genetically modified mice in which the catalytic domain of ADAMTS5 was deleted are resistant to cartilage destruction in an experimental model of osteoarthritis. ADAMTS5 is the major aggrecanase in mouse cartilage in a mouse model of inflammatory arthritis. ADAMTS5 is also useful as a biomarker for prediction of the response to infliximab (IFX) in patients with rheumatoid arthritis.

Fabrication of Tissue-Targeted Nanoparticles

Examples for the preparation of nanopieces for use in individual tissues are described below.

Cartilage/Chondrocytes:
1) 30 µg RNTs in 50 µL water were heated to 99° C. for 3 mins, and then mixed with 0.1 nmol MMP-13 molecular beacon. The resulting mixture was sonicated at 100% power for 10 s.
2) 4.4 µg RNTs in 1 µL water were sonicated at 50% power of a 700 W sonicator for 10 mins, and then mixed with 0.1 nmol miRNA-140. The resulting mixture was sonicated at 100% power for 30 mins.
3) 10 µg RNTs in 10 µL water were sonicated at 100% power of a 700 W sonicator for 5 mins, and then mixed with 0.1 nmol ADAMTS-5 siRNA. The resulting mixture was sonicated at 100% power for 3 mins.

Synovium:
1) 30 µg RNTs in 50 µL water were heated to 99° C. for 3 mins, and then mixed with 0.1 nmol IL-1β molecular beacon on ice. The resulting mixture was sonicated at 100% power for 60 s.
2) 4.4 µg RNTs in 1 µL saline were sonicated at 1% power of a 700 W sonicator for 10 mins, and then mixed with 0.1 nmol IL-1 receptor antagonist protein. The resulting mixture was sonicated at 1% power for 10 s.
3) 10 µg RNTs in 10 µL water were sonicated at 100% power of a 700 W sonicator for 5 mins, and then mixed with 0.1 nmol TNF-α siRNA. The resulting mixture was sonicated at 100% power for 60 s.

Neurons:
1) 15 µg RNTs in 50 µL water at 1% power of a 700 W sonicator for 30 mins, and then mixed with 0.1 nmol VEGF molecular beacon. The resulting mixture was sonicated at 100% power for 60 s.
2) 0.1 µg RNTs in 1 µL saline were heated to 99° C. for 3 mins, and then mixed with 0.1 nmol IL-1 receptor siRNA on ice. The resulting mixture was sonicated at 100% power for 30 mins.
3) 10 µg RNTs were sonicated in 10 µL water at 100% power of a 700 W sonicator for 5 mins, and then mixed with 0.1 nmol MMP-1 siRNA. The resulting mixture was sonicated at 100% power for 3 mins.

Brain/BBB:
1) 20 µg RNTs in 50 µL water were heated to 99° C. for 3 mins, and then mixed with 0.1 nmol MMP-9 molecular beacon on ice. The resulting mixture was sonicated at 100% power for 60 s.
2) 1 µg RNTs in 1 µL saline were sonicated at 10% power of a 700 W sonicator for 10 mins, and then mixed with 0.1 nmol VEGF mRNA. The resulting mixture was sonicated at 10% power for 10 s.
3) 10 µg RNTs in 10 µL water were sonicated at 100% power of a 700 W sonicator for 5 mins, and then mixed with 0.1 nmol TNF-α siRNA. The resulting mixture was sonicated at 100% power for 60 s.

Ocular Tissue:
1) 30 µg RNTs in 50 µL water were heated to 99° C. for 3 mins, and then mixed with 0.1 nmol VEGF molecular beacon on ice. The resulting mixture was sonicated at 100% power for 60 s.
2) 4.4 µg RNTs in 1 µL saline were sonicated at 1% power of a 700 W sonicator for 10 mins, and then mixed with 0.1 nmol VEGF antagonist protein. The resulting mixture was sonicated at 1% power for 10 s.
3) 10 µg RNTs in 10 µL water were sonicated at 100% power of a 700 W sonicator for 5 mins, and then mixed with 0.1 nmol VEGF siRNA. The resulting mixture was sonicated at 100% power for 60 s.

Derm Tissue/Skin:
1) 30 µg RNTs in 50 µL water were heated to 99° C. for 3 mins, and then mixed with 0.1 nmol IL-1β molecular beacon on ice. The resulting mixture was sonicated at 100% power for 60 s.
2) 4.4 µg RNTs in 1 µL saline were sonicated at 1% power of a 700 W sonicator for 10 mins, and then mixed with 0.1 nmol IL-6 siRNA. The resulting mixture was sonicated at 1% power for 10 s.
3) 10 µg RNTs in 10 µL water were sonicated at 100% power of a 700 W sonicator for 5 mins, and then mixed with 0.1 nmol IL-8 siRNA. The resulting mixture was sonicated at 100% power for 60 s.

Tumor:
1) 30 µg RNTs in 50 µL water at 1% power of a 700 W sonicator for 30 mins, and then mixed with 0.1 nmol VEGF molecular beacon. The resulting mixture was sonicated at 100% power for 60 s.
2) 0.1 µg RNTs in 1 µL saline were heated to 99° C. for 3 mins, and then mixed with 0.1 nmol TNF-α siRNA on ice. The resulting mixture was sonicated at 100% power for 30 mins.
3) 10 µg RNTs were sonicated in 104, water at 100% power of a 700 W sonicator for 5 mins, and then mixed with 0.1 nmol MMP-1 siRNA. The resulting mixture was sonicated at 100% power for 3 mins.

Kidney:
1) 30 µg RNTs in 50 µL water were heated to 99° C. for 3 mins, and then mixed with 0.1 nmol IL-12 molecular beacon on ice. The resulting mixture was sonicated at 100% power for 60 s.
2) 4.4 µg RNTs in 1 µL saline were sonicated at 5% power of a 700 W sonicator for 10 mins, and then mixed with 0.1 nmol IL-1 receptor associated protein siRNA. The resulting mixture was sonicated at 1% power for 10 s.
3) 10 µg RNTs in 10 µL water were sonicated at 100% power of a 700 W sonicator for 5 mins, and then mixed with 0.1 nmol IL-8 siRNA. The resulting mixture was sonicated at 100% power for 60 s.

Mucous Membrane:

1) 30 μg RNTs in 50 μL water were heated to 99° C. for 3 mins, and then mixed with 0.1 nmol MMP-13 molecular beacon on ice. The resulting mixture was sonicated at 100% power for 60 s.

2) 4.4 μg RNTs in 1 μL saline were sonicated at 1% power of a 700 W sonicator for 10 mins, and then mixed with 0.1 nmol MMP-9 siRNA. The resulting mixture was sonicated at 1% power for 10 s.

3) 10 μg RNTs in 10 μL water were sonicated at 100% power of a 700 W sonicator for 5 mins, and then mixed with 0.1 nmol MMP-1 siRNA. The resulting mixture was sonicated at 100% power for 60 s.

Lung:

1) 30 μg RNTs in 50 μL water were heated to 99° C. for 3 mins, and then mixed with 0.1 nmol TNF-α molecular beacon on ice. The resulting mixture was sonicated at 50% power for 60 s.

2) 4.4 μg RNTs in 1 μL saline were sonicated at 1% power of a 700 W sonicator for 3 mins, and then mixed with 0.1 nmol MMP-9 siRNA. The resulting mixture was sonicated at 1% power for 5 s.

3) 10 μg RNTs in 10 μL water were sonicated at 50% power of a 700 W sonicator for 1 mins, and then mixed with 0.1 nmol MMP-1 siRNA. The resulting mixture was sonicated at 100% power for 60 s.

Heart:

1) 30 μg RNTs in 50 μL water were heated to 99° C. for 3 mins, and then mixed with 0.1 nmol VEGF molecular beacon. The resulting mixture was sonicated at 100% power for 10 s.

2) 4.4 μg RNTs in 1 μL water were sonicated at 50% power of a 700 W sonicator for 10 mins, and then mixed with 0.1 nmol miRNA-365. The resulting mixture was sonicated at 100% power for 30 mins.

3) 10 μg RNTs in 10 μL water were sonicated at 100% power of a 700 W sonicator for 5 mins, and then mixed with 0.1 nmol IL-1α siRNA. The resulting mixture was sonicated at 100% power for 3 mins.

Coating of Nanopieces, which is another important factor for tissue delivery can also be used to improve the tissue delivery. For example polyethylene glycol (PEG) and dextran are coatings often used.

The invention further provides methods for making composites of rosette nanotubes or components or rosette nanotubes or rosette Nanopieces and therapeutic or diagnostic agents including those known in the art. For example, agents include nucleic acids (DNA or RNA), wherein the RNA can be small RNA such as siRNA and miRNA. In particular, disclosed herein are novel siRNA transport complexes, comprising an unexpectedly advantageous transport vehicle. Methods of the present invention include contacting a transfection complex described herein with one or more cells, where the transfection complex includes a rosette nanotube and one or more nucleic acids such as DNA and RNA, for example siRNA. The rosette nanotube is a carrier that is formed from self-assembled modules as described below and those modules recognized in the art.

Compounds/Modules for Self-Assembly

Modules according to the present disclosure include compounds of Formula I below:

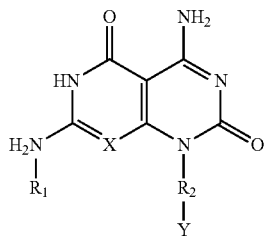

Wherein X is CH or nitrogen, preferably nitrogen; $R_2$ is hydrogen or a linker group for example $(CH_2)_n$ or other linker groups described herein, preferably $(CH_2)_n$; n is an integer of, 1, 2, 3, or 4, n=2 is preferred; Y is absent when $R_2$ is hydrogen or is an amino acid or polypeptide having an amino group covalently bound to an α-carbon of the amino acid and the amino group is covalently bound to the linker group $R_2$, Y is preferred to be lysine arginine, and histidine; and $R_1$ is hydrogen or an aliphatic moiety, such as alkyl, straight or branched chain, saturated or unsaturated; and salts thereof. Preferably $R_1$ is $C_1$ to $C_{10}$ alkyl, $C_1$ to $C_5$ alkyl, $C_1$ to $C_3$ alkyl, or methyl. Compounds within the scope of the invention include those where the Y group can be connected to the linker group either by the amino group or the carboxyl group of the amino acid or polypeptide. An exemplary linker group is shown in the formula below.

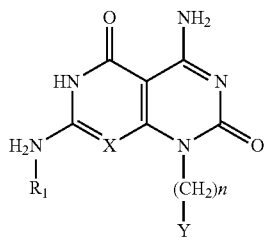

Figure 4:
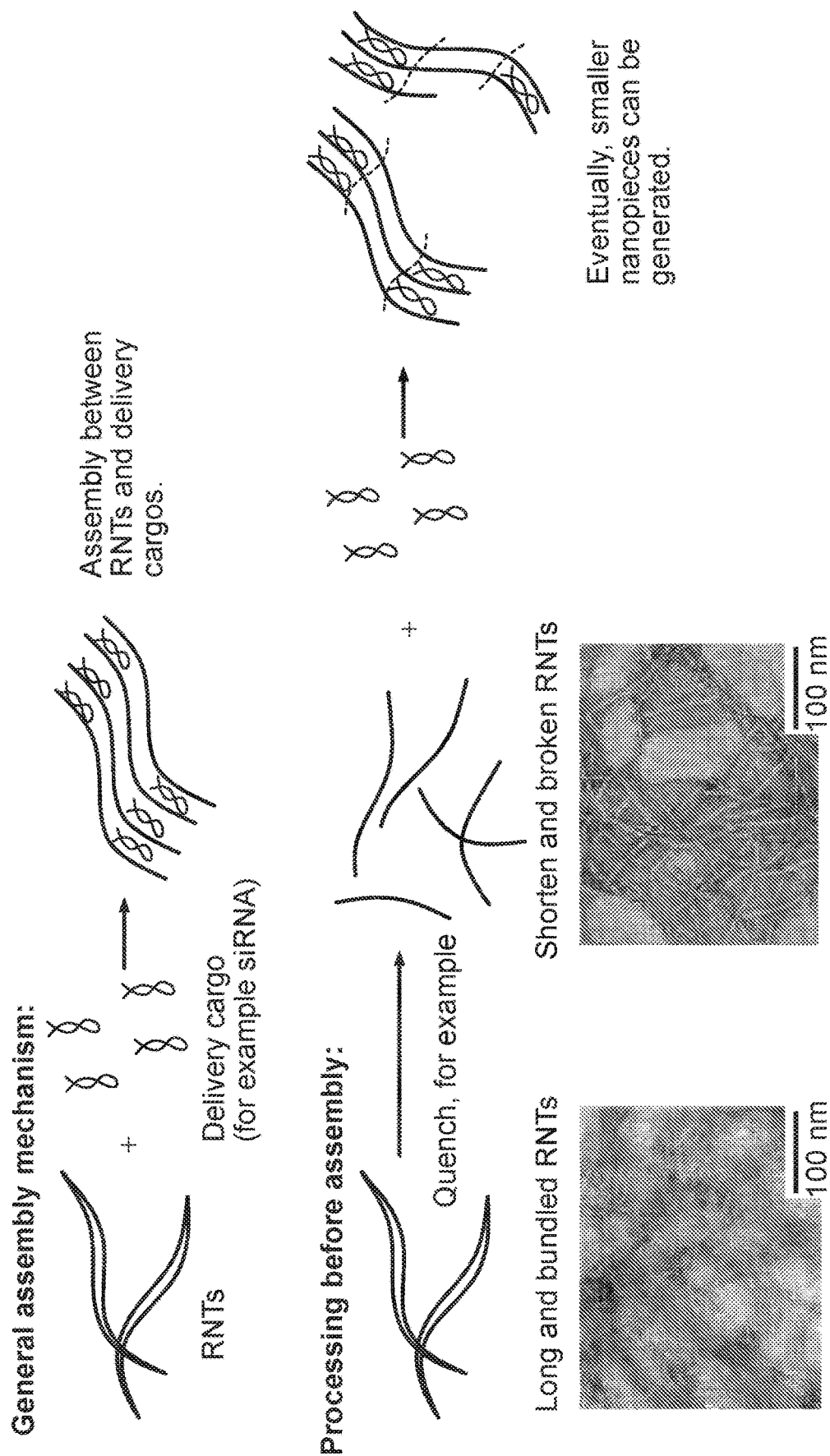
FIG. 4 illustrates scheme 1, which displays an assembly mechanism and processing approaches.

An exemplary module within the scope of Formula I is shown in FIG. 4 along with a schematic representation of a nanotube and an image of nanotubes formed from the exemplary module.

Alternative linker groups $R_2$ can join the Y group to the carbon of the $(CH_2)_n$ group or the N atom either by the amino group or the carboxyl group of the amino acid or polypeptide.

Alternative $R_2$ groups within the scope of the present disclosure are selected from a group comprising:

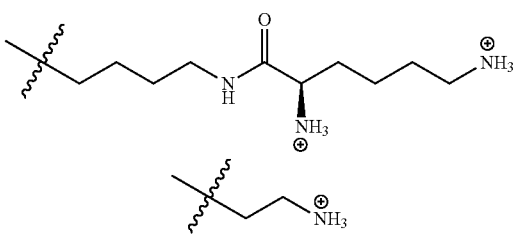

39
-continued

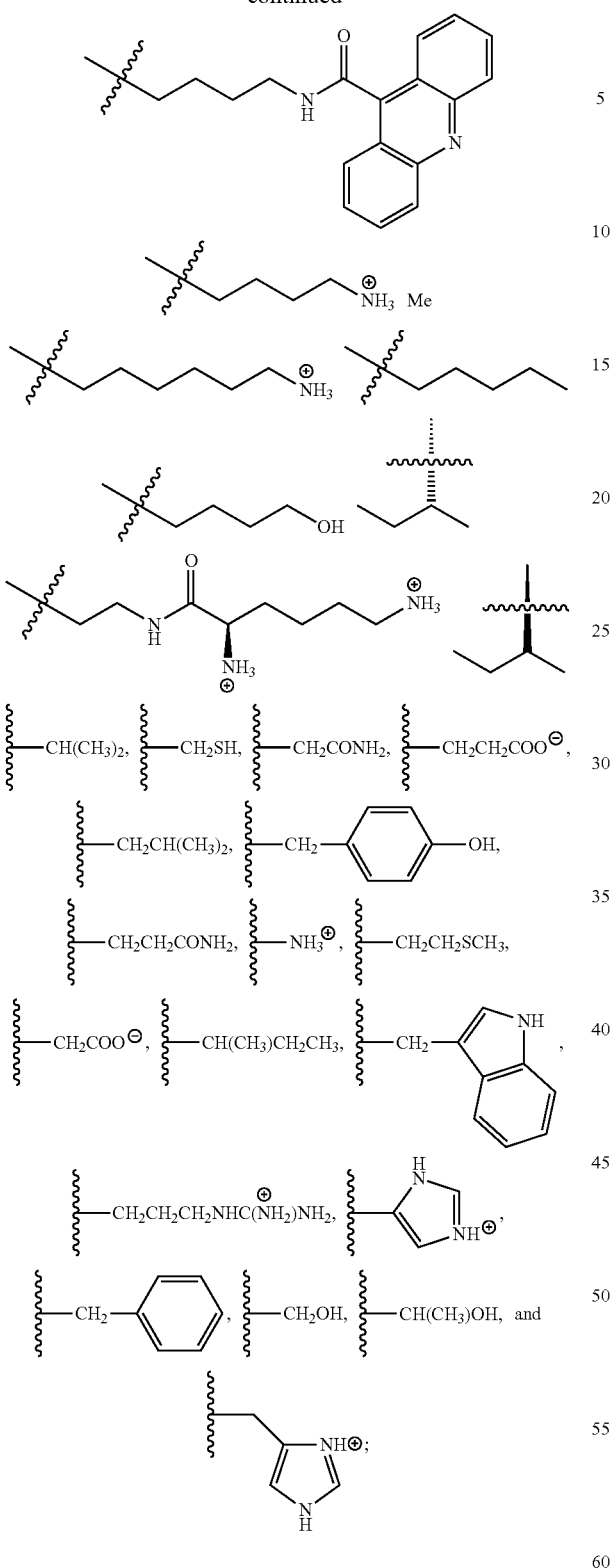

wherein Y is absent.

Compounds of Formula I can be prepared by the methods described in U.S. Pat. No. 6,696,565 hereby incorporated by reference herein in its entirety alone or combined with methods known to those of skill in the art. Rosette nanotubes are made by assembly of compounds of Formula (I).

40

Exemplary compounds of Formula I are shown below:

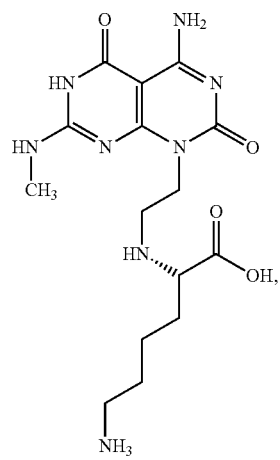

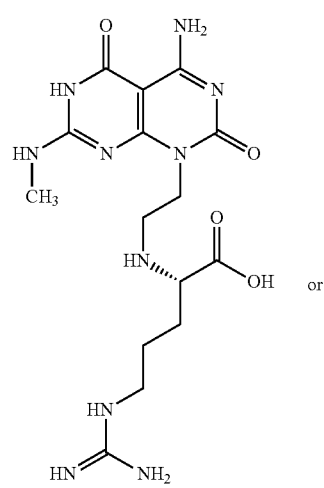

or

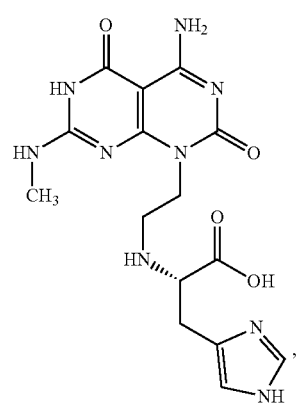

and a salt thereof. In embodiments, the compounds of Formula I are present in zwitterion form. The compounds are shown as below.

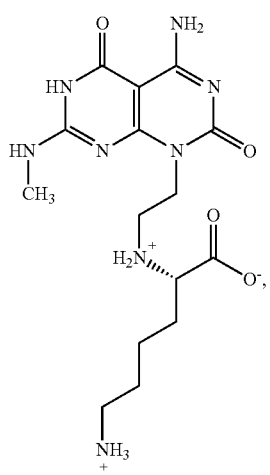
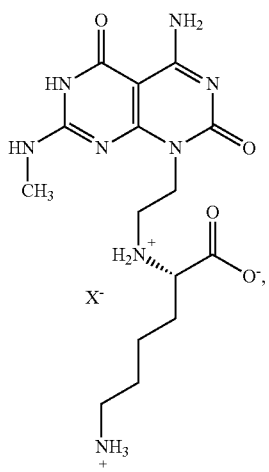
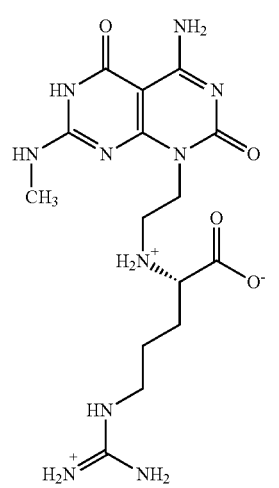
and
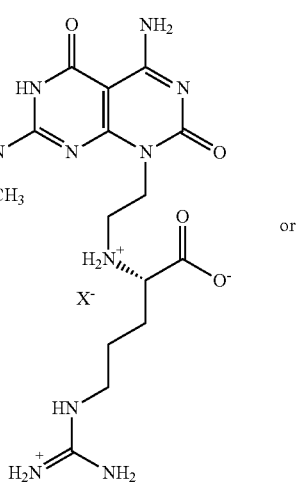
or
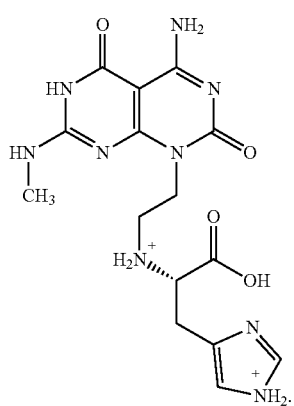
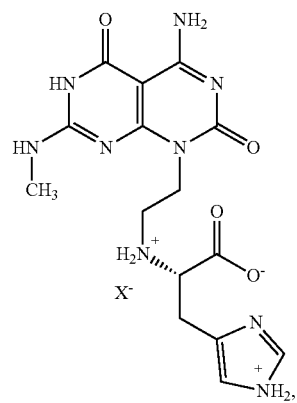
The salt forms thereof may be presented as follows:
wherein X⁻ can be anion such as Cl⁻, or other anionic organic acids.

Modules according to the present disclosure also include compounds of Formula II below:

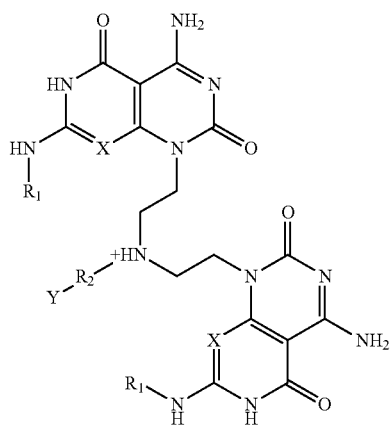

Wherein X is CH or nitrogen preferably nitrogen; $R_2$ is hydrogen or a linker group for example $(CH_2)_n$, preferably $(CH_2)_n$; where n is an integer of, 1, 2, 3, or 4 or $(CH_2)_3CO$ or other linker groups described herein, n=2 is preferred; Y is absent when $R_2$ is hydrogen or is an amino acid or polypeptide having an amino group covalently bound to an α-carbon of the amino acid and the amino group is covalently bound to the linker group $R_2$, Y is preferred to be lysine arginine, and histidine; and $R_1$ is hydrogen or an aliphatic moiety, such alkyl, straight or branched chain, saturated or unsaturated; and salts thereof. Preferably $R_1$ is $C_1$ to $C_{10}$ alkyl, $C_1$ to $C_5$ alkyl, $C_1$ to $C_3$ alkyl, or methyl. An exemplary linker group is shown in the formula below.

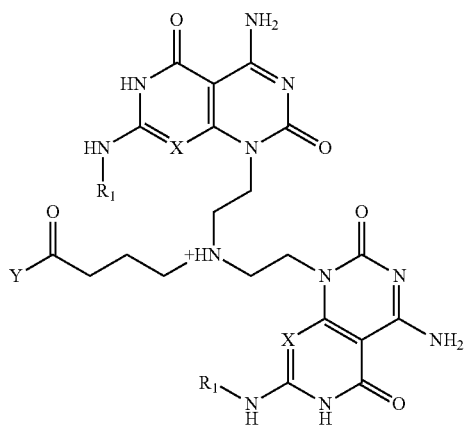

Compounds within the scope of the present disclosure include those where the Y group can be connected to the linker group either by the amino group or the carboxyl group of the amino acid or polypeptide. Alternative $R_2$ groups within the scope of the present disclosure are selected from a group comprising:

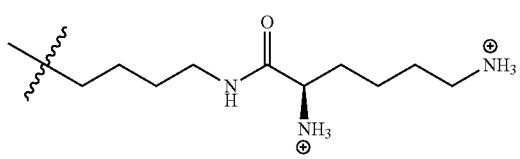

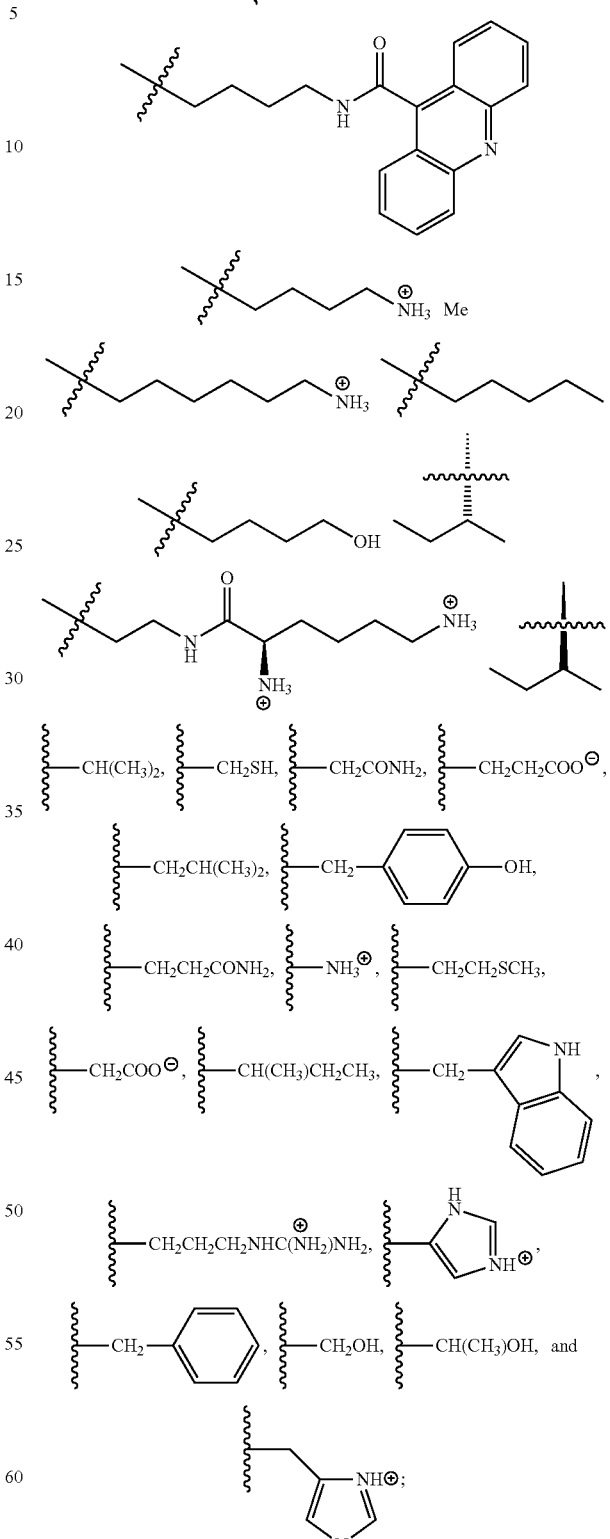

wherein Y is absent. TBL structures are made by the assembly of compounds of Formula (II).

Exemplary compounds of Formula II are shown below:
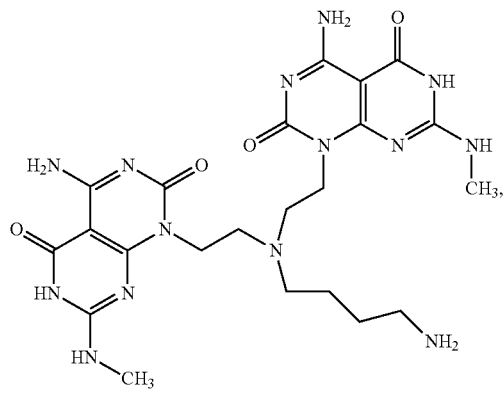
Lysine Functional Group Construct
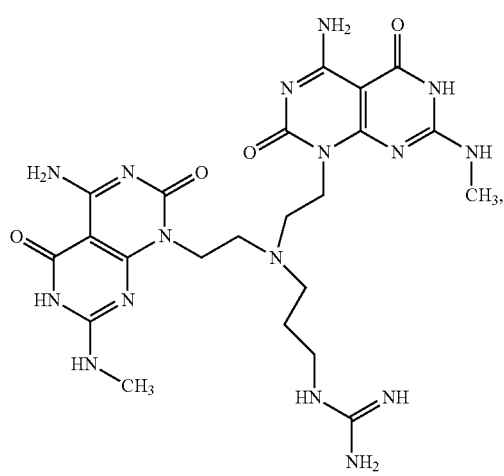
Arginine Functional Group Construct
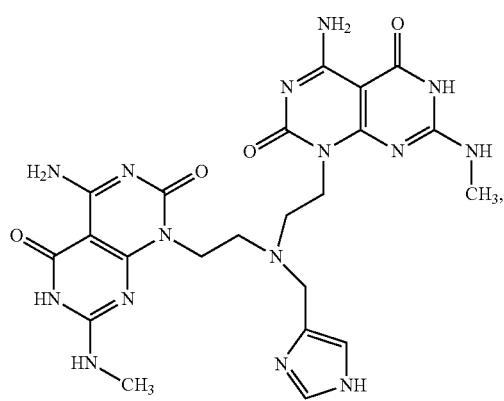
Histidine Functional Group Construct
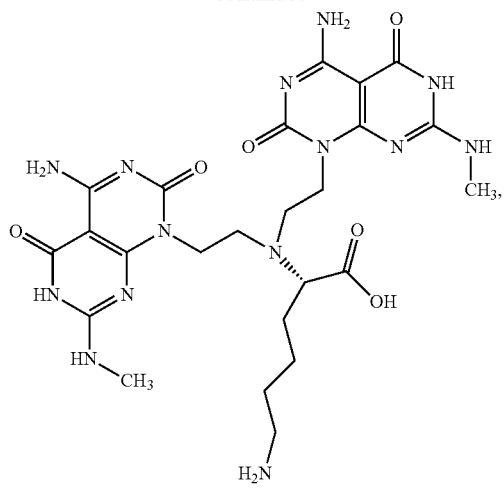
Lysine Amino Acid Construct
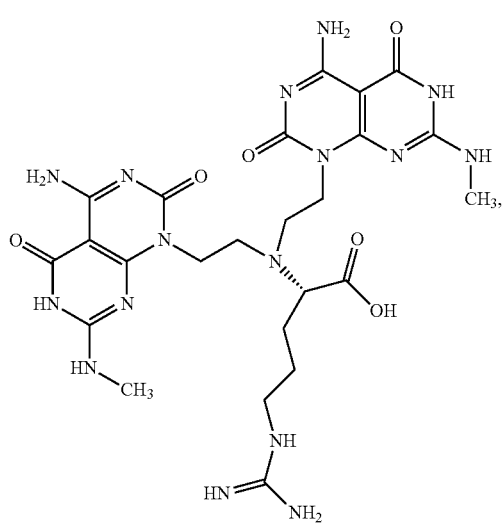
Arginine Amino Acid Construct
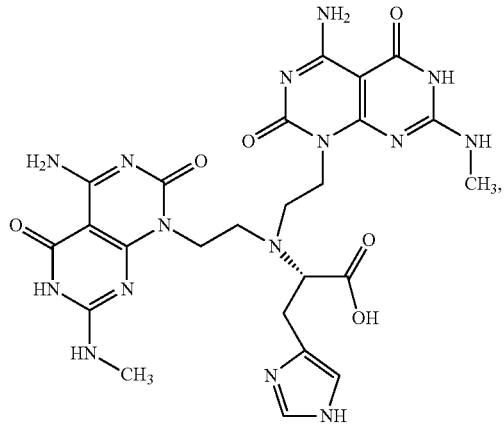
Histidine Amino Acid Construct

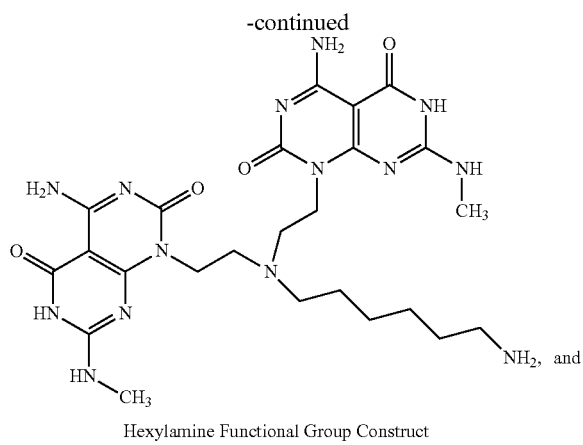

Hexylamine Functional Group Construct

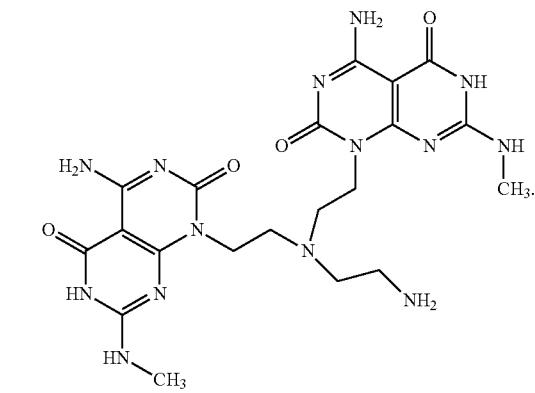

Ethylamine Functional Group Construct

In some embodiments, compounds of formula II comprise amino acid functional group constructs. These compounds contain functional groups present in natural occurring amino acid side chains or may contain the entire amino acid side chain. For example, the lysine functional group construct contains the entire amino acid side chain functionality (—$CH_2CH_2CH_2CH_2NH_3^+$), whereas the histidine functional group construct only contains the heteroaryl imidazole group present in histidine.

In some embodiments, compounds of formula II comprise amino acid analogs. These compounds contain the entire the amino acid or may contain modified and/or unnatural amino acids. For example, the lysine amino acid analog contains the entire amino acid functionality of lysine, whereas the histidine amino acid analog contains a modified histidine amino acid.

In some embodiments the compound of formula II is the Lysine Functional Group Construct:

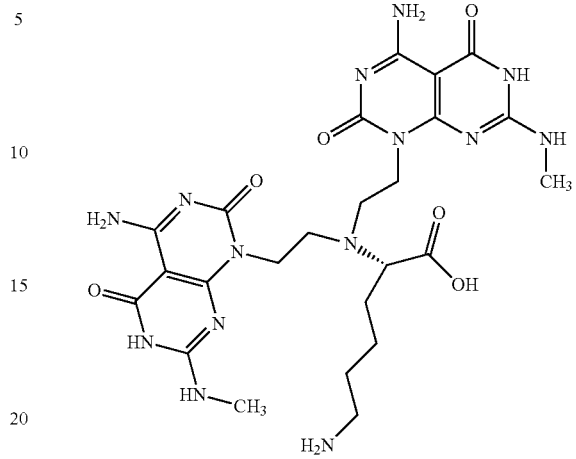

According to certain aspects of the present disclosure, the structure of Formula II is referred to as a twin base with a linker (TBL) or twin base linkers insofar as two similar double ring structures are present as shown in Formula II and are linked to an amino acid or polypeptide. However, it is to be understood that the two double ring structures need not be identical insofar as they may have different X and $R_1$ groups.

Embodiments of the present disclosure involve making composites of rosette nanotubes or components or rosette nanotubes or rosette Nanopieces and therapeutic or diagnostic agents including those known in the art and including nucleic acids, such as DNA or RNA. RNA can be small RNA including siRNA and miRNA. In particular, disclosed herein are novel siRNA transport complexes, comprising an unexpectedly advantageous transport vehicle. Methods of the present invention include contacting a transfection complex described herein with one or more cells, where the transfection complex includes a rosette nanotube and one or more nucleic acids such as DNA and RNA, for example siRNA. The rosette nanotube is a carrier that is formed from self-assembled modules as described below and those modules are recognized in the art.

TBL or twin base linkers comprise structures shown in Formula II and are linked to an amino acid, amino acid side chain structure, or polypeptide; compounds of Formula I may also be linked to an amino acid, amino acid side chain structure, or polypeptide. However, it is to be understood that the two double ring structures need not be identical insofar as they may have different X, Y, and $R_1$ groups.

Amino acids can be divided into amino acid containing hydrophilic side chains, hydrophobic side chains, and electrically charged side chains. See chart below, wherein the side chains are shaded:

According to aspects of the present disclosure, modules (compounds) according to Formula I and Formula II self-assemble into substructures also called supermacrocycles which themselves will self-assemble into nanometer scale architectures or structures such as discrete nanotubular assemblies in water or aqueous solutions. Supermacrocycles are defined herein as being a number of organic molecules covalently or noncovalently bound together so as to form a ring structure. For example, compounds of Formula I will self-assemble into a 6-mer ring structure, sometimes referred to as a rosette. The process of forming nanotubes with the modules of the present disclosure is hierarchical. In particular, the modules of the present invention first self-assemble into supermacrocycles, and then the supermacrocycles self-assembly into nanotubes. Such self-assembly is described in U.S. Pat. No. 6,696,565. For the compounds of Formula II referred to as twin base linkers, the compounds will also assemble into a 6-mer ring structure. However, a single supermacrocycle formed will include two base layers owing to the presence of the two bases in each of the compound of Formula II.

Examples of modules of the present disclosure comprise the compounds of Formula I and Formula II and may include low molecular weight synthetic DNA base analogues referred to by the nomenclature C∧G (Fenniri et al, *J. Am. Chem. Soc.* 2001, 123, 3854-3855) and A∧T. The C∧G moiety, referred to as a single CG motif, possesses the Watson-Crick donor-donor-acceptor of guanine and the acceptor-acceptor-donor of cytosine and undergoes a self-assembly process, fueled by an array of hydrogen bonds, to produce a six-membered supermacrocycle or rosette. Stacking of these rosettes produced a nanotube of very high aspect ratio. Compounds within the scope of the present invention include a twin G∧C motif denoted as $(C∧G)_2$. Like the single C∧G motif, the twin C∧G motif $(C∧G)_2$ also possesses the Watson-Crick donor-donor-acceptor of guanine and the acceptor-acceptor-donor of cytosine and undergoes a self-assembly process, fueled by an array of hydrogen bonds, to produce a six-membered supermacrocycle or ring structure (rosette) of twin configuration. Stacking of these twin rosettes produces a nanotube of very high aspect ratio and higher stability. Analogously, The A∧T moiety, referred to as a single AT motif, also possesses the Watson-Crick donor-donor-acceptor of adenine and the acceptor-acceptor-donor of thymine and undergoes a self-assembly process as well, fueled by an array of hydrogen bonds, to produce a six-membered supermacrocycle or rosette. Stacking of these rosettes produces a nanotube of very high aspect ratio. Compounds within the scope of the present invention include a twin A∧T motif denoted as $(A∧T)_2$. Like the single A∧T motif, the twin A∧T motif $(A∧T)_2$ also possesses the Watson-Crick donor-donor-acceptor of adenine and the acceptor-acceptor-donor of thymine and undergoes a self-assembly process, fueled by an array of hydrogen bonds, to produce a six-membered supermacrocycle or ring structure (rosette) of twin configuration. Stacking of these twin rosettes also produces a nanotube of very high aspect ratio and higher stability.

It should be understood that the above described Formula I and/or Formula II demonstrate that electrostatic, stacking and hydrophobic interactions can be effectively orchestrated by hydrogen bonds to direct the hierarchical assembly and organization of helical nanotubular architectures in an aqueous milieu. Helical nanotubular architectures within the scope of the present invention include those formed entirely from compounds of Formula I. Helical nanotubular architectures within the scope of the present invention include those formed entirely from compounds of Formula II. Further, helical nanotubular architectures within the scope of the present invention include those formed from one or more of the compounds of Formula I and one or more of the compounds of Formula II. For example, a supermacrocycle ring substructure having particular amino acid or polypeptide side chains formed from the compounds of Formula I can be stacked with a supermacrocycle ring substructure having particular amino acid or polypeptide side chains formed from the compounds of Formula II. The rosette substructures formed from the compounds of Formula I and Formula II can be stacked in any desired sequence to form nanotubular structures of the present invention. Utilizing this aspect of the present invention, a wide variety of structurally different modules (e. g, compounds) can be synthesized and self-assembled into supermacrocycles and then nanotubular structures according to methods of the present invention.

Another aspect of the invention is the conversion of nanotubes to nanorods by altering pH, temperature, and usage of physical methods (e.g., sonication, heating and blending) to prepare different sizes of Nanopieces.

Before assembly with delivery cargo, length of nanotubes (based on either Formula I or II) range in size from 1 nm to 999 micron, e.g., 10 nm to 999 nm. Outer width of nantoubes range in size from 0.5 nm to 100 nm, e.g., 1 nm to 10 nm. Inner diameter of nanotubes range in size from 1 angstrom to 10 nm, e.g., 0.5 nm to 5 nm.

After assembly with delivery cargo, length of Nanopieces (based on either Formula I or II) range in size from 1 nm to 999 micron, e.g., 10 nm to 999 nm. Width of Nanopieces range in size from 1 nm to 999 nm, e.g., 10 nm to 100 nm.

Another aspect of the invention is the packaging of drug molecules, e.g., therapeutics and diagnostics, with nanotubes to alter their surface charge and more importantly process these nanotubes into Nanopieces of the right shape and size to penetrate tissue matrix. Therefore, it is not the drug molecules that are released from nanotubes that diffuse into tissue, it is the Nanopieces themselves that penetrate the tissue. Control of the surface charge of the Nanopieces is done via the ratio of delivery cargo and nanotubes and/or nanorods. A further aspect of the invention is the use of coatings for the Nanopieces for tissue delivery. For example, polyethylene glycol and/or dextran are coatings that when used can improve tissue delivery.

A further aspect of the invention is the delivery of cargo into cells. These drug molecules can be nucleic acid, peptides, proteins, aromatic small molecules or negatively charged small molecules.

In some embodiments, the prepared module of the invention has an overall yield of no less than 60%, e.g., no less than 70%, no less than 80%, or no less than 90%.

In some embodiments, the module of the method of the invention contains more than 80% of compound of Formula I or II. In some embodiments, the product of the method of the invention contains more than 85%, 90%, 92%, 95%, 97%, 98%, 98.5%, or 99% of compound of Formula I and/or II. For example, the product is free of undesired byproduct or starting material.

In some embodiments, the nanotube of the invention has an overall yield of no less than 60%, e.g., no less than 70%, no less than 80%, or no less than 90%.

In some embodiments, the nanotube of the method of the invention contains more than 80% of compound of Formula I or II. In some embodiments, the product of the method of the invention contains more than 85%, 90%, 92%, 95%, 97%, 98%, 98.5%, or 99% of compound of Formula I and/or II. For example, the product is free of undesired byproduct or starting material.

In some embodiments, the Nanopieces of the invention has an overall yield of no less than 60%, e.g., no less than 70%, no less than 80%, or no less than 90%.

In some embodiments, the Nanopieces of the method of the invention contains more than 80% of compound of Formula I or II. In some embodiments, the product of the method of the invention contains more than 85%, 90%, 92%, 95%, 97%, 98%, 98.5%, or 99% of compound of Formula I and/or II. For example, the product is free of undesired byproduct or starting material.

According to certain preferred aspects of the present invention, a nanotube is prepared from single base ring structures and twin base ring structures in any desired order. The nanotube can have one or more single base ring structures and one or more twin base ring structures. Likewise, a nanotube within the scope of the present invention can include a plurality of single base ring structures formed from compounds of Formula I and a plurality of twin base ring structures formed from compounds of Formula II stacked together, e.g. one next to the other via hydrogen bonding, to form the nanotube.

Nanotube-Agent Complexes

According to certain aspects, nucleic acids or polypeptides includes small RNA being a duplex of between about 10 to about 30 nucleic acids, between about 15 to about 25 nucleic acids and between about 20 to about 23 nucleic acids, and any values and ranges in between whether overlapping or not. The small RNA can be formed by one or more oligonucleotides. Small RNA includes RNA commonly referred to as interference RNA, dsRNA, ssRNA, saRNA, siRNA or miRNA or their derivatives, analogs, mimics and inhibitors. According to certain aspects, siRNA is involved in the RNA interference (RNAi) pathway, where it interferes with the expression of a specific gene. In addition to their role in the RNAi pathway, siRNAs also act in the RNAi-related pathways. siRNA within the scope of the present disclosure includes double stranded RNA of about 21 nucleotides with a 2 nucleotide 3' overhang on either end of the siRNA. Each siRNA strand has a 5' phosphate group and a 3' hydroxyl (—OH) group. The structure is the result of processing by dicer, an enzyme that converts either long dsRNAs or small hairpin RNAs into siRNAs. Particular exemplary sequences of siRNA are readily available to those of skill in the art through published literature and siRNA is commercially available from, for example, Qiagen. It is to be understood that the present disclosure is not to be limited to any particular siRNA sequence, but rather the present disclosure broadly describes the incorporation of siRNA into or with rosette nanotubes. One of skill in the art will readily recognize that all siRNA sequences, given the similar structure and function of covalently connected nucleotides, can be incorporated into or complexed with rosette nanotubes using the methods described herein and that an exhaustive listing of publicly known siRNA sequences need not be provided herein.

According to additional aspects, DNA includes any DNA desired to be expressed by a cell. DNA includes genes having known functions and expressing known proteins. Likewise, DNA suitable for transfecting a cell will be apparent to those of skill in the art of transfection and gene expression.

Manufacture and Use of Transfection Complexes

The present disclosure is directed to methods of forming a transfection complex, for example, by mixing one or more nucleic acids with fully formed rosette nanotubes or modules that self-assemble into rosette nanotubes, such as the compounds of Formula I or Formula II. According to one aspect, fully formed rosette nanotubes in the form of a powder is dissolved in water and heated to boiling. The solution is then cooled to room temperature. One or more nucleic acids in the form of a solution is then added to the solution of nanotubes at a suitable temperature and for a suitable period of time until a complex of the nanotube and one or more nucleic acids forms. Suitable ratios of the nucleic acid to nanotube include about 0.01:1 (wt/wt) to about 1:0.1 (wt/wt).

The invention is further directed to transfection complexes, which include small RNA, such as siRNA and a rosette nanotube. Transfection complexes in accordance with the present invention may include any of the rosette nanotubes of the present invention in combination with small RNA known to those of skill in the art.

According to certain aspects, cells within the scope of the present invention that can be transfected include osteoblasts, fibroblasts, stem cells, neuronal cells, connective tissue cells, keratinocytes, cardiac myocytes, chondrocytes, proteoglycans, synoviocytes, adipose, phagocytic, blood monocytes, mesenchymal stem cells, neural stem cells, islet cells, hepatocytes, smooth muscle cells, urothelial cells, neurons, Schwann cells, microgial cells, cancerous and non-cancerous cells, epithelial cells, endothelial cells, myofibroblasts, osteoclasts, macrophages, leukocytes, osteocytes, astrocytes etc. and the like. Additional cells include bacterial cells such as *Staphylococcus aureus, Staphylococcus epidermis, Pseudomonas aeruginosa*, MRSA, *E. coli, candida* (yeast), *Candida albacans, Streptococcus pneumoniae, Neisseria meningitides, Haemophilus influenzae, Streptococcus agalactiae, Listeria monocytogenes, Mycoplasma pneumoniae, Chlamydia pneumoniae, Legionella pneumophila, Mycobacterium*, tuberculosis, *Streptococcus pyogenes, Chlamydia trachomatis, Neisseria gonorrhoeae, Treponema pallidum, Ureaplasma urealyticum, Haemophilus ducreyi, Helicobacter pylori, Campylobacter jejuni, Salmonella, Shigella, Clostridium*, Enterobacteriaceae, *Staphylococcus saprophyticus* and the like. The above list is intended to be exemplary and not exhaustive. One of skill in the art will readily be able to identify additional cells within the scope of the present disclosure, which is directed to toward cells present in joints, tissue and/or organs.

In general, a cell to be transfected includes, but is not limited to, any animal, plant or bacterial cell that is susceptible to intracellular delivery of DNA or RNA such as siRNA using the transfection complex of the present invention either in vitro or in vivo. For example, cells from different species such as human, mouse, rat, pig, chicken, etc. may be used according to the present disclosure. Likewise, cells from different tissues or organs, such as cartilage (e.g, ear, nose, rib cage, bronchial tube, intervertebral disc, hyaline, fibrous, elastic), connective tissue (e.g. loose, dense, adipose, fibrous, elastic, lymphoid), conjunctive tissue, fibers (e.g., collagenous, elastic, reticular), synovium, neuronal tissue, muscle tissue, ligament, tendon, busae, fibroblast, beast cells, macrophages from the immune system, and astrocytes from the neuronal system may be used. Likewise, primary cells obtained directly from animals, plants or bacteria may be used and cell lines, such as commercially available immortalized cell, may be used. Likewise, normal cells may be used and diseased cells may be used, such as cancer cells. For example, suitable cellular targets include, without limitation, epithelial cells, endothelial cells, keratinocytes, fibroblasts, muscle cells, hepatocytes, blood cells such as T lymphocytes, B lymphocytes, monocytes, macrophages, neutrophils, eosinophils, megakaryocytes, granulocytes, various stem or progenitor cells, in particular hematopoietic stem or progenitor cells, e.g., as obtained from bone marrow, umbilical cord blood, peripheral blood, fetal liver, and the like. In certain aspects, the cell is selected from the group consisting of synoviocytes, fibroblasts, monocytes, chondrocytes, collagen, endothelial cells, connective tissue cells, neuronal cells, muscle cells, hematopoietic stem cells and tumor cells.

According to certain embodiments, the cells include one or more cells selected from the group consisting of transformed, recombinant, malignant, and primary cell lines. It is believed that the rosette nanotubes of the present invention will be effective as carriers of DNA or RNA such as siRNA in most, if not all cell types and cell lines. Since complexes of the rosette nanotubes and nucleic acids are composed of covalently bound base pairs, one of skill would expect that such complexes will be universally recognized by all cell types for transfecting purposes.

Methods of transfecting cells in accordance with the present invention may also include forming the transfection complex by combining in aqueous media the modules of the rosette nanotube and one or more DNA sequences and/or one or more RNA sequences. The complex is allowed to form. Cells are then contacted with the complex. According to one aspect, one of skill in the art will recognize from the benefit of the present disclosure that doses, concentrations, ratios and conditions of RNT/nucleic acids incorporation can be within ranges. For example, between about 1 µL to about 100 µL, for example 10 µL, of 1 mg/mL RNTs can be mixed with about 1 µL to about 100 µL, for example 20 µL, of 5 µM nucleic acids, such as siRNA, miRNA, nucleic acid probes or other nucleic acids, at a temperature of between about 0° C. to about 37° C. for between about 0.5 hours to about 48 hours and added into 1 mL cell culture medium for transfection. For example, the combination of RNT and nucleic acids can be maintained at 4° C. for 24 hours or can be maintained at room temperature for two hours. Mixing can be accomplished by simple mixing, mixing while heating to about 60° C. to about 100° C., sonication or other methods known to those of skill in the art. If heated, the combination may then be subjected to a temperature of between about 0° C. to about 37° C. for between about 0.5 hours to about 48 hours to result in formation or assembly of the nanotube/nucleic acid complex. For example, nanotubes can be modified to modulate the surface charge of the nanotubes comprising one or more DNA sequence and/or one or more RNA sequences by varying the RNT/nucleic acid ratio. A skilled person in the arts would recognize that cartilage, for example, is a negatively charged tissue matrix and nanotube carrying an overall positive charge would increase the residence time of such Nanopieces in cartilage tissue.

Method of Treatment

The present invention also provides methods of treating tissue, organ and/or joint disease comprising using the complexes or compositions of the present invention. In particular, methods are provided for treating a patient having a tissue, organ or joint disease, by administering to the patient a therapeutically effective amount of a complex or composition of the present invention. For in vivo therapies based on local injection (e.g., intra-articularly, intratumoral, and intramuscularly) the RNT/small RNA complex is advantageously water soluble and so may be administered as an aqueous injection.

According to aspects of the present disclosure, composites of rosette nanotubes and small RNA can be combined with a pharmaceutically acceptable agent and administered as a delivery composition to an individual for therapeutic purposes.

In accordance with certain examples, complexes of the present invention can be incorporated into pharmaceutical compositions suitable for administration. Such compositions typically comprise the complexes disclosed here and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Therapeutic Applications

Also encompassed are methods for treating a patient having a tissue, organ and/or joint disease, by administering to the patient cells that have been transfected by the methods disclosed herein. An aspect of an ex vivo delivery method of the present invention may include for example, (i) removing a cell from a subject; (ii) introducing siRNA into a cell by contacting the cell with a delivery composition (transfection complex or composition comprising such a transfection complex) comprising siRNA and a rosette nanotube; and (iii) reintroducing the cell into the subject. In addition, nanotubes having nucleic acids complexed therewith as described herein may be delivered in vivo to an individual in need of treatment where the nanotubes having nucleic acids complexed therewith enter cells within the individual and the nucleic acids regulate cellular expression of proteins. For example the nucleic acids may silence genes in a therapeutic manner to the extent that a protein is not expressed resulting in treatment or the nucleic acids may be expressed by the cell to produce proteins in a therapeutic manner resulting in treatment.

Examples of joint diseases (e.g. synovial, fibrous, cartilagenoius) potentially treatable with the complex, compositions, and methods include, but are not limited to the following: autoimmune, degenerative, inflammatory, infectious, cancerous, viral, fungal, injured or trauma derived. These joint diseases may be the primary disease or may be caused by an existing disease and/or illness. Examples include polymyalgia rheumatica, rheumatoid arthritis, multiple sclerosis, Charcot's Joint, osteoarthritis, juvenile onset of rheumatoid arthritis (JRA), system lupus erythematosus (SLE), psoriatic arthritis, inflammatory bowel disease (MS) arthritis, Whipple's disease, intestinal lipodystrupjy, ankylosing spondylitis (AS), reactive arthritis, Still's disease, avascular necrosis, bursitis, fibromyalgia, gout, hemochromatosis, hypothyroidism, lupus, Lyme disease, Fifths disease, osteomalacia, osteomyelitis, Paget's disease of bone, pseudogout, rickets, septic arthritis, tendinitis, diabetes, Ehlers-Danlos syndrome, costochondritis, Perthes' disease, Marfan syndrome, rheumatic fever, tubercular arthritis, pigmented villonodular synovitis, scleroderma, polymyositis, erythema nodosum, neuropathic arthropathy, sickle-cell disease, acromegaly, amyloidosis, acute crystal synovitis, pyogenic bacterial infection, scurvy, hemophilia, achondroplasia, herniation, diffuse iodophatic skeletal hyperostosis (DISH), ganglion, lumbar spinal stenosis, sacrolilac joint pain, SAPHO syndrome, polycythemia, Raynaud's phenomenon, hydroxyapatite, Behcet's syndrome, Felt's syndrome, hepatitis B, primary Sjoegrens, and polychondritis.

In another aspect of the invention, joint disease can also be the result of genetics, trauma (e.g., meniscus tears), mechanical injury (e.g., repetitive motion), nutrition deficiencies, and joint mal-alignment. Joints having suffered from an initial injury and/or trauma often develop joint disease over a period of time.

Examples of tissue diseases (e.g. epithelial, connective, muscle and nervous tissue) potentially treatable with the complex, compositions, and methods include, but are not limited to the following: autoimmune, degenerative, inflammatory, infectious, cancerous, viral, fungal, injured or trauma derived. These tissue and/or organ diseases may be the primary disease or may be caused by an existing disease and/or illness. Examples include amyloidosis, atiral fibrillation, convulsion, cramp, dermatomyositis, enchondroma, fibroma, lumbao, heritable connective tissue disorder (e.g., Marfan syndrome, Peyronie's disease, Ehlers-Danlos syndrome, Osteogenesis imperfecta, Stickler syndrome, Alport syndrome, Congenital contractural arachnodactyly), autoimmune connective tissue disorder (e.g., systemic lupus erythematosus (SLE), rheumatoid arthritis, Scleroderma, Sjoegren's syndrome, mixed connective tissue disease, psoriatic arthritis), scurvy, muscle disease (e.g., muscle tumour, muscular dystrophy, disuse atrophy, denervation atrophy, Duchenne muscular dystrophy, facioscapulohumoral muscular dystrophy), hepatic diseasemyasthenia gravis, myopathy, myositis, myositis ossificans, cancer, fibromyalgia, muscle fatigue, spasm, spasticity, sprain, strain, brain injury, spinal cord injury, gliomas, neuroeptheliomatous, hypertension, cardiovascular disease, diabetes, Alzheimer's disease, cystitis, AIDS, rickets, and nerve sheath tumors. Examples of tissues, organs and/or body systems affected by disease and may be treated with the compositions, and methods described therein, but are not limited to the following: Immune system, senory organs (e.g., organs of tase, smell, sight, hearing), digestive system (e.g., mouth, fauces, pharynx, esophagus, abdomen, stomach, small intestine, large intestine, liver, pancreas), urogenital apparatus, endocrinological systemt, metabolism, cardiovascular system (e.g., heart, blood pressure, arteries), hematology (e.g., blood chemistry), urinary organs (e.g., kidneys, ureters, urinary bladder, male urethra, female urethra, male gential organs (e.g., testes and their covering, ductus deferens, vesiculae seminales, ejaculatory ducts, penis, prostate, bulbourethral glands), female genital organs (e.g., ovaries, uterine tube, uterus, vagina, clitoris, Bartholin's glands, external organs, mammae)), ductless glands (e.g., thyroid, parathyroid, thymus, hypophysis cerebri, pineal body, chromaphil and corticol systems, spleen), reproduction, respiratory (e.g., larynx, trachea, bonchi, pleurae, mediastinum, lungs), central nervous system (e.g., nerves, nerve fibers), skin, epithelial (e.g., simple, stratified, pseudostratified columnar, glandular), connective (e.g., loose connective (e.g., areolar, adipose, reticular), and dense connective (e.g., dense regular, dense irregular)), cartilage (e.g., Hyaline, elastic, fibrous), muscle (e.g., skeletal muscle (e.g., type I, II, IIa, IIx, IIb), cardiac muscle, smooth muscle), nervous (e.g., neuron (e.g., motor neurons, interneuron, sensory neuron), neuroglia, spinal cord, nerves, brain).

In another aspect of the invention, cancers can also reside in the joint, tissue and/or organ either as a primary tumor (e.g., sarcoma, hemangiopericytoma, connective tissue neoplasm, chondroma, chondrosarcoma) or as a result of metastasis of a primary tumor at a different location in the body of the subject.

Ex vivo and in vivo gene therapy with siRNA can also be used in joint, tissue, and/or organ disease. These RNAi applications toward joint disease include, but are not limited to, 1) targeting proteins or enzymes relevant in the disease state; 2) targeting or reducing expression of factors that are relevant in the disease state; and 3) targeting genes to maintain or restore joint health and homeostasis. For example, genes of the current invention may include ADAMTS (e.g., ADAMTS-4, ADAMTS-5), MMPs (e.g., MMP-1, MMP-3, MMP-9, MMP-13 and other MMPs), ILs (e.g., IL-1α, IL-1β, IL-2, IL-6, IL-8, IL-12, IL-15, IL-20, IL-21 and other ILs), IL receptors, IL receptor associated proteins, IL receptor antagonists, HLA-DRB1, PADI4, PTPN22, TNFAIP3, megakaryocyte stimulating factor, osteoprotegerin, activator of NF-α ligand, STAT4, CCR6, TNFR-1, TNFR-2, RIP, TRADD, PAD2-PAD4, FOX3, CD-25, FAP, DPP, CD26, MK2, SIRT-1, FoxO3a, miR-24, miR-125-5p, muR-203, miR-140, miR-365, miR-146a, miR-27a, TNF-α, HLA, collagen type II, aggrecan, prostaglandins, immunoglobulins, IFN-γ, GM-CSF, PDGF, FGF, VEGF, BMPs (e.g., BMP-2, BMP-4, BMP-7, and other BMPs), TGF-β, IGF-1, IGF-2 and, their related receptor protein and the like. For example, the following genes or proteins may promote arthritis such as rheumatoid arthritis: ADAMTS, MMPs, ILs, IL receptors, IL receptor associated proteins, HLA, DRB1, PADI4 gene, PTPN22 gene, TNFAIP3 gene, STAT4 gene, TNFR-1, TNFR-2, RIP, TRADD, PAD2-PAD4 proteins, CCR6 gene, miR-24, miR-125a-5p, mIR-365, miR-203, and miR-181a. In embodiments, the anti-miR-181a nucleic acid sequence comprises SEQ ID NO: 228 or SEQ ID NO: 229. Genes and protein can also prevent arthritis such as Juvenile idiopathic arthritis: FOXP3 and CD-25. Moreover, genes and proteins and their receptors and combinations thereof can also inhibit arthritis such as rheumatoid arthritis or osteoarthritis: IL receptor antagonists, MK2, FAP, DPP-4/CD26, SIRT-1/FoxO3a, miR-140 and miR-27a. Lastly, genes and proteins and their receptors and combinations thereof can mediate arthritis progression and joint tissue regeneration (such as cartilage regeneration): FGF, VEGF, BMPs, TGF-β, IGF-1, IGF-2, miR-146a.

Nanopieces deliver siRNA, antisense and/or anti-microRNA to knockdown genes and their related proteins and protein receptors (e.g., ADAMTS, MMPs, IL-1). In some embodiments, the anti-microRNA is anti-miR-24, anti-miR-125a-5p, anti-mIR-365, anti-miR-203, or anti-miR-181a. In an example, the anti-miR-181a nucleic acid sequence comprises SEQ ID NO: 228 or SEQ ID NO: 229. In another example, Nanopieces deliver miRNA and/or mRNA to increase the level of genes and their related proteins and protein receptors. For example, genes and expression their respective encoded proteins and/or corresponding protein receptors that promote arthritis or other joint diseases can be knocked down; while genes and expression of their encoded proteins and/or corresponding protein receptors that inhibit arthritis or other joint diseases can be increased. Gene expression and production of encoded proteins and/or corresponding protein receptors that mediate arthritis progression and joint tissue regeneration can be adjusted (either knocked down or increased) depending on the needs or clinical condition of the patient.

Ex vivo and in vivo gene therapy with siRNA could also be used in cancer of tissue and/or organs. These RNAi applications toward cancer include, but are not limited to, 1) reducing expression of growth factors, reducing proteins that augment the cell cycle (e.g., Raf-1, PI-3 kinase), growth factor receptors (e.g., EGFR, Her-2), or proteins critical for supporting cells of the tumor (e.g., VEGF, VEGFR1-2 for tumor endothelial cells); 2) targeting or reducing expression of factors that are anti-apoptotic (e.g., BCL-2); and 3) targeting proteins or enzymes that reduce immune activation toward tumor.

Cancers or neoplasms contemplated within the scope of the disclosure include, but are not limited to, carcinomas (i.e., malignant tumors derived from epithelial cells such as, for example, common forms of breast, prostate, lung and colon cancer), sarcomas (i.e., malignant tumors derived from connective tissue or mesenchymal cells), lymphomas (i.e., malignancies derived from hematopoietic cells), leukemias (i.e., malignancies derived from hematopoietic cells), germ cell tumors (i.e., tumors derived from totipotent cells. In adults most often found in the testicle or ovary; in fetuses, babies and young children, most often found on the body midline, particularly at the tip of the tailbone), blastic tumors (i.e., a typically malignant tumor which resembles an immature or embryonic tissue) and the like.

Examples of specific neoplasms intended to be encompassed by the present invention include, but are not limited to, acute lymphoblastic leukemia, myeloid leukemia, acute childhood myeloid leukemia, adrenocortical carcinoma, AIDS-related cancers, AIDS-related lymphoma, anal cancer, appendix cancer, astrocytoma (e.g., cerebellar, cerebral), atypical teratoid/rhabdoid tumor, basal cell carcinoma, extrahepatic bile duct cancer, bladder cancer, bone cancer, osteosarcoma and malignant fibrous histiocytoma, brain tumor (e.g., brain stem glioma, central nervous system atypical teratoid/rhabdoid tumors, central nervous system embryonal tumors, cerebellar astrocytoma, cerebral astrocytoma/malignant glioma, craniopharyngioma, ependymoblastoma, ependymoma, medulloblastoma, medulloepithelioma, pineal parenchymal tumors of intermediate differentiation, supratentorial primitive neuroectodermal tumors and/or pineoblastoma, visual pathway and/or hypothalamic glioma, brain and spinal cord tumors), breast cancer, bronchial tumors, Burkitt lymphoma, carcinoid tumor (e.g., gastrointestinal), carcinoma of unknown primary, central nervous system (e.g., atypical teratoid/rhabdoid tumor, embryonal tumors (e.g., lymphoma, primary), cerebellar astrocytoma, cerebral astrocytoma/malignant glioma, cervical cancer, chordoma, chronic lymphocytic leukemia, chronic myelogenous leukemia, chronic myeloproliferative disorders, colon cancer, colorectal cancer, craniopharyngioma, cutaneous T-cell lymphoma, central nervous system embryonal tumors, endometrial cancer, ependymoblastoma, ependymoma, esophageal cancer, Ewing family of tumors, extracranial germ cell tumor, extragonadal germ cell tumor, extrahepatic bile duct cancer, eye cancer (e.g., intraocular melanoma, retinoblastoma), gallbladder cancer, gastric cancer, gastrointestinal tumor (e.g., carcinoid tumor, stromal tumor (gist), stromal cell tumor), germ cell tumor (e.g., extracranial, extragonadal, ovarian), gestational trophoblastic tumor, glioma (e.g., brain stem, cerebral astrocytoma), hairy cell leukemia, head and neck cancer, hepatocellular cancer, Hodgkin lymphoma, hypopharyngeal cancer, hypothalamic and visual pathway glioma, intraocular melanoma, islet cell tumors, Kaposi sarcoma, kidney cancer, large cell tumors, laryngeal cancer (e.g., acute lymphoblastic, acute myeloid), leukemia (e.g., acute myeloid, chronic lymphocytic, chronic myelogenous, hairy cell), lip and/or oral cavity cancer, liver cancer, lung cancer (e.g., non-small cell, small cell), lymphoma (e.g., AIDS-related, Burkitt, cutaneous T cell, Hodgkin, non-Hodgkin, primary central nervous system), Waldenström macroglobulinemia, malignant fibrous histiocytoma of bone and/or osteosarcoma, medulloblastoma, medulloepithelioma, melanoma, merkel cell carcinoma, mesothelioma, metastatic squamous neck cancer, mouth cancer, multiple endocrine neoplasia syndrome, multiple myeloma/plasma cell neoplasm, mycosis fungoides, myelodysplastic syndromes, myelodysplastic/myeloproliferative diseases, myelogenous leukemia (e.g., chronic, acute, multiple), chronic myeloproliferative disorders, nasal cavity and/or paranasal sinus cancer, nasopharyngeal cancer, neuroblastoma, non-Hodgkin lymphoma, non-small cell lung cancer, oral cancer, oral cavity cancer, oropharyngeal cancer, osteosarcoma and/or malignant fibrous histiocytoma of bone, ovarian cancer (e.g., ovarian epithelial cancer, ovarian germ cell tumor, ovarian low malignant potential tumor), pancreatic cancer (e.g., islet cell tumors), papillomatosis, paranasal sinus and/or nasal cavity cancer, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell cancer, renal, pelvis and/or ureter, transitional cell cancer, respiratory tract carcinoma involving the nut gene on chromosome 15, retinoblastoma, rhabdomyosarcoma, salivary gland cancer, sarcoma (e.g., Ewing family of tumors, Kaposi, soft tissue, uterine), Sézary syndrome, skin cancer (e.g., non-melanoma, melanoma, merkel cell), small cell lung cancer, small intestine cancer, soft tissue sarcoma, squamous cell carcinoma, squamous neck cancer with occult primary, metastatic, stomach cancer; supratentorial primitive neuroectodermal tumors; T-cell lymphoma, cutaneous; testicular cancer, throat cancer; thymoma and/or thymic carcinoma, thyroid cancer, transitional cell cancer of the renal, pelvis and/or ureter; trophoblastic tumor, unknown primary site carcinoma, urethral cancer, uterine cancer, endometrial, uterine sarcoma, vaginal cancer, visual pathway and/or hypothalamic glioma, vulvar cancer, Waldenström macroglobulinemia, Wilms tumor and the like. For a review, see the National Cancer Institute's Worldwide Website (cancer.gov/cancertopics/alphalist). One of skill in the art will understand that this list is exemplary only and is not exhaustive, as one of skill in the art will readily be able to identify additional cancers and/or neoplasms based on the disclosure herein.

Examples of primary cancers as joint disease comprise connective tissue neoplasm, hemangiopericytoma, sarcoma, chondroma, chondrosarcoma, bone and the like.

Examples of genetic and/or non-neoplastic diseases potentially treatable with the complex, compositions, and methods include, but are not limited to the following: adenosine deaminase deficiency; purine nucleoside phosphorylase deficiency; chronic granulomatous disease with defective p47phox; sickle cell with HbS, β-thalassemia; Faconi's anemia; familial hypercholesterolemia; phenylketonuria; ornithine transcarbamylase deficiency; apolipoprotein E deficiency; hemophilia A and B; muscular dystrophy; cystic fibrosis; Parkinsons, retinitis pigmentosa, lysosomal storage disease (e.g., mucopolysaccharide type 1, Hunter, Hurler and Gaucher), diabetic retinopathy, human immunodeficiency virus disease virus infection, acquired anemia, cardiac and peripheral vascular disease, osteoporosis and arthritis. In some of these examples of diseases, the therapeutic gene may encode a replacement enzyme or protein of the genetic or acquired disease, an antisense or ribozyme molecule, a decoy molecule, or a suicide gene product.

Recombinant cells may be produced using the complexes of the present invention. Resulting recombinant cells can be delivered to a subject by various methods known in the art. In certain embodiments, the recombinant cells are injected, e.g., subcutaneously or intra-articular. Recombinant blood cells (e.g., hematopoietic stem or progenitor cells) are preferably administered intravenously or intra-articular. The cells can also be encapsulated in a suitable vehicle and then implanted in the subject (see, e.g., Dionne et al. PCT Publication WO92/19195, dated Nov. 12, 1992). The amount of cells administered depends on a variety of factors known in the art, for example, the desired effect, subject state, rate of expression of the chimeric polypeptides, etc., and can readily be determined by one skilled in the art.

Another aspect of the present disclosure provides methods of introducing a therapeutic or diagnostic agent into a cell or tissue matrix using rosette nanotubes. Biologically active agents also called "therapeutic agents" or "drugs" are complexed with rosette nanotubes to form nanotube-drug complex, which can enter the cell and/or tissue and release the drug. A person of skill in the art will recognize the drug as being compounds which include any synthetic or natural element or are compounds which when introduced into the body causes a desired biological response, such as altering body function. Non-limiting examples of drugs or biologically active agents or therapeutic agents include anti-inflammatory agents (e.g., steroidal and non-steroidal), analgesics, anesthetics, chemotherapeutic agents, anti-proliferative agents, cytotoxic agents, steroidal agents, antifungal agents, antiviral agents, immunosuppressive agents, and include small molecules. Further non-limiting examples of drugs or biologically active agents or therapeutic agents include peptides (such as RGD, KRSR, YIGSR, IKVAV and the like), aromatic bioactive molecules such as tamoxifen, dexamethasone, vitamin K and the like, antibiotics such as penicillin, streptomycin, gentamycin and the like, glucosamine, chondroitin, cortisone, glucocorticoids, hydrocortisone, hyaluronic acid, hydrocortisone, gentamycin and the like, and proteins such as bone morphogenetic proteins, matrillins and the like. Drugs or biologically active agents or therapeutic agents may be hydrophobic or hydrophilic. According to one aspect, the rosette nanotubes include hydrophobic moieties within the core portion of the structure where hydrophobic drugs, biologically active agents or therapeutic agents may be located in the composite. According to another aspect, the rosette nanotubes of the present disclosure may have hydrophilic outer surfaces to facilitate administration of the complexes in physiological environments.

Examples of analgesic agents include opioid analgesics and adjuvent analgesics within the scope of the present disclosure that can be complexed with rosette nanotubes include clonidine, tizanidine, gapapentin, pregabalin, lamotrigine, oxcarbazepine, topiramate, levitiracetam, tigabine, zonisamide, carbamazepine, valprioc acid, phenytoin, amitriptyline, nortriptyline, desipramine, imipramine, doxepin, paroxetine, citalopram, escitalopram, fluoxetine, venlafaxine, duloxetine, bupriopion, mexiletine, lidocaine, baclofen, cyclobenzaprine, orphenadrine, metaxalone, methocarbamol, morphine, hydrocodone, hydromorphone, tramadol, oxycodone, oxymorphone, fentanyl, methadone, capsaicin, loperamide, naloxone, demerol, buprenorphine, butorphanol, codeine, levorphanol, meperidine, methadone, nabuphine, propoxyphene, and pentazocine.

Examples of non-opioid and anti-inflammatory agents within the scope of the present disclosure that can be complexed with rosette nanotubes include acetaminophen, aspirin, diflunisal, choline magnesium trisalicylate, salsalate, ibuprofen, naproxen, ketoprofen, fluriprofen, oxaprozin, indomethacin, sulindac, nabumetone, diclofenac, ketorolac, tolectin, piroxicam, meloxicam, mefenamic acid, meclofenamate, celecoxib, allopurinol, dextromethorphan, pegloticase, dexibuprofen, etodolac, fenoprofen, flufenamic acid, flupbiprofen, lornoxicam, loxoprofen, meclofenamic acid, piroxicam, tenoxicam, tolmetin, and tolfenamic acid.

Examples of immunosuppresive agents within the scope of the present disclosure that can be complexed with rosette nanotubes include alkylating agents, antimetabolites, high dose corticosteroids, azathioprine, mycophenolate mofetil, cyclosporine, methotrexate, leflunomide, cyclophosphamide, chlorambucil, nitrogen mustard, abacavir, abciximab, adalimumab, aldesleukin, altretamine, aminoglutethimide, amprevenir, anakinra, anastrozole, aspariginase, azathioprine, basiliximab, betamethasone, bleomycin, busulfan, capecitabine, carboplatin, carmustine, chlorambucil, cidofovir, cisplatin, cladribine, cortisone, cyclosporine, cytarabine, decarbazine, dacuzumab, dactinomycin, daunorubicin, delaviridine, dexamethasone, didanosine, doxorubicin, efavirenz, epirubicin, estramustine, etanercept, etoposide, exemestane, foxuridine, fludarabine, fluorouracil, flutamide, gemcitabine, gemtuzumab ozogamicin, hydrocortisone, hydroxychloroquine, hydroxyurea, idaubicin, ifosphamide, indinavir, infliximab, interferon alpha-2a, interferon alpha-2b, interferon beta-2b, interferon beta-2a, interferon gamma-1b, interleukin-2, irinotecan, isotretinoin, lamivudine, leflunomide, letrozole, leuprolide, mechloethamine, megestrol, melphalan, mercaptopurine, methotrexate, methylpregnisolone, mitomycin, mitotane, mitoxantrone, mycophenolate, nelfinavir, nevirapine, paclitaxel, pegaspargase, penicillamine, pentostatin, pimecroslimus, pipobroman, plicamycin, prednisolone, predisone, priliximab, procarbazine, ritonavir, rituximab, saquinavir, sargamomstim, stavudine, strepozocin, tacrolismus, temozolomide, teniposide, testolactone, thioguanine, thiotepa, trastuzumab, tretinoin, triamcinolone, uracil mustard, valrubucin, vinblastine, vincristine, vinorelbine, zalcitabine, zidovudine.

Examples of antifungal agents within the scope of the present disclosure that can be complexed with rosette nanotubes include polyene, azole, allylamine, morpholine, and antimetabolite antifungal agents, e.g., amphotericin B, candicin, filipin, hamycin, natamycin, nystatin rimocidin, bifonazole, butoconazole, clotrimazole, econozole, fenticonazole, isoconazole, ketoconazole, luiconazole, miconazole, omoconazole, oxiconazole, sertaconazole, sulconazole, tioconazole, albaconazole, fluconazole, isavuconazole, traconazole, posaconazole, ravuconazole, terconazole, voriconazole, abafungin, amorolfin, butenafine, naftifine, terbinafine, anidulafungin, caspofungin, micafungin, benzoic acid, ciclopirox, griseofulvin, tolnaftate, and undecylenic acid.

Examples of antibiotic agent within the scope of the present disclosure that can be complexed with rosette nanotubes include aminoglycosides (e.g., amikacin, gentamicin, kanamycine, neomycine, metilmicin, tobramycin, paromomycin, streptomycin, spectinomycin), anasamycins (e.g., geldanamycin, herbimycin, riflaximin), loracerbef, carbapenems (e.g., ertapenem, doripenem, cilastatin, meropenem), cephalosporin (e.g. cefadroxil, cefazolin, cephalexin, cefaclor, cefamandole, cefoxitin, cefprozil, cefuroxime, cefixime, cefdinir, cefdotoren, cefotaxime, ceftibuten, ceftizoxime, cefepime, ceftaroline, ceftobioprole, teichoplanin, vancomycin, telavancin, clindamycin, lincomycin, daptomycin, azithromycin, clarithromycin, dirithromycin, erythromycin, roxithromycin, troleandomycin, telithromycin, spiramycin, azetreonam, flurazolidone, linezolid, posizolid, radezolid, torezolid, ampicillin, azolocillin, carbenicillin, cloxacillin, dicloxaxillin, pencillin), polypeptides (e.g. bacitracin, colistin, polymyxin B), Quinolones (e.g., ciproflaxin, enoxacin, gemifloxacin, norfloxacin), sulfonamides (e.g., malfenide, sulfamethizole, sulfasalazine, sulfadiazine), tetracyclines (e.g., demeclocycline, minocycline, doxycycline, tetracycline), clofazimine, dapsone, capreomycin, cycloserine, ethambutol, ethionamide, isoniazid, pyrazinamide, riflampicin, rifabutin, rifapentine, streptomycin, arsphenamine, chloramthenicol, foffmycin, fusidic acid, metronidazole, mupirocin, platensimycin, thiamphenicol, tigecycline, tinidazole, and trimethoprim.

Examples of drugs within the scope of the present disclosure that can be complexed with rosette nanotubes include glucosamine, chondroitin, cortisone, glucocorticoids, hydrocortisone, hyaluronic acid, hydrocortisone, and lurbicants (e.g. lubricin).

Examples of anti-cancer drugs within the scope of the present disclosure that can be complexed with rosette nanotubes include bortezomib ([(1R)-3-methyl-1-[[(2S)-1-oxo-3-phenyl-2-[(pyrazinylcarbonyl) amino]propyl]amino] butyl] boronic acid; MG-341; VELCADE®), MG-132 (N-[(phenylmethoxy)carbonyl]-L-leucyl-N-[(1S)-1-formyl-3-methylbutyl]-L-leucinamide); pyrimidine analogs (e.g., 5-fluorouracil, floxuridine, capecitabine, gemcitabine and cytarabine); purine analogs; folate antagonists and related inhibitors (e.g., mercaptopurine, thioguanine, pentostatin and 2-chlorodeoxyadenosine [cladribine]); folic acid analogs (e.g., methotrexate); antimitotic agents, including vinca alkaloids (e.g., vinblastine, vincristine, and vinorelbine) and alkylating agents such as nitrogen mustards (e.g., mechlorethamine, cyclophosphamide and analogs, melphalan, chlorambucil), ethylenimines and methylmelamines (e.g., hexamethylmelamine and thiotepa), alkyl sulfonates-busulfan, nitrosoureas (e.g., carmustine (BCNU) and analogs, streptozocin), trazenes-dacarbazinine (DTIC); microtubule disruptors (e.g., paclitaxel, docetaxel, vincristin, vinblastin, nocodazole, epothilones and navelbine, and teniposide); actinomycin, amsacrine, anthracyclines, bleomycin, busulfan, camptothecin, carboplatin, chlorambucil, cisplatin, cyclophosphamide, Cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide and etoposide (VP 16); dactinomycin (actinomycin D), daunorubicin, doxorubicin (adriamycin), idarubicin, anthracyclines, mitoxantrone, bleomycins, plicamycin (mithramycin) and mitomycin; L-asparaginase; antiplatelet agents; platinum coordination complexes (e.g., cisplatin, carboplatin), procarbazine, hydroxyurea, mitotane, aminoglutethimide; hormones and hormone analogs (e.g., estrogen, tamoxifen, goserelin, bicalutamide, nilutamide); aromatase inhibitors (e.g., letrozole, anastrozole); anticoagulants (e.g., heparin, synthetic heparin salts and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; antisecretory agents (e.g., breveldin); immunosuppressives (e.g., cyclosporine, tacrolimus (FK-506), sirolimus (rapamycin), azathioprine, mycophenolate mofetil); anti-angiogenic compounds (e.g., TNP-470, genistein) and growth factor inhibitors (e.g., vascular endothelial growth factor (VEGF) inhibitors, fibroblast growth factor (FGF) inhibitors, epidermal growth factor (EGF) inhibitors); angiotensin receptor blockers; nitric oxide donors; anti-sense oligonucleotides; antibodies (e.g., trastuzumab (HERCEPTIN®), AVASTIN®, ERBITUX®); cell cycle inhibitors and differentiation inducers (e.g., tretinoin); mTOR (mammalian target of rapamycin) inhibitors (e.g., everolimus, sirolimus); topoisomerase inhibitors e.g., doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan); corticosteroids (e.g., cortisone, dexamethasone, hydrocortisone, methylpednisolone, prednisone, and prenisolone); growth factor signal transduction kinase inhibitors; mitochondrial dysfunction inducers; and caspase activators and the like.

Examples of anti-cancer drugs within the scope of the present disclosure that can be complexed with rosette nanotubes include alemtuzumab; aminoglutethimide; amsacrine; anastrozole; asparaginase; bevacizumab; bicalutamide; bleomycin; bortezomib; buserelin; busulfan; campothecin; capecitabine; carboplatin; carmustine; CeaVac; cetuximab; chlorambucil; cisplatin; cladribine; clodronate; colchicine; cyclophosphamide; cyproterone; cytarabine; dacarbazine; daclizumab; dactinomycin; daunorubicin; dienestrol; diethylstilbestrol; docetaxel; doxorubicin; edrecolomab; epirubicin; epratuzumab; erlotinib; estradiol; estramustine; etoposide; exemestane; filgrastim; fludarabine; fludrocortisone; fluorouracil; fluoxymesterone; flutamide; gemcitabine; gemtuzumab; genistein; goserelin; huJ591; hydroxyurea; ibritumomab; idarubicin; ifosfamide; IGN-101; imatinib; interferon; irinotecan; ironotecan; letrozole; leucovorin; leuprolide; levamisole; lintuzumab; lomustine; MDX-210; mechlorethamine; medroxyprogesterone; megestrol; melphalan; mercaptopurine; mesna; methotrexate; mitomycin; mitotane; mitoxantrone; mitumomab; nilutamide; nocodazole; octreotide; oxaliplatin; paclitaxel; pamidronate; pentostatin; pertuzumab; plicamycin; porfimer; procarbazine; raltitrexed; rituximab; streptozocin; sunitinib; suramin; tamoxifen; temozolomide; teniposide; testosterone; thalidomide; thioguanine; thiotepa; titanocene dichloride; topotecan; tositumomab; trastuzumab; tretinoin; vatalanib; vinblastine; vincristine; vindesine; and vinorelbine and the like.

Examples of NMDA receptor antagonists within the scope of the present disclosure that can be complexed with rosette nanotubes include LY 274614 (decahydro-6-(phosphonomethyl)-3-isoquinolinecarboxylic acid), LY 235959 [(3S,4aR,6S,8aR)-decahydro-6-(phosphonomethyl)-3-isoquinolinecarboxylic acid], LY 233053 ((2R,4S)-rel-4-(1H-tetrazol-5-yl-methyl)-2-piperidine carboxylic acid), NPC 12626 (α-amino-2-(2-phosphonoethyl)-cyclohexanepropanoic acid), reduced and oxidized glutathione, carbamathione, AP-5 (5-phosphono-norvaline), CPP (4-(3-phosphonopropyl)-2-piperazine-carboxylic acid), CGS-19755 (seifotel, cis-4(phono-methyl)-2-piperidine-carboxylic acid), CGP-37849 ((3E)-2-amino-4-methyl-5-phosphono-3-pentenoic acid), CGP 39551 ((3E)-2-amino-4-methyl-5-phosphono-3-pentenoic acid, 1-ethyl ester), SDZ 220-581 [(αS)-α-amino-2'-chloro-5-(phosphonomethyl)-[1,1'-biphenyl]-3-propanoic acid], and S-nitrosoglutathione. amantadine, aptiganel (CERESTAT®, CNS 1102), caroverine, dextrorphan, dextromethorphan, fullerenes, ibogaine, ketamine, lidocaine, memantine, dizocilpine (MK-801), neramexane (MRZ 2/579, 1,3,3,5,5-pentamethyl-cyclohexanamine), NPS 1506 (delucemine, 3-fluoro-γ-(3-fluorophenyl)-N-methyl-benzenepropanamine hydrochloride), phencyclidine, tiletamine and remacemide. acamprosate, arcaine, conantokin-G, eliprodil (SL 82-0715), haloperidol, ifenprodil, traxoprodil (CP-101,606), and Ro 25-6981 [(±)-(R,S)-α-(4-hydroxyphenyl)-β-methyl-4-(phenylmethyl)-1-piperidine propanol]; aminocyclopropanecarboxylic acid (ACPC), 7-chlorokynurenic acid, D-cycloserine, gavestinel (GV-150526), GV-196771A (4,6-dichloro-3-[(E)-(2-oxo-1-phenyl-3-pyrrolidinylidene)methyl]-1H-indole-2-carboxylic acid monosodium salt), licostinel (ACEA 1021), MRZ-2/576 (8-chloro-2,3-dihydropyridazino[4,5-b]quinoline-1,4-dione 5-oxide 2-hydroxy-N,N,N-trimethyl-ethanaminium salt), L-701,324 (7-chloro-4-hydroxy-3-(3-phenoxyphenyl)-2 (1H)-quinolinone), HA-966 (3-amino-1-hydroxy-2-pyrrolidinone), and ZD-9379 (7-chloro-4-hydroxy-2-(4-methoxy-2-methylphenyl)-1,2,5,10-tetra-hydropyridanizo[4,5-b] quinoline-1,10-dione, sodium salt); oxidized and reduced glutathione, S-nitrosoglutathione, sodium nitroprusside, ebselen, and disulfiram, DETC-MeSO, carbamathione; CNQX (1,2,3,4-tetrahydro-7-nitro-2,3-dioxo-6-quinoxalinecarbonitrile) and DNQX (1,4-dihydro-6,7-dinitro-2,3-quinoxalinedione) and the like.

Examples of subtype-specific NMDA receptor antagonists within the scope of the present disclosure that can be complexed with rosette nanotubes include arcaine, argiotoxin636, Co 101244 (PD 174494, Ro 63-1908, 1-[2-(4-hydroxyphenoxy)ethyl]-4-[(4-methylphenyl)methyl-4-piperidinol], despiramine, dextromethorphan, dextrorphan, eliprodil, haloperidol, ifenprodil, memantine, philanthotoxin343, Ro-25-6981 ([(±)-(R*, S*)-α-(4-hydroxyphenyl)-β-methyl-4-(phenylmethyl)-1-piperidine propanol]), traxoprodil (CP-101,606), Ro 04-5595 (1-[2-(4-chlorophenyl)ethyl]-1,2,3,4-tetrahydro-6-methoxy-2-methyl-7-isoquinolinol), CPP [4-(3-phosphonopropyl)-2-piperazinecarboxylic acid], conantokin G, spermine, spermidine, NVP-AAM077 [[[[(1S)-1-(4-bromophenyl)ethyl]amino](1,2,3,4-tetrahydro-2,3-dioxo-5-quinoxalinyl)methyl]-phosphonic acid]; and 1-(phenanthrene-2-carbonyl) piperazine-2,3-dicarboxylic acid and the like.

Examples of anticonvulsants within the scope of the present disclosure that can be complexed with rosette nanotubes include barbiturates (e.g., mephobarbital and sodium pentobarbital); benzodiazepines, such as alprazolam (XANAX®, lorazepam, clonazepam, clorazepate dipotassium, and diazepam (VALIUM®); GABA analogs, such as tiagabine, gabapentin (an α2δ antagonist, NEURONTIN®), and β-hydroxypropionic acid; hydantoins, such as 5,5-diphenyl-2,4-imidazolidinedione (phenytoin, DILANTIN®) and fosphenytoin sodium; phenyltriazines, such as lamotrigine; succinimides, such as methsuximide and ethosuximide; 5H-dibenzazepine-5-carboxamide (carbamazepine); oxcarbazepine; divalproex sodium; felbamate, levetiracetam, primidone; zonisamide; topiramate; and sodium valproate.

Examples of psychiatric drugs within the scope of the present disclosure that can be complexed with rosette nanotubes include Abilify, Adapin, Adartrel, Adderall, Alepam, Alertec, Aloperidin, Alplax, Alprax, Alprazolam, Alviz, Alzolam, Amantadine, Ambien, Amisulpride, Amitriptyline, Amoxapine, Amfebutamone, Anafranil, Anatensol, Ansial, Ansiced, Antabus, Antabuse, Antideprin, Anxiron, Apo-Alpraz, Apo-Primidone, Apo-Sertral, Aponal, Apozepam, Aripiprazole, Aropax, Artane, Asendin, Asendis, Asentra, Ativan, Atomoxetine, Aurorix, Aventyl, Axoren, Beneficat, Benperidol, Bimaran, Bioperidolo, Biston, Brotopon, Bespar, Bupropion, Buspar, Buspimen, Buspinol, Buspirone, Buspisal, Cabaser, Cabergoline, Calepsin, Calcium carbonate, Calcium carbimide, Calmax, Carbamazepine, Carbatrol, Carbolith, Celexa, Chloraldurat, Chloralhydrat, Chlordiazepoxide, Chlorpromazine, Cibalith-S, Cipralex, Citalopram, Clomipramine, Clonazepam, Clozapine, Clozaril, Concerta, Constan, Convulex, Cylert, Dapotum, Daquiran, Daytrana, Defanyl, Dalmane, Damixane, Demolox, Depad, Depakene, Depakote, Depixol, Desyrel, Dostinex, dextroamphetamine, Dexedrine, Diazepam, Didrex, Divalproex, Dogmatyl, Dolophine, Droperidol, Edronax, Efectin, Effexor (Efexor), Eglonyl, Einalon S, Elavil, Elontril, Endep, Epanutin, Epitol, Equetro, Escitalopram, Eskalith, Eskazinyl, Eskazine, Etrafon, Eukystol, Eunerpan, Faverin, Fazaclo, Fevarin, Finlepsin, Fludecate, Flunanthate, Fluoxetine, Fluphenazine, Flurazepam, Fluspi, Fluspirilen, Fluvoxamine, Focalin, Gabapentin, Geodon, Gladem, Glianimon, Halcion, Halomonth, Haldol, Haloperidol, Halosten, Imap, Imipramine, Imovane, JJanimine, Jatroneural, Kalma, Keselan, Klonopin, Lamotrigine, Largactil, Lecital, Levomepromazine, Levoprome, Leponex, Lexapro, Libritabs, Librium, Linton, Liskantin, Lithane, Lithium, Lithizine, Lithobid, Lithonate, Lithotabs, Lorazepam, Loxapac, Loxapine, Loxitane, Ludiomil, Lunesta, Lustral, Luvox, Lyrica, Lyogen, Manegan, Manerix, Maprotiline, Mellaril, Melleretten, Melleril, Melneurin, Melperone, Meresa, Mesoridazine, Metadate, Methamphetamine, Methotrimeprazine, Methylin, Methylphenidate, Minitran, Mirapex, Mirapexine, Moclobemide, Modafinil, Modalina, Modecate, Moditen, Molipaxin, Moxadil, Murelax, Myidone, Mylepsinum, Mysoline, Nardil, Narol, Navane, Nefazodone, Neoperidol, Neurontin, Nipolept, Norebox, Normison, Norpramine, Nortriptyline, Novodorm, Olanzapine, Omca, Oprymea, Orap, Oxazepam, Pamelor, Parnate, Paroxetine, Paxil, Peluces, Pemoline, Pergolide, Permax, Permitil, Perphenazine, Pertofrane, Phenelzine, Phenytoin, Pimozide, Piportil, Pipotiazine, Pragmarel, Pramipexole, Pregabalin, Primidone, Prolift, Prolixin, Promethazine, Prothipendyl, Protriptyline, Provigil, Prozac, Prysoline, Psymion, Quetiapine, Ralozam, Reboxetine, Resimatil, Restoril, Restyl, Requip, Rhotrimine, Risperdal, Risperidone, Rispolept, Ritalin, Rivotril, Ropark, Ropinerole, Rubifen, Rozerem, Sediten, Seduxen, Selecten, Serax, Serenace, Serepax, Serenase, Serentil, Seresta, Serlain, Serlift, Seroquel, Seroxat, Sertan, Sertraline, Serzone, Sevinol, Sideril, Sifrol, Sigaperidol, Sinequan, Sinqualone, Sinquan, Sirtal, Solanax, Solian, Solvex, Songar, Stazepin, Stelazine, Stilnox, Stimuloton, Strattera, Sulpiride, Sulpiride Ratiopharm, Sulpiride Neurazpharm, Surmontil, Symbyax, Symmetrel, Tafil, Tavor, Taxagon, Tegretol, Telesmin, Temazepam, Temesta, Temposil, Terfluzine, Thioridazine, Thiothixene, Thombran, Thorazine, Timonil, Tofranil, Tradon, Tramadol, Tramal, Trancin, Tranax, Trankimazin, Tranquinal, Tranylcypromine, Trazalon, Trazodone, Trazonil, Trialodine, Trevilor, Triazolam, Trifluoperazine, Trihexane, Trihexyphenidyl, Trilafon, Trimipramine, Triptil, Trittico, Troxal, Tryptanol, Ultram-Valium, Valproate, Valproic acid, Valrelease, Vasiprax, Venlafaxine, Vestra, Vigicer, Vivactil, Wellbutrin, Xanax, Xanor, Xydep, Zamhexal, Zeldox, Zimovane, Zispin, Ziprasidone, Zolarem, Zoldac, Zoloft, Zolpidem, Zonalon, Zopiclone, Zotepine, Zydis, Zyprexa and the like.

Examples of miscellaneous drugs within the scope of the present disclosure that can be complexed with rosette nanotubes include nortriptyline, amytriptyline, fluoxetine (PROZAC®), paroxetine HCl (PAXIL®), trimipramine, oxcarbazepine (TRILEPTAL®), eperisone, misoprostol (a prostaglandin $E_1$ analog), latanoprost (a prostaglandin F2 ⓐ analog) melatonin, and steroids (e.g., pregnenolone, triamcinolone acetonide, methylprednisolone, and other anti-inflammatory steroids) and the like.

Examples of antiviral drugs within the scope of the present disclosure that can be complexed with rosette nanotubes include Abacavir, Aciclovir, Acyclovir, Adefovir, Amantadine, Amprenavir, Ampligen, Arbidol, Atazanavir, Atripla (fixed dose drug), Boceprevir, Cidofovir, Combivir (fixed dose drug), Darunavir, Delavirdine, Didanosine, Docosanol, Edoxudine, Efavirenz, Emtricitabine, Enfuvirtide, Entecavir, Entry inhibitors, Famciclovir, Fixed dose combination (antiretroviral), Fomivirsen, Fosamprenavir, Foscarnet, Fosfonet, Fusion inhibitor, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Oseltamivir (Tamiflu), Peginterferon alfa-2a, Penciclovir, Peramivir, Pleconaril, Podophyllotoxin, Protease inhibitor (pharmacology), Raltegravir, Reverse transcriptase inhibitor, Ribavirin, Rimantadine, Ritonavir, Pyramidine, Saquinavir, Stavudine, Synergistic enhancer (antiretroviral), Tea tree oil, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), Zidovudine and the like.

Ex vivo and in vivo therapy and/or diagnostics could also be used in joint disease. These therapeutic and diagnostic applications toward these joint diseases include, but are not limited to, 1) targeting proteins or enzymes relevant in the disease state; 2) targeting or reducing expression of factors that are relevant in the disease state; and 3) targeting genes to maintain or restore joint health and homeostasis. For example, Nanopieces delivery of molecular probes to detect expression of inflammatory markers (e.g., cytokines, MMP, ADAMS) and the like or delivery of therapeutic agents to treat pain, inflammation, infection and the like can be used.

In another example, in vivo imaging technology to detect molecular changes at early stages of arthritis without harming articular cartilage was demonstrated. Osteoarthritis (OA) is one of the most common causes of disability. However, the lack of tools for early diagnosis of OA hampers the prevention and treatment of the disease to decelerate articular cartilage loss and alleviate suffering of patients. The OA Biomarker Initiative has identified a series of biomarkers, including Matrix metalloproteinases (MMP), which are elevated in articular cartilage during OA pathogenesis. However, detection of MMP protein levels or activities in serum may not be sensitive enough, while the more sensitive detection of MMP transcripts requires invasive procedure to obtain biopsy of articular joint tissue. Therefore, there is an urgent need to develop sensitive in vivo imaging technology to detect molecular changes at early stages of arthritis without harming articular cartilage.

Figure 51:
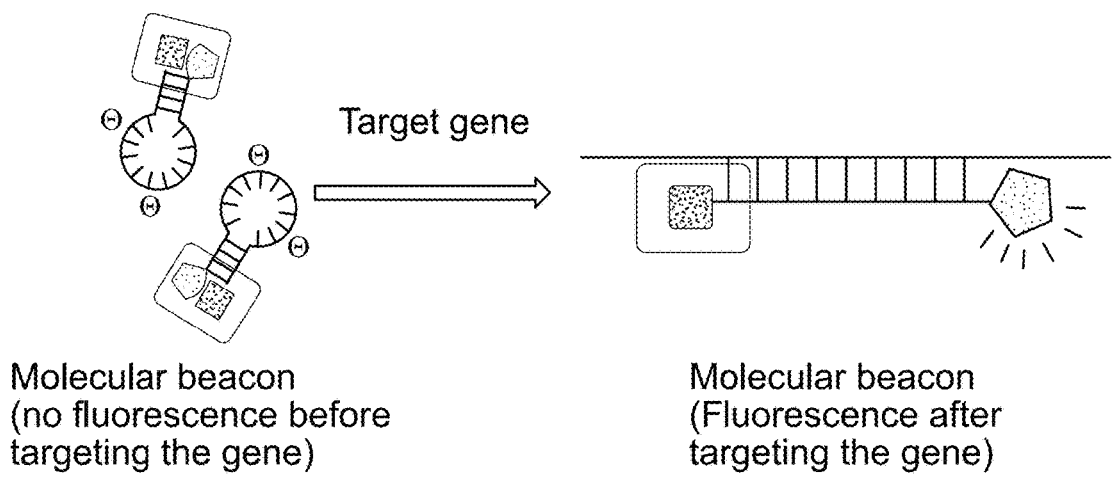
FIG. 51 is a scheme showing molecular beacon (MB) technology.
Figure 52:
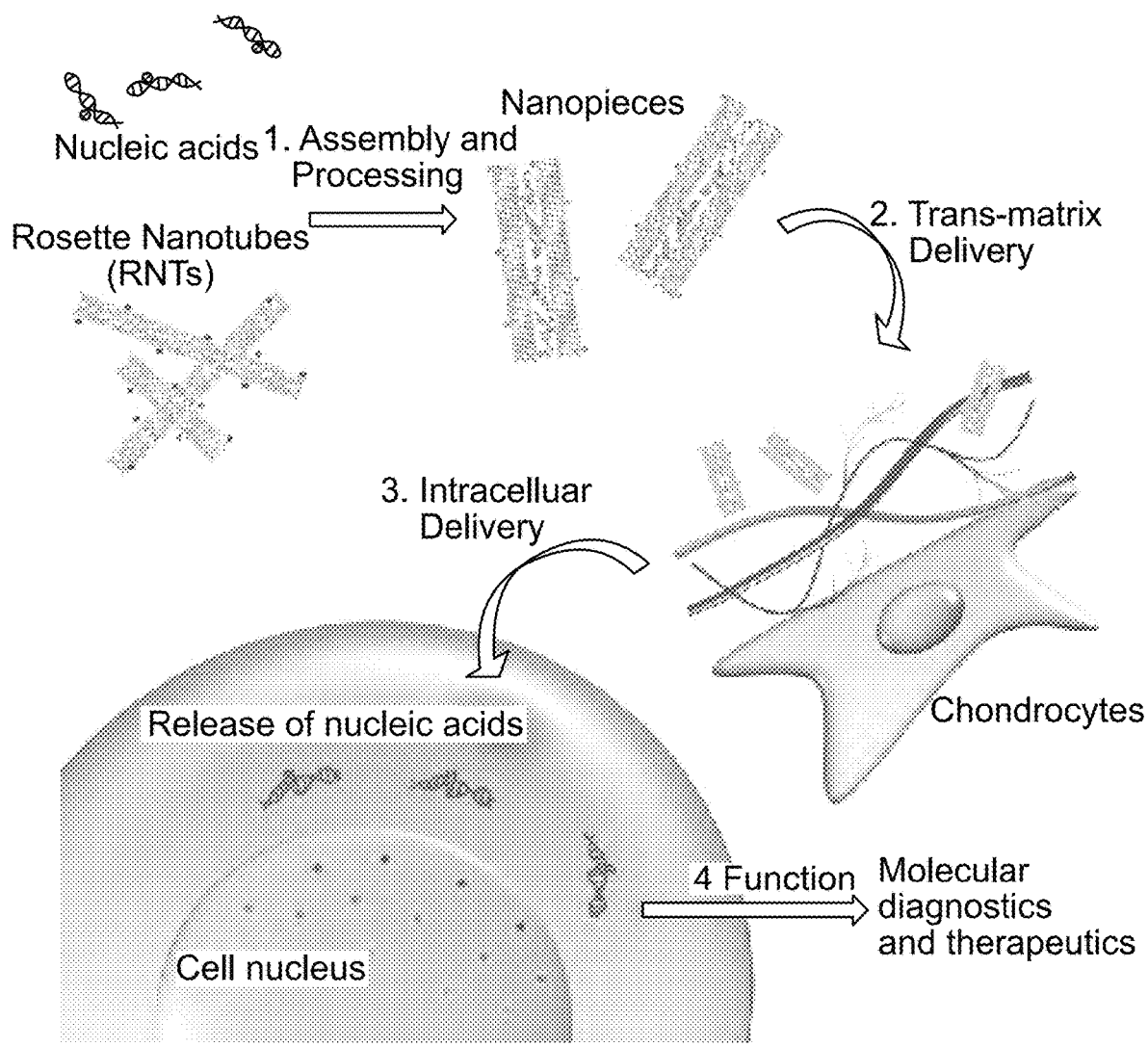
FIG. 52 is a scheme showing trans matrix delivery of Nanopieces into chondrocytes.

Specifically, Molecular beacon (MB) technology provided an intriguing possibility to detect the changes of mRNA levels in live animals in vivo. In fact, molecular beacon (MB) technology (FIG. 51) detected the changes of mRNA levels in live animals in vivo. The Molecular beacon comprises an oligonucleotides loop, double strand stem, and a fluorophore and quencher, which remains non-fluorescent due to the proximity of fluorophore and quencher. Upon entering a cell and hybridizing with its target mRNA, MB emits fluorescence after separation of the fluorophore and quencher (FIG. 52). However, prior to the invention, there was no report of detection of OA using MB due to the significant challenge of in vivo delivery of MB into joint tissues. Detection of OA using MB is challenging because of the in vivo delivery of MB into joint tissues. Early detection of OA in the Destabilizing Medial Meniscus (DMM) mouse OA model using MB to detect induction of MMP-13 transcript, a major matrix proteinase that degrades interstitial collagen matrix during arthritis was shown. In vivo delivery of MMP13 MB using Nanopieces derived from rosette nanotubes were used. Since cartilage is a very negatively charged tissue (containing a huge amount of proteoglycan), the negatively charged Nanopieces intend to bind and accumulate onto and/or into the matrix and/or tissue resulting in much longer retention time to achieve more effective delivery. Different sizes of Nanopieces can be created for different delivery proposes to get into the matrix. For example, cartilage tissue matrix has about 60 nm mesh size of the collagen II fibrillar network and about 20 nm spacing between the side chains of the proteoglycan network. Nanopieces with small sizes (at least one dimension smaller than 60 nm and/or 20 nm) showed excellent efficiency and function in intra-cartilage matrix delivery of siRNA. Adjusting the ratio between RNTs and cargo reagents to yield an overall positive charged surface enabled Nanopieces to adhere with negatively charged matrix and/or tissue components resulting longer retention time.

Intra-joint delivery was thereby achieved with these processed Nanopieces. Delivery of Molecular probes with Nanopiece detected a specific gene expression (or protein activity) along with the co-delivery of a negative control for non-specific signal and an internal positive control to accurately diagnose a target gene expression in a real-time, in-situ and non-invasive manner. Matrix metalloproteinases (MMP) are the major enzymes that degrade the components of the extracellular matrix during arthritis progression. MMP-13, which is usually produced by cartilage and bone, degrade interstitial collagens (types I, II and III) in both OA and RA. Expression of MMP-13 is low in normal cells, whereas in pathologic condition excess MMP-13 production is associated with inflammation. mRNA level of MMP-13 are indicative for arthritis development and MMP-13 is as a good target in early diagnosis of arthritis. However, articular cartilage tissues need to be collected to show the up-regulation of MMP-13 mRNA levels. The combination of molecular beacon and Nanopieces technology detected of OA in vivo in a specific and sensitive manner without harming any joint tissues.

In another example, therapeutic agents complexed with nanotubes can knock down one or multiple disease gene expression (such as via siRNA delivery) and/or up-regulate one or multiple beneficial gene and/or protein (such as via DNA, mRNA or protein delivery) and deliver a variety of cargo types and can deliver multiple cargo reagents at the same time.

Accordingly, the rosette nanotubes of the present disclosure have hollow channels that can be used for drug encapsulation. Rosette nanotubes are able to incorporate water-insoluble drugs into their tubular structures by hydrophobic interactions with the core whereas their hydrophilic outer surface can shield such hydrophobic drugs in a physiological environment for subsequent prolonged release (even into the cell). Rosette nanotubes can also be chemically functionalized with peptides such as Arg-Gly-Asp-Ser-Lys, Lys-Arg-Ser-Arg-Lys, and Gly-Arg-Gly-Asp-Tyr-Lys to deliver growth factors for healthy tissue regeneration, such as healthy bone in osteosarcoma patients, after the delivery of drugs to kill cancer cells.

The rosette nanotubes may also be used in tissue engineering, where living cells are utilized as engineering materials. Applications for tissue engineering are used to repair or replace portions of whole tissues such as bone, cartilage, blood vessels, muscle, etc. Tissues are fabricated in the laboratory from combinations of engineered extracellular matrices ("scaffolds"), cells, and biologically active molecules destined for transplantation. For example, nasal chondrocytes can expand in culture to engineer a cartilage graft. The rosette nanotubes of the current disclosure can be used as scaffolds in tissue engineering methods, e.g. using nasal chondrocytes, as well as a transfer vehicle to deliver therapeutic agents to specific tissues, e.g. cartilage, when using tissue engineering techniques known to a skilled person in the art.

Genes and Proteins Used as Agents/Delivery Cargo

The following Genes and Proteins can be used as agents to complex with Nanotubes and Nanopieces:

The following Genes and Proteins can be used as target gene of siRNA which complex with Nanotubes and Nanopieces:

The mRNA transcript sequence encoding human ADAMTS-5, provided by Genbank Accession No.NM_007038.3, is incorporated herein by reference, and is shown below (SEQ ID NO: 1).

```
   1 ataaattcat tgttccacct cctcgcatct tcacagcgct cgcgctgctc tcggcgctcg
  61 cagctgccga ctggggatga cggcgggcag gaggagaccg cagccgaagg gacacagaca
 121 cgccgcttca ccagctcgcc tcaggctgcc ccctgcatt tttgttttaa ttttacggc
 181 ttttccccct ctctttcttc ccttcctcct ggtcccagca gagccaagga aacccacaaa
 241 ataagaaagg aagtgggccc cggagcttgg aacctccaca gccggcttgt ccagcgcagc
 301 gcggggggcgg gaggctgcgc gcaccagttg ccagcccggt gcgcggtacc tttccttact
 361 tttcttgaaa cagcgatcgt gcctgcattt ggtggttttt tggttttgt ttttttcctt
 421 ttcccgtatt tgctgaatct ccactatccg acttttttt tttaatcttt tctttccccc
 481 ccccccacc ccacctcttt ctggagcacg aatccaaaca ttttcccaag caacaaagaa
 541 aagttcgcac gctggcaccg cagcccggac aggctggcgc tgctgccggg ccccctccc
 601 tccgacactt gactcaatcc tgcaagcaag tgtgtgtgtg tccccatccc ccgccccgtt
 661 aacttcatag caaataacaa atacccataa agtcccagtc gcgcagcccc tccccgcggg
 721 cagcgcacta tgctgctcgg gtgggcgtcc ctgctgctgt gcgcgttccg cctgcccctg
 781 gccgcggtcg gccccgccgc gacacctgcc caggataaag ccgggcagcc tccgactgct
 841 gcagcagccg cccagccccg ccggcggcag ggggaggagg tgcaggagcg agccgagcct
 901 cccggccacc cgcaccccct ggcgcagcgg cgcaggagca aggggctggt gcagaacatc
 961 gaccaactct actccggcgg cggcaaggtg ggctacctcg tctacgcggg cggccggagg
1021 ttcctcttgg acctggagcg agatggttcg gtgggcattg ctggcttcgt gcccgcagga
1081 ggcgggacga gtgcgccctg gcgccaccgg agccactgct tctatcgggg cacagtggac
1141 ggtagtcccc gctctctggc tgtctttgac ctctgtgggg gtctcgacgg cttcttcgcg
1201 gtcaagcacg cgcgctacac cctaaagcca ctgctgcgcg gacccggggc ggaggaagaa
1261 aagggggcgcg tgtacgggga tgggtccgca cggatcctgc acgtctacac ccgcgagggc
1321 ttcagcttcg aggccctgcc gccgcgcgcc agctgcgaaa cccccgcgtc cacaccggag
1381 gcccacgagc atgctccggc gcacagcaac ccgagcggac gcgcagcact ggcctcgcag
1441 ctcttggacc agtccgctct ctcgcccgct ggggctcag gaccgcagac gtggtggcgg
1501 cggcggcgcc gctccatctc ccgggcccgc caggtggagc tgcttctggt ggctgacgcg
1561 tccatggcgc ggttgtatgg ccgggggcctg cagcattacc tgctgaccct ggcctccatc
1621 gccaataggc tgtacagcca tgctagcatc gagaaccaca tccgcctggc cgtggtgaag
1681 gtggtggtgc taggcgacaa ggacaagagc ctggaagtga gcaagaacgc tgccaccaca
1741 ctcaagaact tttgcaagtg gcagcaccaa cacaaccagc tgggagatga ccatgaggag
1801 cactacgatg cagctatcct gtttactcgg gaggatttat gtgggcatca ttcatgtgac
1861 accctgggaa tggcagacgt tggaccata tgttctccag agcgcagctg tgctgtgatt
1921 gaagacgatg gcctccacgc agccttcact gtggctcacg aaatcggaca tttacttggc
1981 ctctcccatg acgattccaa attctgtgaa gagacctttg gttccacaga agataagcgc
2041 ttaatgtctt ccatccttac cagcattgat gcatctaagc cctggtccaa atgcacttca
2101 gccaccatca cagaattcct ggatgatggc catggtaact gtttgctgga cctaccacga
```

-continued

```
2161 aagcagatcc tgggccccga agaactccca ggacagacct acgatgccac ccagcagtgc
2221 aacctgacat tcgggcctga gtactccgtg tgtcccggca tggatgtctg tgctcgcctg
2281 tggtgtgctg tggtacgcca gggccagatg gtctgtctga ccaagaagct gcctgcggtg
2341 gaagggacgc cttgtggaaa ggggagaatc tgcctgcagg gcaaatgtgt ggacaaaacc
2401 aagaaaaaat attattcaac gtcaagccat ggcaactggg gatcttgggg atcctggggc
2461 cagtgttctc gctcatgtgg aggaggagtg cagtttgcct atcgtcactg taataaccct
2521 gctcccagaa acaacggacg ctactgcaca gggaagaggg ccatctaccg ctcctgcagt
2581 ctcatgccct gcccacccaa tggtaaatca tttcgtcatg aacagtgtga ggcaaaaaat
2641 ggctatcagt ctgatgcaaa aggagtcaaa acttttgtgg aatgggttcc caaatatgca
2701 ggtgtcctgc cagcggatgt gtgcaagctg acctgcagag ccaagggcac tggctactat
2761 gtggtatttt ctccaaaggt gaccgatggc actgaatgta ggctgtacag taattccgtc
2821 tgcgtccggg ggaagtgtgt gagaactggc tgtgacggca tcattggctc aaagctgcag
2881 tatgacaagt gcggagtatg tggaggagac aactccagct gtacaaagat tgttggaacc
2941 tttaataaga aaagtaaggg ttacactgac gtggtgagga ttcctgaagg ggcaacccac
3001 ataaaagttc gacagttcaa agccaaagac cagactagat tcactgccta tttagccctg
3061 aaaaagaaaa acggtgagta ccttatcaat ggaaagtaca tgatctccac ttcagagact
3121 atcattgaca tcaatggaac agtcatgaac tatagcggtt ggagccacag ggatgacttc
3181 ctgcatggca tgggctactc tgccacgaag gaaattctaa tagtgcagat tcttgcaaca
3241 gacccccacta aaccattaga tgtccgttat agcttttttg ttcccaagaa gtccactcca
3301 aaagtaaact ctgtcactag tcatggcagc aataaagtgg gatcacacac ttcgcagccg
3361 cagtgggtca cgggcccatg gctcgcctgc tctaggacct gtgacacagg ttggcacacc
3421 agaacggtgc agtgccagga tggaaaccgg aagttagcaa aaggatgtcc tctctcccaa
3481 aggccttctg cgtttaagca atgcttgttg aagaaatgtt agcctgtggt tatgatctta
3541 tgcacaaaga taactggagg attcagcact gatgcagtcg tggtgaacag gaggtctacc
3601 taacgcacag aaagtcatgc ttcagtgaca ttgtcaacag gagtccaatt atgggcagaa
3661 tctgctctct gtgaccaaaa gaggatgtgc actgcttcac gtgacagtgg tgaccttgca
3721 atatagaaaa acttgggagt tattgaacat cccctgggct acaagaaac actgatgaat
3781 gtaaaatcag gggacatttg aagatggcag aactgtctcc cccttgtcac ctacctctga
3841 tagaatgtct ttaatggtat cataatcatt ttcacccata atacacagta gcttcttctt
3901 actgtttgta aatacattct cccttggtat gtcactttat atcccctggt tctattaaaa
3961 tatccatata tatttctata aaaaagtgt ttgaccaaag taggtctgca gctatttcaa
4021 cttccttccg tttccagaaa gagctgtgga tatttactg gaaattaaga acttgctgct
4081 gttttaataa gatgtagtat atttttctgac tacaggagat aaaatttcag tcaaaaaacc
4141 attttgacag caagtatctt ctgagaaatt ttgaaaagta aatagatctc agtgtatcta
4201 gtcacttaaa tacatacacg ggttcattta cttaaaccctt tgactgcctg tatttttttc
4261 aggtagctag ccaaattaat gcataatttc agatgtagaa gtagggtttg cgtgtgtgtg
4321 tgtgatcata ctcaagagtc taaaaactag tttccttgtg ttggaaattt aaaaggaaaa
4381 aaatcgtatt tcactgtgtt ttcaatttat attttcacaa ctactttctc tctccagagc
4441 tttcatctga tatctcacaa tgtatgatat acgtacaaaa cacacagcaa gttttctatc
4501 atgtccaaca cattcaacac tggtatacct cctaccagca agccttaaa atgcatttgt
```

-continued

```
4561 gtttgcttat ttgttttgtt caagggttca gtaagaccta caatgttttg tatttcttga
4621 cttattttat tagaaacatt aaagatcact tggtagttag ccacattgag aagtggttat
4681 cattgttaat gtggttaatg ccaaaaagtg gttaatatta ataagactgt ttccacacca
4741 taggcaataa tttcttaatt taaaaaatct aagtatattc ctattgtact aaatattttt
4801 cccaactgga aagcacttga ttgtacccgt aagtgtttga gtgatgacat gtgatgattt
4861 tcagaaagtt gttgtttttg tttccatagc ctgtttaagt aggttgtaag tttgaatagt
4921 tagacatgga aattatttta taagcacaca cctaaagata tcttttaga tgataaaatg
4981 tacaccccccc catcaccaac ctcacaactt agaaaatcta agttgtttga tttctttggg
5041 atttcttttg ttgtgaaaca ctgcaaagcc aattttttctt tataaaaatt catagtaatc
5101 ctgccaaatg tgcctattgt taaagatttg catgtgaaga tcttagggaa ccactgtttg
5161 agttctacaa gctcatgaga gtttattttt attataagat gttttttaata taaaagaatt
5221 atgtaactga tcactatatt acatcatttc agtgggccag gaaaatagat gtcttgctgt
5281 tttcagtatt ttcttaagaa attgctttta aaacaaataa ttgtttttaca aaaccaataa
5341 ttatcctttg aattttcata gactgactt gcttttgacg tagaaatttt ttttctcaat
5401 aaattatcac tttgagaaat gaggcctgta caaggctgat aacctatatg tgatggagat
5461 cacccaatgc caagggcaga aagcaaacct agttaaatag gtgagaaaaa aataataat
5521 cccagtgcca tttgtctgtg caaagagaat taggagagag gttaatgtta cttttttcca
5581 ttttggaaat aattttaatc aagtaactca aatgtgacaa aattattttt tattttttgt
5641 ggttatattc ccaacaacat taaaaaatac tcgaggcata aatgtagttg tctcctactc
5701 tgcttctctt actatactca tacatttta atatggttta tcaatgattc atgtttccct
5761 caaatagtga tggtttacac ctgtcatgga aacaatccta gagagctcag agcaattaaa
5821 ccactattcc atgcttttaa gtagttttct ccacctttt cttatgagtc tcactagatt
5881 gactgaggaa tgtatgtcta aattcctgga gaagatgata tggattggaa actgaaattc
5941 agagaaatgg agtgttcaat agataccacg aattgtgaac aaagggaaaa ttctatacaa
6001 ctcaatctaa gtcagtccac tttgacttcg tactgtcttt caccttttcca ttgttgcatc
6061 ttgaatttt taaaatgtct agaattcagg atgctagggg ctacttcttt aaaaaaaaaa
6121 aaaaaaaaga attcgtctga aaatgctcag gtttgtaaga atctaatctc acttacataa
6181 ctaagcactc cataataagt tttattaagt acaaagggag ccagaaaaaa tgacatttat
6241 ttcttctaga tcagaaaaat ttaaattaag ccctgccttg ctgtttagaa atatgtgggc
6301 attgttataa tttattcaat aaatttatgt tcctttgcct tcctgtggaa acagttttat
6361 cccactaaac taggaattag gggataaatc acaaacaaaa aaaaagttgc agcactgaaa
6421 aaaagtaatt tattgttttt gcaactggta tgtgaatttg tgtgataaaa ttatttattc
6481 ttatttaaca aaatatgtt caaattttc tatatttaaa atgttttgct gttgtcctac
6541 tttttaattt atgcttcatg tttgtgtata aagtacactt ttcactttg tgagtttaca
6601 taatatacag cactggttgc ttttgtattt ttttacagaa agctttctgt gtgaagcagg
6661 tgtatatgta tatattcctc atgtattctt attctgatac tatcattttt ctttccaagg
6721 aaatttaat ctgtcatgac caatagtgtt cattacttgt gcctatgata ataggttttt
6781 tacatcacat taacactatt tttccaagt cacaaataag aaaaacactt attcaatgaa
6841 acaaggtgca agttttaaat ttgggtacac aaatagccta gaagcttcct acagacgcta
6901 agacacagcc aataatcaga tcctttcact tcatcgagaa acttggacaa gtcgatattg
6961 atgtattaga tgaaagttgt ctacacacaa cttctgaggg atacaaacga taataaaacc
```

-continued

```
7021 aaatgttgtc tgtttctcct ttagaaacac ctcctaaaat taatatcatt tagtctctag 7081 tgtctgtagg attctacaga tgagcacaaa tagattgggt ttgtataaca aatgctaata 7141 gtcataactg tttctacaaa tatggggtgt ccattaagag aatgtgatgt tttcctactg 7201 ctgttgaatc ccatggggtg attataggac ttgaaatagg cagagtcacc tctgatgaca 7261 tcagcttgcc tctgtgattt cacagtctga tcctggcaac aagacaaagc acccttggac 7321 acacagccaa tctctggttg tgatatttcc ccattgattc cttccttgtt aacaaggtca 7381 ttttaatggt tcaggtgagg acagcagcca gattcaaagt ccagaatttg tgctgttaca 7441 tagagttcac actgtcaaat aacattgaat ttaataatga tcaaattttt ctagtagtct 7501 ttggcagagt gtataatctc attggcatga ttggtgaata ttactaatct ctttataatg 7561 aaagatgctt tacaaatacc ttatatttgc taacatttca aaactactaa ataaatgaaa 7621 tagccatgtg tacagaaatg gtcatttaaa gctttaatag aaccaaattc aagacaatgt 7681 atcatttaga cacacagaaa aggaacttgt atgttttccc tattattttt ctcatttgcc 7741 aacaatctat agttttaggt tatcaaacag atagatcaac ttaactggct agtacattga 7801 aaaatcttcc taagaatcct ttgttagcat aatctataga gataatttct caaattatat 7861 catcatgatg catataaact ctataatgta taattgtgtt tcatttattt aatgtatgag 7921 aacatattga aatacaaaac catgcattag ccaaaaaatt ggaatacagg tagtgttcag 7981 atcagcaaaa cattcagtct ggtaaatgcc tgcctggggc tatgatatca ttctcaatgc 8041 aggttttatg gaaaaactaa aagaatatgt tgttagatga tgttggtttt gaaaaaaaaa 8101 agacattaac atacacatta gttagcccag ttaattgcat tctactaata tagttgcaca 8161 ttagcaataa ttttgctgtc tctggtcttt attttgtggc ttcaactaac tggaccatgt 8221 ggactgtaaa ggtcaaatgg aaaaaacgag cagtggcccc tcatcctgta aggtactgct 8281 acatcagagt gacctaaaag tctaacactg tgaggaaaac tgtgatttgt aggaaaaaaa 8341 aaaaaaacaa ataaaaaaca gggcatgctt tttaattttt ttccactttc ctttggcaca 8401 cccaatgaac aattctaatt tttattgagg tgctaacatc tttcgtgacc gactgtcaaa 8461 tgtggtattt ttgagttact attttctac atgattttac agtttgcaag aaagacctct 8521 aagctttgtg tcacggtagg gcacaacttg atactcaaaa tttgaaaaat aagcacatcc 8581 aatgattgtt ttgaccaaca gtggtcagtg acgtaaactg catgtgcatc tgaggacatt 8641 taagggggtca ttaaaatttg aggagcatca ggccggagta gcagactttt agatgagtca 8701 tatttcagca ttcactaagt cctcagcatt ccattcaaac tgtcgtgtat atttggcctg 8761 attttttttc aagctttgca ataatttatg ttattggtaa acacttggtg actatatctc 8821 agccttttct ttaacaactc acaatatatt agaaacacgt ctacctatac tgagagtata 8881 tttacaatag aagaacatac tgtatgtgac tttgtaaagc tagacttttg attaagaaat 8941 atataatctc tggatgctat ttttgcatta tacactcagg cacaacgtaa accttgatgg 9001 ctcatcttgc tacaattacg agttgaaaaa cactacttac gtatttgtat gacctattag 9061 tcagaggaaa tcatacatat gctttgtaaa tagactttgc agataactaa atagactgaa 9121 gaaatatgtt gcatttgata gaagcaattg cataaatatt tggtttctat attagagtct 9181 gtgagtaaag tcaagtaata aacctaagta ggtataacag attttaaac cttgaaactt 9241 gctttgatgg tagagaaaat cattgaagat ttacatactg tatataagat gtaaatgta 9301 cgctgcttat taccctcaat ttttccagaag caatggtata taatgcagtt gaaaaaccaa 9361 aaatcttgga aaactaagac gggtcttgtt taaaatgtct ctcagctttg gcaaccttca
```

-continued

```
9421 aatcttaatc aactatttaa agcattactg tgtcttgtag cctgcattcc acaacagctc 9481 tgttattcag gtaaaagact tgaactgagc cgtttgggac ctatactgta atatttcat 9541 tgaggaacaa tatcctattt tgtaaagcat ttccctatgt gtgactttaa actgtaaaat 9601 taaacactgc ttttgtgggt tcagtgggca taataaatat aaattgtaaa ctaggttaaa 9661 gta
```

The amino acid sequence of human ADAMTS-5 (preproprotein), provided by Genbank Accession No.NP_008969.2, is incorporated herein by reference, and is shown below (SEQ ID NO: 2).

```
  1 mllgwaslll cafrlplaav gpaatpaqdk agqpptaaaa
    aqprrrqgee vqeraeppgh 61 phplaqrrrs kglvqnidql ysgggkvgyl vyaggrrfll
    dlerdgsvgi agfvpagggt 121 sapwrhrshc fyrgtvdgsp rslavfdlcg gldgffavkh
    arytlkpllr gpwaeeekgr 181 vygdgsaril hvytregfsf ealpprasce tpastpeahe
    hapahsnpsg raalasqlld 241 qsalspaggs gpqtwwrrrr rsisrarqve lllvadasma
    rlygrglqhy lltlasianr 301 lyshasienh irlavvkvvv lgdkdkslev sknaattlkn
    fckwqhqhnq lgddheehyd 361 aailftredl cghhscdtlg madvgticsp erscaviedd
    glhaaftvah eighllglsh 421 ddskfceetf gstedkrlms siltsidask pwskctsati
    teflddghgn clldlprkqi 481 lgpeelpgqt ydatqqcnlt fgpeysvcpg mdvcarlwca
    vvrqgqmvcl tkklpavegt 541 pcgkgriclq gkcvdktkkk yystsshgnw gswgswgqcs
    rscgggvqfa yrhcnnpapr 601 nngryctgkr aiyrscslmp cppngksfrh eqceakngyq
    sdakgvktfv ewvpkyagvl 661 padvckltcr akgtgyyvvf spkvtdgtec rlysnsvcvr
    gkcvrtgcdg iigsklqydk 721 cgvcggdnss ctkivgtfnk kskgytdvvr ipegathikv
    rqfkakdqtr ftaylalkkk 781 ngeylingky mistsetiid ingtvmnysg wshrddflhg
    mgysatkeil ivqilatdpt 841 kpldvrysff vpkkstpkvn svtshgsnkv gshtsqpqwv
    tgpwlacsrt cdtgwhtrtv 901 qcqdgnrkla kgcplsqrps afkqcllkkc
```
(Signal peptide AA 1-6; proprotein AA 17-930; mature peptide AA 262-930).

The siRNA used to target human ADAMTS-5 mRNA include following sequences (SEQ ID NO: 3-6):

```
SEQ NO: 3:
5'-GCUCAAAGCUGCAGUAUGA-3'

SEQ NO: 4:
5'-GAAGUCCACUCCAAAAGUA-3'

SEQ NO: 5:
5'-GCACUACGAUGCAGCUAUC-3'

SEQ NO: 6:
5'-CGAAGGAAAUUCUAAUAGU-3'
```

The molecular beacon used to target human ADAMTS-5 mRNA includes the following sequences (SEQ ID NO: 7-9):

```
SEQ NO 7:
5'-CCGGTC TAACATTTCTTCAACAAGCA GACCGG-3'

SEQ NO 8:
5'-CCGGTC TTATACACAAACATGAAGCA GACCGG-3'

SEQ NO 9:
5'-CCGGTC TACATCTTATTAAAACAGCA GACCGG-3'
```

The mRNA transcript sequence encoding human ADAMTS-4, provided by Genbank Accession No.NM_005099.4, is incorporated herein by reference, and is shown below (SEQ ID NO: 10).

```
  1 gggagaacc cacagggaga cccacagaca catatgcacg agagagacag aggaggaaag 61 agacagagac aaaggcacag cggaagaagg cagagacagg gcaggcacag aagcggccca 121 gacagagtcc tacagaggga gaggccagag aagctgcaga agacacaggc agggagagac 181 aaagatccag gaaaggaggg ctcaggagga gagtttggag aagccagacc cctgggcacc 241 tctcccaagc ccaaggacta agttttctcc atttcctta acggtcctca gcccttctga 301 aaactttgcc tctgaccttg gcaggagtcc aagcccccag gctacagaga ggagctttcc 361 aaagctaggg tgtggaggac ttggtgccct agacggcctc agtccctccc agctgcagta 421 ccagtgccat gtcccagaca ggctcgcatc ccgggagggg cttggcaggg cgctggctgt 481 gggagcccca accctgcctc ctgctcccca ttgtgccgct ctcctggctg gtgtggctgc 541 ttctgctact gctggcctct ctcctgccct cagcccggct ggccagcccc ctccccgggg 601 aggaggagat cgtgtttcca gagaagctca acggcagcgt cctgcctggc tcgggcgccc
```

-continued

```
 661 ctgccaggct gttgtgccgc ttgcaggcct ttggggagac gctgctacta gagctggagc
 721 aggactccgg tgtgcaggtc gaggggctga cagtgcagta cctgggccag gcgcctgagc
 781 tgctgggtgg agcagagcct ggcacctacc tgactggcac catcaatgga gatccggagt
 841 cggtggcatc tctgcactgg gatgggggag ccctgttagg cgtgttacaa tatcgggggg
 901 ctgaactcca cctccagccc ctggagggag gcaccctaa ctctgctggg ggacctgggg
 961 ctcacatcct acgccggaag agtcctgcca gcggtcaagg tcccatgtgc aacgtcaagg
1021 ctcctcttgg aagccccagc cccagacccc gaagagccaa gcgctttgct tcactgagta
1081 gatttgtgga gacactggtg gtggcagatg acaagatggc cgcattccac ggtgcgggc
1141 taaagcgcta cctgctaaca gtgatggcag cagcagccaa ggccttcaag cacccaagca
1201 tccgcaatcc tgtcagcttg gtggtgactc ggctagtgat cctggggtca ggcgaggagg
1261 ggccccaagt ggggcccagt gctgcccaga ccctgcgcag cttctgtgcc tggcagcggg
1321 gcctcaacac ccctgaggac tcggaccctg accactttga cacagccatt ctgtttaccc
1381 gtcaggacct gtgtggagtc tccacttgcg acacgctggg tatgctgat gtgggcaccg
1441 tctgtgaccc ggctcggagc tgtgccattg tggaggatga tgggctccag tcagccttca
1501 ctgctgctca tgaactgggt catgtcttca acatgctcca tgacaactcc aagccatgca
1561 tcagtttgaa tgggcctttg agcacctctc gccatgtcat ggcccctgtg atggctcatg
1621 tggatcctga ggagccctgg tcccctgca gtgcccgctt catcactgac ttcctggaca
1681 atggctatgg gcactgtctc ttagacaaac cagaggctcc attgcatctg cctgtgactt
1741 tccctggcaa ggactatgat gctgaccgcc agtgccagct gaccttcggg cccgactcac
1801 gccattgtcc acagctgccg ccgccctgtg ctgccctctg gtgctctggc cacctcaatg
1861 gccatgccat gtgccagacc aaacactcgc cctgggccga tgcacaccc tgcgggcccg
1921 cacaggcctg catgggtggt cgctgcctcc acatggacca gctccaggac ttcaatattc
1981 cacaggctgg tggctggggt ccttggggac catggggtga ctgctctcgg acctgtgggg
2041 gtggtgtcca gttctcctcc cgagactgca cgaggcctgt cccccggaat ggtggcaagt
2101 actgtgaggg ccgccgtacc cgcttccgct cctgcaacac tgaggactgc ccaactggct
2161 cagccctgac cttccgcgag gagcagtgtg ctgcctacaa ccaccgcacc gacctcttca
2221 agagcttccc agggcccatg gactgggttc ctcgctacac aggcgtggcc cccaggacc
2281 agtgcaaact cacctgccag gcccaggcac tgggctacta ctatgtgctg agccacgggt
2341 tggtagatgg gacccctgt tcccggaca gctcctcggt ctgtgtccag ggccgatgca
2401 tccatgctgg ctgtgatcgc atcattggct ccaagaagaa gtttgacaag tgcatggtgt
2461 gcggagggga cggttctggt tgcagcaagc agtcaggctc cttcaggaaa ttcaggtacg
2521 gatacaacaa tgtggtcact atccccgcgg gggccaccca cattcttgtc cggcagcagg
2581 gaaaccctgg ccaccggagc atctacttgg ccctgaagct gccagatggc tcctatgccc
2641 tcaatggtga atacacgctg atgccctccc ccacagatgt ggtactgcct ggggcagtca
2701 gcttgcgcta cagcggggcc actgcagcct cagagacact gtcaggccat gggccactgg
2761 cccagccttt gacactgcaa gtcctagtgg ctggcaaccc ccaggacaca cgcctccgat
2821 acagcttctt cgtgcccggg ccgacccctt caacgccacg ccccactccc caggactggc
2881 tgcaccgaag agcacagatt ctggagatcc ttcggcggcg ccctgggcg ggcaggaaat
2941 aacctcacta tcccggctgc ccttttctggg caccggggcc tcggacttag ctgggagaaa
3001 gagagagctt ctgttgctgc ctcatgctaa gactcagtgg ggagggctg tgggcgtgag
```

```
3061 acctgccct cctctctgcc ctaatgcgca ggctggccct gccctggttt cctgccctgg 3121 gaggcagtga tgggttagtg gatggaaggg gctgacagac agccctccat ctaaactgcc 3181 ccctctgccc tgcgggtcac aggagggagg gggaaggcag ggagggcctg ggccccagtt 3241 gtatttattt agtatttatt cacttttatt tagcaccagg gaaggggaca aggactaggg 3301 tcctggggaa cctgacccct gaccctcat agccctcacc ctggggctag gaaatccagg 3361 gtggtggtga taggtataag tggtgtgtgt atgcgtgtgt gtgtgtgtga aaatgtgtgt 3421 gtgcttatgt atgaggtaca acctgttctg ctttcctctt cctgaatttt attttttggg 3481 aaaagaaaag tcaagggtag ggtgggcctt cagggagtga gggattatct ttttttttt 3541 ttctttcttt ctttcttttt ttttttttgag acagaatctc gctctgtcgc ccaggctgga 3601 gtgcaatggc acaatctcgg ctcactgcat cctccgcctc ccgggttcaa gtgattctca 3661 tgcctcagcc tcctgagtag ctggattac aggctcctgc caccacgccc ggctaatttt 3721 tgttttgttt tgtttggaga cagagtctcg ctattgtcac cagggctgga atgatttcag 3781 ctcactgcaa ccttcgccac ctgggttcca gcaattctcc tgcctcagcc tcccgagtag 3841 ctgagattat aggcacctac caccacgccc ggctaatttt tgtattttta gtagagacgg 3901 ggtttcacca tgttggccag gctggtctcg aactcctgac cttaggtgat ccactcgcct 3961 tcatctccca aagtgctggg attacaggcg tgagccaccg tgcctggcca cgcccaacta 4021 attttgtat ttttagtaga cagggttt caccatgttg gccaggctgc tcttgaactc 4081 ctgacctcag gtaatcgacc tgcctcggcc tcccaaagtg ctgggattac aggtgtgagc 4141 caccacgccc ggtacatatt ttttaaattg aattctacta tttatgtgat ccttttggag 4201 tcagacagat gtggttgcat cctaactcca tgtctctgag cattagattt ctcatttgcc 4261 aataataata cctcccttag aagtttgttg tgaggattaa ataatgtaaa taaagaacta 4321 gcataacact caaaaaaaaa aaaaaaaaa aaaaaaaaaa aaaaaaaaaa aaaaaaaaaa 4381 aaaaaaaaaa aaaaaaaaaa aaaaaaaaaa
```

The amino acid sequence of human ADAMTS-4 (preproprotein), provided by Genbank Accession No.NP_005090.3, is incorporated herein by reference, and is shown below (SEQ ID NO: 11).

```
  1 msqtgshpgr glagrwlwga qpclllpivp lswlvwllll
    llasllpsar lasplpreee 61 ivfpeklngs vlpgsgapar llcrlqafge tllleleqds
    gvqvegltvq ylgqapellg 121 gaepgtyltg tingdpesva slhwdggall gvlqyrgael
    hlqpleggtp nsaggpgahi 181 lrrkspasgq gpmcnvkapl gspsprprra krfaslsrfv
    etlvvaddkm aafhgaglkr 241 ylltvmaaaa kafkhpsirn pvslvvtrlv ilgsgeegpq
    vgpsaaqtlr sfcawqrgln 301 tpedsdpdhf dtailftrqd lcgstcdtl gmadvgtvcd
    parscaived dglqsaftaa 361 helghvfnml hdnskpcisl ngplstsrhv mapvmahvdp
    eepwspcsar fitdfldngy 421 ghclldkpea plhlpvtfpg kdydadrqcq ltfgpdsrhc
    pqlpppcaal wcsghlngha 481 mcqtkhspwa dgtpcgpaqa cmggrclhmd qlqdfnipqa
    ggwgpwgpwg dcsrtcgggv 541 qfssrdctrp vprnggkyce grrtrfrscn tedcptgsal
    tfreeqcaay nhrtdlfksf 601 pgpmdwvpry tgvapqdqck ltcqaqalgy yyvleprvvd
    gtpcspdsss vcvqgrciha 661 gcdriigskk kfdkcmvcgg dgsgcskqsg sfrkfrygyn
    nvvtipagat hilvrqqgnp 721 ghrsiylalk lpdgsyalng eytlmpsptd vvlpgayslr
    ysgataaset lsghgplaqp 781 ltlqvlvagn pqdtrlrysf fvprptpstp rptpqdwlhr
    raqileilrr rpwagrk
```

The siRNA used to target human ADAMTS-4 mRNA includes the following sequences (SEQ ID NO: 12-15):

```
SEQ NO: 12:
5'-CCGCAAUCCUGUCAGCUUG-3'

SEQ NO: 13:
5'-GCGCUUUGCUUCACUGAGU-3'

SEQ NO: 14:
5'-GGACACACGCCUCCGAUAC-3'

SEQ NO: 15:
5'-GCACCGAAGAGCACAGAUU-3'
```

The molecular beacon used to target human ADAMTS-4 mRNA includes the following sequences (SEQ ID NO: 16-18):

```
SEQ NO: 16:
5'-CCGGTC TTTTCACACACACACACACG GACCGG-3'

SEQ NO: 17:
5'-CCGGTC TAAAAATACAAAAATTAGCC GACCGG-3'

SEQ NO: 18:
5'-CCGGTC TTGTCTCTGTCTCTTTCCTC GACCGG-3'
```

The mRNA transcript sequence encoding human MMP-13, provided by Genbank Accession No.NM_002427.3, is incorporated herein by reference, and is shown below (SEQ ID NO: 19).

```
   1 acaacagtcc ccaggcatca ccattcaaga tgcatccagg
     ggtcctggct gccttcctct
  61 tcttgagctg gactcattgt cgggccctgc cccttcccag
     tggtggtgat gaagatgatt
 121 tgtctgagga agacctccag tttgcagagc gctacctgag
     atcatactac catcctacaa
 181 atctcgcggg aatcctgaag gagaatgcag caagctccat
     gactgagagg ctccgagaaa
 241 tgcagtcttt cttcggctta gaggtgactg gcaaacttga
     cgataacacc ttagatgtca
 301 tgaaaaagcc aagatgcggg gttcctgatg tgggtgaata
     caatgttttc cctcgaactc
 361 ttaaatggtc caaaatgaat ttaacctaca gaattgtgaa
     ttacacccct gatatgactc
 421 attctgaagt cgaaaaggca ttcaaaaaag ccttcaaagt
     ttggtccgat gtaactcctc
 481 tgaattttac cagacttcac gatggcattg ctgacatcat
     gatctctttt ggaattaagg
 541 agcatggcga cttctaccca tttgatgggc cctctggcct
     gctggctcat gcttttcctc
 601 ctgggccaaa ttatggagga gatgcccatt ttgatgatga
     tgaaacctgg acaagtagtt
 661 ccaaaggcta caacttgttt cttgttgctg cgcatgagtt
     cggccactcc ttaggtcttg
 721 accactccaa ggaccctgga gcactcatgt ttcctatcta
     cacctacacc ggcaaaagcc
 781 actttatgct tcctgatgac gatgtacaag ggatccagtc
     tctctatggt ccaggagatg
 841 aagacccaa ccctaaacat ccaaaaacgc cagacaaatg
     tgaccctttcc ttatcccttg
 901 atgccattac cagtctccga ggagaaacaa tgatctttaa
     agacagattc ttctggcgcc
 961 tgcatcctca gcaggttgat gcggagctgt ttttaacgaa
     atcattttgg ccagaacttc
1021 ccaaccgtat tgatgctgca tatgagcacc cttctcatga
     cctcatcttc atcttcagag
1081 gtagaaaatt tgggctctt aatggttatg acattctgga
     aggttatccc aaaaaaatat
1141 ctgaactggg tcttccaaaa gaagttaaga agataagtgc
     agctgttcac tttgaggata
1201 caggcaagac tctcctgttc tcaggaaacc aggtctggag
     atatgatgat actaaccata
1261 ttatggataa agactatccg agactaatag aagaagactt
     cccaggaatt ggtgataaag
1321 tagatgctgt ctatgagaaa aatggttata tctatttttt
     caacggaccc atacagtttg
1381 aatacagcat ctggagtaac cgtattgttc gcgtcatgcc
     agcaaattcc attttgtggt
1441 gttaagtgtc tttttaaaaa ttgttattta aatcctgaag
     agcatttggg gtaatacttc
1501 cagaagtgcg gggtagggga agaagagcta tcaggagaaa
     gcttggttct gtgaacaagc
1561 ttcagtaagt tatctttgaa tatgtagtat ctatatgact
     atgcgtggct ggaaccacat
1621 tgaagaatgt tagagtaatg aaatggagga tctctaaaga
     gcatctgatt cttgttgctg
1681 tacaaaagca atggttgatg atacttccca caccacaaat
     gggacacatg gtctgtcaat
1741 gagagcataa tttaaaaata tatttataag gaaatttttac
     aagggcataa agtaaataca
1801 tgcatataat gaataaatca ttcttactaa aaagtataaa
     atagtatgaa aatggaaatt
1861 tgggagagcc atacataaaa gaaataaacc aaaggaaaat
     gtctgtaata atagactgta
1921 acttccaaat aaataatttt cattttgcac tgaggatatt
     cagatgtatg tgcccttctt
1981 cacacagaca ctaacgaaat atcaaagtca ttaaagacag
     gagacaaaag agcagtggta
2041 agaatagtag atgtggcctt tgaattctgt ttaattttca
     cttttggcaa tgactcaaag
2101 tctgctctca tataagacaa atattccttt gcatattata
     aaggataaag aaggatgatg
2161 tcttttt att aaaatatttc aggttcttca gaagtcacac
     attacaaagt taaaattgtt
2221 atcaaaatag tctaaggcca tggcatccct ttttcataaa
     ttatttgatt atttaagact
2281 aaaagttgca ttttaaccct attttaccta gctaattatt
     taattgtcca gtttgtcttg
2341 gatatatagg ctatttcta aagacttgta tagcatgaaa
     taaaatatat cttataaagt
2401 ggaagtatgt atattaaaaa agagacatcc aaattttttt
     ttaaagcagt ctactagatt
2461 gtgatccctt gagatatgga aggatgcctt tttttctctg
     catttaaaaa aatcccccag
2521 cacttcccac agtgcctatt gatacttggg gagggtgctt
     ggcacttatt gaatatgaa
2581 tcggccatca agggaagaac tattgtgctc agagacactg
     ttgataaaaa ctcaggcaaa
2641 gaaaatgaaa tgcatatttg caaagtgtat taggaagtgt
     ttatgttgtt tataataaaa
2701 atatattttc aacagacaaa aaaaaaaaaa aaaaa
```

The amino acid sequence of human MMP-13 (collagenase 3 preproprotein), provided by Genbank Accession No.NP_002418.1, is incorporated herein by reference, and is shown below (SEQ ID NO: 20).

```
  1 mhpgvlaafl flswthcral plpsggdedd lseedlqfae
    rylrsyyhpt nlagilkena 61 assmterlre mqsffglevt gklddntldv mkkprcgvpd
    vgeynvfprt lkwskmnlty 121 rivnytpdmt hsevekafkk afkvwsdvtp lnftrlhdgi
    adimisfgik ehgdfypfdg 181 psgllahafp pgpnyggdah fdddetwtss skgynlflva
    ahefghslgl dhskdpgalm 241 fpiytytgks hfmlpdddvq giqslygpgd edpnpkhpkt
    pdkcdpslsl daitslrget 301 mifkdrffwr lhpqqvdael fltksfwpel pnridaayeh
    pshdlififr grkfwalngy 361 dilegypkki selglpkevk kisaavhfed tglallfsgn
    qvwryddtnh imdkdyprli 421 eedfpgigdk vdavyekngy iyffngpiqf eysiwsnriv
    rvmpansilw c
```
(Signal protein AA 1-19; proprotein AA 20-471; mature peptide AA 104-471).

The siRNA used to target human MMP-13 mRNA includes the following sequences (SEQ ID NO: 21-24):

```
SEQ NO: 21:
5'-UUUCACACACACACACACGC-3'

SEQ NO: 22:
5'-UUUUCACACACACACACACG-3'

SEQ NO: 23:
5'-UAAAAAUACAAAAAUUAGCC-3'

SEQ NO: 24:
5'-UUUGUCUCUGUCUCUUUCCU-3'
```

The molecular beacon used to target human MMP-13 mRNA includes the following sequences (SEQ ID NO: 25-27):

```
SEQ NO 25:
5'-CCGGTC TACACACACCACTTATACCT GACCGG-3'

SEQ NO 26:
5'-CCGGTC TATAATCTCAGCTACTCGGG GACCGG-3'

SEQ NO 27:
5'-CCGGTC AAACAAAACAAAAATTAGCC GACCGG-3'
```

The mRNA transcript sequence encoding human MMP-1variant 2, provided by Genbank Accession No.NM_001145938.1, is incorporated herein by reference, and is shown below (SEQ ID NO: 28).

```
   1 agcatgagtc agacagcctc tggctttctg gaagggcaag
     gactctatat atacagaggg 61 agcttcctag ctgggatatt ggagcagcaa gaggctggga
     agccatcact taccttgcac 121 tgagaaagaa gacaaaggca agttgaaaag cggagaaata
     gtggcccagt ggttgaaaaa 181 ttgaagcaaa tgcaggaatt ctttgggctg aaagtgactg
     ggaaaccaga tgctgaaacc 241 ctgaaggtga tgaagcagcc cagatgtgga gtgcctgatg
     tggctcagtt tgtcctcact 301 gagggaacc ctcgctggga gcaaacacat ctgacctaca
     ggattgaaaa ttacacgcca 361 gatttgccaa gagcagatgt ggaccatgcc attgagaaag
     ccttccaact ctggagtaat 421 gtcacacctc tgacattcac caaggtctct gagggtcaag
     cagacatcat gatatctttt 481 gtcaggggag atcatcggga caactctcct tttgatggac
     ctggaggaaa tcttgctcat 541 gcttttcaac caggcccagg tattggaggg gatgctcatt
     ttgatgaaga tgaaaggtgg 601 accaacaatt cagagagta caacttacat cgtgttgcag
     ctcatgaact cggccattct 661 cttggactct cccattctac tgatatcggg gctttgatgt
     accctagcta caccttcagt 721 ggtgatgttc agctagctca ggatgacatt gatggcatcc
     aagccatata tggacgttcc 781 caaaatcctg tccagcccat cggcccacaa accccaaaag
     cgtgtgacag taagctaacc 841 tttgatgcta taactacgat tcggggagaa gtgatgttct
     ttaaagacag attctacatg 901 cgcacaaatc ccttctaccc ggaagttgag ctcaatttca
     tttctgtttt ctggccacaa 961 ctgccaaatg ggcttgaagc tgcttacgaa tttgccgaca
     gagatgaagt ccggtttttc 1021 aagggaata agtactgggt tgttcaggga cagaatgtgc
     tacacggata ccccaaggac 1081 atctacagct cctttggctt ccctagaact gtgaagcata
     tcgatgctgc tcttttctgag 1141 gaaaacactg gaaaaaccta cttctttgtt gctaacaaat
     actggaggta tgatgaatat 1201 aaacgatcta tggatccagg ttatcccaaa atgatagcac
     atgactttcc tggaattggc 1261 cacaaagttg atgcagtttt catgaaagat ggatttttct
     atttctttca tggaacaaga 1321 caatacaaat ttgatcctaa aacgaagaga attttgactc
     tccagaaagc taatagctgg 1381 ttcaactgca ggaaaaattg aacattacta atttgaatgg
     aaaacacatg gtgtgagtcc 1441 aaagaaggtg ttttcctgaa gaactgtcta ttttctcagt
     cattttttaac ctctagagtc 1501 actgatacac agaatataat cttatttata cctcagtttg
     catatttttt tactatttag 1561 aatgtagccc tttttgtact gatataattt agttccacaa
     atggtgggta caaaaagtca 1621 agtttgtggc ttatggattc atataggcca gagttgcaaa
     gatcttttcc agagtatgca 1681 actctgacgt tgatcccaga gagcagcttc agtgacaaac
     atatcctttc aagacagaaa 1741 gagacaggag acatgagtct ttgccggagg aaaagcagct
     caagaacaca tgtgcagtca 1801 ctggtgtcac cctggatagg caagggataa ctcttctaac
     acaaaataag tgttttatgt 1861 ttggaataaa gtcaaccttg tttctactgt tttatacact
     ttc
```

The amino acid sequence of human MMP-1 (interstitial collagenase isoform 2), provided by Genbank Accession No.NP_001139410.1, is incorporated herein by reference, and is shown below (SEQ ID NO: 29).

```
  1 mqeffglkvt gkpdaetlkv mkqprcgvpd vaqfvltegn prweqthlty rienytpdlp
 61 radvdhaiek afqlwsnvtp ltftkvsegq adimisfvrg dhrdnspfdg pggnlahafq
121 pgpgiggdah fdederwtnn freynlhrva ahelghslgl shstdigalm ypsytfsgdv
181 qlaqddidgi qaiygrsqnp vqpigpqtpk acdskltfda ittirgevmf fkdrfymrtn
241 pfypevelnf isvfwpqlpn gleaayefad rdevrffkgn kywavqgqnv lhgypkdiys
301 sfgfprtvkh idaalseent gktyffvank ywrydeykrs mdpgypkmia hdfpgighkv
361 davfmkdgff yffhgtrqyk fdpktkrilt lqkanswfnc rkn
```

The siRNA used to target human MMP-1 variant 1 mRNA include following sequences (SEQ ID NO: 30-33):

SEQ NO: 30:
5'-UUAGCUUACUGUCACACGC-3'

SEQ NO: 31:
5'-UUAUAUUCAUCAUACCUCC-3'

SEQ NO: 32:
5'-UUGUCUUCUUUCUCAGUGC-3'

SEQ NO: 33:
5'-UUCGUAAGCAGCUUCAAGC-3'

The molecular beacon used to target human MMP-1 variant 1 mRNA includes the following sequences (SEQ ID NO: 34-36):

SEQ NO 34:
5'-CCGGTC TTCGTAAGCAGCTTCAAGC GACCGG-3'

SEQ NO 35:
5'-CCGGTC TAAAGAACATCACTTTCC GACCGG-3'

SEQ NO 36:
5'-CCGGTC TAAAACAGTAGAAACAAGG GACCGG-3'

The mRNA transcript sequence encoding human MMP-9, provided by Genbank Accession No.NM_004994.2, is incorporated herein by reference, and is shown below (SEQ ID NO: 37).

```
   1 agacacctct gccctcacca tgagcctctg gcagccctg gtcctggtgc tcctggtgct
  61 gggctgctgc tttgctgccc ccagacagcg ccagtccacc cttgtgctct tccctggaga
 121 cctgagaacc aatctcaccg acaggcagct ggcagaggaa tacctgtacc gctatggtta
 181 cactcgggtg gcagagatgc gtggagagtc gaaatctctg gggcctgcgc tgctgcttct
 241 ccagaagcaa ctgtccctgc ccgagaccgg tgagctggat agcgccacgc tgaaggccat
 301 gcgaacccca cggtgcgggg tcccagacct gggcagattc caaaccttg agggcgacct
 361 caagtggcac caccacaaca tcacctattg gatccaaaac tactcggaag acttgccgcg
 421 ggcggtgatt gacgacgcct ttgcccgcgc cttcgcactg tggagcgcgg tgacgccgct
 481 caccttcact cgcgtgtaca gccgggacgc agacatcgtc atccagtttg gtgtcgcgga
 541 gcacggagac gggtatccct tcgacgggaa ggacgggctc tgcacacg cctttcctcc
 601 tggcccggc attcagggag acgccatt cgacgatgac gagttgtggt ccctgggcaa
 661 gggcgtcgtg gttccaactc ggtttggaaa cgcagatggc gcggcctgcc acttccccctt
 721 catcttcgag ggccgctcct actctgcctg caccaccgac ggtcgctccg acggcttgcc
 781 ctggtgcagt accacggcca actacgacac cgacgaccgg tttggcttct gccccagcga
 841 gagactctac acccaggacg gcaatgctga tgggaaaccc tgccagtttc cattcatctt
 901 ccaaggccaa tcctactccg cctgcaccac ggacggtcgc tccgacggct accgctggtg
 961 cgccaccacc gccaactacg accgggacaa gctcttcggc ttctgcccga cccgagctga
1021 ctcgacggtg atgggggca actcggcggg ggagctgtgc gtcttcccct tcactttcct
1081 gggtaaggag tactcgacct gtaccagcga gggccgcgga gatgggcgcc tctggtgcgc
1141 taccacctcg aactttgaca gcgacaagaa gtggggcttc tgcccggacc aaggatacag
```

-continued

```
1201 tttgttcctc gtggcggcgc atgagttcgg ccacgcgctg ggcttagatc attcctcagt 1261 gccggaggcg ctcatgtacc ctatgtaccg cttcactgag gggccccct tgcataagga 1321 cgacgtgaat ggcatccggc acctctatgg tcctcgccct gaacctgagc cacggcctcc 1381 aaccaccacc acaccgcagc ccacggctcc ccgacggtc tgccccaccg acccccac 1441 tgtccacccc tcagagcgcc ccacagctgg ccccacaggt cccccctcag ctggccccac 1501 aggtccccc actgctggcc cttctacggc cactactgtg cctttgagtc cggtggacga 1561 tgcctgcaac gtgaacatct tcgacgccat cgcggagatt gggaaccagc tgtatttgtt 1621 caaggatggg aagtactggc gattctctga gggcaggggg agccggccgc agggcccctt 1681 ccttatcgcc gacaagtggc ccgcgctgcc ccgcaagctg gactcggtct ttgaggagcg 1741 gctctccaag aagcttttct tcttctctgg gcgccaggtg tgggtgtaca caggcgcgtc 1801 ggtgctgggc ccgaggcgtc tggacaagct gggcctggga gccgacgtgg cccaggtgac 1861 cgggcccctc cggagtggca gggggaagat gctgctgttc agcgggcggc gcctctggag 1921 gttcgacgtg aaggcgcaga tggtggatcc ccggagcgcc agcgaggtgg accggatgtt 1981 ccccgggggtg cctttggaca cgcacgacgt cttccagtac cgagagaaag cctatttctg 2041 ccaggaccgc ttctactggc gcgtgagttc ccggagtgag ttgaaccagg tggaccaagt 2101 gggctacgtg acctatgaca tcctgcagtg ccctgaggac tagggctccc gtcctgcttt 2161 ggcagtgcca tgtaaatccc cactgggacc aaccctgggg aaggagccag tttgccggat 2221 acaaactggt attctgttct ggaggaaagg gaggagtgga ggtgggctgg gccctctctt 2281 ctcacctttg tttttttgttg gagtgtttct aataaacttg gattctctaa cctttaaaaa 2341 aaaaaaaaaa aaaaaaaaaa aaaaaaaaaa aaaaaaaaaa aaaaaaa
```

The amino acid sequence of human MMP-9 (preproprotein), provided by Genbank Accession No.NP_004985.2, is incorporated herein by reference, and is shown below (SEQ ID NO: 38).

```
  1 mslwqplvlv llvlgccfaa prqrqstivl fpgdlrtnit drqlaeeyly rygytrvaem 61 rgeskslgpa llllqkqlsl petgeldsat lkamrtprcg vpdlgrfqtf egdlkwhhhn 121 itywiqnyse dlpravidda farafalwsa vtpltftrvy srdadiviqf gvaehgdgyp 181 fdgkdgllah afppgpgiqg dahfdddelw slgkgvvvpt rfgnadgaac hfpfifegrs 241 ysacttdgrs dglpwcstta nydtddrfgf cpserlytqd gnadgkpcqf pfifqgqsys 301 acttdgrsdg yrwcattany drdklfgfcp tradstvmgg nsagelcvfp fifigkeyst 361 ctsegrgdgr lwcattsnfd sdkkwgfcpd qgyslflvaa hefghalgld hssvpealmy 421 pmyrftegpp lhkddvngir hlygprpepe prppttttpq ptapptvcpt gpptvhpser 481 ptagptgpps agptgpptag pstattvpls pvddacnvni fdaiaeignq lylfkdgkyw 541 rfsegrgsrp qgpfliadkw palprkldsv feerlskklf ffsgrqvwvy tgasvlgprr 601 ldklglgadv aqvtgalrsg rgkmllfsgr rlwrfdvkaq mvdprsasev drmfpgvpld 661 thdvfqyrek ayfcqdrfyw rvssrselnq vdqvgyvtyd ilqcped
```

(signal protein AA 1-19; proportein AA 20-707; mature protein 107-707)

The siRNA used to target human MMP-9 mRNA include following sequences (SEQ ID NO: 39-42):

SEQ NO: 39:
5'-UUGUCGCUGUCAAAGUUCGAG-3'

SEQ NO: 40:
5'-UUCUUGUCGCUGUCAAAGUUC-3'

SEQ NO: 41:
5'-UUCAACUCACUCCGGGAACUC-3'

SEQ NO: 42:
5'-UUCACGUCGUCCUUAUGCAAG-3'

The molecular beacon used to target human MMP-9 mRNA includes the following sequences (SEQ ID NO:43-45):

SEQ NO: 43:
5'-CCGGTC TTGTCGCTGTCAAAGTTCGGACCGG-3'

SEQ NO: 44:
5'-CCGGTC TTATTAGAAACACTCCAAC GACCGG-3'

SEQ NO: 45:
5'-CCGGTC ATTCACGTCGTCCTTATGC GACCGG-3'

The mRNA transcript sequence encoding human MMP-3, provided by Genbank Accession No.NM_002422.3, is incorporated herein by reference, and is shown below (SEQ ID NO: 46).

```
   1 ctacaaggag gcaggcaaga cagcaaggca tagagacaac atagagctaa gtaaagccag
  61 tggaaatgaa gagtcttcca atcctactgt tgctgtgcgt ggcagtttgc tcagcctatc
 121 cattggatgg agctgcaagg ggtgaggaca ccagcatgaa ccttgttcag aaatatctag
 181 aaaactacta cgacctcaaa aaagatgtga aacagtttgt taggagaaag gacagtggtc
 241 ctgttgttaa aaaaatccga gaaatgcaga agttccttgg attggaggtg acggggaagc
 301 tggactccga cactctggag gtgatgcgca agcccaggtg tggagttcct gatgttggtc
 361 acttcagaac ctttcctggc atcccgaagt ggaggaaaac ccaccttaca tacaggattg
 421 tgaattatac accagatttg ccaaaagatg ctgttgattc tgctgttgag aaagctctga
 481 aagtctggga agaggtgact ccactcacat tctccaggct gtatgaagga gaggctgata
 541 taatgatctc ttttgcagtt agagaacatg gagacttta cccttttgat ggacctggaa
 601 atgttttggc ccatgcctat gcccctgggc cagggattaa tggagatgcc cactttgatg
 661 atgatgaaca atggacaaag gatacaacag ggaccaattt atttctcgtt gctgctcatg
 721 aaattggcca ctccctgggt ctctttcact cagccaacac tgaagctttg atgtacccac
 781 tctatcactc actcacagac ctgactcggt tccgcctgtc tcaagatgat ataaatggca
 841 ttcagtccct ctatggacct cccctgact ccctgagac ccccctggta cccacggaac
 901 ctgtccctcc agaacctggg acgccagcca actgtgatcc tgctttgtcc tttgatgctg
 961 tcagcactct gaggggagaa atcctgatct ttaaagacag gcacttttgg cgcaaatccc
1021 tcaggaagct tgaacctgaa ttgcatttga tctcttcatt ttggccatct cttccttcag
1081 gcgtggatgc cgcatatgaa gttactagca aggacctcgt tttcattttt aaaggaaatc
1141 aattctgggc tatcagagga aatgaggtac gagctggata cccaagaggc atccacaccc
1201 taggtttccc tccaaccgtg aggaaaatcg atgcagccat ttctgataag gaaaagaaca
1261 aaacatattt ctttgtagag gacaaatact ggagatttga tgagaagaga aattccatgg
1321 agccaggctt tcccaagcaa atagctgaag acttccagg gattgactca aagattgatg
1381 ctgtttttga agaatttggg ttcttttatt tctttactgg atcttcacag ttggagtttg
1441 acccaaatgc aaagaaagtg acacacactt tgaagagtaa cagctggctt aattgttgaa
1501 agagatatgt agaaggcaca atatgggcac tttaaatgaa gctaataatt cttcacctaa
1561 gtctctgtga attgaaatgt tcgttttctc ctgcctgtgc tgtgactcga gtcacactca
1621 agggaacttg agcgtgaatc tgtatcttgc cggtcatttt tatgttatta cagggcattc
```

-continued
```
1681 aaatgggctg ctgcttagct tgcaccttgt cacatagagt gatctttccc aagagaaggg 1741 gaagcactcg tgtgcaacag acaagtgact gtatctgtgt agactatttg cttatttaat 1801 aaagacgatt tgtcagttat tttatctt
```

The amino acid sequence of human MMP-3 (preproprotein), provided by Genbank Accession No.NP_002413.1, is incorporated herein by reference, and is shown below (SEQ ID NO: 47).

```
  1 mkslpillll cvavcsaypl dgaargedts mnlvqkylen yydlkkdvkq fvrrkdsgpv 61 vkkiremqkf lglevtgkld sdtlevmrkp rcgvpdvghf rtfpgipkwr kthltyrivn 121 ytpdlpkdav dsavekalkv weevtpltfs rlyegeadim isfavrehgd fypfdgpgnv 181 lahayapgpg ingdahfddd eqwtkdttgt nlflvaahei ghslglfhsa ntealmyply 241 hsltdltrfr lsqddingiq slygpppdsp etplvptepv ppepgtpanc dpalsfdays 301 firgeilifk drhfwrkslr klepelhlis sfwpslpsgv daayevtskd lvfifkgnqf 361 wairgnevra gyprgihtlg fpptvrkida aisdkeknkt yffvedkywr fdekrnsmep 421 gfpkqiaedf pgidskidav feefgffyff tgssqlefdp nakkythtlk snswlnc
(signal peptide AA 1-17; proprotein AA 18-477; mature protein AA 100-477).
```

The siRNA used to target human MMP-3 mRNA include following sequences (SEQ ID NO: 48-51):

```
SEQ NO: 48:
5'-UUCAUCAUCAUCAAAGUGGG-3'

SEQ NO: 49:
5'-UAAUAACAUAAAAAUGACCG-3'

SEQ NO: 50:
5'-UAGUCUACACAGAUACAGUC-3'

SEQ NO: 51:
5'-UAUAUCAUCUUGAGACAGGC-3'
```

The molecular beacon used to target human MMP-3 mRNA includes the following sequences (SEQ ID NO: 52-54):

```
SEQ NO 52:
5'-CCGGTC TATATCATCTTGAGACAGGC GACCGG-3'

SEQ NO 53:
5'-CCGGTC TTTCTCTTCTCATCAAATCT GACCGG-3'

SEQ NO 54:
5'-CCGGTC TAACAAACTGTTTCACATCT GACCGG-3'
```

The mRNA transcript sequence encoding human IL-1 alpha, provided by Genbank Accession No.NM_000575.3, is incorporated herein by reference, and is shown below (SEQ ID NO: 55).

```
  1 accaggcaac accattgaag gctcatatgt aaaaatccat gccttccttt ctcccaatct 61 ccattcccaa acttagccac tggcttctgg ctgaggcctt acgcatacct cccggggctt 121 gcacacacct tcttctacag aagacacacc ttgggcatat cctacagaag accaggcttc 181 tctctggtcc ttggtagagg gctactttac tgtaacaggg ccagggtgga gagttctctc 241 ctgaagctcc atccctcta taggaaatgt gttgacaata ttcagaagag taagaggatc 301 aagacttctt tgtgctcaaa taccactgtt ctcttctcta ccctgcccta accaggagct 361 tgtcacccca aactctgagg tgatttatgc cttaatcaag caaacttccc tcttcagaaa 421 agatggctca ttttccctca aaagttgcca ggagctgcca agtattctgc caattcaccc 481 tggagcacaa tcaacaaatt cagccagaac acaactacag ctactattag aactattatt 541 attaataaat tcctctccaa atctagcccc ttgacttcgg atttcacgat ttctcccttc 601 ctcctagaaa cttgataagt ttcccgcgct tccctttttc taagactaca tgtttgtcat 661 cttataaagc aaaggggtga ataaatgaac caaatcaata acttctggaa tatctgcaaa 721 caacaataat atcagctatg ccatctttca ctatttagc cagtatcgag ttgaatgaac 781 atagaaaaat acaaaactga attcttccct gtaaattccc cgttttgacg acgcacttgt
```

```
 841 agccacgtag ccacgcctac ttaagacaat acaaaaggc gaagaagact gactcaggct
 901 taagctgcca gccagagagg gagtcatttc attggcgttt gagtcagcaa agaagtcaag
 961 atggccaaag ttccagacat gtttgaagac ctgaagaact gttacagtga aaatgaagaa
1021 gacagttcct ccattgatca tctgtctctg aatcagaaat ccttctatca tgtaagctat
1081 ggcccactcc atgaaggctg catggatcaa tctgtgtctc tgagtatctc tgaaacctct
1141 aaaacatcca agcttacctt caaggagagc atggtggtag tagcaaccaa cgggaaggtt
1201 ctgaagaaga gacggttgag tttaagccaa tccatcactg atgatgacct ggaggccatc
1261 gccaatgact cagaggaaga aatcatcaag cctaggtcag caccttttag cttcctgagc
1321 aatgtgaaat acaactttat gaggatcatc aaatacgaat tcatcctgaa tgacgccctc
1381 aatcaaagta taattcgagc caatgatcag tacctcacgg ctgctgcatt acataatctg
1441 gatgaagcag tgaaatttga catgggtgct tataagtcat caaggatga tgctaaaatt
1501 accgtgattc taagaatctc aaaaactcaa ttgtatgtga ctgcccaaga tgaagaccaa
1561 ccagtgctgc tgaaggagat gcctgagata cccaaaacca tcacaggtag tgagaccaac
1621 ctcctcttct tctgggaaac tcacggcact aagaactatt tcacatcagt tgcccatcca
1681 aacttgttta ttgccacaaa gcaagactac tgggtgtgct tggcaggggg gccaccctct
1741 atcactgact ttcagatact ggaaaaccag gcgtaggtct ggagtctcac ttgtctcact
1801 tgtgcagtgt tgacagttca tatgtaccat gtacatgaag aagctaaatc ctttactgtt
1861 agtcatttgc tgagcatgta ctgagccttg taattctaaa tgaatgttta cactctttgt
1921 aagagtggaa ccaacactaa catataatgt tgttatttaa agaacaccct atattttgca
1981 tagtaccaat cattttaatt attattcttc ataacaattt taggaggacc agagctactg
2041 actatggcta ccaaaaagac tctacccata ttacagatgg gcaaattaag gcataagaaa
2101 actaagaaat atgcacaata gcagttgaaa caagaagcca cagacctagg atttcatgat
2161 ttcatttcaa ctgtttgcct tctactttta agttgctgat gaactcttaa tcaaatagca
2221 taagtttctg ggacctcagt tttatcattt tcaaaatgga gggaataata cctaagcctt
2281 cctgccgcaa cagttttttta tgctaatcag ggaggtcatt ttggtaaaat acttcttgaa
2341 gccgagcctc aagatgaagg caaagcacga aatgttattt tttaattatt atttatatat
2401 gtatttataa atatatttaa gataattata atatactata tttatgggaa cccccttcatc
2461 ctctgagtgt gaccaggcat cctccacaat agcagacagt gttttctggg ataagtaagt
2521 ttgatttcat taatacaggg cattttggtc caagttgtgc ttatcccata gccaggaaac
2581 tctgcattct agtacttggg agacctgtaa tcatataata aatgtacatt aattaccttg
2641 agccagtaat tggtccgatc tttgactctt ttgccattaa acttacctgg gcattcttgt
2701 ttcaattcca cctgcaatca agtcctacaa gctaaaatta gatgaactca actttgacaa
2761 ccatgagacc actgttatca aaactttctt ttctggaatg taatcaatgt ttcttctagg
2821 ttctaaaaat tgtgatcaga ccataatgtt acattattat caacaatagt gattgataga
2881 gtgttatcag tcataactaa ataaagcttg caacaaaatt ctctgacaaa aaaaaaaaaa
2941 aaa
```

The amino acid sequence of human IL-1 alpha (proprotein), provided by Genbank Accession No.NP_000566.3, is incorporated herein by reference, and is shown below (SEQ ID NO: 56).

```
  1 makvpdmfed lkncysenee dsssidhlsl nqksfyhvsy gplhegcmdq syslsisets
 61 ktskltfkes mvvvatngkv lkkrrlslsq sitdddleai andseeeiik prsapfsfls
121 nvkynfmrii kyefilndal nqsiirandq yltaaalhnl deavkfdmga yksskddaki
181 tvilrisktq lyvtaqdedq pvllkempei pktitgsetn llffwethgt knyftsvahp
241 nlfiatkqdy wvclaggpps itdfqilenq a (mature peptide AA 113-271).
```

The siRNA used to target human IL-1 alpha mRNA include following sequences (SEQ ID NO: 57-60):

```
SEQ NO: 57:
5'-UUUCUAUGUUCAUUCAACUC-3'

SEQ NO: 58:
5'-UCAUUCAACUCGAUACUGGC-3'

SEQ NO: 59:
5'-UUCAUUCAACUCGAUACUGG-3'

SEQ NO: 60:
5'-UAAUAGUUCUAAUAGUAGCU-3'
```

The molecular beacon used to target human IL-1 alpha mRNA includes the following sequences (SEQ ID NO: 61-63):

```
SEQ NO 61:
5'-CCGGTC TTTCTTAGTTTTCTTATGCC GACCGG-3'

SEQ NO 62:
5'-CCGGTC TAATAGTTCTAATAGTAGC GACCGG-3'

SEQ NO 63:
5'-CCGGTC TATGAACTGTCAACACTGC GACCGG-3'
```

The mRNA transcript sequence encoding human IL-1 beta, provided by Genbank Accession No.NM_000576.2, is incorporated herein by reference, and is shown below (SEQ ID NO: 64).

```
   1 accaaacctc ttcgaggcac aaggcacaac aggctgctct gggattctct tcagccaatc
  61 ttcattgctc aagtgtctga agcagccatg gcagaagtac ctgagctcgc cagtgaaatg
 121 atggcttatt acagtggcaa tgaggatgac ttgttctttg aagctgatgg ccctaaacag
 181 atgaagtgct ccttccagga cctgaccctc tgccctctgg atggcggcat ccagctacga
 241 atctccgacc accactacag caagggcttc aggcaggccg cgtcagttgt tgtggccatg
 301 gacaagctga ggaagatgct ggttccctgc ccacgacct tccaggagaa tgacctgagc
 361 accttctttc ccttcatctt tgaagaagaa cctatcttct cgacacatg ggataacgag
 421 gcttatgtgc acgatgcacc tgtacgatca ctgaactgca cgctccggga ctcacagcaa
 481 aaaagcttgg tgatgtctgg tccatatgaa ctgaaagctc tccacctcca gggacaggat
 541 atggagcaac aagtggtgtt ctccatgtcc tttgtacaag gagaagaaag taatgacaaa
 601 atacctgtgg ccttgggcct caaggaaaag aatctgtacc tgtcctgcgt gttgaaagat
 661 gataagccca ctctacagct ggagagtgta gatcccaaaa attacccaaa gaagaagatg
 721 gaaaagcgat ttgtcttcaa caagatagaa atcaataaca agctggaatt tgagtctgcc
 781 cagttcccca actggtacat cagcacctct caagcagaaa acatgcccgt cttcctggga
 841 gggaccaaag gcggccagga tataactgac ttcaccatgc aatttgtgtc ttcctaaaga
 901 gagctgtacc cagagagtcc tgtgctgaat gtggactcaa tccctagggc tggcagaaag
 961 ggaacagaaa ggttttgag tacggctata gcctggactt tcctgttgtc tacaccaatg
1021 cccaactgcc tgccttaggg tagtgctaag aggatctcct gtccatcagc caggacagtc
1081 agctctctcc tttcagggcc aatccccagc ccttttgttg agccaggcct ctctcacctc
1141 tcctactcac ttaaagcccg cctgacagaa accacggcca catttggttc taagaaaccc
1201 tctgtcattc gctcccacat tctgatgagc aaccgcttcc ctatttattt atttatttgt
1261 ttgtttgttt tattcattgg tctaatttat tcaaggtggg caagaagtag cagtgtctgt
```

```
1321 aaaagagcct agtttttaat agctatggaa tcaattcaat ttggactggt gtgctctctt 1381 taaatcaagt cctttaatta agactgaaaa tatataagct cagattattt aaatgggaat 1441 atttataaat gagcaaatat catactgttc aatggttctg aaataaactt cactgaag
```

The amino acid sequence of human IL-1 beta (proprotein), provided by Genbank Accession No.NP_000567.1, is incorporated herein by reference, and is shown below (SEQ ID NO: 65).

```
  1 maevpelase mmayysgned dlffeadgpk qmkcsfqdld
    lcpldggiql risdhhyskg
 61 frqaasvvva mdklikmlvp cpqtfqendl stffpfifee
    epiffdtwdn eayvhdapvr
121 slnctlrdsq qkslvmsgpy elkalhlqgq dmeqqvvfsm
    sfvqgeesnd kipvalglke
181 knlylscvlk ddkptlqles vdpknypkkk mekrfvfnki
    einnklefes aqfpnwyist
241 sqaenmpvfl ggtkggqdit dftmqfvss
    (mature peptide AA 117-269)
```

The siRNA used to target human IL-1 beta mRNA includes the following sequences (SEQ ID NO: 66-69):

```
SEQ NO: 66:
5'-UUAUCAUCUUUCAACACGCAG-3'

SEQ NO: 67:
5'-UUUUACAGACACUGCUACUUC-3'

SEQ NO: 68:
5'-UUUGUCAUUACUUUCUUCUCC-3'

SEQ NO: 69:
5'-UACAGACACUGCUACUUCUUG-3'
```

The molecular beacon used to target human IL-1 beta mRNA includes the following sequences (SEQ ID NO: 70-72):

```
SEQ NO: 70:
5'-CCGGTC TTTTGTCATTACTTTCTTCTC GACCGG-3'

SEQ NO: 71:
5'-CCGGTC TTTCAGTCTTAATTAAAGGAC GACCGG-3'

SEQ NO: 72:
5'-CCGGTC TTACATAAATTAACTCAGCT GACCGG-3'
```

The mRNA transcript sequence encoding human IL-6, provided by Genbank Accession No.NM_000600.3, is incorporated herein by reference, and is shown below (SEQ ID NO: 73).

```
   1 aatattagag tctcaacccc caataaatat aggactggag atgtctgagg ctcattctgc 61 cctcgagccc accgggaacg aaagagaagc tctatctccc ctccaggagc ccagctatga 121 actccttctc cacaagcgcc ttcggtccag ttgccttctc cctggggctg ctcctggtgt 181 tgcctgctgc cttccctgcc ccagtacccc aggagaaga ttccaaagat gtagccgccc 241 cacacagaca gccactcacc tcttcagaac gaattgacaa acaaattcgg tacatcctcg 301 acggcatctc agccctgaga aaggagacat gtaacaagag taacatgtgt gaaagcagca 361 aagaggcact ggcagaaaac aacctgaacc ttccaaagat ggctgaaaaa gatggatgct 421 tccaatctgg attcaatgag gagacttgcc tggtgaaaat catcactggt cttttggagt 481 ttgaggtata cctagagtac ctccagaaca gatttgagag tagtgaggaa caagccagag 541 ctgtgcagat gagtacaaaa gtcctgatcc agttcctgca gaaaaaggca agaatctag 601 atgcaataac caccctgac ccaaccacaa atgccagcct gctgacgaag ctgcaggcac 661 agaaccagtg gctgcaggac atgacaactc atctcattct gcgcagcttt aaggagttcc 721 tgcagtccag cctgagggct cttcggcaaa tgtagcatgg gcacctcaga ttgttgttgt 781 taatgggcat tccttcttct ggtcagaaac ctgtccactg ggcacagaac ttatgttgtt 841 ctctatggag aactaaaagt atgagcgtta ggacactatt ttaattattt taatttatt 901 aatatttaaa tatgtgaagc tgagttaatt tatgtaagtc atatttatat ttttaagaag 961 taccacttga aacatttat gtattagttt tgaaataata atggaaagtg gctatgcagt 1021 ttgaatatcc tttgtttcag agccagatca tttcttggaa agtgtaggct tacctcaaat
```

-continued

```
1081 aaatggctaa cttatacata tttttaaaga aatatttata ttgtatttat ataatgtata 1141 aatggttttt ataccaataa atggcatttt aaaaaattca gcaaaaaaaa aaaaaaaaaa 1201 a
```

The amino acid sequence of human IL-6 (precursor), provided by Genbank Accession No.NP_000591.1, is incorporated herein by reference, and is shown below (SEQ ID NO: 74).

```
  1 mnsfstsafg pvafslglll vlpaafpapv ppgedskdva aphrqpltss eridkqiryi 61 ldgisalrke tcnksnmces skealaennl nlpkmaekdg cfqsgfneet clvkiitgll 121 efevyleylq nrfesseeqa ravqmstkvl iqflqkkakn ldaittpdpt tnaslltklq 181 aqnqwlqdmt thlilrsfke flqsslralr qm
    (Signal peptide AA 1-29;
    mature peptide AA 30-212).
```

The siRNA used to target human IL-6 mRNA include following sequences (SEQ ID NO: 75-78):

```
SEQ NO: 75:
5'-UAAAAUAGUGUCCUAACGCUC-3'
```

```
SEQ NO: 76:
5'-UCACUACUCUCAAAUCUGUUC-3'

SEQ NO: 77:
5'-UUACUCUUGUUACAUGUCUCC-3'

SEQ NO: 78:
5'-UAACGCUCAUACUUUUAGUUC-3'
```

The molecular beacon used to target human IL-6 mRNA includes the following sequences (SEQ ID NO: 79-81):

```
SEQ NO 79:
5'-CCGGTC TTACTCTTGTTACATGTCYCCGACCTT-3'

SEQ NO 80:
5'-CCGGTC TTACTCTTGTTACATGTCTCCGACCTT-3'

SEQ NO 81:
5'-CCGGTC TACATAAAATGTTTCAAGTGGGACCTT-3'
```

The mRNA transcript sequence encoding human IL-8, provided by Genbank Accession No.NM_000584.3, is incorporated herein by reference, and is shown below (SEQ ID NO: 82).

```
   1 gagggtgcat aagttctcta gtagggtgat gatataaaaa gccaccggag cactccataa 61 ggcacaaact ttcagagaca gcagagcaca caagcttcta ggacaagagc caggaagaaa 121 ccaccggaag gaaccatctc actgtgtgta aacatgactt ccaagctggc cgtggctctc 181 ttggcagcct tcctgatttc tgcagctctg tgtgaaggtg cagttttgcc aaggagtgct 241 aaagaactta gatgtcagtg cataaagaca tactccaaac cttccaccc caaatttatc 301 aaagaactga gagtgattga gagtggacca cactgcgcca acacagaaat tattgtaaag 361 ctttctgatg aagagagct ctgtctggac cccaaggaaa actgggtgca gagggttgtg 421 gagaagtttt tgaagagggc tgagaattca taaaaaaatt cattctctgt ggtatccaag 481 aatcagtgaa gatgccagtg aaacttcaag caaatctact tcaacacttc atgtattgtg 541 tgggtctgtt gtagggttgc cagatgcaat acaagattcc tggttaaatt tgaatttcag 601 taaacaatga atagttttc attgtaccat gaaatatcca gaacatactt atatgtaaag 661 tattatttat ttgaatctac aaaaaacaac aaataatttt taaatataag gattttccta 721 gatattgcac gggagaatat acaaatagca aaattgaggc caagggccaa gagaatatcc 781 gaactttaat ttcaggaatt gaatgggttt gctagaatgt gatatttgaa gcatcacata 841 aaaatgatgg gacaataaat tttgccataa agtcaaattt agctggaaat cctggatttt 901 tttctgttaa atctggcaac cctagtctgc tagccaggat ccacaagtcc ttgttccact 961 gtgccttggt ttctccttta tttctaagtg gaaaaagtat tagccaccat cttacctcac 1021 agtgatgttg tgaggacatg tggaagcact ttaagttttt tcatcataac ataaattatt 1081 ttcaagtgta acttattaac ctatttatta tttatgtatt tatttaagca tcaaatattt 1141 gtgcaagaat ttggaaaaat agaagatgaa tcattgattg aatagttata aagatgttat
```

```
1201 agtaaattta ttttatttta gatattaaat gatgttttat tagataaatt tcaatcaggg 1261 tttttagatt aaacaaacaa acaattgggt acccagttaa attttcattt cagataaaca 1321 acaaataatt ttttagtata agtacattat tgtttatctg aaatttttaat tgaactaaca 1381 atcctagttt gatactccca gtcttgtcat tgccagctgt gttggtagtg ctgtgttgaa 1441 ttacggaata atgagttaga actattaaaa cagccaaaac tccacagtca atattagtaa 1501 tttcttgctg gttgaaactt gtttattatg tacaaataga ttcttataat attatttaaa 1561 tgactgcatt tttaaataca aggctttata tttttaactt taagatgttt ttatgtgctc 1621 tccaaatttt ttttactgtt tctgattgta tggaaatata aaagtaaata tgaaacattt 1681 aaaatataat ttgttgtcaa agtaaaaaaa aaaaaaa
```

The amino acid sequence of human IL-8(precursor), provided by Genbank Accession No.NP_000575.1, is incorporated herein by reference, and is shown below (SEQ ID NO: 83).

```
 1 mtsklavall aaflisaalc egavlprsak elrcqcikty skpfhpkfik elrviesgph 61 canteiivkl sdgrelcldp kenwvqrvve kflkraens
```

The siRNA used to target human IL-8 mRNA include following sequences (SEQ ID NO: 84-87):

SEQ NO: 84:
5'-UUUGUUUAAUCUAAAAACCC-3'

SEQ NO: 85:
5'-UUUACACACAGUGAGAUGGU-3'

SEQ NO: 86:
5'-UUCAAAUAUCACAUUCUAGC-3'

SEQ NO: 87:
5'-UUAUGCACUGACAUCUAAGU-3'

The molecular beacon used to target human IL-8 mRNA includes the following sequences (SEQ ID NO: 88-90):

SEQ NO 88:
5'-CCGGTC TATCACATTCTAGCAAACCC GACCGG-3'

SEQ NO 89:
5'-CCGGTC TACTAGAGAACTTATGCACC GACCGG-3'

SEQ NO 90:
5'-CCGGTC TAGTTCTAACTCATTATTCC GACCGG-3'

The mRNA transcript sequence encoding human IL-1R type 1 variant 1, provided by Genbank Accession No.NM_000877.3, is incorporated herein by reference, and is shown below (SEQ ID NO: 91).

```
  1 gtggccggcg gccggagccg actcggagcg cgcggcgccg gcgggagga gccggagagc 61 ggccgggccg ggcggtgggg gcgccggcct gccccgcgcg ccccagggag cggcaggaat 121 gtgacaatcg cgcgcccgcg caccgaagca ctcctcgctc ggctcctagg gctctcgccc 181 ctctgagctg agccgggttc cgcccggggc tgggatccca tcaccctcca cggccgtccg 241 tccaggtaga cgcaccctct gaagatggtg actccctcct gagaagctgg accccttggt 301 aaaagacaag gccttctcca agaagaatat gaaagtgtta ctcagactta tttgtttcat 361 agctctactg atttcttctc tggaggctga taaatgcaag gaacgtgaag aaaaaataat 421 tttagtgtca tctgcaaatg aaattgatgt tcgtccctgt cctcttaacc caaatgaaca 481 caaggcact ataacttggt ataaagatga cagcaagaca cctgtatcta cagaacaagc 541 ctccaggatt catcaacaca aagagaaact ttggtttgtt cctgctaagg tggaggattc 601 aggacattac tattgcgtgg taagaaattc atcttactgc ctcagaatta aaataagtgc 661 aaaatttgtg gagaatgagc ctaacttatg ttataatgca caagccatat ttaagcagaa 721 actacccgtt gcaggagacg gaggacttgt gtgcccttat atggagtttt ttaaaaatga 781 aataatgag ttacctaaat tacagtggta taaggattgc aaacctctac ttcttgacaa 841 tatacacttt agtggagtca agatagggct catcgtgatg aatgtggctg aaaagcatag 901 agggaactat acttgtcatg catcctacac atacttgggc aagcaatatc ctattacccg 961 ggtaatagaa tttattactc tagaggaaaa caaacccaca aggcctgtga ttgtgagccc
```

-continued

```
1021 agctaatgag acaatggaag tagacttggg atcccagata caattgatct gtaatgtcac 1081 cggccagttg agtgacattg cttactggaa gtggaatggg tcagtaattg atgaagatga 1141 cccagtgcta ggggaagact attacagtgt ggaaaatcct gcaaacaaaa aaggagtac 1201 cctcatcaca gtgcttaata tatcggaaat tgaaagtaga ttttataaac atccatttac 1261 ctgttttgcc aagaatacac atggtataga tgcagcatat atccagttaa tatatccagt 1321 cactaatttc cagaagcaca tgattggtat atgtgtcacg ttgacagtca taattgtgtg 1381 ttctgttttc atctataaaa tcttcaagat tgacattgtg cifiggtaca gggattcctg 1441 ctatgatttt ctcccaataa aagcttcaga tggaaagacc tatgacgcat atatactgta 1501 tccaaagact gttggggaag ggtctacctc tgactgtgat attttttgtgt ttaaagtctt 1561 gcctgaggtc ttggaaaaac agtgtggata taagctgttc atttatgaa gggatgacta 1621 cgttgggaa gacattgttg aggtcattaa tgaaaacgta aagaaaagca gaagactgat 1681 tatcatttta gtcagagaaa catcaggctt cagctggctg ggtggttcat ctgaagagca 1741 aatagccatg tataatgctc ttgttcagga tggaattaaa gttgtcctgc ttgagctgga 1801 gaaaatccaa gactatgaga aaatgccaga atcgattaaa ttcattaagc agaaacatgg 1861 ggctatccgc tggtcagggg actttacaca gggaccacag tctgcaaaga caaggttctg 1921 gaagaatgtc aggtaccaca tgccagtcca gcgacggtca ccttcatcta aacaccagtt 1981 actgtcacca gccactaagg agaaactgca aagagaggct cacgtgcctc tcgggtagca

2041 tggagaagtt gccaagagtt ctttaggtgc ctcctgtctt atggcgttgc aggccaggtt 2101 atgcctcatg ctgacttgca gagttcatgg aatgtaacta tatcatcctt tatccctgag 2161 gtcacctgga atcagattat taagggaata agccatgacg tcaatagcag cccagggcac 2221 ttcagagtag agggcttggg aagatctttt aaaaaggcag taggcccggt gtggtggctc 2281 acgcctataa tcccagcact ttgggaggct gaagtgggtg gatcaccaga ggtcaggagt 2341 tcgagaccag cccagccaac atggcaaaac cccatctcta ctaaaaatac aaaaatgagc 2401 taggcatggt ggcacacgcc tgtaatccca gctacacctg aggctgaggc aggagaattg 2461 cttgaaccgg ggagacggag gttgcagtga gccgagtttg gccactgca ctctagcctg 2521 gcaacagagc aagactccgt ctcaaaaaaa gggcaataaa tgccctctct gaatgtttga 2581 actgccaaga aaaggcatgg agacagcgaa ctagaagaaa gggcaagaag gaaatagcca 2641 ccgtctacag atggcttagt taagtcatcc acagcccaag ggcggggcta tgccttgtct 2701 ggggaccctg tagagtcact gaccctggag cggctctcct gagaggtgct gcaggcaaag 2761 tgagactgac acctcactga ggaagggaga catattcttg gagaactttc catctgcttg 2821 tattttccat acacatcccc agccagaagt tagtgtccga agaccgaatt ttattttaca 2881 gagcttgaaa actcacttca atgaacaaag ggattctcca ggattccaaa gttttgaagt 2941 catcttagct ttccacagga gggagagaac ttaaaaaagc aacagtagca gggaattgat 3001 ccacttctta atgctttcct ccctggcatg accatcctgt cctttgttat tatcctgcat 3061 tttacgtctt tggaggaaca gctccctagt ggcttcctcc gtctgcaatg tcccttgcac 3121 agcccacaca tgaaccatcc ttcccatgat gccgctcttc tgtcatcccg ctcctgctga 3181 aacacctccc aggggctcca cctgttcagg agctgaagcc catgctttcc caccagcatg 3241 tcactcccag accacctccc tgccctgtcc tccagcttcc cctcgctgtc ctgctgtgtg 3301 aattcccagg ttggcctggt ggccatgtcg cctgccccca gcactcctct gtctctgctc 3361 ttgcctgcac ccttcctcct cctttgccta ggaggccttc tcgcattttc tctagctgat 3421 cagaattta ccaaaattca gaacatcctc caattccaca gtctctggga gactttccct
```

```
3481 aagaggcgac ttcctctcca gccttctctc tctggtcagg cccactgcag agatggtggt
3541 gagcacatct gggaggctgg tctccctcca gctggaattg ctgctctctg agggagaggc
3601 tgtggtggct gtctctgtcc ctcactgcct tccaggagca atttgcacat gtaacataga
3661 tttatgtaat gctttatgtt taaaaacatt ccccaattat cttatttaat ttttgcaatt
3721 attctaattt tatatataga gaaagtgacc tattttttaa aaaaatcaca ctctaagttc
3781 tattgaacct aggacttgag cctccatttc tggcttctag tctggtgttc tgagtacttg
3841 atttcaggtc aataacggtc cccctcact ccacactggc acgtttgtga aagaaatga
3901 cattttgcta ggaagtgacc gagtctagga atgcttttat tcaagacacc aaattccaaa
3961 cttctaaatg ttggaatttt caaaaattgt gtttagattt tatgaaaaac tcttctactt
4021 tcatctattc tttccctaga ggcaaacatt tcttaaaatg tttcattttc attaaaaatg
4081 aaagccaaat ttatatgcca ccgattgcag gacacaagca cagttttaag agttgtatga
4141 acatggagag gacttttggt ttttatattt ctcgtattta atatgggtga acaccaactt
4201 ttatttggaa taataatttt cctcctaaac aaaaacacat tgagtttaag tctctgactc
4261 ttgccttttcc acctgctttc tcctgggccc gctttgcctg cttgaaggaa cagtgctgtt
4321 ctggagctgc tgttccaaca gacagggcct agctttcatt tgacacacag actacagcca
4381 gaagcccatg gagcagggat gtcacgtctt gaaaagccta ttagatgttt tacaaattta
4441 attttgcaga ttatttttagt ctgtcatcca gaaaatgtgt cagcatgcat agtgctaaga
4501 aagcaagcca atttggaaac ttaggttagt gacaaaattg gccagagagt gggggtgatg
4561 atgaccaaga attacaagta gaatggcagc tggaatttaa ggagggacaa gaatcaatgg
4621 ataagcgtgg gtggaggaag atccaaacag aaaagtgcaa agttattccc catcttccaa
4681 gggttgaatt ctgaggaag aagacacatt cctagttccc cgtgaacttc ctttgactta
4741 ttgtccccac taaaacaaaa caaaaaactt ttaatgcctt ccacattaat tagattttct
4801 tgcagttttt ttatggcatt ttttttaaaga tgccctaagt gttgaagaag agtttgcaaa
4861 tgcaacaaaa tatttaatta ccggttgtta aaactggttt agcacaattt atattttccc
4921 tctcttgcct ttcttatttg caataaaagg tattgagcca ttttttaaat gacattttttg
4981 ataaattatg tttgtactag ttgatgaagg agtttttttt aacctgttta tataattttg
5041 cagcagaagc caaattttttt gtatattaaa gcaccaaatt catgtacagc atgcatcacg
5101 gatcaataga ctgtacttat tttccaataa aatttttcaaa ctttgtactg ttaaaaaaaa
5161 aaaaaaaaaa
```

The amino acid sequence of human IL-1R type 1 isoform 1 precursor, provided by Genbank Accession No.NP_000868.1, is incorporated herein by reference, and is shown below (SEQ ID NO: 92).

```
  1 mkvllrlicf iallisslea dkckereeki ilvssaneid
    vrpcpinpne hkgtitwykd
 61 dsktpvsteq asrihqhkek lwfvpakved sghyycvvrn
    ssyclrikis akfvenepnl
121 cynaqaifkq klpvagdggl vcpymeffkn ennelpklqw
    ykdckpllld nihfsgvkdr
181 livmnvaekh rgnytchasy tylgkqypit rviefitlee
    nkptrpvivs panetmevdl
241 gsqiqlicnv tgqlsdiayw kwngsvided dpvlgedyys
    venpankrrs tlitvinise
301 iesrfykhpf tcfaknthgi daayiqliyp vtnfqkhmig
    icvtltviiv csvfiykifk
361 idivlwyrds cydflpikas dgktydayil ypktvgegst
    sdcdifvfkv lpevlekqcg
```

-continued

```
421 yklfiygrdd yvgedivevi nenvkksrrl iiilvretsg
    fswlggssee qiamynalvq 481 dgikvvllel ekiqdyekmp esikfikqkh gairwsgdft
    qgpqsaktrf wknvryhmpv 541 qrrspsskhq llspatkekl qreahvplg
    (Signal peptide 1-20;
    mature peptide AA 21-569).
```

The siRNA used to target human IL-1R type 1 variant 1 mRNA include following sequences (SEQ ID NO: 93-96):

SEQ NO: 93:
5'-UUUCUUCUCACAAACGUGCC-3'

SEQ NO: 94:
5'-UUAUACCAAGUUAUAGUGCC-3'

SEQ NO: 95:
5'-UUGUAAAACAUCUAAUAGGC-3'

SEQ NO: 96:
5'-UUUCCACACUGUAAUAGUCU-3'

The molecular beacon used to target human IL-1R type 1 variant 1 mRNA includes the following sequences (SEQ ID NO: 97-99):

SEQ NO 97:
5'-CCGGTC TTTCTTCTCACAAACGTGC GACCGG-3'

SEQ NO 98:
5'-CCGGTC TTAAACACAAAAATATCAC GACCGG-3'

SEQ NO 99:
5'-CCGGTC TTTCCACACTGTAATAGTC GACCGG-3'

The mRNA transcript sequence encoding human TNF-alpha, provided by Genbank Accession No.NM_000594.3, is incorporated herein by reference, and is shown below (SEQ ID NO: 100).

```
   1 cagacgctcc ctcagcaagg acagcagagg accagctaag agggagagaa gcaactacag
  61 acccccctg aaaacaaccc tcagacgcca catccctga caagctgcca ggcaggttct
 121 cttcctctca catactgacc cacggctcca ccctctctcc cctggaaagg acaccatgag
 181 cactgaaagc atgatccggg acgtggagct ggccgaggag gcgctcccca agaagacagg
 241 ggggcccag gctccaggc ggtgcttgtt cctcagcctc ttctccttcc tgatcgtggc
 301 aggcgccacc acgctcttct gcctgctgca ctttggagtg atcggccccc agagggaaga
 361 gttcccagg gacctctctc taatcagccc tctggcccag gcagtcagat catcttctcg
 421 aaccccgagt gacaagcctg tagcccatgt tgtagcaaac cctcaagctg aggggcagct
 481 ccagtggctg aaccgccggg ccaatgccct cctggccaat ggcgtggagc tgagagataa
 541 ccagctggtg gtgccatcag agggcctgta cctcatctac tcccaggtcc tcttcaaggg
 601 ccaaggctgc ccctccaccc atgtgctcct cacccacacc atcagccgca tcgccgtctc
 661 ctaccagacc aaggtcaacc tcctctctgc catcaagagc ccctgccaga gggagacccc
 721 agagggggct gaggccaagc cctggtatga gcccatctat ctgggagggg tcttccagct
 781 ggagaagggt gaccgactca gcgctgagat caatcggccc gactatctcg actttgccga
 841 gtctgggcag gtctactttg ggatcattgc cctgtgagga ggacgaacat ccaaccttcc
 901 caaacgcctc ccctgcccca atcccttat tacccctcc ttcagacacc ctcaacctct
 961 tctggctcaa aaagagaatt gggggcttag ggtcggaacc caagcttaga actttaagca
1021 acaagaccac cacttcgaaa cctgggattc aggaatgtgt ggcctgcaca gtgaagtgct
1081 ggcaaccact aagaattcaa actggggcct ccagaactca ctggggccta cagctttgat
1141 ccctgacatc tggaatctgg agaccaggga gcctttggtt ctggccagaa tgctgcagga
1201 cttgagaaga cctcacctag aaattgacac aagtggacct taggccttcc tctctccaga
1261 tgtttccaga cttccttgag acacggagcc cagccctccc catggagcca gctccctcta
1321 tttatgtttg cacttgtgat tatttattat ttatttatta tttatttatt tacagatgaa
1381 tgtatttatt tgggagaccg gggtatcctg ggggacccaa tgtaggagct gccttggctc
1441 agacatgttt tccgtgaaaa cggagctgaa caataggctg ttcccatgta gcccctggc
1501 ctctgtgcct tcttttgatt atgttttta aatatttat ctgattaagt tgtctaaaca
```

-continued

```
1561  atgctgattt ggtgaccaac tgtcactcat tgctgagcct ctgctcccca ggggagttgt 1621  gtctgtaatc gccctactat tcagtggcga gaaataaagt ttgcttagaa aagaaaaaaa 1681  aaaaaa
```

The amino acid sequence of human TNF-alpha, provided by Genbank Accession No.NP_000585.2, is incorporated herein by reference, and is shown below (SEQ ID NO: 101).

```
  1  mstesmirdv elaeealpkk tggpqgsrrc lflslfsfli vagattlfcl lhfgvigpqr 61  eefprdlsli splaqavrss srtpsdkpva hvvanpqaeg qlqwlnrran allangvelr 121  dnqlvvpseg lyliysqvlf kgqgcpsthv llthtisria vsyqtkvnll saikspcqre 181  tpegaeakpw yepiylggvf qlekgdrlsa einrpdyldf aesgqvyfgi ial (Exemplary regions include residues 36-56 (transmembrane region; residue 80-glycosylation site; 102-

233 tumor necrosis factor site; and residues 105, 106, 111, 153, 160 and 165- receptor binding sites)
```

The siRNA used to target human TNF-alpha mRNA include following sequences (SEQ ID NO: 102-105):

```
SEQ NO: 102:
5'-AAUAAAUAAUCACAAGUGC-3'

SEQ NO: 103:
5'-UAAAAAACAUAAUCAAAAG-3'

SEQ NO: 104:
5'-UAAUAAAUAAUCACAAGUG-3'

SEQ NO: 105:
5'-UUUUCUUUUCUAAGCAAAC-3'
```

The molecular beacon used to target human TNF-alpha mRNA includes the following sequences (SEQ ID NO: 106-108):

```
SEQ NO 106:
5'-CCGGTC AAACATAATCAAAAGAAGG GACCGG-3'

SEQ NO 107:
5'-CCGGTC TAAAAAACATAATCAAAAG GACCGG-3'

SEQ NO 108:
5'-CCGGTC TATTTTAAAAAACATAATC GACCGG-3'
```

The mRNA transcript sequence encoding human VEGF A variant 1, provided by Genbank Accession No.NM_001025366.2, is incorporated herein by reference, and is shown below (SEQ ID NO: 109).

```
  1  tcgcggaggc ttggggcagc cgggtagctc ggaggtcgtg gcgctggggg ctagcaccag 61  cgctctgtcg ggaggcgcag cggttaggtg gaccggtcag cggactcacc ggccagggcg 121  ctcggtgctg gaatttgata ttcattgatc cgggttttat ccctcttctt ttttcttaaa 181  cattttttt taaaactgta ttgtttctcg ttttaattta tttttgcttg ccattcccca 241  cttgaatcgg gccgacggct tggggagatt gctctacttc cccaaatcac tgtggatttt 301  ggaaaccagc agaaagagga aagaggtagc aagagctcca gagagaagtc gaggaagaga 361  gagacgggt cagagagagc gcgcgggcgt gcgagcagcg aaagcgacag gggcaaagtg 421  agtgacctgc ttttgggggt gaccgccgga gcgcggcgtg agccctcccc cttgggatcc 481  cgcagctgac cagtcgcgct gacggacaga cagacagaca ccgccccag ccccagctac 541  cacctcctcc ccggccggcg gcggacagtg gacgcggcgg cgagccgcgg gcaggggccg 601  gagcccgcgc ccggaggcgg ggtgaggggg gtcggggctc gcggcgtcgc actgaaactt 661  ttcgtccaac ttctgggctg ttctcgcttc ggaggagccg tggtccgcgc gggggaagcc 721  gagccgagcg gagccgcgag aagtgctagc tcgggccggg aggagccgca gccggaggag 781  ggggaggagg aagaagagaa ggaagaggag agggggccgc agtggcgact cggcgctcgg 841  aagccgggct catggacggg tgaggcggc gtgtgcgcag acagtgctcc agccgcgcgc 901  gctccccagg ccctggcccg ggcctcgggc cggggaggaa gagtagctcg ccgaggcgcc
```

```
 961  gaggagagcg ggccgcccca cagcccgagc cggagaggga gcgcgagccg cgccggcccc
1021  ggtcgggcct ccgaaaccat gaactttctg ctgtcttggg tgcattggag ccttgccttg
1081  ctgctctacc tccaccatgc caagtggtcc caggctgcac ccatggcaga aggaggaggg
1141  cagaatcatc acgaagtggt gaagttcatg gatgtctatc agcgcagcta ctgccatcca
1201  atcgagaccc tggtggacat cttccaggag taccctgatg agatcgagta catcttcaag
1261  ccatcctgtg tgccctgat gcgatgcggg ggctgctgca atgacgaggg cctggagtgt
1321  gtgcccactg aggagtccaa catcaccatg cagattatgc ggatcaaacc tcaccaaggc
1381  cagcacatag gagagatgag cttcctacag cacaacaaat gtgaatgcag accaaagaaa
1441  gatagagcaa gacaagaaaa aaaatcagtt cgaggaaagg gaaaggggca aaaacgaaag
1501  cgcaagaaat cccggtataa gtcctggagc gtgtacgttg gtgcccgctg ctgtctaatg
1561  ccctggagcc tccctggccc ccatccctgt gggccttgct cagagcggag aaagcatttg
1621  tttgtacaag atccgcagac gtgtaaatgt tcctgcaaaa acacagactc gcgttgcaag
1681  gcgaggcagc ttgagttaaa cgaacgtact tgcagatgtg acaagccgag gcggtgagcc
1741  gggcaggagg aaggagcctc cctcagggtt tcgggaacca gatctctcac caggaaagac
1801  tgatacagaa cgatcgatac agaaaccacg ctgccgccac cacaccatca ccatcgacag
1861  aacagtcctt aatccagaaa cctgaaatga aggaagagga gactctgcgc agagcacttt
1921  gggtccggag ggcgagactc cggcggaagc attcccgggc gggtgaccca gcacggtccc
1981  tcttggaatt ggattcgcca tttattttt cttgctgcta aatcaccgag cccggaagat
2041  tagagagttt tatttctggg attcctgtag acacacccac ccacatacat acatttatat
2101  atatatatat tatatatata taaaaataaa tatctctatt ttatatatat aaaatatata
2161  tattcttttt ttaaattaac agtgctaatg ttattggtgt cttcactgga tgtatttgac
2221  tgctgtggac ttgagttggg aggggaatgt tcccactcag atcctgacag ggaagaggag
2281  gagatgagag actctggcat gatctttttt ttgtcccact tggtggggcc agggtcctct
2341  cccctgccca ggaatgtgca aggccagggc atggggcaa atatgaccca gttttgggaa
2401  caccgacaaa cccagccctg gcgctgagcc tctctacccc aggtcagacg gacagaaaga
2461  cagatcacag gtacagggat gaggacaccg gctctgacca ggagtttggg gagcttcagg
2521  acattgctgt gctttgggga ttccctccac atgctgcacg cgcatctcgc ccccaggggc
2581  actgcctgga agattcagga gcctgggcgg ccttcgctta ctctcacctg cttctgagtt
2641  gcccaggaga ccactggcag atgtcccggc gaagagaaga gacacattgt tggaagaagc
2701  agcccatgac agctccccctt cctgggactc gccctcatcc tcttcctgct ccccttcctg
2761  gggtgcagcc taaaaggacc tatgtcctca caccattgaa accactagtt ctgtcccccc
2821  aggagacctg gttgtgtgtg tgtgagtggt tgaccttcct ccatcccctg gtccttccct
2881  tcccttcccg aggcacagag agacagggca ggatccacgt gcccattgtg gaggcagaga
2941  aaagagaaag tgttttatat acggtactta tttaatatcc cttttaatt agaaattaaa
3001  acagttaatt taattaaaga gtagggtttt ttttcagtat tcttggttaa tatttaattt
3061  caactattta tgagatgtat cttttgctct ctcttgctct cttatttgta ccggttttg
3121  tatataaaat tcatgtttcc aatctctctc tccctgatcg gtgacagtca ctagcttatc
3181  ttgaacagat atttaatttt gctaacactc agctctgccc tccccgatcc cctggctccc
3241  cagcacacat tcctttgaaa taaggtttca atatacatct acatactata tatatatttg
3301  gcaacttgta tttgtgtgta tatatatata tatatgttta tgtatatatg tgattctgat
3361  aaaatagaca ttgctattct gttttttata tgtaaaaaca aaacaagaaa aaatagagaa
```

-continued

```
3421  ttctacatac taaatctctc tcctttttta attttaatat ttgttatcat ttatttattg 3481  gtgctactgt ttatccgtaa taattgtggg gaaaagatat taacatcacg tctttgtctc 3541  tagtgcagtt tttcgagata ttccgtagta catatttatt tttaaacaac gacaaagaaa 3601  tacagatata tcttaaaaaa aaaaaagcat tttgtattaa agaatttaat tctgatctca 3661  aaaaaaaaaa aaaaaaa
```

The amino acid sequence of human VEGF A isoform 1, provided by Genbank Accession No.NP_001020537.2, is incorporated herein by reference, and is shown below (SEQ ID NO: 110).

```
  1  mtdrqtdtap spsyhllpgr rrtvdaaasr gqgpepapgg gvegvgargv alklfvqllg 61  csrfggavvr ageaepsgaa rsassgreep qpeegeeeee keeergpqwr lgarkpgswt 121  geaavcadsa paarapqala rasgrggrva rrgaeesgpp hspsrrgsas ragpgraset 181  mnfllswvhw slalllylhh akwsqaapma egggqnhhev vkfmdvyqrs ychpietlvd 241  ifqeypdeie yifkpscvpl mrcggccnde glecvptees nitmqimrik phqgqhigem 301  sflqhnkcec rpkkdrarqe kksvrgkgkg qkrkrkksry kswsvyvgar cclmpwslpg 361  phpcgpcser rkhlfvqdpq tckcscjntd srckarqlel nertcrcdkp rr
```

The siRNA used to target human VEGF A variant 1 mRNA include following sequences (SEQ ID NO: 111-114):

```
SEQ NO: 111:
5'-UAAAACUCUCUAAUCUUCCGG-3'

SEQ NO: 112:
5'-UUCCUUCUCUUCUUCCUCCUC-3'

SEQ NO: 113:
5'-UAUACACACAAAUACAAGUUG-3'

SEQ NO: 114:
5'-UUAAAACGAGAAACAAUACAG-3'
```

The molecular beacon used to target human VEGF A variant 1 mRNA includes the following sequences (SEQ ID NO: 115-117):

```
SEQ NO 115:
5'-CCGGTC TAAAACTCTCTAATCTTCC GACCGG-3'

SEQ NO 116:
5'-CCGGTC TTTGATCCGCATAATCTGC GACCGG-3'

SEQ NO 117:
5'-CCGGTC TTGAAATTAAATATTAACC GACCGG-3'
```

The mRNA transcript sequence encoding human TGF-beta 1, provided by Genbank Accession No.NM_000660.5, is incorporated herein by reference, and is shown below (SEQ ID NO: 118).

```
  1  agccggtccc cgccgccgcc gcccttcgcg ccctgggcca tctccctccc acctccctcc 61  gcggagcagc cagacagcga gggcccccggc cggggcagg ggggacgccc cgtccggggc 121  acccccccgg ctctgagccg cccgcgggc cggcctcggc ccggagcgga ggaaggagtc 181  gccgaggagc agcctgaggc cccagagtct gagacgagcc gccgccgccc ccgccactgc 241  ggggaggagg gggaggagga gcgggaggag ggacgagctg gtcgggagaa gaggaaaaaa 301  acttttgaga cttttccgtt gccgctggga gccggaggcg cggggacctc ttggcgcgac 361  gctgccccgc gaggaggcag gacttgggga ccccagaccg cctcccttttg ccgccgggga 421  cgcttgctcc ctccctgccc cctacacggc gtccctcagg cgcccccatt ccggaccagc 481  cctcgggagt cgccgacccg gcctcccgca aagactttttc cccagacctc gggcgcaccc 541  cctgcacgcc gccttcatcc ccggcctgtc tcctgagccc ccgcgcatcc tagacccttt 601  ctcctccagg agacggatct ctctccgacc tgccacagat ccctattca agaccaccca 661  ccttctggta ccagatcgcg cccatctagg ttatttccgt gggatactga gacacccccg 721  gtccaagcct cccctccacc actgcgccct tctccctgag gacctcagct ttccctcgag
```

```
 781   gccctcctac cttttgccgg gagacccca gcccctgcag gggcggggcc tccccaccac
 841   accagccctg ttcgcgctct cggcagtgcc gggggcgcc gcctccccca tgccgccctc
 901   cgggctgcgg ctgctgccgc tgctgctacc gctgctgtgg ctactggtgc tgacgcctgg
 961   ccggccggcc gcgggactat ccacctgcaa gactatcgac atggagctgg tgaagcggaa
1021   gcgcatcgag gccatccgcg gccagatcct gtccaagctg cggctcgcca gcccccccgag
1081   ccaggggag gtgccgcccg gcccgctgcc cgaggccgtg ctcgccctgt acaacagcac
1141   ccgcgaccgg gtggccgggg agagtgcaga accggagccc gagcctgagg ccgactacta
1201   cgccaaggag gtcacccgcg tgctaatggt ggaaacccac aacgaaatct atgacaagtt
1261   caagcagagt acacacagca tatatatgtt cttcaacaca tcagagctcc gagaagcggt
1321   acctgaaccc gtgttgctct cccgggcaga gctgcgtctg ctgaggctca agttaaaagt
1381   ggagcagcac gtggagctgt accagaaata cagcaacaat tcctggcgat acctcagcaa
1441   ccggctgctg gcacccagcg actcgccaga gtggttatct tttgatgtca ccggagttgt
1501   gcggcagtgg ttgagccgtg gaggggaaat tgagggcttt cgccttagcg cccactgctc
1561   ctgtgacagc agggataaca cactgcaagt ggacatcaac gggttcacta ccggccgccg
1621   aggtgacctg gccaccattc atggcatgaa ccggcctttc ctgcttctca tggccacccc
1681   gctggagagg gcccagcatc tgcaaagctc ccggcaccgc cgagccctgg acaccaacta
1741   ttgcttcagc tccacggaga agaactgctg cgtgcggcag ctgtacattg acttccgcaa
1801   ggacctcggc tggaagtgga tccacgagcc caagggctac catgccaact tctgcctcgg
1861   gccctgcccc tacatttgga gcctggacac gcagtacagc aaggtcctgg ccctgtacaa
1921   ccagcataac ccgggcgcct cggcggcgcc gtgctgcgtg ccgcaggcgc tggagccgct
1981   gcccatcgtg tactacgtgg gccgcaagcc caaggtggag cagctgtcca acatgatcgt
2041   gcgctcctgc aagtgcagct gaggtcccgc ccgccccgc ccgccccgg caggcccggc
2101   cccaccccgc cccgccccg ctgccttgcc catgggggct gtatttaagg cacccgtgc
2161   cccaagccca cctggggccc cattaaagat ggagagagga ctgcggatct ctgtgtcatt
2221   gggcgcctgc ctgggtctc catccctgac gttcccccac tcccactccc tctctctccc
2281   tctctgcctc ctcctgcctg tctgcactat cctttgcc ggcatcaagg cacaggggac
2341   cagtggggaa cactactgta gttagatcta tttattgagc accttgggca ctgttgaagt
2401   gccttacatt aatgaactca ttcagtcacc atagcaacac tctgagatgc agggactctg
2461   ataacaccca ttttaaaggt gaggaaacaa gcccagagag gttaagggag gagttcctgc
2521   ccaccaggaa cctgctttag tgggggatag tgaagaagac aataaaagat agtagttcag
2581   gcc
```

The amino acid sequence of human TGF-beta 1 (precursor), provided by Genbank Accession No. NP_000651.3, is incorporated herein by reference, and is shown below (SEQ ID NO:119).

```
  1   mppsglrllp lllpllwllv ltpgrpaagl stcktidmel vkrkrieair gqilsklrla
 61   sppsqgevpp gplpeavlal ynstrdrvag esaepepepe adyyakevtr vlmvethnei
121   ydkfkqsths iymffntsel reavpepvll sraelrllrl klkveqhvel yqkysnnswr
181   ylsnrllaps dspewlsfdv tgvvrqwlsr ggeiegfrls ahcscdsrdn tlqvdingft
241   tgrrgdlati hgmnrpflll matpleraqh lqssrhrral dtnycfsste knccvrqlyi
```

-continued

```
301 dfrkdlgwkw ihepkgyhan fclgpcpyiw sldtqyskvl alynqhnpga saapccvpqa 361 leplpivyyv grkpkveqls nmivrsckcs (Signal peptide AA 1-29; mature
    peptide AA 30-278).
```

The siRNA used to target human TGF-beta 1 mRNA include following sequences (SEQ ID NO: 120-123):

```
SEQ NO: 120:
5'-UAUUGUCUUCUUCACUAUC-3'

SEQ NO: 121:
5'-UAGAUCUAACUACAGUAGU-3'

SEQ NO: 122:
5'-UAUAUGCUGUGUGUACUCU-3'

SEQ NO: 123:
5'-UAUAUAUGCUGUGUGUACU-3'
```

The molecular beacon used to target human TGF-beta 1 mRNA includes the following sequences (SEQ ID NO: 124-126):

```
SEQ NO 124:
5'-CCGGTC ATATATGCTGTGTGTACTC GACCGG-3'

SEQ NO 125:
5'-CCGGTC TTTTATTGTCTTCTTCACT GACCGG-3'

SEQ NO 126:
5'-CCGGTC TATATATGCTGTGTGTACT GACCGG-3'
```

The mRNA transcript sequence encoding human TGF-beta 2 variant 1, provided by Genbank Accession No.NM_001135599.2, is incorporated herein by reference, and is shown below (SEQ ID NO: 127).

```
   1 gtgatgttat ctgctggcag cagaaggttc gctccgagcg gagctccaga agctcctgac
  61 aagagaaaga cagattgaga tagagataga aagagaaaga gagaaagaga cagcagagcg
 121 agagcgcaag tgaaagaggc aggggagggg gatggagaat attagcctga cggtctaggg
 181 agtcatccag gaacaaactg aggggctgcc cggctgcaga caggaggaga cagagaggat
 241 ctattttagg gtggcaagtg cctacctacc ctaagcgagc aattccacgt tggggagaag
 301 ccagcagagg ttgggaaagg gtgggagtcc aagggagccc ctgcgcaacc ccctcaggaa
 361 taaaactccc cagccagggt gtcgcaaggg ctgccgttgt gatccgcagg gggtgaacgc
 421 aaccgcgacg gctgatcgtc tgtggctggg ttggcgtttg gagcaagaga aggaggagca
 481 ggagaaggag ggagctggag gctggaagcg tttgcaagcg gcggcggcag caacgtggag
 541 taaccaagcg ggtcagcgcg cgcccgccag ggtgtaggcc acggagcgca gctcccagag
 601 caggatccgc gccgcctcag cagcctctgc ggccctgcg gcacccgacc gagtaccgag
 661 cgccctgcga agcgcaccct cctcccgcg gtgcgctggg ctcgccccca gcgcgcgcac
 721 acgcacacac acacacacac acacacacgc acgcacacac gtgtgcgctt ctctgctccg
 781 gagctgctgc tgctcctgct ctcagcgccg cagtggaagg caggaccgaa ccgctccttc
 841 tttaaatata taaatttcag cccaggtcag cctcggcggc ccccctcacc gcgctcccgg
 901 cgcccctccc gtcagttcgc cagctgccag ccccgggacc ttttcatctc ttccttttg
 961 gccggaggag ccgagttcag atccgccact ccgcacccga gactgacaca ctgaactcca
1021 cttcctcctc ttaaatttat ttctacttaa tagccactcg tctcttttt tccccatctc
1081 attgctccaa gaatttttt cttcttactc gccaaagtca gggttccctc tgcccgtccc
1141 gtattaatat ttccactttt ggaactactg gccttttctt tttaaggaa ttcaagcagg
1201 atacgttttt ctgttgggca ttgactagat tgtttgcaaa agtttcgcat caaaaacaac
1261 aacaacaaaa aaccaaacaa ctctccttga tctatacttt gagaattgtt gatttctttt
1321 ttttattctg acttttaaaa acaacttttt tttccacttt tttaaaaaat gcactactgt
1381 gtgctgagcg cttttctgat cctgcatctg gtcacggtcg cgctcagcct gtctacctgc
1441 agcacactcg atatggacca gttcatgcgc aagaggatcg aggcgatccg cgggcagatc
1501 ctgagcaagc tgaagctcac cagtcccca gaagactatc ctgagcccga ggaagtcccc
1561 ccggaggtga tttccatcta caacagcacc agggacttgc tccaggagaa ggcgagccgg
```

-continued

```
1621   agggcggccg cctgcgagcg cgagaggagc gacgaagagt actacgccaa ggaggtttac
1681   aaaatagaca tgccgccctt cttcccctcc gaaactgtct gcccagttgt tacaacaccc
1741   tctggctcag tgggcagctt gtgctccaga cagtcccagg tgctctgtgg gtaccttgat
1801   gccatcccgc ccactttcta cagaccctac ttcagaattg ttcgatttga cgtctcagca
1861   atggagaaga atgcttccaa tttggtgaaa gcagagttca gagtctttcg tttgcagaac
1921   ccaaaagcca gagtgcctga caacggatt gagctatatc agattctcaa gtccaaagat
1981   ttaacatctc caacccagcg ctacatcgac agcaaagttg tgaaaacaag agcagaaggc
2041   gaatggctct ccttcgatgt aactgatgct gttcatgaat ggcttcacca taaagacagg
2101   aacctgggat ttaaaataag cttacactgt ccctgctgca cttttgtacc atctaataat
2161   tacatcatcc caaataaaag tgaagaacta gaagcaagat ttgcaggtat tgatggcacc
2221   tccacatata ccagtggtga tcagaaaact ataaagtcca ctaggaaaaa aaacagtggg
2281   aagacccac atctcctgct aatgttattg ccctcctaca gacttgagtc acaacagacc
2341   aaccggcgga agaagcgtgc tttggatgcg gcctattgct ttagaaatgt gcaggataat
2401   tgctgcctac gtccacttta cattgatttc aagagggatc tagggtggaa atggatacac
2461   gaacccaaag ggtacaatgc caacttctgt gctggagcat gcccgtattt atggagttca
2521   gacactcagc acagcagggt cctgagctta tataatacca taaatccaga agcatctgct
2581   tctccttgct gcgtgtccca agatttagaa cctctaacca ttctctacta cattggcaaa
2641   acacccaaga ttgaacagct ttctaatatg attgtaaagt cttgcaaatg cagctaaaat
2701   tcttggaaaa gtggcaagac caaaatgaca atgatgatga taatgatgat gacgacgaca
2761   acgatgatgc ttgtaacaag aaaacataag agagccttgg ttcatcagtg ttaaaaaatt
2821   tttgaaaagg cggtactagt tcagacactt tggaagtttg tgttctgttt gttaaaactg
2881   gcatctgaca caaaaaaagt tgaaggcctt attctacatt tcacctactt tgtaagtgag
2941   agagacaaga agcaaatttt ttttaaagaa aaaaataaac actggaagaa tttattagtg
3001   ttaattatgt gaacaacgac aacaacaaca acaacaacaa acaggaaaat cccattaagt
3061   ggagttgctg tacgtaccgt tcctatcccg cgcctcactt gattttctg tattgctatg
3121   caataggcac ccttcccatt cttactctta gagttaacag tgagttattt attgtgtgtt
3181   actatataat gaacgtttca ttgcccttgg aaaataaaac aggtgtataa agtggagacc
3241   aaatactttg ccagaaactc atggatggct taaggaactt gaactcaaac gagccagaaa
3301   aaaagaggtc atattaatgg gatgaaaacc caagtgagtt attatatgac cgagaaagtc
3361   tgcattaaga taaagaccct gaaaacacat gttatgtatc agctgcctaa ggaagcttct
3421   tgtaaggtcc aaaaactaaa aagactgtta ataaaagaaa ctttcagtca gaataagtct
3481   gtaagttttt ttttttcttt ttaattgtaa atggttcttt gtcagtttag taaaccagtg
3541   aaatgttgaa atgttttgac atgtactggt caaacttcag accttaaaat attgctgtat
3601   agctatgcta taggtttttt cctttgtttt ggtatatgta accataccta tattattaaa
3661   atagatggat atagaagcca gcataattga aaacacatct gcagatctct tttgcaaact
3721   attaaatcaa aacattaact actttatgtg taatgtgtaa atttttacca tatttttat
3781   attctgtaat aatgtcaact atgatttaga ttgacttaaa tttgggctct tttaatgat
3841   cactcacaaa tgtatgtttc tttagctgg ccagtacttt tgagtaaagc ccctatagtt
3901   tgacttgcac tacaaatgca ttttttttt aataacattt gccctacttg tgctttgtgt
3961   ttctttcatt attatgacat aagctacctg ggtccacttg tcttttcttt ttttgtttc
```

-continued

```
4021  acagaaaaga tgggttcgag ttcagtggtc ttcatcttcc aagcatcatt actaaccaag
4081  tcagacgtta acaaattttt atgttaggaa aaggaggaat gttatagata catagaaaat
4141  tgaagtaaaa tgttttcatt ttagcaagga tttagggttc taactaaaac tcagaatctt
4201  tattgagtta agaaaagttt ctctaccttg gtttaatcaa tattttttgta aaatcctatt
4261  gttattacaa agaggacact tcataggaaa catcttttc tttagtcagg ttttaatat
4321  tcaggggaa attgaaagat atatatttta gtcgattttt caaaagggga aaaaagtcca
4381  ggtcagcata agtcattttg tgtatttcac tgaagttata aggtttttat aaatgttctt
4441  tgaaggggaa aaggcacaag ccaatttttc ctatgatcaa aaaattcttt cttcctctg
4501  agtgagagtt atctatatct gaggctaaag tttaccttgc tttaataaat aatttgccac
4561  atcattgcag aagaggtatc ctcatgctgg ggttaataga atatgtcagt ttatcacttg
4621  tcgcttattt agctttaaaa taaaaattaa taggcaaagc aatggaatat ttgcagtttc
4681  acctaaagag cagcataagg aggcgggaat ccaaagtgaa gttgtttgat atggtctact
4741  tctttttgg aatttcctga ccattaatta aagaattgga tttgcaagtt tgaaaactgg
4801  aaaagcaaga gatgggatgc cataatagta aacagccctt gtgttggatg taacccaatc
4861  ccagatttga gtgtgtgttg attatttttt tgtcttccac ttttctatta tgtgtaaatc
4921  actttatt ctgcagacat tttcctctca gataggatga cattttgttt tgtattattt
4981  tgtctttcct catgaatgca ctgataatat tttaaatgct ctattttaag atctcttgaa
5041  tctgtttttt tttttttttaa tttgggggtt ctgtaaggtc tttatttccc ataagtaaat
5101  attgccatgg gaggggggtg gaggtggcaa ggaaggggtg aagtgctagt atgcaagtgg
5161  gcagcaatta ttttttgtgtt aatcagcagt acaatttgat cgttggcatg gttaaaaaat
5221  ggaatataag attagctgtt ttgtatttg atgaccaatt acgctgtatt ttaacacgat
5281  gtatgtctgt ttttgtggtg ctctagtggt aaataaatta tttcgatgat atgtggatgt
5341  cttttcctta tcagtaccat catcgagtct agaaaacacc tgtgatgcaa taagactatc
5401  tcaagctgga aaagtcatac cacctttccg attgccctct gtgctttctc ccttaaggac
5461  agtcacttca gaagtcatgc tttaaagcac aagagtcagg ccatatccat caaggataga
5521  agaaatccct gtgccgtctt tttattccct tatttattgc tatttggtaa ttgtttgaga
5581  tttagtttcc atccagcttg actgccgacc agaaaaaatg cagagagatg tttgcaccat
5641  gctttggctt tctggttcta tgttctgcca acgccagggc caaaagaact ggtctagaca
5701  gtatcccctg tagccccata acttggatag ttgctgagcc agccagatat aacaagagcc
5761  acgtgctttc tggggttggt tgtttgggat cagctacttg cctgtcagtt tcactggtac
5821  cactgcacca caaacaaaaa aacccaccct atttcctcca attttttgg ctgctaccta
5881  caagaccaga ctcctcaaac gagttgccaa tctcttaata aataggatta ataaaaaaag
5941  taattgtgac tcaaaaaaaa aaaaaa
```

The amino acid sequence of human TGF-beta 2 isoform 1 precursor, provided by Genbank Accession No. NP_001129071.1, is incorporated herein by reference, and is shown below (SEQ ID NO: 128).

```
  1  mhycvlsafl ilhlvtvals lstcstldmd qfmrkrieai rgqilsklkl tsppedypep
 61  eevppevisi ynstrdllqe kasrraaace rersdeeyya kevykidmpp ffpsetvcpv
121  vttpsgsvgs lcsrqsqvlc gyldaipptf yrpyfrivrf dvsameknas nlvkaefrvf
181  rlqnpkarvp eqrielyqil kskdltsptq ryidskvvkt raegewlsfd vtdavhewlh
241  hkdrnlgfki slhcpcctfv psnnyiipnk seelearfag idgtstytsg dqktikstrk
```

```
301  knsgktphll lmllpsyrle sqqtnrrkkr aldaaycfrn vqdncclrpl yidfkrdlgw 361  kwihepkgyn anfcagacpy lwssdtqhsr vlslyntinp easaspccvs qdleplily 421  yigktpkieq lsnmivksck cs
```

The siRNA used to target human TGF-beta 2 variant 1 mRNA include following sequences (SEQ ID NO: 129-132):

```
SEQ NO: 129:
5'-UAUCUCUAUCUCAAUCUGUC-3'

SEQ NO: 130:
5'-UUCUAUCUCUAUCUCAAUCU-3'

SEQ NO: 131:
5'-UUCUCUUUCUAUCUCUAUCU-3'

SEQ NO: 132:
5'-UCUAUCUCUAUCUCAAUCUG-3'
```

The molecular beacon used to target human TGF-beta 2 variant 1 mRNA includes the following sequences (SEQ ID NO: 133-135):

```
SEQ NO 133:
5'-CCGGTC TTCTATCTCTATCTCAATC GACCGG-3'

SEQ NO 134:
5'-CCGGTC TATCTCTATCTCAATCTGT GACCGG-3'

SEQ NO 135:
5'-CCGGTC TTCTCTTTCTATCTCTATC GACCGG-3'
```

The mRNA transcript sequence encoding human IGF-1 variant 4, provided by Genbank Accession No.NM_000618.3, is incorporated herein by reference, and is shown below (SEQ ID NO: 136).

```
   1  ttttgtagat aaatgtgagg attttctcta aatccctctt ctgtttgcta aatctcactg
  61  tcactgctaa attcagagca gatagagcct gcgcaatgga ataaagtcct caaaattgaa
 121  atgtgacatt gctctcaaca tctcccatct ctctggattt cttttgctt cattattcct
 181  gctaaccaat tcattttcag actttgtact tcagaagcaa tgggaaaaat cagcagtctt
 241  ccaacccaat tatttaagtg ctgcttttgt gatttcttga aggtgaagat gcacaccatg
 301  tcctcctcgc atctcttcta cctggcgctg tgcctgctca ccttcaccag ctctgccacg
 361  gctggaccgg agacgctctg cggggctgag ctggtggatg ctcttcagtt cgtgtgtgga
 421  gacaggggct tttatttcaa caagcccaca gggtatggct ccagcagtcg gagggcgcct
 481  cagacaggca tcgtggatga gtgctgcttc cggagctgtg atctaaggag gctggagatg
 541  tattgcgcac ccctcaagcc tgccaagtca gctcgctctg tccgtgccca gcgccacacc
 601  gacatgccca agacccagaa ggaagtacat ttgaagaacg caagtagagg gagtgcagga
 661  aacaagaact acaggatgta ggaagaccct cctgaggagt gaagagtgac atgccaccgc
 721  aggatccttt gctctgcacg agttacctgt taaactttgg aacacctacc aaaaataag
 781  tttgataaca tttaaaagat gggcgtttcc cccaatgaaa tacacaagta acattccaa
 841  cattgtcttt aggagtgatt tgcaccttgc aaaaatggtc ctggagttgg tagattgctg
 901  ttgatctttt atcaataatg ttctataaa agaaaaaaa aaatatatat atatatatat
 961  cttagtccct gcctctcaag agccacaaat gcatgggtgt tgtatagatc cagttgcact
1021  aaattcctct ctgaatcttg gctgctggag ccattcattc agcaaccttg tctaagtggt
1081  ttatgaattg tttccttatt tgcacttctt tctacacaac tcgggctgtt tgttttacag
1141  tgtctgataa tcttgttagt ctatacccac cacctccctt ataacctttt atatttgccg
1201  aatttggcct cctcaaaagc agcagcaagt cgtcaagaag cacaccaatt ctaacccaca
1261  agattccatc tgtggcattt gtaccaaata taagttggat gcatttatt ttagacacaa
1321  agctttattt ttccacatca tgcttacaaa aagaataat gcaaatagtt gcaactttga
1381  ggccaatcat ttttaggcat atgttttaaa catagaaagt ttcttcaact caaaagagtt
1441  ccttcaaatg atgagttaat gtgcaaccta attagtaact ttcctctttt tattttttcc
1501  atatagagca ctatgtaaat ttagcatatc aattatacag gatatatcaa acagtatgta
```

```
1561  aaactctgtt ttttagtata atggtgctat tttgtagttt gttatatgaa agagtctggc
1621  caaaacggta atacgtgaaa gcaaaacaat aggggaagcc tggagccaaa gatgacacaa
1681  ggggaagggt actgaaaaca ccatccattt gggaagaag gcaaagtccc cccagttatg
1741  ccttccaaga ggaacttcag acacaaaagt ccactgatgc aaattggact ggcgagtcca
1801  gagaggaaac tgtggaatgg aaaaagcaga aggctaggaa ttttagcagt cctggtttct
1861  ttttctcatg gaagaaatga acatctgcca gctgtgtcat ggactcacca ctgtgtgacc
1921  ttgggcaagt cacttcacct ctctgtgcct cagtttcctc atctgcaaaa tgggggcaat
1981  atgtcatcta cctacctcaa aggggtggta taaggtttaa aaagataaag attcagattt
2041  tttttaccct gggttgctgt aagggtgcaa catcagggcg cttgagttgc tgagatgcaa
2101  ggaattctat aaataaccca ttcatagcat agctagagat tggtgaattg aatgctcctg
2161  acatctcagt tcttgtcagt gaagctatcc aaataactgg ccaactagtt gttaaaagct
2221  aacagctcaa tctcttaaaa cacttttcaa aatatgtggg aagcatttga ttttcaattt
2281  gattttgaat tctgcatttg gttttatgaa tacaaagata agtgaaaaga gagaaaggaa
2341  aagaaaaagg agaaaaacaa agagatttct accagtgaaa ggggaattaa ttactctttg
2401  ttagcactca ctgactcttc tatgcagtta ctacatatct agtaaaacct cgtttaatac
2461  tataaataat attctattca ttttgaaaaa cacaatgatt ccttcttttc taggcaatat
2521  aaggaaagtg atccaaaatt tgaaatatta aataatatc taataaaaag tcacaaagtt
2581  atcttcttta acaaacttta ctcttattct tagctgtata tacattttt taaaagtttg
2641  ttaaaatatg cttgactaga gtttccagtt gaaaggcaaa aacttccatc acaacaagaa
2701  atttcccatg cctgctcaga agggtagccc ctagctctct gtgaatgtgt tttatccatt
2761  caactgaaaa ttggtatcaa gaaagtccac tggttagtgt actagtccat catagcctag
2821  aaaatgatcc ctatctgcag atcaagattt tctcattaga acaatgaatt atccagcatt
2881  cagatctttc tagtcacctt agaactttt ggttaaaagt acccaggctt gattatttca
2941  tgcaaattct atattttaca ttcttggaaa gtctatatga aaaacaaaaa taacatcttc
3001  agttttctc ccactgggtc acctcaagga tcagaggcca ggaaaaaaaa aaaaaagact
3061  ccctggatct ctgaatatat gcaaaaagaa ggccccattt agtggagcca gcaatcctgt
3121  tcagtcaaca agtattttaa ctctcagtcc aacattattt gaattgagca cctcaagcat
3181  gcttagcaat gttctaatca ctatggacag atgtaaaaga aactatacat cattttttgcc
3241  ctctgcctgt tttccagaca tacaggttct gtggaataag atactggact cctcttccca
3301  agatggcact tcttttttatt tcttgtcccc agtgtgtacc ttttaaaatt attccctctc
3361  aacaaaactt tataggcagt cttctgcaga cttaacgtgt tttctgtcat agttagatgt
3421  gataattcta agagtgtcta tgacttatt ccttcactta attctatcca cagtcaaaaa
3481  tcccccaagg aggaaagctg aaagatgcac tgccatatta tctttcttaa cttttccaa
3541  cacataatcc tctccaactg gattataaat aaattgaaaa taactcatta taccaattca
3601  ctatttattt ttttaatgaa ttaaaactag aaaacaaatt gatgcaaacc ctggaagtca
3661  gttgattact atatactaca gcagaatgac tcagatttca tagaaaggag caaccaaaat
3721  gtcacaaccc aaaactttac aagctttgct tcagaattag attgctttat aattcttgaa
3781  tgaggcaatt tcaagatatt tgtaaaagaa cagtaaacat tggtaagaat gagcttttcaa
3841  ctcataggct tatttccaat ttaattgacc atactggata cttaggtcaa atttctgttc
3901  tctcttcccc aaataatatt aaagtattat ttgaactttt taagatgagg cagttcccct
```

```
3961  gaaaaagtta atgcagctct ccatcagaat ccactcttct agggatatga aaatctctta
4021  acacccaccc tacatacaca gacacacaca cacacacaca cacacacaca cacacacaca
4081  ttcaccctaa ggatccaatg gaatactgaa agaaatcac ttccttgaaa attttattaa
4141  aaaacaaaca aacaaacaaa aagcctgtcc acccttgaga atccttcctc tccttggaac
4201  gtcaatgttt gtgtagatga aaccatctca tgctctgtgg ctccagggtt tctgttacta
4261  ttttatgcac ttgggagaag gcttagaata aaagatgtag cacattttgc tttcccattt
4321  attgtttggc cagctatgcc aatgtggtgc tattgtttct ttaagaaagt acttgactaa
4381  aaaaaaaaga aaaaagaaa aaaaagaaag catagacata ttttttttaaa gtataaaaac
4441  aacaattcta tagatagatg gcttaataaa atagcattag gtctatctag ccaccaccac
4501  cttcaactt tttatcactc acaagtagtg tactgttcac caaattgtga atttgggggt
4561  gcagggcag gagttggaaa ttttttaaag ttagaaggct ccattgtttt gttggctctc
4621  aaacttagca aaattagcaa tatattatcc aatcttctga acttgatcaa gagcatggag
4681  aataaacgcg ggaaaaaaga tcttataggc aaatagaaga atttaaaaga taagtaagtt
4741  ccttattgat ttttgtgcac tctgctctaa aacagatatt cagcaagtgg agaaaataag
4801  aacaaagaga aaaaatacat agatttaccct gcaaaaaata gcttctgcca aatcccccctt
4861  gggtattctt tggcatttac tggtttatag aagacattct cccttcaccc agacatctca
4921  aagagcagta gctctcatga aaagcaatca ctgatctcat ttgggaaatg ttggaaagta
4981  tttccttatg agatgggggt tatctactga taaagaaaga atttatgaga aattgttgaa
5041  agagatggct aacaatctgt gaagattttt tgtttcttgt ttttgttttt tttttttttt
5101  tactttatac agtctttatg aatttcttaa tgttcaaaat gacttggttc ttttcttctt
5161  tttttatatc agaatgagga ataataagtt aaacccacat agactcttta aaactatagg
5221  ctagatagaa atgtatgttt gacttgttga agctataatc agactattta aaatgttttg
5281  ctatttttaa tcttaaaaga ttgtgctaat ttattagagc agaacctgtt tggctctcct
5341  cagaagaaag aatctttcca ttcaaatcac atggctttcc accaatattt tcaaaagata
5401  aatctgattt atgcaatggc atcatttatt ttaaaacaga agaattgtga aagtttatgc
5461  ccctcccttg caaagaccat aaagtccaga tctggtaggg gggcaacaac aaaaggaaaa
5521  tgttgttgat tcttggtttt ggattttgtt ttgttttcaa tgctagtgtt taatcctgta
5581  gtacatattt gcttattgct attttaatat tttataagac cttcctgtta ggtattagaa
5641  agtgatacat agatatcttt tttgtgtaat ttctatttaa aaaagagaga agactgtcag
5701  aagctttaag tgcatatggt acaggataaa gatatcaatt taaataacca attcctatct
5761  ggaacaatgc ttttgttttt taaagaaacc tctcacagat aagacagagg cccagggat
5821  ttttgaagct gtctttattc tgcccccatc ccaacccagc ccttattatt ttagtatctg
5881  cctcagaatt ttatagaggg ctgaccaagc tgaaactcta gaattaaagg aacctcactg
5941  aaaacatata tttcacgtgt tccctctttt ttttttttcct ttttgtgaga tggggtctcg
6001  cactgtcccc caggctggag tgcagtggca tgatctcggc tcactgcaac ctccacctcc
6061  tgggtttaag cgattctcct gcctcagcct cctgagtagc tgggattaca ggcacccacc
6121  actatgcccg gctaatttttt tggatttttta atagagacgg ggttttacca tgttggccag
6181  gttggtctca aactcctgac cttgtgattt gcccgcctca gcctcccaaa ttgctgggat
6241  tacaggcatg agccaccaca ccctgcccat gtgttccctc ttaatgtatg attacatgga
6301  tcttaaacat gatccttctc tcctcattct tcaactatct ttgatggggt ctttcaaggg
6361  gaaaaaaatc caagcttttt taaagtaaaa aaaaaaaaag agaggacaca aaaccaaatg
```

-continued

```
6421  ttactgctca actgaaatat gagttaagat ggagacagag tttctcctaa taaccggagc 6481  tgaattacct ttcactttca aaaacatgac cttccacaat ccttagaatc tgccttttt 6541  tatattactg aggcctaaaa gtaaacatta ctcattttat tttgcccaaa atgcactgat 6601  gtaaagtagg aaaaataaaa acagagctct aaaatccctt tcaagccacc cattgacccc 6661  actcaccaac tcatagcaaa gtcacttctg ttaatccctt aatctgattt tgtttggata 6721  tttatcttgt acccgctgct aaacacactg caggagggac tctgaaacct caagctgtct 6781  acttacatct tttatctgtg tctgtgtatc atgaaaatgt ctattcaaaa tatcaaaacc 6841  tttcaaatat cacgcagctt atattcagtt tacataaagg ccccaaatac catgtcagat 6901  cttttggta aaagagttaa tgaactatga gaattgggat tacatcatgt attttgcctc 6961  atgtattttt atcacactta taggccaagt gtgataaata aacttacaga cactgaatta 7021  atttccctg ctactttgaa accagaaaat aatgactggc cattcgttac atctgtctta 7081  gttgaaaagc atattttta ttaaattaat tctgattgta tttgaaatta ttattcaatt 7141  cacttatggc agaggaatat caatcctaat gacttctaaa aatgtaacta attgaatcat 7201  tatcttacat ttactgttta ataagcatat tttgaaaatg tatggctaga gtgtcataat 7261  aaaatggtat atctttcttt agtaattaca ttaaaattag tcatgtttga ttaattagtt 7321  c
```

The amino acid sequence of human IGF-1 isoform 4 preproprotein, provided by Genbank Accession No.NP_000609.1, is incorporated herein by reference, and is shown below (SEQ ID NO: 137).

```
  1  mgkisslptq lfkccfcdfl kvkmhtmsss hlfylalcll tftssatagp eticgaelvd
 61  alqfvcgdrg fyfnkptgyg sssrrapqtg ivdeccfrsc dlrrlemyca plkpaksars
121  vraqrhtdmp ktqkevhlkn asrgsagnkn yrm
```

The siRNA used to target human IGF-1 variant 4 mRNA include following sequences (SEQ ID NO: 138-141):

```
SEQ NO: 138:
5'-UAAACUGAAUAUAAGCUGC-3'

SEQ NO: 139:
5'-UAAAAAAAUAUGUCUAUGC-3'

SEQ NO: 140:
5'-UUUAACAGGUAACUCGUGC-3'

SEQ NO: 141:
5'-UAACAAACUACAAAAUAGC-3'
```

The molecular beacon used to target human IGF-1 variant 4 mRNA includes the following sequences (SEQ ID NO: 142-144):

```
SEQ NO 142:
5'-CCGGTC TAAACTGAATATAAGCTGCG GACCGG-3'

SEQ NO 143:
5'-CCGGTC TTTAAATTCTTCTATTTGCC GACCGG-3'

SEQ NO 144:
5'-CCGGTC TAATCAACTGACTTCCAGGGGACCGG-3'
```

The mRNA transcript sequence encoding human BMP-2, provided by Genbank Accession No.NM_001200.2, is incorporated herein by reference, and is shown below (SEQ ID NO: 145).

```
  1  ccacaaaggg cacttggccc cagggctagg agagcgaggg gagagcacag ccacccgcct 61  cggcggcccg ggactcggct cgactcgccc gagaatgcgc ccgaggacga cggggcgcca 121  gagccgcggt gctttcaact ggcgagcgcg aatgggggtg cactggagta aggcagagtg 181  atgcggggg gcaactcgcc tggcaccgag atcgccgccg tgcccttccc tggacccggc 241  gtcgcccagg atggctgccc cgagccatgg gccgcgcgg agctagcgcg gagcgcccga 301  ccctcgaccc ccgagtcccg gagccggccc cgcgcggggc cacgcgtccc tcgggcgctg
```

```
 361   gttcctaagg aggacgacag caccagcttc tcctttctcc cttcccttcc ctgccccgca
 421   ctcctccccc tgctcgctgt tgttgtgtgt cagcacttgg ctggggactt cttgaacttg
 481   cagggagaat aacttgcgca ccccactttg cgccggtgcc tttgccccag cggagcctgc
 541   ttcgccatct ccgagcccca ccgcccctcc actcctcggc cttgcccgac actgagacgc
 601   tgttcccagc gtgaaaagag agactgcgcg gccggcaccc gggagaagga ggaggcaaag
 661   aaaaggaacg gacattcggt ccttgcgcca ggtcctttga ccagagtttt tccatgtgga
 721   cgctcttttca atggacgtgt ccccgcgtgc ttcttagacg gactgcggtc tcctaaaggt
 781   cgaccatggt ggccgggacc cgctgtcttc tagcgttgct gcttcccag gtcctcctgg
 841   gcggcgcggc tggcctcgtt ccggagctgg gccgcaggaa gttcgcggcg cgtcgtcgg
 901   gccgcccctc atcccagccc tctgacgagg tcctgagcga gttcgagttg cggctgctca
 961   gcatgttcgg cctgaaacag agacccaccc ccagcaggga cgccgtggtg ccccccctaca
1021   tgctagacct gtatcgcagg cactcaggtc agccgggctc acccgccccca gaccaccggt
1081   tggagagggc agccagccga gccaacactg tgcgcagctt ccaccatgaa gaatctttgg
1141   aagaactacc agaaacgagt gggaaaacaa cccggagatt cttctttaat ttaagttcta
1201   tccccacgga ggagtttatc acctcagcag agcttcaggt tttccgagaa cagatgcaag
1261   atgctttagg aaacaatagc agtttccatc accgaattaa tatttatgaa atcataaaac
1321   ctgcaacagc caactcgaaa ttccccgtga ccagactttt ggacaccagg ttggtgaatc
1381   agaatgcaag caggtgggaa agttttgatg tcaccccgc tgtgatgcgg tggactgcac
1441   agggacacgc caaccatgga ttcgtggtgg aagtggccca cttggaggag aaacaaggtg
1501   tctccaagag acatgttagg ataagcaggt ctttgcacca agatgaacac agctggtcac
1561   agataaggcc attgctagta acttttggcc atgatggaaa agggcatcct ctccacaaaa
1621   gagaaaaacg tcaagccaaa cacaaacagc ggaaacgcct taagtccagc tgtaagagac
1681   acccttttgta cgtggacttc agtgacgtgg ggtggaatga ctggattgtg gctcccccgg
1741   ggtatcacgc cttttactgc cacggagaat gccctttcc tctggctgat catctgaact
1801   ccactaatca tgccattgtt cagacgttgg tcaactctgt taactctaag attcctaagg
1861   catgctgtgt cccgacagaa ctcagtgcta tctcgatgct gtaccttgac gagaatgaaa
1921   aggttgtatt aaagaactat caggacatgg ttgtggaggg ttgtgggtgt cgctagtaca
1981   gcaaaattaa atacataaat atatatatat atatatattt tagaaaaaag aaaaaaacaa
2041   acaaacaaaa aaaccccacc ccagttgaca ctttaatatt tcccaatgaa gactttattt
2101   atggaatgga atggaaaaaa aaacagctat tttgaaaata tatttatatc tacgaaaaga
2161   agttgggaaa acaaatattt taatcagaga attattcctt aaagatttaa atgtatttta
2221   gttgtacatt ttatatgggt tcaaccccag cacatgaagt ataatggtca gatttatttt
2281   gtatttattt actattataa ccacttttta ggaaaaaaat agctaatttg tatttatatg
2341   taatcaaaag aagtatcggg tttgtacata atttccaaa aattgtagtt gttttcagtt
2401   gtgtgtattt aagatgaaaa gtctacatgg aaggttactc tggcaaagtg cttagcacgt
2461   ttgctttttt gcagtgctac tgttgagttc acaagttcaa gtccagaaaa aaaaagtgga
2521   taatccactc tgctgacttt caagattatt atattattca attctcagga atgttgcaga
2581   gtgattgtcc aatccatgag aatttacatc cttattaggt ggaatatttg gataagaacc
2641   agacattgct gatctattat agaaactctc ctcctgcccc ttaatttaca gaaagaataa
2701   agcaggatcc atagaaataa ttaggaaaac gatgaacctg caggaaagtg aatgatggtt
```

```
2761   tgttgttctt ctttcctaaa ttagtgatcc cttcaaaggg gctgatctgg ccaaagtatt 2821   caataaaacg taagatttct tcattattga tattgtggtc atatatattt aaaattgata 2881   tctcgtggcc ctcatcaagg gttggaaatt tatttgtgtt ttacctttac ctcatctgag 2941   agctctttat tctccaaaga acccagtttt ctaactttttt gcccaacacg cagcaaaatt 3001   atgcacatcg tgttttctgc ccaccctctg ttctctgacc tatcagcttg cttttctttc 3061   caaggttgtg tgtttgaaca catttctcca aatgttaaac ctatttcaga taataaatat 3121   caaatctctg gcatttcatt ctataaagtc
```

The amino acid sequence of human BMP-2 preproprotein, provided by Genbank Accession No.NP_001191.1, is incorporated herein by reference, and is shown below (SEQ ID NO: 146).

```
  1   mvagtrclla lllpqvllgg aaglypelgr rkfaaassgr pssqpsdevl sefelrllsm 61   fglkqrptps rdavvppyml dlyrrhsgqp gspapdhrle raasrantvr sfhheeslee 121   lpetsgkttr rfffnlssip teefitsael qvfreqmqda lgnnssfhhr iniyeiikpa 181   tanskfpvtr lldtrlvnqn asrwesfdvt pavmrwtaqg hanhgfvvev ahleekqgvs 241   krhvrisrsl hqdehswsqi rpllvtfghd gkghplhkre krqakhkqrk rlkssckrhp 301   lyvdfsdvgw ndwivappgy hafychgecp fpladhlnst nhaivqtlvn svnskipkac 361   cvptelsais mlyldenekv vlknyqdmvv egcgcr (Signal protein AA 1-23;
      proprotein AA 24-396; mature protein AA 283-396).
```

The siRNA used to target human BMP-2 mRNA include following sequences (SEQ ID NO: 147-150):

```
SEQ NO: 147:
5'-UUGUGAACUCAACAGUAGC-3'

SEQ NO: 148:
5'-UUAAUUUUGCUGUACUAGC-3'

SEQ NO: 149:
5'-UAAAACACAAAUAAAUUUC-3'

SEQ NO: 150:
5'-UUCUUUCUGUAAAUUAAGG-3'
```

The molecular beacon used to target human BMP-2 mRNA includes the following sequences (SEQ ID NO: 151-153):

```
SEQ NO: 151:
5'-CCGGTC TAATACAAAATAAATCTG GACCGG-3'

SEQ NO: 152:
5'-CCGGTC AAAACACAAATAAATTTCC GACCGG-3'

SEQ NO: 153:
5'-CCGGTC TTCATTCTCGTCAAGGTAC GACCGG-3'
```

The mRNA transcript sequence encoding human BMP-4 variant 1, provided by Genbank Accession No.NM_001202.3, is incorporated herein by reference, and is shown below (SEQ ID NO: 154).

```
  1   aagaggagga aggaagatgc gagaaggcag aggaggaggg agggagggaa ggagcgcgga 61   gcccggcccg gaagctaggt gagtgtggca tccgagctga gggacgcgag cctgagacgc 121   cgctgctgct ccggctgagt atctagcttg tctccccgat gggattcccg tccaagctat 181   ctcgagcctg cagcgccaca gtccccggcc ctcgcccagg ttcactgcaa ccgttcagag 241   gtccccagga gctgctgctg gcgagcccgc tactgcaggg acctatggag ccattccgta 301   gtgccatccc gagcaacgca ctgctgcagc ttccctgagc ctttccagca gtttgttca 361   agattggctg tcaagaatca tggactgtta ttatatgcct tgttttctgt caagacacca

421   tgattcctgg taaccgaatg ctgatggtcg ttttattatg ccaagtcctg ctaggaggcg 481   cgagccatgc tagtttgata cctgagacgg ggaagaaaaa agtcgccgag attcagggcc 541   acgcgggagg acgccgctca gggcagagcc atgagctcct gcgggacttc gaggcgacac 601   ttctgcagat gtttgggctg cgccgccgcc cgcagcctag caagagtgcc gtcattccgg
```

-continued

```
 661   actacatgcg ggatctttac cggcttcagt ctggggagga ggaggaagag cagatccaca
 721   gcactggtct tgagtatcct gagcgcccgg ccagccgggc caacaccgtg aggagcttcc
 781   accacgaaga acatctggag aacatcccag ggaccagtga aaactctgct tttcgtttcc
 841   tctttaacct cagcagcatc cctgagaacg aggtgatctc ctctgcagag cttcggctct
 901   tccgggagca ggtggaccag ggccctgatt gggaaagggg cttccaccgt ataaacattt
 961   atgaggttat gaagccccca gcagaagtgg tgcctgggca cctcatcaca cgactactgg
1021   acacgagact ggtccaccac aatgtgacac ggtgggaaac ttttgatgtg agccctgcgg
1081   tccttcgctg gacccgggag aagcagccaa actatgggct agccattgag gtgactcacc
1141   tccatcagac tcggacccac cagggccagc atgtcaggat tagccgatcg ttacctcaag
1201   ggagtgggaa ttggcccag ctccggcccc tcctggtcac ctttggccat gatggccggg
1261   gccatgcctt gacccgacgc cggagggcca agcgtagccc taagcatcac tcacagcggg
1321   ccaggaagaa gaataagaac tgccggcgcc actcgctcta tgtggacttc agcgatgtgg
1381   gctggaatga ctggattgtg gccccaccag gctaccaggc cttctactgc catggggact
1441   gccccttttcc actggctgac cacctcaact caaccaacca tgccattgtg cagaccctgg
1501   tcaattctgt caattccagt atccccaaag cctgttgtgt gcccactgaa ctgagtgcca
1561   tctccatgct gtacctggat gagtatgata aggtggtact gaaaaattat caggagatgg
1621   tagtagaggg atgtgggtgc cgctgagatc aggcagtcct tgaggataga cagatataca
1681   caccacacac acacaccaca tacaccacac acacgttc ccatccactc acccacacac
1741   tacacagact gcttccttat agctggactt ttatttaaaa aaaaaaaaa aaaaggaaaa
1801   aatccctaaa cattcaccttt gaccttattt atgactttac gtgcaaatgt tttgaccata
1861   ttgatcatat attttgacaa aatatattta taactacgta ttaaaagaaa aaaataaaat
1921   gagtcattat tttaaaggta aaaaaaaaa aaaaaaa
```

The amino acid sequence of human BMP-4 preproprotein, provided by Genbank Accession No. NP_001193.2, is incorporated herein by reference, and is shown below (SEQ ID NO: 155).

```
  1    mipgnrmlmv vllcqvllgg ashaslipet gkkkvaeiqg haggrrsgqs hellrdfeat
 61    llqmfglrrr pqpsksavip dymrdlyrlq sgeeeeeqih stgleyperp asrantvrsf
121    hheehlenip gtsensafrf lfnlssipen evissaelrl freqvdqgpd wergfhrini
181    yevmkppaev vpghlitrll dtrlvhhnvt rwetfdvspa vlrwtrekqp nyglaievth
241    lhqtrthqgq hvrisrslpq gsgnwaqlrp llvtfghdgr ghaltrrrra krspkhhsqr
301    arkknkncrr hslyvdfsdv gwndwivapp gyqafychgd cpfpladhln stnhaivqtl
361    vnsvnssipk accvptelsa ismlyldeyd kvvlknyqem vvegcgcr  (Signal peptide AA 1-24)
```

The siRNA used to target human BMP-4 variant 1 mRNA include following sequences (SEQ ID NO: 156-159):

SEQ NO: 156:
5'-UAAUAAAACGACCAUCAGCA-3'

SEQ NO: 157:
5'-UAUCUGUCUAUCCUCAAGGA-3'

SEQ NO: 158:
5'-UUCUUAUUCUUCUUCCUGGC-3'

SEQ NO: 159:
5'-UAAUAAAACGACCAUCAGC-3'

The molecular beacon used to target human BMP-4 variant 1 mRNA includes the following sequences (SEQ ID NO: 160-162):

SEQ NO 160:
5'-CCGGTC TATCTGTCTATCCTCAAGG GACCGG-3'

SEQ NO 161:
5'-CCGGTC TCTCAGGTATCAAACTAGC GACCGG-3'

SEQ NO 162:
5'-CCGGTC TTTGTCAAAATATATGATC GACCGG-3'

The mRNA transcript sequence encoding human BMP-7, provided by Genbank Accession No.NM_001719.2, is incorporated herein by reference, and is shown below (SEQ ID NO: 163).

```
   1  agcgcgtacc actctggcgc tcccgaggcg gcctcttgtg cgatccaggg cgcacaaggc
  61  tgggagagcg ccccggggcc cctgctatcc gcgccggagg ttggaagagg gtgggttgcc
 121  gccgcccgag ggcgagagcg ccagaggagc gggaagaagg agcgctcgcc cgcccgcctg
 181  cctcctcgct gcctccccgg cgttggctct ctggactcct aggcttgctg gctgctcctc
 241  ccacccgcgc ccgcctcctc actcgccttt tcgttcgccg gggctgcttt ccaagccctg
 301  cggtgcgccc gggcgagtgc ggggcgaggg gcccggggcc agcaccgagc aggggcggg
 361  ggtccgggca gagcgcggcc ggccggggag gggccatgtc tggcgcgggc gcagcggggc
 421  ccgtctgcag caagtgaccg agcggcgcgg acggccgcct gccccctctg ccacctgggg
 481  cggtgcgggc ccggagcccg gagcccgggt agcgcgtaga gccggcgcga tgcacgtgcg
 541  ctcactgcga gctgcggcgc cgcacagctt cgtggcgctc tgggcacccc tgttcctgct
 601  gcgctccgcc ctggccgact tcagcctgga caacgaggtg cactcgagct tcatccaccg
 661  gcgcctccgc agccaggagc ggcgggagat gcagcgcgag atcctctcca ttttgggctt
 721  gccccaccgc ccgcgcccgc acctccaggg caagcacaac tcggcaccca tgttcatgct
 781  ggacctgtac aacgccatgg cggtggagga gggcggcggg cccggcggcc agggcttctc
 841  ctaccoctac aaggccgtct tcagtaccca gggcccccct ctggccagcc tgcaagatag
 901  ccatttcctc accgacgccg acatggtcat gagcttcgtc aacctcgtgg aacatgacaa
 961  ggaattcttc cacccacgct accaccatcg agagttccgg tttgatcttt ccaagatccc
1021  agaagggaa gctgtcacgg cagccgaatt ccggatctac aaggactaca tccgggaacg
1081  cttcgacaat gagacgttcc ggatcagcgt ttatcaggtg ctccaggagc acttgggcag
1141  ggaatcggat ctcttcctgc tcgacagccg taccctctgg gcctcggagg agggctggct
1201  ggtgtttgac atcacagcca ccagcaacca ctgggtggtc aatccgcggc acaacctggg
1261  cctgcagctc tcggtggaga cgctggatgg gcagagcatc aaccccaagt ggcgggcct
1321  gattgggcgg cacgggcccc agaacaagca gcccttcatg gtggctttct tcaaggccac
1381  ggaggtccac ttccgcagca tccggtccac ggggagcaaa cagcgcagcc agaaccgctc
1441  caagacgccc aagaaccagg aagccctgcg gatggccaac gtggcagaga acagcagcag
1501  cgaccagagg caggcctgta agaagcacga gctgtatgtc agcttccgag acctgggctg
1561  gcaggactgg atcatcgcgc tgaaggcta cgccgcctac tactgtgagg gggagtgtgc
1621  cttccctctg aactcctaca tgaacgccac caaccacgcc atcgtgcaga cgctggtcca
1681  cttcatcaac ccggaaacgg tgcccaagcc ctgctgtgcg cccacgcagc tcaatgccat
1741  ctccgtcctc tacttcgatg acagctccaa cgtcatcctg aagaaataca gaaacatggt
1801  ggtccgggcc tgtggctgcc actagctcct ccgagaattc agacccttg gggccaagtt
1861  tttctggatc ctccattgct cgccttggcc aggaaccagc agaccaactg cctttgtga
1921  gaccttcccc tccctatccc caactttaaa ggtgtgagag tattaggaaa catgagcagc
1981  atatggcttt tgatcagttt ttcagtggca gcatccaatg aacaagatcc tacaagctgt
```

-continued

```
2041    gcaggcaaaa cctagcagga aaaaaaaaca acgcataaag aaaaatggcc gggccaggtc
2101    attggctggg aagtctcagc catgcacgga ctcgtttcca gaggtaatta tgagcgccta
2161    ccagccaggc cacccagccg tgggaggaag ggggcgtggc aagggtggg cacattggtg
2221    tctgtgcgaa aggaaaattg acccggaagt tcctgtaata aatgtcacaa taaaacgaat
2281    gaatgaaaat ggttaggacg ttacagatat attttcctaa acaatttatc cccatttctc
2341    ggtttatcct gatgcgtaaa cagaagctgt gtcaagtgga gggcggggag gtccctctcc
2401    attccctaca gttttcatcc tgaggcttgc agaggcccag tgtttaccga ggtttgccca
2461    aatccaagat ctagtgggag gggaaagagc aaatgtctgc tccgaggagg gcggtgtgtt
2521    gatctttgga ggaaaaatat gttctgttgt tcagctggat ttgccgtggc agaaatgaaa
2581    ctaggtgtgt gaaatacccg cagacatttg ggattggctt ttcacctcgc cccagtggta
2641    gtaaatccat gtgaaattgc agaggggaca aggacagcaa gtaggatgga acttgcaact
2701    caaccctgtt gttaagaagc accaatgggc cgggcacagt agctcccacc tgtaatccca
2761    gcactttggg aggctgaggt gggcggatca tttgaggtca ggagttcgag accagcctgg
2821    ccaacatggt gaaacccat ctctactaaa aatacaaaaa ttagccgggc atggtggcac
2881    gcacctgtaa tcccagctac tctggaggct gaggcaggag aattgcttga ccccagagg
2941    tggaggttgc agtgagccaa gatcgtccca ctgcactcca gcttgggtga caaaacaaga
3001    ctccatctca aagaaaaaa aaaacagcac caatgaagcc tagttctcca cgggagtggg
3061    gtgagcagga gcactgcaca tcgccccagt ggaccctctg gtctttgtct gcagtggcat
3121    tccaaggctg ggccctggca agggcacccg tggctgtctc ttcatttgca gacctgatc
3181    agaagtctct gcaaacaaat ttgctccttg aattaagggg gagatggcat aataggaggt
3241    ctgatgggtg caggatgtgc tggacttaca ttgcaaatag aagccttgtt gagggtgaca
3301    tcctaaccaa gtgtcccgat ttggaggtgg catttctgac gtggctcttg gtgtaagcct
3361    gccttgcctt ggctggtgag tcccataaat agtatgcact cagcctccgg ccacaaacac
3421    aaggcctagg ggagggctag actgtctgca aacgttttct gcatctgtaa agaaaacaag
3481    gtgatcgaaa actgtggcca tgtggaaccc ggtcttgtgg gggactgttt ctccatcttg
3541    actcagacag ttcctggaaa caccggggct ctgtttttat tttctttgat gtttttcttc
3601    tttagtagct tgggctgcag cctccactct ctagtcactg gggaggagta ttttttgtta
3661    tgtttggttt catttgctgg cagagctggg gcttttttgtg tgatccctct tggtgtgagt
3721    tttctgaccc aaccagcctc tggttagcat catttgtaca tttaaacctg taaatagttg
3781    ttacaaagca aagagattat ttatttccat ccaaagctct tttgaacacc ccccccctt
3841    taatccctcg ttcaggacga tgagcttgct ttccttcaac ctgtttgttt tcttatttaa
3901    gactatttat taatggttgg accaatgtac tcacagctgt tgcgtcgagc agtccttagt
3961    gaaaattctg tataaataga caaatgaaa agggtttgac cttgcaataa aaggagacgt
4021    ttggttctgg caaaaaaaaa aaaaaaaa
```

The amino acid sequence of human BMP-7 precursor, provided by Genbank Accession No. NP_001710.1, is incorporated herein by reference, and is shown below (SEQ ID NO: 164).

```
  1  mhvrslraaa phsfvalwap lfllrsalad fsldnevhss fihrrlrsqe rremqreils
 61  ilglphrprp hlqgkhnsap mfmldlynam aveegggpgg qgfsypykav fstqgpplas
121  lqdshfltda dmvmsfvnlv ehdkeffhpr yhhrefrfdl skipegeavt aaefriykdy
```

-continued

```
181 irerfdnetf risvyqvlqe hlgresdlfl ldsrtlwase egwlvfdita tsnhwvvnpr 241 hnlglqlsve tldgqsinpk lagligrhgp qnkqpfmvaf fkatevhfrs irstgskqrs 301 qnrsktpknq ealrmanvae nsssdqrqac kkhelyvsfr dlgwqdwiia pegyaayyce 361 gecafplnsy mnatnhaivq tlvhfinpet vpkpccaptq lnaisvlyfd dssnvilkky 421 rnmvvracgc h (signal peptide AA 1-29; mature peptide AA 293-431).
```

The siRNA used to target human BMP-7 mRNA include following sequences (SEQ ID NO: 165-168):

SEQ NO: 165: 5'-UUCCUAAUACUCUCACACC-3'

SEQ NO: 166: 5'-UAACAAAAAAUACUCCUCC-3'

SEQ NO: 167: 5'-UAAAUAAGAAAACAAACAGG-3'

SEQ NO: 168: 5'-UUCCUAAUACUCUCACACCU-3'

The molecular beacon used to target human BMP-7 mRNA includes the following sequences (SEQ ID NO: 169-171):

SEQ NO 169: 5'-CCGGTC TAACAAAAAATACTCCTCCC GACCGG-3'

SEQ NO 170: 5'-CCGGTC TTGTAACAACUATTTACAGG GACCGG-3'

SEQ NO 171: 5'-CCGGTC TAAATAAGAAAACAAACAG GACCGG-3'

The mRNA transcript sequence encoding human IL-1 receptor antagonist variant 3, provided by Genbank Accession No.NM_000577.4, is incorporated herein by reference, and is shown below (SEQ ID NO: 172).

```
   1 gggcagctcc accctgggag ggactgtggc ccaggtactg cccgggtgct actttatggg 61 cagcagctca gttgagttag agtctggaag acctcagaag acctcctgtc ctatgaggcc 121 ctcccatgg ctttagagac gatctgccga ccctctggga gaaaatccag caagatgcaa 181 gccttcagaa tctgggatgt taaccagaag accttctatc tgaggaacaa ccaactagtt 241 gctggatact tgcaaggacc aaatgtcaat ttagaagaaa agatagatgt ggtacccatt 301 gagcctcatg ctctgttctt gggaatccat ggagggaaga tgtgcctgtc ctgtgtcaag 361 tctggtgatg agaccagact ccagctggag gcagttaaca tcactgacct gagcgagaac 421 agaaagcagg acaagcgctt cgccttcatc cgctcagaca gtggccccac caccagtttt 481 gagtctgccg cctgccccgg ttggttcctc tgcacagcga tggaagctga ccagcccgtc 541 agcctcacca atatgcctga cgaaggcgtc atggtcacca aattctactt ccaggaggac 601 gagtagtact gcccaggcct gcctgttccc attcttgcat ggcaaggact gcagggactg 661 ccagtccccc tgccccaggg ctcccggcta tgggggcact gaggaccagc cattgagggg 721 tggaccctca gaaggcgtca caacaacctg gtcacggac tctgcctcct cttcaactga 781 ccagcctcca tgctgcctcc agaatggtct ttctaatgtg tgaatcagag cacagcagcc 841 cctgcacaaa gcccttccat gtcgcctctg cattcaggat caaaccccga ccacctgccc 901 aacctgctct cctcttgcca ctgcctcttc ctccctcatt ccaccttccc atgccctgga 961 tccatcaggc cacttgatga cccccaacca agtggctccc acaccctgtt ttacaaaaaa 1021 gaaaagacca gtccatgagg gaggttttta agggtttgtg gaaaatgaaa attaggattt 1081 catgattttt tttttcagt ccccgtgaag gagagccctc catttggaga ttatgttctt 1141 tcggggagag gctgaggact taaaatattc ctgcatttgt gaaatgatgg tgaaagtaag 1201 tggtagcttt tcccttcttt ttcttctttt tttgtgatgt cccaacttgt aaaaattaaa 1261 agttatggta ctatgttagc cccataattt tttttttcct tttaaaacac ttccataatc 1321 tggactcctc tgtccaggca ctgctgccca gcctccaagc tccatctcca ctccagattt 1381 tttacagctg cctgcagtac tttacctcct atcagaagtt tctcagctcc caaggctctg 1441 agcaaatgtg gctcctgggg gttctttctt cctctgctga aggaataaat tgctccttga
```

-continued

```
1501 cattgtagag cttctggcac ttggagactt gtatgaaaga tggctgtgcc tctgcctgtc 1561 tcccccaccg ggctgggagc tctgcagagc aggaaacatg actcgtatat gtctcaggtc 1621 cctgcagggc caagcaccta gcctcgctct tggcaggtac tcagcgaatg aatgctgtat 1681 atgttgggtg caaagttccc tacttcctgt gacttcagct ctgttttaca ataaaatctt 1741 gaaaatgcct aaaaaaaaa aaaaaaaaa aaaaaaaaa aaaaaaaaa aaaaaaaaa 1801 aa
```

The amino acid sequence of human IL-1 receptor antagonist isoform 3, provided by Genbank Accession No.NP_000568.1, is incorporated herein by reference, and is shown below (SEQ ID NO: 173).

```
  1 maleticrps grksskmqaf riwdvnqktf ylrnnqlvag ylqgpnvnle ekidvvpiep 61 halflgihgg kmclscvksg detrlqleav nitdlsenrk qdkrfafirs dsgpttsfes 121 aacpgwflct ameadqpvsl tnmpdegvmv tkfyfqede
```

The Pre-miRNA sequence of human microRNA140, provided by Genbank Accession NO: NR 029681.1, is incorporated herein by reference, and is shown below (SEQ ID NO: 174).

5'-UGUGUCUCUCUCUGUGUCCUGCCAGUGGUUUUACCCUAUGGUAGGUU

ACGUCAUGCUGUUCUACCACAGGGUAGAACCACGGACAGGAUACCGGGGC

ACC-3'

And mature microRNA140 (SEQ ID NO: 175).

5'-caguggguuuuacccuauggua-3'

The Pre-miRNA sequence of human microRNA365, provided by Genbank Accession NO: NR_029854.1, is incorporated herein by reference, and is shown below (SEQ ID NO: 176).

5'-ACCGCAGGGAAAAUGAGGGACUUUUGGGGGCAGAUGUGUUUCCAUUC

CACUAUCAUAAUGCCCCUAAAAAUCCUUAUUGCUCUUGCA-3'

And mature microRNA365 (SEQ ID NO: 177):

5'-AGGGACUUUUGGGGGCAGAUGUG-3'

The Pre-miRNA sequence of human microRNA125a, provided by Genbank Accession NO: NR_029693.1, is incorporated herein by reference, and is shown below (SEQ ID NO: 178).

5'-UGCCAGUCUCUAGGUCCCUGAGACCCUUUAACCUGUGAGGACAUCCA

GGGUCACAGGUGAGGUUCUUGGGAGCCUGGCGUCUGGCC-3'

And two mature microRNA125a (SEQ ID NO: 179-180):

```
SEQ ID NO: 179:
hsa-mir-125a-5p: 5'-ucccugagacccuuuaaccuguga 3' \

SEQ ID NO: 180:
hsa-mir-125a-3p: 5'-acaggugagguucuugggagcc 3'
```

The mRNA sequence encoding human IL-15, provided by Genbank Accession No. BC018149.2, is incorporated herein by reference, and is shown below (SEQ ID NO: 181).

```
  1 actccgggtg gcaggcgccc ggggaatcc cagctgactc gctcactgcc ttcgaagtcc 61 ggcgccccc gggagggaac tgggtggccg caccctcccg gctgcggtgg ctgtcgcccc 121 ccaccctgca gccaggactc gatggaggta cagagctcgg cttctttgcc ttgggagggg 181 agtggtggtg gttgaaaggg cgatggaatt ttccccgaaa gcctacgccc agggcccctc 241 ccagctccag cgttaccctc cggtctatcc tactggccga gctgccccgc cttctcatgg 301 ggaaaactta gccgcaactt caattttttgg ttttttccttt aatgacactt ctgaggctct 361 cctagccatc ctcccgcttc cggaggagcg cagatcgcag gtcccttttgc ccctggcgtg 421 cgactcccta ctgcgctgcg ctcttacggc gttccaggct gctggctagc gcaaggcggg 481 ccgggcaccc cgcgctccgc tgggagggtg agggacgcgc gtctggcggc cccagccaag 541 ctgcgggttt ctgagaagac gctgtcccgc agccctgagg gctgagttct gcacccagtc 601 aagctcagga aggccaagaa aagaatccat tccaatatat ggccatgtgg ctctttggag
```

-continued

```
 661 caatgttcca tcatgttcca tgctgctgac gtcacatgga gcacagaaat caatgttagc
 721 agatagccag cccatacaag atcgtattgt attgtaggag gcatcgtgga tggatggctg
 781 ctggaaaccc cttgccatag ccagctcttc ttcaatactt aaggatttac cgtggctttg
 841 agtaatgaga atttcgaaac cacatttgag aagtatttcc atccagtgct acttgtgttt
 901 acttctaaac agtcattttc taactgaagc tggcattcat gtcttcattt tgggctgttt
 961 cagtgcaggg cttcctaaaa cagaagccaa ctgggtgaat gtaataagtg atttgaaaaa
1021 aattgaagat cttattcaat ctatgcatat tgatgctact ttatatacgg aaagtgatgt
1081 tcacccccagt tgcaaagtaa cagcaatgaa gtgctttctc ttggagttac aagttatttc
1141 acttgagtcc ggagatgcaa gtattcatga tacagtagaa aatctgatca tcctagcaaa
1201 caacagtttg tcttctaatg ggaatgtaac agaatctgga tgcaaagaat gtgaggaact
1261 ggaggaaaaa aatattaaag aattttttgca gagttttgta catattgtcc aaatgttcat
1321 caacacttct tgattgcaat tgattctttt taaagtgttt ctgttattaa caaacatcac
1381 tctgctgctt agacataaca aaacactcgg catttcaaat gtgctgtcaa aacaagtttt
1441 tctgtcaaga agatgatcag accttggatc agatgaactc ttagaaatga aggcagaaaa
1501 atgtcattga gtaatatagt gactatgaac ttctctcaga cttactttac tcattttttt
1561 aatttattat tgaaattgta catatttgtg gaataatgta aaatgttgaa taaaaatatg
1621 tacaagtgtt gtttttttaag ttgcactgat attttaccctc ttattgcaaa atagcatttg
1681 tttaagggtg atagtcaaat tatgtattgg tggggctggg taccaatgct gcaggtcaac
1741 agctatgctg gtaggctcct gcctgtgtgg aaccactgac tactggctct cattgacttc
1801 cttactaagc atagcaaaca gaggaagaat ttgttatcag taagaaaaag aagaactata
1861 tgtgaatcct cttctttaca ctgtaattta gttattgatg tataaagcaa ctgttatgaa
1921 ataagaaat tgcaataact ggcaaaaaaa aaaaaaaaa aaaaaaaa
```

The atg start and stop codons are bolded and underlined.
The amino acid sequence of human IL-15, provided by Genbank Accession No. AAH18149.1, is incorporated herein by reference, and is shown below (SEQ ID NO: 182).

(SEQ ID NO: 182)
```
  1 mriskphlrs isiqcylcll lnshflteag ihvfilgcfs aglpkteanw vnvisdlkki
 61 edliqsmhid atlytesdvh psckvtamkc fllelqvisl esgdasihdt venliilann
121 slssngnvte sgckeceele eknikeflqs fvhivqmfin ts
```

The mRNA sequence encoding human IL-20 (interleukin-20 precursor), provided by Genbank Accession No. NM_018724.3, is incorporated herein by reference, and is shown below (SEQ ID NO: 183).

```
  1 ctttgaattc ctagctcctg tggtctccag atttcaggcc taagatgaaa gcctctagtc
 61 ttgccttcag ccttctctct gctgcgtttt atctcctatg gactccttcc actggactga
121 agacactcaa tttgggaagc tgtgtgatcg ccacaaacct tcaggaaata cgaaatggat
181 tttctgagat acggggcagt gtgcaagcca agatggaaa cattgacatc agaatcttaa
241 ggaggactga gtctttgcaa gacacaaagc ctgcgaatcg atgctgcctc ctgcgccatt
301 tgctaagact ctatctggac agggtattta aaaactacca gaccccctgac cattatactc
361 tccggaagat cagcagcctc gccaattcct ttcttaccat caagaaggac ctccggctct
```

-continued

```
421 gtcatgccca catgacatgc cattgtgggg aggaagcaat gaagaaatac agccagattc 481 tgagtcactt tgaaaagctg gaacctcagg cagcagttgt gaaggctttg ggggaactag 541 acattcttct gcaatggatg gaggagacag aatag gagga aagtgatgct gctgctaaga 601 atattcgagg tcaagagctc cagtcttcaa tacctgcaga ggaggcatga ccccaaacca 661 ccatctcttt actgtactag tcttgtgctg gtcacagtgt atcttattta tgcattactt 721 gcttccttgc atgattgtct ttatgcatcc ccaatcttaa ttgagaccat acttgtataa 781 gattttgta atatctttct gctattggat atatttatta gttaatatat ttatttattt 841 tttgctattt aatgtattta ttttttact tggacatgaa actttaaaaa aattcacaga 901 ttatatttat aacctgacta gagcaggtga tgtattttta tacagtaaaa aaaaaaaacc 961 ttgtaaattc tagaagagtg gctagggggg ttattcattt gtattcaact aaggacatat 1021 ttactcatgc tgatgctctg tgagatattt gaaattgaac caatgactac ttaggatggg 1081 ttgtggaata agttttgatg tggaattgca catctaccct acaattactg accatcccca 1141 gtagactccc cagtcccata attgtgtatc ttccagccag gaatcctaca cggccagcat 1201 gtatttctac aaataaagtt ttctttgcat aacaaaaaaa aaaaaaaaaa aa
```

The atg start and stop codons are bolded and underlined. The amino acid sequence of human IL-20 (interleukin-20 precursor), provided by Genbank Accession No. NP_061194.2, is incorporated herein by reference, and is shown below (SEQ ID NO: 184).

```
  1 mkasslafsl lsaafyllwt pstglktlnl gscviatnlq eirngfseir gsvqakdgni 61 dirilrrtes lqdtkpanrc cllrhllrly ldrvfknyqt pdhytlrkis slansfltik 121 kdlrlchahm tchcgeeamk kysqilshfe klepqaavvk algeldillq wmeete
```

The mRNA sequence encoding human PADI4 (protein-arginine deiminase type-4), provided by Genbank Accession No. NM_012387.2, is incorporated herein by reference, and is shown below (SEQ ID NO: 185).

```
(SEQ ID NO: 185)
  1 acagccagag ggacgagcta gcccgacgat ggcccagggg acattgatcc gtgtgacccc 61 agagcagccc acccatgccg tgtgtgtgct gggcaccttg actcagcttg acatctgcag 121 ctctgccccc gaggactgca cgtccttcag catcaacgcc tccccagggg tggtcgtgga 181 tattgcccac ggccctccag ccaagaagaa atccacaggt tcctccacat ggcccctgga 241 ccctgggta gaggtgaccc tgacgatgaa agtggccagt ggtagcacag gcgaccagaa 301 ggttcagatt tcatactacg gacccaagac tccaccagtc aaagctctac tctacctcac 361 cggggtggaa atctccttgt gcgcagacat cacccgcacc ggcaaagtga agccaaccag 421 agctgtgaaa gatcagagga cctggacctg gggcccttgt ggacagggtg ccatcctgct 481 ggtgaactgt gacagagaca atctcgaatc ttctgccatg gactgcgagg atgatgaagt 541 gcttgacagc gaagacctgc aggacatgtc gctgatgacc ctgagcacga agacccccaa 601 ggacttcttc acaaaccata cactggtgct ccacgtggcc aggtctgaga tggacaaagt 661 gagggtgttt caggccacac ggggcaaact gtcctccaag tgcagcgtag tcttgggtcc 721 caagtggccc tctcactacc tgatggtccc cggtggaaag cacaacatgg acttctacgt 781 ggaggccctc gctttcccgg acaccgactt cccggggctc attaccctca ccatctccct
```

-continued

```
 841 gctggacacg tccaacctgg agctccccga ggctgtggtg ttccaagaca gcgtggtctt 901 ccgcgtggcg ccctggatca tgaccccaa cacccagccc ccgcaggagg tgtacgcgtg 961 cagtattttt gaaaatgagg acttcctgaa gtcagtgact actctggcca tgaaagccaa 1021 gtgcaagctg accatctgcc ctgaggagga gaacatggat gaccagtgga tgcaggatga 1081 aatggagatc ggctacatcc aagccccaca caaaacgctg cccgtggtct tcgactctcc 1141 aaggaacaga ggcctgaagg agtttcccat caaacgcgtg atgggtccag attttggcta 1201 tgtaactcga gggccccaaa caggggtat cagtggactg gactcctttg ggaacctgga 1261 agtgagcccc ccagtcacag tcaggggcaa ggaatacccg ctgggcagga ttctcttcgg 1321 ggacagctgt tatcccagca atgacagccg gcagatgcac caggccctgc aggacttcct 1381 cagtgcccag caggtgcagg ccctgtgaa gctctattct gactggctgt ccgtgggcca 1441 cgtggacgag ttcctgagct tgtgccagc acccgacagg aagggcttcc ggctgctcct 1501 ggccagcccc aggtcctgct acaaactgtt ccaggagcag cagaatgagg ccacgggga 1561 ggccctgctg ttcgaaggga tcaagaaaaa aaacagcag aaaataaaga acattctgtc 1621 aaacaagaca ttgagagaac ataattcatt tgtggagaga tgcatcgact ggaaccgcga 1681 gctgctgaag cgggagctgg gcctggccga gagtgacatc attgacatcc cgcagctctt 1741 caagctcaaa gagttctcta aggcggaagc tttttccc aacatggtga acatgctggt 1801 gctagggaag cacctgggca tccccaagcc cttcgggccc gtcatcaacg gccgctgctg 1861 cctggaggag aaggtgtgtt ccctgctgga gccactgggc ctccagtgca ccttcatcaa 1921 cgacttcttc acctaccaca tcaggcatgg ggaggtgcac tgcggcacca acgtgcgcag 1981 aaagcccttc tccttcaagt ggtggaacat ggtgccctga gccatcttc cctggcgtcc 2041 tctccctcct ggccagatgt cgctgggtcc tctgcagtgt ggcaagcaag agctcttgtg 2101 aatattgtgg ctccctgggg gcggccagcc ctcccagcag tggcttgctt tcttctcctg 2161 tgatgtccca gtttcccact ctgaagatcc aacatggtc ctagcactgc acactcagtt 2221 ctgctctaag aagctgcaat aaagttttt taagtcactt tgtac
```

The atg start and stop codons are bolded and underlined. The amino acid sequence of human PADI4 (protein-arginine deiminase type-4) provided by Genbank Accession No. NP_036519.2, is incorporated herein by reference, and is shown below (SEQ ID NO: 186).

The mRNA sequence encoding human HLA-DRB1, provided by Genbank Accession No. HQ267233.1, is incorporated herein by reference, and is shown below (SEQ ID NO: 187).

```
                                                    (SEQ ID NO: 186)
  1 maqgtlirvt peqpthavcv lgtltqldic ssapedctsf sinaspgvvv diahgppakk 61 kstgsstwpl dpgvevtltm kvasgstgdq kvqisyygpk tppvkallyl tgveislcad 121 itrtgkvkpt ravkdqrtwt wgpcgqgail lvncdrdnle ssamdcedde vldsedlqdm 181 slmtlstktp kdfftnhtiv lhvarsemdk vrvfqatrgk lsskcsvvlg pkwpshylmv 241 pggkhnmdfy vealafpdtd fpglitltis lldtsnlelp eavvfqdsvv frvapwimtp 301 ntqppqevya csifenedfl ksvttlamka kcklticpee enmddqwmqd emeigyiqap 361 hktlpvvfds prnrglkefp ikrvmgpdfg yvtrgpqtgg isgldsfgnl evsppvtvrg 421 keyplgrilf gdscypsnds rqmhqalqdf lsaqqvqapv klysdwlsvg hvdeflsfvp 481 apdrkgfrll lasprscykl fqeqqneghg eallfegikk kkqqkiknil snktlrehns 541 fvercidwnr ellkrelgla esdiidipql fklkefskae affpnmvnml vlgkhlgipk 601 pfgpvingrc cleekvcsll eplglqctfi ndfftyhirh gevhcgtnvr rkpfsfkwwn 661 mvp
```

```
  1 atggtgtgtc tgaggctccc tggaggctcc tgcatggcag ttctgacagt gacactgatg
 61 gtgctgagct ccccactggc tttggctggg gacaccagac cacgtttctt ggaggaggtt
121 aagtttgagt gtcatttctt caacgggacg gagcgggtgc ggttgctgga aagacgcgtc
181 cataaccaag aggagtacgc gcgctacgac agcgacgtgg gggagtaccg ggcggtgacg
241 gagctggggc ggcctgatgc cgagtactgg aacagccaga aggacctcct ggagcggagg
301 cgtgccgcgg tggacaccta ctgcagacac aactacgggg ttggtgagag cttcacagtg
361 cagcggcgag ttcaacctaa ggtgactgtg tatccttcaa agacccagcc cctgcagcac
421 cacaacctcc tggtctgttc tgtgaatggt ttctatccag gcagcattga agtcaggtgg
481 ttccggaacg gccaggaaga gaagactggg gtggtgtcca cgggcctgat ccagaatgga
541 gactggacct tccagaccct ggtgatgctg gaaacagttc ctcagagtgg agaggtttac
601 acctgccaag tggagcaccc aagtgtgatg agccctctca cagtggaatg gagagcacgg
661 tctgaatctg cacagagcaa gatgctgagt ggagtcgggg gctttgtgct gggcctgctc
721 ttccttgggg ccgggctgtt catctacttc aggaatcaga aggacactc tggacttccg
781 ccaacaggat tcctgagctg a
```

The atg start and stop codons are bolded and underlined.
The amino acid sequence of human HLA-DRB1, provided by Genbank Accession No. ADZ73424.1, is incorporated herein by reference, and is shown below (SEQ ID NO: 188).

(SEQ ID NO: 188)
```
  1 myclrlpggs cmavltvtlm vlssplalag dtrprfleev kfechffngt ervrllerry
 61 hnqeeyaryd sdvgeyravt elgrpdaeyw nsqkdllerr raavdtycrh nygvgesftv
121 qrrvqpkvtv ypsktqplqh hnllvcsvng fypgsievrw frngqeektg vvstgliqng
181 dwtfqtivml etvpqsgevy tcqvehpsvm spltvewrar sesaqskmls gvggfvlgll
241 flgaglfiyf rnqkghsglp ptgfls
```

The mRNA sequence encoding human PTPN22 provided by Genbank Accession No. BC071670.1, is incorporated herein by reference, and is shown below (SEQ ID NO: 189).

```
  1 ggtgtctcgg ccatgacaca catttgacat gccctccctc aacctactta tagactattt
 61 ttcttgctct gcagcatgga ccaaagagaa attctgcaga gttcctggat tgaggcccaa
121 agcaagaaaa ttactaaaga ggagtttgcc aatgaatttc tgaagctgaa aaggcaatct
181 accaagtaca aggcagacaa aacctatcct acaactgtgg ctgagaagcc caagaatatc
241 aagaaaaaca gatataagga tattttgccc tatgattata gccgggtaga actatccctg
301 ataacctctg atgaggattc cagctacatc aatgccaact tcattaaggg agtttatgga
361 cccaaggctt atattgccac ccagggtcct ttatctacaa ccctcctgga cttctggagg
421 atgatttggg aatatagtgt ccttatcatt gttatgcat gcatggagta tgaaatggga
481 aagaaaagt gtgagcgcta ctgggctgag ccaggagaga tgcagctgga atttggccct
541 ttctctgtat cctgtgaagc tgaaaaaagg aaatctgatt atataatcag gactctaaaa
601 gttaagttca atagtgaaac tcgaactatc taccagtttc attacaagaa ttggccagac
661 catgatgtac cttcatctat agaccctatt cttgagctca tctgggatgt acgttgttac
721 caagaggatg acagtgttcc catatgcatt cactgcagtg ctggctgtgg aaggactggt
781 gttatttgtg ctattgatta tacatggatg ttgctaaaag atgggagtca agcaaagcat
```

-continued

```
 841 tgtattcctg agaaaaatca cactctccaa gcagactctt attctcctaa tttaccaaaa 901 agtaccacaa aagcagcaaa aatgatgaac caacaaagga caaaaatgga aatcaaagaa 961 tcttcttcct ttgactttag gacttctgaa ataagtgcaa agaagagct agttttgcac 1021 cctgctaaat caagcacttc ttttgacttt ctggagctaa attacagttt tgacaaaaat 1081 gctgacacaa ccatgaaatg gcagacaaag gcatttccaa tagttgggga gcctcttcag 1141 aagcatcaaa gtttggattt gggctctctt ttgtttgagg gatgttctaa ttctaaacct 1201 gtaaatgcag caggaagata ttttaattca aaggtgccaa taacacggac caaatcaact 1261 cctttttgaat tgatacagca gagagaaacc aaggaggtgg acagcaagga aaacttttct 1321 tatttggaat ctcaaccaca tgattcttgt tttgtagaga tgcaggctca aaaagtaatg 1381 catgtttctt cagcagaact gaattattca ctgccatatg actctaaaca ccaaatacgt 1441 aatgcctcta atgtaaagca ccatgactct agtgctcttg gtgtatattc ttacatacct 1501 ttagtggaaa atccttattt ttcatcatgg cctccaagtg gtaccagttc taagatgtct 1561 cttgatttac ctgagaagca agatggaact gttttttcctt cttctctgtt gccaacatcc 1621 tctacatccc tcttctctta ttacaattca catgattctt tatcactgaa ttctccaacc 1681 aatatttcct cactattgaa ccaggagtca gctgtactag caactgctcc aaggatagat 1741 gatgaaatcc cccctccact tcctgtacgg acacctgaat catttattgt ggttgaggaa 1801 gctggagaat tctcaccaaa tgttcccaaa tccttatcct cagctgtgaa ggtaaaaatt 1861 ggaacatcac tggaatgggg tggaacatct gaaccaaaga aatttgatga ctctgtgata 1921 cttagaccaa gcaagagtgt aaaactccga agtcctaaat cagaactaca tcaagatcgt 1981 tcttctcccc cacctcctct cccagaaaga actctagagt ccttcttcct tgccgatgaa 2041 gattgtatgc aggcccaatc tatagaaaca tattctacta gctatcctga caccatggaa 2101 aattcaacat cttcaaaaca gacactgaag actcctggaa aaagtttcac aaggagtaag 2161 agtttgaaaa ttttgcgaaa catgaaaaag agtatctgta attcttgccc accaaacaag 2221 cctgcagaat ctgttcagtc aaataactcc agctcatttc tgaattttgg ttttgcaaac 2281 cgttttttcaa aacccaaagg accaaggaat ccaccaccaa cttggaatat taataaaac 2341 tccagattta taataatatg ggctgcaagt cacctgcaa ataaaactac tagaatactg 2401 ctagttaaaa taagtgctct atatgcataa tatcaaatat gaagatatgc taatgtgtta 2461 atagctttta aaagaaaagc aaaatgccaa taagtgccag ttttgcattt tcatatcatt 2521 tgcattgagt tgaaaactgc aaataaaagt ttgtcacttg agcttatgta cagaatgcta 2581 tatgagaaac acttttagaa tggatttatt tttcattttt gccagttatt tttattttct 2641 tttacttttt tacataaaca taaacttcaa aaggtttgta agatttggat ctcaactaat 2701 ttctacattg ccagaatata ctataaaaag ttaaaaaaaa aacttacttt gtgggttgca 2761 atacaaactg ctcttgacaa tgactattcc ctgacagtta tttttgccta aatggagtat 2821 accttgtaaa tcttcccaaa tgttgtggaa aactggaata ttaagaaaat gagaaattat 2881 atttattaga ataaaatgtg caaataatga caattatttg aatgtaacaa ggaattcaac 2941 tgaaatcctg ataagtttta accaaagtca ttaaattacc aattctagaa aagtaatcaa 3001 tgaaatataa tagctatctt ttggtagcaa aagatataaa ttgtatatgt ttatacagga 3061 tctttcagat catgtgcaat ttttatctaa ccaatcagaa atactagttt aaaatgaatt 3121 tctatatgaa tatggatctg ccataagaaa atctagttca actctaattt tatgtagtaa 3181 ataaattggc aggtaattgt ttttacaaag aatccacctg acttcccta atgcattaaa
```

-continued

```
3241 aatattttta tttaaataac tttatttata acttttagaa acatgtagta ttgtttaaac 3301 atcatttgtt cttcagtatt tttcatttgg aagtccaata gggcaaattg aatgaagtat 3361 tattatctgt ctcttgtagt acaatgtatc caacagacac tcaataaact ttttggttgt 3421 taaaaaaaaa aaaaaa
```

The atg start and stop codons are bolded and underlined.
The amino acid sequence of human PTPN22, provided by Genbank Accession No. AAH716701.1, is incorporated herein by reference, and is shown below (SEQ ID NO: 190).

```
                                                           (SEQ ID NO: 190)
  1 mdqreilqkf ldeaqskkit keefaneflk lkrqstkyka dktypttvae kpknikknry 61 kdilpydysr velslitsde dssyinanfi kgvygpkayi atqgplsttl ldfwrmiwey 121 svliivmacm eyemgkkkce rywaepgemq lefgpfsysc eaekrksdyi irtlkvkfns 181 etrtiyqfhy knwpdhdvps sidpileliw dvrcyqedds vpicihcsag cgrtgvicai 241 dytwmllkdg sqakhcipek nhtlqadsys pnlpksttka akmmnqqrtk meikesssfd 301 frtseisake elvlhpakss tsfdflelny sfdknadttm kwqtkafpiv geplqkhqsl 361 dlgsllfegc snskpvnaag ryfnskvpit rtkstpfeli qqretkevds kenfsylesq 421 phdscfvemq aqkvmhvssa elnyslpyds khqirnasnv khhdssalgv ysyiplvenp 481 yfsswppsgt sskmsldlpe kqdgtvfpss llptsstslf syynshdsls lnsptnissl 541 lnqesavlat apriddeipp plpvrtpesf ivveeagefs pnvpkslssa vkvkigtsle 601 wggtsepkkf ddsvilrpsk svklrspkse lhqdrssppp plpertlesf fladedcmqa 661 qsietystsy pdtmenstss kqtlktpgks ftrskslkil rnmkksicns cppnkpaesv 721 qsnnsssfln fgfanrfskp kgprnppptw ni
```

The mRNA sequence encoding human TNFAIP3 provided by Genbank Accession No. BC114480.1, is incorporated herein by reference, and is shown below (SEQ ID NO: 191).

```
  1 ccggagaggt gttggagagc acaatggctg aacaagtcct tcctcaggct ttgtatttga 61 gcaatatgcg gaaagctgtg aagatacggg agagaactcc agaagacatt tttaaaccta 121 ctaatgggat cattcatcat tttaaaacca tgcaccgata cacactggaa atgttcagaa 181 cttgccagtt ttgtcctcag tttcgggaga tcatccacaa agccctcatc gacagaaaca 241 tccaggccac cctggaaagc cagaagaaac tcaactggtg tcgagaagtc cggaagcttg 301 tggcgctgaa aacgaacggt gacggcaatt gcctcatgca tgccacttct cagtacatgt 361 ggggcgttca ggacacagac ttggtactga ggaaggcgct gttcagcacg ctcaaggaaa 421 cagacacacg caactttaaa ttccgctggc aactggagtc tctcaaatct caggaatttg 481 ttgaaacggg gctttgctat gatactcgga actggaatga tgaatgggac aatcttatca 541 aaatggcttc cacagacaca cccatggccc gaagtggact tcagtacaac tcactggaag 601 aaatacacat atttgtcctt tgcaacatcc tcagaaggcc aatcattgtc atttcagaca 661 aaatgctaag aagtttggaa tcaggttcca atttcgcccc tttgaaagtg ggtggaattt 721 acttgcctct ccactggcct gcccaggaat gctacagata ccccattgtt ctcggctatg 781 acagccatca ttttgtaccc ttggtgaccc tgaaggacag tgggcctgaa atccgagctg 841 ttccacttgt taacagagac cggggaagat tgaagactt aaaagttcac tttttgacag
```

-continued

```
 901 atcctgaaaa tgagatgaag gagaagctct taaaagagta cttaatggtg atagaaatcc
 961 ccgtccaagg ctgggaccat ggcacaactc atctcatcaa tgccgcaaag ttggatgaag
1021 ctaacttacc aaaagaaatc aatctggtag atgattactt tgaacttgtt cagcatgagt
1081 acaagaaatg gcaggaaaac agcgagcagg ggaggagaga ggggcacgcc cagaatccca
1141 tggaaccttc cgtgccccag ctttctctca tggatgtaaa atgtgaaacg cccaactgcc
1201 ccttcttcat gtctgtgaac acccagcctt tatgccatga gtgctcagag aggcggcaaa
1261 agaatcaaaa caaactccca aagctgaact ccaagccggg ccctgagggg ctccctggca
1321 tggcgctcgg ggcctctcgg ggagaagcct atgagccctt ggcgtggaac cctgaggagt
1381 ccactgggggg gcctcattcg gccccaccga cagcacccag ccctttcctg ttcagtgaga
1441 ccactgccat gaagtgcagg agccccggct gccccttcac actgaatgtg cagcacaacg
1501 gattttgtga acgttgccac aacgcccggc aacttcacgc cagccacgcc ccagaccaca
1561 caaggcactt ggatcccggg aagtgccaag cctgcctcca ggatgttacc aggacattta
1621 atgggatctg cagtacttgc ttcaaaagga ctacagcaga ggcctcctcc agcctcagca
1681 ccagcctccc tccttcctgt caccagcgtt ccaagtcaga tccctcgcgg ctcgtccgga
1741 gcccctcccc gcattcttgc cacagagctg gaaacgacgc ccctgctggc tgcctgtctc
1801 aagctgcacg gactcctggg gacaggacgg ggacgagcaa gtgcagaaaa gccggctgcg
1861 tgtattttgg gactccagaa aacaagggct tttgcacact gtgtttcatc gagtacagag
1921 aaaacaaaca ttttgctgct gcctcaggga aagtcagtcc cacagcgtcc aggttccaga
1981 acaccattcc gtgcctgggg agggaatgcg gcacccttgg aagcaccatg tttgaaggat
2041 actgccagaa gtgtttcatt gaagctcaga atcagagatt tcatgaggcc aaaaggacag
2101 aagagcaact gagatcgagc cagcgcgagg atgtgcctcg aaccacacaa agcacctcaa
2161 ggcccaagtg cgcccgggcc tcctgcaaga acatcctggc ctgccgcagc gaggagctct
2221 gcatggagtg tcagcatccc aaccaggaga tgggccctgg ggccaccgg ggtgagcctg
2281 cccccgaaga cccccccaag cagcgttgcc gggcccccgc ctgtgatcat tttggcaatg
2341 ccaagtgcaa cggctactgc aacgaatgct tcagttcaa gcagatgtat ggctaaccgg
2401 aaacaggtgg gtcacctcct gcaagaagtg gggcctcgag ctgtcagtca tcatggtgct
2461 atcctctgaa cccctcagct gccactgcaa cagtgggctt aagggtgtct gagcaggaga
2521 ggaaagataa gctcttcgtg gtgcccacga tgctcaggtt tggtaacccg ggagtgttcc
2581 caggtggcct tagaaagcaa agcttgtaac tggcaaggga tgatgtcaga ttcagcccaa
2641 ggttcctcct ctcctaccaa gcaggaggcc aggaacttct ttggacttgg aaggtgtgcg
2701 gggactggcc gaggccctg caccctgcgc atcaggactg cttcatcgtc ttggctgaga
2761 aagggaaaag acacacaagt cgcgtgggtt ggagaagcca gagccattcc acctcccctc
2821 ccccagcatc tctcagagat gtgaagccag atcctcatgg cagcgaggcc ctctgcaaga
2881 agctcaagga agctcaggga aaatggacgt attcagagag tgtttgtagt tcatggtttt
2941 tccctacctg cccggttcct ttcctgagga cccggcagaa atgcagaacc atccatggac
3001 tgtgattctg aggctgctga gactgaacat gttcacattg acagaaaaac aagctgctct
3061 ttataatatg cacctttaa aaattagaa tattttactg ggaagacgtg taactctttg
3121 ggttattact gtctttactt ctaaagaagt tagcttgaac tgaggagtaa aagtgtgtac
3181 atatataata taccttaca ttatgtatga gggattttt taaattatat tgaaatgctg
3241 ccctagaagt acaataggaa ggctaaataa taataacctg ttttctggtt gttgttgggg
3301 catgagcttg tgtatacact gcttgcataa actcaaccag ctgccttttt aaagggagct
```

-continued

```
3361 ctagtcctttt ttgtgtaatt cactttattt attttattac aaacttcaag attatttaag 3421 cgaagatatt tcttcagctc tggggaaaat gccacagtgt tctcctgaga gaacatcctt 3481 gctttgagtc aggctgtggg caagttcctg accacaggga gtaaattggc ctctttgata 3541 cacttttgct tgcctcccca ggaaagaagg aattgcatcc aaggtataca tacatattca 3601 tcgatgtttc gtgcttctcc ttatgaaact ccagctatgt aataaaaaac tatactctgt 3661 gttctgttaa tgcctctgag tgtcctacct ccttggagat gagatagggga aggagcaggg 3721 atgagactgg caatggtcac agggaaagat gtggcctttt gtgatggttt tattttctgt 3781 taacactgtg tcctgggggg gctgggaagt cccctgcatc ccatg
```

The atg start and stop codons are bolded and underlined.
The amino acid sequence of human TNFAIP3, provided by Genbank Accession No. AAI14481.1, is incorporated herein by reference, and is shown below (SEQ ID NO: 192).

```
  1 maeqvlpqal ylsnmrkavk irertpedif kptngiihhf ktmhrytlem frtcqfcpqf 61 reiihkalid rniqatlesq kklnwcrevr klvalktngd gnclmhatsq ymwgvqdtdl 121 vlrkalfstl ketdtrnfkf rwqleslksq efvetglcyd trnwndewdn likmastdtp 181 marsglqyns leeihifylc nilrrpiivi sdkmlisles gsnfaplkvg giylplhwpa 241 qecyrypivl gydshhfvpl vtlkdsgpei ravplvnrdr grfedlkvhf ltdpenemke 301 kllkeylmvi eipvqgwdhg tthlinaakl deanlpkein lvddyfelvq heykkwqens 361 eqgrreghaq npmepsvpql slmdvkcetp ncpffmsvnt qplchecser rqknqnklpk 421 lnskpgpegl pgmalgasrg eayeplawnp eestggphsa pptapspflf settamkcrs 481 pgcpftlnvq hngfcerchn arqlhashap dhtrhldpgk cqaclqdvtr tfngicstcf 541 krttaeasss lstslppsch qrsksdpsrl vrspsphsch ragndapagc lsqaartpgd 601 rtgtskcrka gcvyfgtpen kgfcticfie yrenkhfaaa sgkvsptasr fqntipclgr 661 ecgtlgstmf egycqkcfie aqnqrfheak rteeqlrssq advprttqs tsrpkcaras 721 cknilacrse elcmecqhpn qrmgpgahrg epapedppkq rcrapacdhf gnakcngycn 781 ecfqfkqmyg
```

The mRNA sequence encoding human STAT4 provided by Genbank Accession No. L78440.1, is incorporated herein by reference, and is shown below (SEQ ID NO: 193).

```
  1 gctttctcct agggactgtg aggggcgctt ctgactttgg acttgagcac tgcctgggac 61 ctgtgctgag agagcgctag catgtctcag tggaatcaag tccaacagtt agaaatcaag 121 tttttggagc aggtggatca attctatgat gacaactttc ccatggaaat tcggcatctg 181 ttggcccaat ggattgaaaa tcaagactgg gaggcagctt ctaacaatga aaccatggca 241 acgattcttc ttcaaaactt gttaatacaa ctggatgaac agttaggtcg tgtttccaaa 301 gagaaaaacc tactcttgat acacaatcta aaaagaatta ggaaggtcct tcagggaaaa 361 tttcatggaa atccaatgca tgtagctgtg gttatttcaa actgtttaag ggaagagagg 421 agaatattgg ctgcagccaa catgcctgtc caggggcctc tagagaaatc cttacaaagt 481 tcttcagttt cagaaagaca gaggaatgtg gagcacaaag tggctgccat taaaaacagt 541 gtgcagatga cagaacaaga taccaaatac ttagaagatc tgcaagacga atttgactac 601 aggtataaaa caattcagac aatggatcag agtgacaaga atagtgccat ggtgaatcag
```

-continued

```
 661 gaagttttga cactgcagga aatgcttaac agcctcgatt tcaagagaaa ggaggctctc
 721 agtaaaatga cccaaatcat ccatgagaca gacctgttaa tgaacaccat gctcatagaa
 781 gagctgcaag actggaagcg gcggcagcaa atcgcctgca tcggggtcc actccacaat
 841 gggctcgacc agcttcagaa ctgctttaca ctattggcag aaagtctttt ccaactgaga
 901 aggcaattgg agaaactaga ggagcaatct accaaaatga catatgaagg tgatcccatt
 961 ccaatgcaaa gaactcacat gctagaaaga gtcaccttct tgatctacaa ccttttcaag
1021 aactcatttg tggttgagcg acagccatgt atgccaaccc accctcagag gccgttggta
1081 cttaaaaccc taattcagtt cactgtaaaa ctaaggctac taataaaatt gccagaacta
1141 aactatcagg taaaggttaa ggcatcaatt gacaagaatg tttcaactct aagcaaccga
1201 agatttgtac tttgtggaac taatgtcaaa gccatgtcta ttgaagaatc ttccaatggg
1261 agtctctcag tagaatttcg acatttgcaa ccaaaggaaa tgaagtccag tgctggaggt
1321 aaaggaaatg agggctgtca catggtgact gaagaacttc attccataac gtttgaaaca
1381 cagatctgcc tctatggcct gaccatagat ttggagacca gctcattgcc tgtggtgatg
1441 atttccaatg tcagtcagtt acctaatgct tgggcatcca tcatttggta caacgtgtca
1501 accaacgatt cccagaactt ggttttcttt aataatcctc cacctgccac attgagtcaa
1561 ctactggagg tgatgagctg gcagttttca tcgtacgttg gtcgtggtct taactcagat
1621 caactccata tgctggcaga gaagcttaca gtccaatcta gctacagtga tggtcacctc
1681 acctgggcca gtctctgcaa ggaacattta cctggtaaat catttacctt ttggacatgg
1741 cttgaagcaa tattggatct aattaagaaa cacattcttc ccctttggat tgatgggtat
1801 gtcatgggct tgttagcaa agagaaggaa cggctgttgc taaaggataa aatgcctggc
1861 acctttttat taagattcag tgaaagccat ctcggaggaa taactttcac ctgggtggac
1921 cattctgaaa gtggggaagt gagattccac tctgtagaac cctacaataa aggccggttg
1981 tctgctctgc cattcgctga catcctgcga gactacaaag ttattatggc tgaaaacatt
2041 cctgaaaacc ctctgaagta cctatatcct gacattccca agacaaagc cttcggtaaa
2101 cactacagct ctcagccttg cgaagtttca agaccaacag aaaggggtga caaaggttat
2161 gttccttctg tttttatccc catctcaaca atccgaagtg attcaacaga gccacattct
2221 ccatcagacc ttcttcccat gtctccaagt gtgtatgcgg tgttgagaga aaacctgagt
2281 cccacaacaa ttgaaactgc aatgaagtct ccttattctg ctgaatgaca ggataaactc
2341 tgacgcacca agaaaggaag caaatgaaaa agtttaaaga ctgttctttg cccaataacc
2401 acattttatt tcttcagctt tgtaaatacc aggttctagg aaatgtttga catctgaagc
2461 tctcttcaca ctcccgtggc actcctcaat tgggagtgtt gtgactgaaa tgcttgaaac
2521 caaagcttca gataaacttg caagataaga caactttaag aaaccagtgt taataacaat
2581 attaacag
```

55

The atg start and stop codons are bolded and underlined. The amino acid sequence of human STAT4, provided by Genbank Accession No. AAB05605.1, is incorporated herein by reference, and is shown below (SEQ ID NO: 194).

```
  1 msqwnqvqql eikfleqvdq fyddnfpmei rhllaqwien qdweaasnne tmatillqnl
 61 liqldeqlgr vskeknllli hnlkrirkvl qgkfhgnpmh vawisnclr eerrilaaan
121 mpvqgpleks lqsssyserq rnvehkvaai knsvqmteqd tkyledlqde fdyryktiqt
```

-continued

```
181 mdqsdknsam vnqevltlqe mlnsldfkrk ealskmtqii hetdllmntm lieelqdwkr 241 rqqiaciggp lhngldqlqn cftllaeslf qlrrqlekle eqstkmtyeg dpipmqrthm 301 lervtfliyn lfknsfvver qpcmpthpqr plvlktliqf tvklrllikl pelnyqvkvk 361 asidlmvstl snrrfvlcgt nvkamsiees sngslsvefr hlqpkemkss aggkgnegch 421 mvteelhsit fetqiclygl tidletsslp vvmisnvsql pnawasiiwy nvstndsqnl 481 vffnnpppat lsqllevmsw qfssyvgrgl nsdqlhmlae kltvqssysd ghltwakfck 541 ehlpgksftf wtwleaildl ikkhilplwi dgyvmgfvsk ekerllkdk mpgtfllrfs 601 eshlggitft wvdhsesgev rfhsvepynk grlsalpfad ilrdykvima enipenpk 661 lypdipkdka fgkhyssqpc evsrptergd kgyvpsvfip istirsdste phspsdllpm 721 spsvyavlre nlspttieta mkspysae
```

The mRNA sequence encoding human CCR6 provided by Genbank Accession No. AY242126.1, is incorporated herein by reference, and is shown below (SEQ ID NO: 195).

```
   1 atgagcgggg aatcaatgaa tttcagcgat gttttcgact ccagtgaaga ttattttgtg 61 tcagtcaata cttcatatta ctcagttgat tctgagatgt tactgtgctc cttgcaggag 121 gtcaggcagt tctccaggct atttgtaccg attgcctact ccttgatctg tgtctttggc 181 ctcctgggga atattctggt ggtgatcacc Mgcttttt ataagaaggc caggtctatg 241 acagacgtct atctcttgaa catggccatt gcagacatcc tctttgttct tactctccca 301 ttctgggcag tgagtcatgc cactggtgcg tgggttttca gcaatgccac gtgcaagttg 361 ctaaaaggca tctatgccat caactttaac tgcgggatgc tgctcctgac ttgcattagc 421 atggaccggt acatcgccat tgtacaggcg actaagtcat tccggctccg atccagaaca 481 ctaccgcgca gcaaaatcat ctgccttgtt gtgtgggggc tgtcagtcat catctccagc 541 tcaacttttg tcttcaacca aaaatacaac acccaaggca gcgatgtctg tgaacccaag 601 taccagactg tctcggagcc catcaggtgg aagctgctga tgttggggct tgagctactc 661 tttggtttct ttatcccttt gatgttcatg atattttgtt acacgttcat tgtcaaaacc 721 ttggtgcaag ctcagaattc taaaaggcac aaagccatcc gtgtaatcat agctgtggtg 781 cttgtgtttc tggcttgtca gattcctcat aacatggtcc tgcttgtgac ggctgcaaat 841 ttgggtaaaa tgaaccgatc ctgccagagc gaaaagctaa ttggctatac gaaaactgtc 901 acagaagtcc tggctttcct gcactgctgc ctgaaccctg tgctctacgc ttttattggg 961 cagaagttca gaaactactt tctgaagatc ttgaaggacc tgtggtgtgt gagaaggaag 1021 tacaagtcct caggcttctc ctgtgccggg aggtactcag aaaacatttc tcggcagacc 1081 agtgagaccg cagataacga caatgcgtcg tccttcacta tgtga
```

The atg start and stop codons are bolded and underlined. The amino acid sequence of human CCR6, provided by Genbank Accession No. AA092293.1, is incorporated herein by reference, and is shown below (SEQ ID NO: 196).

```
   1 msgesmnfsd vfdssedyfv svntsyysvd semllcslqe vrqfsrlfvp iayslicvfg 61 llgnilvvit fafykkarsm tdvyllnmai adilfvltlp fwayshatga wvfsnatckl 121 lkgiyainfn cgmlllicis mdryiaivqa tksfrlisrt l prskiiclv vwglsviiss 181 stfvfnqkyn tqgsdvcepk yqtvsepirw kllmlglell fgffiplmfm ifcytfivkt
```

-continued 241 lvqaqnskrh kairviiavv lvflacqiph nmvllvtaan lgkmnrscqs ekligytktv 301 tevlaflhcc lnpvlyafig qkfrnyflki lkdlwcyrrk ykssgfscag rysenisrqt 361 setadndnas sftm The mRNA sequence encoding human TNFR-1 (tumor necrosis factor receptor 1) provided by Genbank Accession No. NM 001065.3, is incorporated herein by reference, and is shown below (SEQ ID NO: 197).

```
   1 ctcctccagc tcttcctgtc ccgctgttgc aacactgcct cactcttccc ctcccacctt
  61 ctctcccctc ctctctgctt taattttctc agaattctct ggactgaggc tccagttctg
 121 gcctttgggg ttcaagatca ctgggaccag gccgtgatct ctatgcccga gtctcaaccc
 181 tcaactgtca ccccaaggca cttgggacgt cctggacaga ccgagtcccg ggaagcccca
 241 gcactgccgc tgccacactg ccctgagccc aaatggggga gtgagaggcc atagctgtct
 301 ggcatgggcc tctccaccgt gcctgacctg ctgctgccac tggtgctcct ggagctgttg
 361 gtgggaatat acccctcagg ggttattgga ctggtccctc acctagggga cagggagaag
 421 agagatagtg tgtgtcccca aggaaaatat atccaccctc aaaataattc gatttgctgt
 481 accaagtgcc acaaaggaac ctacttgtac aatgactgtc caggcccggg gcaggatacg
 541 gactgcaggg agtgtgagag cggctccttc accgcttcag aaaaccacct cagacactgc
 601 ctcagctgct ccaaatgccg aaaggaaatg ggtcaggtgg agatctcttc ttgcacagtg
 661 gaccgggaca ccgtgtgtgg ctgcaggaag aaccagtacc ggcattattg gagtgaaaac
 721 cttttccagt gcttcaattg cagcctctgc ctcaatggga ccgtgcacct cctgcccag
 781 gagaaacaga acaccgtgtg cacctgccat gcaggttct ttctaagaga aaacgagtgt
 841 gtctcctgta gtaactgtaa gaaaagcctg gagtgcacga agttgtgcct accccagatt
 901 gagaatgtta agggcactga ggactcaggc accacagtgc tgttgcccct ggtcattttc
 961 tttggtcttt gcctttatc cctcctcttc attggtttaa tgtatcgcta ccaacggtgg
1021 aagtccaagc tctactccat tgtttgtggg aaatcgacac tgaaaaaga gggggagctt
1081 gaaggaacta ctactaagcc cctggcccca aacccaagct tcagtcccac tccaggcttc
1141 accccaccc tgggcttcag tcccgtgccc agttccacct tcacctccag ctccacctat
1201 acccccggtg actgtcccaa ctttgcggct ccccgcagag aggtggcacc accctatcag
1261 ggggctgacc ccatccttgc gacagccctc gcctccgacc catccccaa cccccttcag
1321 aagtgggagg acagcgccca caagccacag agcctagaca ctgatgaccc cgcgacgctg
1381 tacgccgtgg tggagaacgt gccccgttg cgctggaagg aattcgtgcg gcgcctaggg
1441 ctgagcgacc acgagatcga tcggctggag ctgcagaacg ggcgctgcct gcgcgaggcg
1501 caatacagca tgctggcgac ctggaggcgg cgcacgccgc ggcgcgaggc cacgctggag
1561 ctgctgggac gcgtgctccg cgacatggac ctgctgggct gcctggagga catcgaggag
1621 gcgctttgcg gccccgccgc cctcccgccc gcgcccagtc ttctcagatg aggctgcgcc
1681 cctgcgggca gctctaagga ccgtcctgcg agatcgcctt ccaaccccac ttttttctgg
1741 aaaggagggg tcctgcaggg gcaagcagga gctagcagcc gcctacttgg tgctaaccc
1801 tcgatgtaca tagcttttct cagctgcctg cgcgccgccg acagtcagcg ctgtgcgcgc
1861 ggagagaggt gcgccgtggg ctcaagagcc tgagtgggtg gtttgcgagg atgagggacg
1921 ctatgcctca tgcccgtttt gggtgtcctc accagcaagg ctgctcgggg gcccctggtt
1981 cgtccctgag cctttttcac agtgcataag cagtttttt tgtttttgtt ttgttttgtt
```

-continued

```
2041 ttgtttttaa atcaatcatg ttacactaat agaaacttgg cactcctgtg ccctctgcct 2101 ggacaagcac atagcaagct gaactgtcct aaggcagggg cgagcacgga acaatggggc 2161 cttcagctgg agctgtggac ttttgtacat acactaaaat tctgaagtta aagctctgct 2221 cttggaaaaa aaaaaaaaaa aaaaaaaaaa aaaaaaaa
```

The atg start and stop codons are bolded and underlined.
The amino acid sequence of human TNFR-1 (tumor necrosis factor receptor 1), provided by Genbank Accession No. NP_001056.1, is incorporated herein by reference, and is shown below (SEQ ID NO: 198).

```
  1 mglstvpdll lplvllellv giypsgvigl vphlgdrekr dsvcpqgkyi hpqnnsicct 61 kchkgtylyn dcpgpgqdtd crecesgsft asenhlrhcl scskcrkemg qveissctvd 121 rdtvcgcrkn qyrhywsenl fqcfncslcl ngtvhlscqe kqntvctcha gfflrenecv 181 scsnckksle ctklclpqie nvkgtedsgt tvllplviff glcllsllfi glmyryqrwk 241 sklysivcgk stpekegele gtttkplapn psfsptpgft ptlgfspvps stftssstyt 301 pgdcpnfaap rrevappyqg adpilatala sdpipnplqk wedsahkpqs ldtddpatly 361 avvenvpplr wkefvrrlgl sdheidrlel qngrclreaq ysmlatwrrr tprreatlel 421 lgrvlrdmdl lgcledieea lcgpaalppa psllr
```

The mRNA sequence encoding human TNFR-2 provided by Genbank Accession No. M55994.1, is incorporated herein by reference, and is shown below (SEQ ID NO: 199).

```
   1 gaattcggcg cagcggagcc tggagagaag gcgctgggct gcgagggcgc gagggcgcga 61 gggcaggggg caaccggacc ccgcccgcac ccatggcgcc cgtcgccgtc tgggcgcgcg 121 tggccgtcgg actggagctc tgggctgcgg cgcacgcctt gcccgcccag gtggcattta 181 caccctacgc cccggagccc gggagcacat gccggctcag agaatactat gaccagacag 241 ctcagatgtg ctgcagcaag tgctcgccgg ccaacatgc aaaagtcttc tgtaccaaga 301 cctcggacac cgtgtgtgac tcctgtgagg acagcacata cacccagctc tggaactggg 361 ttcccgagtg cttgagctgt ggctcccgct gtagctctga ccaggtggaa actcaagcct 421 gcactcggga acagaaccgc atctgcacct gcaggcccgg ctggtactgc gcgctgagca 481 agcaggaggg gtgccggctg tgcgcgccgc tgcgcaagtg ccgcccgggc ttcggcgtgg 541 ccagaccagg aactgaaaca tcagacgtgg tgtgcaagcc ctgtgccccg ggacgttct 601 ccaacacgac ttcatccacg gatatttgca ggccccacca gatctgtaac gtggtggcca 661 tccctgggaa tgcaagcagg gatgcagtct gcacgtccac gtcccccacc cggagtatgg 721 ccccaggggc agtacactta ccccagccag tgtccacacg atcccaacac acgcagccaa 781 ctccagaacc cagcactgct ccaagcacct ccttcctgct cccaatgggc ccagccccc 841 cagctgaagg gagcactggc gacttcgctc ttccagttgg actgattgtg ggtgtgacag 901 ccttgggtct actaataata ggagtggtga actgtgtcat catgacccag gtgaaaaaga 961 agcccttgtg cctgcagaga gaagccaagg tgcctcactt gcctgccgat aaggcccggg 1021 gtacacaggg ccccgagcag cagcacctgc tgatcacagc gccgagctcc agcagcagct 1081 ccctggagag ctcggccagt gcgttggaca gaagggcgcc cactcggaac cagccacagg 1141 caccaggcgt ggaggccagt ggggccgggg aggcccgggc cagcaccggg agctcagatt
```

-continued

```
1201 cttcccctgg tggccatggg acccaggtca atgtcacctg catcgtgaac gtctgtagca 1261 gctctgacca cagctcacag tgctcctccc aagccagctc cacaatggga gacacagatt 1321 ccagcccctc ggagtccccg aaggacgagc aggtcccctt ctccaaggag gaatgtgcct 1381 ttcggtcaca gctggagacg ccagagaccc tgctggggag caccgaagag aagcccctgc 1441 cccttggagt gcctgatgct gggatgaagc ccagttaacc aggccggtgt gggctgtgtc 1501 gtagccaagg tgggctgagc cctggcagga tgaccctgcg aagggccct ggtccttcca 1561 ggcccccacc actaggactc tgaggctctt tctgggccaa gttcctctag tgccctccac 1621 agccgcagcc tccctctgac ctgcaggcca agagcagagg cagcgggttg tggaaagcct 1681 ctgctgccat ggtgtgtccc tctcggaagg ctggctgggc atggacgttc ggggcatgct 1741 ggggcaagtc cctgactctc tgtgacctgc cccgcccagc tgcacctgcc agcctggctt 1801 ctggagccct tgggtttttt gtttgtttgt ttgtttgttt gtttgtttct cccctgggc 1861 tctgccccag ctctggcttc cagaaaaccc cagcatcctt ttctgcagag gggctttctg 1921 gagaggaggg atgctgcctg agtcacccat gaagacagga cagtgcttca gcctgaggct 1981 gagactgcgg gatggtcctg gggctctgtg cagggaggag gtggcagccc tgtagggaac 2041 ggggtccttc aagttagctc aggaggcttg gaaagcatca cctcaggcca ggtgcagtcc 2101 ctcacgccta tgatcccagc actttgggag gctgaggcgg gtggatcacc tgaggttagg 2161 agttcgagac cagcctggcc aacatggtaa acccccatct ctactaaaaa tacagaaatt 2221 agccgggcgt ggtggcgggc acctatagtc ccagctactc agaagcctga ggctgggaaa 2281 tcgtttgaac ccgggaagcg gaggttgcag ggagccgaga tcacgccact gcactccagc 2341 ctgggcgaca gagcgagagt ctgtctcaaa agaaaaaaaa aaaaaccga attc
```

The atg start and stop codons are bolded and underlined. The amino acid sequence of human TNFR-2, provided by Genbank Accession No. AAA36755.1, is incorporated herein by reference, and is shown below (SEQ ID NO: 200).

```
  1 mapvavwaal avglelwaaa halpaqvaft pyapepgstc rlreyydqta qmccskcspg
 61 qhakvfctkt sdtvcdsced stytqlwnwv peclscgsrc ssdqvetqac treqnrictc
121 rpgwycalsk qegcrlcapl rkcrpgfgva rpgtetsdvv ckpcapgtfs nttsstdicr
181 phqicnvvai pgnasrdavc tstsptrsma pgavhlpqpv strsqhtqpt pepstapsts
241 fllpmgpspp aegstgdfal pvglivgvta lglliigvvn cvimtqvkkk plclqreakv
301 phlpadkarg tqgpeqqhll itapsssss lessasaldr raptrnqpqa pgveasgage
361 arastgssds spgghgtqvn vtcivnvcss sdhssqcssq asstmgdtds spsespkdeq
421 vpfskeecaf rsqletpetl lgsteekplp lgvpdagmkp s
(Signall peptide AA 1-22; mature peptide AA 23-461).
```

The mRNA sequence encoding human cell death protein (RIP) provided by Genbank Accession No. U25994.1, is incorporated herein by reference, and is shown below (SEQ ID NO: 201).

```
  1 gacgtgaaga gtttaaagaa agagtattca aacgaaaatg cagttgtgaa gagaatgcag
 61 tctcttcaac ttgattgtgt ggcagtacct tcaagccggt caaattcagc cacagaacag
121 cctggttcac tgcacagttc ccagggactt gggatgggtc ctgtggagga gtcctggttt
181 gctccttccc tggagcaccc acaagaagag aatgagccca gcctgcagag taaactccaa
```

```
241 gacgaagcca actaccatct ttatggcagc cgcatggaca ggcagacgaa acagcagccc 301 agacagaatg tggcttacaa cagagaggag gaaaggagac gcagggtctc ccatgaccct 361 tttgcacagc aaagacctta cgagaatttt cagaatacag agggaaaagg cactgtttat 421 tccagtgcag ccagtcatgg taatgcagtg caccagccat cagggctcac cagccaacct 481 caagtactgt atcagaacaa tggattatat agctcacatg gctttggaac aagaccactg 541 gatccaggaa cagcaggtcc cagagtttgg tacaggccaa ttccaagtca tatgcctagt 601 ctgcataata tcccagtgcc tgagaccaac tatctaggaa attctcccac catgccattc 661 agctccttgc caccaacaga tgaatctata aaatatacca tatacaatag tactggcatt 721 cagattggag cctacaatta tatggagatt ggtgggacga gttcatcact actagacagc 781 acaaatacga acttcaaaga agagccagct gctaagtacc aagctatctt tgataatacc 841 actagtctga cggataaaca cctggaccca atcagggaaa atctgggaaa gcactggaaa 901 aactgtgccc gtaaactggg cttcacacag tctcagattg atgaaattga ccatgactat 961 gagcgagatg gactgaaaga aaaggtttac cagatgctcc aaaagtgggt gatgagggaa 1021 ggcataaagg gagccacggt ggggaagctg gcccaggcgc tccaccagtg ttccaggatc 1081 gaccttctga gcagcttgat ttacgtcagc cagaactaac cctggatggg ctacggcagc 1141 tgaagtggac gcctcactta gtggataacc ccagaaagtt ggctgcctca gagcattcag 1201 aattctgtcc tcactgatag gggttctgtg tctgcagaaa
```

The atg start and stop codons are bolded and underlined. The amino acid sequence of human RIP, provided by Genbank Accession No. AAC50137.1, is incorporated herein by reference, and is shown below (SEQ ID NO: 202).

```
  1 dvkslkkeys nenavvkrmq slqldcvavp ssrsnsateq pgslhssqgl gmgpveeswf 61 apslehpqee nepslqsklq deanyhlygs rmdrqtkqqp rqnvaynree errrrvshdp 121 faqqrpyenf qntegkgtvy ssaashgnav hqpsgltsqp qvlyqnngly sshgfgtrpl 181 dpgtagprvw yrpipshmps lhnipvpetn ylgnsptmpf sslpptdesi kytiynstgi 241 qigaynymei ggtsssllds tntnfkeepa akyqaifdnt tsltdkhldp irenlgkhwk 301 ncarklgftq sqideidhdy erdglkelwy qmlqkwvmre gikgatvgkl aqalhqcsri 361 dllssliyvs qn
```

The mRNA sequence encoding human TRADD provided by Genbank Accession No. NM_003789.3, is incorporated herein by reference, and is shown below (SEQ ID NO: 203).

```
  1 gcacacccgg aagcggcgga gtagagcgga gcctggcggg cgtgggaacc caggccccgc 61 cgaggcggcc aggaggtgag atggcagctg ggcaaaatgg gcacgaagag tgggtgggca 121 gcgcatacct gtttgtggag tcctcgctgg acaaggtggt cctgtcggat gcctacgcgc 181 accccagca gaaggtggca gtgtacaggg ctctgcaggc tgccttggca gagagcggcg 241 ggagcccgga cgtgctgcag atgctgaaga tccaccgcag cgacccgcag ctgatcgtgc 301 agctgcgatt ctgcgggcgg cagccctgtg gccgcttcct ccgcgcctac cgcgaggggg 361 cgctgcgcgc cgcgctgcag aggagcctgg cggccgcgct cgcccagcac tcggtgccgc 421 tgcaactgga gctgcgcgcc ggcgccgagc ggctggacgc tttgctggcg gacgaggagc 481 gctgtttgag ttgcatccta gcccagcagc ccgaccggct ccgggatgaa gaactggctg
```

-continued

```
 541 agctggagga tgcgctgcga aatctgaagt gcggctcggg ggcccggggt ggcgacgggg 601 aggtcgcttc ggcccccttg cagcccccgg tgccctctct gtcggaggtg aagccgccgc 661 cgccgccgcc acctgcccag acttttctgt tccagggtca gcctgtagtg aatcggccgc 721 tgagcctgaa ggaccaacag acgttcgcgc gctctgtggg tctcaaatgg cgcaaggtgg 781 ggcgctcact gcagcgaggc tgccgggcgc tgcgggaccc ggcgctggac tcgctggcct 841 acgagtacga gcgcgaggga ctgtacgagc aggccttcca gctgctgcgg cgcttcgtgc 901 aggccgaggg ccgccgcgcc acgctgcagc gcctggtgga ggcactcgag gagaacgagc 961 tcaccagcct ggcagaggac ttgctgggcc tgaccgatcc caatggcggc ctggcctaga 1021 ccaggggtgc agccagcttt tggagaacct ggatggcctt agggttcctt ctgcggctat 1081 tgctgaaccc ctgtccatcc acgggaccct gaaactccac ttggcctatc tgctggacct 1141 gctggggcag agttgattgc cttccccagg agccagacca ctgggggtgc atcattgggg 1201 attctgcctc aggtactttg atagagtgtg gggtgggggg gacctgctttg ggagatcagc 1261 ctcaccttct cccatcccag aagcggggct tacagccagc ccttacagtt tcactcatga 1321 agcaccttga tctttggtgt cctggacttc atcctgggtg ctgcagatac tgcagtgaag 1381 taaaacagga atcaatcttg cctgccccca gctcacactc agcgtgggac cccgaatgtt 1441 aagcaatgat aataaagtat aacacggatt ttgatgtgag aaaaaaaaaa aaaaaa
```

The atg start and stop codons are bolded and underlined.
The amino acid sequence of human TRADD, provided by Genbank Accession No. NP_00370.1, is incorporated herein by reference, and is shown below (SEQ ID NO: 204).

```
  1 maagqnghee wvgsaylfve ssldlwvlsd ayahpqqkva vyralqaala esggspdvlq 61 mlkihrsdpq livqlrfcgr qpcgrflray regalraalq rslaaalaqh svplqlelra 121 gaerldalla deerclscil aqqpdrlide elaeledalr nlkcgsgarg gdgevasapl 181 qppvpslsev kpppppppaq tflfqgqpvv nrplslkdqq tfarsvglkw rkvgrslqrg 241 cralrdpald slayeyereg lyeqafqllr rfvqaegrra tlqrlveale eneltslaed 301 llgltdpngg la
```

The mRNA sequence encoding human PADI2 (protein-arginine deiminase type-2) provided by Genbank Accession No. NM_007365.2, is incorporated herein by reference, and is shown below (SEQ ID NO: 205).

```
  1 gcaggctgct ggagaaggcg cacctgctgc aggtgctccc ggccgccccg gaccagcgag 61 cgcgggcact gcggcgggga ggatgctgcg cgagcggacc gtgcggctgc agtacgggag 121 ccgcgtggag gcggtgtacg tgctgggcac ctacctctgg accgatgtct acagcgcggc 181 cccagccggg gcccaaacct tcagcctgaa gcactcggaa cacgtgtggg tggaggtggt 241 gcgtgatggg gaggctgagg aggtggccac caatggcaag cagcgctggc ttctctcgcc 301 cagcaccacc ctgcgggtca ccatgagcca ggcgagcacc gaggccagca gtgacaaggt 361 caccgtcaac tactatgacg aggaagggag cattcccatc gaccaggcgg ggctcttcct 421 cacagccatt gagatctccc tggatgtgga cgcagaccgg gatggtgtgg tggagaagaa 481 caacccaaag aaggcatcct ggacctgggg ccccagggc caggggggcca tcctgctggt 541 gaactgtgac cgagagacac cctggttgcc caaggaggac tgccgtgatg agaaggtcta
```

-continued

```
 601 cagcaaggaa gatctcaagg acatgtccca gatgatcctg cggaccaaag gccccgaccg
 661 cctccccgcc ggatacgaga tagttctgta catttccatg tcagactcag acaaagtggg
 721 cgtgttctac gtggagaacc cgttcttcgg ccaacgctat atccacatcc tgggccggcg
 781 gaagctctac catgtggtca agtacacggg tggctccgcg gagctgctgt tcttcgtgga
 841 aggcctctgt ttccccgacg agggcttctc aggcctggtc tccatccatg tcagcctgct
 901 ggagtacatg gcccaggaca ttcccctgac tcccatcttc acggacaccg tgatattccg
 961 gattgctccg tggatcatga cccccaacat cctgcctccc gtgtcggtgt tgtgtgctg
1021 catgaaggat aattacctgt tcctgaaaga ggtgaagaac cttgtggaga aaccaactg
1081 tgagctgaag gtctgcttcc agtacctaaa ccgaggcgat cgctggatcc aggatgaaat
1141 tgagtttggc tacatcgagg ccccccataa aggcttcccc gtggtgctgg actctccccg
1201 agatggaaac ctaaaggact tccctgtgaa ggagctcctg gcccagatt ttggctacgt
1261 gacccgggag cccctctttg agtctgtcac cagccttgac tcatttggaa acctggaggt
1321 cagtccccca gtgaccgtga acggcaagac atacccgctt ggccgcatcc tcatcgggag
1381 cagcttttcct ctgtctggtg gtcggaggat gaccaaggtg gtgcgtgact tcctgaaggc
1441 ccagcaggtg caggcgcccg tggagctcta ctcagactgg ctgactgtgg gccacgtgga
1501 tgagttcatg tcctttgtcc ccatccccgg cacaaagaaa ttcctgctac tcatggccag
1561 cacctcggcc tgctacaagc tcttccgaga gaagcagaag gacggccatg gagaggccat
1621 catgttcaaa ggcttgggtg ggatgagcag caagcgaatc accatcaaca agattctgtc
1681 caacgagagc cttgtgcagg agaacctgta cttccagcgc tgcctagact ggaaccgtga
1741 catcctcaag aaggagctgg gactgacaga gcaggacatc attgacctgc ccgctctgtt
1801 caagatggac gaggaccacc gtgccagagc cttcttccca aacatggtga acatgatcgt
1861 gctggacaag gacctgggca tccccaagcc attcgggcca caggttgagg aggaatgctg
1921 cctggagatg cacgtgcgtg gcctcctgga gccctgggc ctcgaatgca ccttcatcga
1981 cgacatttct gcctaccaca aatttctggg ggaagtccac tgtggcacca acgtccgcag
2041 gaagcccttc accttcaagt ggtggcacat ggtgccctga cctgccaggg gccctggcgt
2101 ttgcctcctt cgcttagttc tccagaccct ccctcacacg cccagagcct tctgctgaca
2161 tggactggac agccccgctg ggagacctt gggacgtggg gtggaatttg gggtatctgt
2221 gccttgccct ccctgagagg ggcctcagtg tcctctgaag ccatccccag tgagcctcga
2281 ctctgtccct gctgaaaata gctgggccag tgtctctgta gccctgacat aaggaacaga
2341 acacaacaaa acacagcaaa ccatgtgccc aaactgctcc ccaaagaatt ttgagtctct
2401 aatctgacac tgaatgaggg gagaagggaa ggagattctg ggattgccag ttcttccagc
2461 agccatgctc tgaaaatcaa ggtagaatcc atggaaaggg accccaggac cccgggaccc
2521 tagacgtatc ttgaactgcc atcgtcattt caaatacatc tccctcaggg tttccaggtg
2581 gccaccccca attattcatt ccttaccaac ctctcaaatc ctcttggctt tctctctgca
2641 gtgtggacac tgttggctag tcctccccac tccctgaggg tccagtaagt tagcttagaa
2701 ccttcctgga aacatttcat ctgagcaggt ttccccacgt gtgggatgct ccttttgcct
2761 catctgtctc agggatgcag gctcccccgc atgcatgggg atttctcccc agaccagcat
2821 acttgtgacc tgagagttca atgcgtaaag atgcccctgg tcagccatat ccatcttctc
2881 ttgcctggtc cttgattctc tggccgctcc ctgaccttcc tcttccact gccttgactt
2941 tcttcctttt tattcctggt gccatctgtc caggcagcta acaagaact tgttcgccag
3001 cagccagatt caggccttcc caggggcata ataagtgacc agcccctcct ctccggacat
```

-continued

```
3061 cagatccaac acataaggac cctggcctac cctccagccc aacagccagt tctgggtcag 3121 ctgccaactt aggggtggtt tgattatccc attgaaattc accagtgcct ttgccaaaga 3181 ccctctcatt tggacatacc cagattcatt ccctggctcc aactgaaaag actcagtttc 3241 aatcgttaaa agttccttta gggccagaag aataaatgaa ttataatccc attttgaaga 3301 accgatttat aaccaatgaa aaggttataa tgtaatttat attcttggag gaacaagatt 3361 ttcatttggg attatttcct tcaaccattc aacaaacatt tgttgtatgc cactaagcgc 3421 caggcacggc gttgggctct gcaaacacag tggttagtag cagtctggac ctggtcccta 3481 ctggcatgga acccatcact ccccaacatg caaagcccac atttaaaggc cagcctctgc 3541 cccttcagtg atgcgctctt tagaaatgcc agtccactat attcagaaat ccgcagggca 3601 caaaacttcc agcaagtcac tgttgtggtg aaatgggcag tgggggtggg gggtcttctt 3661 taaacaggcc cccttcccat ctacctagcc agtacccatc caatgagtcc ccagagcctc 3721 cagaagctgt tgtctcctct ctggggacag cagctcctgc ctttggaggc caaagcccca 3781 gatctctcca gccccagagc tgaaaacacc aagtgcctat ttgagggtgt ctgtctggag 3841 acttagagtt tgtcatgtgt gtgtgtgtgt ttggttaatg tgggtttatg ggttttcttt 3901 cttttttttc tttttttttt tagtctacat taggggaag tgagcgcctc ccatgtgcag 3961 acagtgtgtc tttatagatt tttctaaggc tttccccaat gatgtcggta atttctgatg 4021 tttctgaagt tcccaggact cacacacccg ttcccatctc acttgcccac ccagtgtgac 4081 aaccctcggt gtggatatac ccccgtggac tcatggctct tccccacccc cactttctat 4141 aaatgtaggc ctagaatacg cttctctgtt gcaaaactca gctaagttcc tgcttccacc 4201 ttgatgttga aatatcttat gtaagagggc aggggatgtc gtgaagatgg caagaagaac 4261 acagtttcaa atttctggaa aagagcctgt ggtggagatc taaagatgtt tagggaagag 4321 ctcgactaaa gaacaatgaa ataaatggtc caggggaag tca
```

The atg start and stop codons are bolded and underlined. The amino acid sequence of human PADI2 (protein-arginine deiminase type-2), provided by Genbank Accession No. NP_031391.2, is incorporated herein by reference, and is shown below (SEQ ID NO: 206).

The mRNA sequence encoding human PAD3 (PADI3) provided by Genbank Accession No. NM_016233.2, is incorporated herein by reference, and is shown below (SEQ ID NO: 207).

```
  1 mlrertvrlq ygsrveavyv lgtylwtdvy saapagaqtf slkhsehvwv evvrdgeaee 61 vatngkqrwl lspsttlrvt msqasteass dkvtvnyyde egsipidqag lfltaieisl 121 dvdadrdgvv eknnpkkasw twgpegqgai llvncdretp wlpkedcrde lwyskedlkd 181 msqmilrtkg pdrlpagyei vlyismsdsd kvgvfyvenp ffgqiyihil grrklyhvvk 241 ytggsaellf fveglcfpde gfsglvsihv slleymaqdi pltpiftdtv ifriapwimt 301 pnilppvsvf vccmkdnylf lkevknlvek tncelkvcfq ylnrgdrwiq deiefgyiea 361 phkgfpvvld sprdgnlkdf pvkellgpdf gyvtreplfe svtsldsfgn levsppvtvn 421 gktyplgril igssfplsgg ilmtkvvrdf lkaqqvqapv elysdwltvg hvdefmsfvp 481 ipgtkkflll mastsacykl frekqkdghg eaimfkglgg msskritink ilsneslvqe 541 nlyfqrcldw nrdilkkelg lteqdiidlp alfkmdedhr araffpnmvn mivldkdlgi 601 pkpfgpqvee ecclemhvrg lleplglect fiddisayhk flgevhcgtn vrrkpftfkw 661 whmvp
```

```
   1 agtgttgggg ttggcggcca cagctaagtc caacaccagc atgtcgctgc agagaatcgt
  61 gcgtgtgtcc ctggagcatc ccaccagcgc ggtgtgtgtg gctggcgtgg agaccctcgt
 121 ggacatttat gggtcagtgc ctgagggcac agaaatgttt gaggtctatg ggacgcctgg
 181 cgtggacatc tacatctctc ccaacatgga gaggggccgg gagcgtgcag acaccaggcg
 241 gtggcgcttt gacgcgactt tggagatcat cgtggtcatg aactccccca gcaatgacct
 301 caacgacagc catgttcaga tttcctacca ctccagccat gagcctctgc ccctggccta
 361 tgcggtgctc tacctcacct gtgttgacat ctctctggat tgcgacctga actgtgaggg
 421 aaggcaggac aggaactttg tagacaagcg gcagtgggtc tgggggccca gtgggtatgg
 481 cggcatcttg ctggtgaact gtgaccgtga tgatccgagc tgtgatgtcc aggacaattg
 541 tgaccagcac gtgcactgcc tgcaagacct ggaagacatg tctgtcatgg tcctgcggac
 601 gcagggccct gcagccctct tgatgaccaa caaacttgtc ctccatacct ccagctatga
 661 tgccaaacgg gcacaggtct tccacatctg cggtcctgag gatgtgtgtg aggcctatag
 721 gcatgtgctg ggccaagata aggtgtccta tgaggtaccc cgcttgcatg ggatgaggga
 781 gcgcttcttc gtggaaggcc tgtccttccc tgatgccggc ttcacaggac tcatctcctt
 841 ccatgtcact ctgctggacg actccaacga ggatttctcg gcatccccta tcttcactga
 901 cactgtggtg ttccgagtgg caccctggat catgacgccc agcactctgc caccctaga
 961 ggtgtatgtg tgccgtgtga ggaacaacac gtgttttgtg gatgcggtgg cagagctggc
1021 caggaaggcc ggctgcaagc tgaccatctg cccacaggcc gagaaccgca acgaccgctg
1081 gatccaggat gagatggagc tgggctacgt tcaggcgccg cacaagaccc tcccggtggt
1141 ctttgactcc ccaaggaatg gggaactgca ggatttccct tacaaaagaa tcctgggtcc
1201 agattttggt tacgtgactc gggaaccacg cgacaggtct gtgagtggcc tggactcctt
1261 tgggaacctg gaggtcagcc ctccagtggt ggccaatggg aaagagtacc ccctggggag
1321 gatcctcatt gggggcaacc tgcctgggtc aagtggccgc agggtcaccc aggtggtgcg
1381 ggacttcctc catgcccaga aggtgcagcc ccccgtggag ctctttgtgg actggttggc
1441 cgtgggccat gtggatgagt ttctgagctt tgtccctgcc cccgatggga agggcttccg
1501 gatgctcctg gccagccctg ggcctgcttc aagctcttc caggaaaagc agaagtgtgg
1561 ccacgggagg gccctcctgt tccaggggg tgttgatgat gagcaggtca agaccatctc
1621 catcaaccag gtgctctcca ataaagacct catcaactac aataagtttg tgcagagctg
1681 catcgactgg aaccgtgagg tgctgaagcg ggagctgggc ctggcagagt gtgacatcat
1741 tgacatccca cagctcttca agaccgagag gaaaaaagca acggccttct tccctgactt
1801 ggtgaacatg ctggtgctgg ggaagcacct gggcatcccc aagcccttg ggcccatcat
1861 caatggctgc tgctgcctgg aggagaaggt gcggtccctg ctggagccgc tgggcctcca
1921 ctgcaccttc attgatgact cactccata ccacatgctg catggggagg tgcactgtgg
1981 caccaatgtg tgcagaaagc ccttctcttt caagtggtgg aacatggtgc ctgagacag
2041 ctcccaccca ccatcctgtc ccctggggc gggcattggc ccaggtggtg gagacagaga
2101 caggcccctg aacgataagc accaagagac cccaaggctc cagatggaac actgagggtg
2161 accgtccctc tcagaagcct tttccctgga agtgtccatg cctcacctgc aacccatgtg
2221 gttctcagac ttgaatcttc tcggcccccc aaaaagaagg acctcatttc ttatagcctc
2281 tcctgtgatt caacacaacc catggagatg tccccttctc actctgaaat catccatttg
2341 gggacaaatc cacattgggg tctagaaaca tccacgtatc tcatcagcca tcttgtcctg
2401 tgcatcctaa cagaggaagg atccatgatt ctgctttggt ccaattgctt cctctctgca
```

-continued

```
2461 gaggaacaac cctaaaacca gaccactcca cgcaggacag gcaggagaga ttcttcctaa 2521 agcctccccc ataaaaaggg agctgtggat ccacttagat cagggcggaa ccatattca 2581 cccggccaag ctcctgccca gatgttgacc ctcacccagc gtgagctgtc acatagtagg 2641 agcttctaga tgcatgtgga agcaatgaga gttgtccctt agccttataa actccccatg 2701 atctgacatg cagaaatcca gccttgtcca gaatcctcct ggaatttctt ggagacgaaa 2761 gtatctgggg gattgttggg tactagggag actgggtaca agggtgaaaa gtagttccca 2821 taatacacat ggttgactat ggtgatccac cttgtgatgg ttaatattag gtgtctggag 2881 aaggttgctt cattggccct gggacttctc tctgcaggag gagagaacgc tgcctctcct 2941 ctggattggt ctcaggctct ctgttggcct ttggtcagcg tttccacatc ctgctctgct 3001 gcaggagagg gggctaaggg gctggatcca ccaaggcagc tcacagcggg aaaactctgg 3061 gaatgaacca ctgaattcag gggatggggg tggggggggcg gttctcgagg tgtgtgccag 3121 ctacacgtgt gttctgtatg ggtccagctg cgtttccatc actcgctaat aaatcaacag 3181 aaacacaaa
```

The atg start and stop codons are bolded and underlined. The amino acid sequence of human PADI3 (PAD3), provided by Genbank Accession No. NP_057317.2, is incorporated herein by reference, and is shown below (SEQ ID NO: 208).

```
  1 mslqrivrvs lehptsavcv agvetivdiy gsvpegtemf evygtpgvdi yispnmergr 61 eradtrrwrf datleiivvm nspsndlnds hvqisyhssh eplplayavl yltcvdisld 121 cdlncegrqd rnfvdkrqwv wgpsgyggil lvncdrddps cdvqdncdqh vhclqdledm 181 svmvlrtqgp aalfddhklv lhtssydakr aqvfhicgpe dvceayrhvl gqdkvsyevp 241 rlhgdeerff veglsfpdag ftglisfhvt llddsnedfs aspiftdtvv frvapwimtp 301 stlpplevyv crvrnntcfv davaelarka gcklticpqa enrndrwiqd emelgyvqap 361 hktlpvvfds prngelqdfp ykrilgpdfg yvtreprdrs vsgldsfgnl evsppvvang 421 keyplgrili ggnlpgssgr rvtqvvrdfl haqkvqppve lfvdwlavgh vdeflsfvpa 481 pdgkgfrmll aspgacfklf qekqkcghgr allfqgvvdd eqvktisinq vlsnkdliny 541 nkivqscidw nrevlkrelg laecdiidip qlfkterkka taffpdlvnm lvlgkhlgip 601 kpfgpiingc ccleekvrsl leplglhctf iddftpyhml hgevhcgtnv crkpfsfkww 661 nmvp
```

The mRNA sequence encoding human FOXP3 provided by Genbank Accession No. EF534714.1, is incorporated herein by reference, and is shown below (SEQ ID NO: 209).

```
  1 atgcccaacc ccaggcctgg caagccctcg gcccctccct tggcccttgg cccatcccca 61 ggagcctcgc ccagctggag ggctgcaccc aaagcctcag acctgctggg ggcccggggc 121 ccagggggaa ccttccaggg ccgagatctt cgaggcgggg cccatgcctc ctcttcttcc 181 ttgaacccca tgccaccatc gcagctgcag ctgcccacac tgccctagt catggtggca 241 ccctccgggg cacggctggg cccttgccc cacttacagg cactcctcca ggacaggcca 301 catttcatgc accagctctc aacggtggat gccacgcccc ggacccctgt gctgcaggtg 361 caccccctgg agagcccagc catgatcagc ctcacaccac ccaccaccgc cactggggtc
```

-continued

```
 421 ttctccctca aggcccggcc tggcctccca cctgggatca acgtggccag cctggaatgg 481 gtgtccaggg agccggcact gctctgcacc ttcccaaatc ccagtgcacc caggaaggac 541 agcacccttt cggctgtgcc ccagagctcc tacccactgc tggcaaatgg tgtctgcaag 601 tggcccggat gtgagaaggt cttcgaagag ccagaggact tcctcaagca ctgccaggcg 661 gaccatcttc tggatgagaa gggcagggca caatgtctcc tccagagaga gatggtacag 721 tctctggagc agcagctggt gctggagaag gagaagctga gtgccatgca ggcccacctg 781 gctgggaaaa tggcactgac caaggcttca tctgtggcat catccgacaa gggctcctgc 841 tgcatcgtag ctgctggcag ccaaggccct gtcgtcccag cctggtctgg ccccgggag 901 gcccctgaca gcctgtttgc tgtccggagg cacctgtggg gtagccatgg aaacagcaca 961 ttcccagagt tcctccacaa catggactac ttcaagttcc acaacatgcg accccctttc 1021 acctacgcca cgctcatccg ctgggccatc ctggaggctc cagagaagca gcggacactc 1081 aatgagatct accactggtt cacacgcatg tttgccttct tcagaaacca tcctgccacc 1141 tggaagaacg ccatccgcca caacctgagt ctgcacaagt gctttgtgcg ggtggagagc 1201 gagaagggg ctgtgtggac cgtggatgag ctggagttcc gcaagaaacg gagccagagg 1261 cccagcaggt gttccaaccc tacacctggc ccctga
```

The atg start and stop codons are bolded and underlined. The amino acid sequence of human FOXP3, provided by Genbank Accession No. ABQ15210.1, is incorporated herein by reference, and is shown below (SEQ ID NO: 210).

```
  1 mpnprpgkps apslalgpsp gaspswraap kasdllgarg pggtfqgrdl rggahassss 61 lnpmppsqlq lptlplvmva psgarlgplp hlqallqdrp hfmhqlstvd ahartpvlqv 121 hplespamis ltppttatgv fslkarpglp pginvaslew vsrepallct fpnpsaprkd 181 stlsavpqss ypllangvck wpgcekvfee pedflkhcqa dhlldekgra qcllqremvq 241 sleqqlvlek eklsamqahl agkmaltkas svassdkgsc civaagsqgp vvpawsgpre 301 apdslfavrr hlwgshgnst fpeflhnmdy flahnmrppf tyatlirwai leapekqrtl 361 neiyhwftrm faffrnhpat wknairhnls lhkcfvrves ekgavwtvde lefrkkrsqr 421 psrcsnptpg p
```

The mRNA sequence encoding human IL2RA (CD-25) provided by Genbank Accession No. NM_000417.2, is incorporated herein by reference, and is shown below (SEQ ID NO: 211).

```
                                                          (SEQ ID NO: 211)
  1 ggcagtttcc tggctgaaca cgccagccca atacttaaag agagcaactc ctgactccga 61 tagagactgg atgacccac aagggtgaca gcccaggcgg accgatcttc ccatcccaca 121 tcctccggcg cgatgccaaa agaggctga cggcaactgg gccttctgca gagaaagacc 181 tccgcttcac tgccccggct ggtcccaagg gtcaggaaga tggattcata cctgctgatg 241 tggggactgc tcacgttcat catggtgcct ggctgccagg cagagctctg tgacgatgac 301 ccgccagaga tcccacacgc acattcaaa gccatgcct acaaggaagg aaccatgttg 361 aactgtgaat gcaagagagg tttccgcaga ataaaaagcg ggtcactcta tatgctctgt 421 acaggaaact ctagccactc gtcctgggac aaccaatgtc aatgcacaag ctctgccact 481 cggaacacaa cgaaacaagt gacacctcaa cctgaagaac agaaagaaag gaaaaccaca
```

-continued

```
 541 gaaatgcaaa gtccaatgca gccagtggac caagcgagcc ttccaggtca ctgcagggaa 601 cctccaccat gggaaaatga agccacagag agaatttatc atttcgtggt ggggcagatg 661 gtttattatc agtgcgtcca gggatacagg gctctacaca gaggtcctgc tgagagcgtc 721 tgcaaaatga cccacgggaa gacaaggtgg acccagcccc agctcatatg cacaggtgaa 781 atggagacca gtcagtttcc aggtgaagag aagcctcagg caagcccga aggccgtcct 841 gagagtgaga cttcctgcct cgtcacaaca acagattttc aaatacagac agaaatggct 901 gcaaccatgg agacgtccat atttacaaca gagtaccagg tagcagtggc cggctgtgtt 961 ttcctgctga tcagcgtcct cctcctgagt gggctcacct ggcagcggag acagaggaag 1021 agtagaagaa caatctagaa aaccaaaaga acaagaattt cttggtaaga agccgggaac 1081 agacaacaga agtcatgaag cccaagtgaa atcaaaggtg ctaaatggtc gcccaggaga 1141 catccgttgt gcttgcctgc gttttggaag ctctgaagtc acatcacagg acacggggca 1201 gtggcaacct tgtctctatg ccagctcagt cccatcagag agcgagcgct acccacttct 1261 aaatagcaat ttcgccgttg aagaggaagg gcaaaaccac tagaactctc catcttattt 1321 tcatgtatat gtgttcatta aagcatgaat ggtatggaac tctctccacc ctatatgtag 1381 tataaagaaa gtaggttta cattcatctc attccaactt cccagttcag gagtcccaag 1441 gaaagcccca gcactaacgt aaatacacaa cacacacact ctaccctata caactggaca 1501 ttgtctgcgt ggttcctttc tcagccgctt ctgactgctg attctcccgt tcacgttgcc 1561 taataaacat ccttcaagaa ctctgggctg ctacccagaa atcattttac ccttggctca 1621 atcctctaag ctaaccccct tctactgagc cttcagtctt gaatttctaa aaacagagg 1681 ccatggcaga ataatctttg ggtaacttca aaacggggca gccaaaccca tgaggcaatg 1741 tcaggaacag aaggatgaat gaggtcccag gcagagaatc atacttagca aagtttacc 1801 tgtgcgttac taattggcct cttaagagt tagtttcttt gggattgcta tgaatgatac 1861 cctgaatttg gcctgcacta atttgatgtt tacaggtgga cacacaaggt gcaaatcaat 1921 gcgtacgttt cctgagaagt gtctaaaac accaaaaagg gatccgtaca ttcaatgttt 1981 atgcaaggaa ggaaagaaag aaggaagtga agagggagaa gggatggagg tcacactggt 2041 agaacgtaac cacggaaaag agcgcatcag gcctggcacg gtggctcagg cctataaccc 2101 cagctcccta ggagaccaag gcgggagcat ctcttgaggc caggagtttg agaccagcct 2161 gggcagcata gcaagacaca tccctacaaa aaattagaaa ttggctggat gtggtggcat 2221 acgcctgtag tcctagccac tcaggaggct gaggcaggag gattgcttga gcccaggagt 2281 tcgaggctgc agtcagtcat gatggcacca ctgcactcca gcctgggcaa cagagcaaga 2341 tcctgtcttt aaggaaaaaa agacaagatg agcataccag cagtccttga acattatcaa 2401 aaagttcagc atattagaat caccgggagg ccttgttaaa agagttcgct gggcccatct 2461 tcagagtctc tgagttgttg gtctggaata gagccaaatg ttttgtgtgt ctaacaattc 2521 ccaggtgctg ttgctgctgc tactattcca ggaacacact ttgagaacca ttgtgttatt 2581 gctctgcacg cccacccact ctcaactccc acgaaaaaaa tcaacttcca gagctaagat 2641 ttcggtggaa gtcctggttc catatctggt gcaagatctc ccctcacgaa tcagttgagt 2701 caacattcta gctcaacaac atcacacgat taacattaac gaaaattatt catttgggaa 2761 actatcagcc agttttcact tctgaagggg caggagagtg ttatgagaaa tcacggcagt 2821 tttcagcagg gtccagattc agattaaata actatttct gtcatttctg tgaccaacca 2881 catacaaaca gactcatctg tgcactctcc ccctccccct tcaggtatat gttttctgag 2941 taaagttgaa aagaatctca gaccagaaaa tatagatata tatttaaatc ttacttgagt
```

-continued

```
3001 agaactgatt acgactttg ggtgttgagg ggtctataag atcaaaactt ttccatgata 3061 atactaagat gttatcgacc atttatctgt ccttctctca aaagtgtatg gtggaatttt 3121 ccagaagcta tgtgatacgt gatgatgtca tcactctgct gttaacatat aataaattta 3181 ttgctattgt ttataaaaga ataaatgata tttttt
```

The atg start and stop codons are bolded and underlined.
The amino acid sequence of human IL2RA (CD-25), provided by Genbank Accession No. NP_000408, is incorporated herein by reference, and is shown below (SEQ ID NO: 212).

```
                                                        (SEQ ID NO: 212)
  1 mdsyllmwgl ltfimvpgcq aelcdddppe iphatfkama ykegtmlnce ckrgfrriks 61 gslymictgn sshsswdnqc qctssatrnt tkqvtpqpee qkerkttemq spmqpvdqas 121 lpghcreppp weneateriy hfvvgqmvyy qcvqgyralh rgpaesvckm thgktrwtqp 181 qlictgemet sqfpgeekpq aspegrpese tsclvtttdf qiqtemaatm etsiftteyq 241 vavagcvfll isvillsglt wqrrqrksrr ti
```

(Signal protein AA 1-21; mature protein AA 22-272).

The mRNA sequence encoding human FAP (fibroblast activation protein) provided by Genbank Accession No. NM_001291807.1, is incorporated herein by reference, and is shown below (SEQ ID NO: 213).

```
   1 aagaacgccc ccaaaatctg tttctaattt tacagaaatc ttttgaaact tggcacggta 61 ttcaaaagtc cgtggaaaga aaaaaacctt gtcctggctt cagcttccaa ctacaaagac 121 agacttggtc cttttcaacg gttttcacag atccagtgac ccacgctctg aagacagaat 181 tagctaactt tcaaaaacat ctggaaaaat gaagacttgg gtaaaaatcg tatttggagt 241 tgccacctct gctgtgcttg ccttattggt gatgtgcatt gtcttacgcc cttcaagagt 301 tcataactct gaagaaaata caatgagagc actcacactg aaggatattt taaatggaac 361 attttcttat aaaacatttt ttccaaactg gatttcagga caagaatatc ttcatcaatc 421 tgcagataac aatatagtac tttataatat tgaaacagga caatcatata ccatttgag 481 taatagaacc atgctttgga gatactctta cacagcaaca tattcatctc atgaccttag 541 caatggagaa tttgtaagag gaatgagct tcctcgtcca attcagtatt tatgctggtc 601 gcctgttggg agtaaattag catatgtcta tcaaaacaat atctatttga aacaaagacc 661 aggagatcca ccttttcaaa taacatttaa tggaagagaa ataaaatat ttaatgaat 721 cccagactgg gttatgaag aggaaatgct tgctacaaaa tatgctctct ggtggtctcc 781 taatggaaaa tttttggcat atgcggaatt taatgatacg gatataccag ttattgccta 841 ttcctattat ggcgatgaac aatatcctag aacaataaat attccatacc caaaggctgg 901 agctaagaat cccgttgttc ggatatttat tatcgatacc acttaccctg cgtatgtagg 961 tccccaggaa gtgcctgttc agcaatgat agcctcaagt gattattatt tcagttggct 1021 cacgtgggtt actgatgaac gagtatgttt gcagtggcta aaaagagtcc agaatgtttc 1081 ggtcctgtct atatgtgact tcagggaaga ctggcagaca tgggattgtc caagaccca 1141 ggagcatata gaagaaagca gaactggatg ggctggtgga ttctttgttt caacaccagt 1201 tttcagctat gatgccattt cgtactacaa aatatttagt gacaaggatg gctacaaaca
```

```
-continued
1261 tattcactat atcaaagaca ctgtggaaaa tgctattcaa attacaagtg gcaagtggga 1321 ggccataaat atattcagag taacacagga ttcactgttt tattctagca atgaatttga 1381 agaatacect ggaagaagaa acatctacag aattagcatt ggaagctatc ctccaagcaa 1441 gaagtgtgtt acttgccatc taaggaaaga aaggtgccaa tattacacag caagtttcag 1501 cgactacgcc aagtactatg cacttgtctg ctacggccca ggcatcccca tttccaccct 1561 tcatgatgga cgcactgatc aagaaattaa aatcctggaa gaaaacaagg aattggaaaa 1621 tgctttgaaa aatatccagc tgcctaaaga ggaaattaag aaacttgaag tagatgaaat 1681 tactttatgg tacaagatga ttcttcctcc tcaatttgac agatcaaaga agtatccctt 1741 gctaattcaa gtgtatggtg gtccctgcag tcagagtgta aggtctgtat ttgctgttaa 1801 ttggatatct tatcttgcaa gtaaggaagg gatggtcatt gccttggtgg atggtcgagg 1861 aacagctttc caaggtgaca aactcctcta tgcagtgtat cgaaagctgg gtgtttatga 1921 agttgaagac cagattacag ctgtcagaaa attcatagaa atgggtttca ttgatgaaaa 1981 aagaatagcc atatggggct ggtcctatgg aggatacgtt tcatcactgg cccttgcatc 2041 tggaactggt cttttcaaat gtggtatagc agtggctcca gtctccagct gggaatatta 2101 cgcgtctgtc tacacagaga gattcatggg tctcccaaca aaggatgata tcttgagca 2161 ctataagaat tcaactgtga tggcaagagc agaatatttc agaaatgtag actatcttct 2221 catccacgga acagcagatg ataatgtgca ctttcaaaac tcagcacaga ttgctaaagc 2281 tctggttaat gcacaagtgg atttccaggc aatgtggtac tctgaccaga accacggctt 2341 atccggcctg tccacgaacc acttatacac ccacatgacc cacttcctaa agcagtgttt 2401 ctctttgtca gactaaaaac gatgcagatg caagcctgta tcagaatctg aaaaccttat 2461 ataacccct cagacagttt gcttatttta tttttatgt tgtaaaatgc tagtataaac 2521 aaacaaatta atgttgttct aaaggctgtt aaaaaaaaga tgaggactca gaagttcaag 2581 ctaaatattg tttacatttt ctggtactct gtgaaagaag agaaaaggga gtcatgcatt 2641 ttgctttgga cacagtgttt tatcacctgt tcatttgaag aaaaataata aagtcagaag 2701 ttcaagtgct aaaaaaaaaa aaaaaaaaa aaaaaaaaa
```

The atg start and stop codons are bolded and underlined. The amino acid sequence of human FAP (fibroblast activation protein), provided by Genbank Accession No. NP_001278736.1, is incorporated herein by reference, and is shown below (SEQ ID NO: 214).

```
  1 mktwvkivfg vatsavlall vmcivhpsr  vhnseentmr altlkdilng tfsyktffpn 61 wisgqeylhq sadnnivlyn ietgqsytil snrtmlwrys ytatyyiydl sngefvrgne 121 lprpiqylcw spvgsklayv yqnniylkqr pgdppfqitf ngrenkifng ipdwvyeeem 181 latkyalwws pngkflayae fndtdipvia ysyygdeqyp rtinipypka gaknpvvrif 241 iidttypayv gpqevpvpam iassdyyfsw ltwvtdervc lqwlkrvqnv svlsicdfre 301 dwqtwdcpkt qehieesrtg waggffvstp vfsydaisyy kifsdkdgyk hihyikdtve 361 naiqitsgkw eainifrvtq dslfyssnef eeypgrrniy risigsypps kkcvtchlrk 421 ercqyytasf sdyakyyalv cygpgipist lhdgrtdqei kileenkele nalkniqlpk 481 eeikklevde itlwykmilp pqfdrskkyp lliqvyggpc sqsvrsvfav nwisylaske 541 gmvialvdgr gtafqgdkll yavyrklgvy evedqitavr kfiemgfide kriaiwgwsy 601 ggyvsslala sgtglfkcgi avapvsswey yasvyterfm glptkddnle hyknstvmar
```

-continued
```
661 aeyfrnvdyl lffigtaddnv hfqnsaqiak alvnaqvdfq amwysdqnhg lsglstnhly
721 thmthflkqc fslsd
```

The mRNA sequence encoding human DPP4 (dipeptidyl peptidase 4) provided by Genbank Accession No. NM_001935.3, is incorporated herein by reference, and is shown below (SEQ ID NO: 215).

```
   1   ctttcactgg caagagacgg agtcctgggt ttcagttcca gttgcctgcg gtgggctgtg
  61   tgagtttgcc aaagtccect gccctctctg ggtctcggtt ccctcgcctg tccacgtgag
 121   gttggaggag ctgaacgccg acgtcatttt tagctaagag ggagcagggt ccccgagtcg
 181   ccggcccagg gtctgcgcat ccgaggccgc gcgccctttc ccctccccca cggctcctcc
 241   gggccccgca ctctgcgccc cggctgccgc ccagcgccct acaccgccct caggggggcc
 301   tcgcgggctc ccccggccg ggatgccagt gccccgcgcc acgcgcgcct gctcccgcgc
 361   cgcctgccct gcagcctgcc cgcggcgcct ttatacccag cgggctcggc gctcactaat
 421   gtttaactcg gggccgaaac ttgccagcgg cgagtgactc caccgcccgg agcagcggtg
 481   caggacgcgc gtctccgccg cccgcggtga cttctgcctg cgctccttct ctgaacgctc
 541   acttccgagg agacgccgac gatgaagaca ccgtggaagg ttcttctggg actgctgggt
 601   gctgctgcgc ttgtcaccat catcaccgtg cccgtggttc tgctgaacaa aggcacagat
 661   gatgctacag ctgacagtcg caaaacttac actctaactg attacttaaa aaatacttat
 721   agactgaagt tatactcctt aagatggatt tcagatcatg aatatctcta caaacaagaa
 781   aataatatct tggtattcaa tgctgaatat ggaaacagct cagtttctct tggagaacagt
 841   acatttgatg agtttggaca ttctatcaat gattattcaa tatctcctga tgggcagttt
 901   attctcttag aatacaacta cgtgaagcaa tggaggcatt cctacacagc ttcatatgac
 961   atttatgatt taaataaaag gcagctgatt acagaagaga ggattccaaa caacacacag
1021   tgggtcacat ggtcaccagt gggtcataaa ttggcatatg tttggaacaa tgacatttat
1081   gttaaaattg aaccaaattt accaagttac agaatcacat ggacggggaa agaagatata
1141   atatataatg gaataactga ctgggtttat gaagaggaag tcttcagtgc ctactctgct
1201   ctgtggtggt ctccaaacgg cactttttta gcatatgccc aatttaacga cacagaagtc
1261   ccacttattg aatactcctt ctactctgat gagtcactgc agtacccaaa gactgtacgg
1321   gttccatatc caaaggcagg agctgtgaat ccaactgtaa agttctttgt tgtaaataca
1381   gactctctca gctcagtcac caatgcaact tccatacaaa tcactgctcc tgcttctatg
1441   ttgatagggg atcactactt gtgtgatgtg acatgggcaa cacaagaaag aatttctttg
1501   cagtggctca ggaggattca gaactattcg gtcatggata tttgtgacta tgatgaatcc
1561   agtggaagat ggaactgctt agtggcacgg caacacattg aaatgagtac tactggctgg
1621   gttggaagat ttaggccttc agaacctcat tttacccttg atggtaatag cttctacaag
1681   atcatcagca tgaagaagg ttacagacac atttgctatt ccaaataga taaaaaagac
1741   tgcacatta ttacaaaagg cacctgggaa gtcatcggga tagaagctct aaccagtgat
1801   tatctatact acattagtaa tgaatataaa ggaatgccag gaggaaggaa tctttataaa
1861   atccaactta gtgactatac aaaagtgaca tgcctcagtt gtgagctgaa tccggaaagg
1921   tgtcagtact attctgtgtc attcagtaaa gaggcgaagt attatcagct gagatgttcc
1981   ggtcctggtc tgccctcta tactctacac agcagcgtga atgataaagg gctgagagtc
2041   ctggaagaca attcagcttt ggataaaatg ctgcagaatg tccagatgcc ctccaaaaaa
```

```
2101  ctggacttca ttattttgaa tgaaacaaaa ttttggtatc agatgatctt gcctcctcat
2161  tttgataaat ccaagaaata tcctctacta ttagatgtgt atgcaggccc atgtagtcaa
2221  aaagcagaca ctgtcttcag actgaactgg gccacttacc ttgcaagcac agaaaacatt
2281  atagtagcta gctttgatgg cagaggaagt ggttaccaag gagataagat catgcatgca
2341  atcaacagaa gactgggaac atttgaagtt gaagatcaaa ttgaagcagc cagacaattt
2401  tcaaaaatgg gatttgtgga caacaaacga attgcaattt ggggctggtc atatggaggg
2461  tacgtaacct caatggtcct gggatcggga agtggcgtgt tcaagtgtgg aatagccgtg
2521  gcgcctgtat cccggtggga gtactatgac tcagtgtaca cagaacgtta catgggtctc
2581  ccaactccag aagacaacct tgaccattac agaaattcaa cagtcatgag cagagctgaa
2641  aattttaaac aagttgagta cctccttatt catggaacag cagatgataa cgttcacttt
2701  cagcagtcag ctcagatctc caaagccctg gtcgatgttg gagtggattt ccaggcaatg
2761  tggtatactg atgaagacca tggaatagct agcagcacag cacaccaaca tatatatacc
2821  cacatgagcc acttcataaa acaatgtttc tctttaccttagcacctcaa ataccatgc
2881  catttaaagc ttattaaaac tcattttgt tttcattatc tcaaaactgc actgtcaaga
2941  tgatgatgat ctttaaaata cacactcaaa tcaagaaact taaggttacc tttgttccca
3001  aatttcatac ctatcatctt aagtagggac ttctgtcttc acaacagatt attccttac
3061  agaagtttga attatccggt cgggttttat tgtttaaaat catttctgca tcagctgctg
3121  aaacaacaaa taggaattgt ttttatggag gctttgcata gattccctga gcaggatttt
3181  aatctttttc taactggact ggttcaaatg ttgttctctt ctttaaaggg atggcaagat
3241  gtgggcagtg atgtcactag ggcagggaca ggataagagg gattagggag agaagatagc
3301  agggcatggc tgggaaccca agtccaagca taccaacacg agcaggctac tgtcagctcc
3361  cctcggagaa gagctgttca cagccagact ggcacagttt tctgagaaag actattcaaa
3421  cagtctcagg aaatcaaata tgcaaagcac tgacttctaa gtaaaaccac agcagttgaa
3481  aagactccaa agaaatgtaa gggaaactgc cagcaacgca ggcccccagg tgccagttat
3541  ggctataggt gctacaaaaa cacagcaagg gtgatgggaa agcattgtaa atgtgctttt
3601  aaaaaaaaat actgatgttc ctagtgaaag aggcagcttg aaactgagat gtgaacacat
3661  cagcttgccc tgttaaaaga tgaaaatatt tgtatcacaa atcttaactt gaaggagtcc
3721  ttgcatcaat ttttcttatt tcatttcttt gagtgtctta attaaaagaa tattttaact
3781  tccttggact cattttaaaa aatggaacat aaaatacaat gttatgtatt attattccca
3841  ttctacatac tatggaattt ctcccagtca tttaataaat gtgccttcat ttttcagaa
3901  aaaaaaaaa aaa
```

The atg start and stop codons are bolded and underlined.
The amino acid sequence of human DPP-4 (dipeptidyl peptidase 4), provided by Genbank Accession No. NP_001926.2, is incorporated herein by reference, and is shown below (SEQ ID NO: 216).

```
  1  mktpwkvllg llgaaalvti itvpvvllnk gtddatadsr ktythdylk  ntyrlklysl
 61  rwisdheyly kqennilvfn aeygnssvfl enstfdefgh sindysispd gqfilleyny
121  vkqwrhsyta sydiydlnkr qliteeripn ntqwvtwspv ghklayvwnn diyvkiepnl
181  psyritwtgk ediiyngitd wvyeeevfsa ysalwwspng tflayaqfnd tevplieysf
241  ysdeslqypk tvrvpypkag avnptvkffv vntdslssvt natsiqitap asmligdhyl
```

-continued

```
301  cdvtwatqer  islqwlrriq  nysvmdicdy  dessgrwncl  varqhiemst  tgwvgrfrps
361  ephftldgns  fykiisneeg  yrhicyfqid  kkdctfitkg  twevigieal  tsdylyyisn
421  eykgmpggrn  lykiqlsdyt  kvtclsceln  percqyysvs  fskeakyyql  rcsgpglply
481  tlhssvndkg  lrvlednsal  dkmlqnvqmp  skkldfiiln  etkfwyqmil  pphfdkskky
541  pllldvyagp  csqkadtvfr  lnwatylast  eniivasfdg  rgsgyqgdki  mhainrrlgt
601  fevedqieaa  rqfskmgfvd  nkriaiwgws  yggyvtsmvl  gsgsgvfkcg  iavapvsrwe
661  yydsvytery  mglptpednl  dhyrnstvms  raenfkqvey  llihgtaddn  vhfqqsaqis
721  kalvdvgvdf  qamwytdedh  giasstahqh  iythmshfik  qcfslp
```

15

The mRNA sequence encoding human CD26 provided by Genbank Accession No. M74777.1, is incorporated herein by reference, and is shown below (SEQ ID NO: 217).

```
   1  gacgccgacg  atgaagacac  cgtggaaggt  tcttctggga  ctgctgggtg  ctgctgcgct
  61  tgtcaccatc  atcaccgtgc  ccgtggttct  gctgaacaaa  ggcacagatg  atgctacagc
 121  tgacagtcgc  aaaacttaca  ctctaactga  ttacttaaaa  aatacttata  gactgaagtt
 181  atactcctta  agatggattt  cagatcatga  atatctctac  aaacaagaaa  ataatatctt
 241  ggtattcaat  gctgaatatg  gaaacagctc  agttttcttg  gagaacagta  catttgatga
 301  gtttggacat  tctatcaatg  attattcaat  atctcctgat  gggcagttta  ttctcttaga
 361  atacaactac  gtgaagcaat  ggaggcattc  ctacacagct  tcatatgaca  tttatgattt
 421  aaataaaagg  cagctgatta  cagaagagag  gattccaaac  aacacacagt  gggtcacatg
 481  gtcaccagtg  ggtcataaat  tggcatatgt  ttggaacaat  gacatttatg  ttaaaattga
 541  accaaattta  ccaagttaca  gaatcacatg  gacggggaaa  gaagatataa  tatataatgg
 601  aataactgac  tgggtttatg  aagaggaagt  cttcagtgcc  tactctgctc  tgtggtggtc
 661  tccaaacggc  acttttttag  catatgccca  atttaacgac  acagaagtcc  cacttattga
 721  atactccttc  tactctgatg  agtcactgca  gtacccaaag  actgtacggg  ttccatatcc
 781  aaaggcagga  gctgtgaatc  caactgtaaa  gttctttgtt  gtaaatacag  actctctcag
 841  ctcagtcacc  aatgcaactt  ccatacaaat  cactgctcct  gcttctatgt  tgataggga
 901  tcactacttg  tgtgatgtga  catgggcaac  acaagaaaga  atttctttgc  agtggctcag
 961  gaggattcag  aactattcgg  tcatggatat  ttgtgactat  gatgaatcca  gtggaagatg
1021  gaactgctta  gtggcacggc  aacacattga  atgagtact  actggctggg  ttggaagatt
1081  taggccttca  gaacctcatt  ttacccttga  tggtaatagc  ttctacaaga  tcatcagcaa
1141  tgaagaaggt  tacagacaca  tttgctattt  ccaaatagat  aaaaaagact  gcacatttat
1201  tacaaaaggc  acctgggaag  tcatcgggat  agaagctcta  accagtgatt  atctatacta
1261  cattagtaat  gaatataaag  gaatgccagg  aggaaggaat  ctttataaaa  tccaacttag
1321  tgactataca  aaagtgacat  gcctcagttg  tgagctgaat  ccggaaaggt  gtcagtacta
1381  ttctgtgtca  ttcagtaaag  aggcgaagta  ttatcagctg  agatgttccg  gtcctggtct
1441  gccctctat   actctacaca  gcagcgtgaa  tgataaaggg  ctgagagtcc  tggaagacaa
1501  ttcagctttg  gataaaatgc  tgcagaatgt  ccagatgccc  tccaaaaaac  tggacttcat
1561  tattttgaat  gaaacaaaat  tttggtatca  gatgatcttg  cctcctcatt  ttgataaatc
1621  caagaaatat  cctctactat  tagatgtgta  tgcaggccca  tgtagtcaaa  aagcagacac
1681  tgtcttcaga  ctgaactggg  ccacttacct  tgcaagcaca  gaaaacatta  tagtagctag
```

```
-continued
1741  ctttgatggc agaggaagtg gttaccaagg agataagatc atgcatgcaa tcaacagaag
1801  actgggaaca tttgaagttg aagatcaaat tgaagcagcc agacaatttt caaaaatggg
1861  atttgtggac aacaaacgaa ttgcaatttg gggctggtca tatggagggt acgtaacctc
1921  aatggtcctg ggatcaggaa gtggcgtgtt caagtgtgga atagccgtgg cgcctgtatc
1981  ccggtgggag tactatgact cagtgtacac agaacgttac atgggtctcc caactccaga
2041  agacaacctt gaccattaca gaaattcaac agtcatgagc agagctgaaa attttaaaca
2101  agttgagtac ctccttattc atggaacagc agatgataac gttcactttc agcagtcagc
2161  tcagatctcc aaagccctgg tcgatgttgg agtggatttc caggcaatgt ggtatactga
2221  tgaagaccat ggaatagcta gcagcacagc acaccaacat atatatcccc acatgagcca
2281  cttcataaaa caatgtttct ctttacctta gcacctcaaa ataccatgcc atttaaagct
2341  tattaaaact catttttgtt ttcattatct caaaactgca ctgtcaagat gatgatgatc
2401  tttaaaatac acactcaaat caagaaactt aaggttacct ttgttcccaa atttcatacc
2461  tatcatctta agtagggact tctgtcttca aacagatta ttaccttaca gaagtttgaa
2521  ttatccggtc gggttttatt gtttaaaatc atttctgcat cagctgctga aacaacaaat
2581  aggaattgtt tttatggagg ctttgcatag attccctgag caggatttta atcttttttct
2641  aactggactg gttcaaatgt tgttctcttc tttaaaggga tggcaagatg tgggcagtga
2701  tgtcactagg gcagggacag gataagaggg attagggaga gaagatagca gggcatggct
2761  gggaacccaa gtccaagcat accaacacga ccaggctact gtcagctccc ctcggagaaa
2821  actgtgcagt ctgcgtgtga acagctcttc tcctttagag cacaatggat ctcgagggat
2881  cttccatacc taccagttct gcgcctcgag gccgcgactc taga
```

The atg start and stop codons are bolded and underlined. The amino acid sequence of human CD26, provided by Genbank Accession No. AAA51943.1, is incorporated herein by reference, and is shown below (SEQ ID NO: 218).

```
  1  mktpwkvllg llgaaalvti itvpvvllnk gtddatadsr ktytltdylk ntyrlklysl
 61  rwisdheyly kqennilvfn aeygnssvfl enstfdefgh sindysispd gqfilleyny
121  vkqwrhsyta sydiydlnkr qliteeripn ntqwvtwspv ghklayvwnn diyvkiepnl
181  psyritwtgk ediiyngitd wvyeeevfsa ysalwwspng tflayaqfnd tevplieysf
241  ysdeslqypk tvrvpypkag avnptvkffv vntdslssvt natsiqitap asmligdhyl
301  cdvtwatqer islqwlrriq nysvmdicdy dessgrwncl varqhiemst tgwvgrfrps
361  ephftldgns fykiisneeg yrhicyfqid kkdctfitkg twevigieal tsdylyyisn
421  eykgmpggrn lykiqlsdyt kvtclsceln percqyysvs fskeakyyql rcsgpglply
481  tlhssvndkg lrvlednsal dkmlqnvqmp skkldfiiln etkfwyqmil pphfdkskky
541  pllldvyagp csqkadtvfr lnwatylast eniivasfdg rgsgyqgdki mhainttlgt
601  fevedqieaa rqfskmgfvd nkriaiwgws yggyvtsmvl gsgsgvfkcg iavapvsrwe
661  yydsvytery mglptpednl dhyrnstvms raenfkqvey llihgtaddn vhfqqsaqis
721  kalvdvgvdf qamwytdedh giasstahqh iythmshfik qcfslp
```

The mRNA sequence encoding human SIRT1 provided by Genbank Accession No. JQ768366.1, is incorporated herein by reference, and is shown below (SEQ ID NO: 219).

```
   1  atgattggca cagatcctcg aacaattctt aaagatttat tgccggaaac aatacctcca
  61  cctgagttgg atgatatgac actgtggcag attgttatta atatcctttc agaaccacca
 121  aaaaggaaaa aaagaaaaga tattaataca attgaagatg ctgtgaaatt actgcaagag
 181  tgcaaaaaaa ttatagttct aactggagct ggggtgtctg tttcatgtgg aatacctgac
 241  ttcaggtcaa gggatggtat ttatgctcgc cttgctgtag acttcccaga tcttccagat
 301  cctcaagcga tgtttgatat tgaatatttc agaaaagatc caagaccatt cttcaagttt
 361  gcaaaggaaa tatatcctgg acaattccag ccatctctct gtcacaaatt catagccttg
 421  tcagataagg aaggaaaact acttcgcaac tatacccaga acatagacac gctggaacag
 481  gttgcgggaa tccaaaggat aattcagtgt catggttcct ttgcaacagc atcttgcctg
 541  atttgtaaat acaaagttga ctgtgaagct gtacgaggag ctcttttta g tcaggtagtt
 601  cctcgatgtc ctaggtgccc agctgatgaa ccgcttgcta tcatgaaacc agagattgtg
 661  ttttttggtg aaaatttacc agaacagttt catagagcca tgaagtatga caaagatgaa
 721  gttgacctcc tcattgttat tgggtcttcc ctcaaagtaa gaccagtagc actaattcca
 781  agttccatac cccatgaagt gcctcagata ttaattaata gagaaccttt gcctcatctg
 841  cattttgatg tagagcttct tggagactgt gatgtcataa ttaatgaatt gtgtcatagg
 901  ttaggtggtg aatatgccaa actttgctgt aaccctgtaa agctttcaga aattactgaa
 961  aaacctccac gaacacaaaa agaattggct tatttgtcag agttgccacc cacacctctt
1021  catgtttcag aagactcaag ttcaccagaa agaacttcac caccagattc ttcagtgatt
1081  gtcacacttt tagaccaagc agctaagagt aatgatgatt tagatgtgtc tgaatcaaaa
1141  ggttgtatgg aagaaaaacc acaggaagta caaacttcta ggaatgttga agtattgct
1201  gaacagatgg aaaatccgga tttgaagaat gttggttcta gtactgggga gaaaaatgaa
```

The atg start and stop codons are bolded and underlined.

The amino acid sequence of human SIRT1, provided by Genbank Accession No. JQ768366.1, is incorporated herein by reference, and is shown below (SEQ ID NO: 220).

```
   1  migtdprtil kdllpetipp pelddmtlwq ivinilsepp krkkrkdint iedavkllqe
  61  ckkiivltga gvsvscgipd frsrdgiyar lavdfpdlpd pqamfdieyf rkdprpffkf
 121  akeiypgqfq pslchkfial sdkegkllrn ytqnidtleq vagiqriiqc hgsfatascl
 181  ickykvdcea vrgalfsqvv prcprcpade plaimkpeiv ffgenlpeqf hramkydkde
 241  vdllivigss lkvrpvalip ssiphevpqi linreplphl hfdvellgdc dviinelchr
 301  lggeyaklcc npvklseite kpprtqkela ylselpptpl hvsedssspe rtsppdssvi
 361  vtlldqaaks nddldvsesk gcmeekpqev qtsrnvesia eqmenpdlkn vgsstgekne
```

The mRNA sequence encoding human FoxO3a (forkhead box 03) provided by Genbank Accession No. NM_001455.3, is incorporated herein by reference, and is shown below (SEQ ID NO: 221).

```
   1  gcgcgaggcc gtcgattcgc tcgcggctcc atcgcggcct ggccgggggg cggtgtctgc
  61  tgcgccaggt tcgctggccg cacgtcttca ggtcctcctg ttcctgggag gcgggcgcgg
 121  caggactggg aggtggcggc agcgggcgag gactcgccga ggacggggct ccggcccggg
```

-continued

```
 181  ataaccaact ctccttctct cttctttggt gcttccccag gcggcggcgg cggcgcccgg
 241  gagccggagc cttcgcggcg tccacgtccc tcccccgctg caccccgccc cggcgcgaga
 301  ggagagcgcg agagccccag ccgcgggcgg gcgggcggcg aagatggcag aggcaccggc
 361  ttccccgcc ccgctctctc cgctcgaagt ggagctggac ccggagttcg agcccagag
 421  ccgtccgcga tcctgtacgt ggccctgca aaggccgag ctccaagcga gccctgccaa
 481  gccctcgggg gagacggccg ccgactccat gatccccgag gaggaggacg atgaagacga
 541  cgaggacggc gggggacggg ccggctcggc catggcgatc ggcggcggcg gcgggagcgg
 601  cacgctgggc tccgggctgc tccttgagga ctcggcccgg gtgctggcac ccggagggca
 661  agaccccggg tctgggccag ccaccgcggc gggcgggctg agcgggggta cacaggcgct
 721  gctgcagcct cagcaaccgc tgccaccgcc gcagccgggg gcggctgggg gctccgggca
 781  gccgaggaaa tgttcgtcgc ggcggaacgc ctggggaaac ctgtcctacg cggacctgat
 841  cacccgcgcc atcgagagct ccccggacaa acggctcact ctgtcccaga tctacgagtg
 901  gatggtgcgt tgcgtgccct acttcaagga taagggcgac agcaacagct ctgccggctg
 961  gaagaactcc atccggcaca acctgtcact gcatagtcga ttcatgcggg tccagaatga
1021  gggaactggc aagagctctt ggtggatcat caaccctgat gggggaaga gcggaaaagc
1081  cccccggcgg cgggctgtct ccatggacaa tagcaacaag tataccaaga gccgtggccg
1141  cgcagccaag aagaaggcag ccctgcagac agccccgaa tcagctgacg acagtccctc
1201  ccagctctcc aagtggcctg gcagcccac gtcacgcagc agtgatgagc tggatgcgtg
1261  gacggacttc cgttcacgca ccaattctaa cgccagcaca gtcagtggcc gcctgtcgcc
1321  catcatggca agcacagagt tggatgaagt ccaggacgat gatgcgcctc tctcgcccat
1381  gctctacagc agctcagcca gcctgtcacc ttcagtaagc aagccgtgca cggtggaact
1441  gccacggctg actgatatgg caggcaccat gaatctgaat gatgggctga ctgaaaacct
1501  catggacgac ctgctggata acatcacgct cccgccatcc cagccatcgc ccactggggg
1561  actcatgcag cggagctcta gcttcccgta taccaccaag ggctcgggcc tgggctcccc
1621  aaccagctcc tttaacagca cggtgttcgg accttcatct ctgaactccc tacgccagtc
1681  tcccatgcag accatccaag agaacaagcc agctaccttc tcttccatgt cacactatgg
1741  taaccagaca ctccaggacc tgctcacttc ggactcactt agccacagcg atgtcatgat
1801  gacacagtcg gacccccttga tgtctcaggc cagcaccgct gtgtctgccc agaattcccg
1861  ccggaacgtg atgcttcgca atgatccgat gatgtccttt gctgccagc ctaaccaggg
1921  aagtttggtc aatcagaact tgctccacca ccagcaccaa acccagggcg ctcttggtgg
1981  cagccgtgcc ttgtcgaatt ctgtcagcaa catgggcttg agtgagtcca gcagccttgg
2041  gtcagccaaa caccagcagc agtctcctgt cagccagtct atgcaaaccc tctcggactc
2101  tctctcaggc tcctccttgt actcaactag tgcaaacctg cccgtcatgg gccatgagaa
2161  gttccccagc gacttggacc tggacatgtt caatgggagc ttggaatgtg acatggagtc
2221  cattatccgt agtgaactca tggatgctga tgggttggat tttaactttg attccctcat
2281  ctccacacag aatgttgttg gtttgaacgt ggggaacttc actggtgcta agcaggcctc
2341  atctcagagc tgggtgccag gctgaaggat cactgaggaa ggggaagtgg gcaaagcaga
2401  ccctcaaact gacacaagac ctacagagaa aacccttgc caaatctgct ctcagcaagt
2461  ggacagtgat accgtttaca gcttaacacc tttgtgaatc ccacgccatt ttcctaaccc
2521  agcagagact gttaatggcc ccttaccctg ggtgaagcac ttacccttgg aacagaactc
```

-continued

```
2581  taaaaagtat gcaaaatctt ccttgtacag ggtggtgagc cgcctgccag tggaggacag
2641  caccccctcag caccacccac cctcattcag agcacaccgt gagcccccgt cggccattct
2701  gtggtgtttt aatattgcga tggtttatgg gacgttttaa gtgttgttct tgtgtttgtt
2761  ttcctttgac tttctgagtt tttcacatgc attaacttgc ggtattttttc tgttaaaatg
2821  ttaaccgtcc ttcccctagc aaatttaaaa acagaaagaa aatgttgtac cagttaccat
2881  tccgggttcg agcatcacaa gcttttgagc gcatggaact ccataaacta acaaattaca
2941  taaactaaag ggggattttc tttcttcttt tgtttggtag aaaattatcc ttttctaaaa
3001  actgaacaat ggcacaattg tttgctatgt gcacccgtcc aggacagaac cgtgcatagg
3061  caaaaggagt ggagcacagc gtccggccca gtgtgtttcc ggttctgagt cagggtgatc
3121  tgtggacggg accccagcac caagtctacg ggtgccagat cagtagggcc tgtgatttcc
3181  tgtcagtgtc ctcagctaat gtgaacagtg ttggtctgct ggttagaaac tagaatattg
3241  atattttcag gaaagaaatc agctcagctc tccactcatt gccaaatgtc actaaagggt
3301  ttagttttaa ggagaaagaa aaggaaaaaa aaaaaaaaca aaaaagtcct gttttgctttt
3361  gcagaacaaa tgaacttaca ggtgagcatt aagcttgcag tgagaaatgt gcgaagagta
3421  aaaacccaag tcaatgctga ggcagttcta acttcactgt tttcctaaat acacatcctt
3481  gattatttc agccttgcta tataatctga tctgctagaa gtgtatgagt gagaggcaat
3541  agcatacaaa ctgatttttt aaatataagc ttaggttgta attgtacaag tgactcaatg
3601  gaagtacaaa atagggcagt tttaactttt tttttctgctt ctatggatttt catttttgttg
3661  tgttttcaaa aagttatggt gctgtatagg tgcttttctgt ttaacctgga aagtgtgatt
3721  atattcgtta ccttctttgg tagacggaat agttgggacc acctttggta cataagaaat
3781  tggtataacg atgctctgat tagcacagta tatgcatact tctccaaagt gatatatgaa
3841  gactcttttc tttgcataaa aagcattagg catataaatg tataaatata ttttatcatg
3901  tacagtacaa aaatggaacc ttatgcatgg gccttaggaa tacaggctag tatttcagca
3961  cagacttccc tgcttgagtt cttgctgatg cttgcaccgt gacagtgggc accaacacag
4021  acgtgccacc caaccccctg cacacaccac cggccaccag gggccccctt gtgcgccttg
4081  gctttataac tcctctgggg gtgatattgg tggtgatcac agctcctagc ataatgagag
4141  ttccatttgg tattgtcaca cgtctcctgc ctcgcttggg ttgccatgtt tgagcgatgg
4201  ccctgttgat ttcaccctgc cttttactga atctgtaaat tgttgtgcaa ttgtggttat
4261  agtagactgt agcacattgc cttttctaaa ctgctacatg tttataatct tcatttttaa
4321  agtatgtgta atttttttaa gtatgtattc tattcatatg gtctgcttgt cagtgagcca
4381  gacttgctta ctatattcct ttataataat gctagccact tcctggattc tttagtaatg
4441  tgctgtatgc aagaactttc cagtagcagt gaaggagggt tgcctctcca agcttcctaa
4501  gggatgctgc cctgtgtggg gatgcattgc agaggcacta gtagcatggg ggctagagtg
4561  gggagcgaga tgtaaaaggg tgggggggata ggagaattcc agagtgcttc cagcattagg
4621  gtcctgagaa cttctgagtt cagagaaaca tgcaaagtga ctaacaaaat agctacttac
4681  cttttgcagtt ttacagaccc tgggagctgc tttgggagtg agaaaggcaa ccctccaatg
4741  tgtttcaact ttaaaatgtt gaattctttt cagacatggt atctcattta ttctcctttt
4801  ctagcgtttg ttgaatttca ggcagaatgt cttacagaat gtcctagaac cagattatca
4861  tttaatctga aacagctgag gaagggacag agaaggtaca agggcaaggc agcacaaaac
4921  agatcaggag aatgaagagg gaatgctttg gttttttgtt ttgttttgtt ttttctttt
4981  caagtaacta aaacagcatc tacatgtaga gtgttgtgga gagctgagac cagggtaaag
```

-continued

```
5041  tcaagtgcag catcagtact gcgagaccca ccagcccctg gagagggtca gccgagaatc
5101  tggtagtgaa gcctgtctag ggtcccggca ccctcaccct cagccacctg cagagaggcc
5161  agggccccag agactagcct ggttctgaag tgggcagggg tgctgccaga gccctctgcc
5221  ccttatgttg agaccctgct ttcaggacag gccagccgtt ggccaccatg tcacattctg
5281  agtgagtgtc acaggtccct aacaataatt ttctgatctg gagcatatca gcagaatgct
5341  tagcctcaag gggcctggca gctgtaatgt ttgatttatg atgagaacta tccgaggcca
5401  cccttggcct ctaaataagc tgctctaggg agccgcctac ttttttgatga gaaattagaa
5461  gagtacctaa tgttgaaaac atgacatgcg ctcttgggat ctgctgttct ctccagggct
5521  ccagaacctg atacctgtta ccaaagctag gaaagagctt tatcacaagc cttcactgtc
5581  ctggcatgag aactggctgc caggctcagt gtaccccatt aactgtgaat gaatctgagc
5641  ttggtttcct ttattgcttc ctctgcaata tgattgctga aacacatttt aaaaattcag
5701  aagcttgtca ctcctgttaa tgggaggatc agtcacacat gtgtagtaca aggcggactt
5761  tgtgtttgtt tttggtgtta attttttagca ttgtgtgtgt tgcttcccca ccctgaggag
5821  aggacaccat ggcttactac tcaggacaag tatgccccgc tcagggtgtg atttcaggtg
5881  gcttccaaac ttgtacgcag tttaaagatg gtggggacag actttgcctc tacctagtga
5941  accccactta agaataagg agcatttgaa tctcttggaa aaggccatga agaataaagc
6001  agtcaaaaag aagtcctcca tgttggtgcc aaggacttgc gagggaaat aaaaatgtta
6061  tccagcctga ccaacatgga gaaacccccgt ctccattaaa aatacaaaat tagcctggca
6121  tggtggcgca tgcctgtaat cccagctact ctggaggctg aggcaggaga atcgcttgaa
6181  cccaggaggc ggaggtcgca gtgagccgag atcatgccag tgcactccag cctgggtaac
6241  aagagtgaaa ctccgtgtca aaaaaaaaaa aaaaatgtta ctcatcctct ctgaaagcaa
6301  aaaggaaacc ctaacagctc tgaactctgg ttttatttt cttgctgtat ttgggtgaac
6361  attgtatgat taggcataat gttaaaaaaa aaaattttt tttggtagaa atgcaatcac
6421  cagtaaagag gtacgaaaaa gctagcctct ctcagagacc ggggaggcag agtactacta
6481  gaggaagtga agttctgatg gaatcatgcc tgtcaaatga ggtcttgaag cggatgccca
6541  aataaaagag tatattttat ctaaatctta agtgggtaac attttatgca gtttaaatga
6601  atggaatatt ttcctcttgt ttagttgtat ctgtttgtat ttttctttga tgaatgattg
6661  gtcatgaggc ctcttgccac actccagaaa tacgtgtgcg gctgctttta agaactatgt
6721  gtctggtcac ttatttctct aaaattatct cattgcctgg caatcagtct tctcttgtat
6781  acttgtccta gcacattatg tacatgggaa atgtaaacaa atgtgaagga ggaccagaaa
6841  aattagttaa tatttaaaaa aatgtattgt gcattttggc ttcacatgtt taacttttt
6901  taagaaaaaa gttgcatgaa tggaaaaaaa aatctgtata cagtatctgt aaaaactatc
6961  ttatctgttt caattccttg ctcatatccc atataatcta gaactaaata tggtgtgtgg
7021  ccatatttaa acacctgaga gtcaagcagt tgagactttg atttgaagca cctcatcctt
7081  ctttcaatgc gaacactatc atatggcatt cttactgagg attttgtcta accatatgtt
7141  gccatgaatt aactctgccg cctttcttaa ggatcaaaac cagtttgatt tgggaatctt
7201  ccccttttcca atgaaatag agatgcagta cttaactttc cttggtgttt gtagatattg
7261  ccttgtgtat tccacttaaa accgtaatct agtttgtaaa agagatggtg acgcatgtaa
7321  ataaagcatc agtgacactc t
```

The atg start and stop codons are bolded and underlined. The amino acid sequence of human FoxO3a (forkhead box 03), provided by Genbank Accession No. NP_001446.1, is incorporated herein by reference, and is shown below (SEQ ID NO: 222).

```
                                                          (SEQ ID NO: 222)
  1    maeapaspap lspleveldp efepqsrprs ctwplqrpel qaspakpsge taadsmipee 61    eddeddedgg gragsamaig ggggsgtlgs gllledsarv lapggqdpgs gpataaggls 121    ggtqallqpq qplpppqpga aggsgqprkc ssrrnawgnl syadlitrai esspdkrltl 181    sqiyewmvrc vpyfkdkgds nssagwknsi rhnlslhsrf mrvqnegtgk sswwiinpdg 241    gksgkaprrr aysmdnsnky tksrgraakk kaalqtapes addspsqlsk wpgsptsrss 301    deldawtdfr srtnsnastv sgrlspimas teldevqddd aplspmlyss saslspsvsk 361    pctvelprlt dmagtmnlnd gltenlmddl ldnitlppsq psptgglmqr sssfpyttkg 421    sglgsptssf nstvfgpssl nslrqspmqt iqenkpatfs smshygnqtl qdlltsdsls 481    hsdvmmtqsd plmsqastav saqnsrrnvm lrndpmmsfa aqpnqgslvn qnllhhqhqt 541    qgalggsral snsvsnmgls essslgsakh qqqspvsqsm qtlsdslsgs slystsanlp 601    vmghekfpsd ldldmfngsl ecdmesiirs elmdadgldf nfdslistqn vvglnvgnft 661    gakqassqsw vpg
```

The mRNA sequence encoding human MiR-24 provided by Genbank Accession No. AF480527.1, is incorporated herein by reference, and is shown below (SEQ ID NO: 223).

```
                    (SEQ ID NO: 223)
  1    tggctcagtt cagcaggaac ag
```

The mRNA sequence encoding human MiR-125a-5p (hsa-mir-125a) provided by Genbank Accession No. LM608509.1, is incorporated herein by reference, and is shown below (SEQ ID NO: 224).

```
  1    tgccagtctc taggtccctg agaccctta acctgtgagg acatccaggg tcacaggtga 61    ggttcttggg agcctggcgt ctggcc
```

The mRNA sequence encoding human MiR-203a (MiR-203), provided by Genbank Accession No. NR_029620.1, is incorporated herein by reference, and is shown below (SEQ ID NO: 225).

```
  1    gtgttgggga ctcgcgcgct gggtccagtg gttcttaaca gttcaacagt tctgtagcgc 61    aattgtgaaa tgtttaggac cactagaccc ggcgggcgcg gcgacagcga
```

The mRNA sequence encoding human MiR-140, provided by Genbank Accession No. NR_029681.1, is incorporated herein by reference, and is shown below (SEQ ID NO: 226).

```
  1    tgtgtctctc tctgtgtcct gccagtggtt tacccctatg gtaggttacg tcatgctgtt 61    ctaccacagg gtagaaccac ggacaggata ccggggcacc
```

The mRNA sequence encoding human MiR-27a, provided by Genbank Accession No. NR_029501.1, is incorporated herein by reference, and is shown below (SEQ ID NO: 227).

```
  1   ctgaggagca gggcttagct gcttgtgagc agggtccaca ccaagtcgtg ttcacagtgg 61   ctaagttccg cccccag
```

The mRNA sequence encoding human miR-181a, provided by Genbank Accession No. NR_029611.1 and is shown below (SEQ ID NO: 228).

```
  1   agaagggcta tcaggccagc cttcagagga ctccaaggaa cattcaacgc 51   tgtcggtgag tttgggattt gaaaaaacca ctgaccgttg actgtacctt 101   ggggtcctta
```

The mRNA sequence encoding mouse miR-181a, provided by Genbank Accession No. NR_029568.1, is incorporated herein by reference, and is shown below (SEQ ID NO: 231).

```
  1   ccatggaaca ttcaacgctg tcggtgagtt tgggattcaa aaacaaaaaa 51   accaccgacc gttgactgta ccttgg
```

Formulation and Dosing

In accordance with certain examples, a pharmaceutical composition of the invention is formulated to be compatible with its intended route of administration. For treatment of autoimmune disease, administration of cargo-loaded nanopieces (complexes) is carried out by systemic administration, e.g., intravenously. In some examples, the compositions may be administered by injection or infusion into a localized tissue site, e.g., into an articulating joint or by inhalation, transdermally, orally, rectally, transmucosally, intestinally, parenterally, intramuscularly, intra-articularly, subcutaneously, intravenously or other suitable methods that will be readily selected by the person of ordinary skill in the art, given the benefit of this disclosure. For example, solutions or suspensions used for parenteral, intradermal, intra-articular, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as ethylenediamine tetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral and/or intra-articular preparation can be enclosed in ampules, disposable syringes or multiple dose vials made of glass or plastic.

A biologically acceptable medium includes, but is not limited to, any and all solvents, dispersion media, and the like which may be appropriate for the desired route of administration of the complexes of the present disclosure. The use of such media for pharmaceutically active substances is known in the art. Except insofar as any conventional media or agent is incompatible with the activity of the small molecule, protein, polypeptide and/or peptide, its use in the pharmaceutical preparation of the invention is contemplated. Suitable vehicles and formulations are described, for example, in the book *Remington's Pharmaceutical Sciences* (Remington's Pharmaceutical Sciences. Mack Publishing Company, Easton, Pa., USA 1985). These vehicles include injectable formulations.

The complexes of the present invention may be administered by any suitable route. For example, a pharmaceutical preparation may be administered in tablets or capsules, by injection, by infusion, by inhalation, topically (e.g., by lotion or ointment), by suppository, by controlled release patch, or the like.

The complexes described herein may be administered to an individual (e.g., a human or animal such as a non-human primate) for therapy by any suitable route of administration, including intravenously, orally, nasally, rectally, intravaginally, parenterally, intra-articularly, intracisternally, topically, buccally, sublingually, epidurally and the like. Intra-articular administration is useful for local treatment of disease and flare-up, e.g. pain in joints, synovitis and the like.

Regardless of the route of administration selected, the pharmaceutical compositions of the present invention are formulated into pharmaceutically acceptable dosage forms such as described below or by other conventional methods known to those of skill in the art. Actual dosage levels of the pharmaceutical compositions described herein may be varied so as to obtain an amount of the compound which is effective to achieve the desired therapeutic response for a particular patient, composition, and mode of administration, without being toxic to the patient.

Joint disease is treated using the complexes or compositions described herein. For example, methods are provided for treating a patient having a joint disease, by administering to the patient a therapeutically effective amount of a complex or composition of the present invention. For in vivo therapies based on local injection (e.g., intratumoral, intraarticularly, intramuscularly, into the peritoneal cavity, and aerosolized treatments) the RNT/small RNA complex is advantageously water soluble and so may be administered as an aqueous injection.

Figure 66:
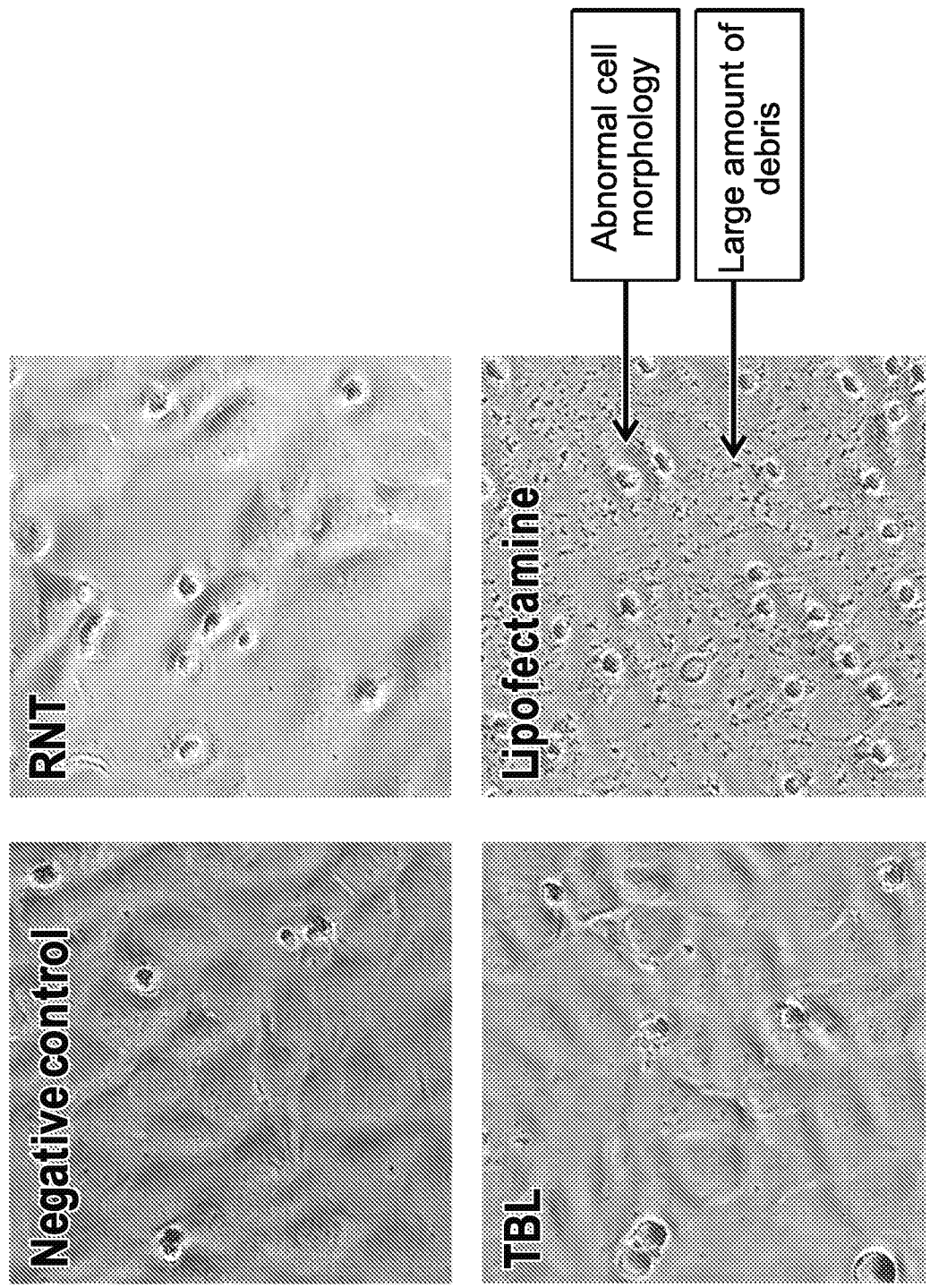
FIG. 66 is a series of images showing that cells with Nanopiece (RNT or TBL) delivery maintain normal cell morphology, indicating excellent biocompatibility of Nanopiece; while delivery with lipid-based vehicles led to abnormal cell morphology and large amount of debris, suggesting cyto-toxicity of lipid-based vehicles.

The selected dosage level will depend upon a variety of factors including the activity of a particular compound or ester, salt or amide thereof, the route of administration, the time of administration, the rate of excretion of the particular compound being employed, the duration of the treatment, other drugs, compounds and/or materials used in combination with the particular complex employed, the age, sex, weight, condition, general health and prior medical history of the patient being treated, and like factors well known in the medical arts. A physician, veterinarian or research scientist having ordinary skill in the art can readily determine and prescribe the effective amount of the pharmaceutical composition required. For example, the physician, veterinarian or research scientist could start doses of the compounds of the invention employed in the pharmaceutical composition at levels lower than that required in order to achieve the desired therapeutic effect and gradually increase the dosage until the desired effect is achieved. Furthermore, different delivery materials are used to administer different doses and dose ranges. For example, Nanopieces demonstrate good biocompatibility and low toxicity. Previous studies have demonstrated no significant toxicity with an administration of 25 μg delivery nanotubes (RNTs) in vivo (Journeay W S, et al. Int J Nanomedicine. 2008; 3(3):373-83). Even with a 50 μg dose, inflammation that resulted from RNTs was resolved after 7 days. In comparison, some conventional delivery materials such as carbon nanotubes, can cause inflammation at much lower doses the resulting in inflammation that can last for two months. In the current system, a 5 μg dose of RNT in Nanopiece was effective in the delivery of cargo. Therefore, the effective doses of RNT Nanopieces are significantly lower than their toxic doses, providing a good therapeutic index. Moreover, RNTs or TBLs showed a lower toxicity than lipid-based delivery vehicles. In FIG. 66, ATDC5 cells were cultured with no additives (negative control), Nanopieces of 0.1 nmol non-targeting siRNA with 10 μg of RNT, Nanopieces of 0.1 nmol non-targeting siRNA with 2.5 μg TBL, or 0.1 nmol non-targeting siRNA with 6 μg Lipofectamine 2000. After 24 hours, ATDC5 cells cultured with Lipofectamine 2000 showed abnormal cell morphology and large amount of cell debris, however, cells cultured with either RNT nanopiece or TBL nanopiece presented normal morphology as the negative control.

In general, a suitable daily dose of a compound of the invention will be that amount of the compound which is the lowest dose effective to produce a therapeutic effect. Such an effective dose will generally depend upon the factors described above. Generally, doses of the compounds of this invention for a patient will range from about 0.0001 to about 100 mg per kilogram of body weight per day, or from about 0.001 to 30 mg/kg body weight, from about 0.01 to 25 mg/kg body weight, from about 0.1 to 20 mg/kg body weight, from about 1 to 10 mg/kg, from about 2 to 9 mg/kg, from about 3 to 8 mg/kg, from about 4 to 7 mg/kg, or from about 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of biologically active agent can include a single treatment or, preferably, can include a series of treatments. It will also be appreciated that the effective dosage for treatment may increase or decrease over the course of a particular treatment. Changes in dosage may result from the results of diagnostic assays.

If desired, the effective daily dose of the active compound may be administered as one, two, three, four, five, six or more sub-doses administered separately at appropriate intervals throughout the day, optionally, in unit dosage forms. In certain embodiments, an effective dose is given every other day, twice a week, once a week or once a month.

A complex of the invention can be administered as such or in admixtures with pharmaceutically acceptable carriers and can also be administered in conjunction with other antimicrobial agents such as penicillin, cephalosporin, aminoglycosides, glycopeptides and the like. Conjunctive therapy includes sequential, simultaneous and separate administration of an active compound in such a way that the therapeutic effects of the first administered compound are still present when a subsequent administration is performed.

Another aspect of the present disclosure provides pharmaceutically acceptable compositions comprising a therapeutically effective amount of one or more of the complexes described herein, formulated together with one or more pharmaceutically acceptable carriers (additives) and/or diluents. As described in detail below, the pharmaceutical compositions of the present disclosure may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection or intraarticularly as, for example, a sterile solution or suspension; (3) topical application, for example, as a cream, ointment or spray applied to the skin; or (4) intravaginally or intrarectally, for example, as a pessary, cream or foam. However, in certain embodiments the subject complexes may be simply dissolved or suspended in sterile water.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in compositions of the present invention.

Examples of pharmaceutically acceptable antioxidants include but are not limited to: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention may conveniently be presented in unit dosage form and may be prepared by any methods well known in the pharmaceutical art. The amount of active ingredient which can be combined with a carrier material to produce a single dosage form will vary depending upon the individual being treated and the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, from about 5 percent to about 70 percent, from about 10 percent to about 30 percent, from about 15 percent to about 25 percent, or from about 18 percent to about 22 percent. In an alternative embodiment, compounds of the present invention can be administered per se, e.g., in the absence of carrier material.

Methods of preparing the formulations or compositions of the present invention include the step of associating a complex described herein with a carrier and, optionally, one or more accessory ingredients. In general, the formulations are prepared by uniformly associating a complex of the present invention with liquid carriers, finely divided solid carriers, or both, and, optionally, shaping the product.

Formulations suitable for oral administration may be in the form of capsules, cachets, pills, tablets, lozenges (using a flavored basis, such as sucrose and acacia or tragacanth), powders, granules, as a solution or a suspension in an aqueous or non-aqueous liquid, as an oil-in-water or water-in-oil liquid emulsion, as an elixir or syrup, as pastilles (using an inert base, such as gelatin and glycerin, or sucrose and acacia) and/or as mouth washes and the like, each containing a predetermined amount of a complex of the present invention as an active ingredient. A complex of the present invention may also be administered as a bolus, electuary or paste.

Ointments, pastes, creams and gels may contain, in addition to a complex of the present disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a complex of the present disclosure, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a complex of the present invention to the body. Such dosage forms can be made by dissolving or dispersing the complex in the proper medium. Absorption enhancers can also be used to increase the flux of the complex across the skin. The rate of such flux can be controlled by either providing a rate controlling membrane or dispersing the complex in a polymer matrix or gel.

Pharmaceutical compositions of this invention suitable for parenteral administration comprise one or more complexes of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol asorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Injectable depot forms are made by forming microencapsule matrices of the complexes in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly (anhydrides). Depot injectable formulations are also prepared by entrapping the drug in liposomes or microemulsions which are compatible with body tissue.

In accordance with certain examples, complexes of the present invention can be incorporated into pharmaceutical compositions suitable for administration. Such compositions typically comprise the complexes disclosed here and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In accordance with certain examples, a pharmaceutical composition of the invention is formulated to be compatible with its intended route of administration. Such pharmaceutical compositions may be administered by inhalation, intraarticularly, transdermally, orally, rectally, transmucosally, intestinally, parenterally, intramuscularly, subcutaneously, intravenously or other suitable methods that will be readily selected by the person of ordinary skill in the art, given the benefit of this disclosure. For example, solutions or suspensions used for parenteral, intraarticularly, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

The present disclosure is directed to methods of forming a delivery complex, for example, by mixing one or more agents with fully formed rosette nanotubes or modules that self-assemble into rosette nanotubes, such as the compounds of Formula I or Formula II. According to one aspect, fully formed rosette nanotubes in the form of a powder is dissolved in water and heated to boiling. The solution is then cooled to room temperature. One or more agents is then added to the solution of nanotubes at a suitable temperature and for a suitable period of time until a complex of the nanotube and one or more agents forms. Suitable ratios of the nucleic acid to nanotube include about 0.01:1 (wt/wt) to about 1:0.1 (wt/wt).

Definitions

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclicf) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. Likewise, preferred cycloalkyls have from 3-10 carbon atoms in their ring structure, and more preferably have 5, 6 or 7 carbons in the ring structure. The ranges provided above are inclusive of all values between the minimum value and the maximum value.

The term "alkyl" includes both "unsubstituted alkyls" and "substituted alkyls", the latter of which refers to alkyl moieties having one or more substituents replacing hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amino, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The alkyl groups may also contain one or more heteroatoms within the carbon backbone. Preferably the heteroatoms incorporated into the carbon backbone are oxygen, nitrogen, sulfur, and combinations thereof. In certain embodiments, the alkyl group contains between one and four heteroatoms.

"Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

"Halogen", as used herein, refers to fluorine, chlorine, bromine, or iodine.

The term "optionally substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aryloxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

The term "amino acid" is inclusive of the 20 common amino acids, as well as "nonstandard amino acids," for example, D-amino acids and chemically (or biologically) produced derivatives of "common" amino acids, including for example, β-amino acids. Accordingly, amino acids according to the present disclosure include the commonly known amino acids such as glycine (Gly, G), alanine (Ala, A), valine (Val, V), leucine (Leu, L), isoleucine (Ile, I), proline (Pro, P), hydroxyproline, phenylalanine (Phe, F), tyrosine (Tyr, Y), tryptophan (Trp, W) cysteine (Cys, C), methionine (Met, M) serine (Ser, S), o-phosphoserine, threonine (Thr, T), lysine (Lys, K), arginine (Arg, R), histidine (His, H), aspartate (Asp, D), glutamate (Glu, E), γ-carboxyglutamate, asparagine (Asn, N), glutamine (Gln, Q) and the like. Amino acids also include stereoisomers thereof and compounds structurally similar to the amino acids or modifications or derivatives thereof. Exemplary amino acids within the scope of the present disclosure include lysine, arginine, serine, glycine, aspartate and the like. The amino acids of the present disclosure are modified only at their terminal amine group.

Aminoe acids are composed of amine (—$NH_2$) and carboxylic acid (—COOH) functional groups, along with a side-chain specific to each amino acid. The key elements of an amino acid are carbon, hydrogen, oxygen, and nitrogen, though other elements are found in the side-chains of certain amino acids.

In the structure shown below, Z represents a side-chain specific to each amino acid. The carbon atom next to the carboxyl group (which is therefore numbered 2 in the carbon chain starting from that functional group) is called the α-carbon. Amino acids containing an amino group bonded directly to the alpha carbon are referred to as alpha amino acids.

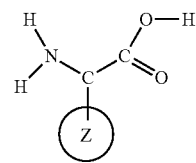

Figure 69:
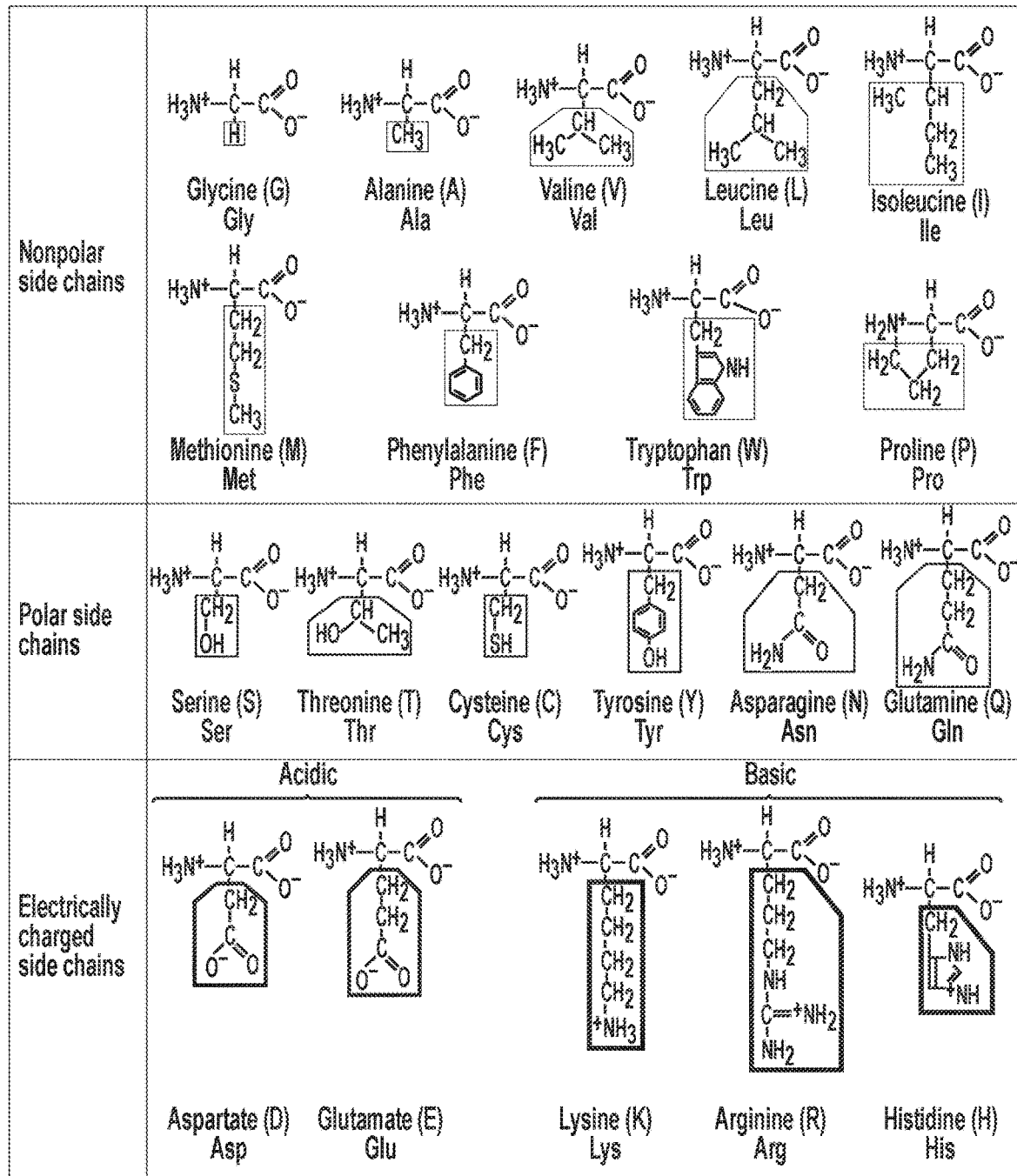
FIG. 69 shows amino acids containing hydrophilic side chains, hydrophobic side chains, and electrically charged side chains, respectively.
Figure 70:
FIG. 70 is a schematic showing a strategy for RNA therapeutics delivery.
Figure 72:
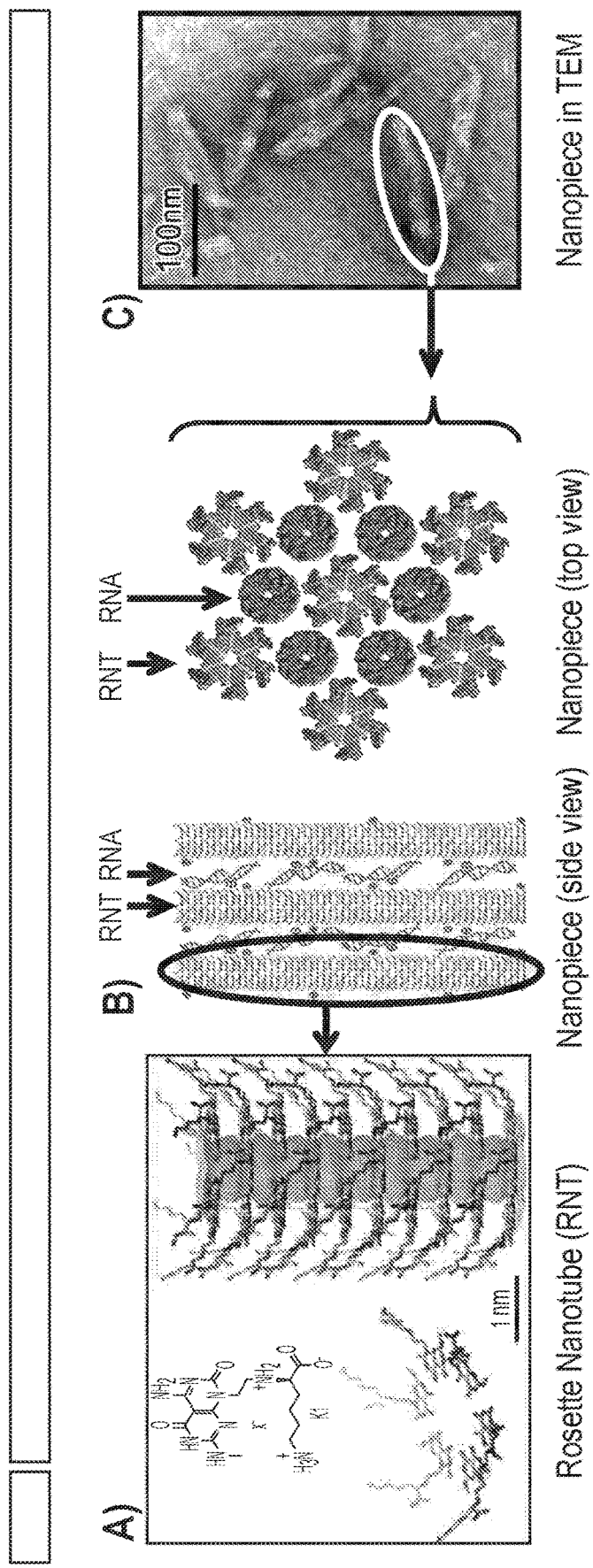
FIG. 72 is a schematic showing a $NP^{JAK1/RNA}$ assembly and property.
Figure 74:
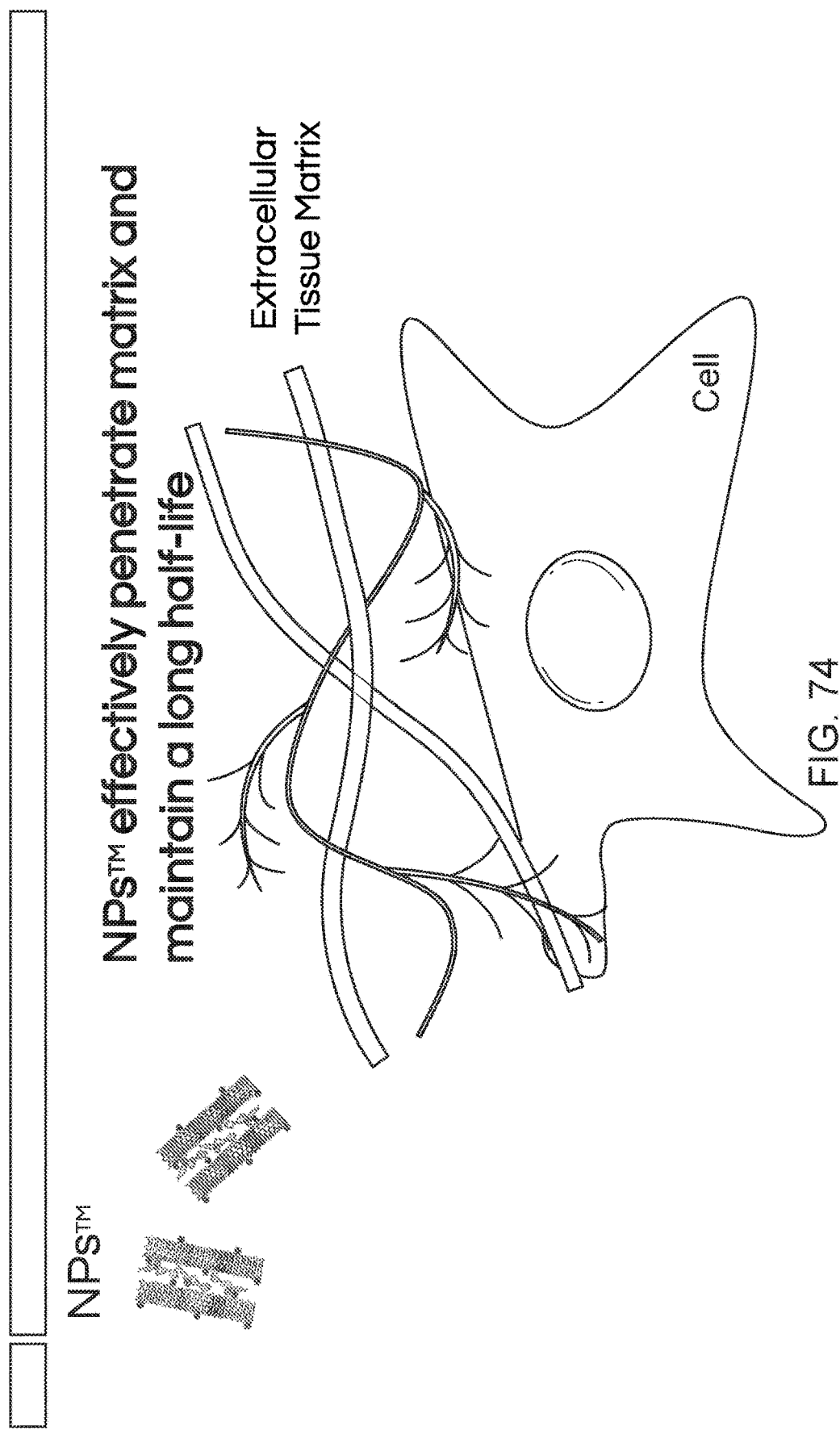
FIG. 74 is a schematic showing a Nanopiece™ tissue penetration.
Figure 75:
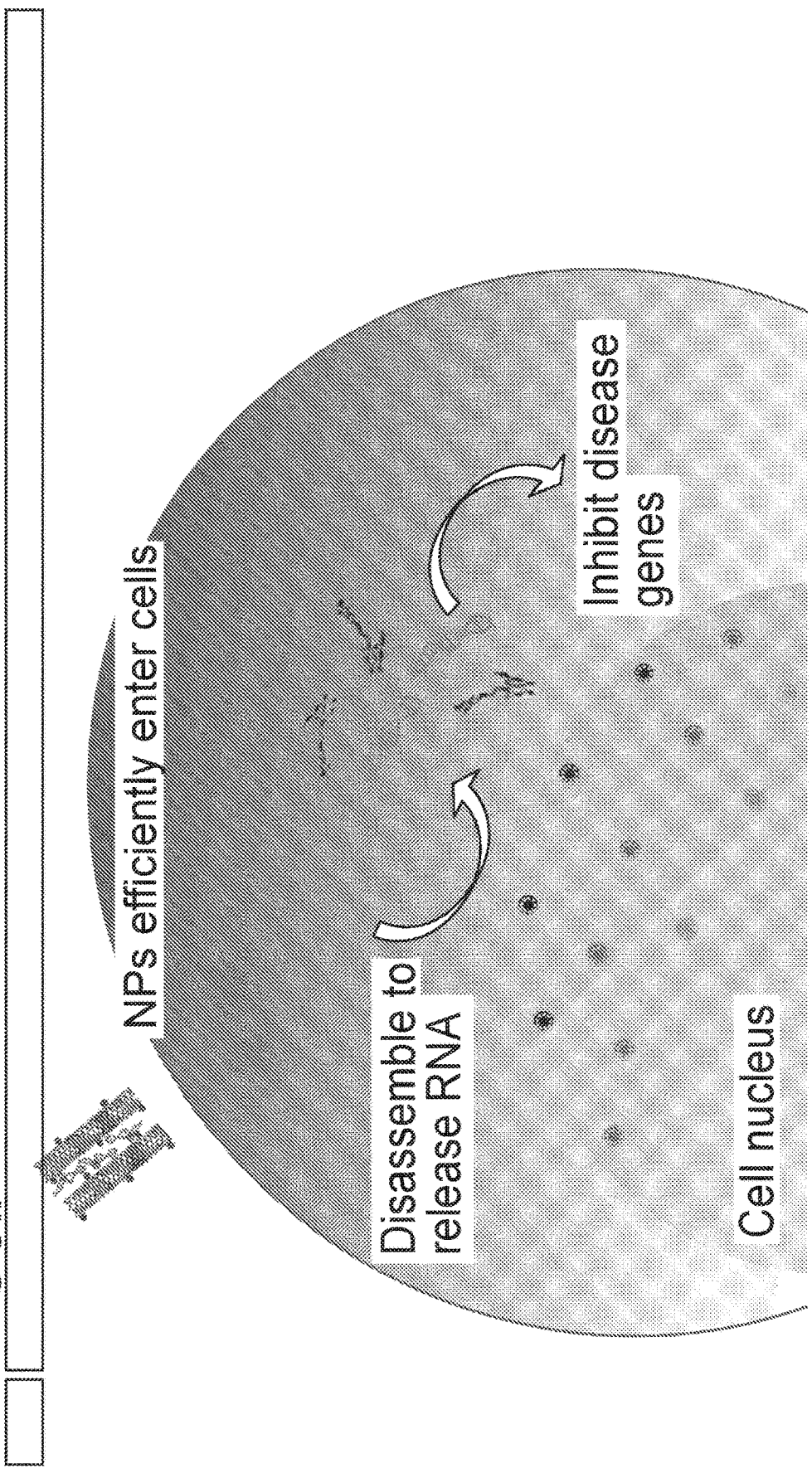
FIG. 75 is a schematic showing a Nanopiece™ target delivery within cell.
Figure 76:
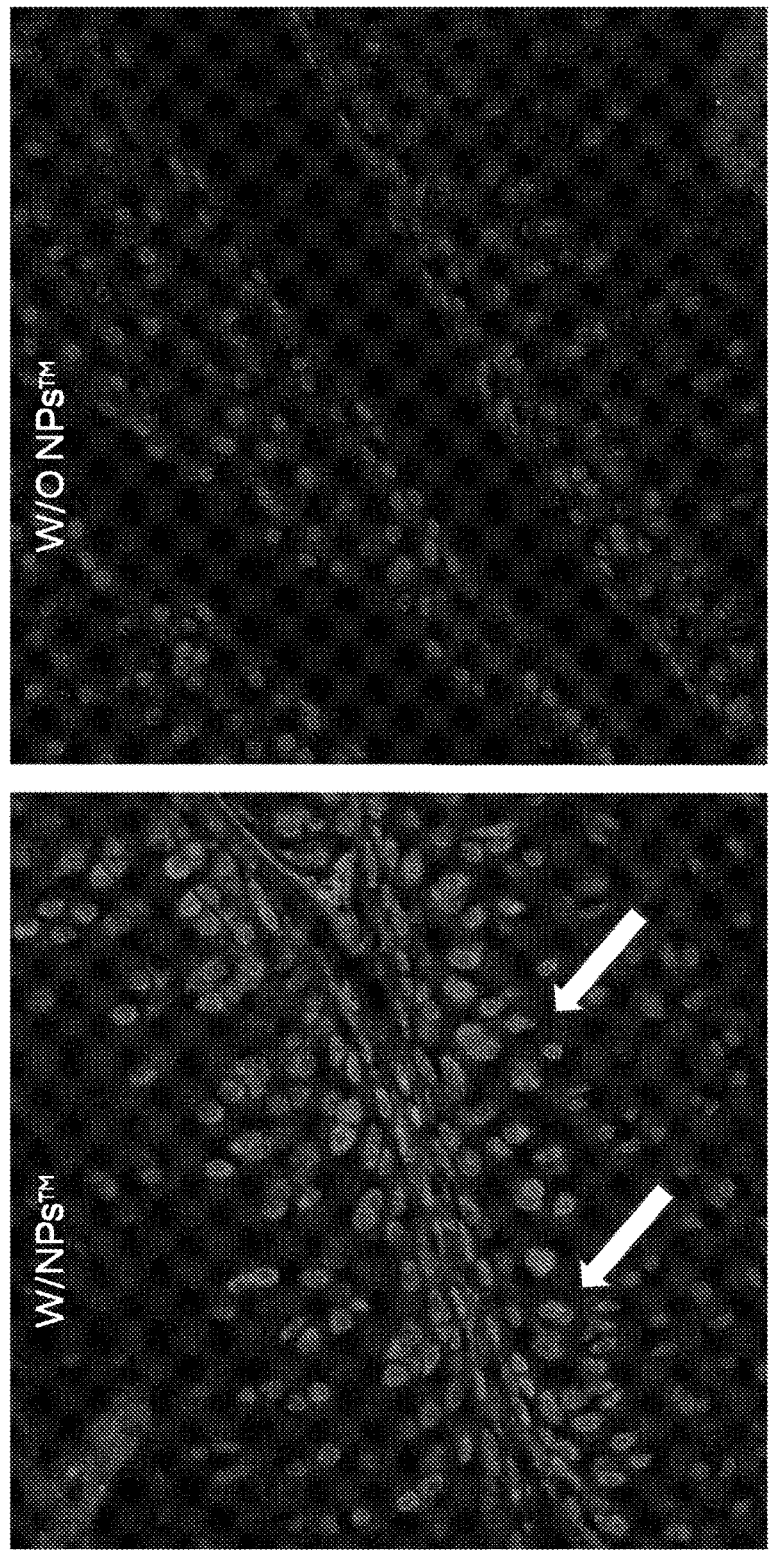
FIG. 76 is a schematic showing targeted in vivo delivery.
Figure 78:
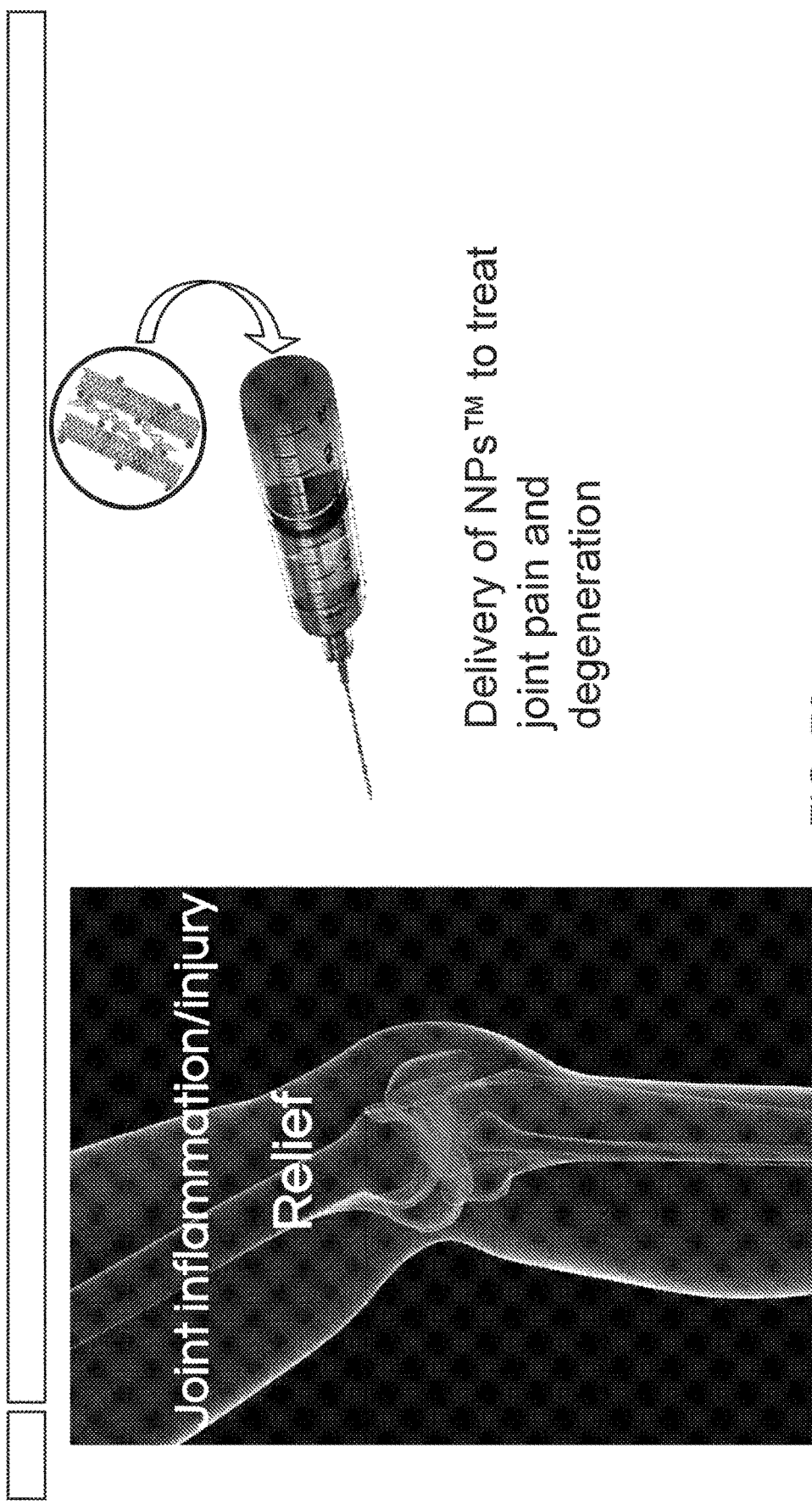
FIG. 78 is a schematic showing a therapeutic strategy for PTJI.
Figure 80:
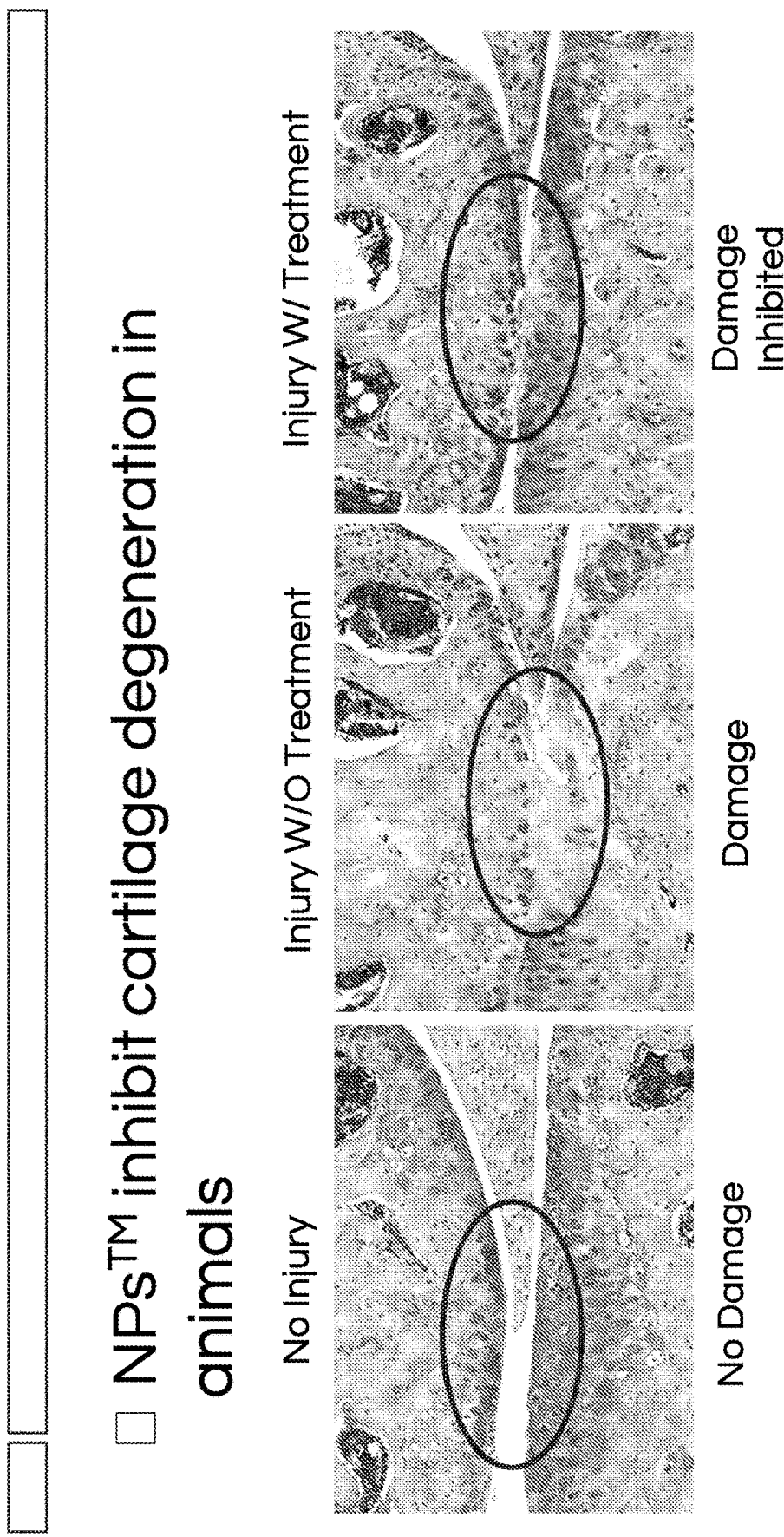
FIG. 80 is a schematic showing that a Nanopiece™ inhibits cartilage degeneration.
Figure 84:
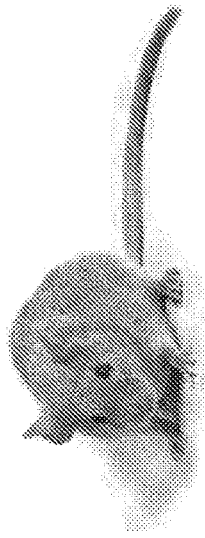
FIG. 84 is a schematic showing a therapeutic approach using siRNA and inhibition of TNF-α gene expression.
Figure 85:
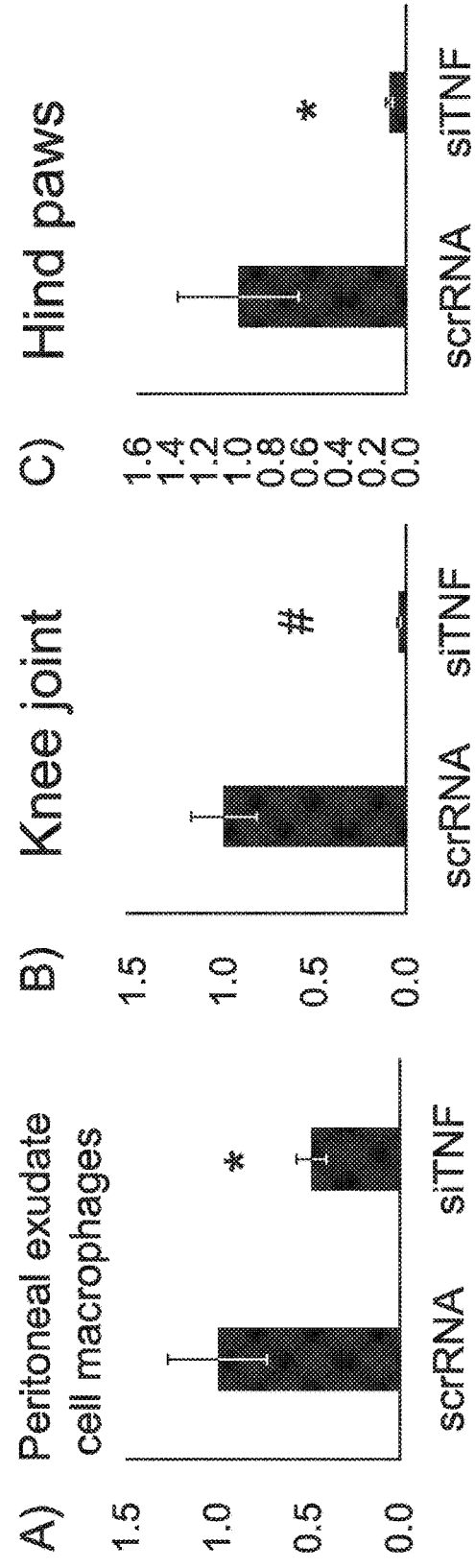
FIG. 85 is a series of bar graphs showing that TNF-α siRNA (SiTNF)/nanopiece (NP) treatment inhibits TNF-α mRNA levels in CIA mice.
Figure 86:
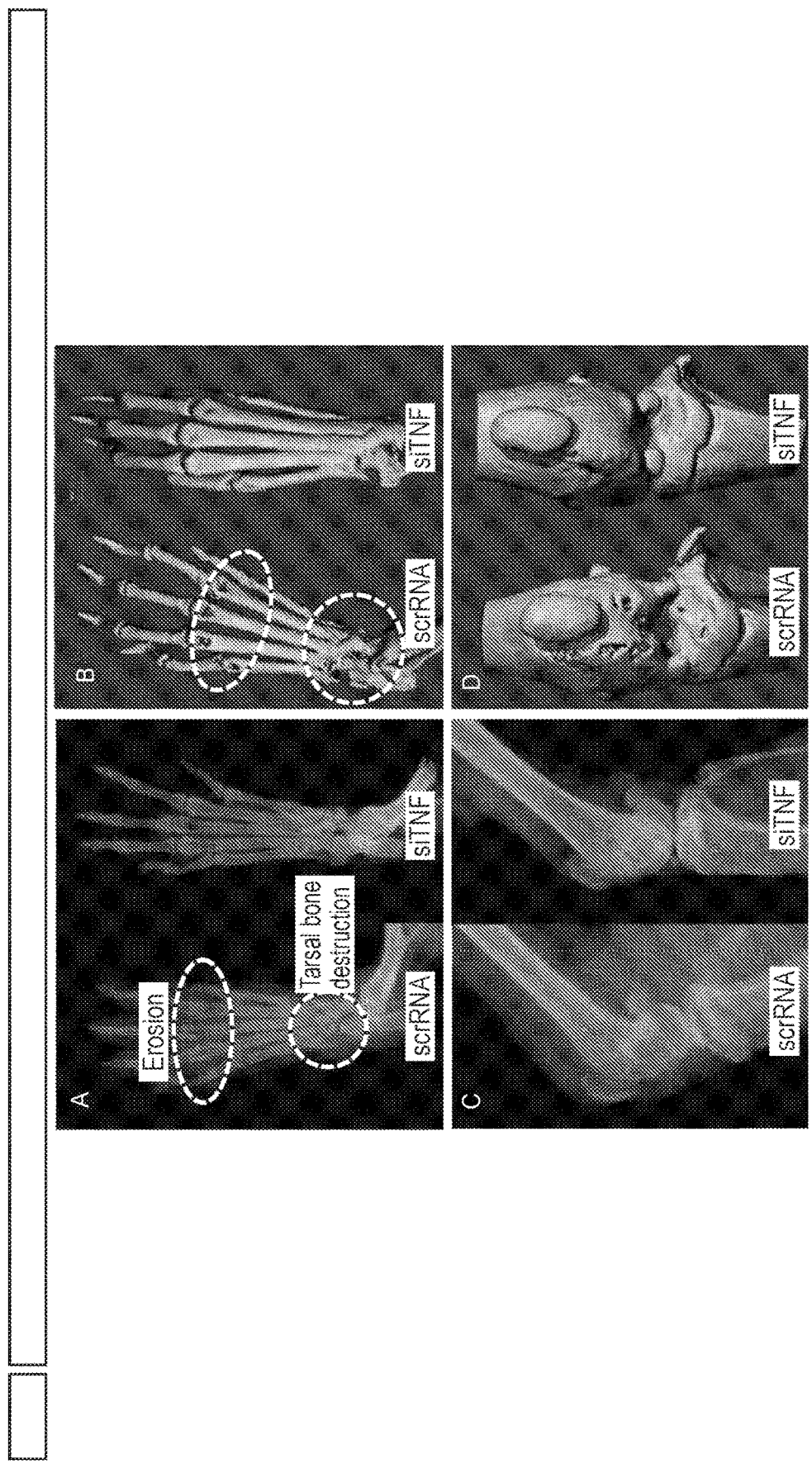
FIG. 86 is a series of photographs showing that SiTNF/NP treatment inhibits bone erosions and destruction in CIA mice.

Amino acids can be divided into amino acid containing hydrophilic side chains, hydrophobic side chains, and electrically charged side chains. See FIG. 69, wherein the side chains are shaded.

The term "peptide" is inclusive of both straight and branched amino acid chains, as well as cyclic amino acid chains, which comprise at least 2 amino acid residues. The terms "peptide" and "polypeptide" are used interchangeably herein. Accordingly, polypeptides according to the present disclosure include two or more amino acids covalently linked together. According to one aspect, the two or more amino acids are covalently linked together at least in part by one or more peptide bonds. The polypeptides of the present disclosure are modified only at their terminal amine group. For example, the peptide or fragment of a full-length protein comprises 2, 5, 10, 50, 100, 200, 500 600, 700, 750, 800, 900, 1000 or more amino acids in length or up to the full length of a reference protein.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the invention may comprise natural nucleic acid sequences and variants thereof, artificial nucleic acid sequences, or a combination of such sequences. As used herein, one of skill in the art will understand that the term "nucleic acid probe" includes probes known as molecular beacons which include synthetic oligonucleotide hybridization probes that can report the presence of specific nucleic acids in homogenous solutions or in cells. Species of molecular beacons include hairpin shaped molecules with a detectable marker such as an internally quenched fluorophore whose fluorescence is restored when they bind to a target nucleic acid sequence. Technically, molecular beacons can be designed to target any gene and can be linked with fluorescent molecules of different fluorescence wavelengths.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Examples of modified nucleotides include, but are not limited to 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety, sugar moiety or phosphate backbone.

The term "small RNA" is used as it is in the art, and includes a duplex of RNA (30 bases or less in each strand) that targets mRNA. Small RNA may be chemically or enzymatically synthesized. Small RNA in accordance with the present invention may be incorporated and then activated in RISC (RNA-induced silencing complex).

A "therapeutically effective amount" is an amount necessary to prevent, delay or reduce the severity of the onset of disease, or an amount necessary to arrest or reduce the severity of an ongoing disease, and also includes an amount necessary to enhance normal physiological functioning.

The word "transfect" is broadly used herein to refer to introduction of an exogenous compound, such as a polynucleotide sequence, into a prokaryotic or eukaryotic cell; the term includes, without limitation, introduction of an exogenous nucleic acid into a cell, which may result in a permanent or temporary alteration of genotype in an immortal or non-immortal cell line. Accordingly, embodiments of the present disclosure include the introduction of a polynucleotide sequence to either be expressed or to inhibit expression of a target gene.

As may be used herein, the terms "drug," biologically active agent," and "therapeutic agent" are used interchangeably and are intended to include, but are not limited to, those compounds recognized by persons of skill in the art as being biologically active agents, or drugs or therapeutic agents and include any synthetic or natural element or compound which when introduced into the body causes a desired biological response, such as altering body function.

As used herein, the terms "parenteral administration" and "administered parenterally" are intended to include, but are not limited to, modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal injection, intrasternal injection, infusion and the like.

As used herein, the terms "systemic administration," "administered systemically," "peripheral administration" and "administered peripherally" are intended to include, but are not limited to, the administration of a compound, drug or other material other than directly into the central nervous system, such that it enters an individual's system and, thus, is subject to metabolism and other like processes, such as, for example, subcutaneous administration.

The term "treatment," as used herein, is intended to include, but is not limited to, prophylaxis, therapy and cure. A patient or individual receiving treatment is any animal in need, such as humans, non-human primates, and other mammals such as horses, camels, cattle, swine, sheep, poultry, goats, rabbits, mice, guinea pigs, dogs, cats and the like.

As used herein, the term "therapeutically effective amount" is intended to include, but is not limited to, an amount of a compound, material, or composition comprising a complex of the present invention which is effective for producing a desired therapeutic effect in at least a subpopulation of cells in an animal and thereby altering (e.g., reducing or increasing) the biological consequences of one or more pathways in the treated cells, at a reasonable benefit/risk ratio.

As used herein, the term "pharmaceutically acceptable" is intended to include, but is not limited to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, a "pharmaceutically acceptable agent" (such as a salt, carrier, excipient or diluent) is a component which (1) is compatible with the RNT/small RNA composites in that it can be included in the delivery composition without eliminating the capacity of the RNT/small RNA composites to transfect cells and deliver small RNA; and (2) where the delivery composition is intended for therapeutic uses, is suitable for use with an animal (e.g., a human) without undue adverse side effects, such as toxicity, irritation, and allergic response. Side effects are "undue" when their risk outweighs the benefit provided by the pharmaceutical agent.

As used herein, the term "pharmaceutically acceptable carrier" is intended to include, but is not limited to, a pharmaceutically acceptable material, composition or vehicle, such as a liquid or solid filler, diluent, excipient, solvent or encapsulating material, involved in carrying or transporting the complexes of the present disclosure from one organ, or portion of the body, to another organ, or portion of the body. Each carrier must be "acceptable" in the sense of being compatible with the other ingredients of the formulation and not unduly dangerous to the patient. Examples of materials which can serve as pharmaceutically acceptable carriers include but are not limited to: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations, which could easily be determined by one of skill in the art.

Chemical compounds, polynucleotides, polypeptides, and oligosaccharides of the invention are purified and/or isolated. Purified defines a degree of sterility that is safe for administration to a human subject, e.g., lacking infectious or toxic agents. Specifically, as used herein, an "isolated" or "purified" compound, nucleic acid molecule, polynucleotide, polypeptide, protein or oligosaccharide, is substantially free of other cellular material, or culture medium when produced by recombinant techniques, or chemical precursors or other chemicals when chemically synthesized. For example, purified compositions are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, thin layer chromatography, or high-performance liquid chromatography (HPLC) analysis. For example, a purified compound refers to a one that has been separated from other proteins, lipids, and nucleic acids with which it is naturally associated. Preferably, the compound constitutes at least 10, 20, 50, 70, 80, 90, 95, 99-100% by dry weight of the purified preparation.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) or polypeptide is free of the amino acid sequences or nucleic acid sequences that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which, in the naturally-occurring genome of the organism from which the DNA of the invention is derived, flank the gene. For example, the purified or isolated nucleic acid is a siRNA. The term covers, e.g., (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically as well as any nucleic acids that have been altered chemically and/or that have modified backbones.

A small interfering RNA (siRNA), also known as short interfering RNA or silencing RNA, is a class of double-stranded RNA molecules, 20-25 base pairs in length, similar to miRNA, and operating within the RNA interference (RNAi) pathway. It interferes with the expression of specific genes with complementary nucleotide sequences by degrading mRNA after transcription, preventing translation. They are produced from dsRNA or hairpin looped RNA which, after entering a cell is split by an RNase III-like enzyme, called Dicer, using RNase or restriction enzymes. The siRNA may then incorporated into a multi-subunit protein complex called RNAi-induced silencing complex (RISC).

As used therein, the term "patient" is intended to include a mammal suffering from a disease. Such a mammal can be a human or another animal such as a companion animal (e.g., dog or cat) or a performance animal or livestock animal (e.g., an equine, bovine, porcine animal).

EXAMPLES

The following examples are specific embodiments of the present invention but are not intended to limit it.

Example 1

Nanopieces that include RNTs and exemplary cargo or payload compounds were manufactured. Cargo agents assemble with RNTs into Nanopieces. Then, taking siRNA Nanopiece as an example, it was demonstrated that Nanopieces can be intentionally processed into different sizes and charge for matrix penetration, e.g. preferential delivery of the cargo to specific tissue types. For example, Nanopieces with a net positive charge were made to deliver payload compounds to negatively charged tissue such as cartilage.

The relation between RNT/siRNA ratio and surface charge was evaluated. Selecting the ratio to result in a net positive charge on Nanopieces, Nanopieces have better binding and longer retention time on negatively charged tissue matrix (e.g., human articular cartilage).

For in vitro and in vivo delivery studies, cartilage was used as an example, because cartilage is an avascular tissue with high matrix component, which is a challenging tissue for drug delivery. Other target matrix and/or tissue can be used and the net charge of the Nanopiece tuned for preferential targeting to a selected tissue. It was shown that the processed Nanopieces were efficiently delivered into cartilage matrix from various species, as well as inside chondrocytes. The delivered Nanopieces were fully functional. A composite of polyethylene glycol (PEG) was used to increase Nanopiece delivery efficiency in a protein-rich environment (such as serum). Rat and mouse models showed that the processed Nanopieces successfully achieved trans-matrix and/or tissue delivery in vivo.

For diagnostics, MMP-13 molecular beacons for disease gene detection were co-delivered with non-targeting scrambled molecular beacons as a non-specific signal negative control and GAPDH molecular beacons as an internal house-keeping gene control. Fluorescence signal was accurately translated into gene expression level exemplary of a non-invasive approach to detect real-time, in-situ gene expression in living animals.

For therapeutics, cytokine (IL-1β) was used to stimulate cartilage degeneration mimicking arthritis, especially rheumatoid arthritis. With Nanopiece delivery of IL-1 receptor siRNA, IL-1 receptor expression was knocked down in chondrocytes in mouse cartilage in vivo, so that cartilage degeneration genes (such as MMP-13, MMP-9) were down-regulated and cartilage anabolic genes (such as Col II) were up-regulated.

Nanopieces were used to deliver ADAMTS-5 siRNA into knee joints of mice with cytokine (IL-1α and retinoic acid) stimulation. Cartilage degeneration was significantly inhibited. To mimic osteoarthritis progression, destabilization of medial meniscus (DMM) was conducted on knee joints of mice. With Nanopiece delivery of ADAMTS-5 siRNA, osteoarthritis progression was prevented. These data indicate the Nanopieces are useful to prevent and/or inhibit cartilage degeneration and arthritis progression.

Example 2

Successful assembly of RNTs into Nanopieces was shown, (see ARROWS) and they were used to deliver various types of cargo reagents including small nucleic acids (siRNA, FIG. 1), long nucleic acids (plasmid DNA, FIG. 2), peptide or protein (Matrilin-3, FIG. 3) as well as small molecules.

Example 2.1

Nanopieces containing SiRNA as cargo were manufactured as follows. 24, of a 50 μM siRNA solution was mixed with 10 μL of a 1 mg/mL RNTs mixture. The resulting mixture was sonicated for 60 s. Dilution factors can range from 1 to 504, for preparing the siRNA-RNTs complex mixture and sonication times of the resulting mixture can vary from 1 to 600 s. Results are shown in FIG. 1.

Example 2.2

Figure 2:
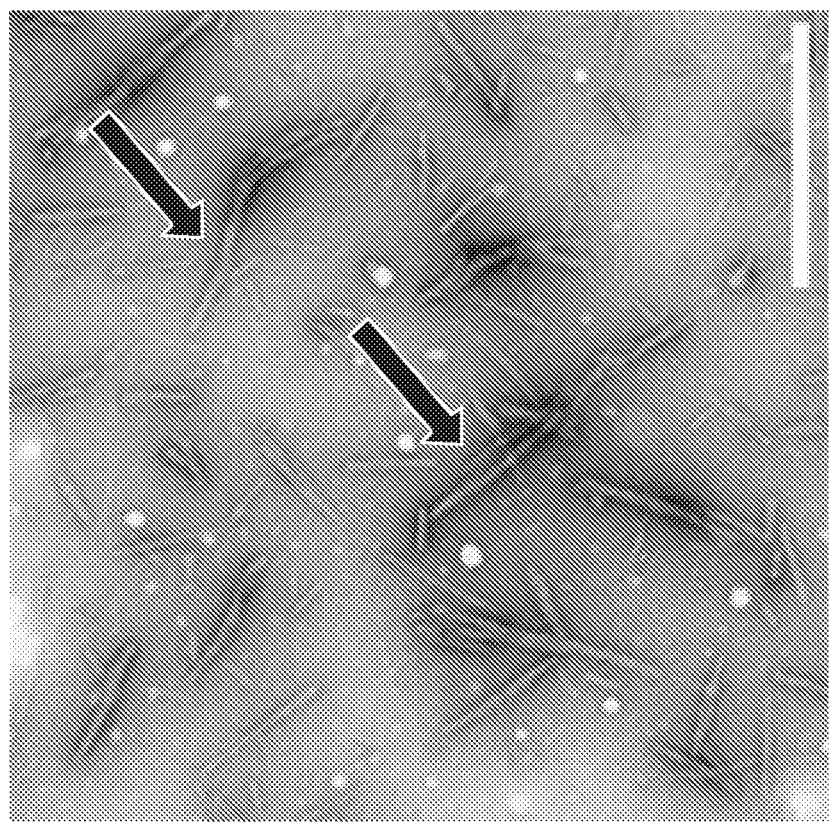
FIG. 2 is an illustration showing an assembly between RNTs with plasmid DNA.

Nanopieces containing DNA were manufactured as follows. 0.5 μg DNA was mixed with 104, of a 1 mg/mL RNTs solution. The resulting mixture was sonicated for 60 s. Dilution factors can range from 1 to 504, for preparing the DNA-RNTs complex mixture and sonication times of the resulting mixture can vary from 1 to 600 s. Results are shown in FIG. 2.

Example 2.3

Figure 3:
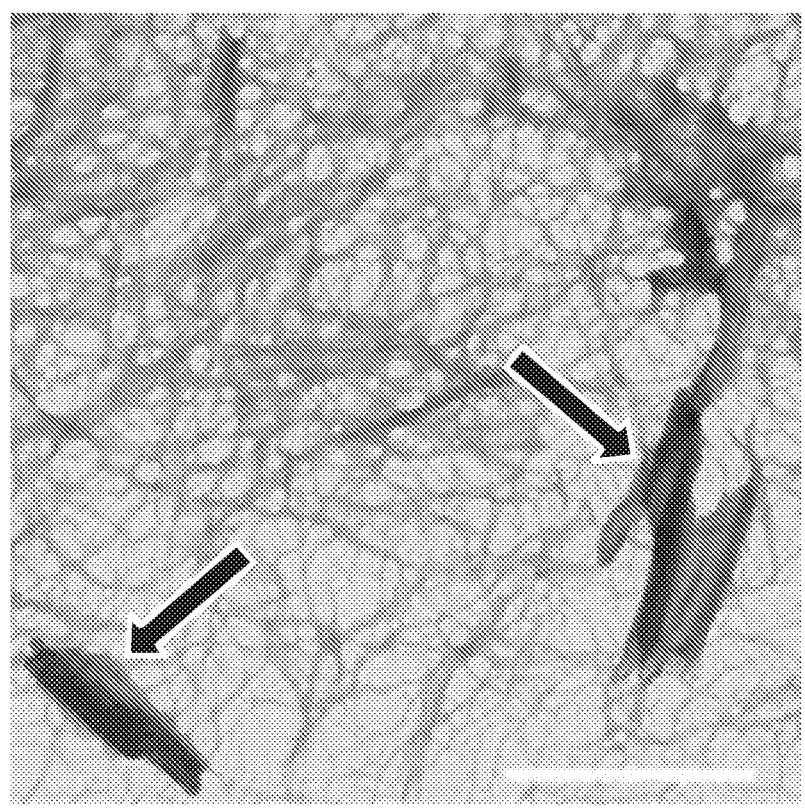
FIG. 3 is an illustration showing an assembly between RNTs with Matrilin-3.

Nanopieces containing Matrilin as cargo were manufactured as follows. 104, of a 100 μg/mL Matrilin (MATN) protein solution was mixed with 10 μL of a 1 mg/mL RNTs. The resulting mixture was then sonicated for 60 s. Dilution factors can range from 1 to 504, for preparing the MATN-RNTs complex mixture and sonication times of the resulting mixture can vary from 1 to 600 s. Results are shown in FIG. 3.

Example 3

Design and Processing of Nanopieces

FIG. 4 shows an exemplary assembly mechanism. Processing methods were designed before, during and after assembly to manipulate the sizes of Nanopieces. Taking quench and sonication as examples of processing methods before assembly, FIGS. 6 and 7 demonstrate the formation of smaller Nanopieces compared with those generated under standard conditions (FIG. 5). FIGS. 8 and 9 represent size distributions of examples of processing methods during and after assembly. Small Nanopieces were delivered into cells as shown in FIG. 10.

Example 3.1

FIGS. 5A-9B demonstrate Nanopieces of different sizes and width that were imaged under a transmission electron microscope, and their length and width were analyzed with Image J software.

Nanopieces of different lengths and widths were prepared using the following exemplary procedures.

Figure 5A:
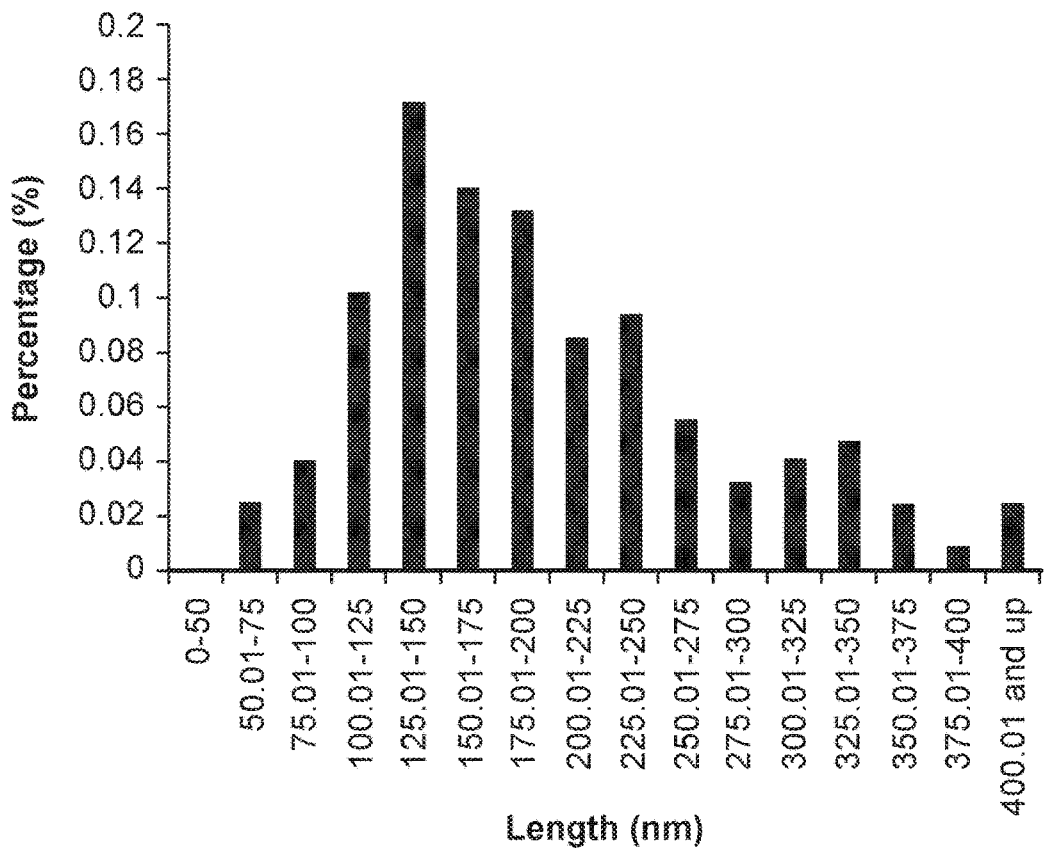
FIG. 5A is a bar graph of the size distribution of Nanopieces assembled under standard conditions.
Figure 5B:
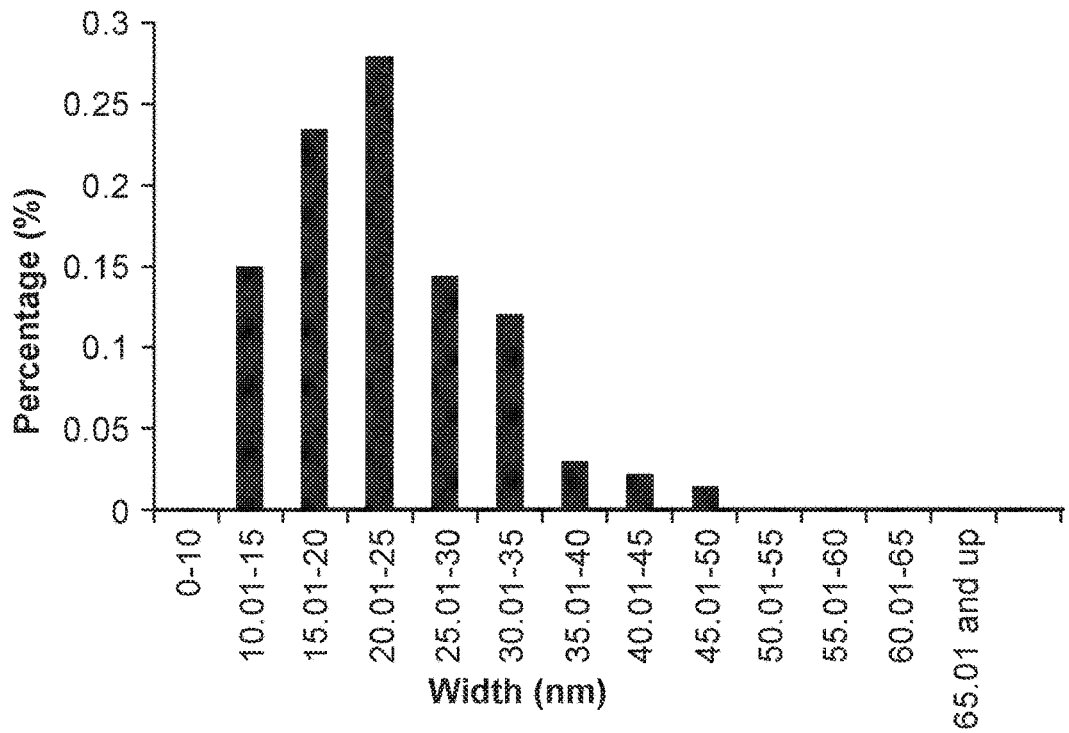
FIG. 5B is a bar graph of the width distribution of Nanopieces assembled under standard conditions.

Example 3.1A 5 ug of RNT in 5 uL water was mixed with 50 pmol siRNA in 10 uL water, and then the mixture was sonicated for 2 min to produce Nanopieces (FIGS. 5A and 5B)

Figure 6A:
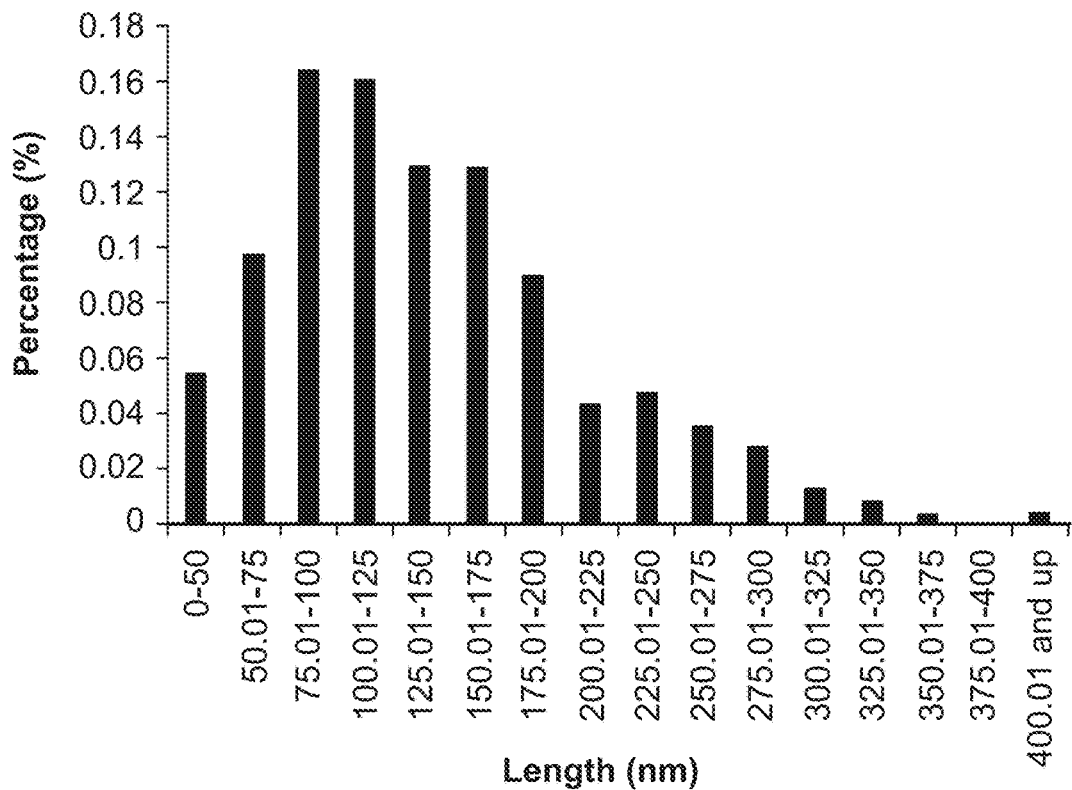
FIG. 6A is a bar a graph of the size distribution of Nanopieces processed before assembly (quench).
Figure 6B:
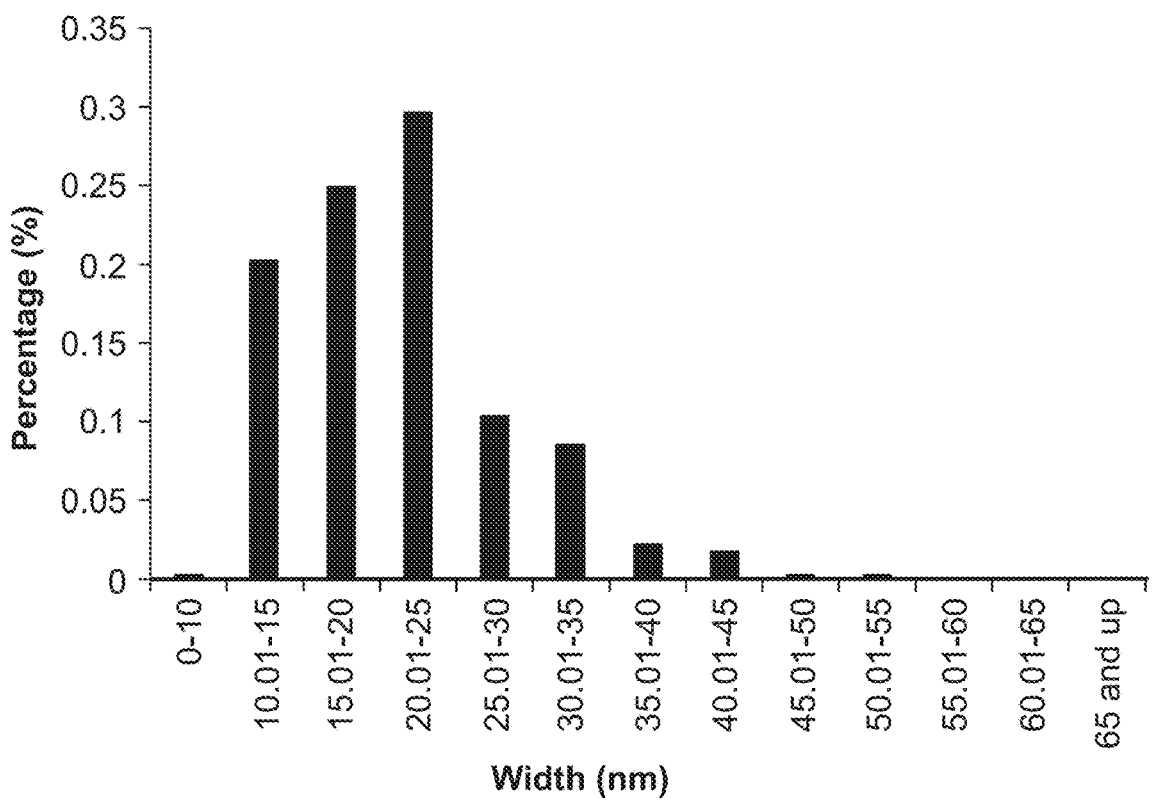
FIG. 6B is a bar graph of the width distribution of Nanopieces processed before assembly (quench).

Example 3.1B 5 ug of RNT in 5 uL water is heated to 95° C. for 10 min, and then the solution is immediately putted on ice. After totally cooling down to 0° C., RNT solution is mixed with 50 pmol siRNA in 10 uL water, and then the mixture is sonicated for 2 min to produce Nanopieces (FIGS. 6A and 6B).

Figure 7A:
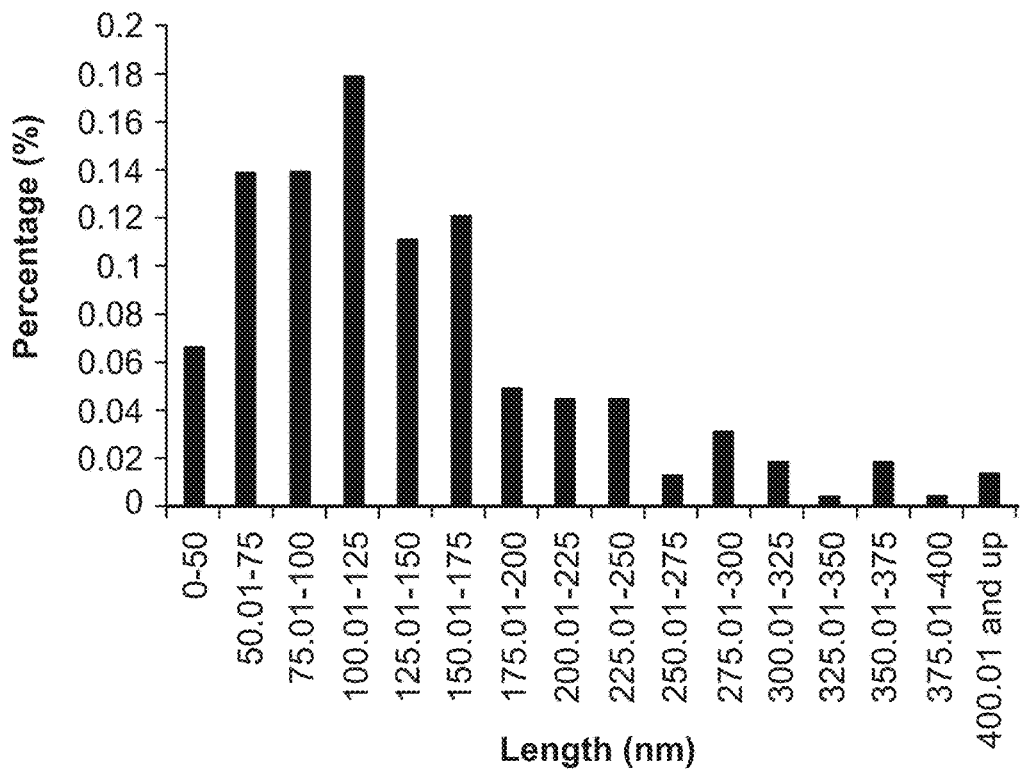
FIG. 7A is a bar graph of the size distribution of Nanopieces processed before assembly (sonication).
Figure 7B:
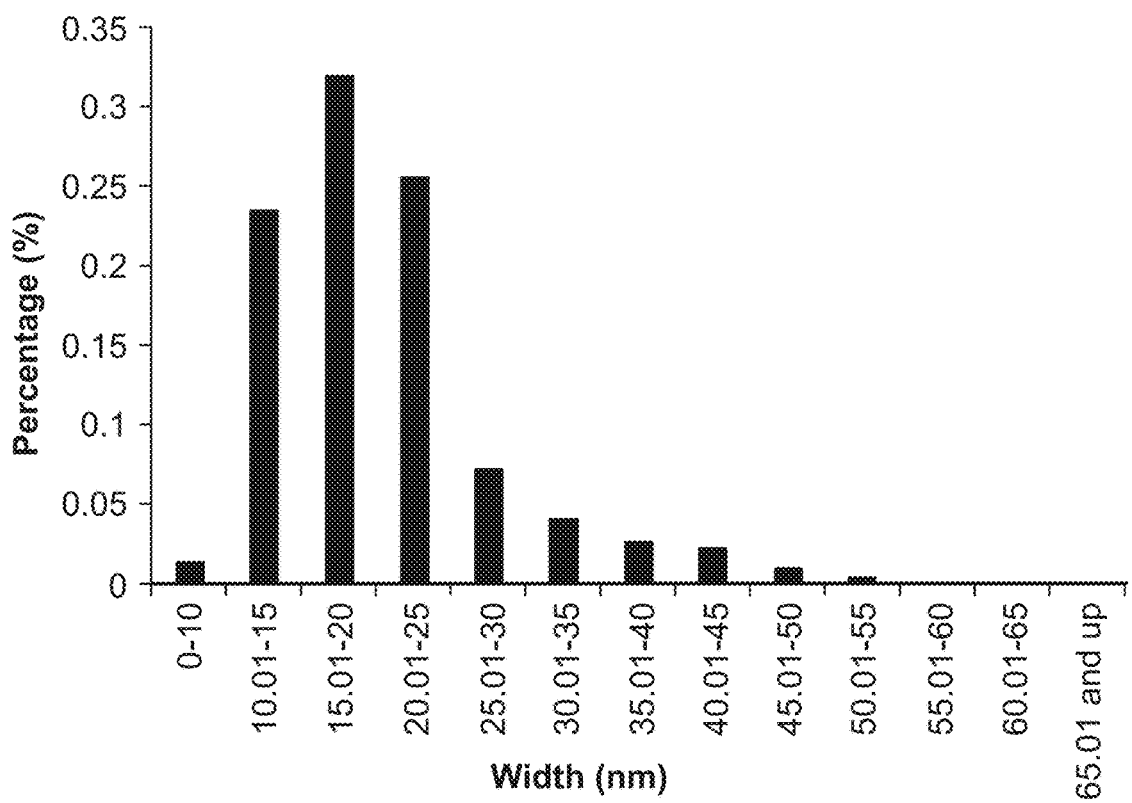
FIG. 7B is a bar graph of the width distribution of Nanopieces processed before assembly (sonication).

Example 3.1C 5 ug of RNT in 5 uL water is heated to 95° C. for 10 min, and then the solution is immediately subjected to sonication for 5 min. The resulting RNT solution is mixed with 50 pmol siRNA in 10 uL water, and then the mixture is sonicated for 2 min to produce Nanopieces (FIGS. 7A and 7B).

Figure 8A:
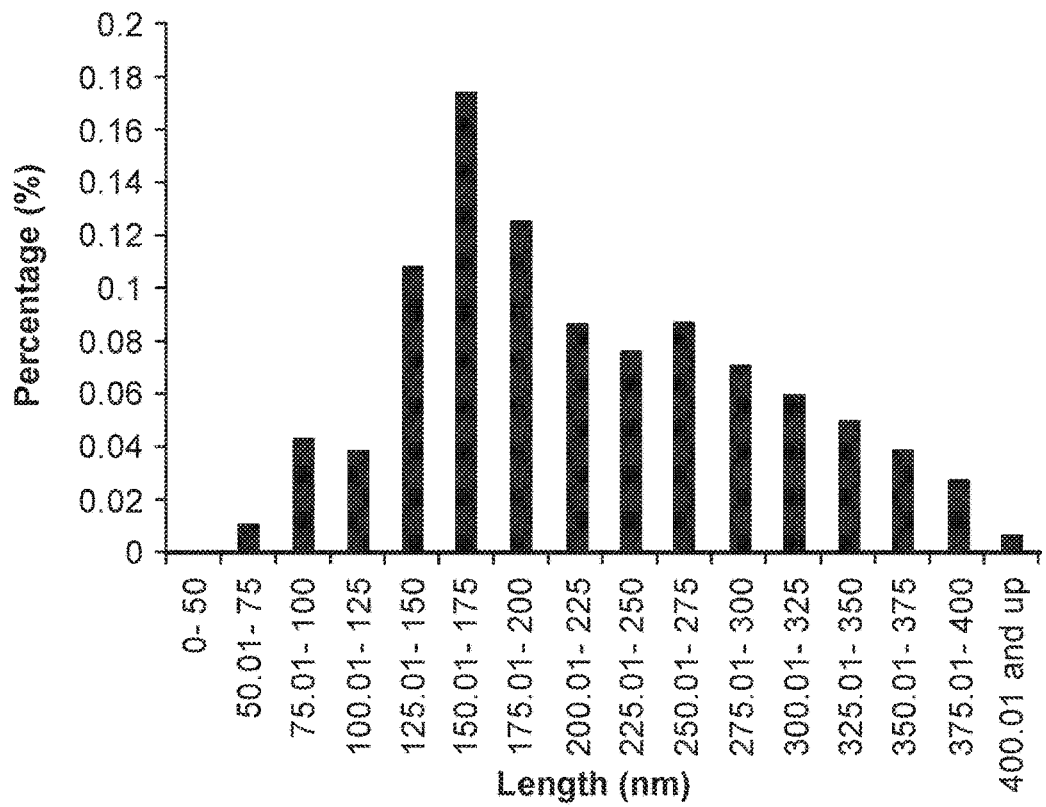
FIG. 8A is a bar graph of the size distribution of Nanopieces processed during assembly (increasing ionic strength).
Figure 8B:
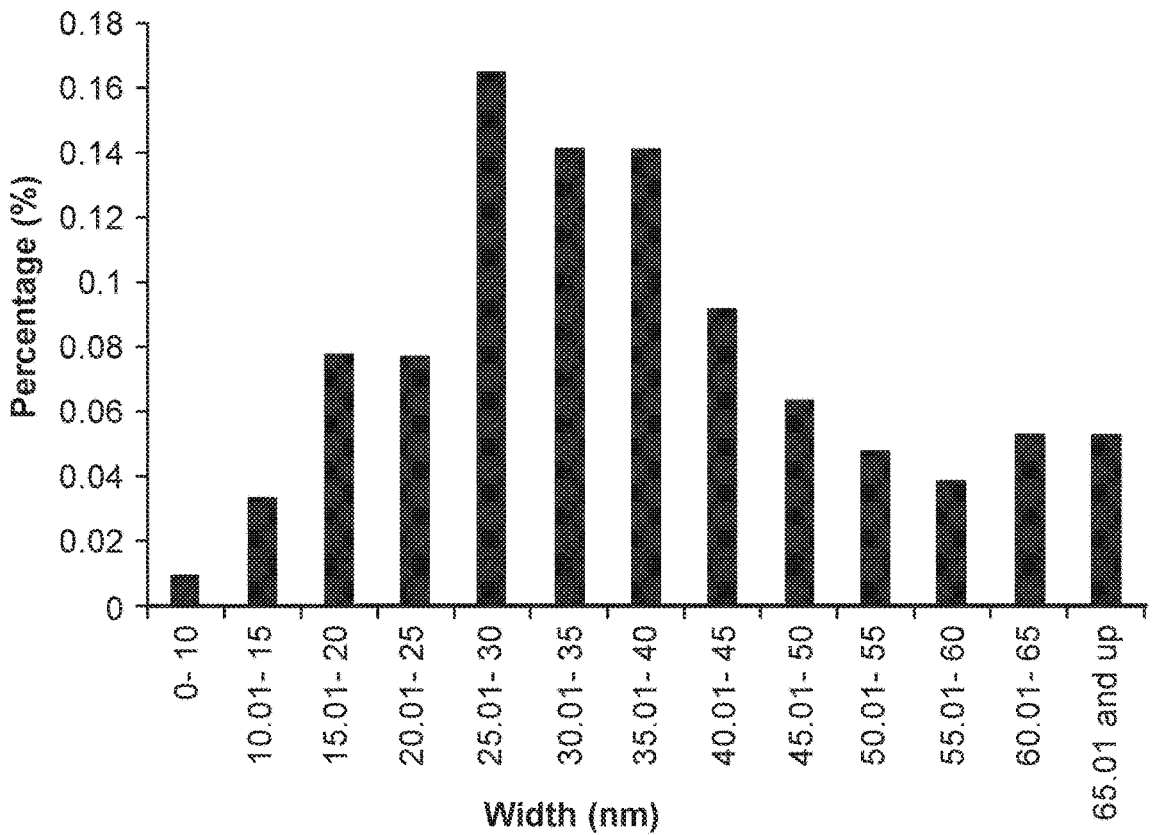
FIG. 8B is a bar graph of the width distribution of Nanopieces processed during assembly (increasing ionic strength).

Example 3.1D 5 ug of RNT in 5 uL in water is mixed with 50 pmol siRNA in 10 uL 0.9% saline, and then the mixture is sonicated for 2 min to produce Nanopieces (FIGS. 8A and 8B).

Figure 9A:
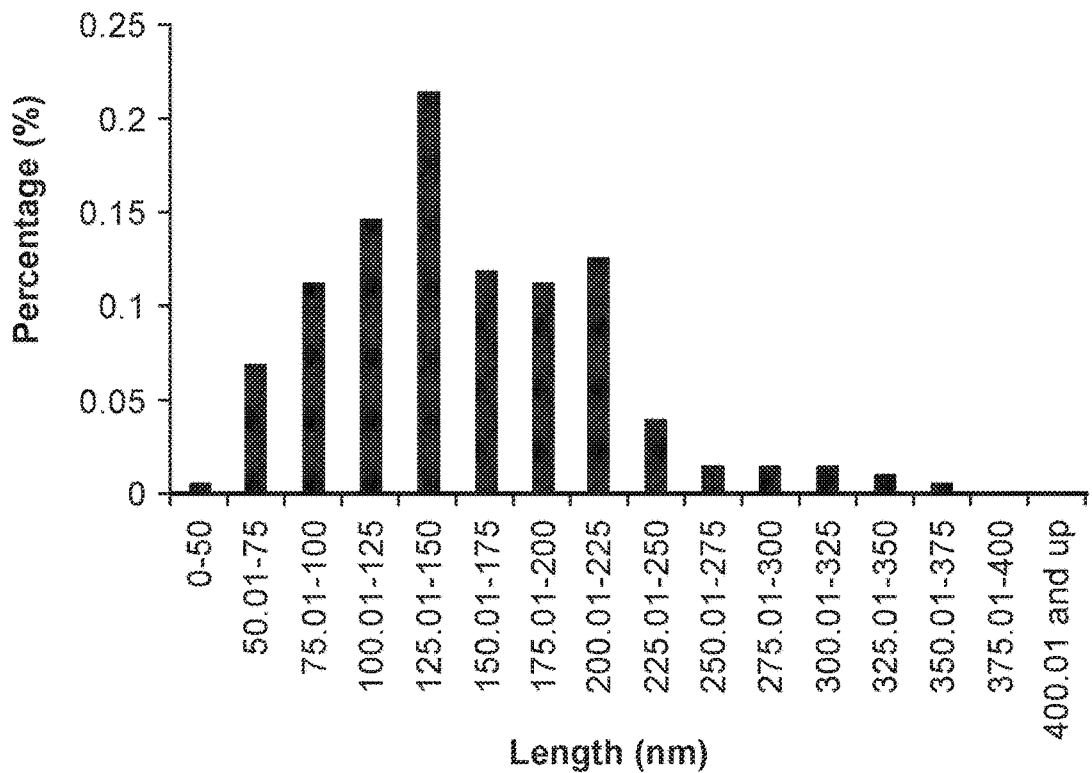
FIG. 9A is a bar graph of the size distribution of Nanopieces processed after assembly (increasing sonication time).
Figure 9B:
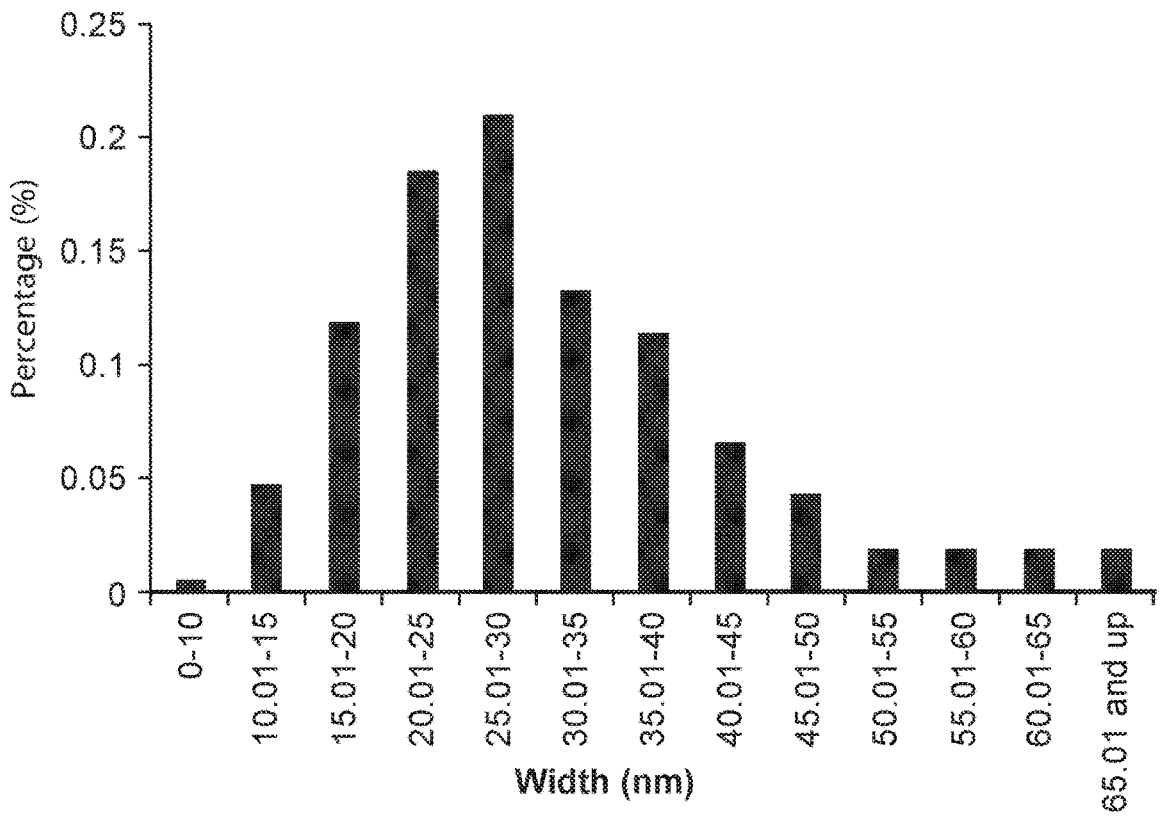
FIG. 9B is a bar graph of the width distribution of Nanopieces processed after assembly (increasing sonication time).
Figure 10:
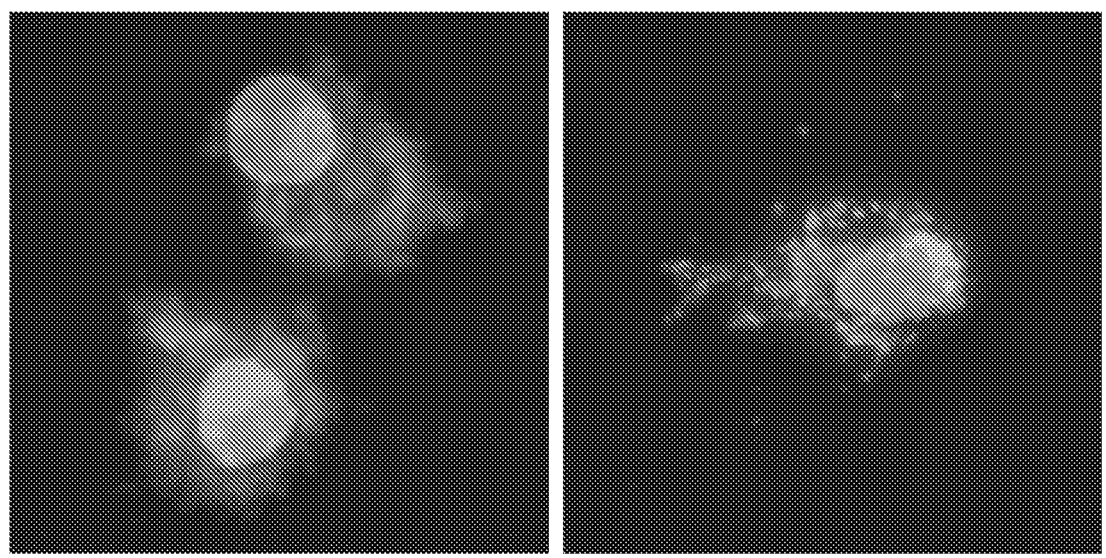
FIG. 10 is a series of images showing Nanopieces assembled before processing (Left) and after processing with sonication (Right) were delivered into cells.

Example 3.1E 5 ug of RNT in 5 uL in water is mixed with 50 pmol siRNA in 10 uL water, and then the mixture is sonicated for 4 min to produce Nanopieces (FIGS. 9A and 9B).

Example 3.2

FIG. 10 shows that fluorescence labeled RNA was delivered into cells using unprocessed and processed Nanopieces. The Nanopieces were added to chondrocytes and the cells were maintained under standard cell culture conditions for 24 h. Left Panel of FIG. 10 shows unprocessed nanopieces, while the right panel of FIG. 10 shows processed Nanopieces being delivered into cells.

Example 3.3

Various types of Nanopieces and their processing methods are described. Nanotubes are converted into nanorods. As shown in FIG. 4, the use of physical methods (sonication, blending, microwave and/or quenching) or chemical methods (altering pH, adding organic solvents, and/or adding of aromatic chemicals) convert nanotubes into homogenous shorter/longer nanorods to result in shorter/longer Nanopieces compared to standard conditions. (FIGS. 5-7). Nanorods were produced via either sonicating RNTs, or heating RNTs to 90° C., and then quenching them on ice. RNTs or Nanorods were used to form Nanopieces. Nanopieces were characterized using transmission electron microscope and their length and width were analyzed with Image J software.

Example 3.4

Figure 11:
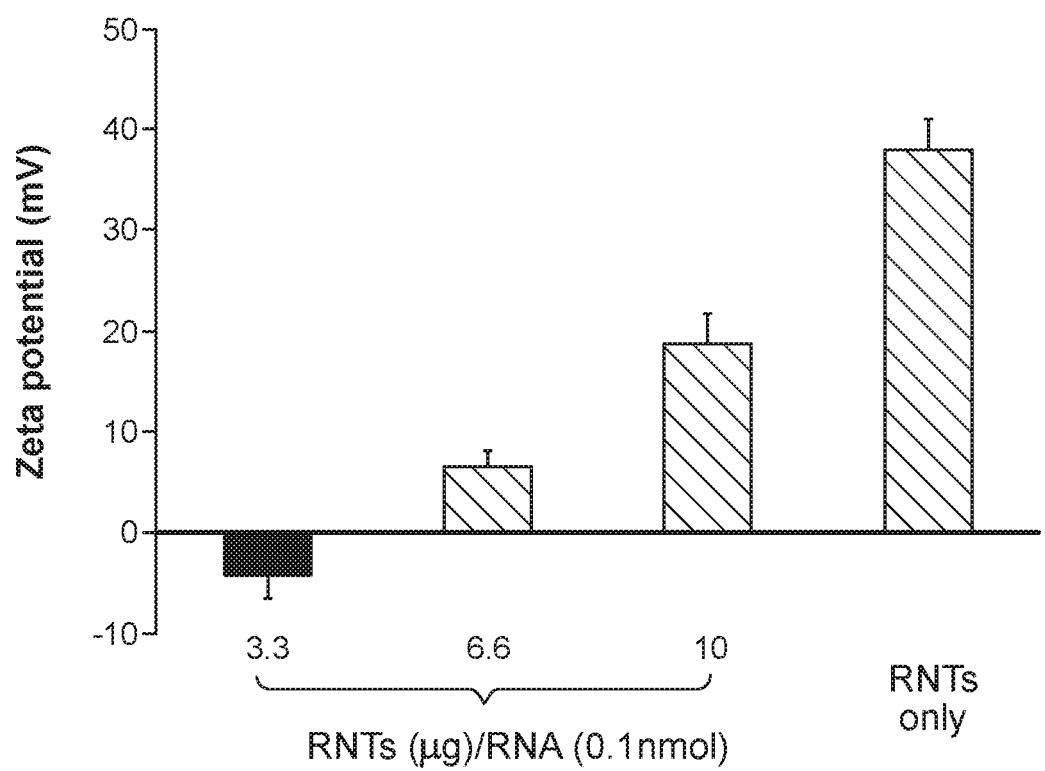
FIG. 11 is a graph showing the Zeta potential (reflecting surface charge) of Nanopieces with different RNT/siRNA ratios.

Various types of Nanopieces and their processing methods are used to customize the physical characteristics, e.g., length and width, and/or chemical characteristics e.g., surface charge of the delivery vehicle. Two major conditions can be altered: i) assembly conditions (ionic strength, pH and concentration) to achieve Nanopieces with various sizes; and ii) the ratio between nanotubes/nanorods and delivery cargos to achieve different surface charge for the delivery of cargo into different tissues. For example, an increase in ionic strength can be used in the assembly solution to generate longer and wider Nanopieces compared to when using standard conditions (FIG. 4 and FIG. 7). An increase in the ratio of RNTs over siRNA resulted in an increase of the surface positive charge of Nanopieces (FIG. 11). FIG. 8 shows that RNTs and siRNA were dissolved in saline to form Nanopieces as described in the previous sections. Nanopieces were imaged under a transmission electron microscope, and their length and width were analyzed with Image J software. FIG. 11 shows the different ratios of RNTs and siRNA that were used to form Nanopieces. The surface charge (as measured by Zeta potential; mV) of Nanopieces was determined via Nanosizer.

Example 3.5

Figure 56:
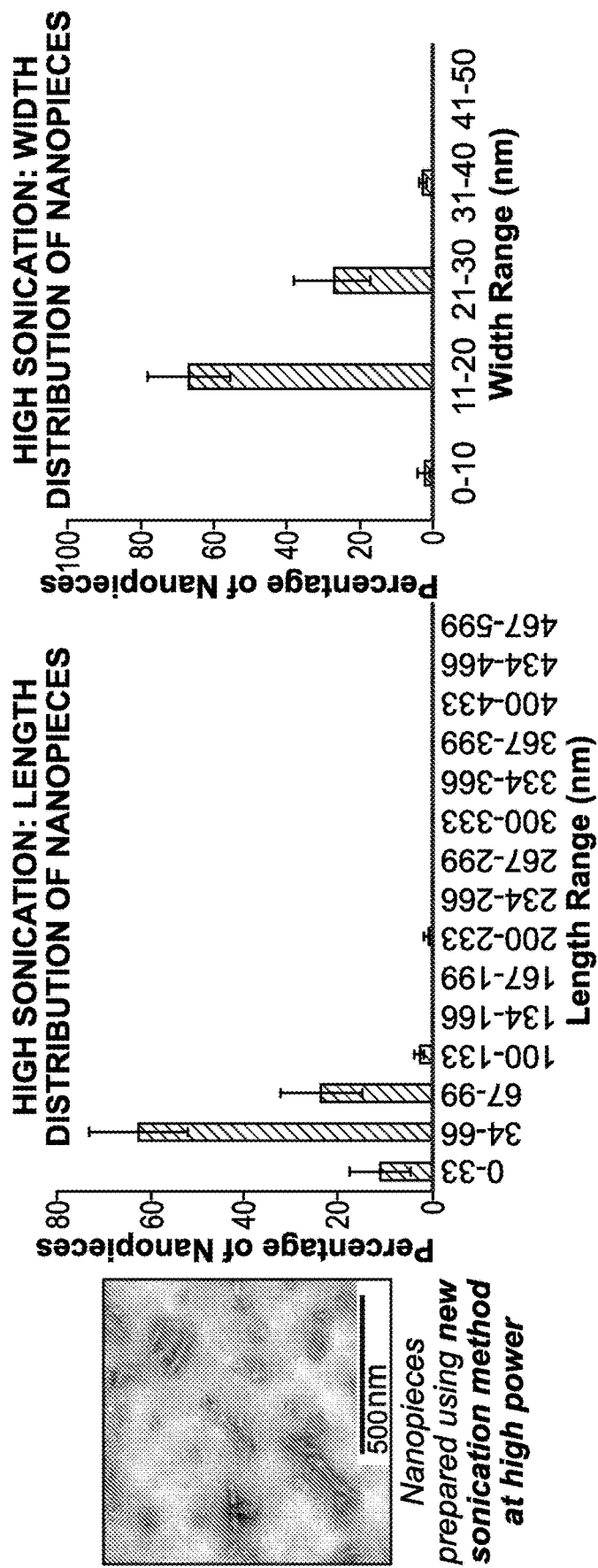
FIG. 56 is a series of graphs an images showing Nanopieces size and morphology with increasing sonication power.
Figure 56:
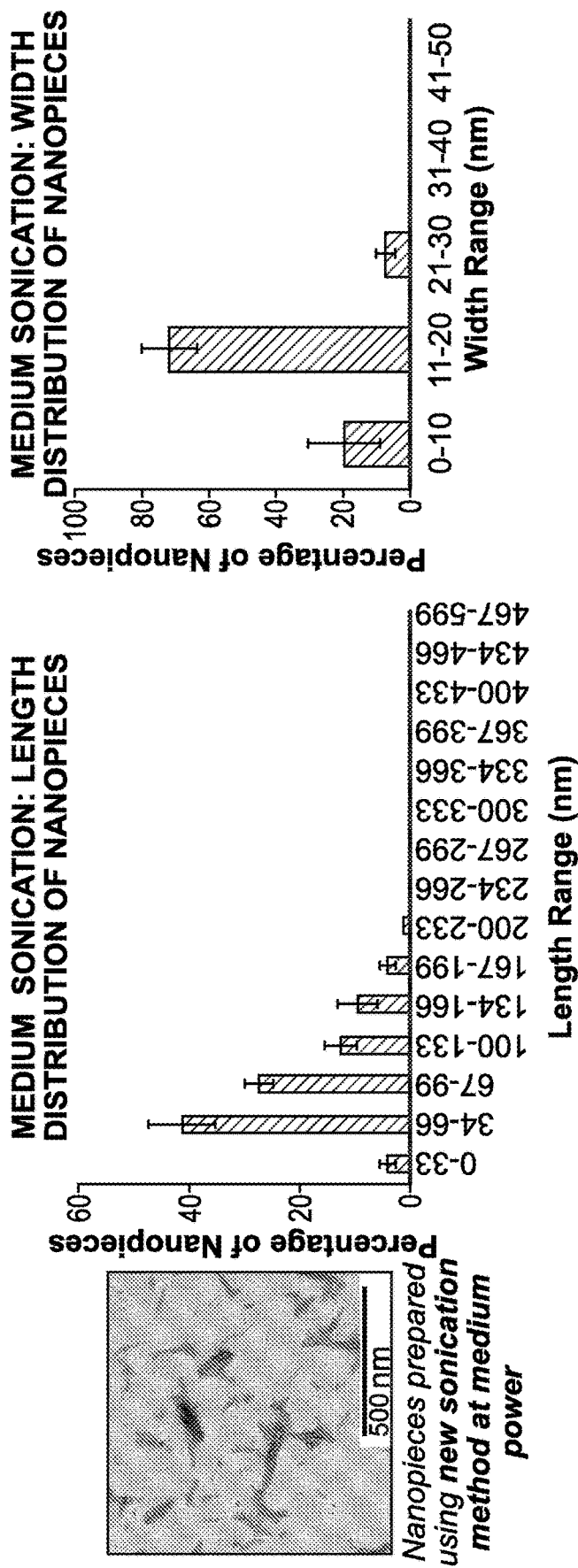
Figure 56:
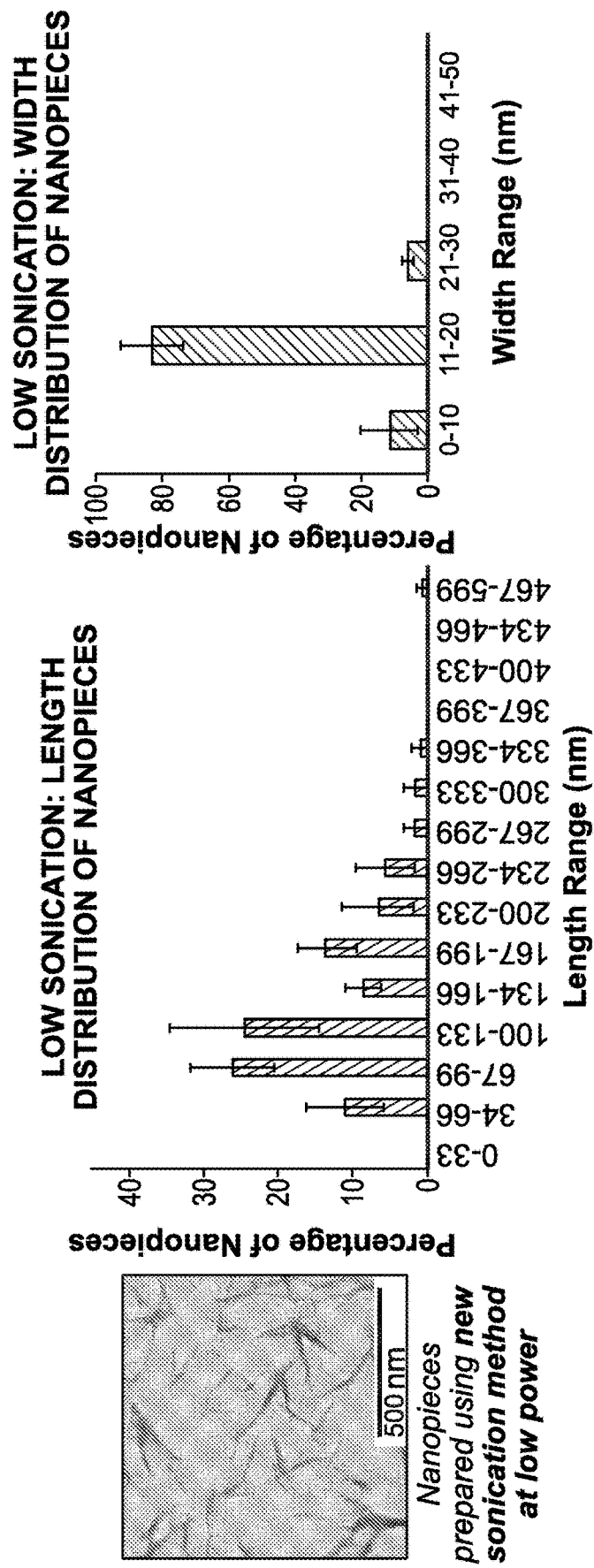
Figure 56:
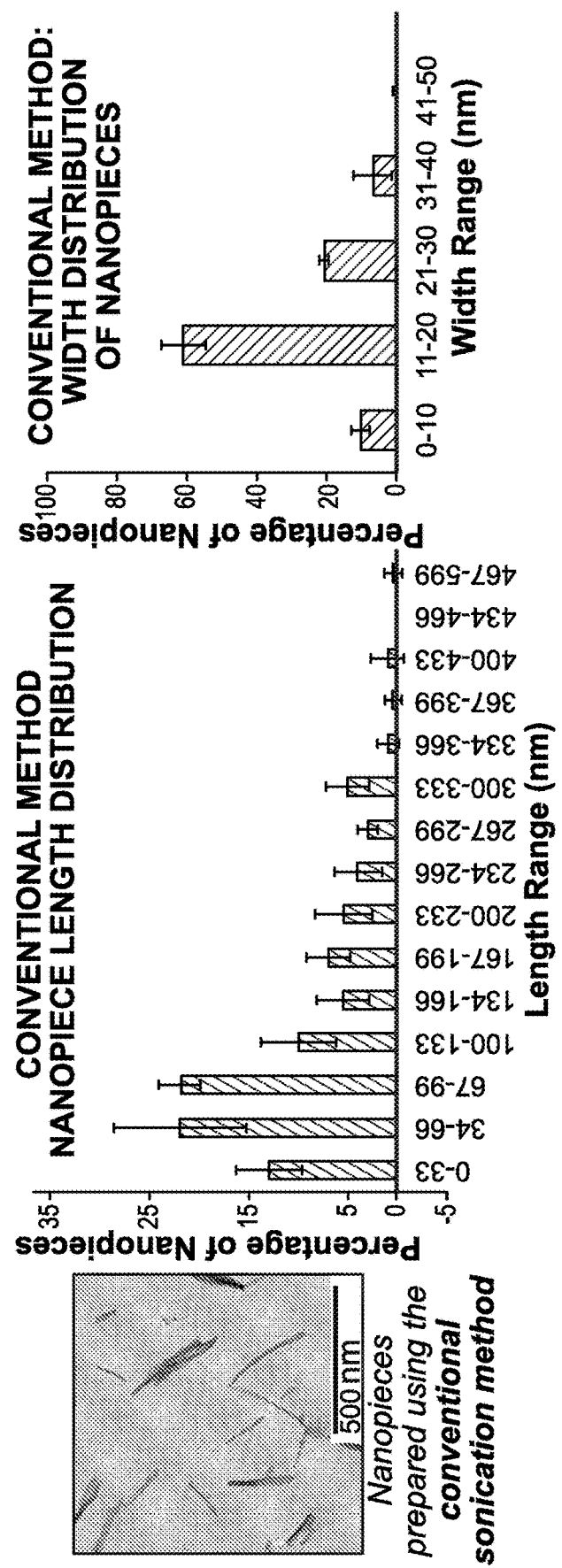
Figure 57:
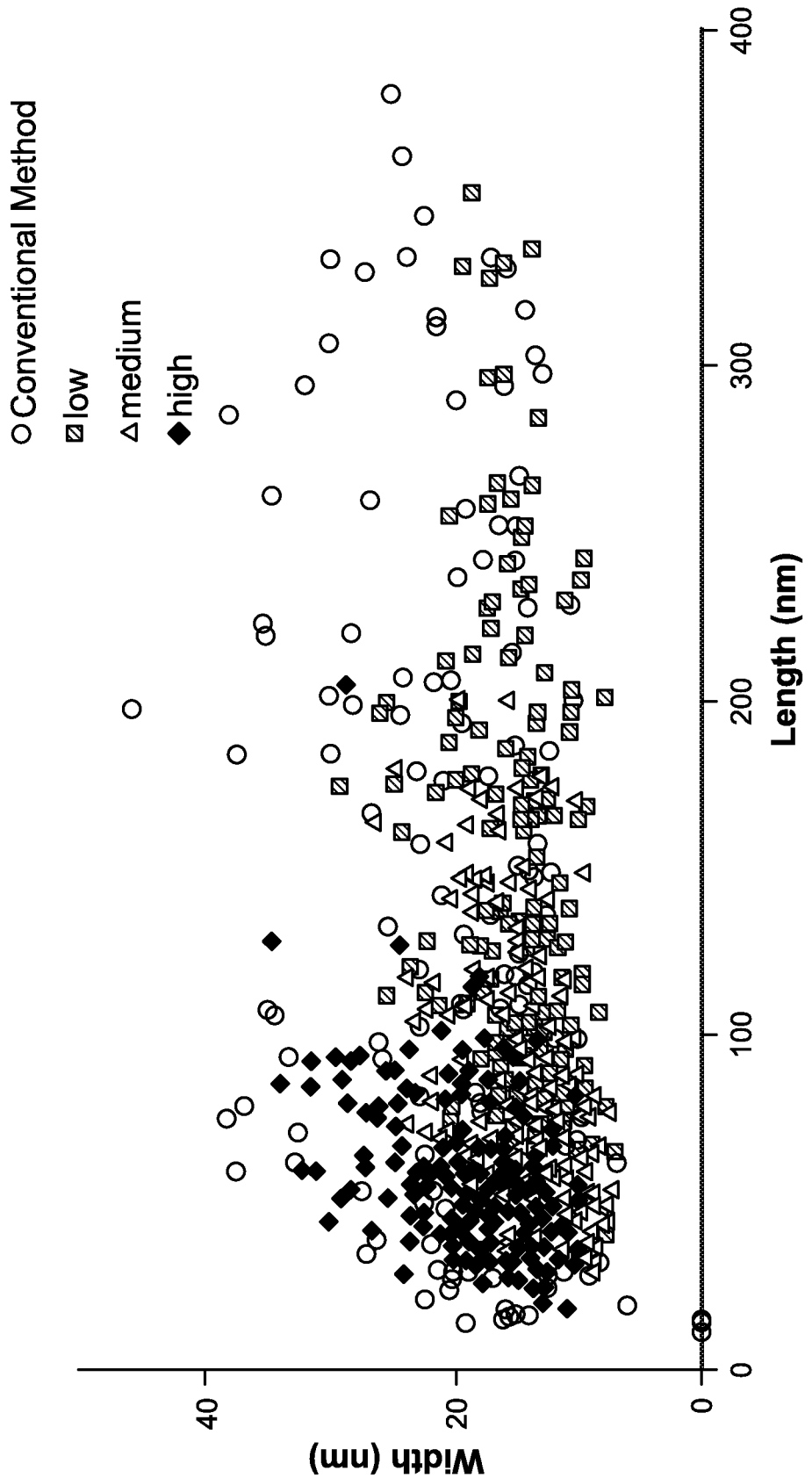
FIG. 57 is a scatter plot of Nanopieces size and morphology with increasing sonication power.

Processing after assembly included physical methods, e.g., using different power of soinication, heating, blending and/or microwave; or chemical methods, like altering of pH and adding of aromatic chemicals. For example, the use of low, medium and high power of sonication resulted in Nanopieces with different size (length) and morphology (aspect ratio, which is equal to length/width) (FIGS. 4, 56, and 57). FIGS. 56-57 shows that Nanopieces were formed under standard conditions or were processed with different sonication powers (low power is 10% of maximum amplitude of a 700 W sonicator; medium is 50% and high is 100%). Nanopieces were imaged under a transmission electron microscope, and their length and width were analyzed with Image J software.

Example 3.6

Figure 20:
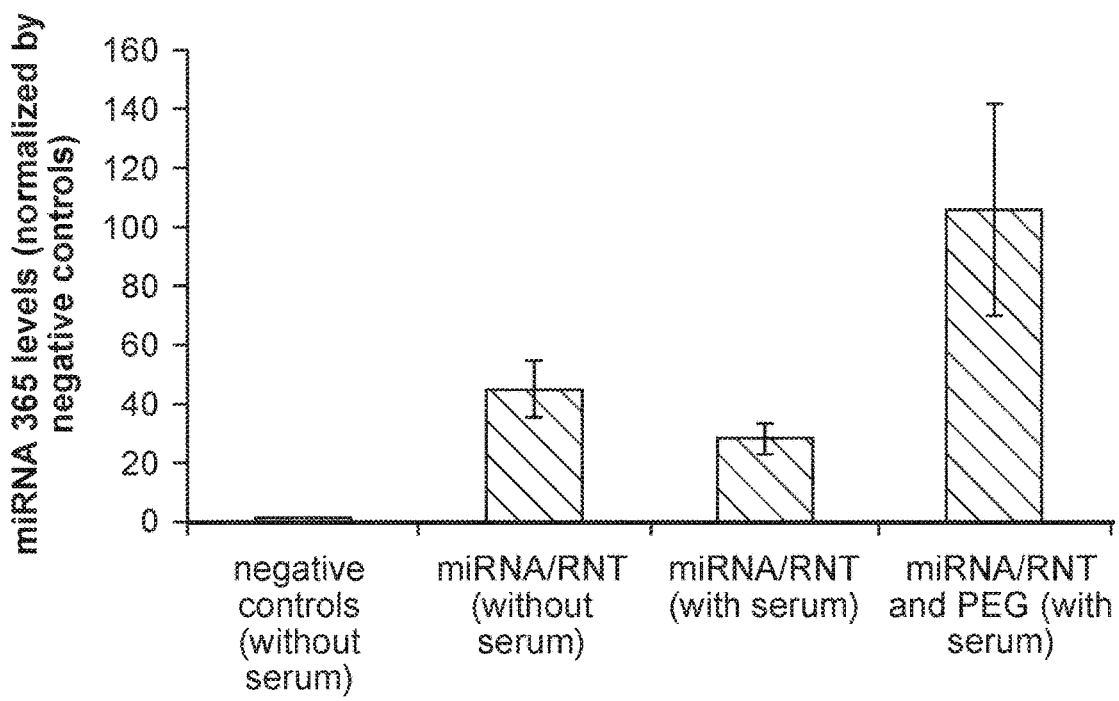
FIG. 20 is a graph showing functional delivery of processed miRNA365/RNT Nanopieces with and/or without PEG into human cartilage tissue matrix and inside chondrocytes in the serum and serum-free medium.
Figure 58:
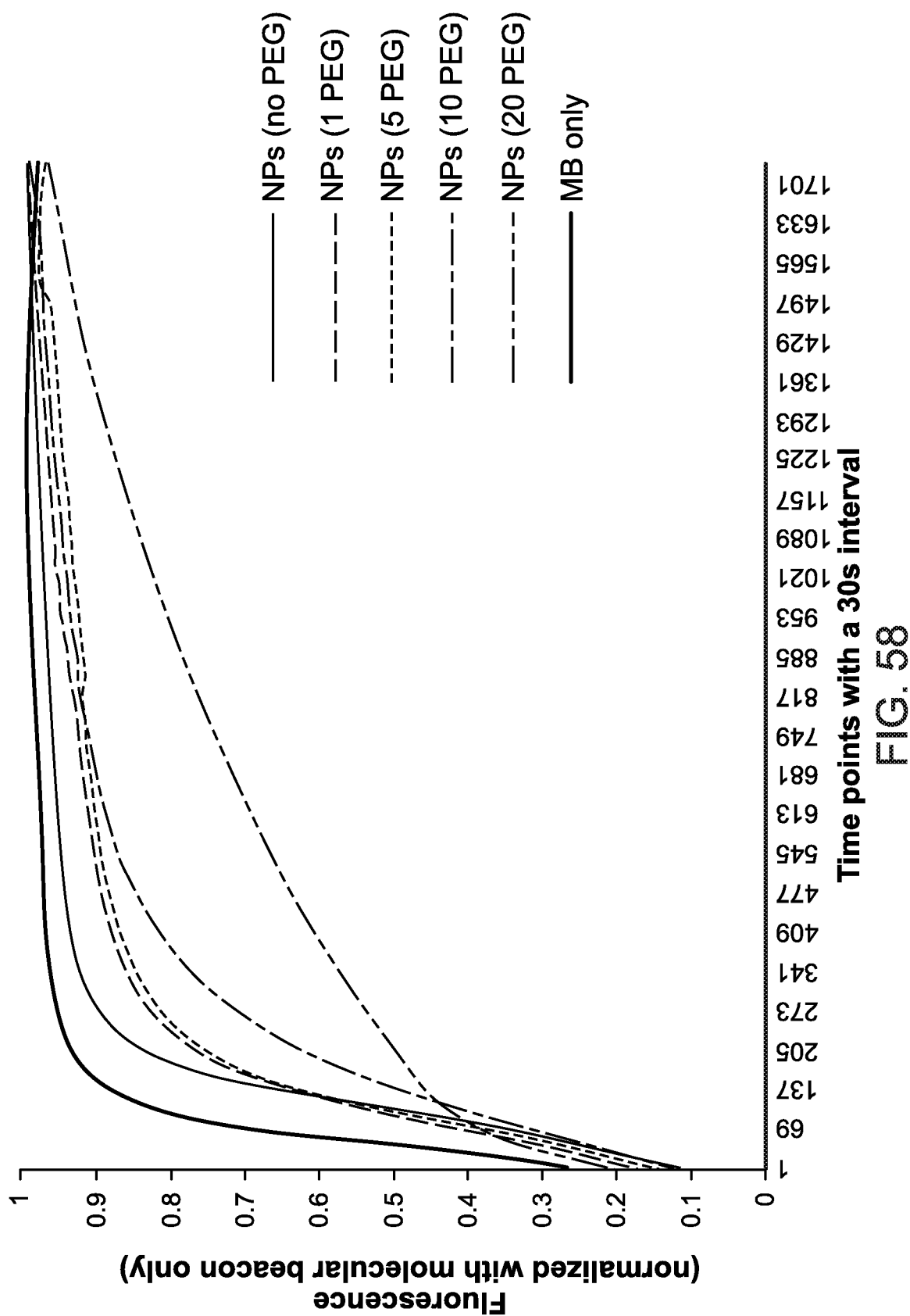
FIG. 58 is a line graph showing the stability of Nanopieces with different molar-excess ratios of PEG.
Figure 59:
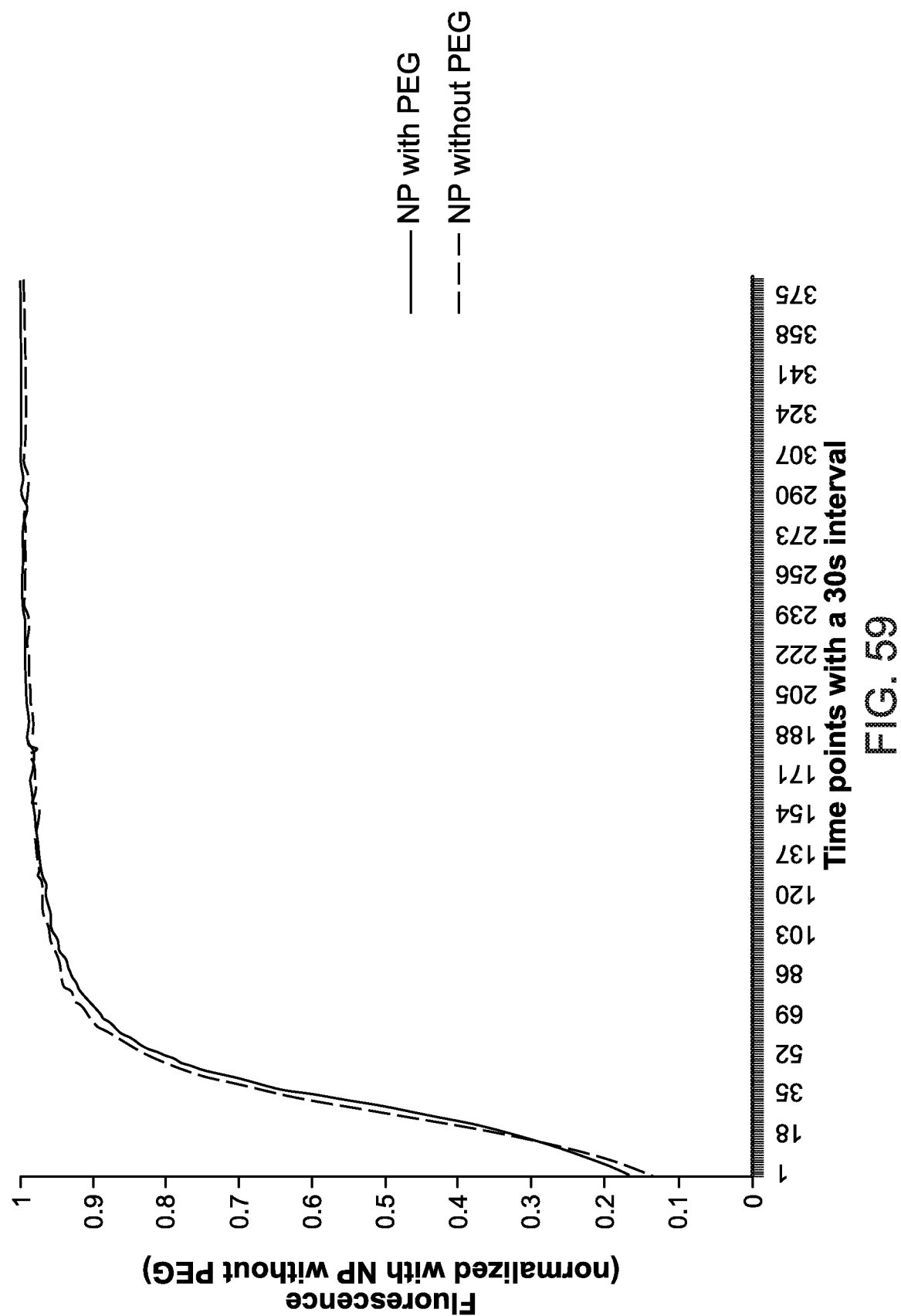
FIG. 59 is a line graph showing the stability of Nanopieces with and without non-covalent linked PEG.

Nanopieces are optionally coated. Coating of Nanopieces with PEG facilitated Nanopieces delivery into tissue matrix, especially in a protein-rich environment, such as in the presence of serum (FIG. 20). Although Nanopieces doubled the half-life of delivery cargos (such as molecular beacon, MB) in serum, a covalent linked PEG coating had a 6-time longer half-life than MB only (FIG. 58). Moreover, non-covalent linked PEG only had marginal difference on Nanopieces in terms of stability in serum (FIG. 59). FIGS. 58-59 shows that molecular beacons delivered with/without Nanopieces were soaked in serum. For PEG coating, PEG (MW 400) was either covalently linked or non-covalently coated on Nanopieces. A fluorescence plate read was determined half-life of MBs.

Example 3.6

Nanopieces of different sizes and length were prepared using the following procedure:

Step A: Quench before assembly: heating 5 ug RNT in water to 50-99° C. for 10 s-10 mins, then immediately putting it on ice, and mixing with 50 pmol siRNA, then, sonicating for 30 s-2 mins to produce Nanopieces.

Step B: Sonication before assembly: sonicating 5 ug RNT in water to 50-99° C. for 10 s-10 mins, and mixing with 50 pmol siRNA, then, sonicating for 30 s-2 mins to produce Nanopieces.

Step C: Increase ionic strength: mixing 5 ug RNT with 50 pmol siRNA in saline, then, sonicating for 30 s-2 mins to produce Nanopieces.

Step D: Increase sonication time after assembly: mixing 5 ug RNT with 50 pmol siRNA, then, sonicating for 2 mins-10 mins to produce Nanopieces.

Modification of Parameters:

|  | Size of Nanopieces | |
| --- | --- | --- |
| Factors | High/Long | Low/Short |
| Heating temperature for quench | Small (Avg. length 10 nm~149 nm; Avg. width diameter 10~29 nm) | Large (Avg. length 150 nm~500 nm; Avg. width diameter 10~29 nm) |
| Heating time for quench | Small (Avg. length 10 nm~149 nm; Avg. width diameter 10~29 nm) | Large (Avg. length 150 nm~500 nm; Avg. width diameter 10~29 nm) |
| Sonication time before assembly | Small (Avg. length 10 nm~149 nm; Avg. width diameter 10~29 nm) | Large (Avg. length 150 nm~500 nm; Avg. width diameter 10~29 nm) |
| Sonication power before assembly | Small (Avg. length 10 nm~149 nm; Avg. width diameter 10~29 nm) | Large (Avg. length 150 nm~500 nm; Avg. width diameter 10~29 nm) |
| Sonication time after assembly | Small (Avg. length 10 nm~149 nm; Avg. width diameter 10~29 nm) | Large (Avg. length 150 nm~500 nm; Avg. width diameter 10~29 nm) |
| Sonication power after assembly | Small (Avg. length 10 nm~149 nm; Avg. width diameter 10~29 nm) | Large (Avg. length 150 nm~500 nm; Avg. width diameter 10~29 nm) |
| Ionic strength | Vary Large (Avg. length 150 nm~999 micon; Avg. width diameter 30~100 nm) | Small (Avg. length 10 nm~149 nm; Avg. width diameter 10~29 nm) |

|  | Charge of Nanopieces | |
| --- | --- | --- |
|  | Strong/High | Weak/Low |
| RNT/RNA ratio | Positive | Negative |
| Negative charge from the cargo (such as RNA other nucleic acids or proteins) | Negative | Positive |

| Nanopiece properties | Size | | Surface Charge | |
| --- | --- | --- | --- | --- |
|  | Small | Large | Negative | Positive |
| Suitable cells or tissues | High and dense extracellular matrix content | Low and loose extracellular matrix content | Positively charged or neutral cell membrane/ extracellular matrix | Negatively charged or neutral cell membrane/ extracellular matrix |

Example 4

Surface Charge and Matrix/Tissue Binding

Figure 12:
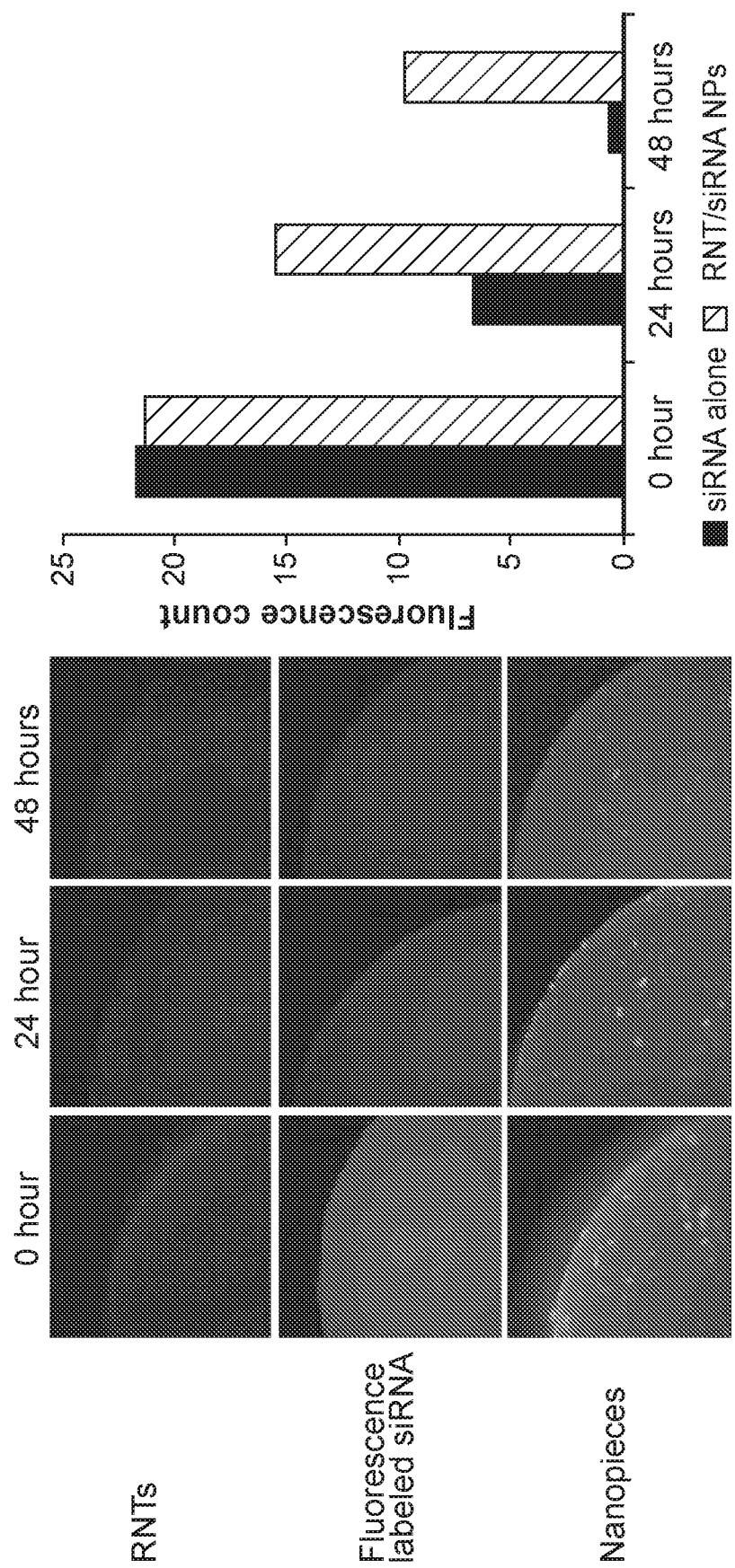
FIG. 12 shows a series of images and a bar graph illustrating cartilage binding with RNTs, fluorescence labeled siRNA and RNT/siRNA Nanopieces on articular cartilage.

Surface charge of Nanopieces were tuned or customized via controlling RNT/delivery cargo ratio (e.g., RNT/siRNA as an example, FIG. 11). Adjusting 4.4 µg~30 µg RNTs per 0.1 nmol RNA yielded positively charged Nanopieces. These Nanopieces exhibited excellent binding to negatively charged tissue and/or matrix, as shown in FIG. 12; light grey area and spots are the fluorescence signals from siRNA alone or siRNA. Nanopieces with more than 30 ug RNT per 0.1 nmol RNA are also positively charged. Generally, the ratio will not exceed 30 ug per 0.1 nmol RNA.

Example 4.1

Fluorescence labeled RNA with and without Nanopieces was added onto porcine articular cartilage for 1 h. Then, the cartilage was soaked in HBSS buffer at 37° C. The remaining RNA was analyzed using a fluorescence microscope.

Example 5

Trans-Matrix/Tissue Delivery

Results showed that processed fluorescence labeled siRNA/RNT Nanopieces successfully penetrated into cartilage (FIG. 13). Moreover, it was further demonstrated that GAPDH molecular beacon/RNT Nanopieces not only penetrate into the tissue matrix but also inside cells (FIGS. 14-16). Effective trans-matrix and/or tissue delivery was demonstrated with a variety of species. Light gray areas within FIG. 14-16 around the cell nucleus are the fluorescence signals from molecular beacons.)

Example 5.1

Fluorescence labeled RNA was delivered with and without Nanopieces and was soaked with porcine cartilage. After 24 hours, the cartilage was sectioned and the individual sections were observed under a fluorescence microscope (FIG. 13).

Example 5.2

Fluorescence GAPDH molecular beacon was delivered with and without Nanopieces and soaked with mouse cartilage. After 24 hours, the cartilage was then sectioned and the individual sections were observed under a fluorescence microscope (FIG. 14).

Example 5.3

Fluorescence GAPDH molecular beacon was delivered with and without Nanopieces and soaked with human cartilage. After 24 hours, the cartilage was then sectioned and the individual sections were observed under a fluorescence microscope (FIG. 15).

Example 5.4

Fluorescence GAPDH molecular beacon was delivered with and without Nanopieces and soaked with chicken cartilage. After 24 hours, the cartilage was then sectioned and the individual sections were observed under a fluorescence microscope (FIG. 16).

Example 5.5

Figure 60:
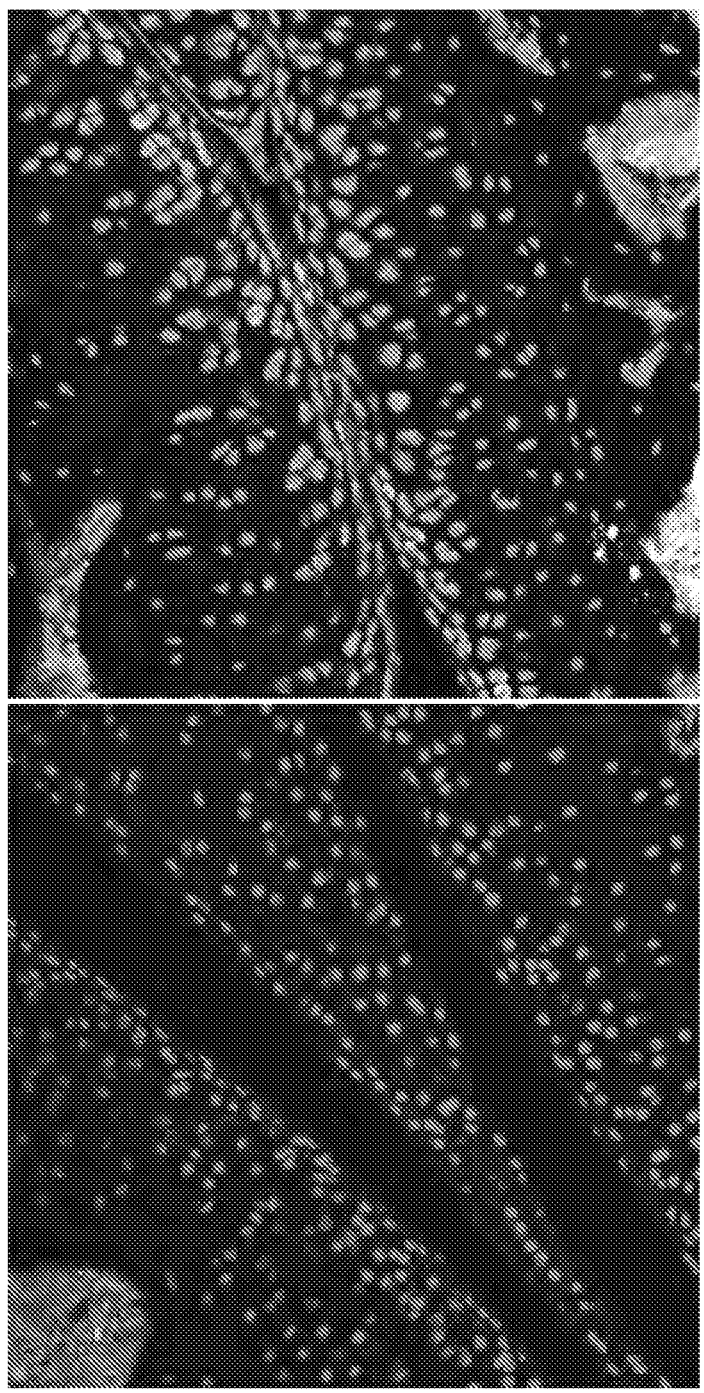
FIG. 60 is an image showing the delivery of small Nanopieces into articular cartilage to result in fluorescence comparted to controls (MB only).
Figure 61:
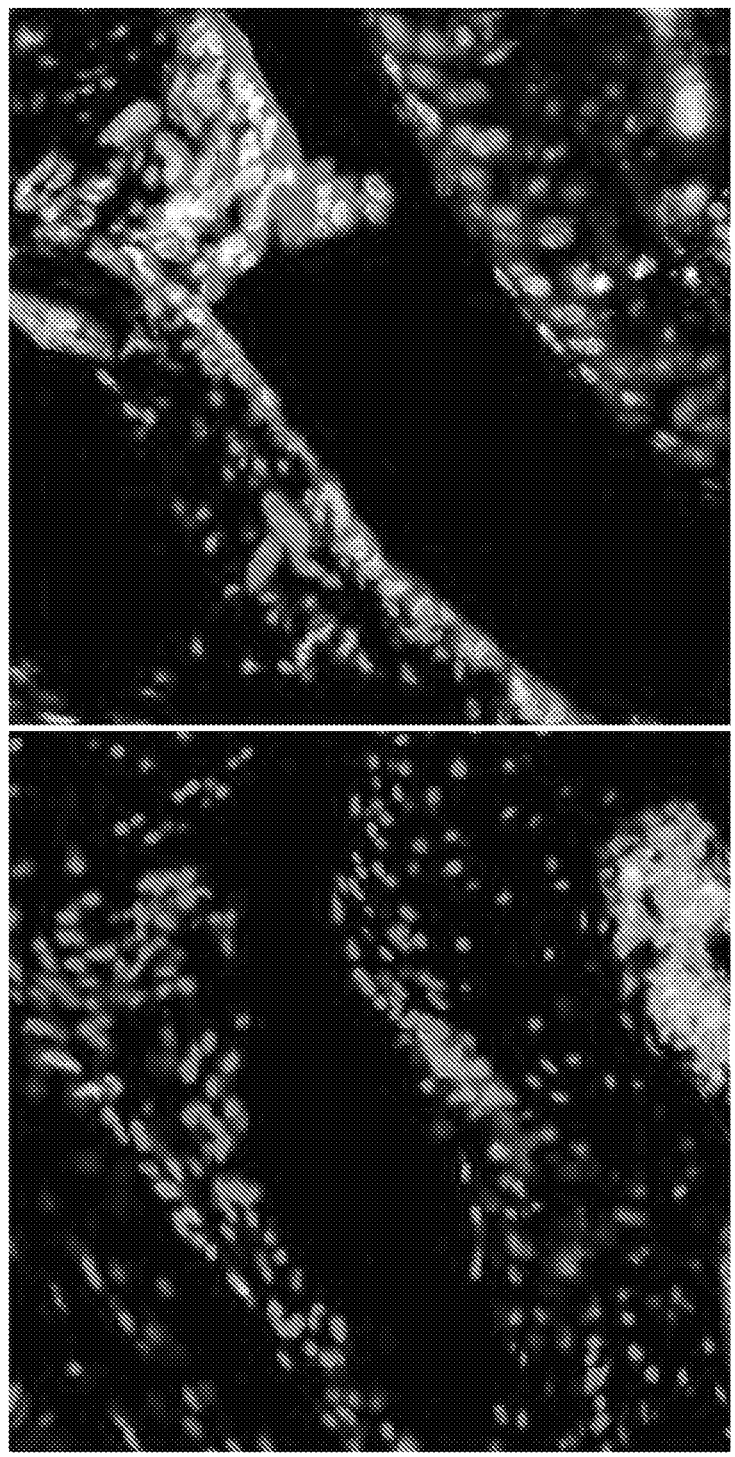
FIG. 61 is an image showing the delivery of both large and small Nanopieces into synovium to result in fluorescence compared with controls (MB only).

Applications of various types of Nanopieces: Various types of Nanopieces can be used for delivery into different tissues or organs as desired. For example, co-injection of small Nanopieces (Avg. length ~110 nm, Avg. width ~20 nm) (SMALL means Avg. length 10 nm~149 nm; Avg. width diameter 10~29 nm) to deliver GAPDH MBs with fluorescence and very large Nanopieces (Avg. length ~250 nm, Avg. width ~33 nm) (LARGE means Avg. length 150 nm~999micon; Avg. width diameter 30~100 nm) to deliver GAPDH MBs also with fluorescence into knee joints of mice were carried out. Small Nanopieces could be delivered into both cartilage and synovium, while large Nanopieces could only be delivered into synovium (FIGS. 60-61). (Bright area/spots around cell nuclei in FIG. 60-61 are the fluorescence signal from molecular beacons delivered via different sizes of Nanopieces.) Therefore, selective delivery into synovium with processed large Nanopieces was achieved.

Figure 63:
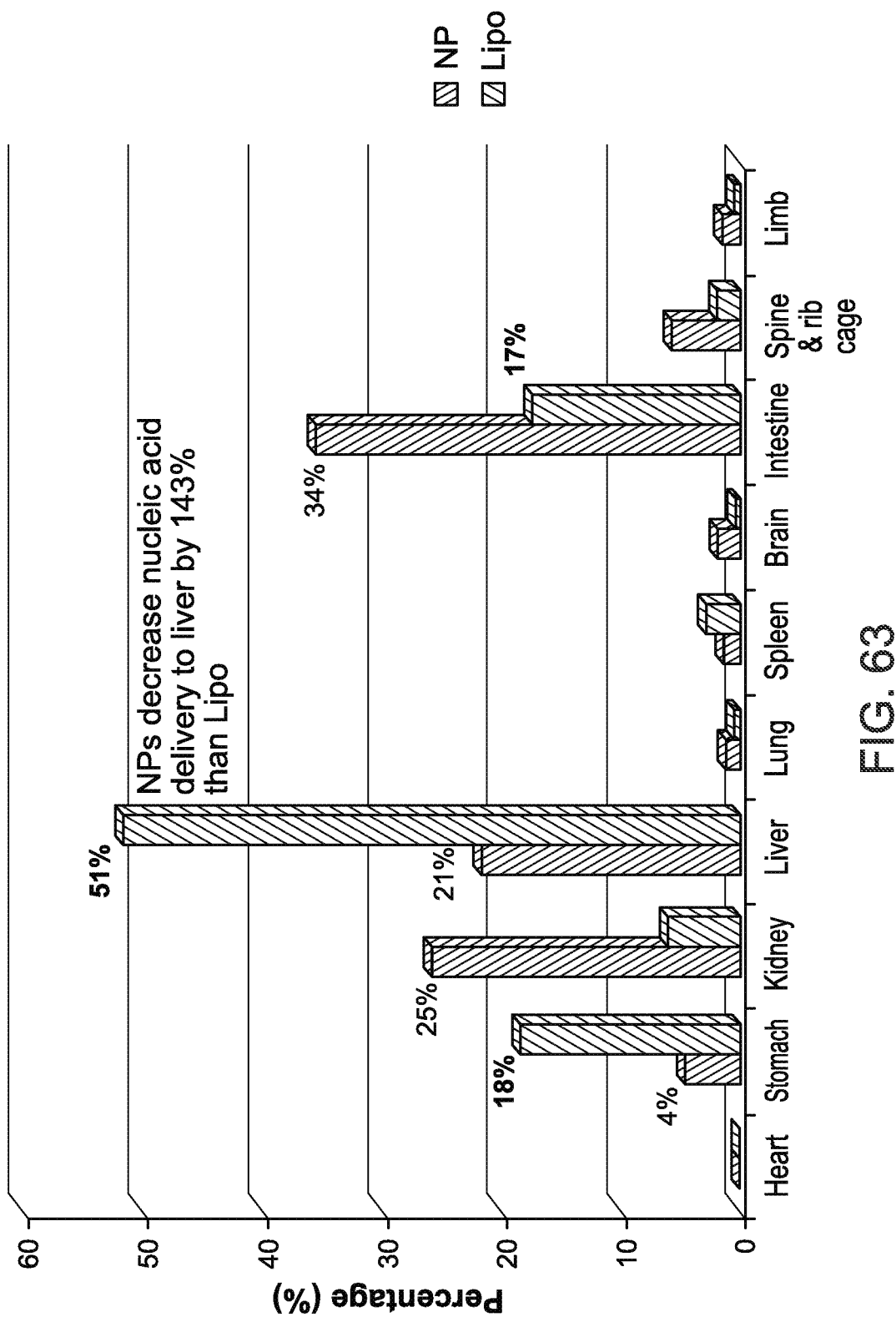
FIG. 63 is a bar graph showing the decreased liver capture with small Nanopieces compared to lipid vehicles.
Figure 64:
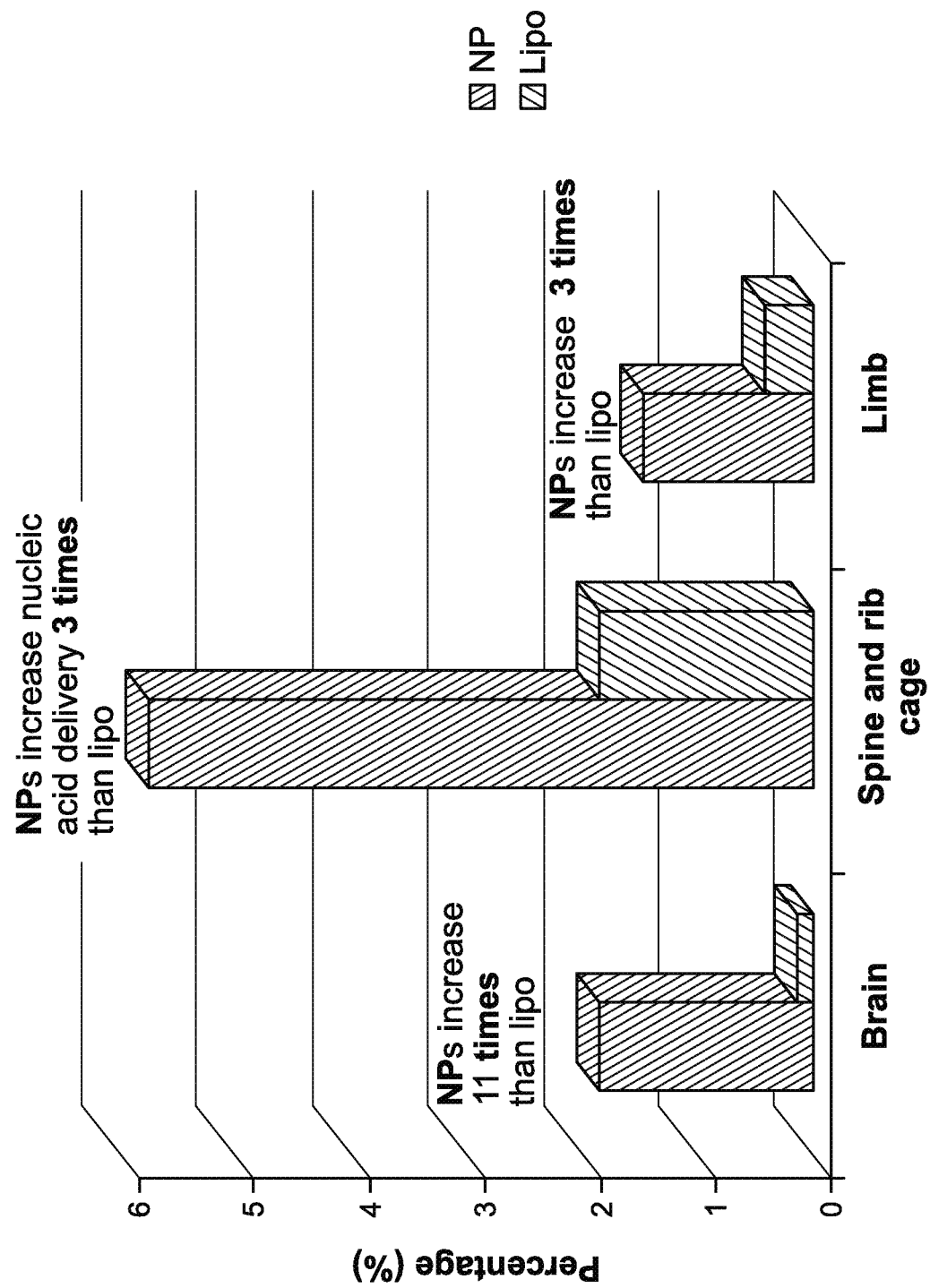
FIG. 64 is a bar graph showing increased delivery into tissues or organs with dense matrix with small Nanopieces.
Figure 65:
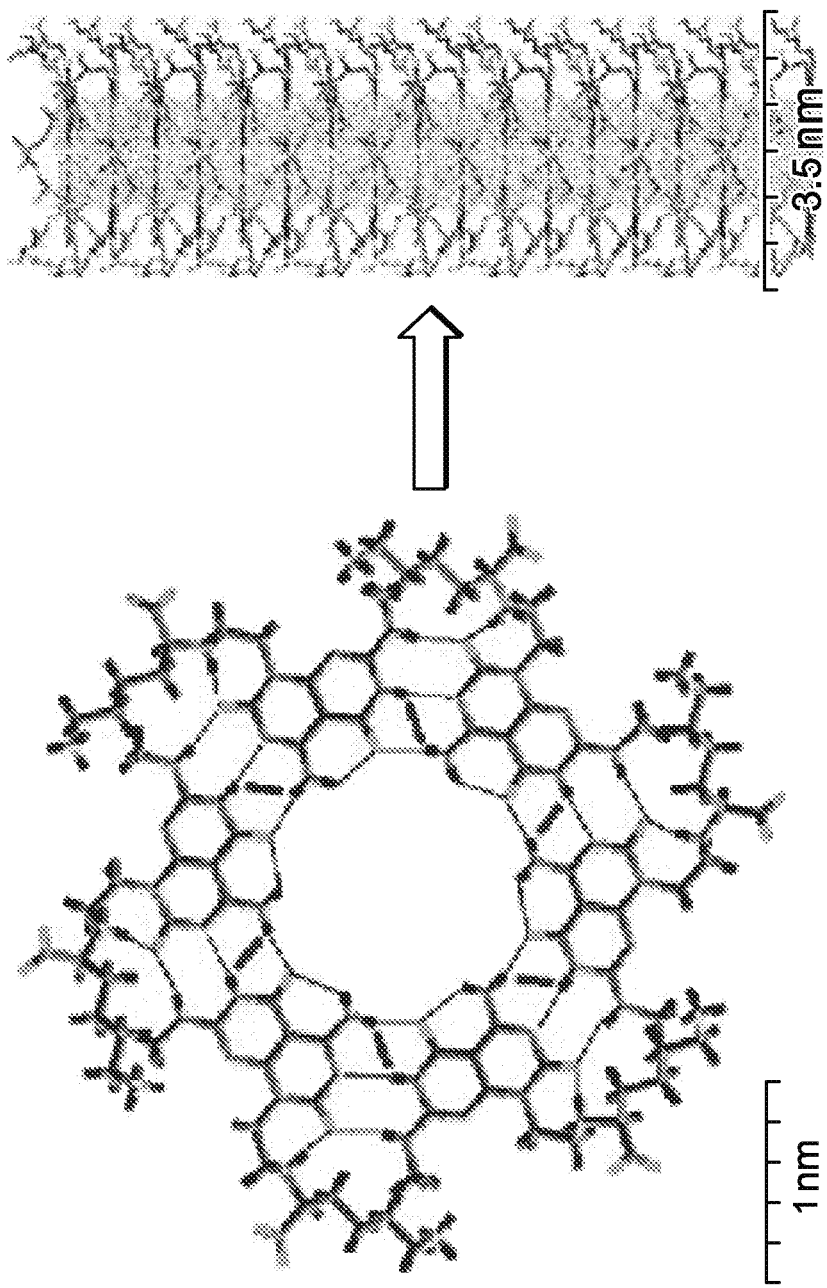
FIG. 65 is an illustration showing a structure of RNT. It is a long tubular structure with outside diameter of 3.5 nm, and inside diameter of 1.1 nm.

Another example was the use of small Nanopieces. Systemic injection of small Nanopieces into mice was carried out. Compared with conventional lipid delivery vehicles, small Nanopieces were found to be able to increase penetration into tissues and organs with dense matrix, which are difficult to infiltrate (such as brain, rib, spine and limb), as well as decreased liver capture (FIGS. 62-63). FIGS. 60-61 shows fluorescence labeled GAPDH molecular beacon delivered with small Nanopieces and also fluorescence labeled GAPDH molecular beacon delivered with large Nanopieces were co-injected into mouse knee joints, and the fluorescence signal was observed under a fluorescence microscope. FIGS. 62-64 shows Far fluorescence labeled GAPDH molecular beacon delivered with Nanopieces or with lipid particles were injected into mice via resto-orbital injection. After 24 hours, the mice were sacrificed and dissected. The fluorescence signal in each organs or tissue was recorded and via a fluorescence molecular tomography.

Example 6

Function

Figure 17:
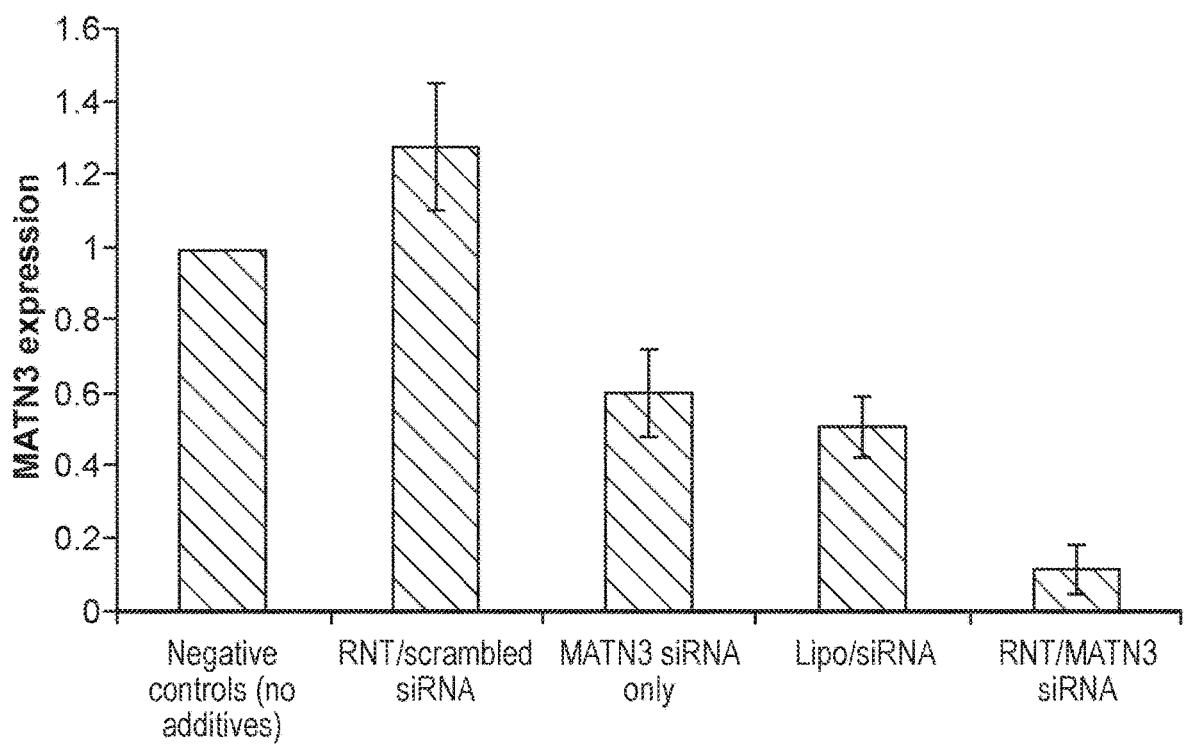
FIG. 17 is a graph showing functional delivery of processed MATN3 siRNA/RNT Nanopieces into mouse cartilage tissue matrix and inside chondrocytes.
Figure 18:
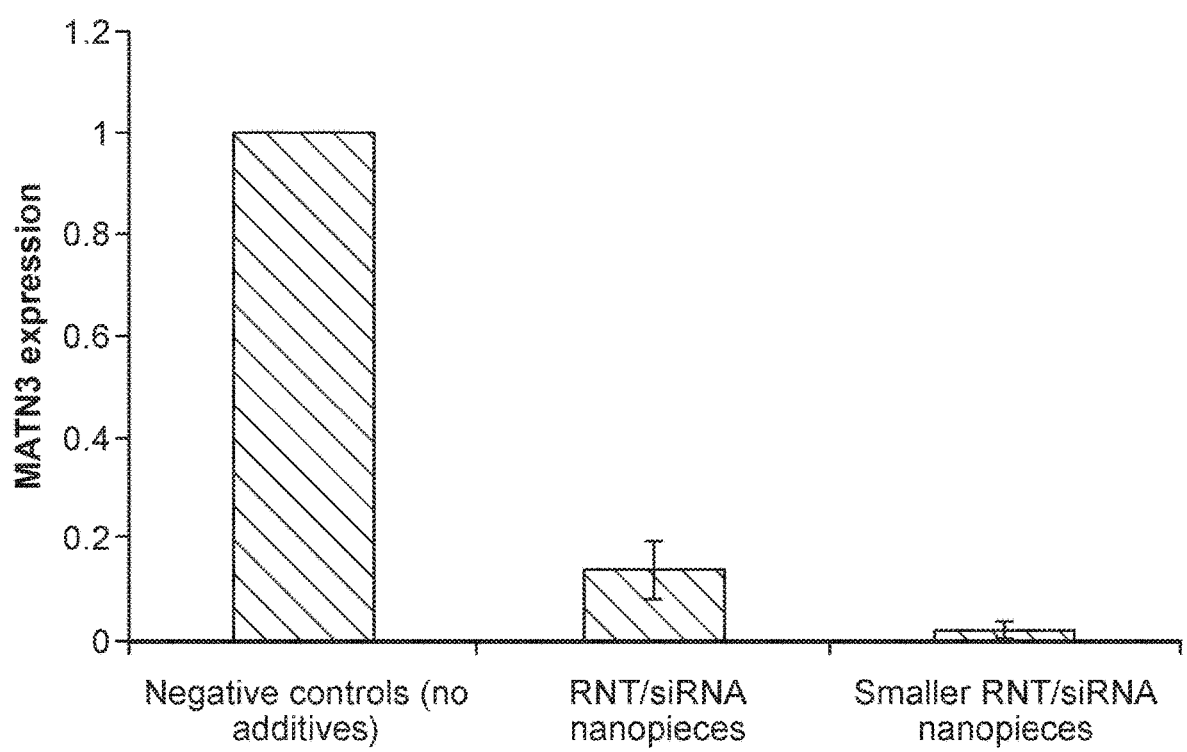
FIG. 18 is a graph showing functional delivery of processed MATN3 siRNA/RNT Nanopieces into mouse cartilage tissue matrix and inside chondrocytes.
Figure 19:
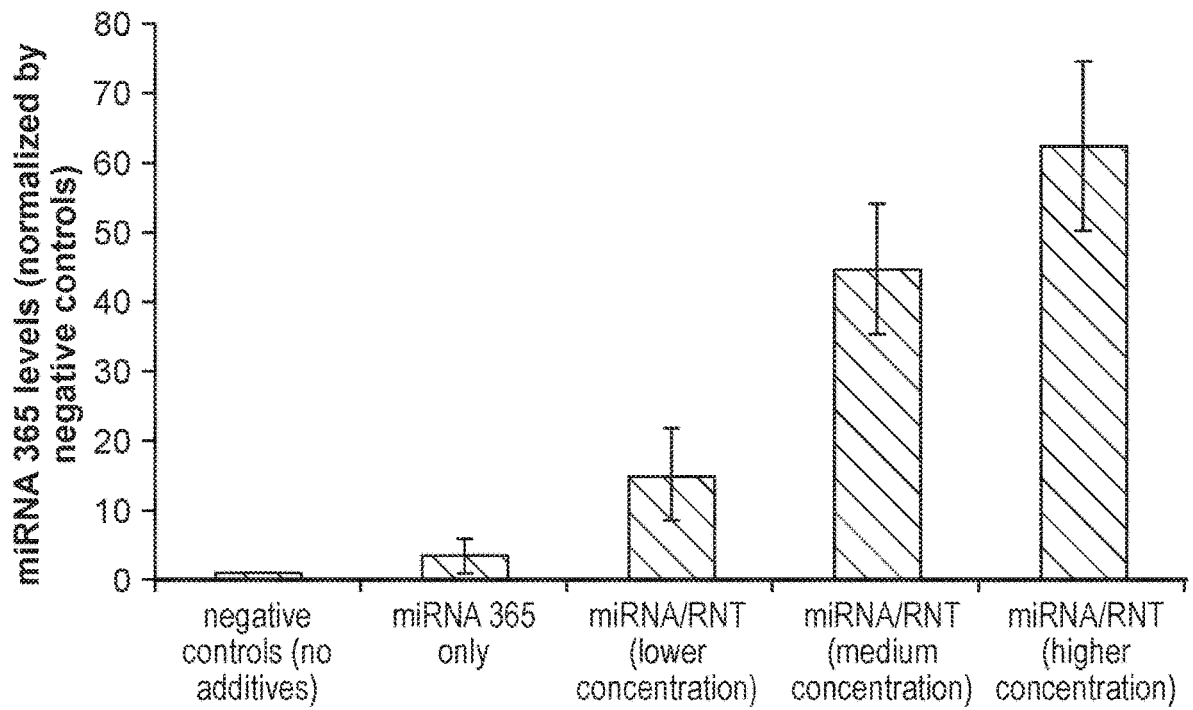
FIG. 19 is a graph showing functional delivery of processed miRNA365/RNT Nanopieces into human cartilage tissue matrix and inside chondrocytes.

Results showed delivery of Matrilin-3 (MATN3) siRNA/RNT Nanopieces into the mouse cartilage tissue matrix and cells with excellent biological function (FIGS. 17 and 18). Moreover, miRNA-365/RNT Nanopieces were functional, when delivered into human cartilage tissue matrix and cells (FIG. 19). The smaller processed Nanopieces resulted in higher Nanopiece delivery efficacy.

Example 6.1

MATN-3 siRNA was delivered with and without Nanopieces or Lipofectamine 2000 and soaked with mouse cartilage. The MATN-3 gene expression was determined via real time RT-PCR (FIG. 17).

Example 6.2

MATN-3 siRNA was delivered with unprocessed or processed Nanopieces and was soaked with mouse cartilage. The MATN-3 gene expression was determined via real time RT-PCR (FIG. 18).

Example 6.3

Various doses of miR-365 (0.1, 0.5 and 1.0 nmol) were delivered with Nanopieces and were soaked with human cartilage. The miR-365 expression was determined via real time RT-PCR (FIG. 19).

Example 7

Compositions

FIG. 20 shows that a composite of PEG increases Nanopiece delivery efficiency in a protein-rich environment (such as serum).

Example 8

In Vivo Delivery

Figure 21:
FIG. 21 is an image showing injection of reagents into mouse knee joints.
Figure 22:
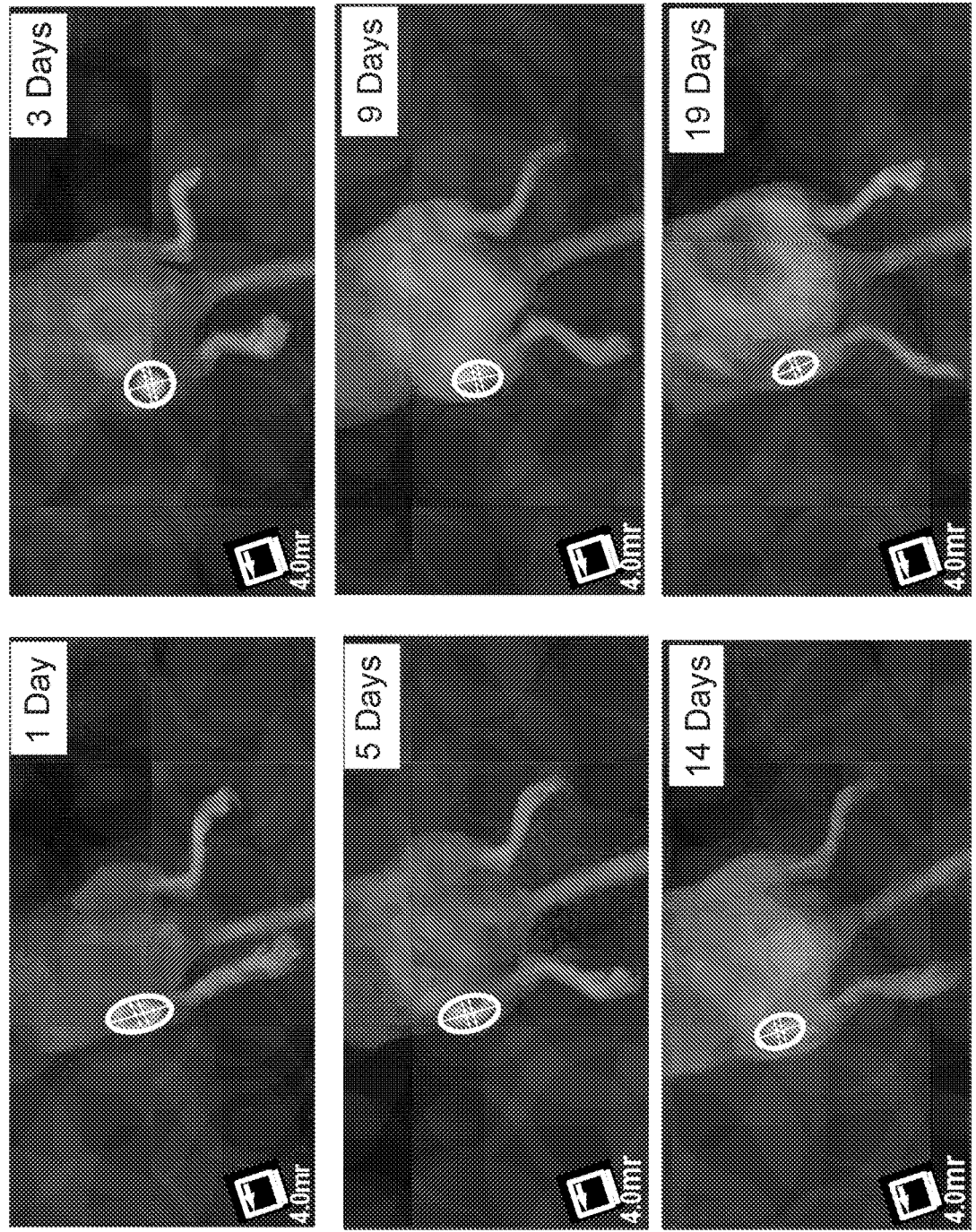
FIG. 22 is a series of images showing fluorescent signals in mouse cartilage tissue matrix over time by injecting processed RNT/beacon Nanopieces.
Figure 23:
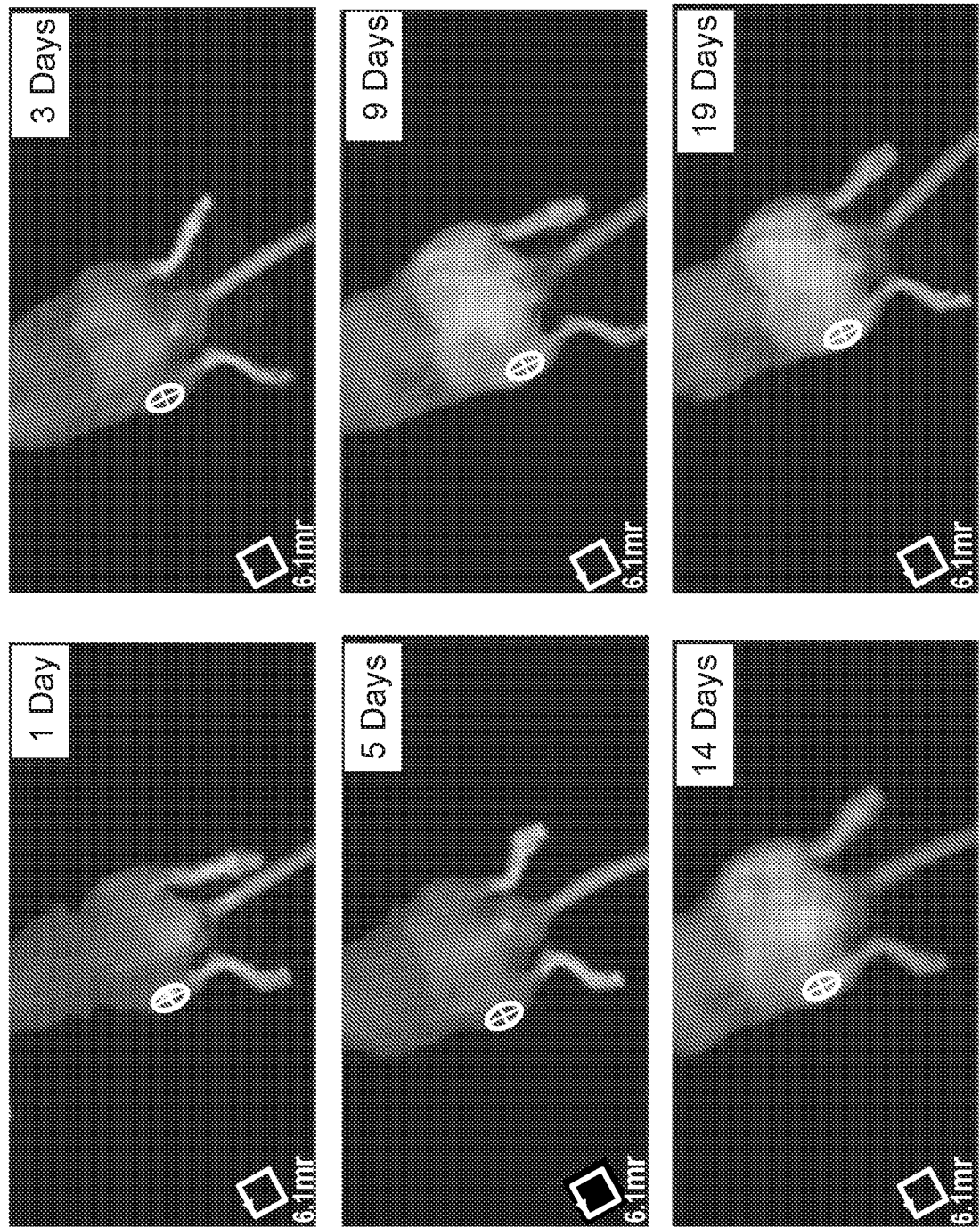
FIG. 23 is a series of images showing fluorescent signals in mouse cartilage tissue matrix over time by injecting molecular beacon only.
Figure 24:
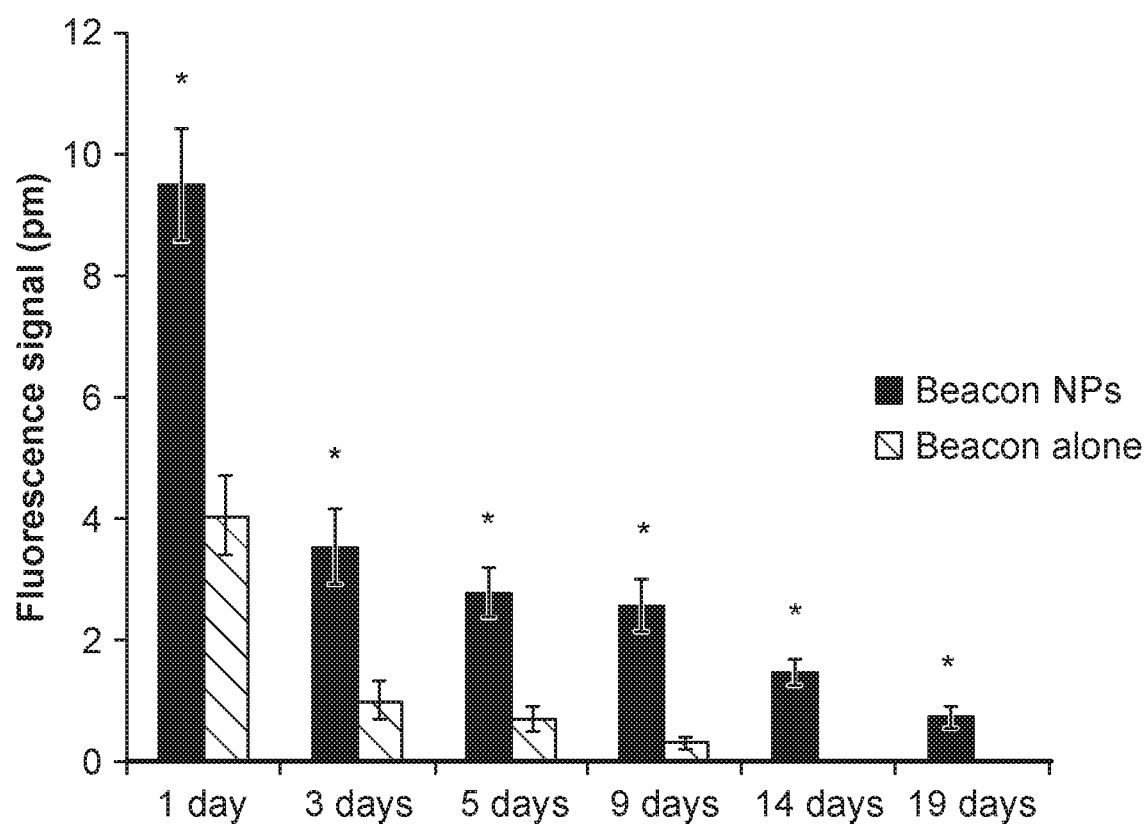
FIG. 24 is a graph showing quantitative fluorescent signals in mouse cartilage tissue matrix over time.
Figure 25:
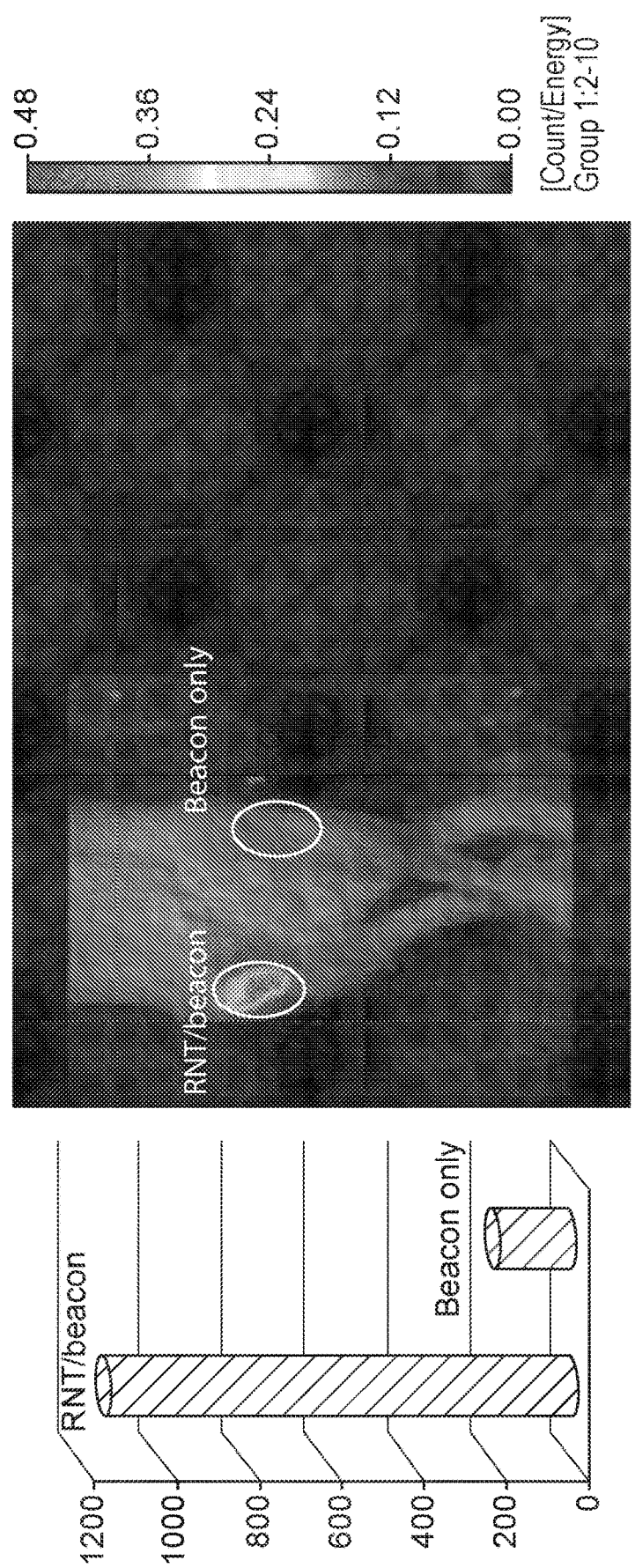
FIG. 25 is a graph and an image showing in vivo delivery of processed RNT/beacon Nanopieces into rat cartilage tissue matrix and inside chondrocytes compared with beacon only.
Figure 26:
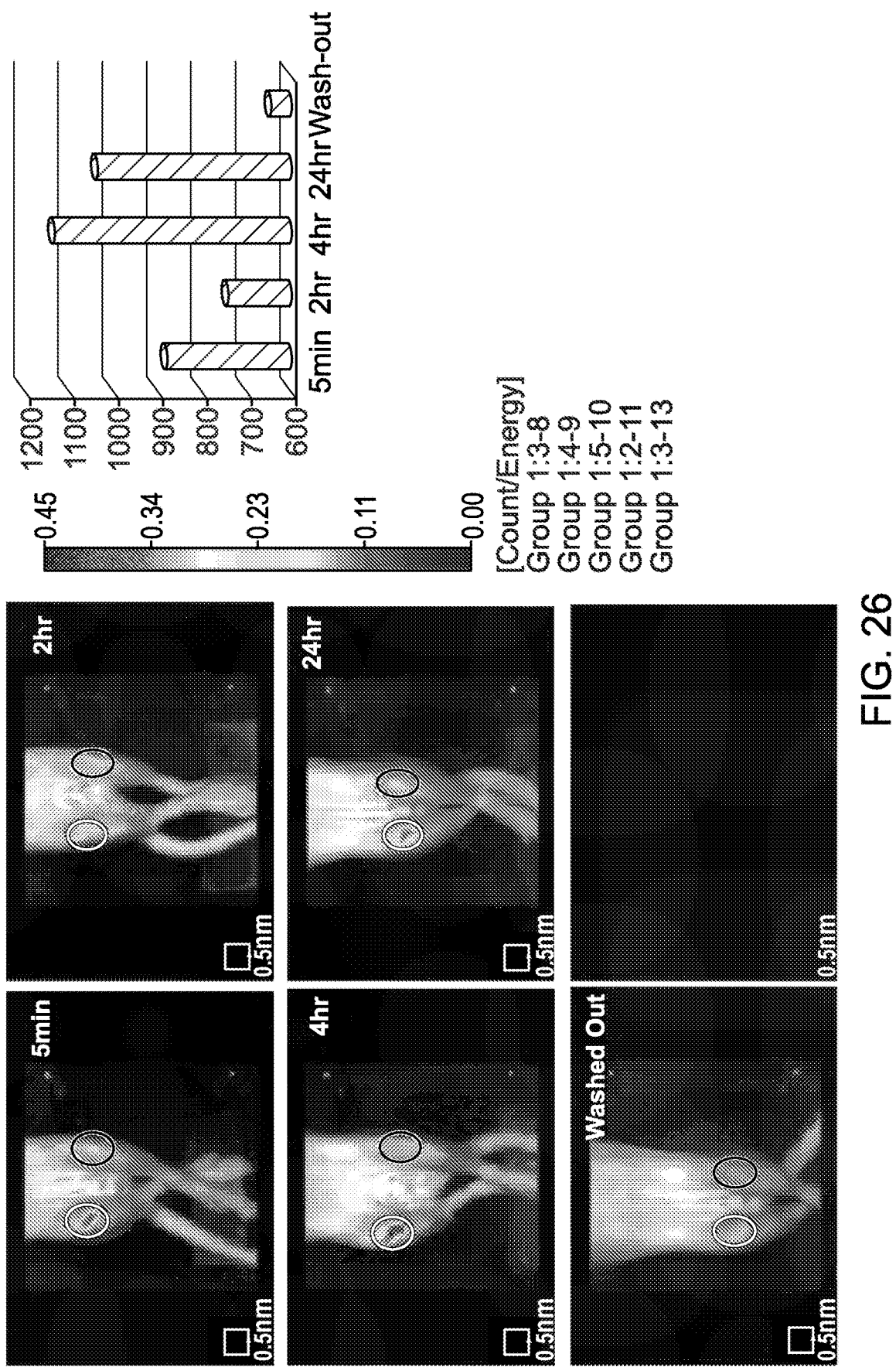
FIG. 26 is a series of images and a bar graph showing qualitative (Left) and quantitative (Right) in vivo delivery of processed RNT/beacon Nanopieces into rat cartilage tissue matrix and inside chondrocytes compared with beacon only.
Figure 27:
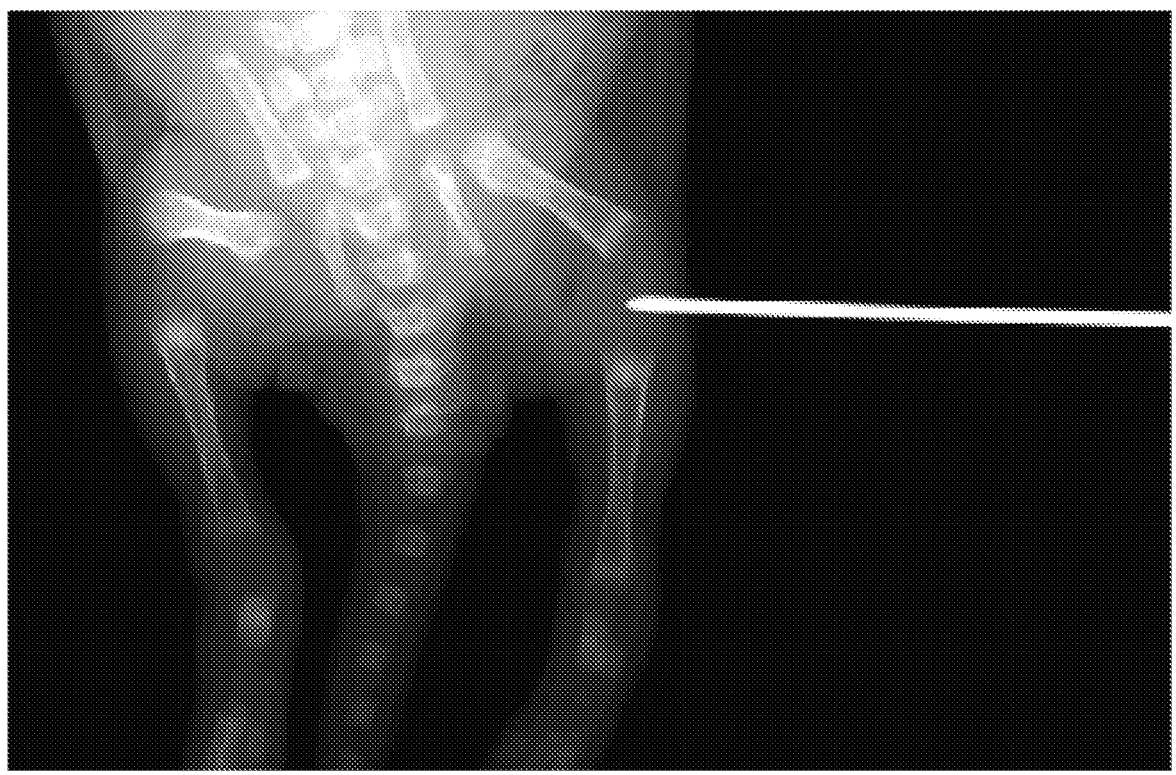
FIG. 27 is an image showing injection of reagents into baby mouse joints.

FIGS. 21 and 27 show injection of Nanopieces into an articulating joint. Injection of GAPDH molecular beacon/RNT Nanopieces into knee joints of a mouse (FIG. 21) resulted in a significant fluorescence signal compared with beacon only (in the absence of RNT Nanopieces). The signal lasted more than 2 weeks in the knees (FIGS. 22-24). In rats, a significant fluorescence signal was also obtained by injecting GAPDH molecular beacon/RNT Nanopieces into knee joints. The fluorescence signal was robust after washing out the adhered fluorescence molecules on the articular surface (FIGS. 25-26). Matrilin-3 siRNA Nanopieces were injected into knees of baby one-week-old mice and was found to be functional. Histology slides of cartilage sections confirmed the successful delivery of the Nanopieces (FIG. 28; light grey areas around the cell nuclei illustrate the fluorescence signal from molecular beacons. Effective in vivo trans-matrix/tissue delivery of processed Nanopieces (Nanopieces) was demonstrated in these experiments.

Example 8.1

Fluorescence labeled GAPDH molecular beacon was delivered with and without Nanopieces and injected into mouse knee joints. The fluorescence signal was recorded via fluorescence molecular tomography (FIGS. 22-24).

Example 8.2

Fluorescence labeled GAPDH molecular beacon was delivered with and without Nanopieces and injected into rat knee joints. The fluorescence signal was recorded via fluorescence molecular tomography (FIGS. 25-26).

Example 8.3

Figure 28:
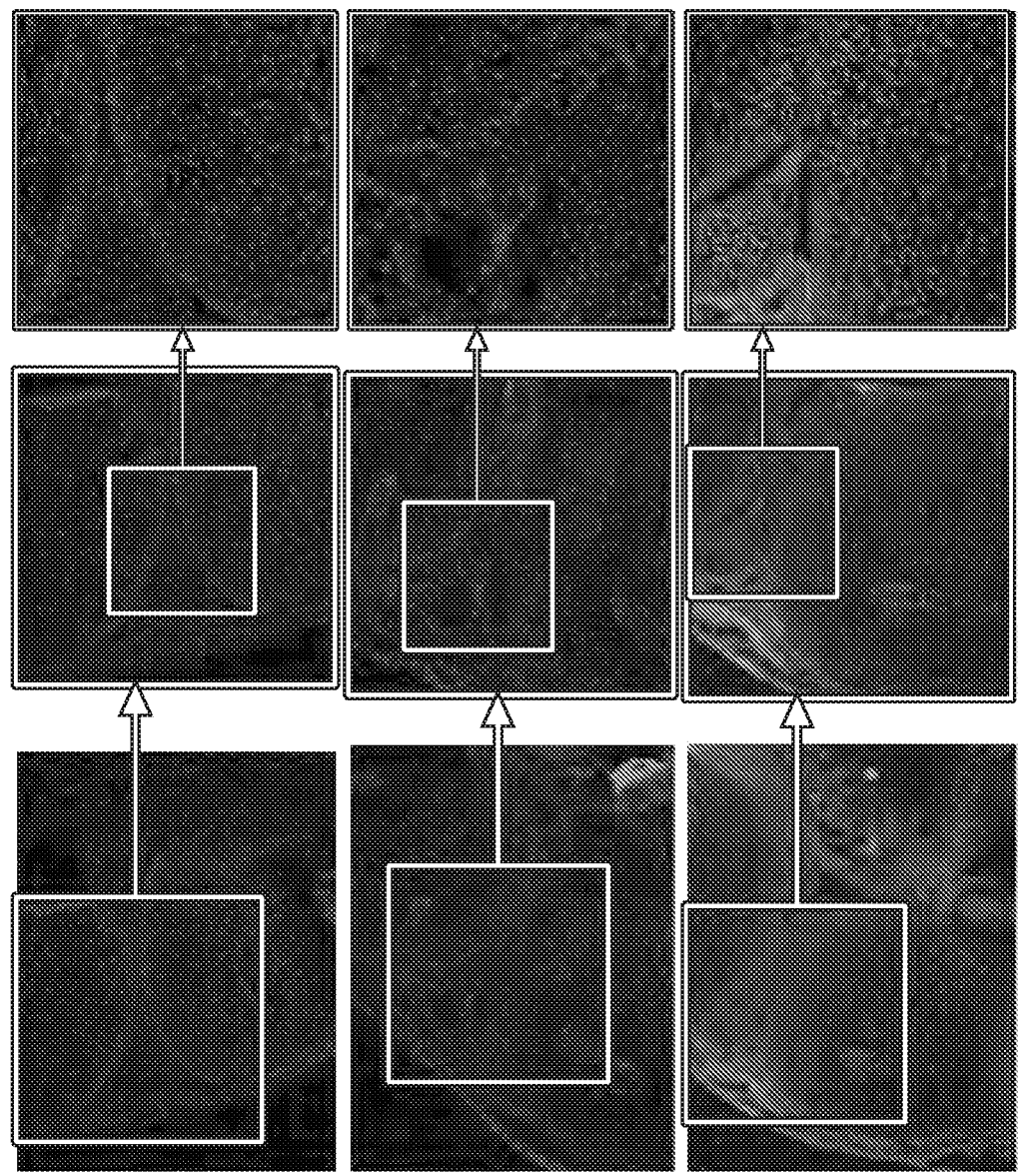
FIG. 28 is a series of images showing histology sections of cartilage delivered with RNTs only (Top), beacon only (Middle) and RNT/beacon Nanopieces (Bottom).

Fluorescence labeled GAPDH molecular beacon was delivered with and without Nanopieces and injected into baby mouse knee joints. The mouse was sacrificed and knee joint was sectioned for observation under a fluorescence microscope (FIGS. 27-28; light grey areas around the nuclei in FIG. 28 illustrate the fluorescence signal from molecular beacons.

Example 9

Diagnostics

Figure 29:
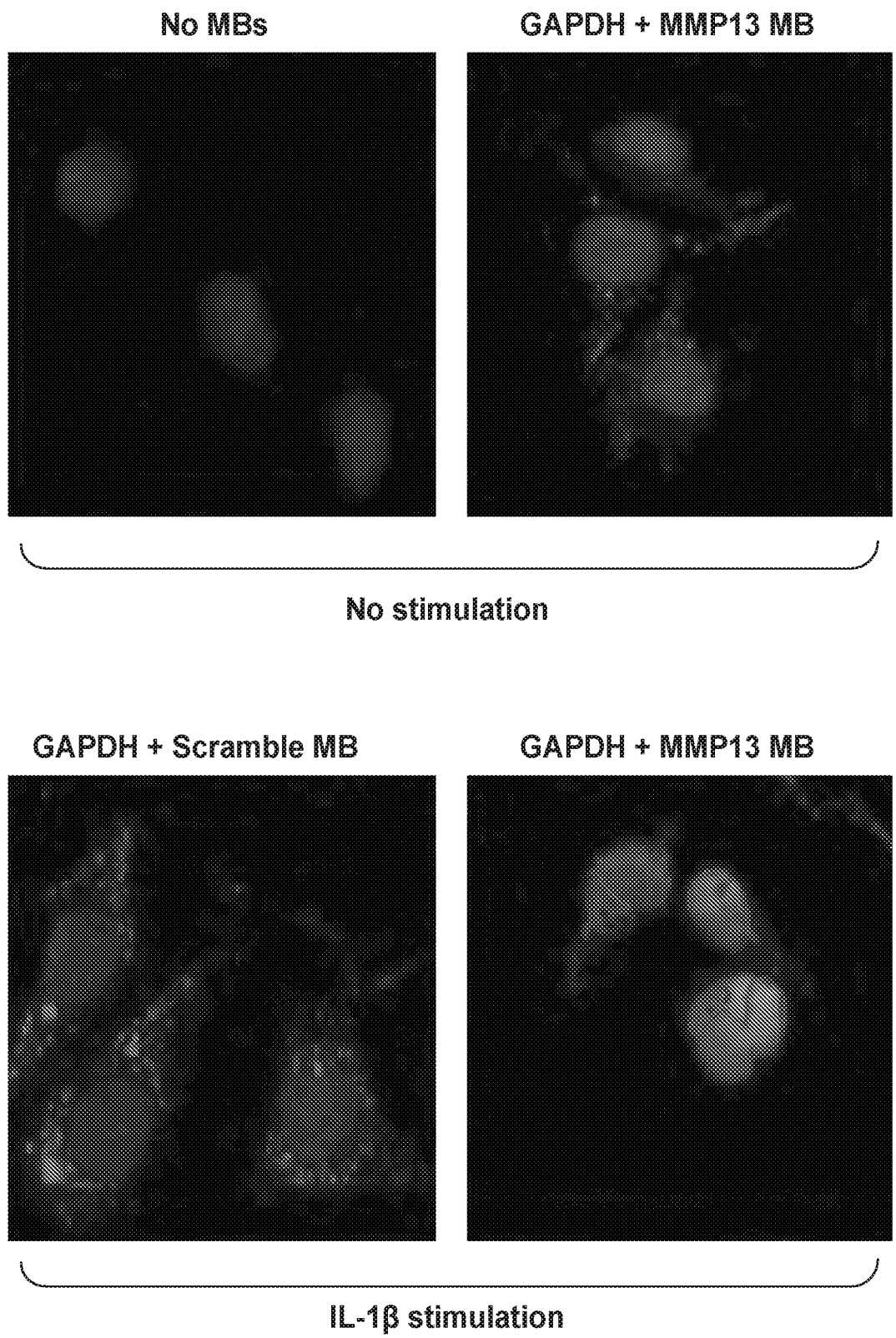
FIG. 29 is a series of images showing in vitro validation of MMP-13 molecular beacon.

To detect OA progression, MMP-13 was selected as a target gene. MMP-13 molecular beacon was designed and its function validated in vitro. As shown in FIG. 29, MMP-13 molecular beacon was delivered by methods described herein and found to emit fluorescence in chondrocytes after stimulation. Light areas shown in in FIG. 29 illustrate the fluorescence signal from molecular beacons. The MMP-13 molecular beacon was prepared according to the following procedure:
  Step one: Pre-heat RNT nanotubes solution, then quench it by placing tube on ice.
  Step two: Sonicate RNT nanotubes solution.
  Step three: Dilute MMP-13 molecular beacon or IL-1 beta receptor siRNA in water, then mix with RNT nanotubes solution in a certain ratio (50 pmol siRNA or 100 pmol molecular beacon to 5 ug RNT), then vertex well.
  Step four: Sonicate the mixture described in Step three, then spin all liquid down. MMP-13 molecular beacon or IL-1 beta receptor Nanopieces was assembled after Step four.
*Standard preparation only includes Step three and Step four. Joint preparation includes all steps.

Figure 30:
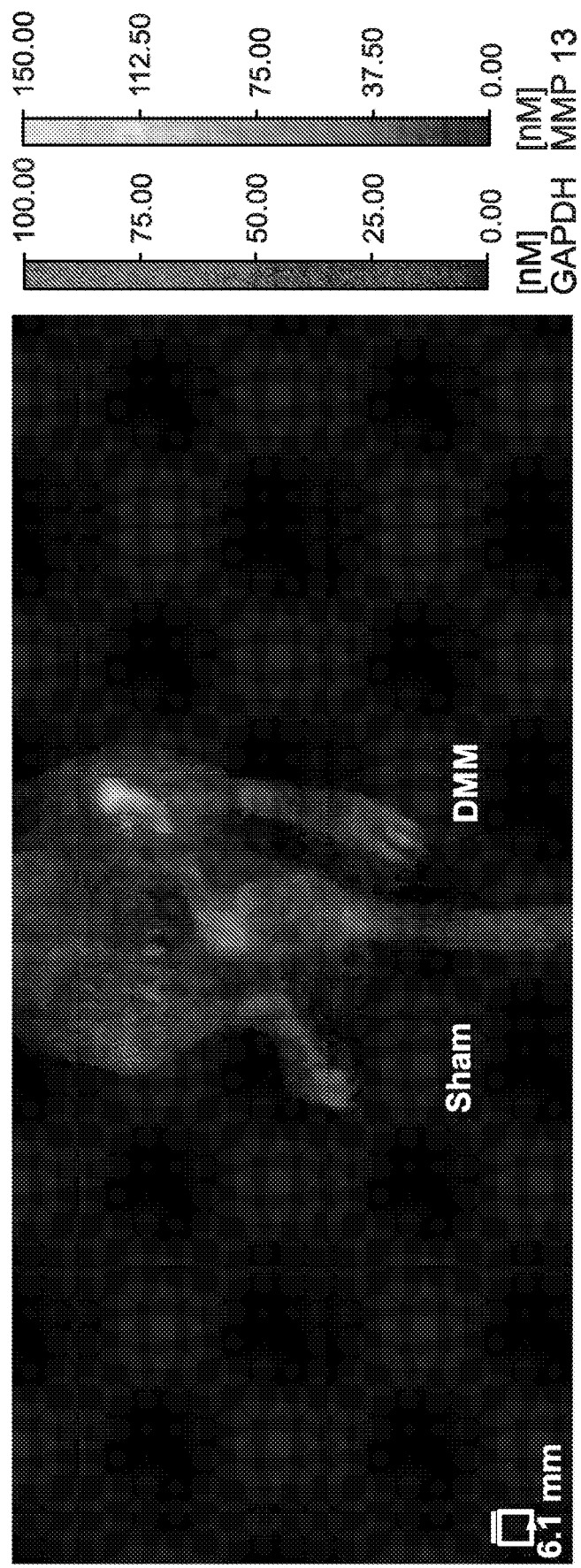
FIG. 30 is an image showing comparison of fluorescence signal between DMM and Sham knees (dark grey is GAPDH; light grey is MMP-13).
Figure 31:
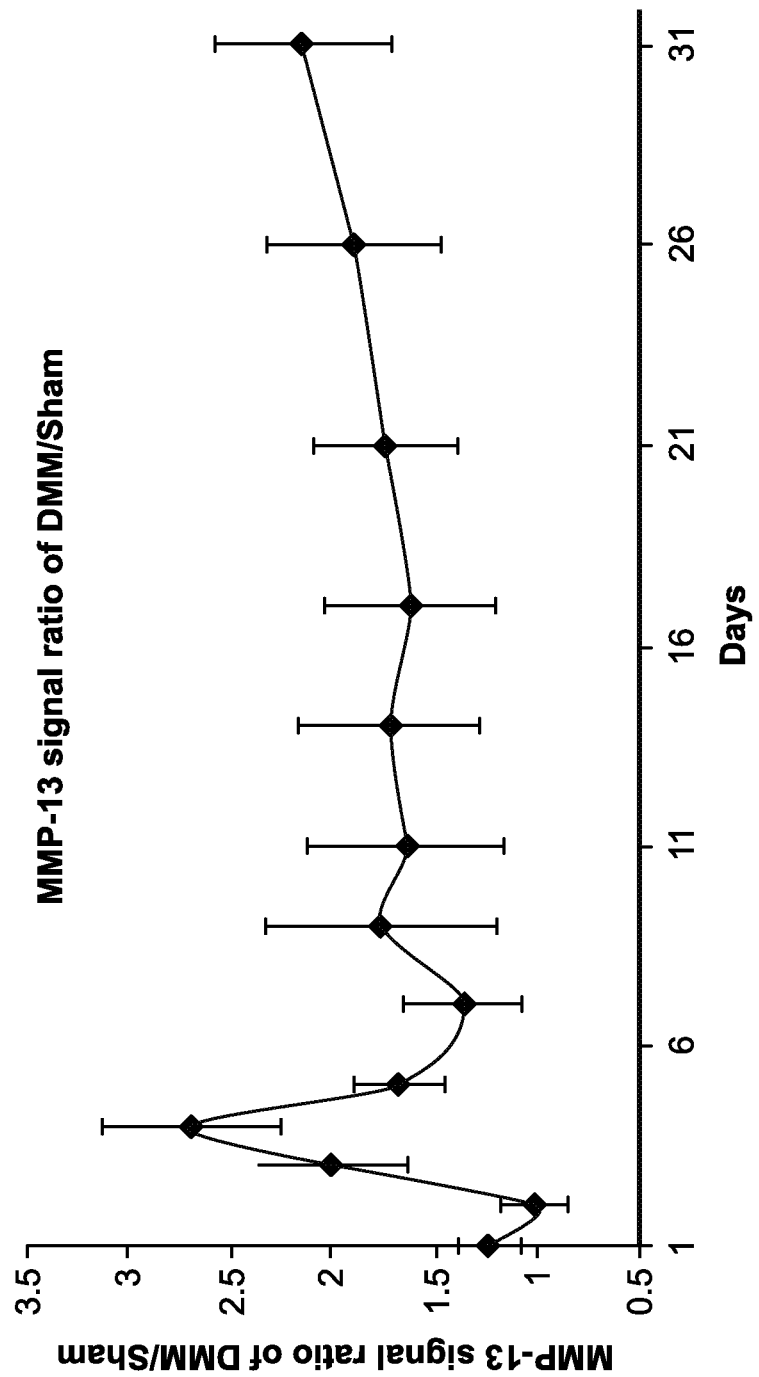
FIG. 31 is a graph showing DMM/Sham MMP-13 signal over time.
Figure 32:
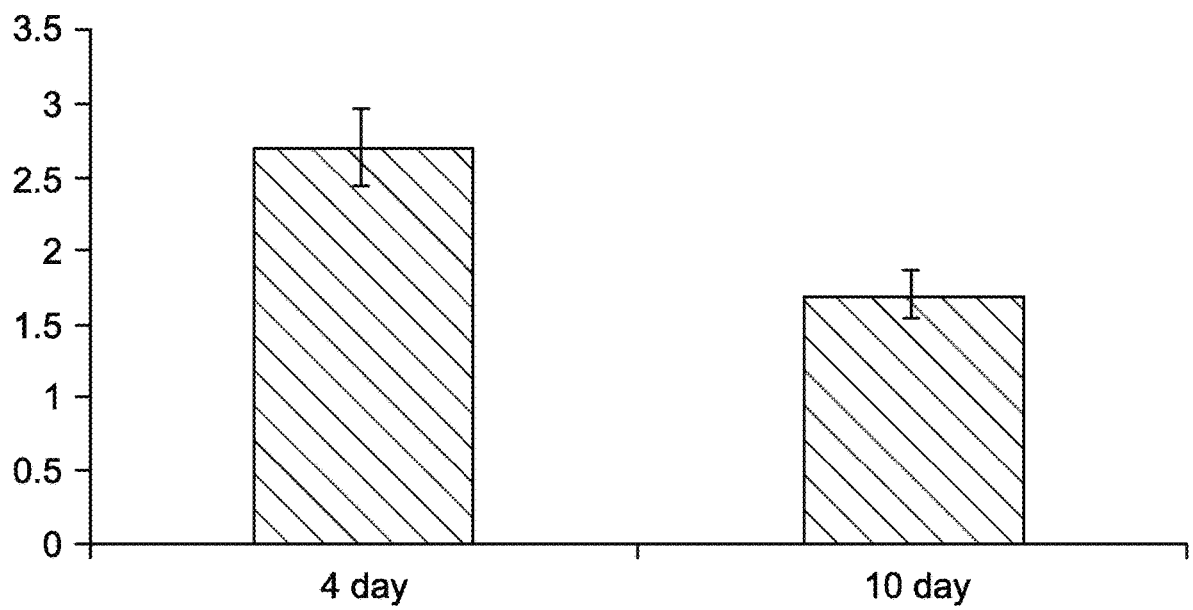
FIG. 32 is a graph showing DMM knee relative MMP-13 expression level.

For in vivo diagnosis, the medial meniscus (DMM) was destabilized to induce OA on one knee of the mice, whereas on the other knee a sham surgery was performed. Right after surgery, MMP-13 molecular beacon was delivered for target gene detection together with a non-targeting scrambled molecular beacon as a non-specific signal serving as a negative control. In addition a GAPDH molecular beacon for an internal house-keeping gene control was also administered. After 4 days, the knee with OA induction, showed a significantly stronger signal than the sham knee (FIG. 30). Moreover, using such a real-time, in-situ, non-invasive diagnosis approach, the signals between DMM and sham were quantitatively compared in a time-depend curve (FIG. 31). Methods were provided to continuously monitor a specific gene expression during OA progression in living animals. Moreover, animals were sacrificed at day 4 and day 11 to determine their MMP-13 expression level via real time RT-PCR. Results showed that the non-invasive diagnostic technology described herein accurately detected gene expression level compared with PCR (FIG. 32).

Figure 37:
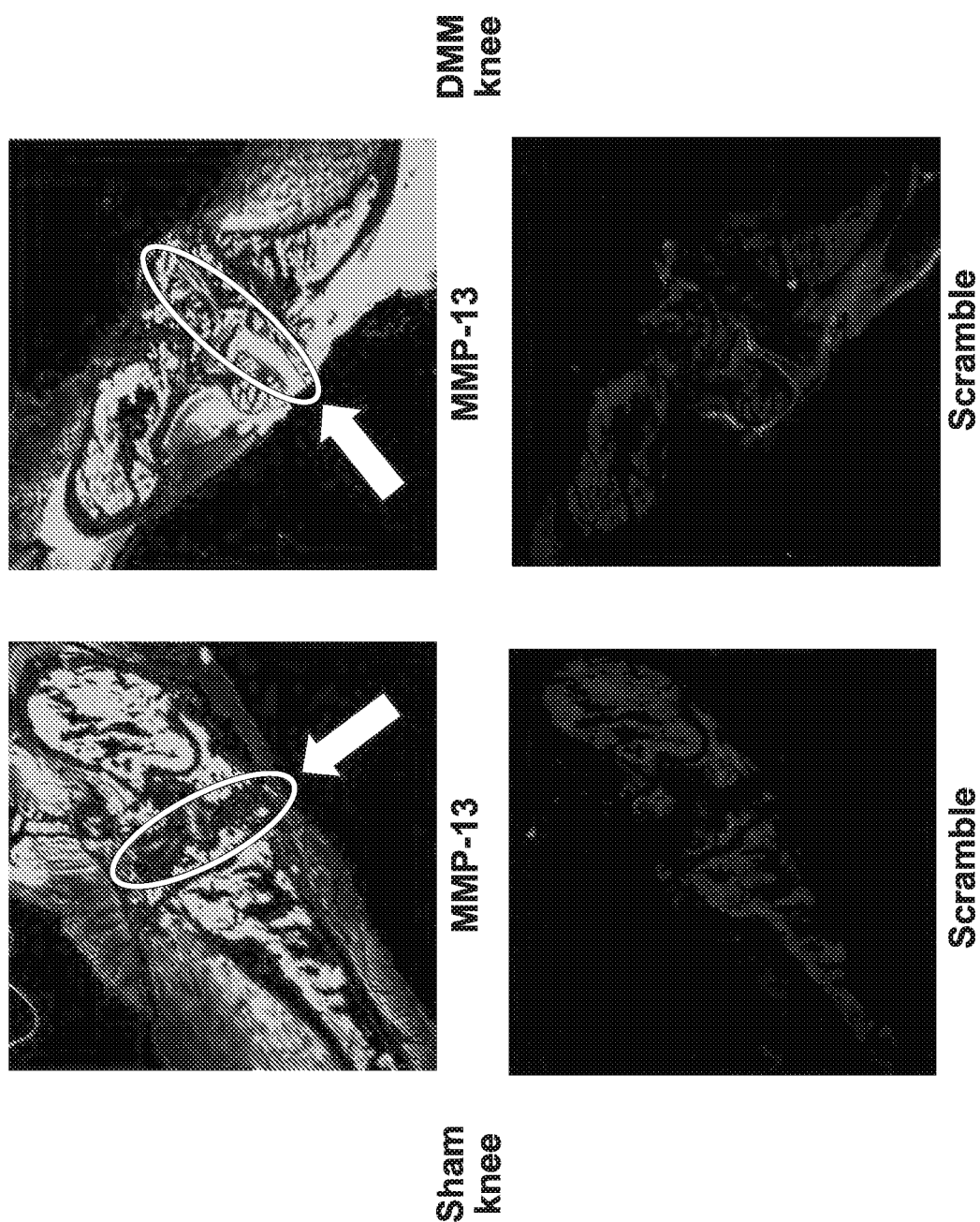
FIG. 37 is a series of images showing a comparison with fluorescence signal from scrambled molecular beacon, signal from MMP-13 molecular beacon indicating the area of MMP-13 expression and articular cartilage degeneration.
Figure 38:
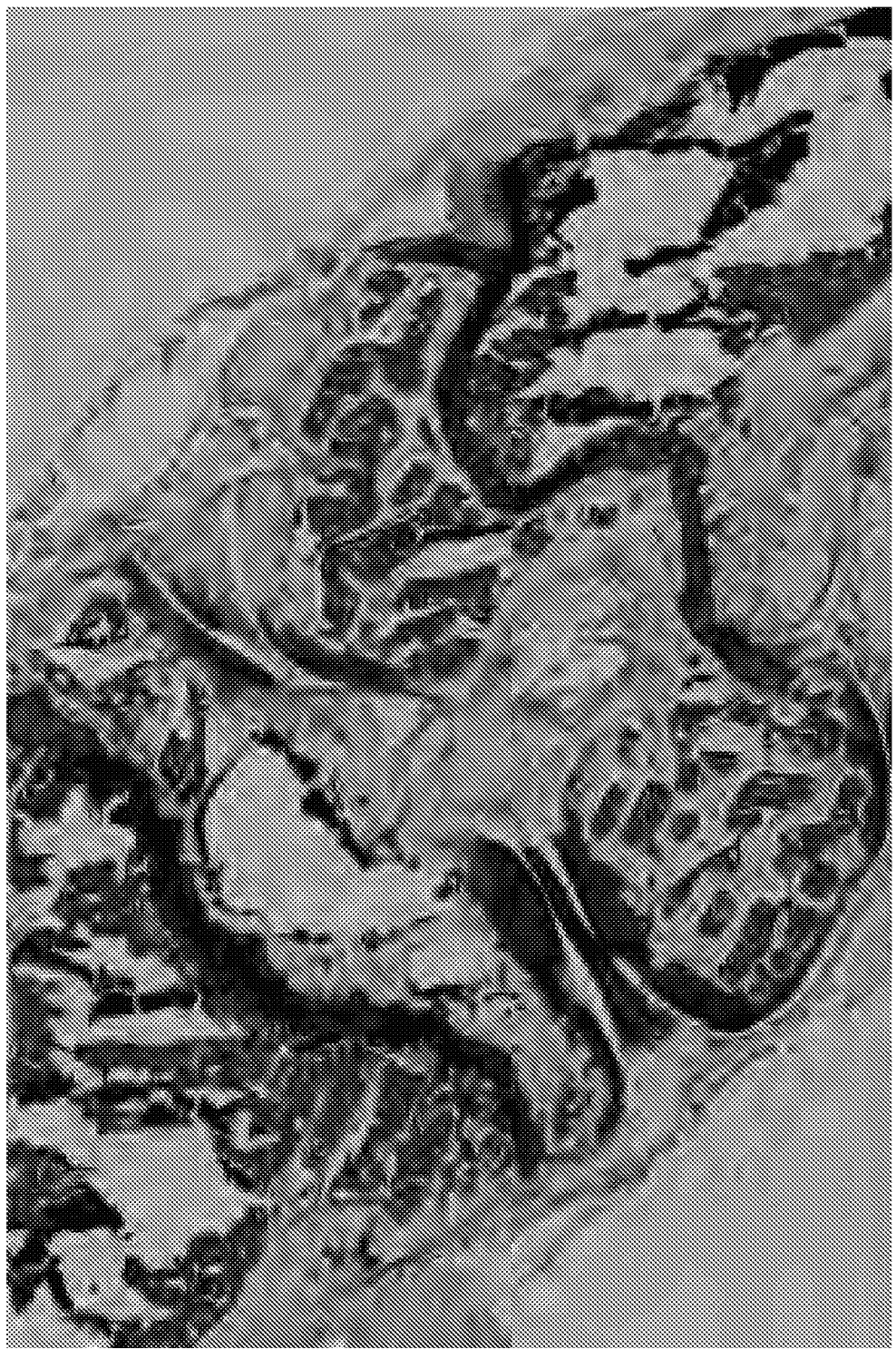
FIG. 38 is an image of histology staining of a mouse knee joint after DMM surgery. The area of cartilage degeneration is the same as what was indicated by MMP-13 molecular beacon.

Fluorescence and histology analysis showed that the damaged articular cartilage surface was the area emitting fluorescence signal from MMP-13 molecular beacon (FIGS. 37-38). In FIG. 37, ARROWs indicate the fluorescence signal as a result from MMP-13 molecular beacon. In FIG. 38, the dark grey color in articular cartilage was aggrecan staining. DMM surgery resulted in loss of aggrecan staining and damage to articular cartilage.

Figure 39:
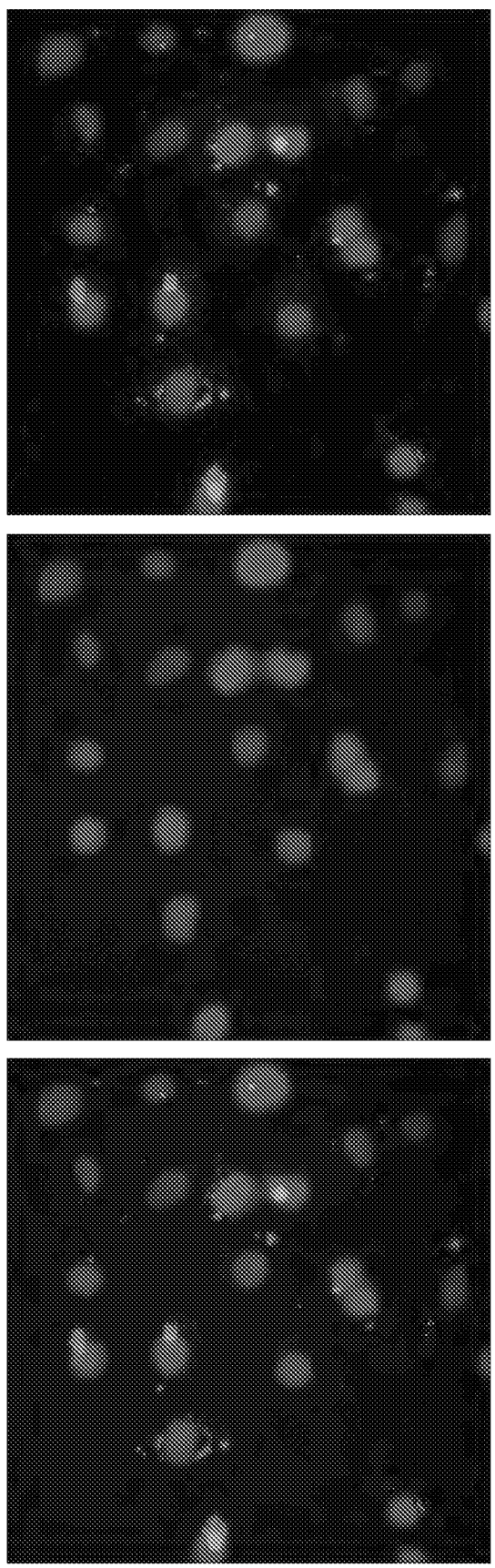
FIG. 39 is a series of images showing GAPDH and Scrambled molecular beacon delivered by Nanopieces into chondrocytes with stimulation.
Figure 41:
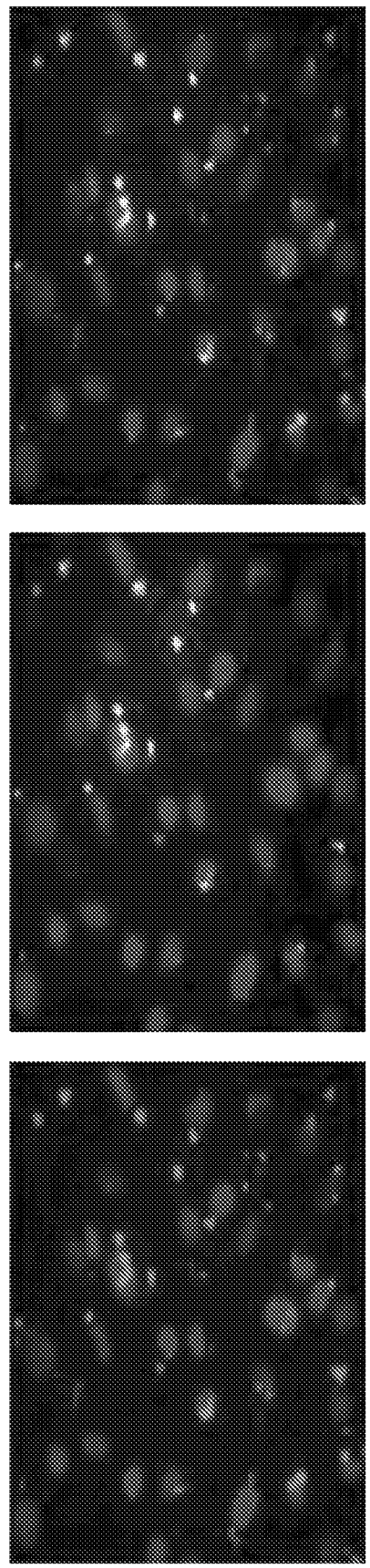
FIG. 41 is a series of images showing GAPDH and ADAMTS-5 molecular beacon was delivered by Nanopieces into chondrocytes with stimulation.
Figure 42:
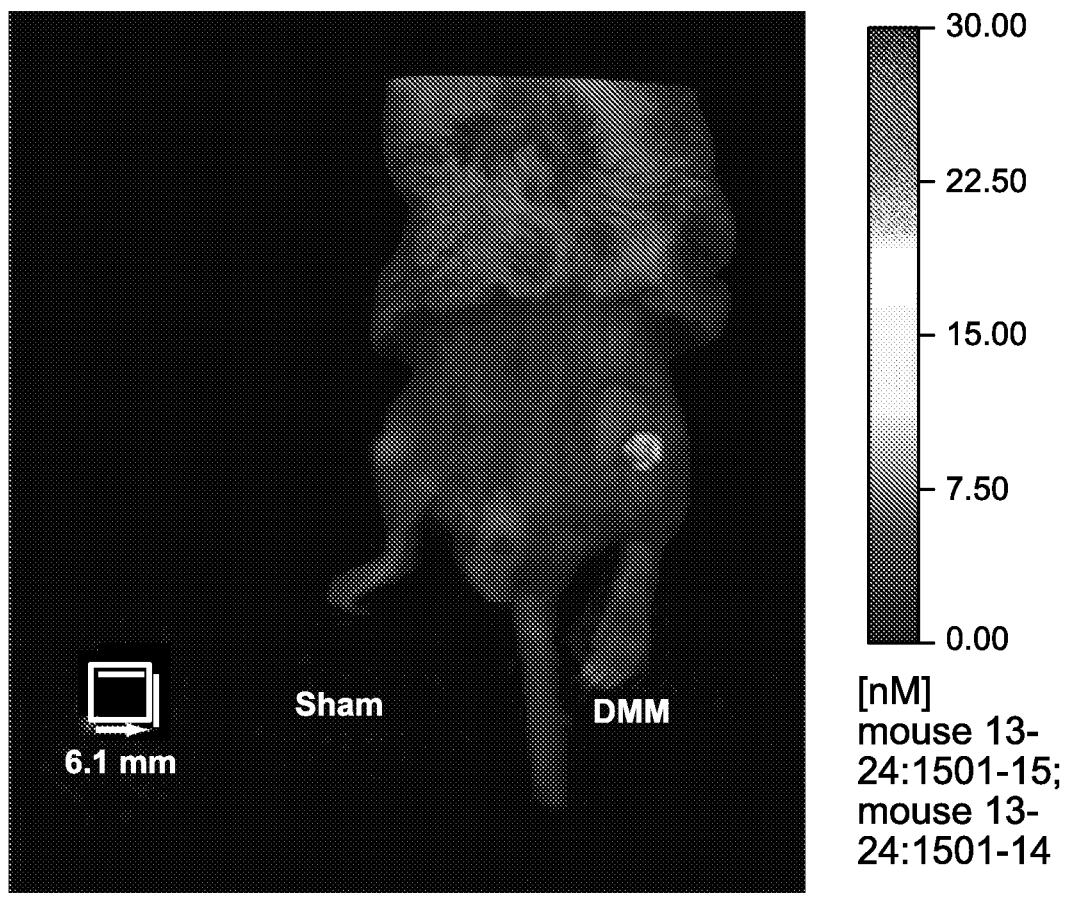
FIG. 42 is an image of fluorescence signal of ADAMTS-5 molecular beacon in DMM and Sham knees on day 6 after surgery.
Figure 43:
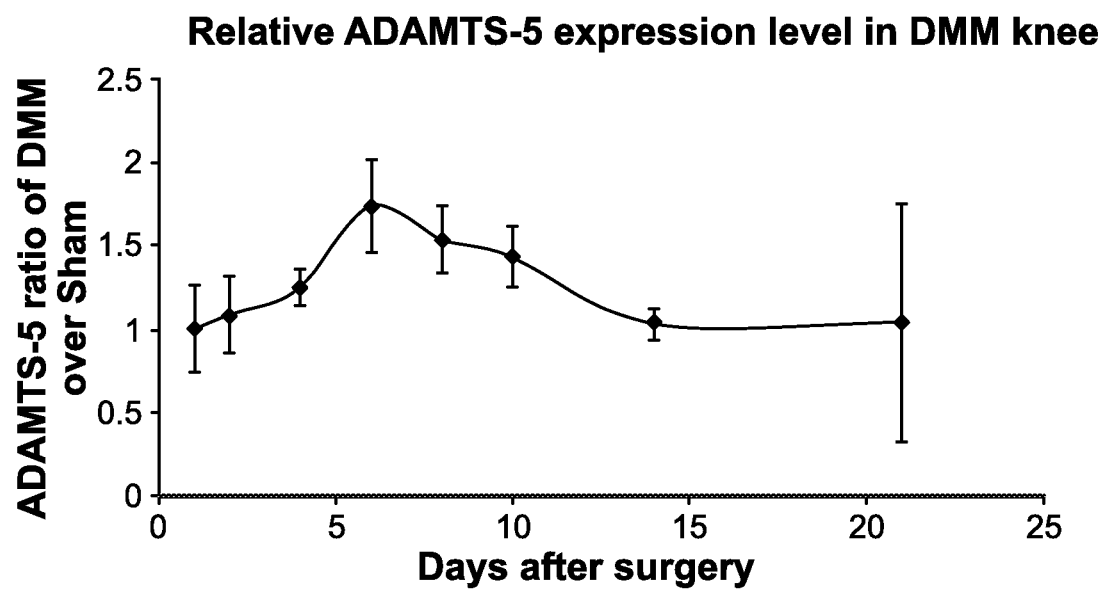
FIG. 43 is a graph showing fluorescence signal ratio of ADAMTS-5 molecular beacon in DMM knees over Sham knees after surgery.

In addition to MMP-13, ADAMTS-5 molecular beacon for OA diagnosis was also shown. Again, the ability of this molecular beacon to detect ADAMTS-5 gene expression in vitro was demonstrated (FIGS. 39-41; light grey areas around the cell nuclei in FIG. 39-41 are the fluorescence signal from molecular beacons. RED channel showed signal from GAPDH beacons; while GREEN channel showed signal from ADAMTS-5 or Scrambled beacons. The upregulation pattern of ADAMTS-5 during OA development was also shown (FIGS. 42-43).

These data indicate that the methods are useful for accurate and specific gene expression detection, thereby permitting reliable diagnosis in a real-time, in-situ and in a non-invasive manner in living animals.

Example 9.1

Fluorescence labeled GAPDH molecular beacon and fluorescence labeled MMP-13 molecular beacon or fluorescence labeled scrambled molecular beacon delivered with Nanopieces was added into chondrocytes under standard cell culture conditions or stimulated with 10 ng/mL IL-1β (FIG. 29).

Using an established method (Tyagi et al Nat. Biotech, 1998, 16:49-53), MBs were designed to target mouse MMP-13 or GAPDH mRNA with a fluorophore/quench pair. Scramble sequence MB (Scramble) was verified to not bind with any mouse mRNA via BLAST. In vitro delivery and validation: MBs were delivered into chondrocytes by Nanopieces. Specifically, after stimulation with IL-1β for 24 hours, chondrocytes were co-transfected GAPDH and scramble MBs or GAPDH and MMP-13 MBs via Nanopieces. Real time RT-PCR and fluorescence microscopy were used to verify the stimulation of MMP-13 expression and the successful fluorescence signal resulted from MMP-13 MB.

To test the efficacy of mRNA detection in chondrocytes using MBs delivered by Nanopieces, primary mouse chondrocytes were transfected with MBs either with or without IL-1β treatment. Before IL-1β treatment, the housekeeping GAPDH MB was detected while the MMP-13 MB was not (FIG. 29, left panels). In contrast, after IL-1β treatment, both GAPDH MB and MMP-13 MB were detected, indicating the induction of MMP-13 mRNA levels by IL-1β (FIG. 29, right panels). Realtime rtPCR showed that MMP-13 mRNA level was up-regulated by about 10 times upon IL-1β stimulation. In contrast, Scramble MB transfection did not show any fluorescence, indicating that the fluorescence of MMP-13 MB was not due to non-specific degradation.

Example 9.2

Figure 50:
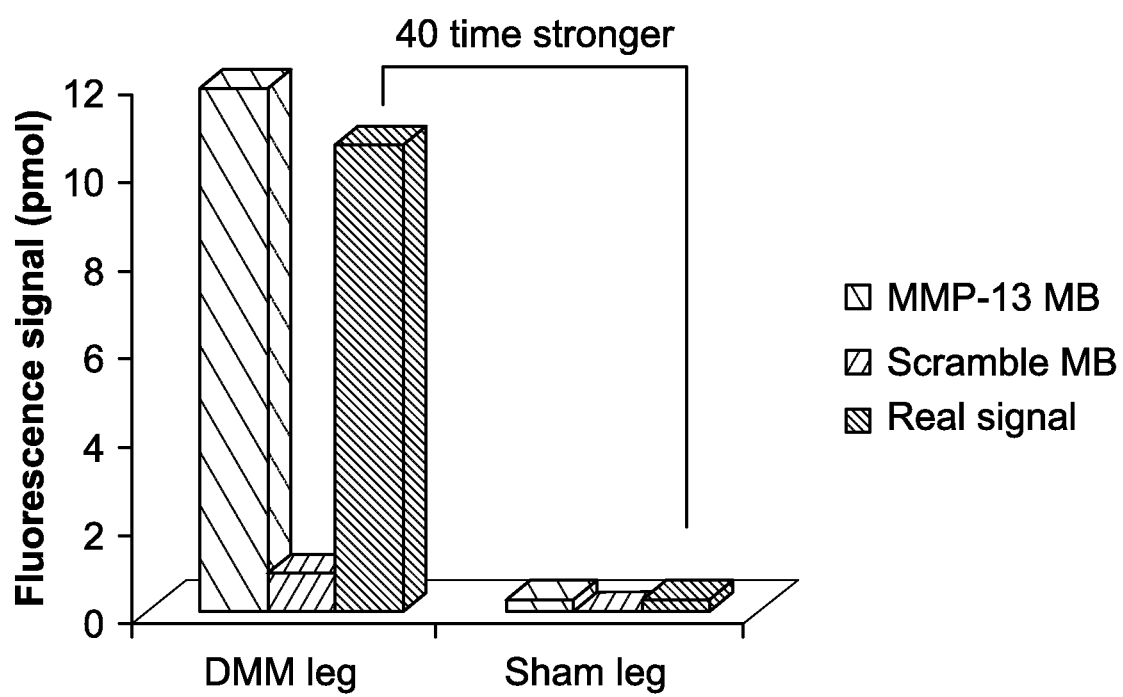
FIG. 50 is a graph showing quantitative analysis of fluorescence signal in mouse knee.

Fluorescence labeled GAPDH, MMP-13 and Scrambled molecular beacon delivered with Nanopieces was injected into mouse knee joints after destabilization of medial meniscus (DMM) surgery or Sham surgery, and then the fluorescence signal was recorded and analyzed via a fluorescence molecular tomography (FIGS. 30-31). DMM or sham surgeries were performed on 10-week-old 129SVE male mice to induce osteoarthritis. One week after surgery, MMP-13 and scramble MBs with different fluorophores delivered by Nanopieces were injected into knee joints of mice. Small animal fluorescence molecular tomography (FMT) was used to determine the fluorescence signal that resulted from MMP-13 expression in the live animals for 3 weeks. The Scramble MB showed low fluorescence in both DMM and Sham surgery knee joints. After subtracting Scramble MB basal level signals, MMP-13 MB real signal was about 40 times stronger in the DMM leg than the sham leg (FIGS. 50, and 54-55). Such MMP-13 MB signals persisted, even for 3 weeks after injection of MBs.

Example 9.3

Mouse knee joint cartilage was isolated 4 days or 10 days after DMM or Sham surgery, and MMP-13 expression was determined via real time RT-PCR (FIG. 32).

Example 9.4

Fluorescence labeled MMP-13 molecular beacon and Scrambled molecular beacon delivered with Nanopieces was injected into mouse knee joints after DMM or Sham surgery. After 30 days, the animals were sacrificed and their knee joints were sectioned for histology and fluorescence scan (FIGS. 37-38).

Example 9.5

Fluorescence labeled GAPDH molecular beacon, fluorescence labeled ADAMTS-5 molecular beacon or fluorescence labeled Scrambled molecular beacon delivered with Nanopieces was added into chondrocytes under standard cell culture conditions or stimulated with 10 ng/mL IL-1α and 10 μM retinoic acid (FIGS. 39-41).

Example 9.6

Fluorescence labeled GAPDH, ADAMTS-5 and Scrambled molecular beacon delivered with Nanopieces was injected into mouse knee joints after DMM or Sham surgery, and then the fluorescence signal was recorded and analyzed via a fluorescence molecular tomography (FIGS. 42-43). FIG. 42 shows a stronger fluorescence signal resulting from ADAMTS-5 molecular beacon in DMM surgery leg than Sham leg. FIG. 43 shows the pattern of ADAMTS-5 expression after surgery.

Example 10

Therapeutics

Figure 33:
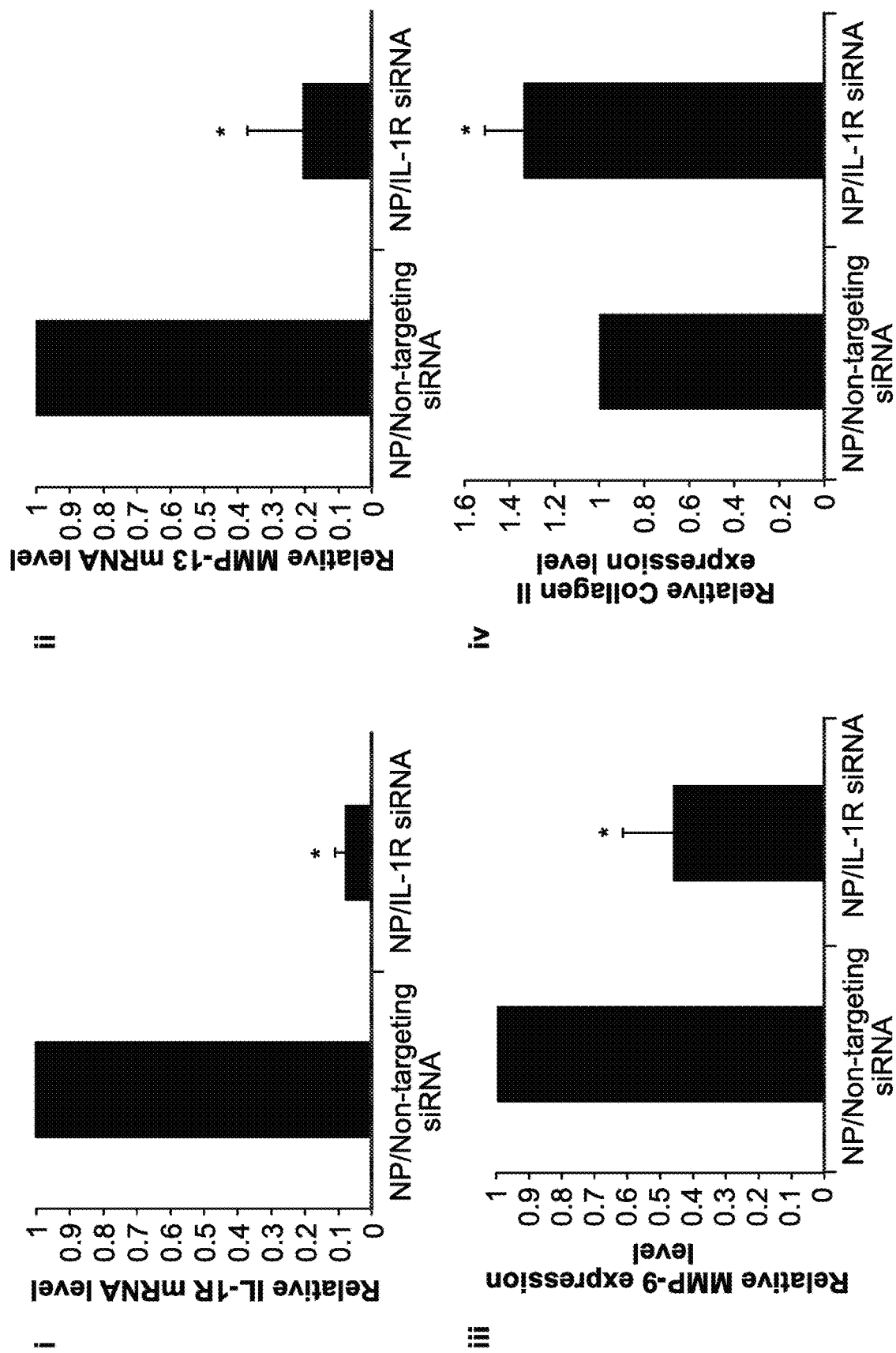
FIG. 33 is a series of graphs showing relative IL-1R, MMP-13, MMP-9 and Col II gene expression level after therapeutically knock down of IL-1R.

IL-1 receptor (IL-1R) siRNA/Nanopieces were injected into one knee of mice and non-targeting scrambled siRNA/Nanopiece was injected into the other knee. Cartilage degeneration was stimulated with catabolic cytokine (such as IL-1β) in both knees mimicking an inflammation environment during arthritis. Successful knock down of IL-1R in chondrocytes in mouse cartilage was observed with Nanopiece delivery of IL-1R siRNA in vivo (FIG. 33). Moreover, cartilage degeneration genes (such as MMP-13 and MMP-9, FIG. 33) were down-regulated and cartilage anabolic genes (such as Col II, FIG. 33) were up-regulated.

Nanopieces were used to deliver ADAMTS-5 siRNA into knee joints of mice that had been treated with cytokines (IL-1α and retinoic acid). Results showed that cartilage degeneration and aggrecan cleavage was significantly inhibited after ADAMTS-5 siRNA treatment (FIG. 34). In the top two panels, the dark grey color in articular cartilage was aggrecan staining. Without ADAMTS-5 siRNA treatment, aggrecan staining is weaker than the treatment group, indicating loss of aggrecan. In the bottom two panels, dark staining around the cell nuclei was epitope staining from aggrecan cleavage. Without ADAMTS-5 siRNA treatment, the staining is stronger than the treatment group, indicating cleavage of aggrecan.

Figure 35:
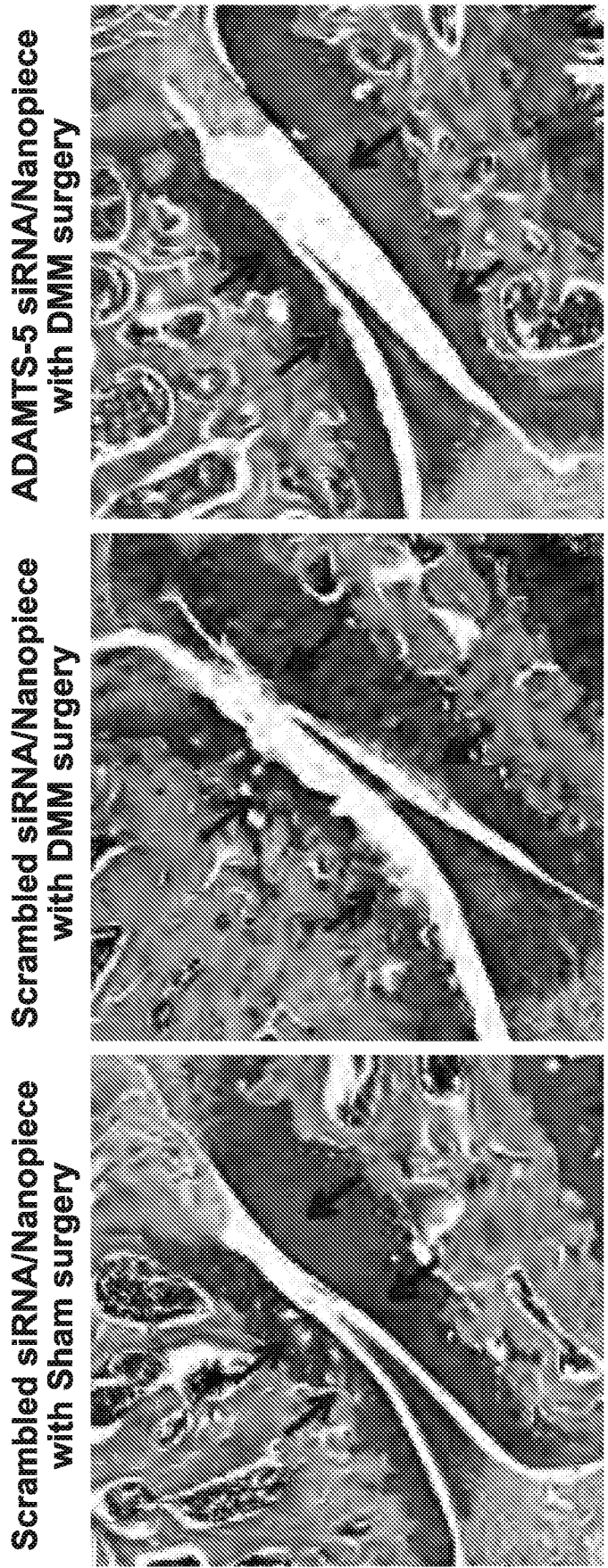
FIG. 35 is a series of images showing histology of mouse knee joints. ADAMTS-5 siRNA/Nanopiece greatly inhibited cartilage degeneration after DMM surgery.
Figure 36:
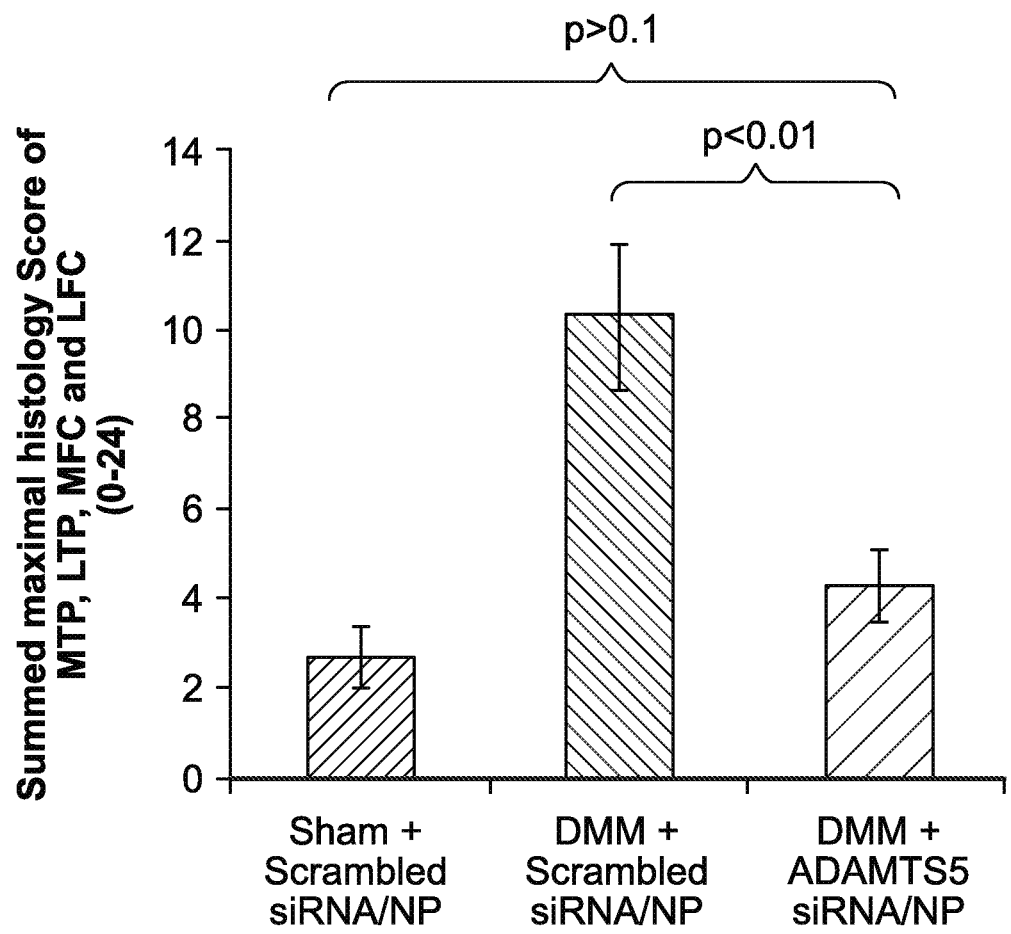
FIG. 36 is a graph showing histology evaluation of mouse knee joints. ADAMTS-5 siRNA/Nanopiece prevents osteoarthritis progression after DMM surgery.

To mimic osteoarthritis progression, DMM surgery on knee joints of mice was conducted. Osteoarthritis progression was shown to be prevented or slowed with Nanopiece delivery of ADAMTS-5 siRNA (FIGS. 35 and 36). In FIG. 35, the dark grey color in articular cartilage was aggrecan staining. A RROWs point out loss of aggrecan staining or damage to articular cartilage in the groups without ADAMTS-5 siRNA treatment; while with treatment, there was very little loss of aggrecan or damage to articular cartilage. Also, immunohisology results showed that aggrecan cleavage was inhibited with delivery of ADAMTS-5 siRNA (FIG. 46). In FIG. 46, dark staining around cell nuclei was epitope staining from aggrecan cleavage. Without ADAMTS-5 siRNA treatment, the staining is stronger than the treatment group, indicating cleavage of aggrecan.

Figure 44:
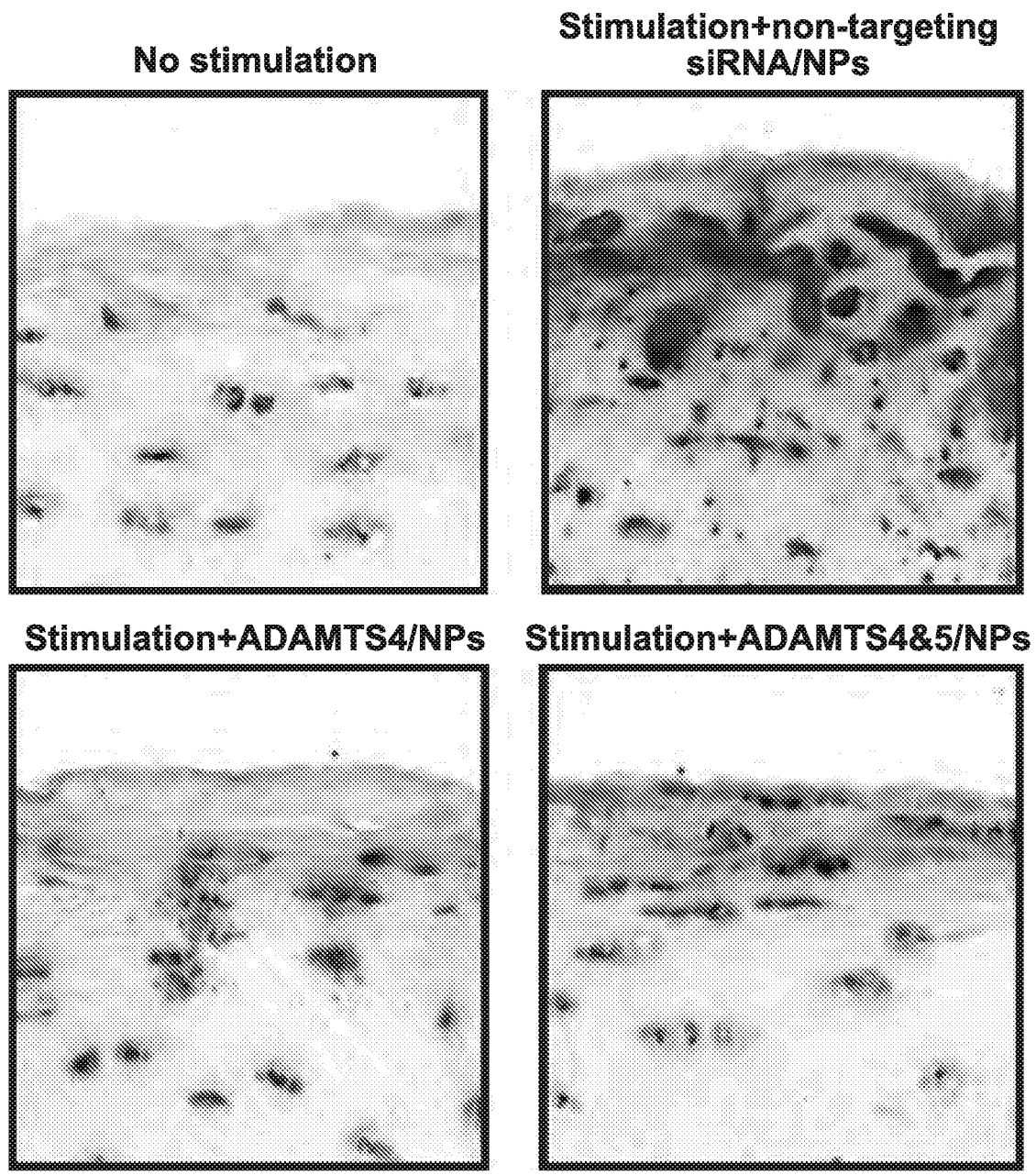
FIG. 44 is a series of images illustrating immunohistochemistry results (staining is epitope from aggrecan cleavage) of human articular cartilage. ADAMTS-4 siRNA and combination of ADAMTS-4&5 siRNA/Nanopieces greatly inhibited Aggrecan cleavage with cytokine stimulation.
Figure 45:
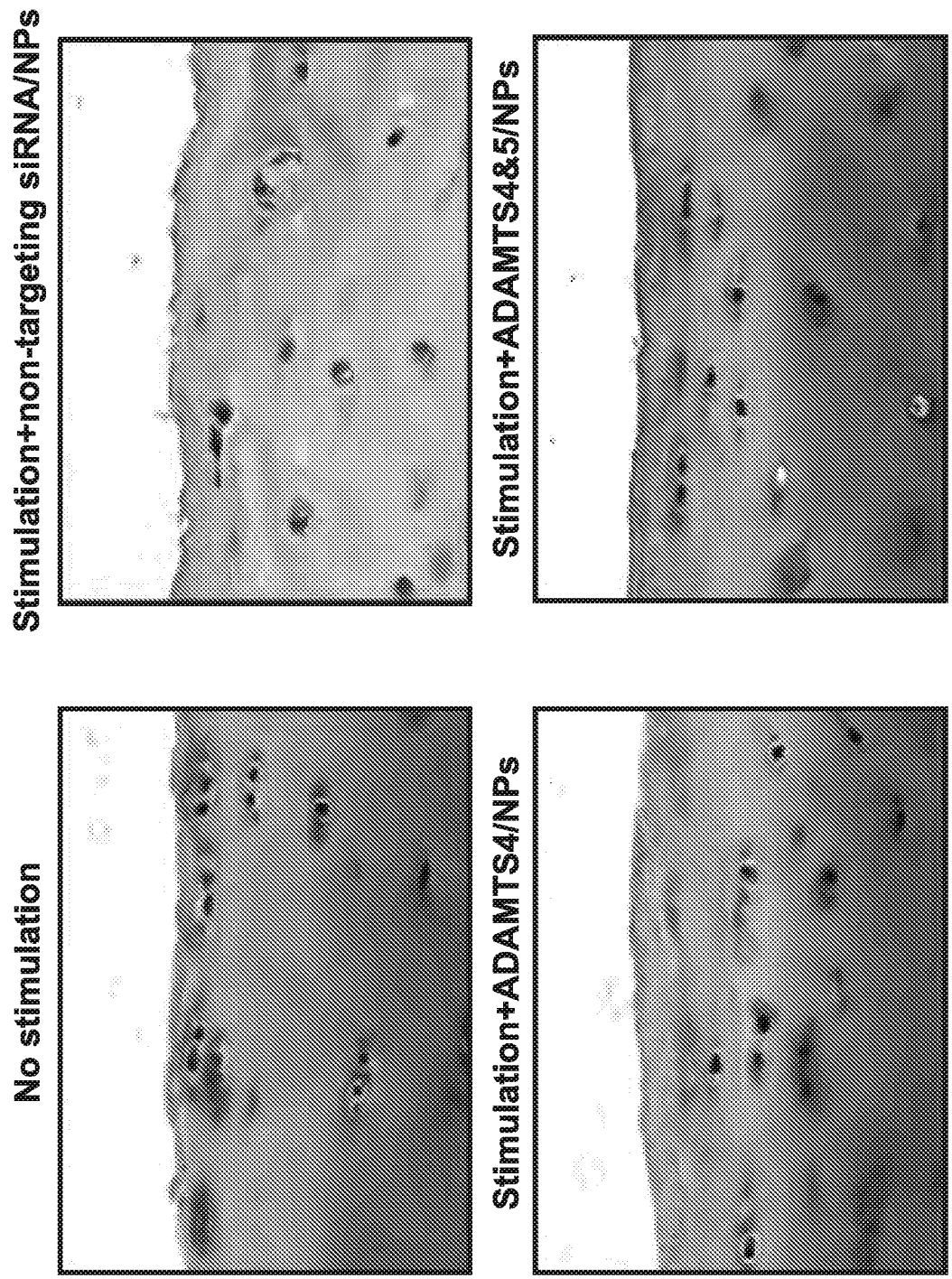
FIG. 45 is a series of images showing histology results (staining is proteoglycan) of human articular cartilage. ADAMTS-4 siRNA and combination of ADAMTS-4&5 siRNA/Nanopieces greatly inhibited cartilage degradation with cytokine stimulation.

In addition, ADAMTS-5 siRNA was delivered via Nanopieces to human cartilage ex vivo. Protection of human cartilage from cytokine-induced cartilage degradation was demonstrated (FIGS. 44-45). In FIG. 44, dark staining around cell nuclei was epitope staining from aggrecan cleavage. Without ADAMTS-4 or 5 siRNA treatment, the staining is stronger than the treatment group, indicating cleavage of aggrecan. In FIG. 45, dark color in articular cartilage was aggrecan staining. Without ADAMTS-4 or 5 siRNA treatment, aggrecan staining is weaker than the treatment group, indicating loss of aggrecan.

These data indicate that the methods are useful to prevent and/or inhibit cartilage degeneration and arthritis progression.

Example 11

Synthesis

Example 11.1

RNTs and TBLs to form Nanopieces are made by first synthesizing a module [(e.g., compound of Formula I or compound of Formula II, respectively]. Nanotubes (RNTs or TBLs) are then processed (Processing-1, Processing-2) to make nanorods and Nanopieces, respectively (see, e.g., FIG. 53). A module for making a Nanopiece was synthesized according to methods described in U.S. Pat. No. 6,696,565 and subsequently purified prior to using the same in the preparation of functional Nanopieces. Liquid chromatography purification was used to purify the synthetic products derived from Formula I and/or Formula II to ensure the success of forming functional and low toxic Nanopieces. In liquid chromatography, trifluoroacetic acid (TFA) is usually applied to keep an acidic eluent environment. Due to known toxicity of TFA or fluoride residual, which made isolated materials undesirable for preclinical and clinical studies, a modification to include hydrochloric acid (HCl) or phosphoric acid during the purification process was developed as an alternative TFA.

Liquid chromatography was performed on C18 reverse-phase column, and Agilent 1260 Infinity Quaternary HPLC System was used. One example of gradient used in isolation is shown below:

| Time | 0 min | 10 min | 15 min |
|---|---|---|---|
| Percentage of Solvent A | 90 | 65 | 0 |
| Percentage of Solvent B | 0 | 25 | 90 |
| Percentage of Solvent C | 10 | 10 | 10 |

*Solvent A is $H_2O$, Solvent B is 100% acetonitrile, and Solvent C is 0.05N hydrochloric acid.

Figure 47:
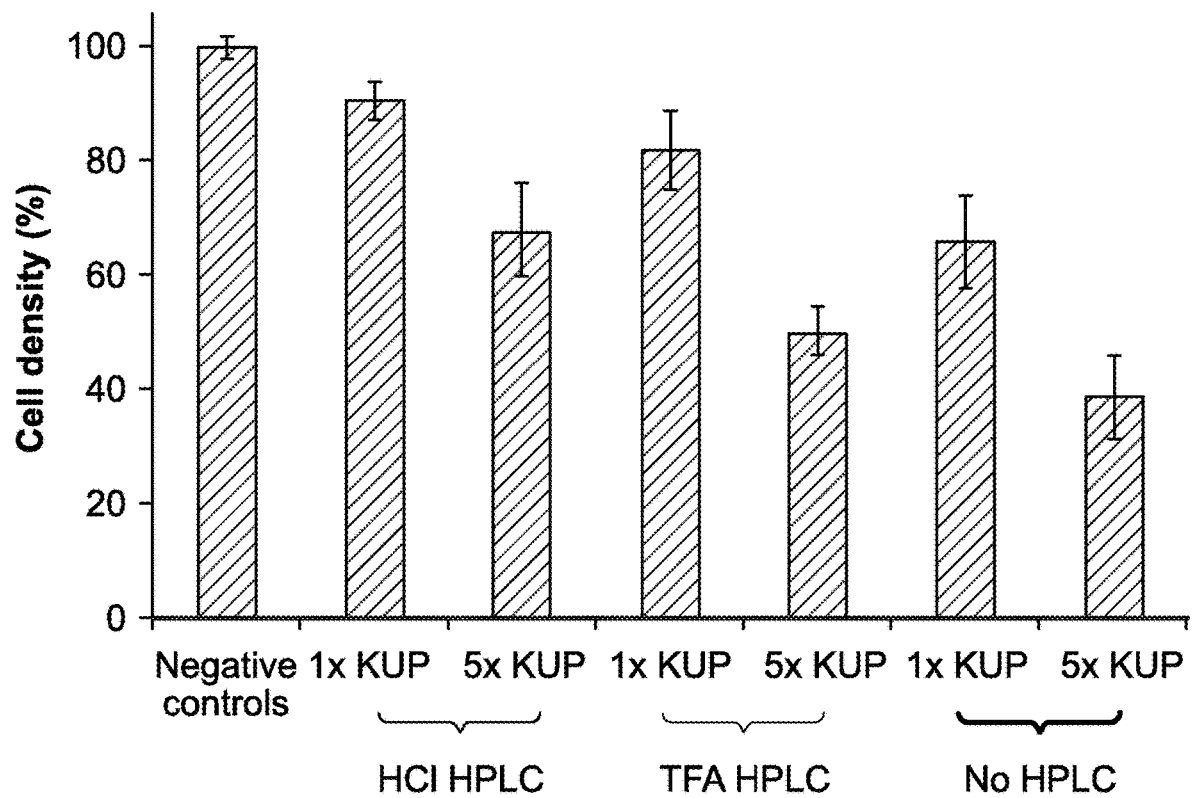
FIG. 47 is a graph showing cell toxicity studies of RNTs purified using HPLC chromatography with HCl or TFA as a modifier.

The cell toxicity was evaluated using a standard cell viability test. ATDC5 cells were treated with RNTs, and after 48 hours cell viability normalized to negative controls (as 100). Results are showed in FIG. 47. These results demonstrate successful isolation of modules using a modified HPLC purification method to obtain RNTs. Using HCl instead of TFA in this purification process avoided the presence of fluorine containing contaminates within the module, which contributed to the toxicity of the resulting nanotube. Thus, use of HPLC decreased the toxicity of RNTs and use of HCl versus TFA further decreased the cytotoxicity. Molecular modules, e.g, TBLs were therefore isolated by applying HCl in liquid chromatography purification. This purification scheme is applicable for module I compounds (for RNT assembly and for module II compounds for TBL assembly) to yield functional Nanopieces with low toxicity.

Example 11.2

Figure 48:
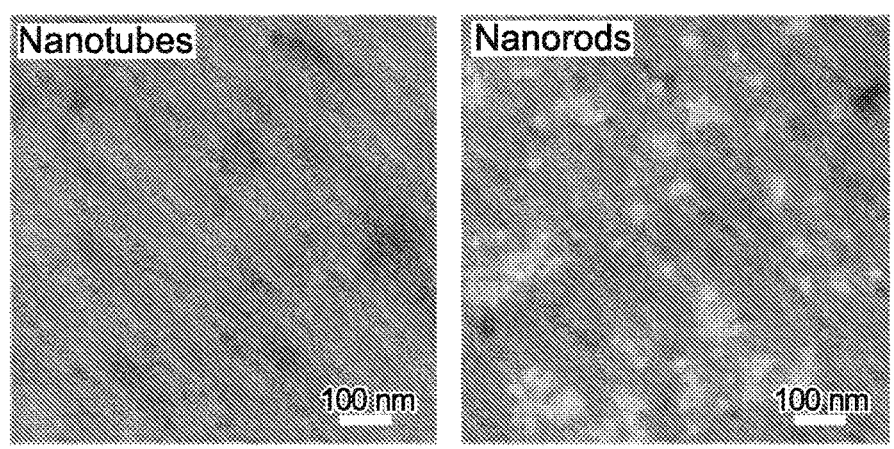
FIG. 48 is a series of images showing the conversion of nanotubes to nanorods.

Conversion of nanotubes (such as RNTs and TBLs) into nanorods was accomplished according to a process called "processing-1" (FIG. 53). In Processing-1, nanotubes are converted into short and homogeneous nanorods. This is very important to produce Nanopieces small enough to penetrate some types of tissue matrices for introduction of therapeutics into the tissue. Conversion of nanotubes to nanorods can be accomplished by altering pH, temperature, and/or using physical methods (such as sonicating, heating and blending (e.g. homogenizer)), and/or addition of aromatic chemicals. Different sizes of Nanopieces can be produced (FIGS. 5, 6 and 48). Based on the Nanopiece assembly mechanism, the processing approach may include at least one of the following: 1) before assembly, controlling the length and bundle of RNTs via changing physical and/or chemical conditions such as temperature, molecule motion and/or vibration (like sonication) and pH; 2) during assembly, adjusting assembly conditions via changing physical and/or chemical conditions including concentrations, pH and ionic strength to enhance and/or reduce the formation and stacking of Nanopieces; 3) after assembly, breaking long or stacked Nanopieces by via changing physical and/or chemical conditions including enhancing molecule motion/vibration (like sonication).

Example 11.3

Figure 49:
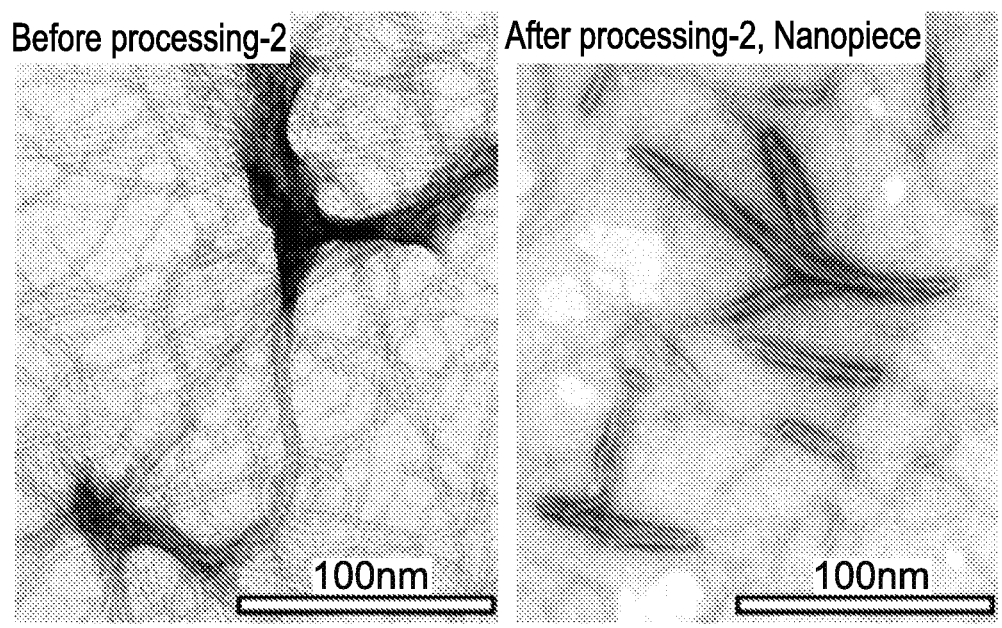
FIG. 49 is a series of images showing the generation of Nanopieces before and after "processing-2".

Preparation of Nanopieces was accomplished by a process called "processing-2" (FIG. 55). Processing-2 occurs after the incorporation between nanotubes or nanorods with delivery cargo and formation of bundles, ribbons or other agglomerates. These agglomerates can then be transformed to Nanopieces (FIG. 49). The size of the Nanopieces can be changed with changes in pH, ionic strength, temperature and concentration (FIGS. 4, 7-9).

FIGS. 15-23 and 26-32 demonstrated the successful tissue delivery after combining the above methods in Examples 11.1-11.3.

Example 11.4

Preparation of small and large lipid Nanoparticles was accomplished using the procedures described below.

Preparation of large lipid nanoparticles with IL-1R siRNA (sphere shape 110 nm to 180 nm diameter):
1) Dissolve siRNA in 20 mM citrate buffer (pH 5.0, nuclease free) to achieve a concentration of 50 µM.
2) Dissolve DSPC, cholesterol, DODMA, and DSG-PEG (20:48:2:30 molar ratio) in absolute, anhydrous ethanol, and then add nuclease free water to achieve a concentration of 90% ethanol.
3) The total concentration of lipid in solution is then adjusted to 20 mM.
4) 1 µL of siRNA and 1 µL of lipid solutions are heated to 37° C., then mix at the same temperature and dilute with 8 uL nuclease free water. Sit at least 30 minutes before use.

Preparation of small lipid Nanoparticles with IL-1R siRNA (sphere shape 70 nm to 120 nm diameter):
1) Dissolve siRNA in 10 mM citrate, 30 mM NaCl (pH 6.0, nuclease free) to achieve a concentration of 50 µM.
2) Dissolve DSPC, DSG-PEG, cholesterol, SPDiOC18, and DOTMA (10:10:39.8:0.2:40 molar ratio) in absolute, anhydrous ethanol, and then add an aqueous buffer (50 mM citrate, pH 4.0, nuclease free) to achieve a final concentration of 40% ethanol.
3) The total concentration of lipid in solution is then adjusted to 20 mM.
4) Extrude the lipid solution through two nuclepore polycarbonate filters (100 nm, 10 passes).
5) 1 µL extruded lipid solution and 1 µL siRNA are mixed under constant vortex, then dialyzed in PBS overnight to increase the pH to about 7.4.

Figure 67:
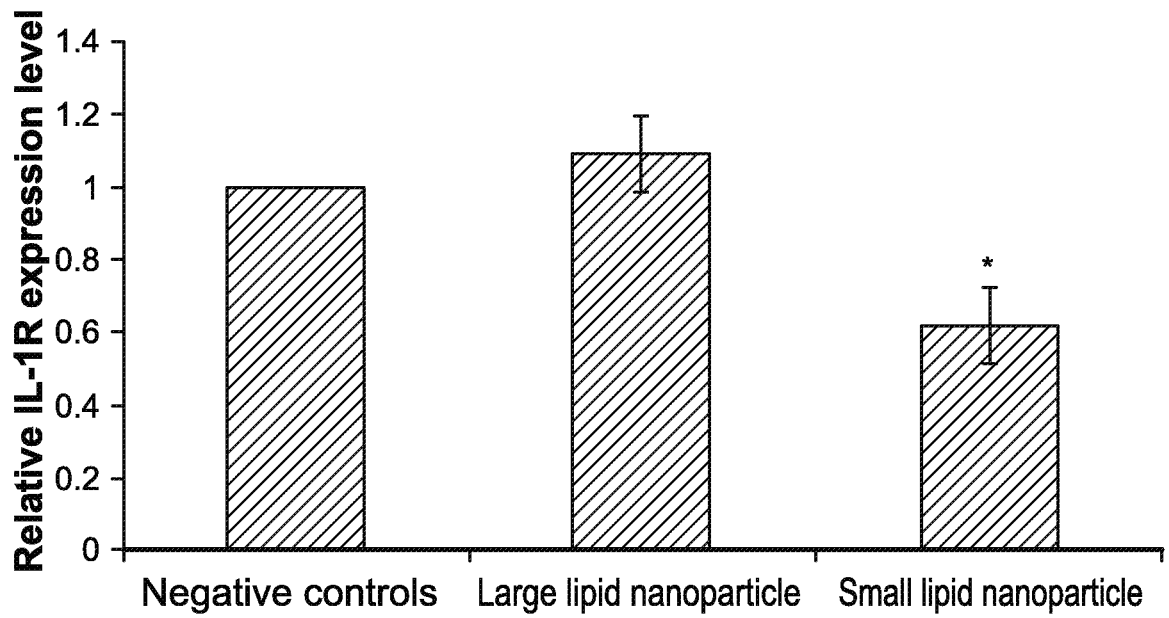
FIG. 67 is a bar graph showing PCR results of IL-1R expression levels of large and small lipid nanoparticles ($*p<0.05$ compared to negative controls and large lipid nanoparticle).

FIG. 67 shows successful localization/delivery of cargo to cartilage tissue using nucleic acid-loaded lipid nanoparticles. The small siRNA lipid nanoparticles localized to, penetrated cartilage tissue, and inhibited expression of the target gene.

Example 11.5

Preparation of small and large polymer Nanoparticles was accomplished using the procedures described below.
Preparation of large and small polymer Nanoparticles with IL-1R siRNA:
1) Dissolve poly-lysine (PLL) (molecular weight, 15 kDa-30 kDa) in nuclease free water to 0.2 mg/mL.
2) Dialyze to remove salt (HBr).
3) Lyophilize.

To prepare large PLL/siRNA nanoparticles (100-250 nm diameter):
1) Dissolve siRNA and PLL in 0.15M NaCl to concentrations of 10 µM and 25 µM, respectively.
2) Quickly add 1 uL 50 µM siRNA solution to 15 uL 100 µg/mL PLL and pipette well at room temperature.
3) Pipette and let sit for at least 30 minutes before use.

To prepare small PLL/siRNA nanoparticles (50-75 nm diameter):
1) Dissolve siRNA and PLL in nuclease free water to concentrations of 50 µM and 100 µg/mL, respectively.
2) Quickly add 1 uL 50 µM siRNA solution to 15 uL 100 µg/mL PLL and pipette well at room temperature.
3) Use within 30 minutes of reaction.

Figure 68:
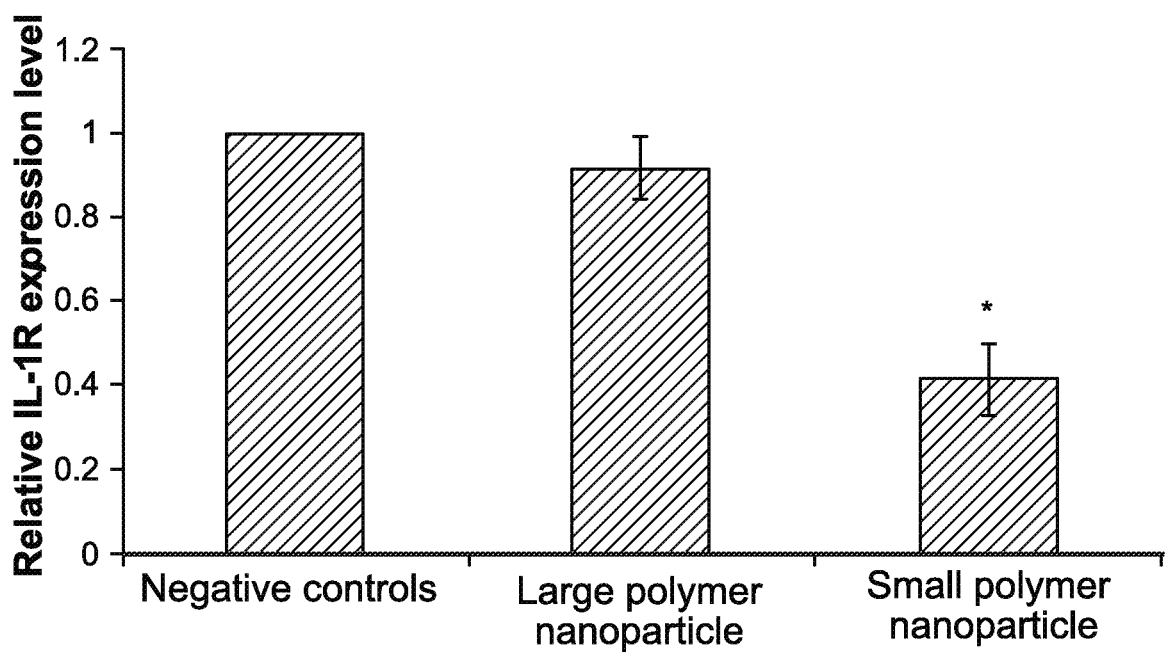
FIG. 68 is a bar graph showing PCR results of IL-1R expression levels of large and small polymer nanoparticles ($*p<0.05$ compared to negative controls and large polymer nanoparticle).

FIG. 68 shows successful localization/delivery of cargo to cartilage tissue using nucleic acid-loaded polymer nanoparticles. The small siRNA polymer nanoparticles localized to, penetrated cartilage tissue, and inhibited expression of the target gene.

FIGS. 67 and 68 demonstrated the successful tissue delivery of the above prepared lipid or polymer nanoparticles. Animals were injected with prepared large/small lipid or polymer nanoparticles delivered with IL-1R siRNA to right knees of mice. (Animal left knees were used as negative controls). After 24 hours, euthanized animals were euthanized and their knee cartilage was collected for real time RT-PCR. These data indicate that cargo-loaded nanostructures such as RNTs comprising compounds of Formula I, TBLs comprising compounds of Formula II, as well as lipid nanoparticles, and polymer nanoparticles successfully deliver cargo to target tissues.

Example 12

A Non-Invasive, Early, and Sensitive Detection of Osteoarthritis Through In Vivo Imaging of MMP-13 mRNA Levels by Molecular Beacon (MB) and Nanopiece Delivery Technology MBs were designed to target MMP-13 or GAPDH mRNA with a fluorophore/quench pair using a mouse model. Scramble sequence MB (Scramble) was verified to not bind with any mouse mRNA via BLAST. To demonstrate in vitro delivery and validation; MBs were delivered into chondrocytes by Nanopieces. After stimulation with IL-1β for 24 hours, chondrocytes were co-transfected GAPDH (red) and scramble (green) MBs or GAPDH (red) and MMP-13 (green) MBs via Nanopieces. Real time RT-PCR and fluorescence microscopy were used to verify the stimulation of MMP-13 expression, and a successful fluorescence signal resulted from using a MMP-13 MB.

Destabilization of the medial meniscus (DMM) surgery and in vivo delivery: DMM or sham surgeries were performed on 10-week-old 129SVE male mice to induce osteoarthritis. One week after surgery, MMP-13 and scramble MBs with different fluorophores delivered by Nanopieces were injected into knee joints of mice. Small animal fluorescence molecular tomography (FMT) was used to determine the fluorescence signal resulted from MMP-13 expression in the live animals for 3 weeks.

To test the in vitro efficacy of mRNA detection in chondrocytes using MBs delivered by Nanopieces, primary mouse chondrocytes were transfected with MBs either with or without IL-1β treatment. Before IL-1β treatment, the housekeeping GAPDH MB (red) was detected while the MMP-13 MB (green) was not. In contrast, after IL-1β treatment, both GAPDH MB (red) and MMP-13 MB (green) were detected, indicating the induction of MMP-13 mRNA levels by IL-1β. Realtime rtPCR showed that MMP-13 mRNA level was up-regulated by about 10 times upon IL-1β stimulation. In contrast, Scramble MB transfection did not show any green fluorescence, suggesting that the fluorescence of MMP-13 MB was not due to non-specific degradation.

To evaluate in vivo efficacy, the following studies were carried out. After DMM surgery, MMP-13 MB was delivered intra-articularly to the knee joint of adult mice with Scramble MB that emits fluorescence at a different wavelength than MMP-13 MB. Only a week after surgery, the DMM surgery leg displayed a strong MMP-13 signal than the contralateral Sham surgery leg (FIG. 2, left panel). In contrast, the Scramble MB showed very low fluorescence in both DMM and Sham surgery knee joints. After subtracting Scramble MB basal level signals, MMP-13 MB real signal was about 40 times stronger in the DMM leg than the sham leg. Such MMP-13 MB signals persist, even for 3 weeks after injection of MBs.

MMP-13 MB delivered by Nanopiece technology represents a sensitive tool to detect pro-inflammatory degenerative conditions as evidenced with chondrocytes in vitro and in OA animal models in vivo. This technology detects pathogenesis of OA at an early stage (within a week) in a mild OA model (DMM). A high sensitivity was achieved due to the detection at the mRNA level and the high efficiency of MB intracellular delivery by Nanopieces. The combination of molecular beacon and Nanopieces technology provided a powerful tool for early detection of OA in vivo in a specific and sensitive manner without harming any joint tissues.

Matrix metalloproteinases (MMP) are the major enzymes that degrade the components of the extracellular matrix during arthritis progression. MMP-13, which is usually produced by cartilage and bone, degrade interstitial collagens (types I, II and III) in both OA and RA. Expression of MMP-13 is low in normal cells, whereas in pathologic condition excess MMP-13 production is associated with inflammation. Thus, mRNA level of MMP-13 is useful as a diagnostic and prognostic tool for assessment of arthritis development. Therefore MMP-13 is recognized as a reliable target in early diagnosis of arthritis. These data indicate that intra-articular injection of Nanopieces+payload were successfully introduced into joint tissue and that the payload was functionally active after delivery.

The system and compositions described herein overcame the difficulty of accurately translating molecular beacon signal into MMP-13 mRNA expression level. MMP-13 upregulation pattern was demonstrated during OA progression using the Nanopiece-delivered beacons. Compared to earlier and current research and clinical methods, Nanopiece-Molecular Beacon technology achieved much earlier and more sensitive detection.

Example 13

Delivery of RNAi and Oligonucleotide Therapeutics and Diagnostics Via Self-Assembled Nanopieces™

The compositions and methods described herein represent the next generation of therapeutics RNA delivery. Schematic self-assembled Nanopieces' associated with RNAi (e.g., siRNA) and/or oligonucleotide for the use in therapeutics and diagnostics are shown in FIGS. 70-88.

Given the benefit of the above disclosure and description of exemplary embodiments, it will be apparent to those skilled in the art that numerous alternative and different embodiments are possible in keeping with the general principles of the invention disclosed here. Those skilled in this art will recognize that all such various modifications and alternative embodiments are within the true scope and spirit of the invention. While the invention has been illustrated and described in detail in the drawings and foregoing description, such illustration and description is to be considered as exemplary and not restrictive in character, it being understood that, only the preferred embodiments have been shown and described and that all changes and modifications that come within the spirit of the invention are desired to be protected. The appended claims are intended to cover all such modifications and alternative embodiments. It should be understood that the use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc. Ref-

Example 14

Systemic RNA Interference Therapy for Rheumatoid Arthritis Joints Through Delivery of Cargo-Loaded Nanopieces The compositions and methods described herein can be used for systemic RNA interference (RNAi) therapy for arthritis (e.g., for rheumatoid arthritis-affected joints).

Rheumatoid arthritis (RA) is a disease which causes inflammatory synovitis and cartilage and bone destruction in the joints (McInnes I B, Schett G., The pathogenesis of rheumatoid arthritis. N Engl J Med. 2011 Dec. 8; 365(23): 2205-19, and Choy E H, Panayi G S. Cytokine pathways and joint inflammation in rheumatoid arthritis. N Engl J Med. 2001 Mar. 22; 344(12):907-16. Review). In the past, Non-Steroidal Anti-Inflammatory Drugs (NSAIDs) and corticosteroid had been used to decrease the pain in patients with RA. Currently, disease-modifying anti-rheumatic drugs (DMARDs) (i.e. methotrexate) and anti-cytokine drugs are the most common therapeutics for RA (Okamura K, et al., Efficacy at 52 weeks of daily clinical use of iguratimod in patients with rheumatoid arthritis. Mod Rheumatol. 2015 July; 25(4):534-9, Okamura K, et al. Efficacy of the clinical use of iguratimod therapy in patients with rheumatoid arthritis. Mod Rheumatol. 2015 March; 25(2):235-40, Yonemoto Y, et al. Comparison of golimumab 100-mg monotherapy to golimumab 50 mg plus methotrexate in patients with rheumatoid arthritis: Results from a multicenter, cohort study. Mod Rheumatol.2016; 26(1):24-8, Okamura K, et al., Evaluation of tocilizumab therapy in patients with rheumatoid arthritis based on FDG-PET/CT. BMC Musculoskelet Disord. 2014 Nov. 22; 15:393, and Okamura K, et al. The assessment of biologic treatment in patients with rheumatoid arthritis using FDG-PET/CT. Rheumatology (Oxford). 2012 August; 51(8):1484-91).

Anti-cytokine drugs such as tumor necrosis factor-α (TNF-α) antibody are targeting either the cytokine or the receptor. These play a regulatory role in the development and progression of RA and have been remarkable in improving the life quality of RA patients. Although most patients have lower disease activities using these drugs, there are still many patients who continue to suffer from joint destruction associated with RA because of the antibody against the protein drug or some adverse effects (van Schouwenburg P A, et al., Immunogenicity of anti-TNF biologic therapies for rheumatoid arthritis. Nat Rev Rheumatol. 2013 March; 9(3):164-72, and Yi H, et al. Induced production of anti-etanercept antibody in collagen-induced arthritis. Mol Med Rep. 2014 June; 9(6):2301-8). Thus, new therapeutic approaches other than protein drugs against RA are needed.

RNA interference (RNAi) therapy may be used for treatment (Kole R, et al., RNA therapeutics: beyond RNA interference and antisense oligonucleotides. Nat Rev Drug Discov. 2012 Jan. 20; 11(2):125-40, Inoue A, et al. Comparison of anti-rheumatic effects of local RNAi-based therapy in collagen induced arthritis rats using various cytokine genes as molecular targets. Mod Rheumatol. 2009; 19(2):125-33, Howard K A, et al., Chitosan/siRNA nanoparticle-mediated TNF-alpha knockdown in peritoneal macrophages for anti-inflammatory treatment in a murine arthritis model. Mol Ther. 2009 January; 17(1):162-8, Lee S J, et al. TNF-α gene silencing using polymerized siRNA/thiolated glycol chitosan nanoparticles for rheumatoid arthritis. Mol Ther. 2014 February; 22(2):397-408, Komano Y, et al., Arthritic joint-targeting small interfering RNA-encapsulated liposome: implication for treatment strategy for rheumatoid arthritis. J Pharmacol Exp Ther. 2012 January; 340(1):109-13, Khoury M, et al. Efficient new cationic liposome formulation for systemic delivery of small interfering RNA silencing tumor necrosis factor alpha in experimental arthritis. Arthritis Rheum. 2006 June; 54(6):1867-77, Khoury M, et al. Efficient suppression of murine arthritis by combined anticytokine small interfering RNA lipoplexes. Arthritis Rheum. 2008 August; 58(8):2356-67, Scheinman R I, et al., Functionalized STAT1 siRNA nanoparticles regress rheumatoid arthritis in a mouse model. Nanomedicine (Lond). 2011 December; 6(10):1669-82, Kanazawa T, et al., Systemic delivery of small interfering RNA targeting nuclear factor KB in mice with collagen-induced arthritis using arginine-histidine-cysteine based oligopeptide-modified polymer nanomicelles. Int J Pharm. 2016 Dec. 30; 515(1-2):315-323, and Luo X, et al. Adenovirus-Mediated Small Interfering RNA Targeting TAK1 Ameliorates Joint Inflammation with Collagen-Induced Arthritis in Mice. Inflammation. 2017 June; 40(3):894-903).

However, existing RNA interference-based therapies are limited in their use because of drawbacks and limitations such as the lack of an effective delivery vehicle. The compositions and methods of the invention overcome the drawbacks and limitations of earlier approached. To maximize the efficacy of RNAi therapy for RA, a systemic administration will have to be done without any adverse effects. The RNAi carrier must also have high delivery efficiency and specificity to appropriate targets of RNAi. Because of these requirements, it is necessary to explore new RNAi therapy for RA. The nanopiece-siRNA complexes described herein are characterized by such advantages.

The delivery vehicle and therapeutic described herein was a nucleobase derived nanotube complex that surrounds small interfering RNA (siRNA) named Janus Base with amine or lysine (K); JBaK nanopieces (NPs). These were consisting of siRNA and non-covalent nanotubes of a small biomimetic molecule.

Suppression of TNF-α through the RNAi method described herein regulated the synovial inflammation of the joints and decreased the joint destruction in a mouse RA model. siRNA was administered against TNF-α with JBaK NPs systemically in RA mouse model and evaluated the inflammation of the synovium and the destruction of joints.

Example 14.1 Methods

Preparation of siRNA and JBaK NPs Complex

Figures 89A, 89B, 89C:
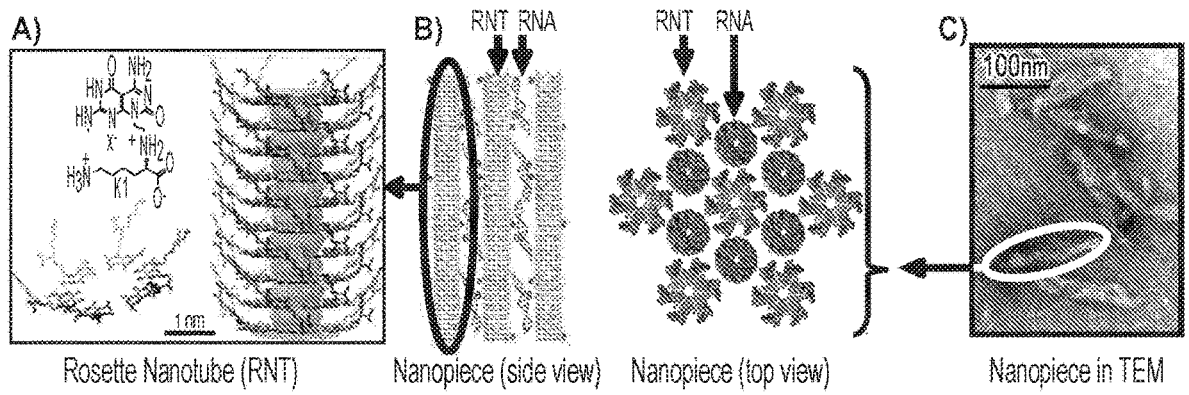
FIG. 89A-C are images and results of the NP Rosette Nanotube.

To deliver siRNA, a nucleobase derived nanotube complex named JBaK (Janus Base with amine or lysine (K)) was used. JBaK molecules was designed to combine two components: 1) nucleobase with hydrogen-bond donors and acceptors on two faces respectively, thus forming a Janus base, 2) a hydrophilic side chain containing amine or lysine. With this design, two faces of Janus base are complementary to each other to from a hydrophilic backbone, just like nucleobase; the amine or lysine containing side chains holding positive charge are stretching out to align the whole structure into a tubular shape (FIG. 89A-89C).

JBaK NPs were formed through a self-assembly process of JBaK nanotube and siRNA under specific conditions. JBaK nanotube was synthesized and verified through a 12-step total chemical synthesis procedure. JBaK nanotubes were formed using compounds of formula (I) or salts thereof. As shown in FIG. 89A, JBaK nanotubes were formed from a compound having a structure of

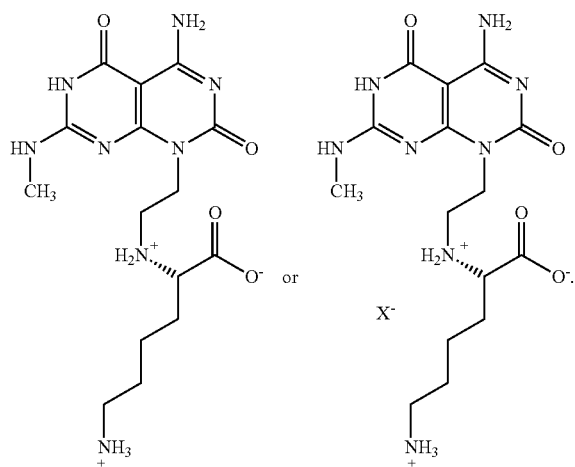

In Vitro Delivery of siRNA siRNA was delivered to macrophages using the nanopiece-siRNA complex (siRNA cargo-loaded nanopieces). The macrophage cell line, RAW264.7, was purchased from ATCC and cultured with Dulbecco's Modified Eagle's Medium (DMEM) (#30-2002). To evaluate the in vitro TNF-α gene silencing efficacy in activated macrophages, the RAW264.7 cells were seeded in 12-well plate (100,000 cells/well) and cultured with Lipopolysaccharides (LPS) (100 ng) for 24 hours. Then, the activated RAW264.7 cells were transfected with siRNA for mouse TNF-α (siTNF) or mouse non-target siRNA (scrRNA) encapsulated within JBaK NPs. After 24 hours, total RNA was extracted from treated cells using an RNeasy RNA isolation kit (QIAGEN), then generated cDNA using iScript™ cDNA synthesis kit (Bio-Rad) according to the manufacturer's instructions. The cDNA of each sample was amplified by real-time quantitative PCR (RT-qPCR). The sequence of the primer used to detect mouse TNF-α were purchased from Integrated DNA technology (Iowa, USA) (forward 5'-AAG CCT GTA GCC CAC GTC GTA-3' (SEQ ID NO: 229); reverse 5'-GGC ACC ACT AGT TGG TTG TCT TTG-3' (SEQ ID NO: 230)). Relative transcript levels were calculated using the delta-delta Ct (ΔΔCt) method, normalized to rRNA 18S expression.

Arthritis Induction for Collagen-Induced Arthritis

Collagen induced arthritis (CIA), a recognized model for rheumatoid arthritis, was generated in 8-week-old DBA/1J mice. 7 week-old mice were purchased from the Jackson Laboratory (JAX stock #000670) and housed under standard conditions at a temperature of 70° F., with 40-60% humidity and a 12 hour light/dark-cycle. CIA was achieved according to the manufacturer's instruction. Briefly, murine CIA was induced in 8 week-old male DBA/1J mice by single immunization with bovine type II collagen and complete Freund's adjuvant (Chondrex, USA) via subcutaneous injection. Arthritis develops 3.5-4 weeks after the first immunization.

Arthritis Score and Paw Measurement

The mice were examined for signs of joint inflammation three times a week under anesthesia. The severity of arthritis was evaluated using the following clinical scoring method; 0, normal, 1, mild redness, slight swelling of ankle or wrist, 2, moderate swelling of ankle or wrist, 3, severe swelling including some digits, ankle, and foot, and 4, maximally inflamed. The clinical score was defined as the sum of the scores of all four paws of each mouse. In addition, the thickness of each paw was measured by digital caliper (Thermo Fisher Scientific, USA) at the same time as clinical assessment.

Systemic Delivery of siRNA

ON-TARGETplus siRNA (Dharmacon, USA) for mouse TNF-α (siTNF) or mouse non-target siRNA (scrRNA) were encapsulated within JBaK NPs and administered to CIA mice, via retro-orbital injections twice per week from 21 days to 49 days after the first induction of arthritis.

Gene Expression Analysis of Mice Tissue, ELISA and Histology

At week 4, after twice injections of siRNA, the CIA mice were euthanized and paws were used to prepare the total RNA using an RNeasy RNA isolation kit (QIAGEN, USA). Peritoneal exudate cell macrophages (PECs) were also collected from each mice in the following method. 5 ml of ice-cold phosphate buffered saline was injected into abdominal space. After three minutes with mild massage, the injected fluid was aspirated with the syringe, then centrifuged at 4° C., 1,000 rpm for 5 min. Discard supernatant and re-suspend cell pellet in DMEM. The cells are allowed to adhere to the substrate by culturing them 2 hr at 37° C. Nonadherent cells are removed by gently washing three times with warm PBS.

At week 8, the serum TNF-α levels were measured by ELISA (Mouse TNF-alpha Quantikine ELISA Kit, R&D systems). The foot and knee were collected for the histological examination. TNF-α gene expression was quantified using real-time quantitative PCR using the QuantiTect SYBR Green PCR kit (Qiagen). The 18S and 36B4 ribosomal RNA were used for normalization. For the histological analyses, the decalcified knee joints were cut into thin thickness sections and H&E staining and Safranin-O and fast green staining were performed.

Images and Bone Volume Analysis

X-ray images and high-resolution (10 μm isometric) 3D volume images using a desktop μCT scanner (MicroCT40, Scanco Medical. Tube Settings: 55 kVp and 145 μA. 300 ms integration time) were generated. Standard trabecular bone indices (e.g. bone volumetric density (Bone volume/Total volume; BV/TV), bone mineral density (BMD), trabecular number, trabecular thickness and trabecular separation of the subchondral bone) were calculated from manually-outlined volumes of interest in the distal femur, proximal tibia and calcaneus using the scanner's built-in analysis routines.

Statistics

Statistical analysis was conducted using SPSS version 22 (IBM Inc., Chicago, Ill., USA). Paired t-test, Mann-Whitney U test, One-way ANOVA and Turkey's post-hoc analyses were used for statistical analysis. Error bars represent one standard error (SE) of the mean.

Example 14.2 Results

In Vitro Delivery Optimization

The expression level of TNF-α mRNA were examined by RT-PCR and 50% suppression was observed in RAW264.7 cells with LPS stimulation.

Knocking Down Efficacy for Mice TNF-α Gene Expression

Figure 90A:
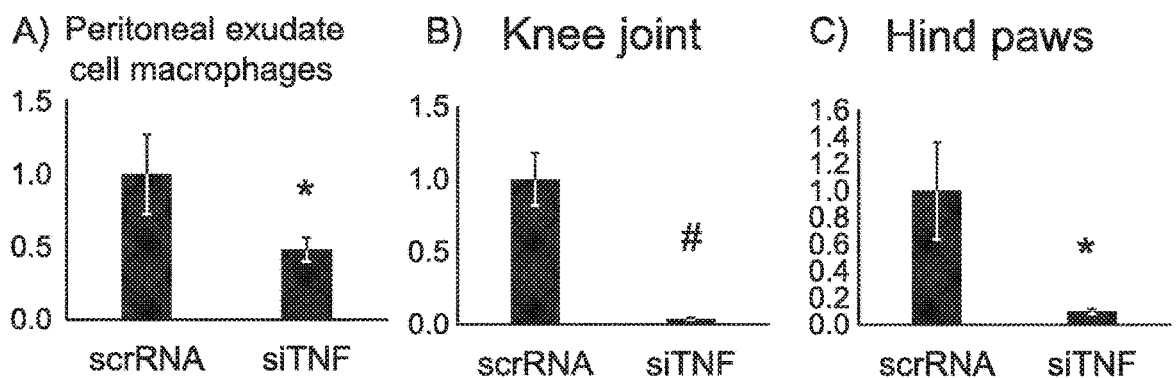
FIG. 90A-90B are graphs showing the TNF-α expression.

After systemic delivery of siTNF in NPs via retro-orbital injections for two times, at the time of week 4, the TNF-α mRNA expression levels were significantly suppressed in peritoneal exudate cell macrophages (PECs) from abdominal cavity, knee joints, and hind paws in comparison to NP delivery of scrambled siRNA in CIA mice (FIG. 90A). NP systemic delivery achieved 96% (FIG. 90A, panel B (middle) and 90% (FIG. 90A panel c, right) knockdown of TNF-α mRNA levels in knee and hind paw joints respectively, indicating NP delivery can achieve highly efficient RNAi in joint tissues.

Serum TNF-α Levels in Each Treatment

Figure 90B:
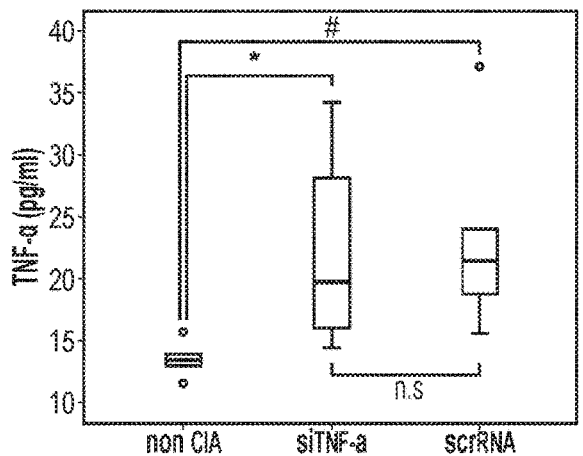

At the end of systemic treatment with siRNA/NP, the serum TNF-α levels were measured with ELISA assay and there was no significant difference between siTNF treated mice and scrRNA treated mice (FIG. 90B).

Clinical Evaluation of CIA Mice

Figure 91A:
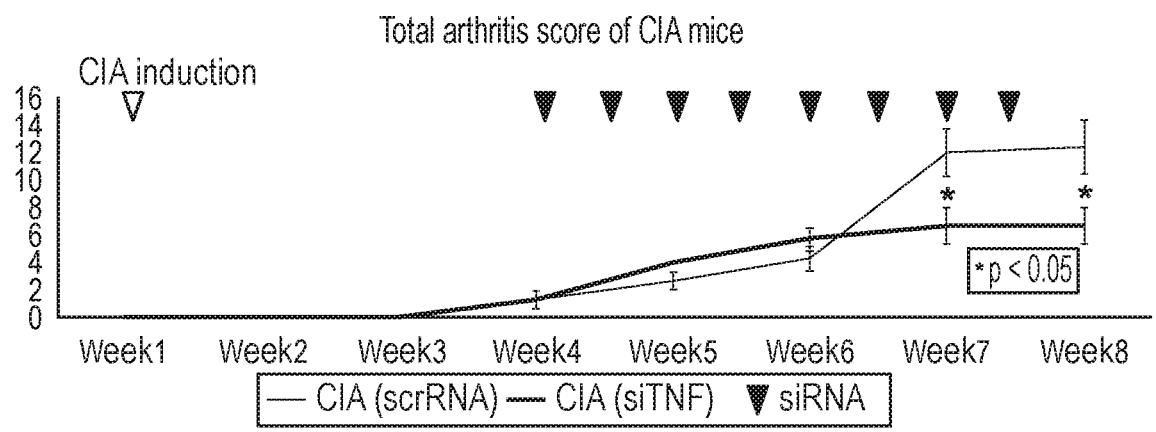
FIGS. 91A and 91B are graphs showing the total arthritis score and mechanical pain threshold.

Total arthritis score was significantly reduced in siTNF treatment group in comparison with the sham treatment group (scrRNA) after CIA induction for 7 and 8 weeks (FIG. 91A). There were also decreased paw thickness in siTNF treated group in those weeks.

Evaluation of Nociception Under siRNA Delivery

Figure 91B:
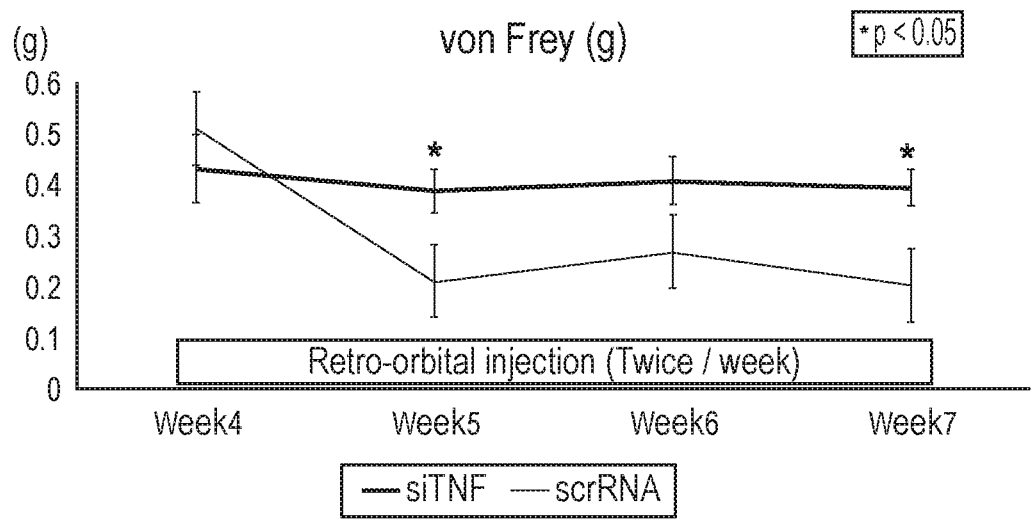

To evaluate nociception under siRNA treatments, von Frey test were performed during the therapies. siTNF mice had higher mechanical nociception threshold than scrRNA mice (FIG. 91B).

Evaluation of Joint Images and Bone Structure

Figure 92:
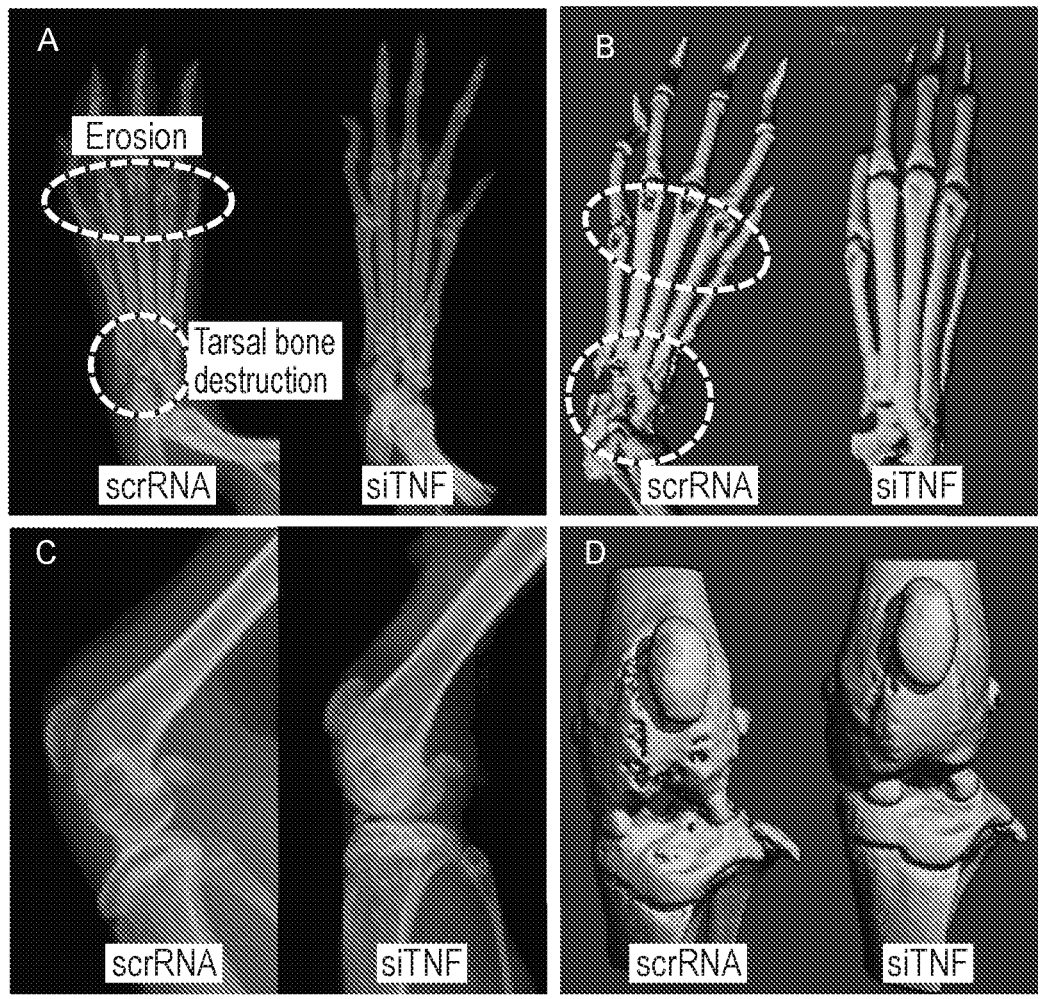
Figure 93A:
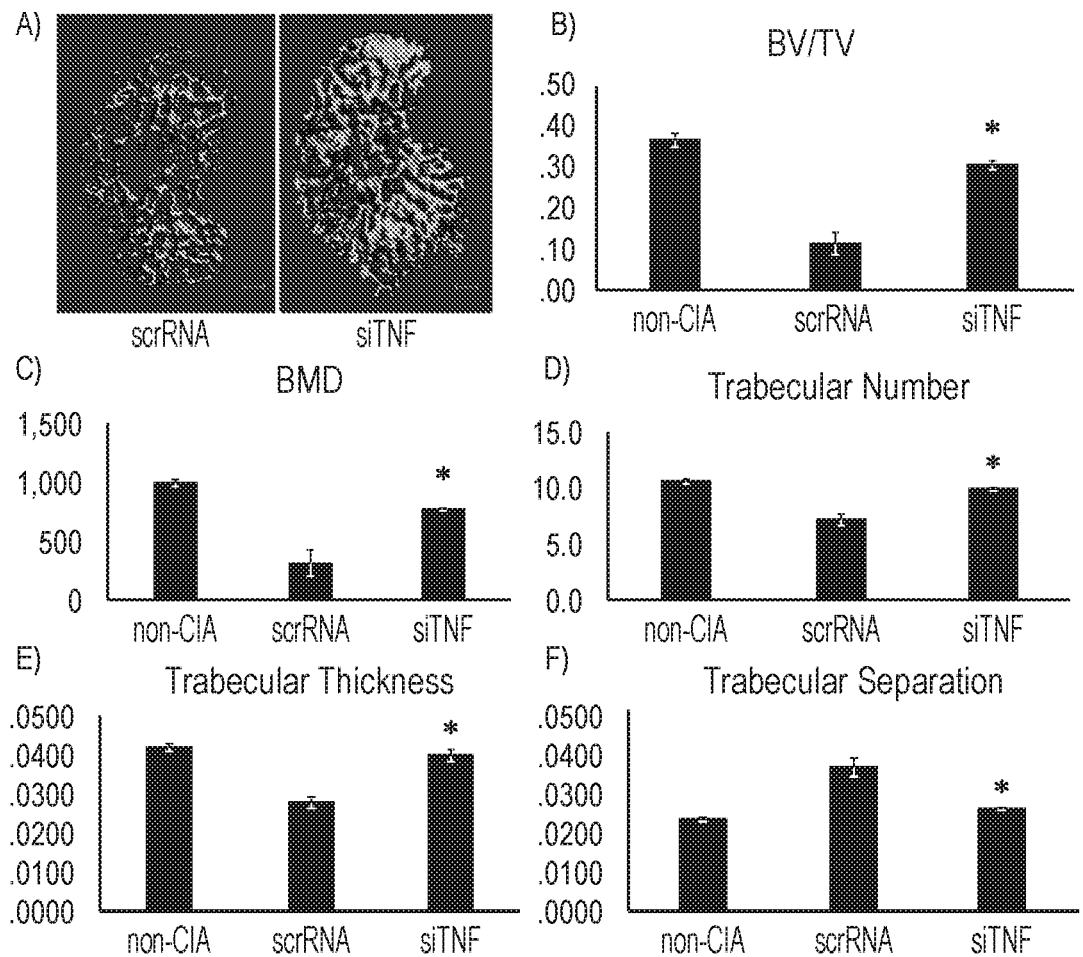
FIG. 93A-93C depict μCT images of subchondral bone from the tibia (FIG. 93A), femur (FIG. 93B), and calcaneus (FIG. 93). In each of the panels (a) represents subchondral bone, (b) represents the BV/TV, (c) represents BMD, (d) represents the trabecular number, (e) represents the trabecular thickness, both of which were (trabecular number and trabecular thickness) significantly higher in siTNF mice compared to scrRNA mice. The trabecular separation in siTNF mice was significantly narrower than scrRNA mice (panel f); n=5-7*P<0.005, #p=0.074. siTNF: TNF-α siRNA, scrRNA: non-target siRNA, BV: Bone Volume, TV: Total Volume, CIA: collagen induced arthritis.
Figure 93B:
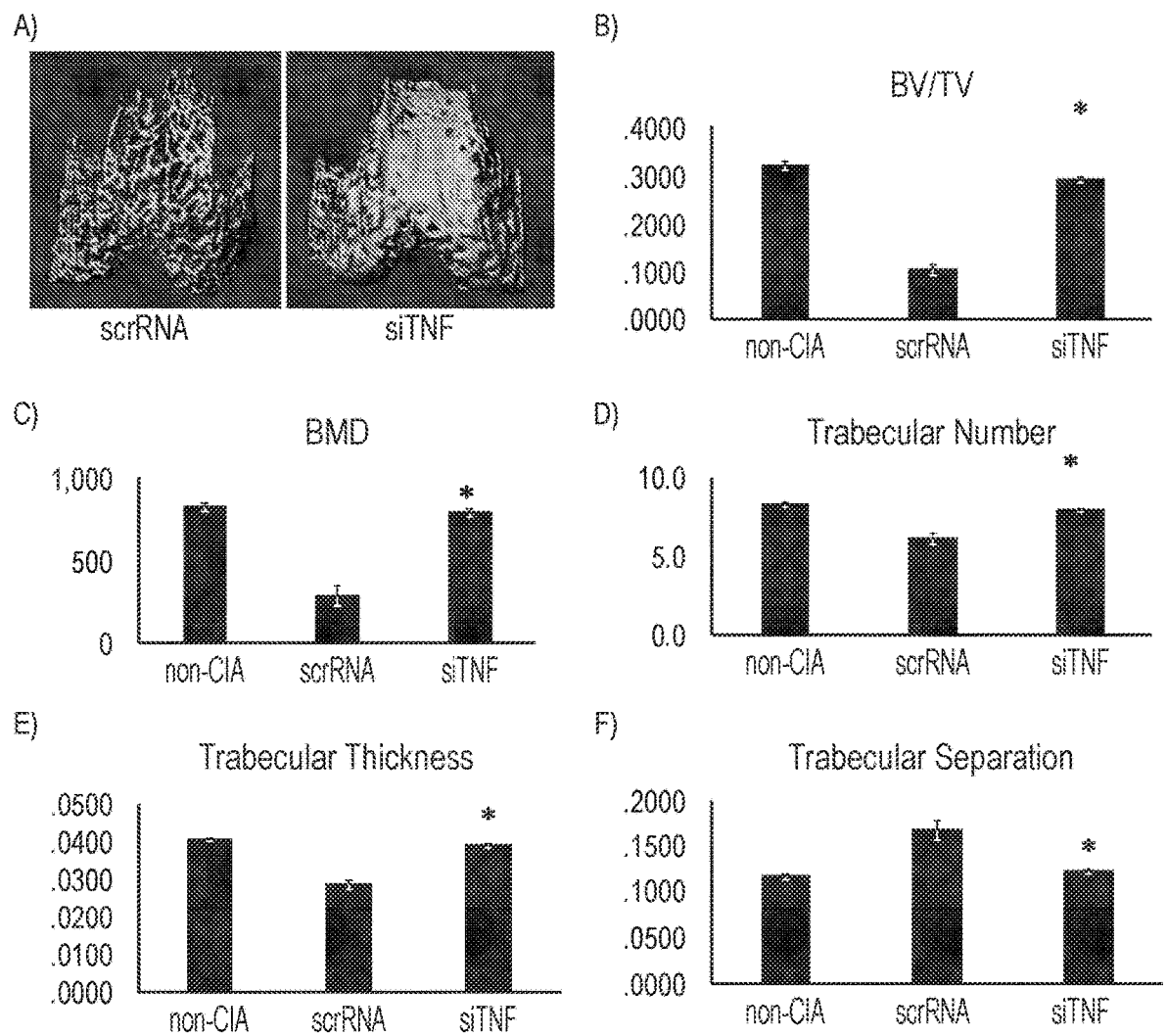
Figure 93C:
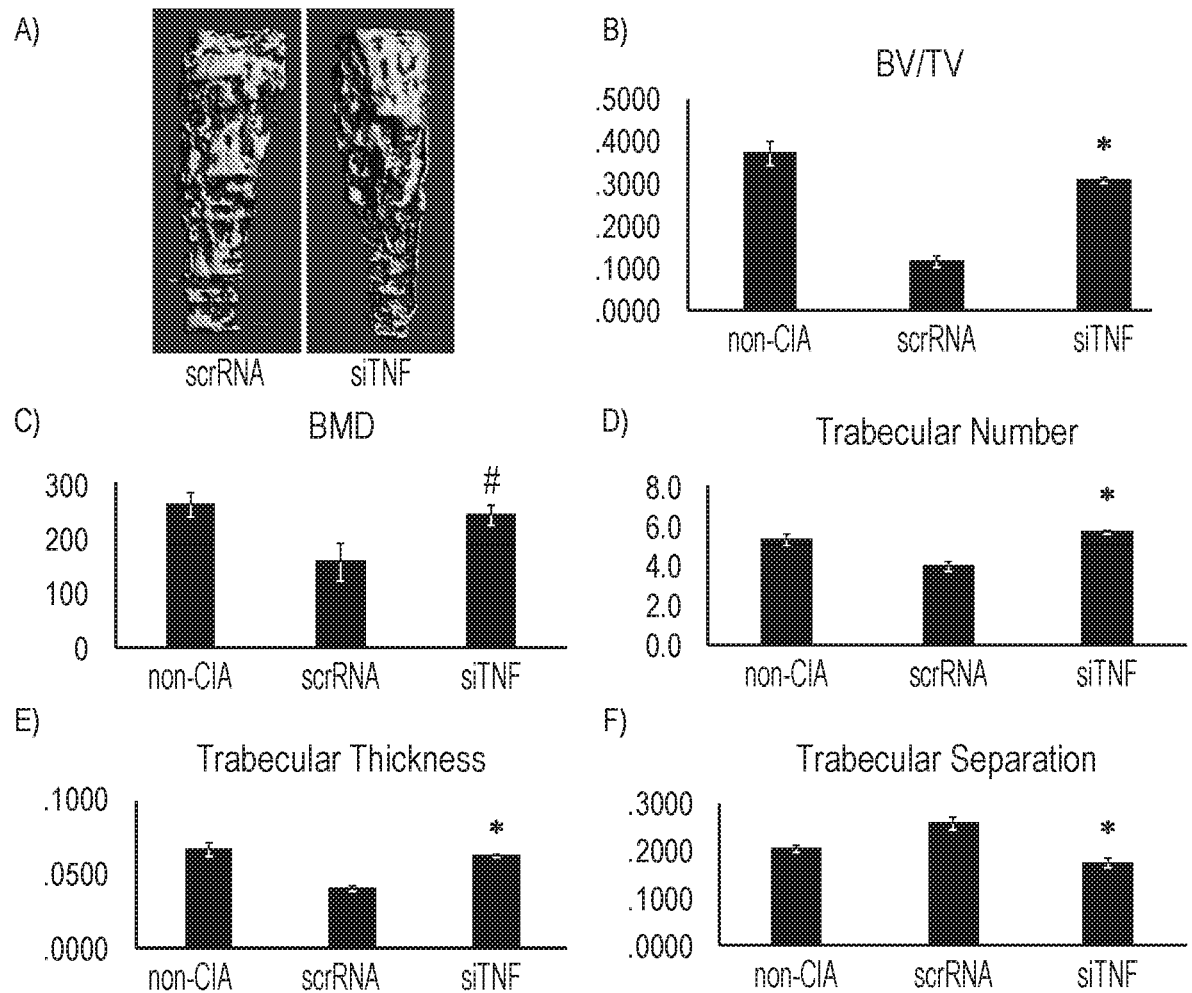

The siTNF treatment inhibited the bone erosions, and joint destructions (FIG. 92). From the quantitative analyses with μCT images of subchondral bone of tibia, the bone volume/total volume (BV/TV) with siTNF treatment was significantly higher than those with scrRNA (FIG. 93A, panel (b)). There were also significant improvement of bone mineral density (BMD) (FIG. 93A, panel (c)), trabecular number (FIG. 93A, panel (d)), trabecular thickness (FIG. 93A, panel (e)) and the trabecular separation (FIG. 93A, panel (f)) in siTNF mice compared to scrRNA mice. The same tendency was also observed with femur and calcaneus with each treatment mice (FIGS. 93B and 93C).

Histological Analyses

Figure 94:
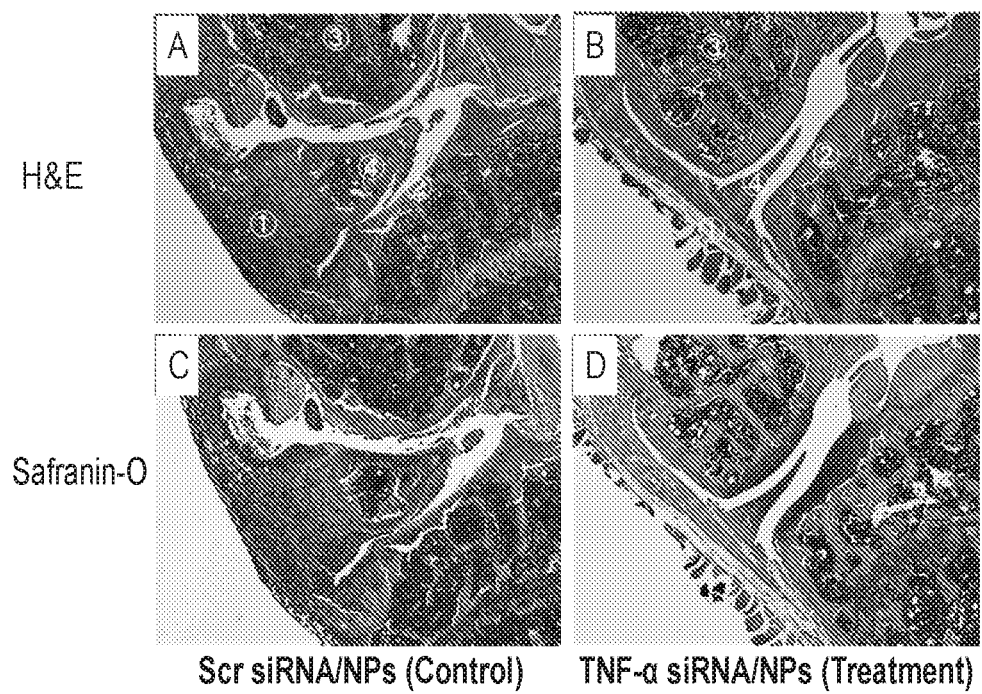
FIG. 94A-94D represent a series of H&E and Safranin O staining images of CIA mice knee joints. H&E and Safranin O staining TNF-α siRNA/NP treatment inhibited synovium inflammation (FIG. 94A), cartilage degradation (FIG. 94B), bone loss (FIG. 94C), and meniscus destruction (FIG. 94D) in CIA mice. Representative histological images of knee joint of CIA mice. Scr siRNA: non-target siRNA, CIA: collagen induced arthritis, NPs: Nanopieces.

There were 1) synovial inflammation, 2) cartilage degradation, 3) bone loss, and 4) meniscus destruction in control CIA mice (FIG. 94A) and the siTNF treatment inhibited these changes (FIGS. 94B and 94D). Therefore, this treatment inhibited RA pathology in CIA mice.

Example 14.3

The data demonstrated that 1) Systemic delivery of siRNA by NPs is achieved with high efficacy (>90%) in knocking down TNF-α gene expression in joint tissues, indicating its superiority in infiltrating peripheral joints for treatment of joint diseases such as the autoimmune disease, RA; and 2) Knocking down TNF-α mRNA in the joint tissues reduced the severity of inflammation and joint swelling, increased the threshold for the mechanical pain and inhibited bone erosion and reduction of joint destruction and BMD in arthritis mice.

CIA model mice (Takagishi K, et al., Effects of cyclosporin on collagen induced arthritis in mice. Ann Rheum Dis. 1986 April; 45(4):339-44, and Seeuws S, et al. A multiparameter approach to monitor disease activity in collagen-induced arthritis. Arthritis Res Ther. 2010; 12(4): R160 Epub 2010 Aug. 23) shares both immunological and pathological features with human RA, therefore it has been used extensively to study the pathogenesis of RA and for testing therapeutics. Previous reports have demonstrated siTNF therapy to CIA mice (Howard K A, et al., Chitosan/siRNA nanoparticle-mediated TNF-alpha knockdown in peritoneal macrophages for anti-inflammatory treatment in a murine arthritis model. Mol Ther. 2009 January; 17(1):162-8, Lee S J, et al. TNF-α gene silencing using polymerized siRNA/thiolated glycol chitosan nanoparticles for rheumatoid arthritis. Mol Ther. 2014 February; 22(2):397-408, Komano Y, et al., Arthritic joint-targeting small interfering RNA-encapsulated liposome: implication for treatment strategy for rheumatoid arthritis. J Pharmacol Exp Ther. 2012 January; 340(1):109-13, and Khoury M, et al. Efficient new cationic liposome formulation for systemic delivery of small interfering RNA silencing tumor necrosis factor alpha in experimental arthritis. Arthritis Rheum. 2006 June; 54(6): 1867-77) Another report targeting interleukin (IL)-1, IL-6 and IL-18 simultaneously was also demonstrated (Khoury M, et al. Efficient suppression of murine arthritis by combined anticytokine small interfering RNA lipoplexes. Arthritis Rheum. 2008 August; 58(8):2356-67). The target of siRNA therapy was not only the cytokine but the other molecules involved in the inflammation such as Signal Transducers and Activator of Transcription (STAT)-1, nuclear factor-kappa B (NF-κB) and transforming growth factor beta-activated kinase 1 (TAK-1) (Scheinman R I, et al., Functionalized STAT1 siRNA nanoparticles regress rheumatoid arthritis in a mouse model. Nanomedicine (Lond). 2011 December; 6(10):1669-82, Kanazawa T, et al., Systemic delivery of small interfering RNA targeting nuclear factor KB in mice with collagen-induced arthritis using arginine-histidine-cysteine based oligopeptide-modified polymer nanomicelles. Int J Pharm. 2016 Dec. 30; 515(1-2):315-323, and Luo X, et al. Adenovirus-Mediated Small Interfering RNA Targeting TAK1 Ameliorates Joint Inflammation with Collagen-Induced Arthritis in Mice. Inflammation. 2017 June; 40(3):894-903). For the deliveries of these siRNAs, most used adenovirus, polymers, and lipid. From the point of the clinical application, these carriers were not enough to deliver siRNA safely to animal and/or human body. The compositions and methods described herein utilize a nucleobase derived nanotube complex called JBaK Nanopieces (NPs) was used. This RNA carrier had high delivery efficiency and specificity to appropriate targets of RNAi in CIA mice. From the quantitative analyses for treated tissue with siTNF, there was the high efficiency of gene inhibition both in knee joints and hind paws, leading to the reduction of total arthritis score of CIA mice, validating the use of this NPs in the treatment of CIA mice.

Since these RNAi therapies utilizes encapsulated RNA rather than protein as a therapeutic, it circumvents the protein drug resistance problem (van Schouwenburg P A, et al., Immunogenicity of anti-TNF biologic therapies for rheumatoid arthritis. Nat Rev Rheumatol. 2013 March; 9(3):164-72) for some patients. Furthermore, RNAi therapy inhibits the synthesis of cytokines rather than neutralizing them after they are made, it may be used as an alternative approach for RA therapy in the cases protein drug is ineffective.

A large number of RA patients had suffered from fragile bone structures and related fractures during their entire stage of life. In order to overcome this situation, physicians need to treat the bone structure of patients with RA. In this study, CIA mice were used for the evaluation of bone microstructures. Seeuws S et al revealed that the cartilage and bone damages were observed using X-ray and μCT in CIA mice model (Seeuws S, et al. A multiparameter approach to monitor disease activity in collagen-induced arthritis. Arthritis Res Ther. 2010; 12(4):R160). They treated CIA mice with etanercept (ETN) or abatacept, both are biological DMARDs (bDMARDs), and these treatments reduced bone erosions in CIA mice.

Some previous reports demonstrated that the usage of bDMARDs had not increased, but prevented decreases in the bone mineral density (BMD) of the hip, spine and/or hand in human RA patients (Marotte H, et al. A 1-year case-control study in patients with rheumatoid arthritis indicates prevention of loss of bone mineral density in both responders and nonresponders to infliximab. Arthritis Res Ther. 2007; 9(3):R61, Wijbrandts C A, et al., Bone mineral density in rheumatoid arthritis patients 1 year after adalimumab therapy: arrest of bone loss. Ann Rheum Dis. 2009; 68(3):373-376, and Bertoldi 1, et al. Disease activity and bone density of mcp joints in patients with rheumatoid and psoriatic arthritis: is there a correlation?—a study in patients treated with methotrexate and an anti-TNF a agent). Regarding the mice RA model, Lee J H investigated the microstructure of tibial epiphysis (Lee J H, et al. Changes in microarchitectural characteristics at the tibial epiphysis induced by collagen-induced rheumatoid arthritis over time. Clin Intery Aging. 2012; 7:373-82) and Hyoju Y I et al evaluated the bone volume, BMD, and trabecular structure after the treatment with ETN for CIA mice and reported the improvement of bone loss in the knee joints of these mice (Yi H, et al. Induced production of anti-etanercept antibody in collagen-induced arthritis. Mol Med Rep. 2014 June; 9(6):2301-8). Lee S J et al also demonstrated that siTNF reduced the bone destruction and improved bone volume of hind paws and knee joints (Lee S J, et al. TNF-α gene silencing using polymerized siRNA/thiolated glycol chitosan nanoparticles for rheumatoid arthritis. Mol Ther. 2014 February; 22(2):397-408).

The data described herein showed that the siTNF therapy improved the bone volume of tibia, femur, and calcaneus in CIA mice and inhibited pathological changes in mice joints. Additionally, the results also revealed that the siRNA therapy improved the BMD and bone trabecular structures in those areas. These results indicated that systemic administration of siTNF with JBaK NPs not only decreased the arthritis score but improved the bone microstructure and joint component in RA murine model.

siTNF therapy increased the bone volume. The previous reports demonstrated that the increase of bone resorption in cancellous bone caused by upregulation of the expression of DKK-1 and regulation of the RANKL/RANK/osteoprotegerin (OPG) signaling pathway (Taketa T, et al. Selective cyclooxygenase-2 inhibitor prevents reduction of trabecular bone mass in collagen-induced arthritic mice in association with suppression of RANKL/OPG ratio and IL-6 mRNA expression in synovial tissues but not in bone marrow cells. J Bone Miner Metab. 2008; 26(2):143-51, Lubberts E, et al. Increase in expression of receptor activator of nuclear factor kappaB at sites of bone erosion correlates with progression of inflammation in evolving collagen-induced arthritis. Arthritis Rheum. 2002 November; 46(11):3055-64, Wu Q, et al. Secondary osteoporosis in collagen-induced arthritis rats. J Bone Miner Metab. 2016 September; 34(5):500-16, and Kato G, et al. The inhibitory effects of a RANKL-binding peptide on articular and periarticular bone loss in a murine model of collagen-induced arthritis: a bone histomorphometric study. Arthritis Res Ther. 2015 Sep. 12; 17:251), and the systemic OPG and anti-TNF-α antibody therapy prevented bone loss in CIA mice through distinct mechanisms involving decreased bone resorption and preserved bone formation (Saidenberg-Kermanac'h N, et al. TNF-alpha antibodies and osteoprotegerin decrease systemic bone loss associated with inflammation through distinct mechanisms in collagen-induced arthritis. Bone. 2004 November; 35(5): 1200-7). The siTNF therapy can affect these signaling pathway(s).

Some reports demonstrated that treatments for RA rodent model improved the mechanical hypersensitivity in those animals (Gao X H, et al. A store-operated calcium channel inhibitor attenuates collagen-induced arthritis. Br J Pharmacol. 2015 June; 172(12):2991-3002 and Baddack-Werncke U, et al. Cytotoxic T cells modulate inflammation and endogenous opioid analgesia in chronic arthritis. J Neuroinflammation. 2017 Feb. 6; 14(1):30). Although there is no report about the change of nociception during siTNF treatment, the suppression of TNF-α expression has been reported to improve the neuropathic pain (Nakanishi M, et al. Go-sha-jinki-Gan (GJG) ameliorates allodynia in chronic constriction injury-model mice via suppression of TNF-α expression in the spinal cord. Mol Pain. 2016 Jun. 13; 12, Kim H K, et al., Pentoxifylline Ameliorates Mechanical Hyperalgesia in a Rat Model of Chemotherapy-Induced Neuropathic Pain. Pain Physician. 2016 May; 19(4):E589-600, and Li Y, et al., Curcumin attenuates diabetic neuropathic pain by downregulating TNF-α in a rat model. Int J Med Sci. 2013; 10(4):377-81). The results herein indicated that siTNF therapy with JBaK NPs pushed up the threshold of nociception and attenuated the mechanical hypersensitivity in CIA mice.

A difference in the knocking down rate of TNF-α between in vitro macrophage cell line and the tissue from the knee and hind paw of CIA mice was observed. The difference was that the cell line was the activated macrophages and the tissue contained other kinds of cells such as T cell and fibroblast. In the body of CIA model mice, those cells are positively and/or negatively stimulated with each other (Choy E H, Panayi G S. Cytokine pathways and joint inflammation in rheumatoid arthritis. N Engl J Med. 2001 Mar. 22; 344(12):907-16). Therefore, it might be possible the RNAi therapy herein with JBaK NPs acted to those cells at the peripheral joints, leading to the high-rate knocking down of TNF-α. Since the knocking down rate of TNF-α in the PECs from abdominal cavity was almost same to the results of macrophage cell line, the target of the current therapy might be not only macrophages but other immune-activated cells.

From the fact that the serum concentration of TNF-α was not changed at the end of 8 weeks while the RA progression were inhibited, the significance may be that a) this siRNA drug works differently than the protein drug which lowers the active TNF-α concentrations, b) it may have less side effects since TNF-α protein level was not overly suppressed, and c) it suggests that the potential mechanism of action may be early on, by inhibiting immune cells infiltration in the joint. Therefore, even if the TNF-α concentration recovers, the infiltration event has occurred earlier in the disease process and thus the disease process was inhibited even if TNF-α level was increased in the serum. Thus, knockdown TNF-α mRNA levels in the joint may be critical to inhibiting RA.

Example 14.4

This data described herein demonstrate that RNAi/NP therapy is highly efficacious in inhibiting cytokine expression in the joint and progression of arthritis and bone destruction in mouse RA model. This systemic siRNA administration technology has great potential to treat RA patients if the results in humans match those in mice.

Example 14.5

Relevant Abbreviations bDMARDs: biological DMARDs, BMD: bone mineral density, BV: bone volume, CIA: Collagen induced arthritis, DMARDs: disease-modifying anti-rheumatic drugs, DMEM: Dulbecco's Modified Eagle's Medium, ETN: etanercept, JBaK: Janus Base with amine or lysine (K), LPS: Lipopolysaccharides RA: rheumatoid arthritis, NF-κB: nuclear factor-kappa B, NPs: nanopieces, NSAIDs: Non-Steroidal Anti-Inflammatory Drugs, OPG: osteoprotegerin, RANK: Receptor activator of NF-κB, RANKL: Receptor activator of NF-κB ligand, PECs: Peritoneal exudate cell macrophages, RNAi: RNA interference, RT-qPCR: real-time quantitative PCR, scrRNA: non-target siRNA, siRNA: small interfering RNA, siTNF: siRNA for mouse TNF-α, STAT: Signal Transducers and Activator of Transcription, TAK: transforming growth factor beta-activated kinase, TNF-α: tumor necrosis factor-α, TV: total volume

What is claimed:

1. A method of treating rheumatoid arthritis comprising the systemic administration of an effective amount of a rosette nanopiece and a nucleic acid, wherein said nanopiece comprises a compound of Formula I or Formula II,

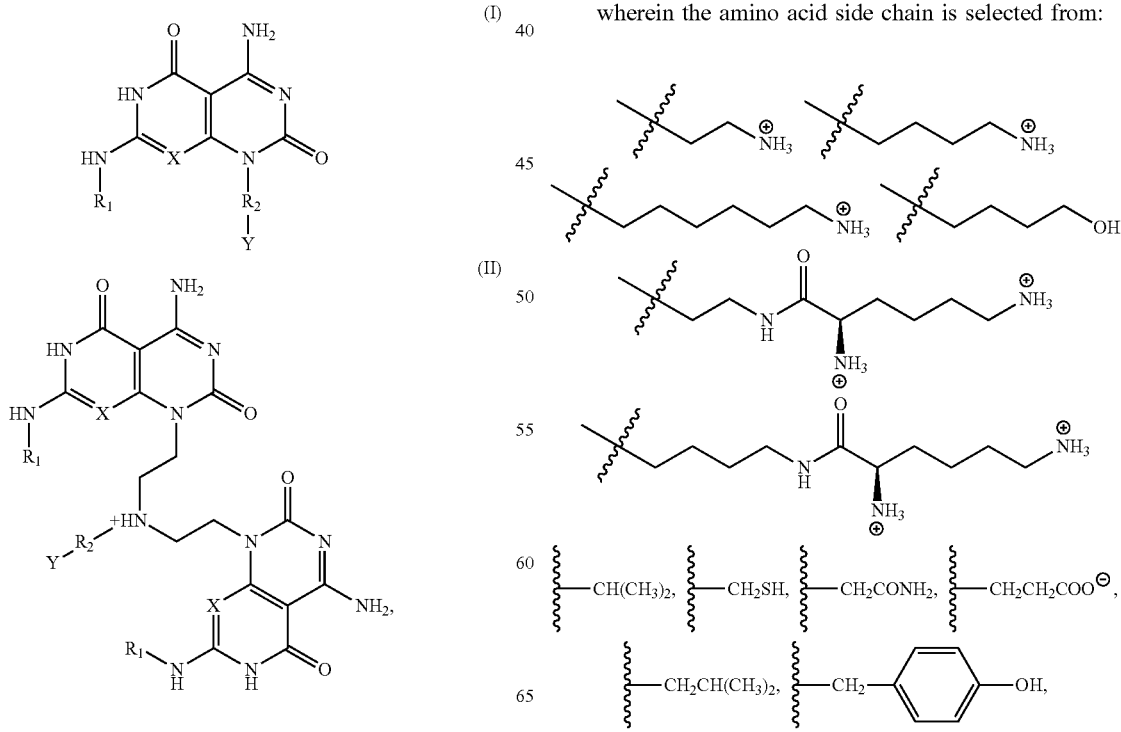

or a salt thereof, wherein,
X is CH or N;
$R_2$ is hydrogen or a linker group;
Y is absent when $R_2$ is hydrogen or is an amino acid or polypeptide;
$R_1$ is hydrogen or aliphatic,
wherein the amino acid side chain is selected from:

-continued

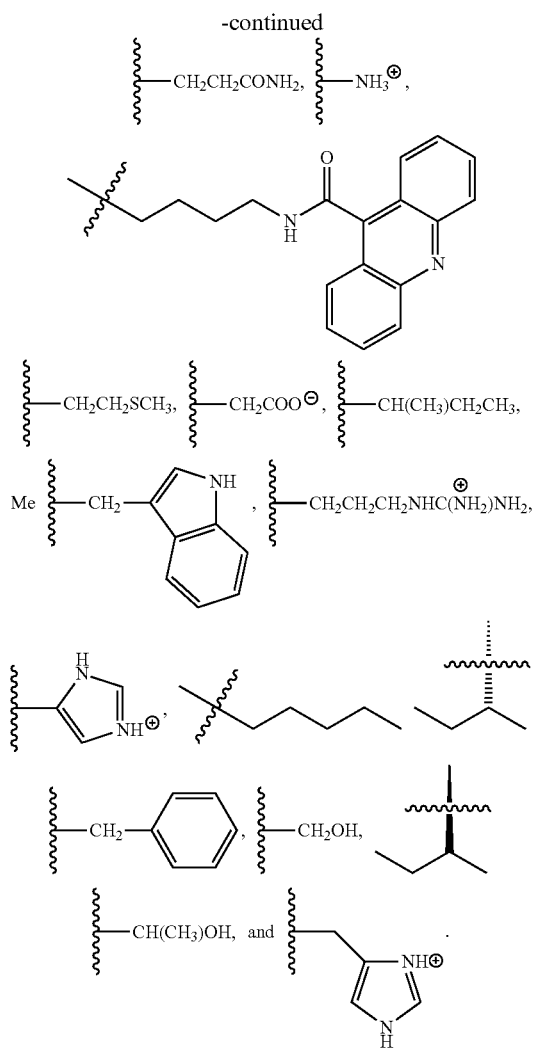

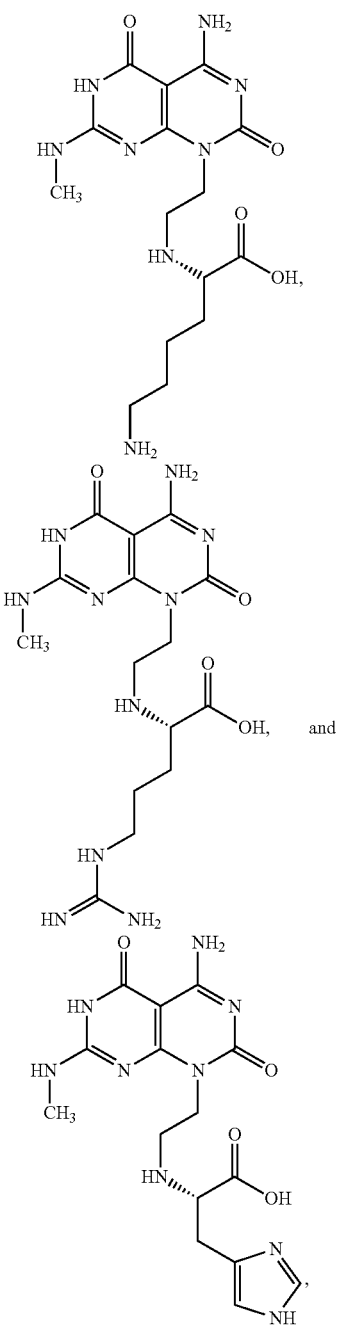

wherein, the compounds of Formula (I), Formula (II), or a salt thereof, or a combination of Formula (I) and Formula (II) self-assemble to form a nanotube, and wherein the nucleic acid comprises an siRNA selected from the group consisting of TNF-α siRNA, a sequence comprising AAG CCT GTA GCC CAC GTC GTA (SEQ ID NO: 229), a sequence comprising GGC ACC ACT AGT TGG TTG TCT TTG (SEQ ID NO: 230), an anti-miR-181a comprising SEQ ID NO: 228, and an anti-miR-181a comprising SEQ ID NO: 229.

2. The method of claim 1, wherein the nanopiece comprises a compound selected from or a salt thereof.

* * * * *